US012377083B2

(12) United States Patent
Lou et al.

(10) Patent No.: US 12,377,083 B2
(45) Date of Patent: Aug. 5, 2025

(54) LYSOPHOSPHATIDIC ACID RECEPTOR ANTAGONIST AND PREPARATION METHOD THEREFOR

(71) Applicant: WUHAN LL SCIENCE AND TECHNOLOGY DEVELOPMENT CO., LTD., Hubei (CN)

(72) Inventors: Jun Lou, Hubei (CN); Yongkai Chen, Hubei (CN); Wei Peng, Hubei (CN); Yihan Zhang, Hubei (CN); Xiaodan Guo, Hubei (CN); Li Liu, Hubei (CN); Junhua Liu, Hubei (CN); Lina Qian, Hubei (CN); Chaodong Wang, Hubei (CN)

(73) Assignee: WUHAN LL SCIENCE AND TECHNOLOGY DEVELOPMENT CO., LTD., Hubei (CN)

( * ) Notice: Subject to any disclaimer, the term of this patent is extended or adjusted under 35 U.S.C. 154(b) by 1056 days.

(21) Appl. No.: 17/310,092

(22) PCT Filed: Jan. 15, 2020

(86) PCT No.: PCT/CN2020/072186
§ 371 (c)(1),
(2) Date: Jul. 15, 2021

(87) PCT Pub. No.: WO2020/147739
PCT Pub. Date: Jul. 23, 2020

(65) Prior Publication Data
US 2022/0079928 A1    Mar. 17, 2022

(30) Foreign Application Priority Data

Jan. 15, 2019  (CN) .......................... 201910037048.2

(51) Int. Cl.
| | | |
|---|---|---|
| *A61K 31/4439* | (2006.01) |
| *A61K 31/415* | (2006.01) |
| *A61K 31/4164* | (2006.01) |
| *A61K 31/42* | (2006.01) |
| *A61K 31/421* | (2006.01) |
| *A61K 31/425* | (2006.01) |
| *A61K 31/426* | (2006.01) |
| *A61P 11/00* | (2006.01) |
| *C07D 207/333* | (2006.01) |
| *C07D 207/34* | (2006.01) |
| *C07D 213/65* | (2006.01) |
| *C07D 231/12* | (2006.01) |
| *C07D 231/16* | (2006.01) |
| *C07D 231/40* | (2006.01) |
| *C07D 233/64* | (2006.01) |
| *C07D 233/68* | (2006.01) |
| *C07D 235/12* | (2006.01) |

(Continued)

(52) U.S. Cl.
CPC ........ *A61K 31/4439* (2013.01); *A61K 31/415* (2013.01); *A61K 31/4164* (2013.01); *A61K 31/42* (2013.01); *A61K 31/421* (2013.01); *A61K 31/425* (2013.01); *A61K 31/426* (2013.01); *A61P 11/00* (2018.01); *C07D 231/12* (2013.01); *C07D 233/64* (2013.01); *C07D 261/08* (2013.01); *C07D 261/14* (2013.01); *C07D 263/32* (2013.01); *C07D 275/02* (2013.01); *C07D 277/24* (2013.01); *C07D 401/04* (2013.01); *C07D 413/04* (2013.01)

(58) Field of Classification Search
CPC .............. A61K 31/4439; A61K 31/415; A61K 31/4164; A61K 31/42; A61K 31/421; A61K 31/425; A61K 31/426; C07D 231/12; C07D 233/64; C07D 261/08; C07D 261/14; C07D 263/32; C07D 275/02; C07D 277/24; C07D 401/04; C07D 413/04; C07D 207/333; C07D 207/34; C07D 213/65; C07D 231/16; C07D 231/40; C07D 233/68; C07D 235/12; C07D 237/08; C07D 239/26; C07D 261/10; C07D 261/18; C07D 263/34; C07D 277/64; C07D 401/14; C07D 403/04; C07D 405/04; C07D 405/14; C07D 409/04; C07D 413/06; C07D 417/04; C07D 498/08; C07D 231/56; C07D 263/48; C07D 277/22; A61P 11/00; A61P 1/00; A61P 1/16; A61P 3/10; A61P 9/00; A61P 9/10; A61P 9/12; A61P 11/06; A61P 13/00; A61P 13/12; A61P 25/00; A61P 25/08; A61P 25/16; A61P 25/28; A61P 27/02; A61P 29/00; A61P 35/00; A61P 37/00; C07F 5/025; C07F 5/02
See application file for complete search history.

(56) References Cited

U.S. PATENT DOCUMENTS

2017/0360759 A1    12/2017  Cheng et al.

FOREIGN PATENT DOCUMENTS

| CN | 104066729 A | 9/2014 |
| CN | 104411690 A | 3/2015 |

(Continued)

*Primary Examiner* — Samantha L Shterengarts
*Assistant Examiner* — Sagar Patel
(74) *Attorney, Agent, or Firm* — NKL Law; Allen Xue

(57) ABSTRACT

Certain compounds are lysophosphatidic acid receptor antagonists have high LPAR1 antagonist activity and selectivity, low toxicity, good metabolic stability, promising pharmaceutical development prospects, and may be used for preventing or treating LPAR1-related diseases or illnesses. The IC50 values of some of the compounds may be as low as 300 nM or below, even 50 nM or below. In addition, CC50 value range of the compounds may be as high as 200

(Continued)

μM or above. Furthermore, the compounds have good metabolic stability in humans, mice and rats.

3 Claims, No Drawings

(51) Int. Cl.
| | |
|---|---|
| *C07D 237/08* | (2006.01) |
| *C07D 239/26* | (2006.01) |
| *C07D 261/08* | (2006.01) |
| *C07D 261/10* | (2006.01) |
| *C07D 261/14* | (2006.01) |
| *C07D 261/18* | (2006.01) |
| *C07D 263/32* | (2006.01) |
| *C07D 263/34* | (2006.01) |
| *C07D 275/02* | (2006.01) |
| *C07D 277/24* | (2006.01) |
| *C07D 277/64* | (2006.01) |
| *C07D 401/04* | (2006.01) |
| *C07D 401/14* | (2006.01) |
| *C07D 403/04* | (2006.01) |
| *C07D 413/04* | (2006.01) |

(56) References Cited

FOREIGN PATENT DOCUMENTS

| | | |
|---|---|---|
| CN | 104418820 A | 3/2015 |
| WO | 2008076754 A2 | 6/2008 |
| WO | 2017223016 A1 | 12/2017 |
| WO | 2019126084 A1 | 6/2019 |
| WO | 2019126085 A1 | 6/2019 |
| WO | 2019126086 A1 | 6/2019 |
| WO | 2019126098 A1 | 6/2019 |
| WO | 2019126099 A1 | 6/2019 |
| WO | 2020060915 A1 | 3/2020 |
| WO | 2020081410 A2 | 4/2020 |

LYSOPHOSPHATIDIC ACID RECEPTOR ANTAGONIST AND PREPARATION METHOD THEREFOR

The present application is a U.S. national stage entry of PCT International Application No. PCT/CN2020/072186, filed Jan. 15, 2020, which claims the priority of Chinese Patent No. 201910037048.2 filed on Jan. 15, 2019 with China National Intellectual Property Administration, titled "LYSOPHOSPHATIDIC ACID RECEPTOR ANTAGONIST AND PREPARATION METHOD THEREFOR", which is incorporated herein by reference in its entirety.

TECHNICAL FIELD

The present invention relates to the technical field of pharmaceutical chemistry, and in particular relates to a lysophosphatidic acid receptor antagonist and a preparation method therefor.

BACKGROUND

To date, six LPA receptors (LPARs), LPAR1 to LPAR6, have been discovered. Lysophosphatidic acid receptor 1 (LPAR1) is a G protein-coupled receptor that mediates the growth factor-like activity of lysophosphatidic acid (LPA), which plays an important role in the development of cancers, especially breast cancer and ovarian cancer. siRNA silencing of LPA1 or the use of LPA1 antagonists lead to the reduction of tumor burden in bone tissues and soft tissues; additionally, LPA signaling can protect individuals from infection-induced inflammation; LPA receptor agonists may be effective in protecting patients with acute radiation syndrome; the upregulation of LPA activity is associated with the fibrosis observed in systemic scleroderma.

No drug is available on the market that, as an LPAR1 inhibitor, treats numerous conditions, including idiopathic pulmonary fibrosis. Therefore, the development of novel compounds capable of inhibiting LPAR1 activity is of great significance for treating diseases.

SUMMARY

To solve the technical problem of the insufficiency of LPAR1 antagonist in the prior art, the present invention provides a lysophosphatidic acid receptor antagonist and a preparation method therefor. The compounds disclosed herein feature high antagonistic activity against LPAR1, good selectivity, low toxicity and good metabolic stability.

The present invention solves the above technical problems by the following technical schemes.

The present invention provides a compound of formula (I), and a stereoisomer, a tautomer, an isotopically labeled compound, a nitrogen oxide, a solvate, a polymorph, a metabolite, an ester, a pharmaceutically acceptable salt or a prodrug thereof,

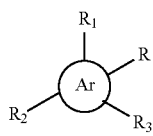

Formula (I)

wherein,

is selected from $C_{6-20}$ aryl and 5-20 membered heteroaryl; preferably

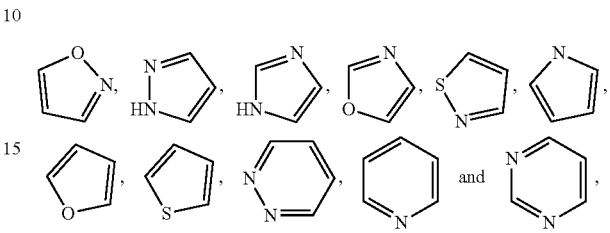

more preferably

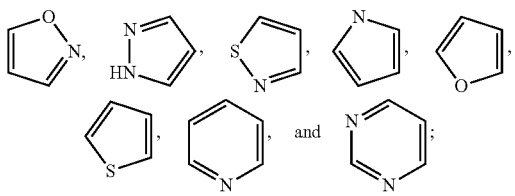

$R_1$, $R_2$, $R_3$ and R can be at any position of

$R_1$ is selected from H, and $C_{1-40}$ alkyl unsubstituted or optionally substituted with one, two or more $R_a$; preferably, $R_1$ is selected from $C_{1-40}$ alkyl unsubstituted or optionally substituted with one, two or more $R_a$, e.g., methyl;

$R_2$ is selected from halogen, COOH, OH, SH, CN, $NO_2$, $NH_2$, $C_{1-40}$ haloalkyl, and the following groups unsubstituted or optionally substituted with one, two or more $R_b$: $C_{1-40}$ alkyl, $C_{1-40}$ alkoxy, $C_{1-40}$ alkylthio, $C_{2-40}$ alkenyl, $C_{2-40}$ alkenyloxy, $C_{2-40}$ alkenylthio, $C_{2-40}$ alkynyl, $C_{2-40}$ alkynyloxy, $C_{2-40}$ alkynylthio, $C_{3-20}$ cycloalkyl, $C_{3-20}$ cycloalkylthio, 3-20 membered heterocyclyl, 3-20 membered heterocyclyloxy, 3-20 membered heterocyclylthio, $C_{6-20}$ aryl, $C_{6-20}$ aryloxy, $C_{6-20}$ arylthio, 5-20 membered heteroaryl, 5-20 membered heteroaryloxy, 5-20 membered heteroarylthio, $—R_4—O—R_5$, $—R_4—R_5$ and $—O—R_5$; $R_4$ is selected from the following groups unsubstituted or optionally substituted with one, two or more $R_b$: $C_{6-20}$ aryl, 5-20 membered heteroaryl and 3-14 membered heterocyclyl; preferably, $R_4$ is selected from the following groups unsubstituted or optionally substituted with one, two or more $R_b$: $C_{6-20}$ aryl and 5-20 membered heteroaryl, e.g., phenyl,

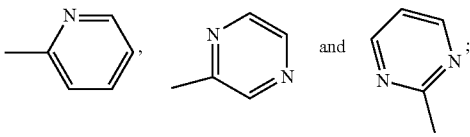

$R_5$ is selected from the following groups unsubstituted or optionally substituted with one, two or more $R_b$: $C_{3-20}$ cycloalkyl, $C_{6-20}$ aryl and 5-20 membered heteroaryl; preferably, $R_5$ is selected from $C_{3-20}$ cycloalkyl unsubstituted or optionally substituted with one, two or more $R_b$, e.g., cyclohexyl;

$R_3$ is selected from the following groups unsubstituted or optionally substituted with one, two or more $R_c$: $C_{1-40}$ alkyl, $C_{1-40}$ alkoxy, $C_{1-40}$ haloalkyl, —$OR_8$, —$R_6$—O—$R_8$, —NH—$R_8$, —$R_6$—NH—$R_8$,

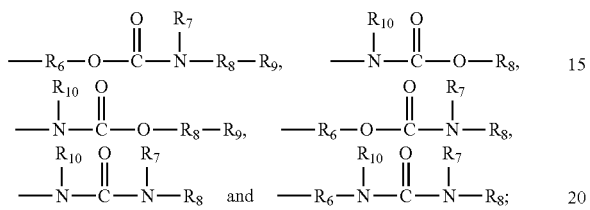

any position of the above groups can be substituted with $R_c$, that is, any position of $R_6$, $R_7$, $R_8$, $R_9$ and $R_{10}$ can be substituted with $R_c$; $R_6$ and $R_7$ are the same or different, and are each independently selected from the following groups unsubstituted or optionally substituted with one, two or more $R_c$: $C_{1-40}$ alkyl and $C_{3-20}$ cycloalkyl; preferably, $R_6$ and $R_7$ are selected from $C_{1-40}$ alkyl unsubstituted or optionally substituted with one, two or more $R_c$, e.g., methyl; $R_8$ is selected from the following groups unsubstituted or optionally substituted with one, two or more $R_c$: $C_{1-40}$ alkyl, $C_{3-20}$ cycloalkyl, $C_{6-20}$ aryl, 5-20 membered heteroaryl and 3-20 membered heterocyclyl; preferably, $R_8$ is selected from the following groups unsubstituted or optionally substituted with one, two or more $R_c$: $C_{3-20}$ cycloalkyl and 3-20 membered heterocyclyl. For example, $R_8$ is selected from cyclopropyl, cyclobutyl, cyclopentyl, oxetane, oxocyclopentane, oxocyclohexane, tetrahydrofuran, tetrahydropyran,

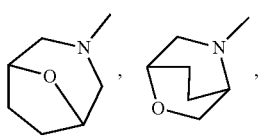

phenyl and methylphenyl; $R_9$ is selected from $C_{6-20}$ aryl unsubstituted or optionally substituted with one, two or more $R_c$; $R_{10}$ is selected from H, and the following groups unsubstituted or optionally substituted with one, two or more $R_c$: $C_{1-40}$ alkyl and $C_{3-20}$ cycloalkyl;

wherein, any of $R_7$, $R_8$, $R_9$ and $R_{10}$, together with the N atoms connected thereto, can form the following ring system unsubstituted or optionally substituted with one, two or more $R_e$: 3-20 membered heterocyclyl;

R is selected from H, OH, $NH_2$, CN, $NO_2$, halogen, $C_{1-40}$ haloalkyl, and the following groups unsubstituted or optionally substituted with one, two or more $R_f$: $C_{1-40}$ alkyl, $C_{3-20}$ cycloalkyl, $C_{2-40}$ alkenyl and $C_{1-40}$ alkoxy; preferably, R is selected from F, Cl, CN, and $C_{1-40}$ haloalkyl, and wherein $C_{1-40}$ haloalkyl, for example, is selected from $C_{1-40}$ fluoroalkyl, e.g., $CF_3$;

each $R_a$, $R_b$, $R_c$, $R_e$ and $R_f$ is the same or different, and is independently selected from halogen, COOH, OH, SH, CN, =O, $NO_2$, $NH_2$, $C_{1-40}$ haloalkyl, and the following groups unsubstituted or optionally substituted with one, two or more $R_d$: $C_{1-40}$ alkyl, $C_{1-40}$ alkoxy, $C_{1-40}$ alkylthio, $C_{2-40}$ alkenyl, $C_{2-40}$ alkenyloxy, $C_{2-40}$ alkenylthio, $C_{2-40}$ alkynyl, $C_{2-40}$ alkynyloxy, $C_{2-40}$ alkynylthio, $C_{3-20}$ cycloalkyl, $C_{3-20}$ cycloalkyloxy, $C_{3-20}$ cycloalkylthio, 3-20 membered heterocyclyl, 3-20 membered heterocyclyloxy, 3-20 membered heterocyclylthio, $C_{6-20}$ aryl, $C_{6-20}$ aryloxy, $C_{6-20}$ arylthio, 5-20 membered heteroaryl, 5-20 membered heteroaryloxy and 5-20 membered heteroarylthio;

each $R_d$ is the same or different, and is independently selected from OH, $C_{1-40}$ alkyl, $C_{2-40}$ alkenyl, $C_{2-40}$ alkynyl, $C_{3-20}$ cycloalkyl, 3-20 membered heterocyclyl, $C_{6-20}$ aryl and 5-20 membered heteroaryl; preferably, $R_b$ is selected from COOH, halogen, $C_{1-40}$ haloalkyl and $C_{1-40}$ alkyl; for example, $R_b$ is selected from COOH, F, methyl and $C_{1-40}$ fluoroalkyl; and $C_{1-40}$ fluoroalkyl is selected from $CF_3$, $CH_2F$ and $CHF_2$. According to an embodiment of the present invention,

is selected from $C_{6-14}$ aryl and 5-14 membered heteroaryl; preferably

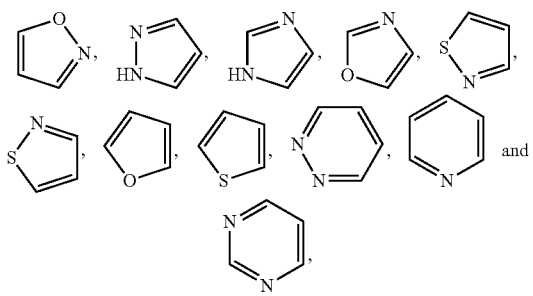

more preferably

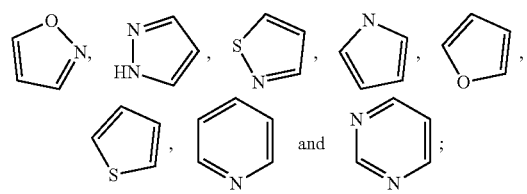

$R_1$ is selected from H, and $C_{1-6}$ alkyl unsubstituted or optionally substituted with one, two or more $R_a$; preferably, $R_1$ is selected from $C_{1-6}$ alkyl unsubstituted or optionally substituted with one, two or more $R_a$, e.g., methyl;

$R_2$ is selected from halogen, COOH, OH, SH, CN, $NO_2$, $NH_2$, $C_{1-40}$ haloalkyl, and the following groups unsubstituted or optionally substituted with one, two or more $R_b$: $C_{1-6}$ alkyl, $C_{1-6}$ alkoxy, $C_{1-6}$ alkylthio, $C_{2-10}$ alkenyl, $C_{2-10}$ alkenyloxy, $C_{2-10}$ alkenylthio, $C_{2-10}$ alkynyl, $C_{2-10}$ alkynyloxy, $C_{2-10}$ alkynylthio, $C_{3-14}$ cycloalkyl, $C_{3-14}$ cycloalkylthio, 3-14 membered heterocyclyl, 3-14 membered heterocyclyloxy, 3-14 membered heterocyclylthio, $C_{6-14}$ aryl, $C_{6-14}$ aryloxy, $C_{6-14}$ arylthio, 5-14 membered heteroaryl, 5-14 membered heteroaryloxy, 5-14 membered heteroarylthio, —R$_4$—O—R$_5$, —R$_4$—R$_5$ and —O—R$_5$; R$_4$ is selected from the following groups unsubstituted or optionally substituted with one, two or more R$_b$: C$_{6-14}$ aryl, 5-14 membered heteroaryl and 3-14 membered heterocyclyl; preferably, R$_4$ is selected from C$_{6-14}$ aryl unsubstituted or optionally substituted with one, two or more R$_b$, e.g., phenyl,

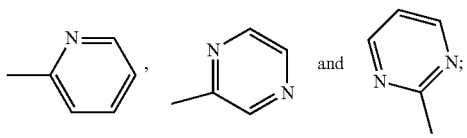

R$_5$ is selected from the following groups unsubstituted or optionally substituted with one, two or more R$_b$: C$_{3-14}$ cycloalkyl, C$_{6-14}$ aryl and 5-14 membered heteroaryl; preferably, R$_5$ is selected from C$_{3-14}$ cycloalkyl unsubstituted or optionally substituted with one, two or more R$_b$, e.g., cyclohexyl; for example, R$_b$ is selected from COOH, halogen, C$_{1-6}$ haloalkyl and C$_{1-6}$ alkyl;

R$_3$ is selected from the following groups unsubstituted or optionally substituted with one, two or more R$_c$:

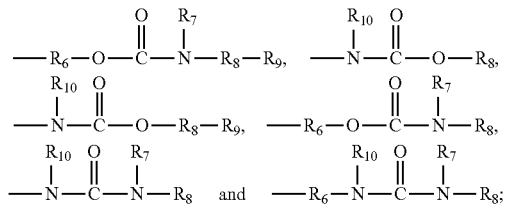

any position of the above groups can be substituted with R$_c$, that is, any position of R$_6$, R$_7$, R$_8$, R$_9$ and R$_{10}$ can be substituted with R$_c$;

R$_6$ and R$_7$ are the same or different, and are each independently selected from the following groups unsubstituted or optionally substituted with one, two or more R$_c$: C$_{1-6}$ alkyl and C$_{3-14}$ cycloalkyl; preferably, R$_6$ and R$_7$ are selected from C$_{1-6}$ alkyl unsubstituted or optionally substituted with one, two or more R$_c$, e.g., methyl;

R$_8$ is selected from the following groups unsubstituted or optionally substituted with one, two or more R$_c$: C$_{1-6}$ alkyl, C$_{3-14}$ cycloalkyl, C$_{6-14}$ aryl, 5-14 membered heteroaryl and 3-14 membered heterocyclyl; preferably, R$_8$ is selected from the following groups unsubstituted or optionally substituted with one, two or more R$_c$: C$_{3-14}$ cycloalkyl and 3-20 membered heterocyclyl, for example, R$_8$ is selected from cyclopropyl, cyclobutyl, cyclopentyl, oxetane, oxocyclopentane, oxocyclohexane, tetrahydrofuran, tetrahydropyran,

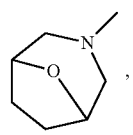

phenyl and methylphenyl; R$_9$ is selected from C$_{6-14}$ aryl unsubstituted or optionally substituted with one, two or more R$_c$; R$_{10}$ is selected from H, and the following groups unsubstituted or optionally substituted with one, two or more R$_c$: C$_{1-6}$ alkyl and C$_{3-14}$ cycloalkyl; or, any of R$_7$, R$_8$, R$_9$ and R$_{10}$, together with the N atoms connected thereto, can form the following ring system unsubstituted or optionally substituted with one, two or more R$_e$: 3-14 membered heterocyclyl; R is selected from H, OH, NH$_2$, CN, NO$_2$, halogen, C$_{1-6}$ haloalkyl, and the following groups unsubstituted or optionally substituted with one, two or more R$_f$: C$_{1-6}$ alkyl, C$_{3-14}$ cycloalkyl, C$_{2-10}$ alkenyl and C$_{1-6}$ alkoxy; preferably, R is selected from H, F, Cl, CN, and C$_{1-6}$ haloalkyl, and wherein C$_{1-6}$ haloalkyl, for example, is selected from C$_{1-6}$ fluoroalkyl, e.g., CF$_3$;

R$_a$, R$_b$, R$_c$, R$_e$ and R$_f$ are defined as above.

As an example,

is selected from the following ring systems:

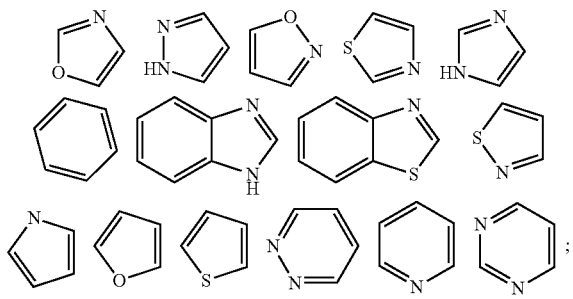

R$_1$ is selected from H, CH$_3$ and cyclopropyl;

R$_2$ is selected from the following groups:

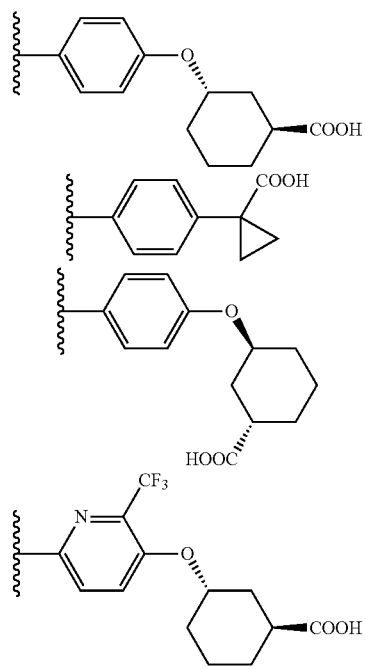

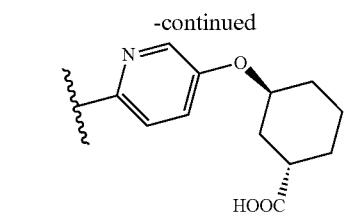
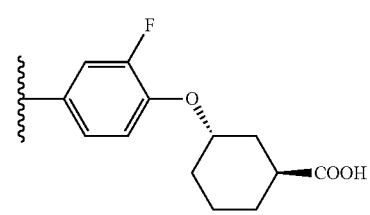
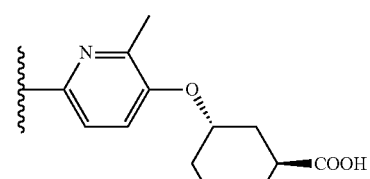
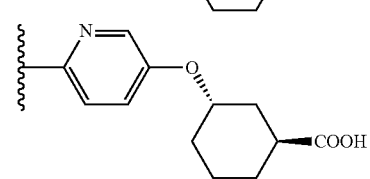
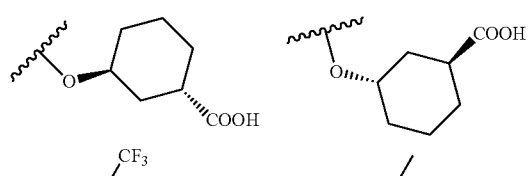
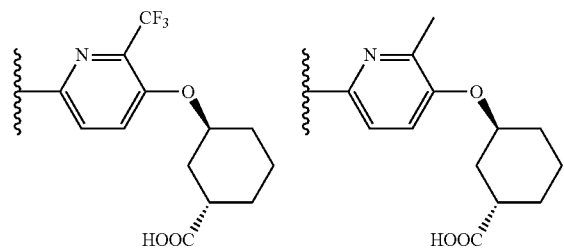
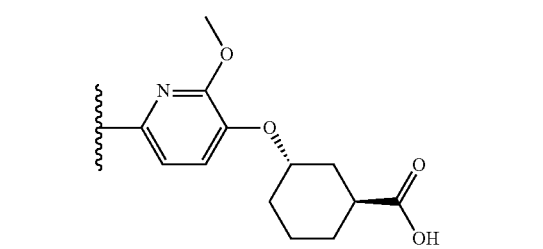
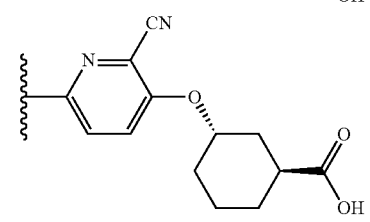
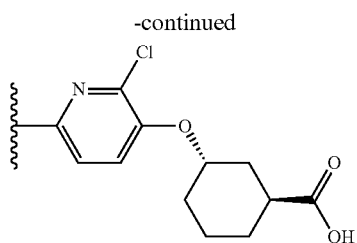
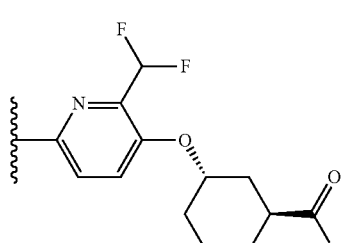
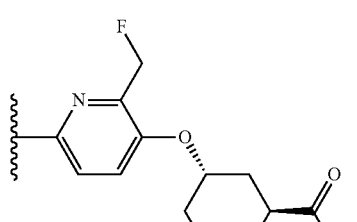
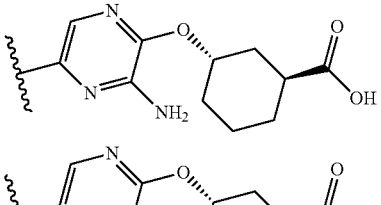
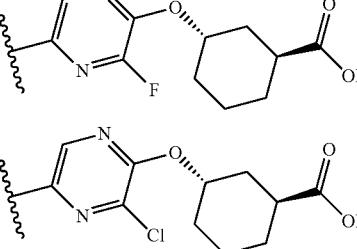
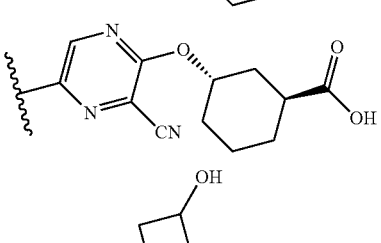
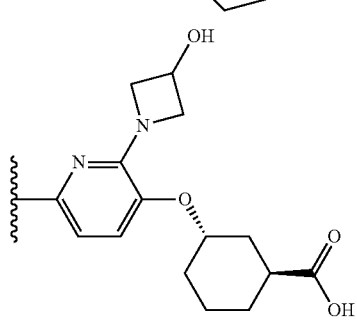

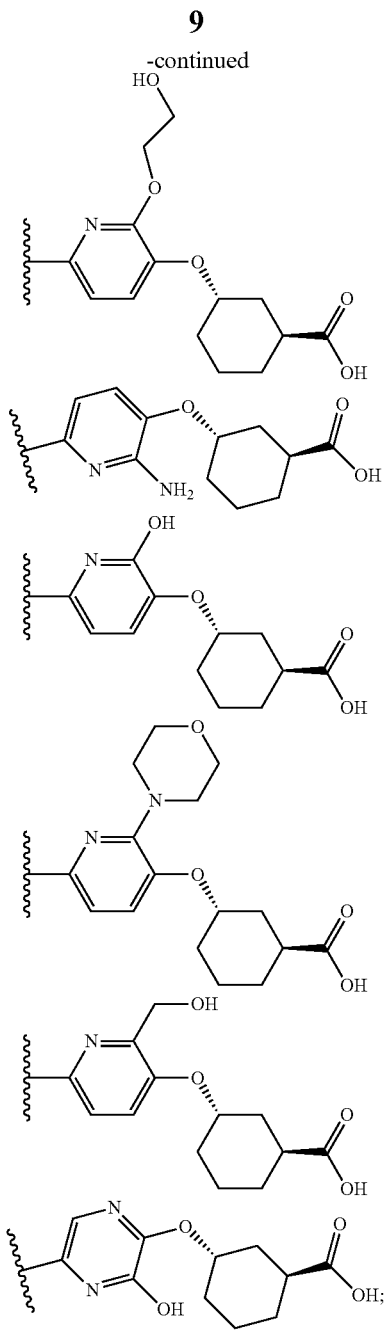
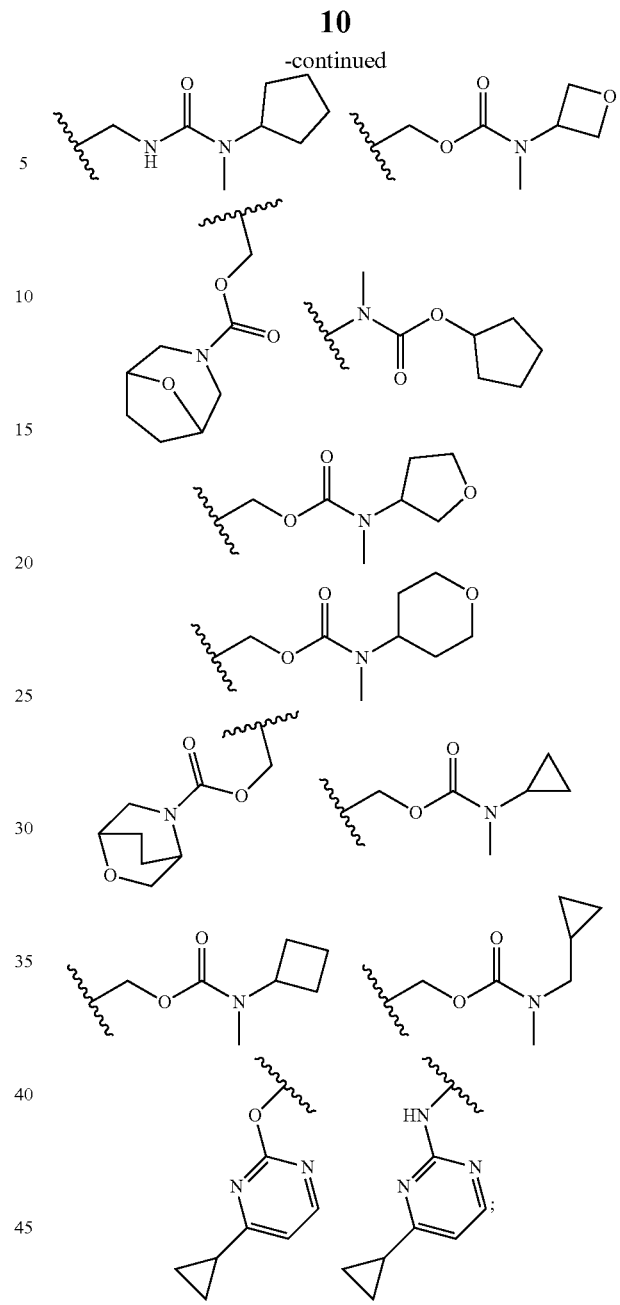
R is selected from H, F, Cl, CN, cyclopropyl and CF$_3$;
As an example, the compound of formula (I) includes, but is not limited to, the following compounds:
R$_3$ is selected from the following groups:
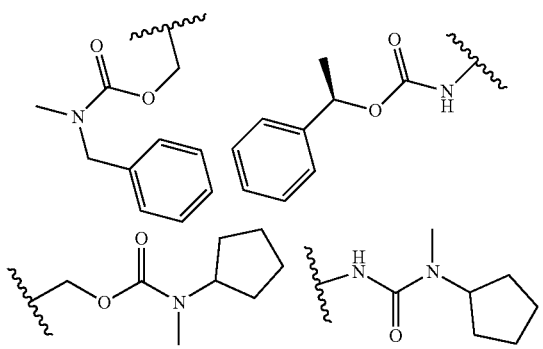
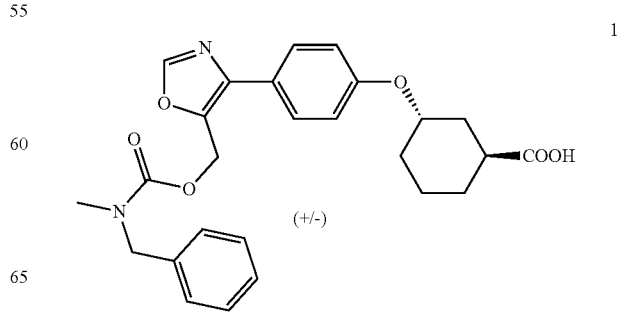

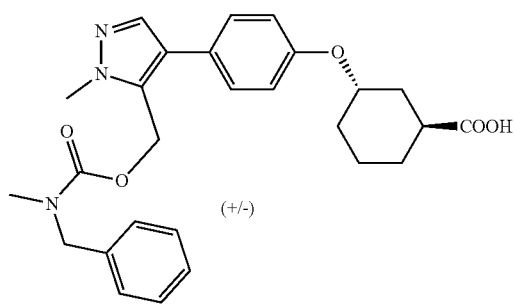
2
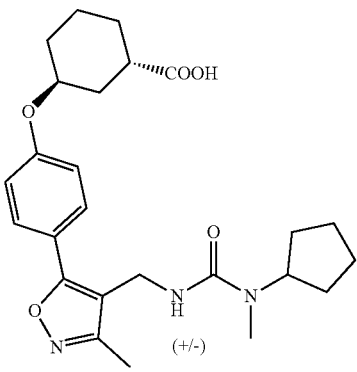
5
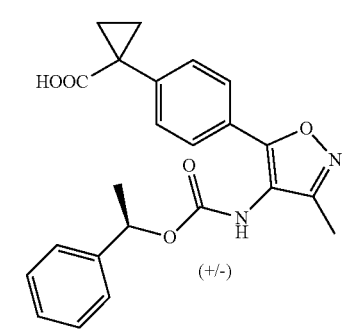
3
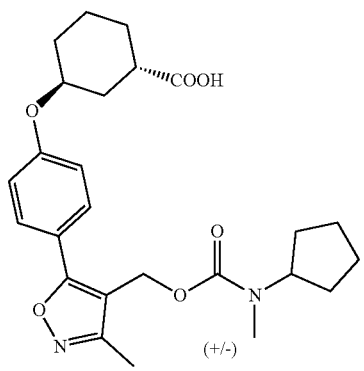
4
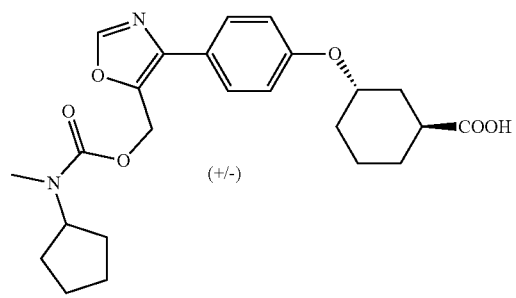
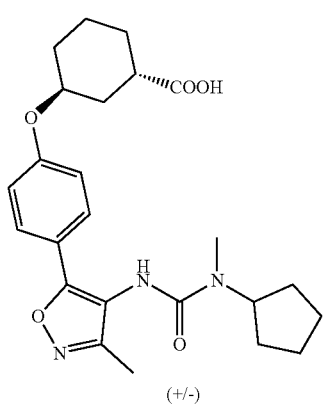
5
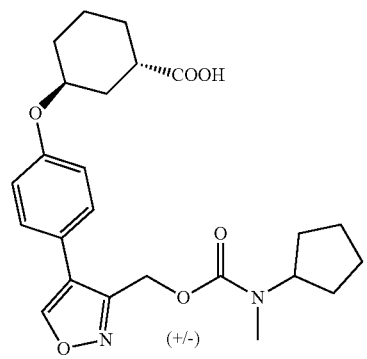

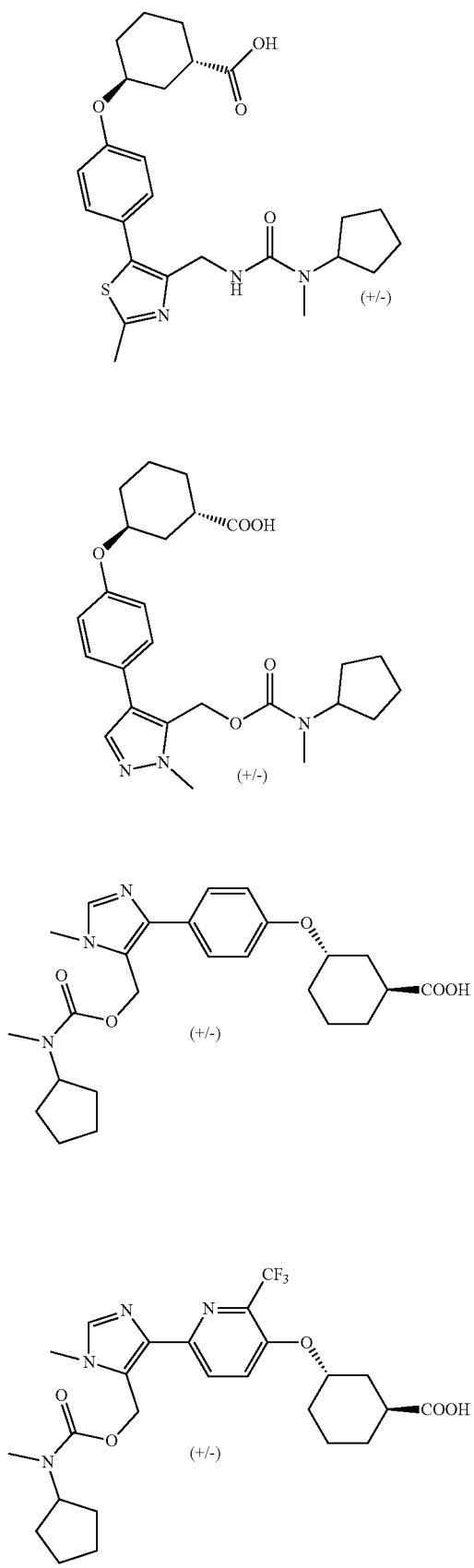
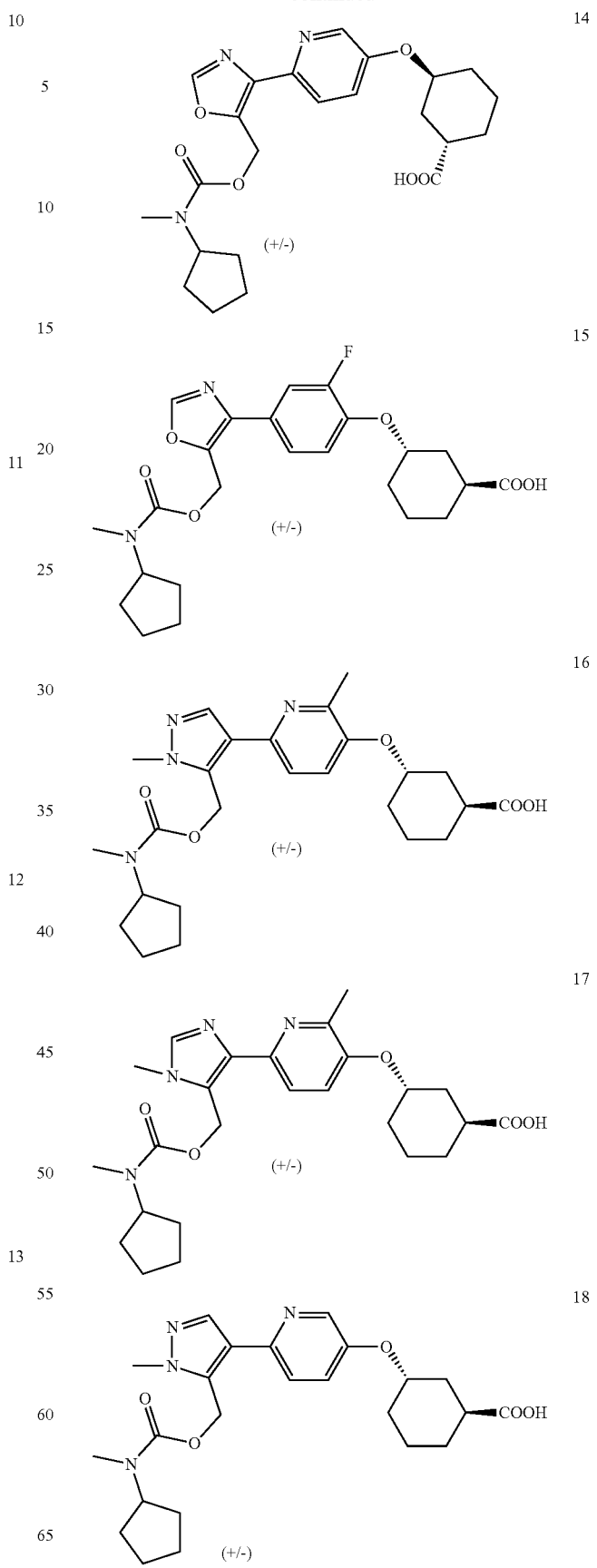

-continued
19
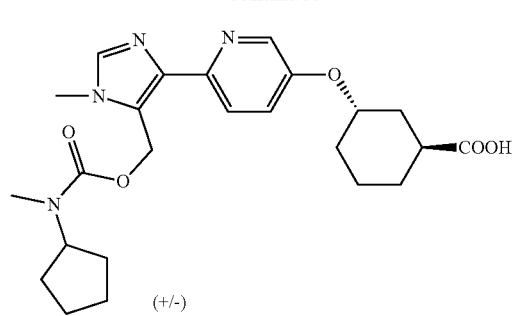
(+/-)
20
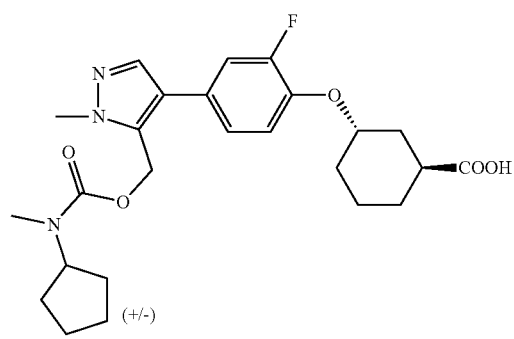
(+/-)
21
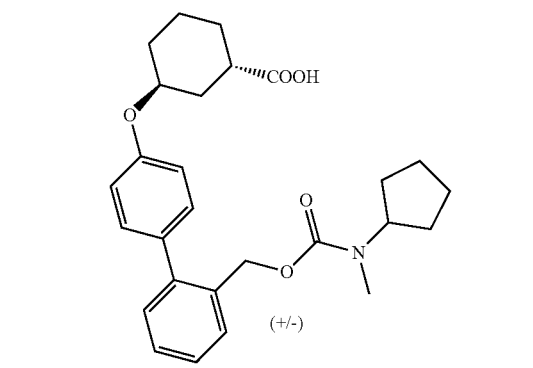
(+/-)
22
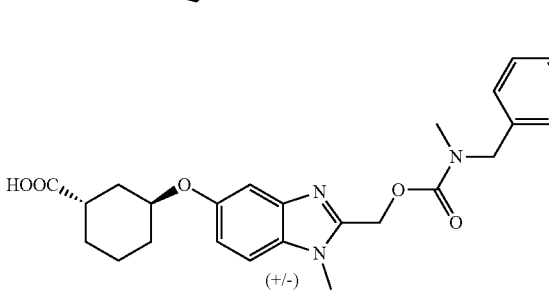
(+/-)
23
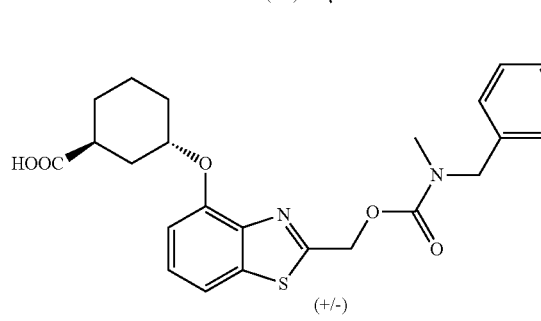
(+/-)
-continued
24
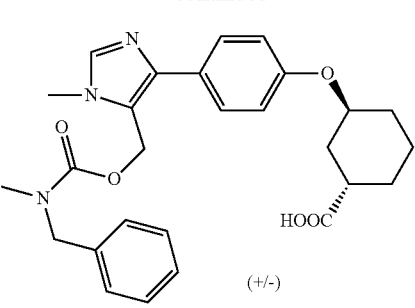
(+/-)
25
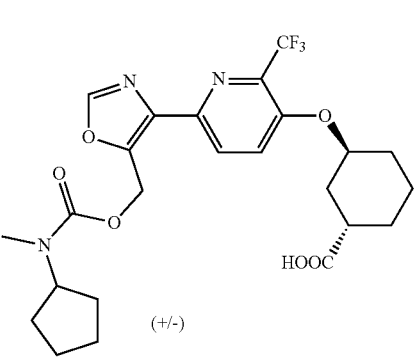
(+/-)
26
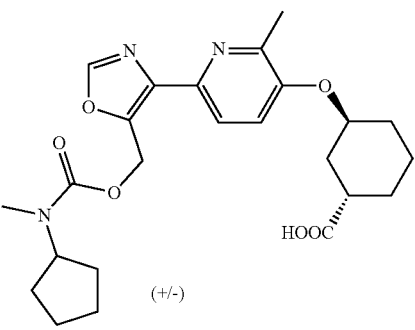
(+/-)
27
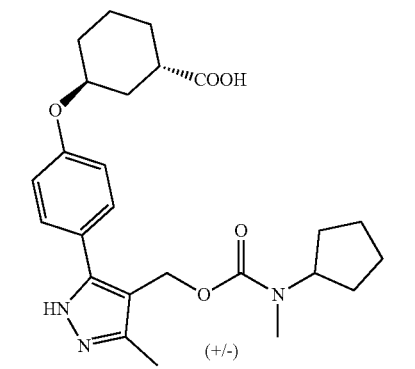
(+/-)

-continued
28
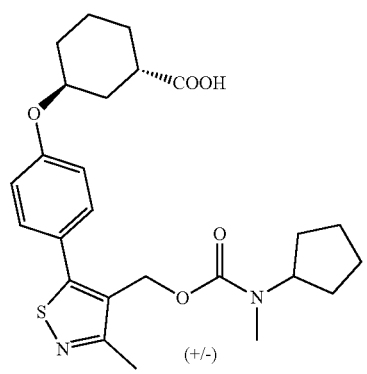
(+/-)
29
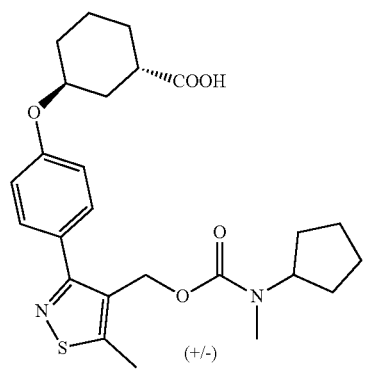
(+/-)
30
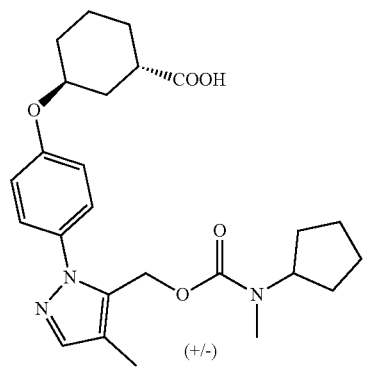
(+/-)
31
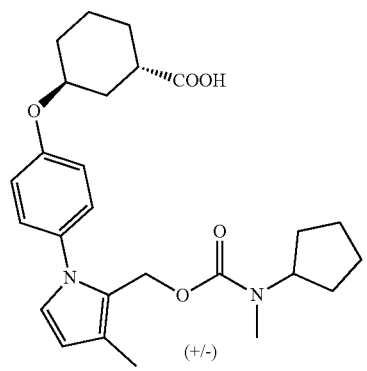
(+/-)
-continued
32
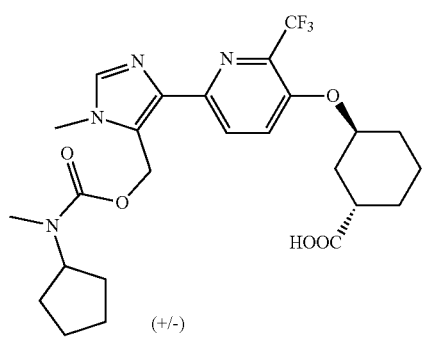
(+/-)
33
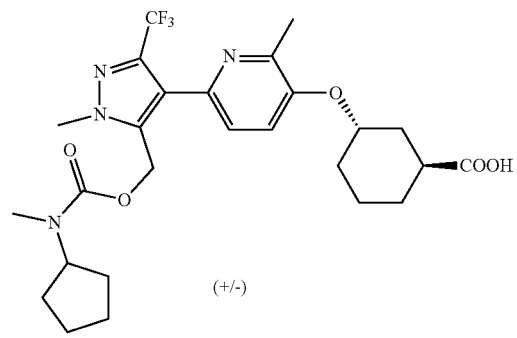
(+/-)
34
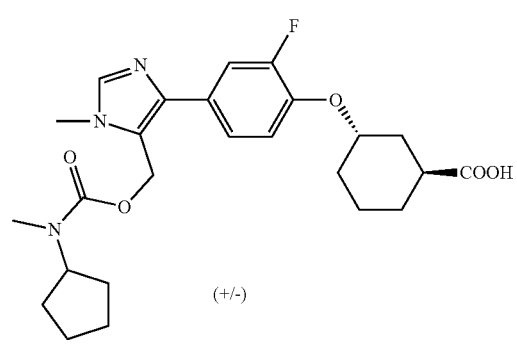
(+/-)
35
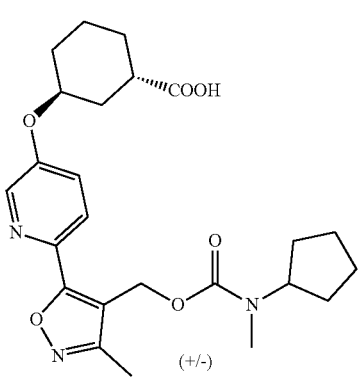
(+/-)

36
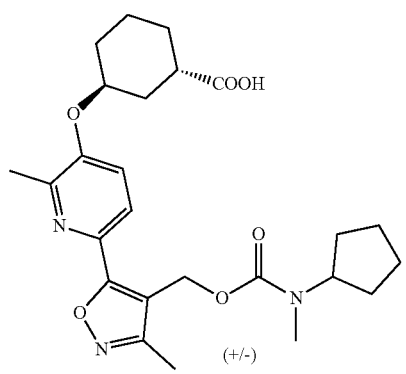
(+/-)
37
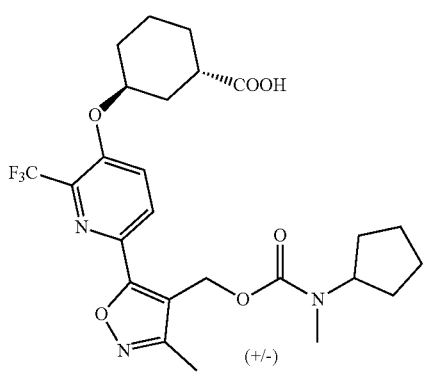
(+/-)
38
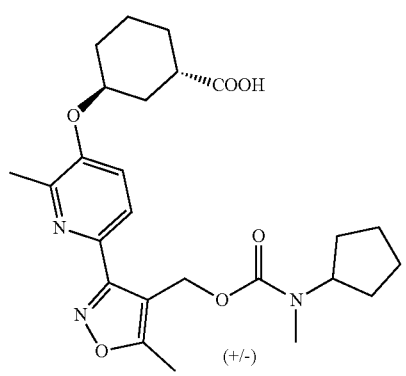
(+/-)
39
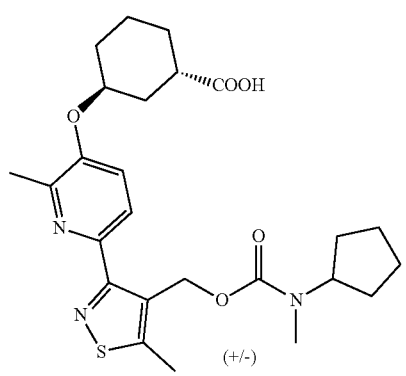
(+/-)
40
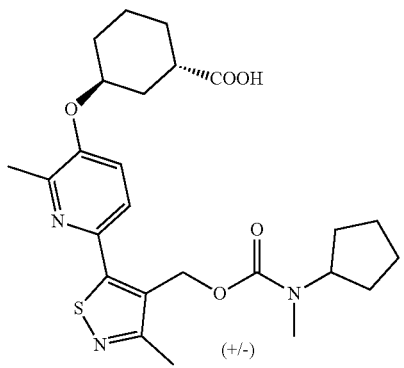
(+/-)
41
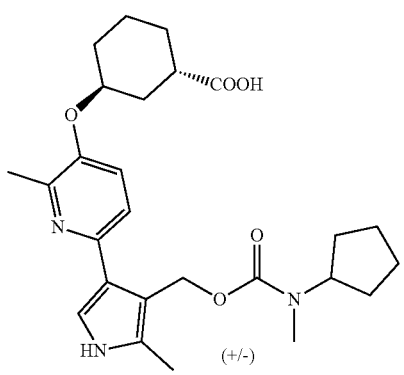
(+/-)
42
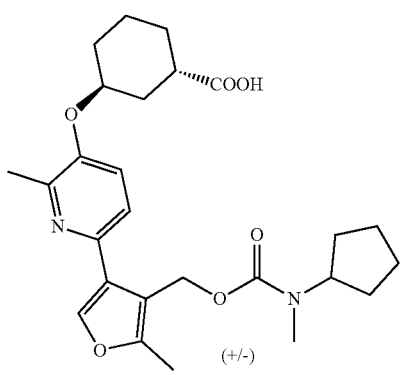
(+/-)
43
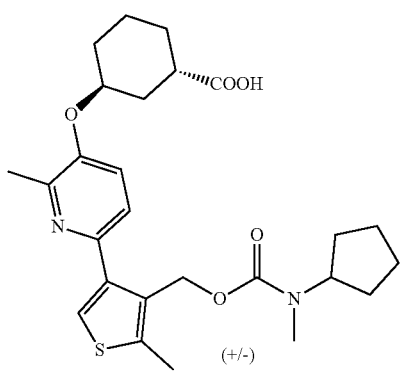
(+/-)

44
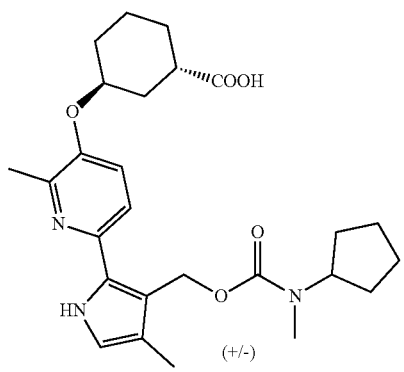
(+/-)
45
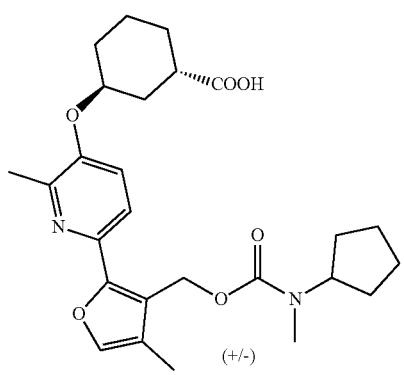
(+/-)
46
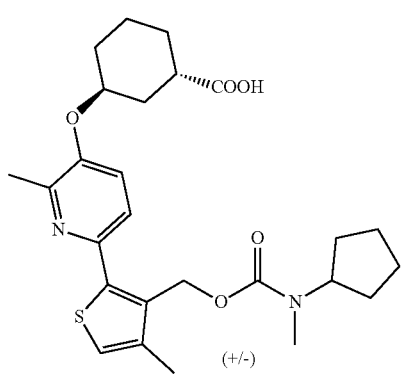
(+/-)
47
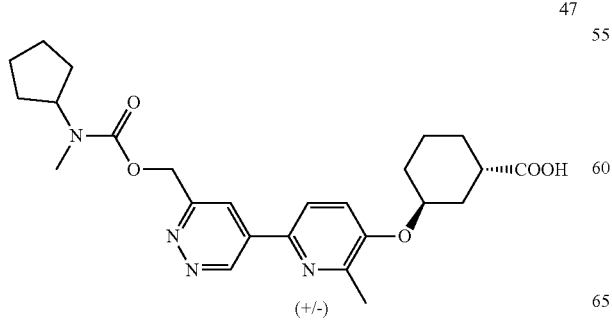
(+/-)
48
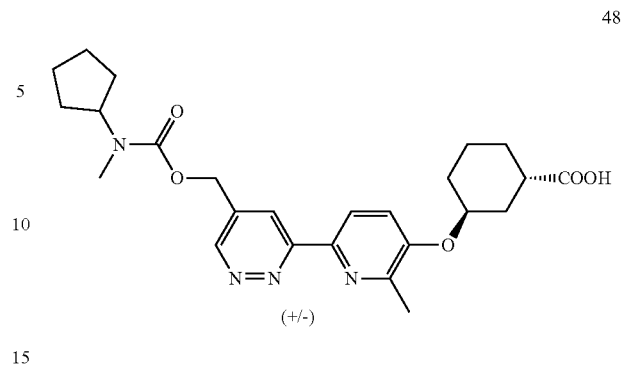
(+/-)
49
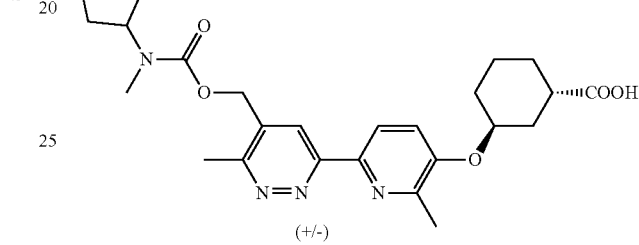
(+/-)
50
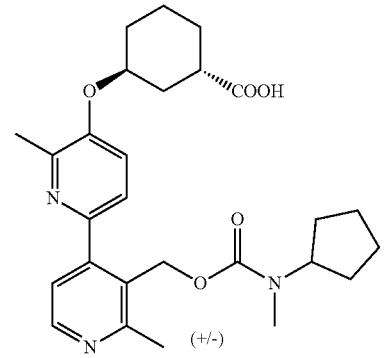
(+/-)
51
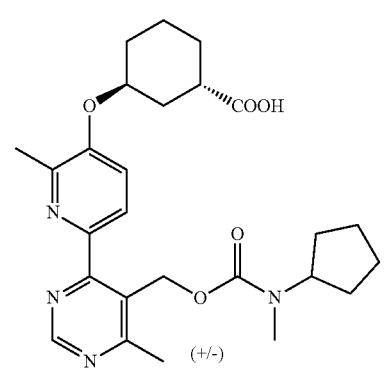
(+/-)

23
-continued
52
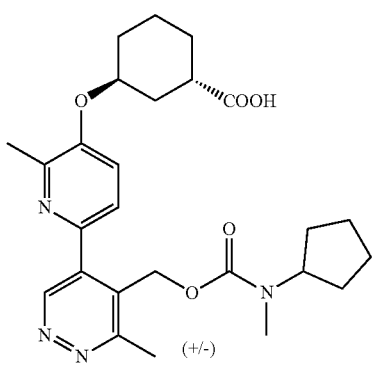
(+/-)
53
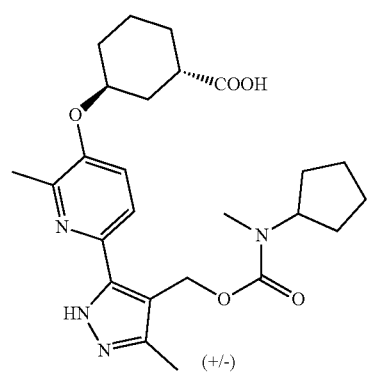
(+/-)
54
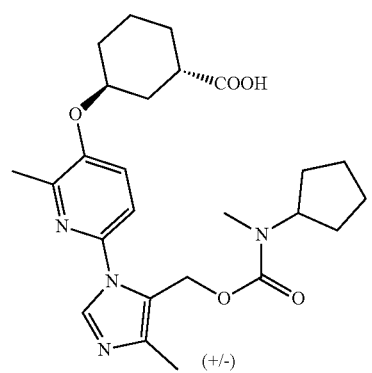
(+/-)
55
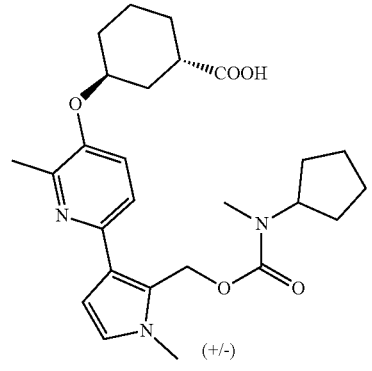
(+/-)
24
-continued
56
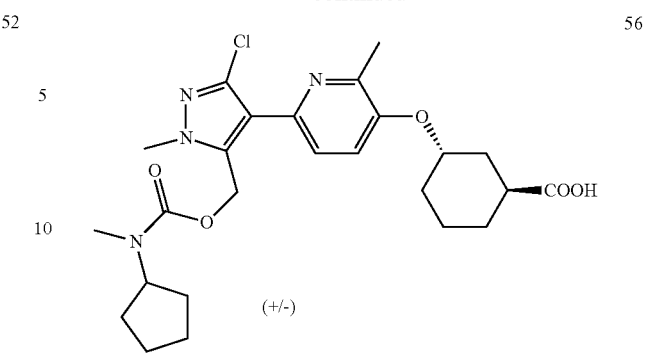
(+/-)
57
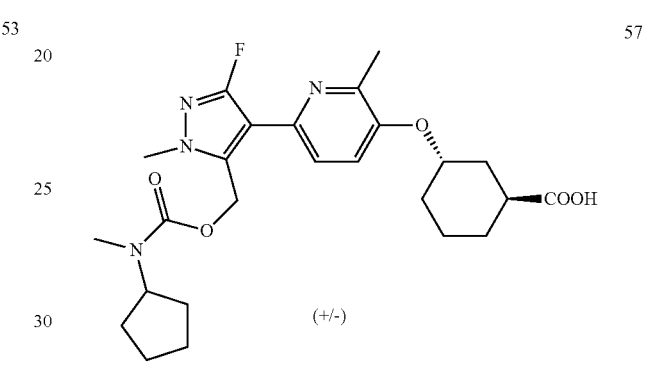
(+/-)
58
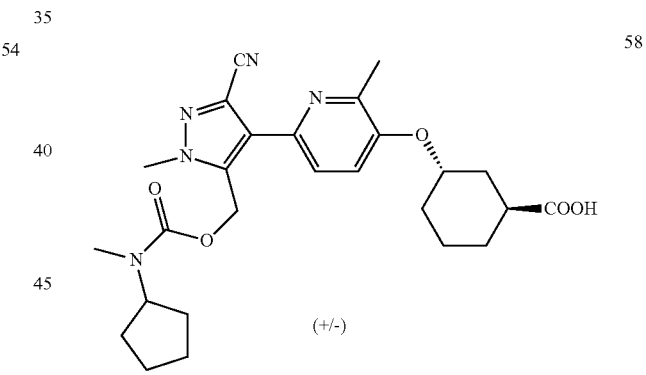
(+/-)
59
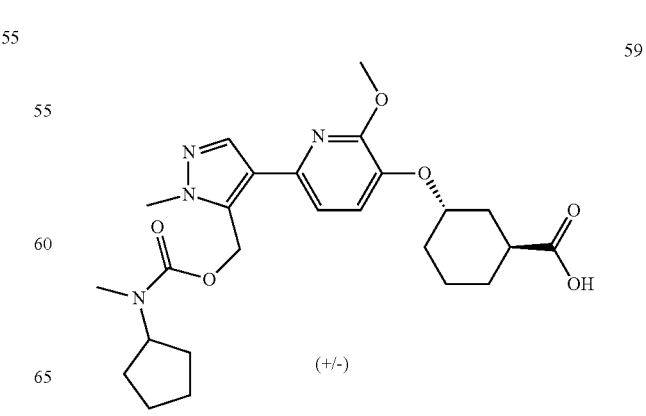
(+/-)

60
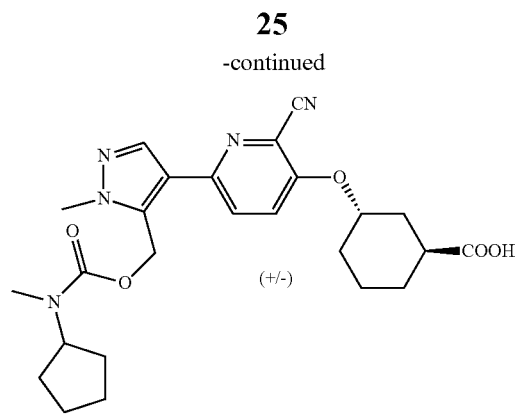
(+/-)
61
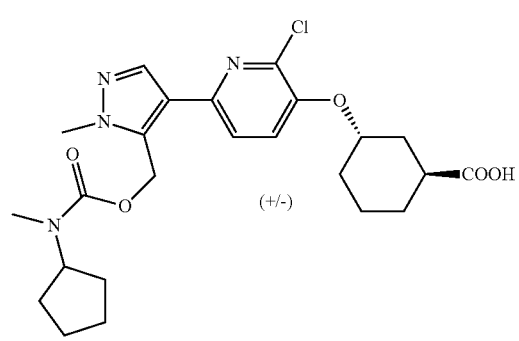
(+/-)
62
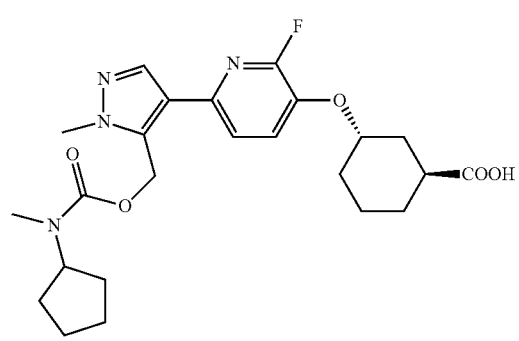
(+/-)
63
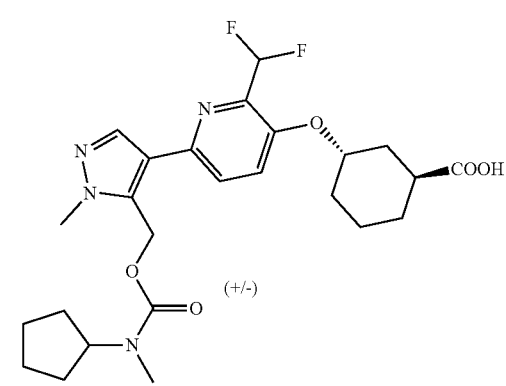
(+/-)
64
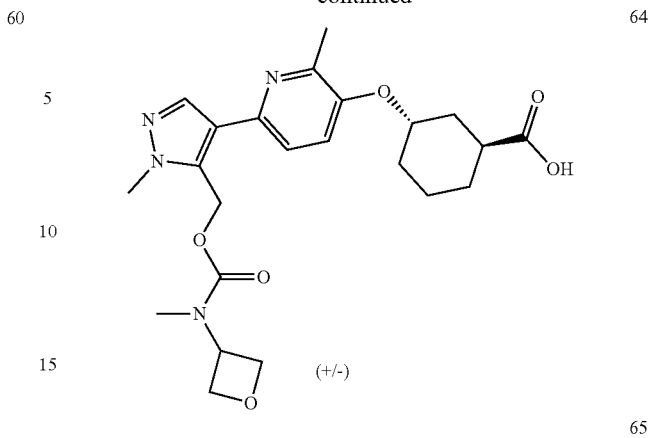
(+/-)
65
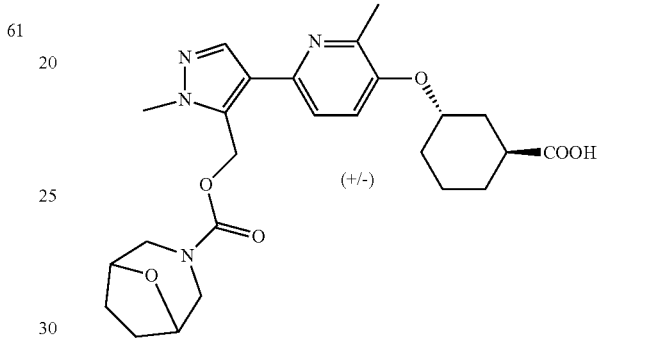
(+/-)
66
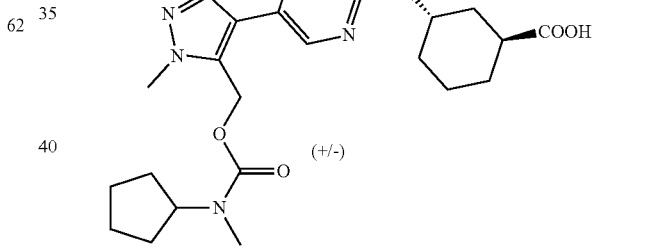
(+/-)
67
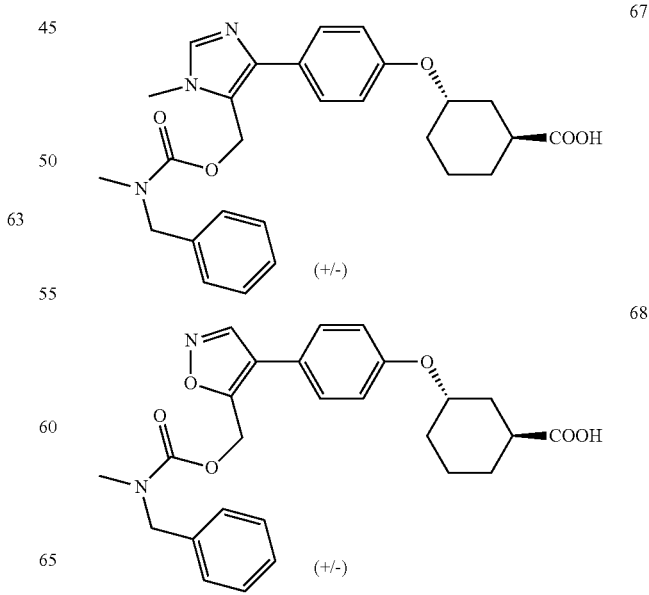
(+/-)
68
(+/-)

69
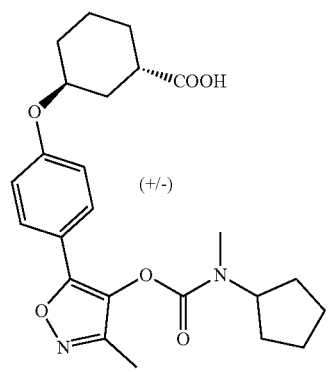
70
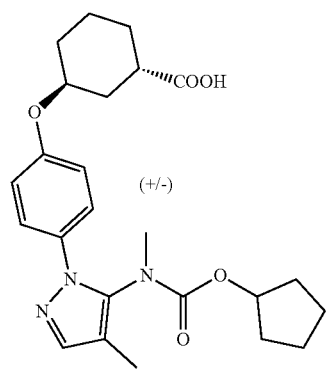
71
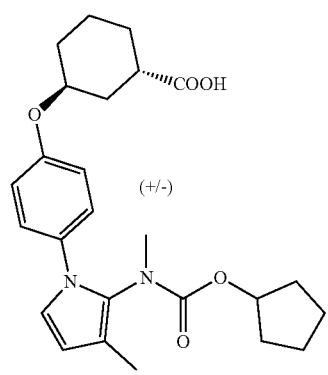
72
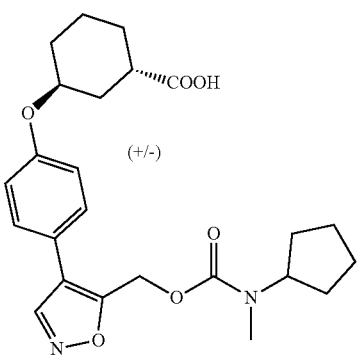
73
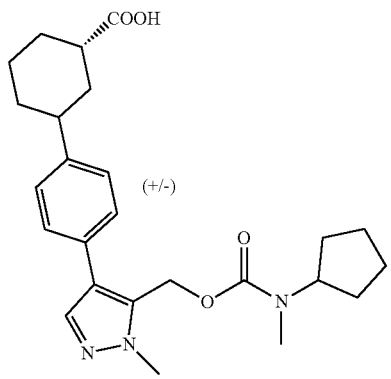
74
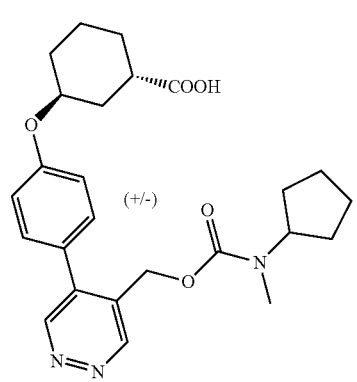
75
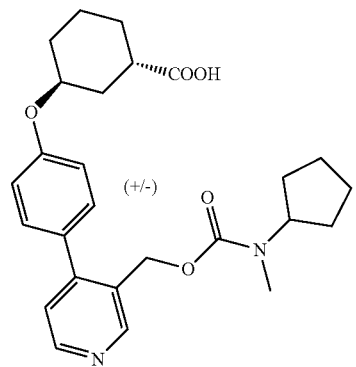
76
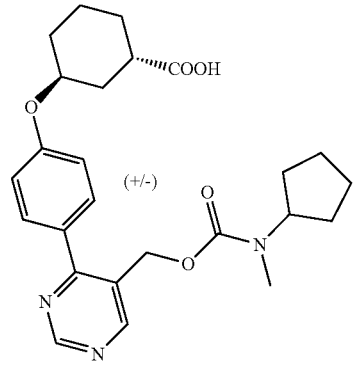

77
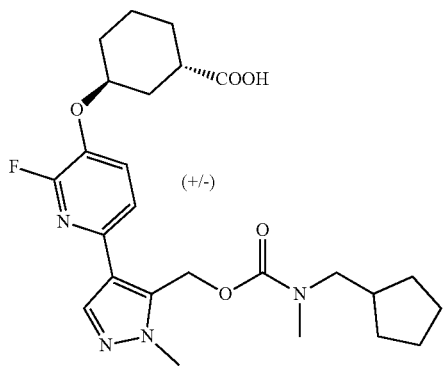
78
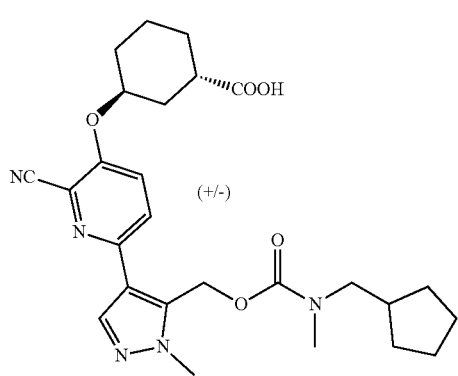
79
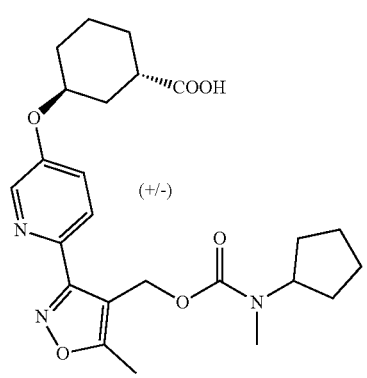
80
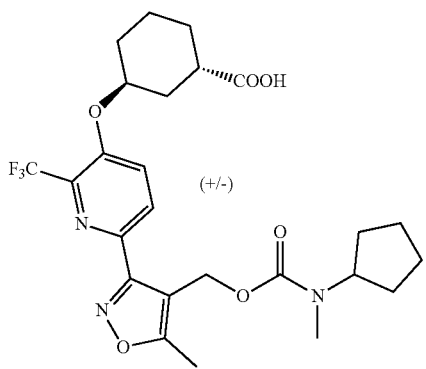
81
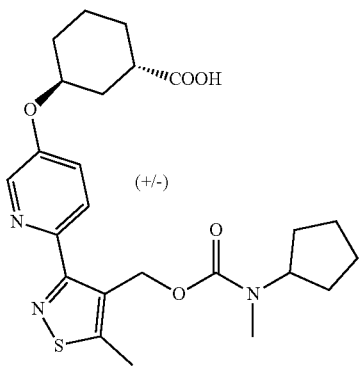
82
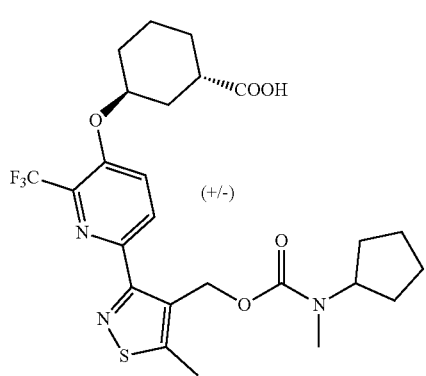
83
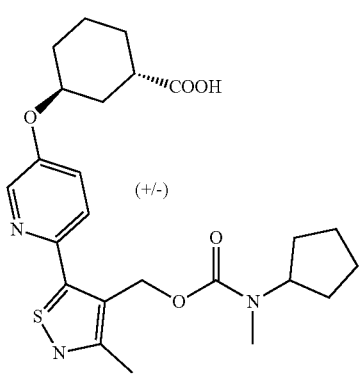
84
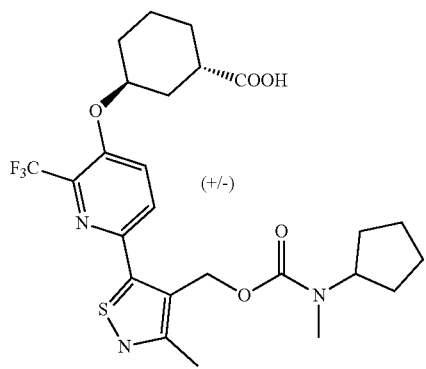

85
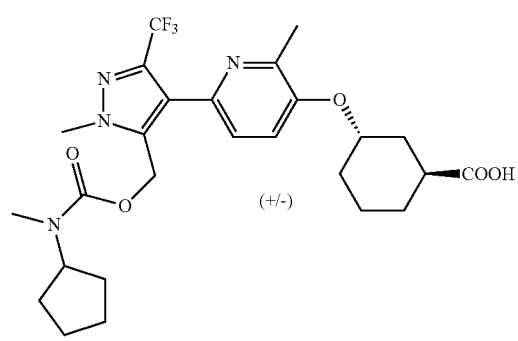
(+/-)
86
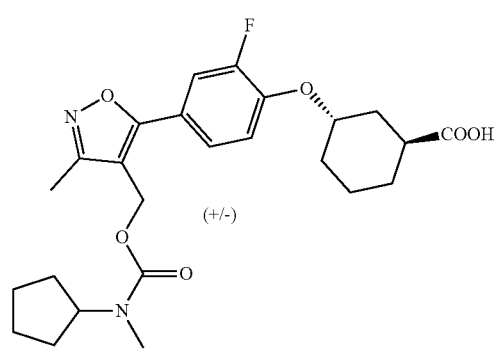
(+/-)
87
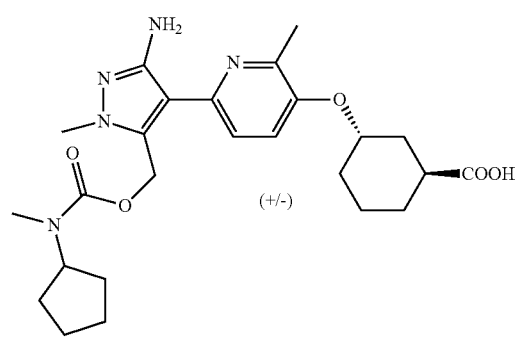
(+/-)
88
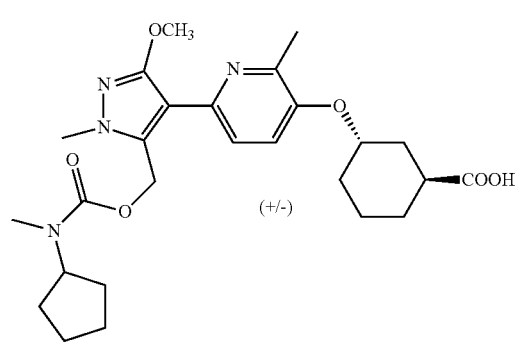
(+/-)
89
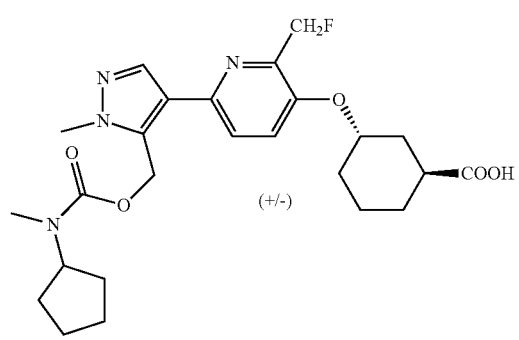
(+/-)
90
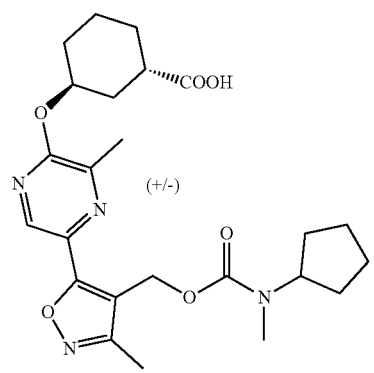
(+/-)
91
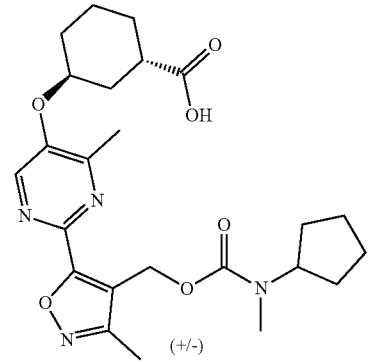
(+/-)
92
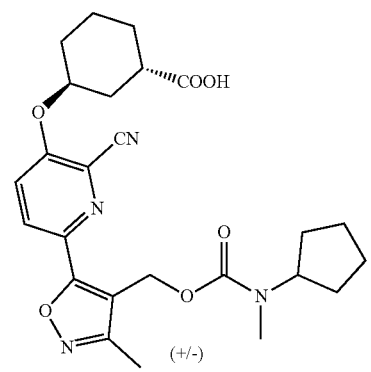
(+/-)

93
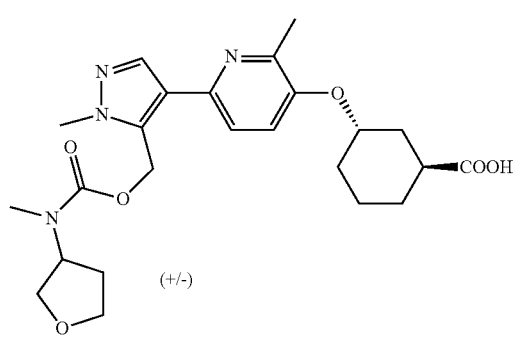
(+/-)
94
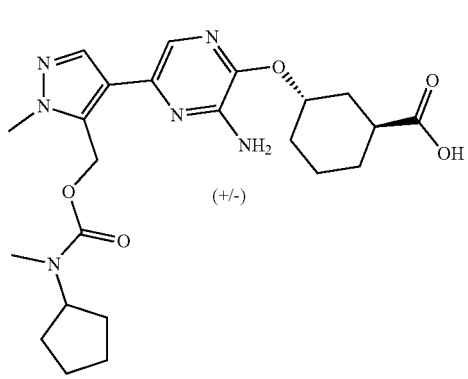
(+/-)
95
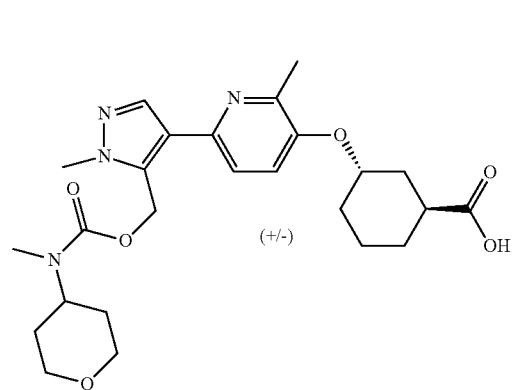
(+/-)
96
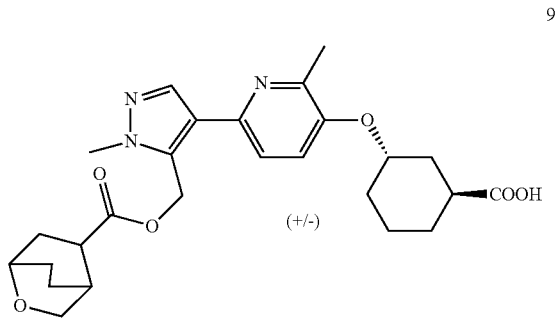
(+/-)
97
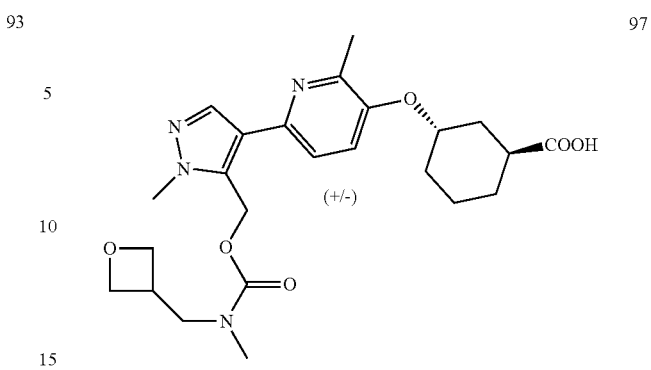
(+/-)
98
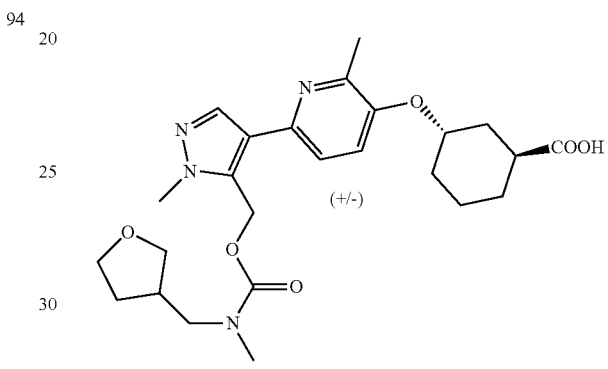
(+/-)
99
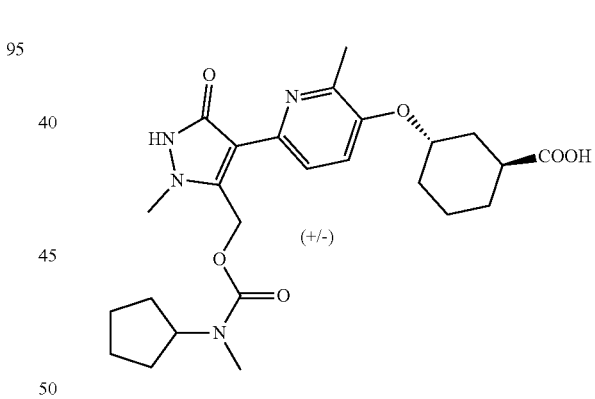
(+/-)
100
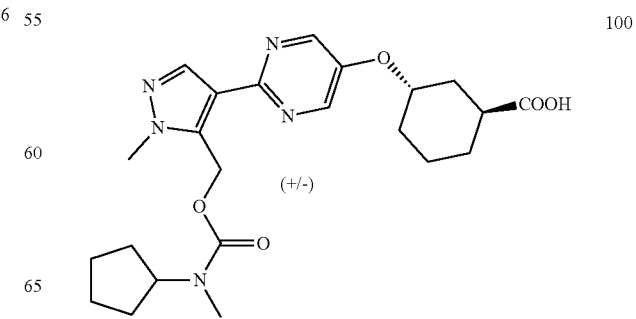
(+/-)

101 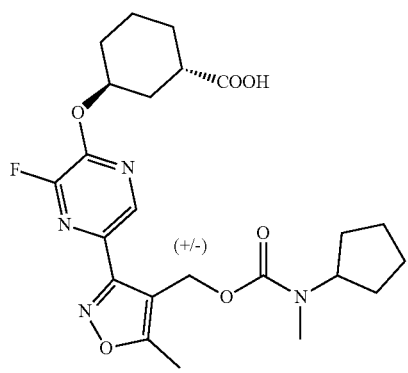 (+/-)
102 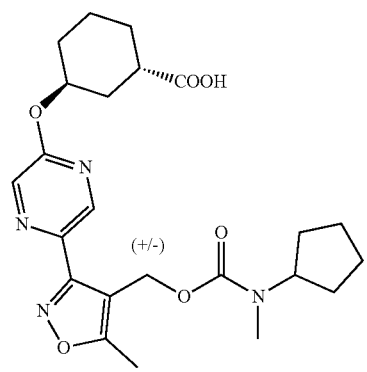 (+/-)
103 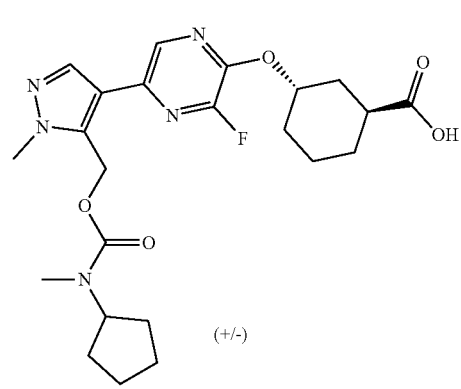 (+/-)
104 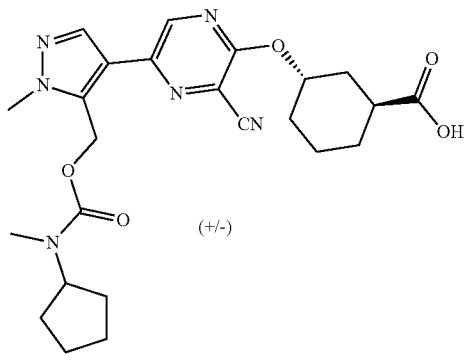 (+/-)
105 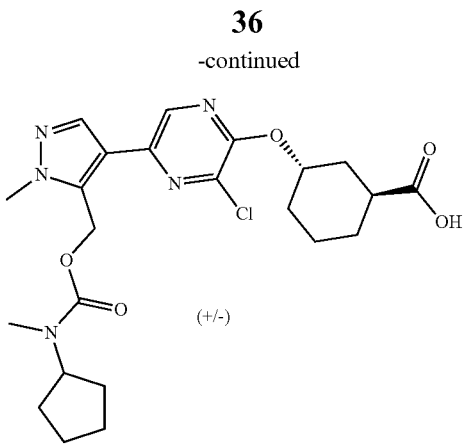 (+/-)
106 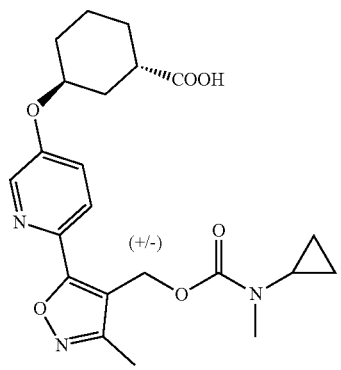 (+/-)
107 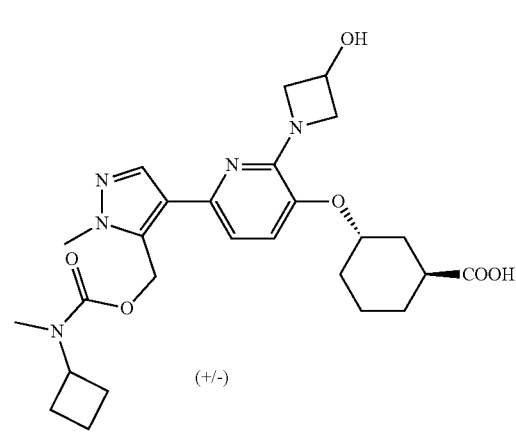 (+/-)
108 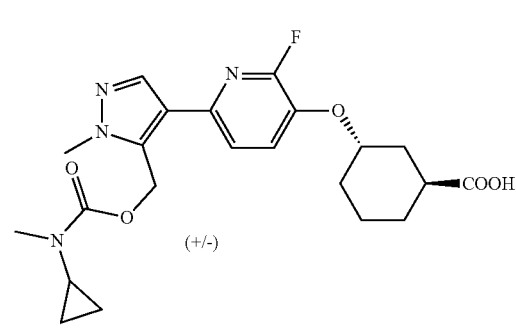 (+/-)

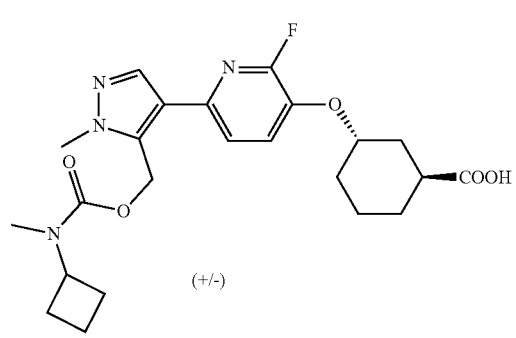
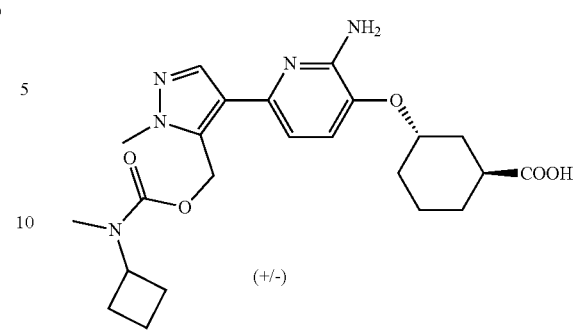
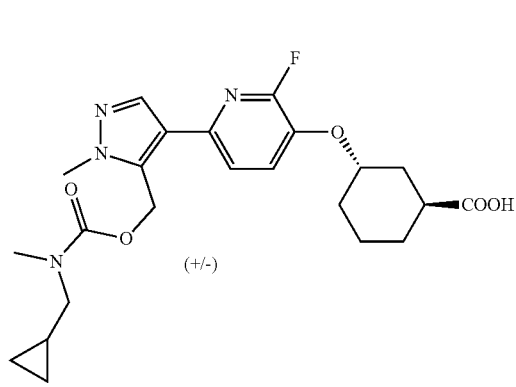
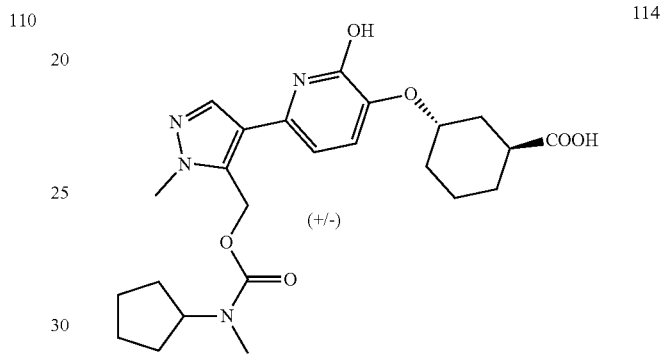
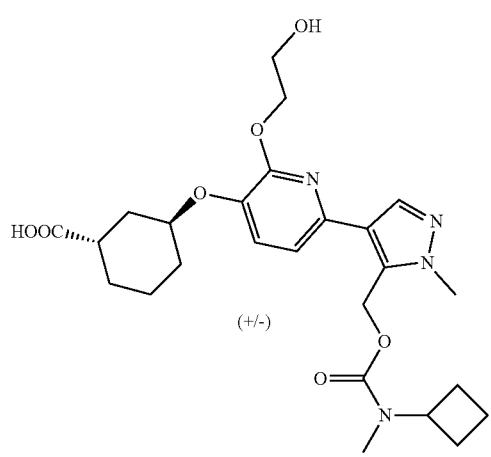
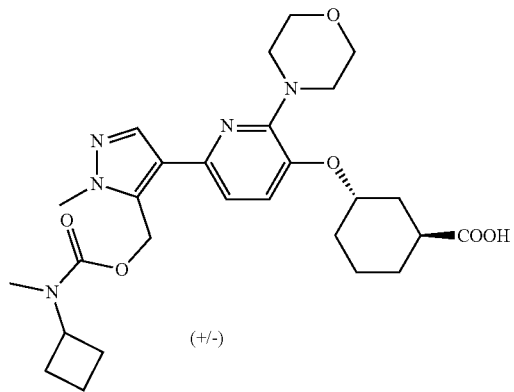
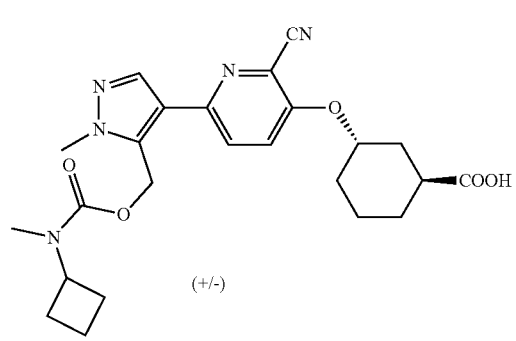
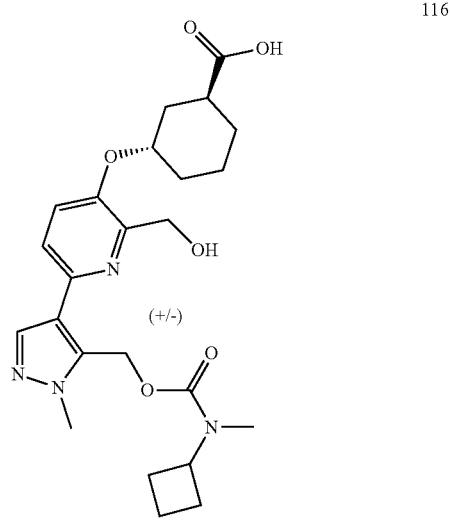

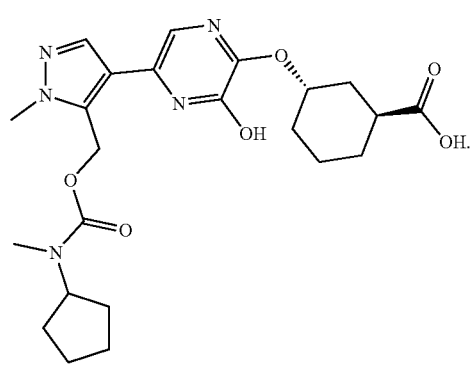
117
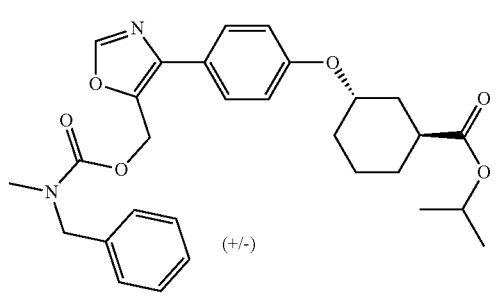
1-14
The present invention also provides compounds shown as below:
1-8
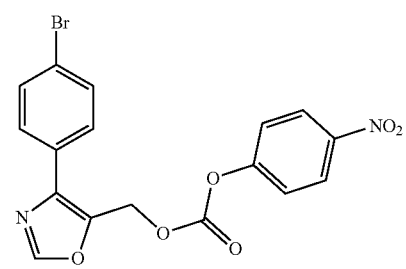
2-7
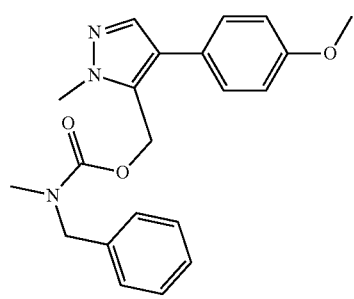
1-9
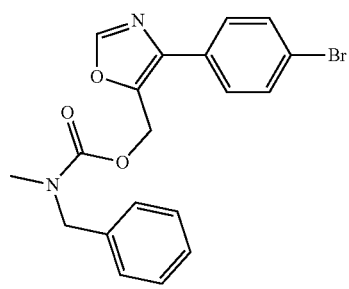
2-8
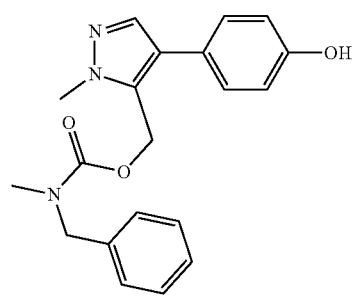
1-11
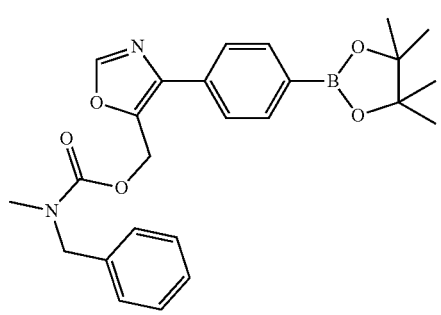
2-10
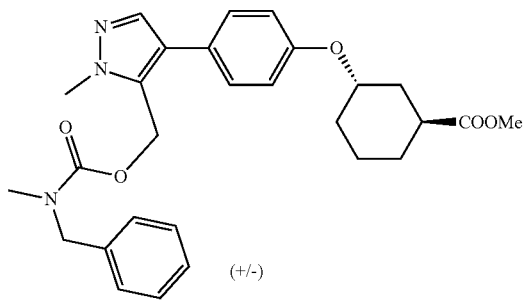
1-12
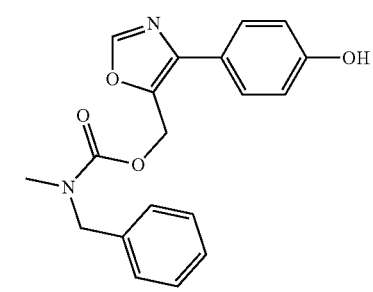
3-7
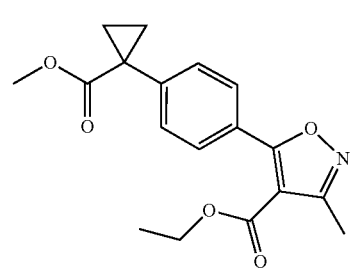

3-8
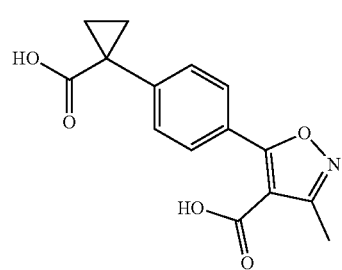
3-9
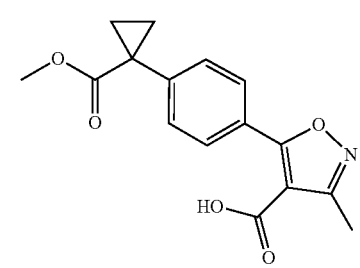
3-11
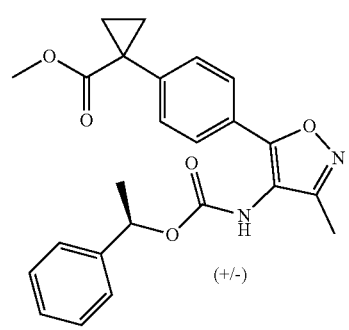
4-7
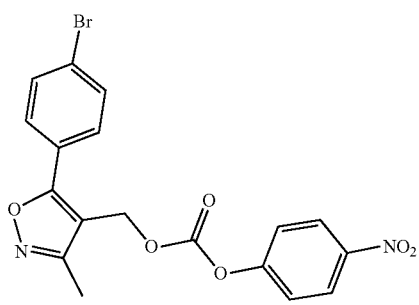
4-9
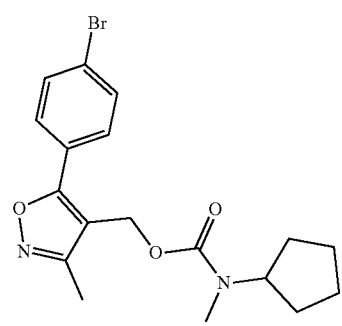
4-10
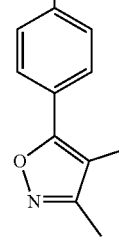
4-11
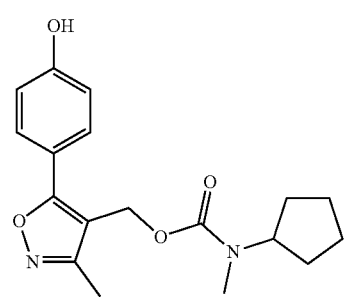
4-13
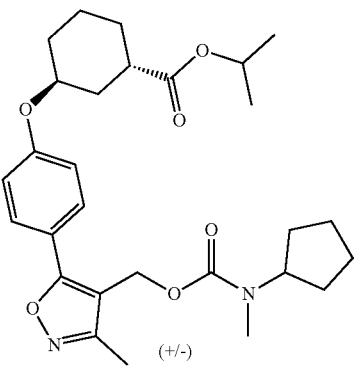
5-2
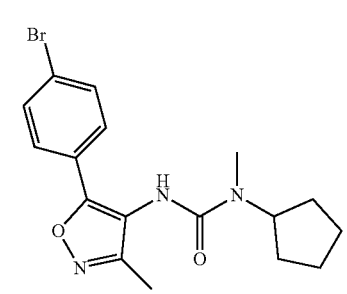

| 43 -continued | 44 -continued |
|---|---|
| 5-3 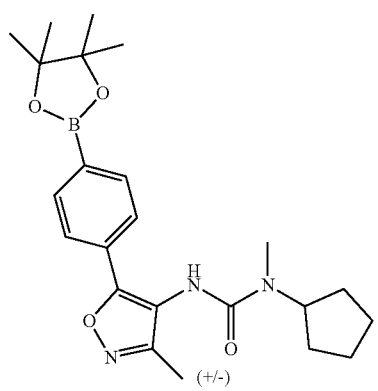 (+/-) | 6-3 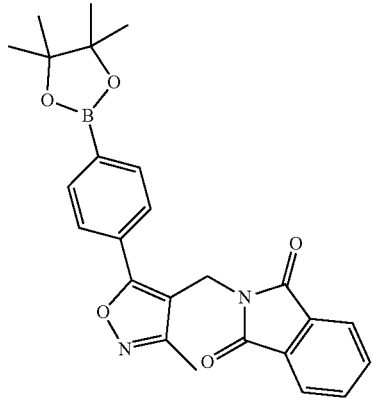 |
| 5-4 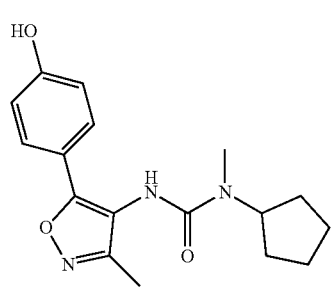 | 6-4 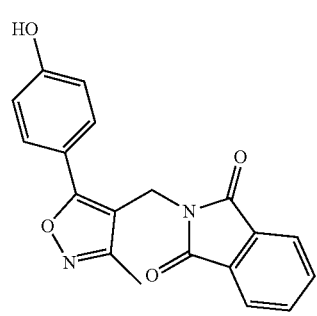 |
| 5-5 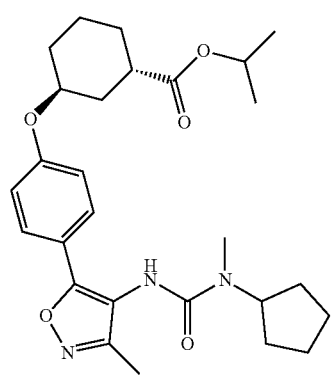 | 6-5 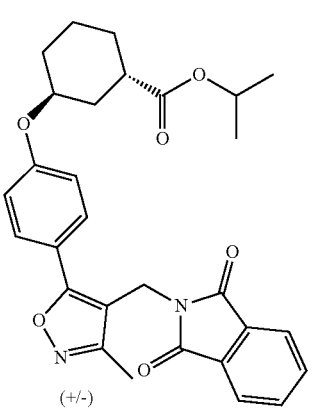 (+/-) |
| 6-2 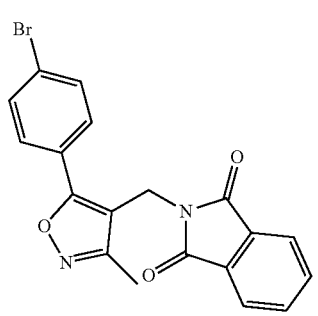 | 6-6 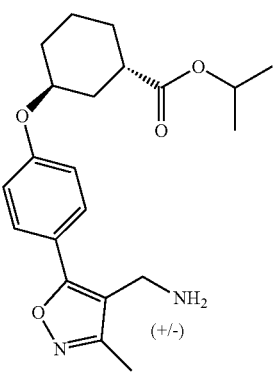 (+/-) |

6-7
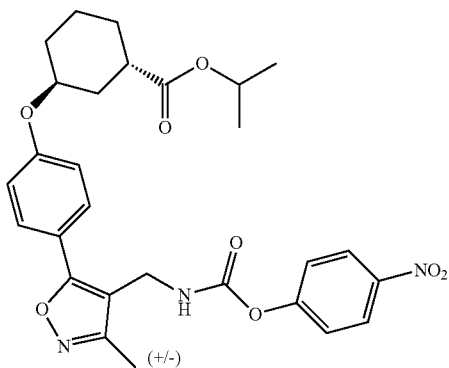
6-8
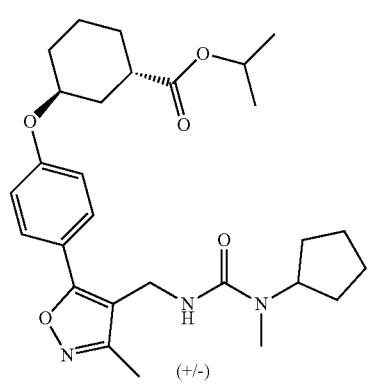
7-8
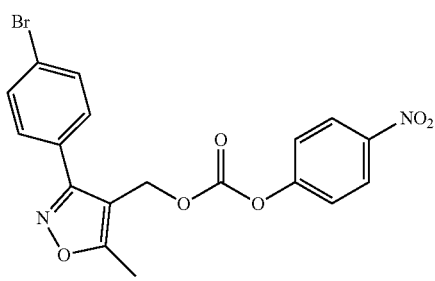
7-9
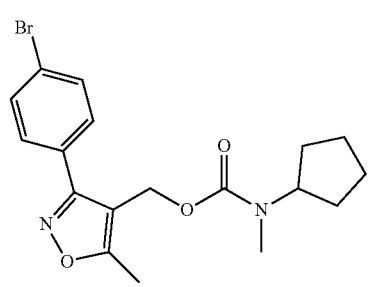
7-10
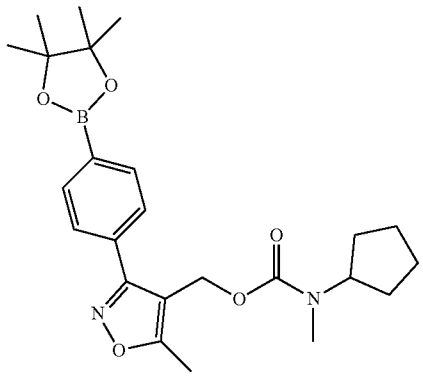
7-11
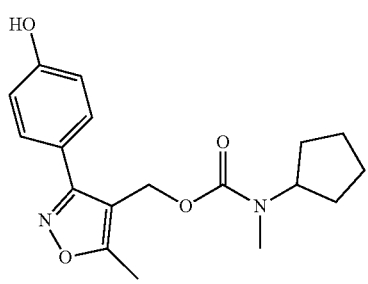
7-12
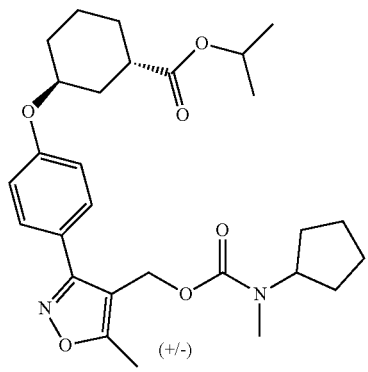
8-4
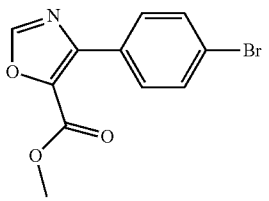
8-5
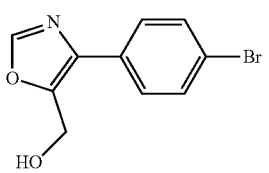

8-6
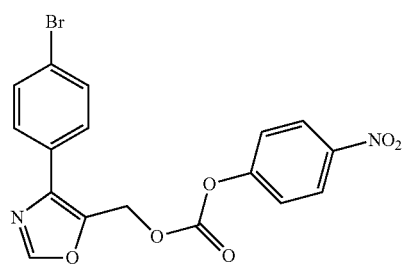
8-7
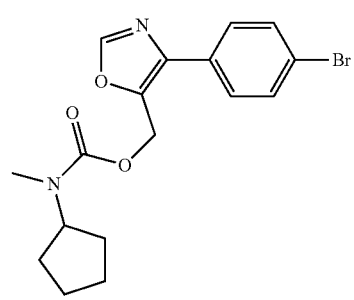
8-8
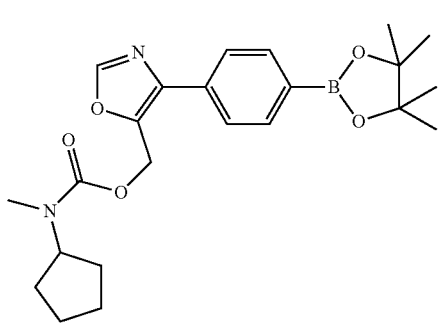
8-9
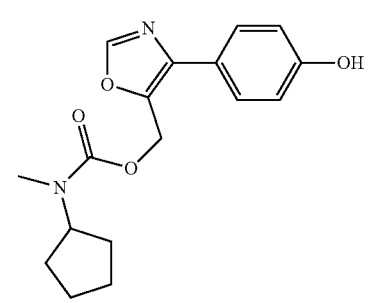
8-10
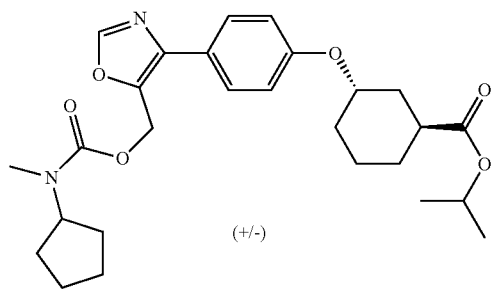
(+/-)
9-4
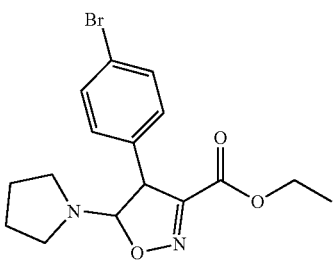
9-5
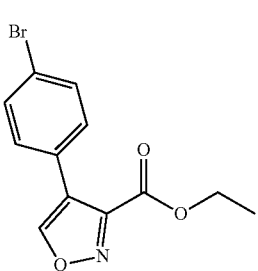
9-6
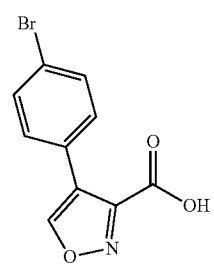
9-7
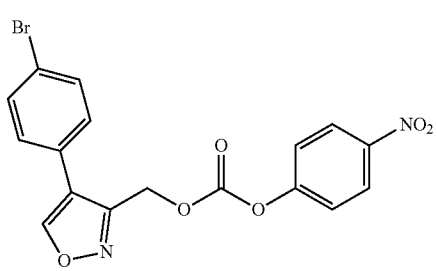
9-8
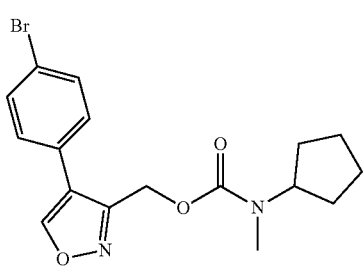

9-9
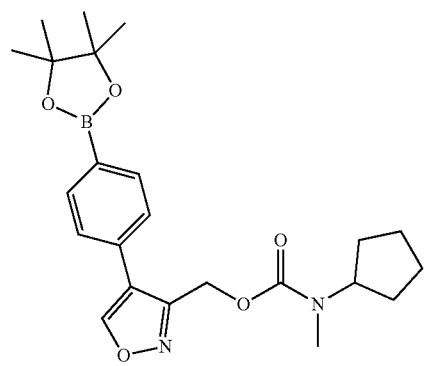
9-10
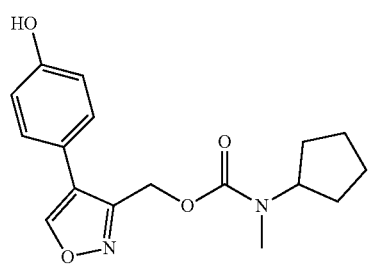
9-11
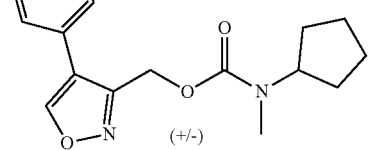
(+/-)
10-5
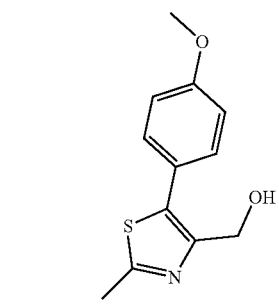
10-6
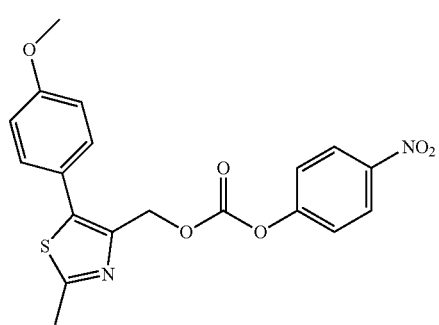
10-7
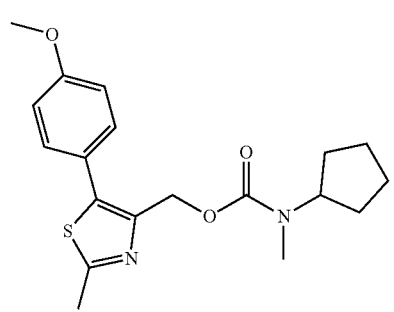
10-8
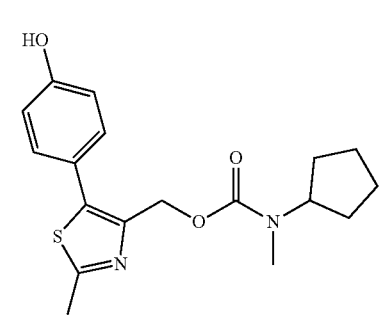
10-9
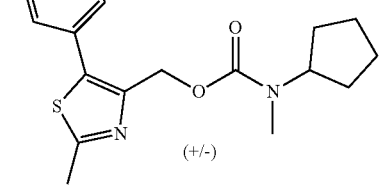
(+/-)
11-5
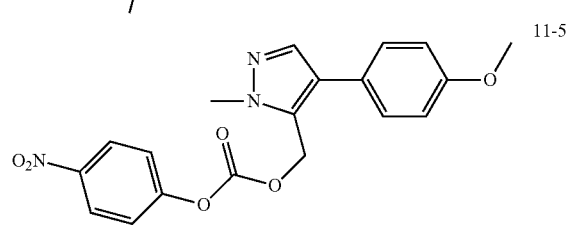
11-6
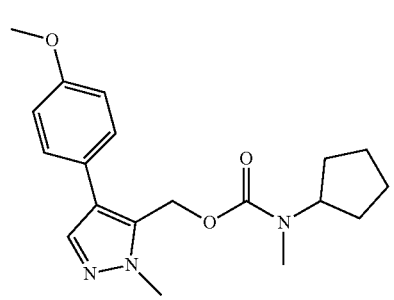

11-7
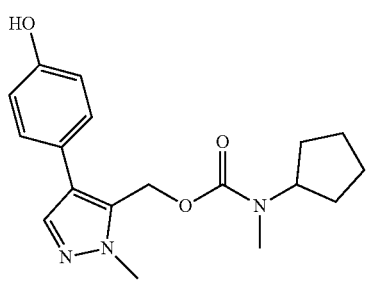
11-8
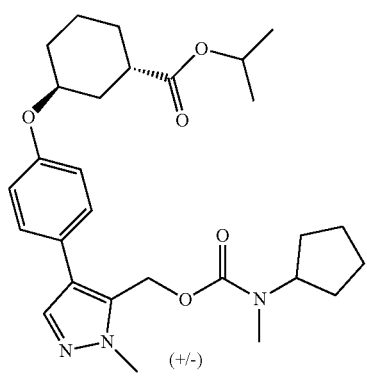
12-5
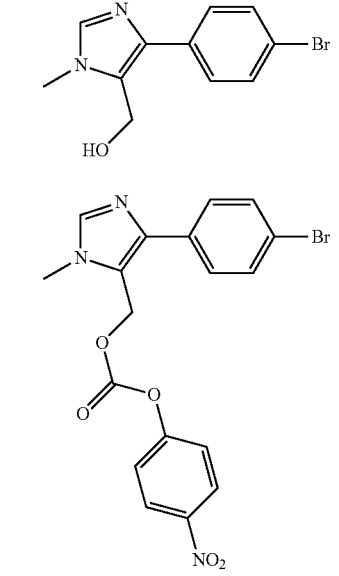
12-6
12-7
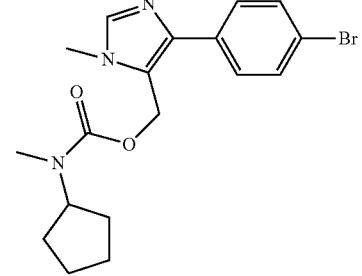
12-8
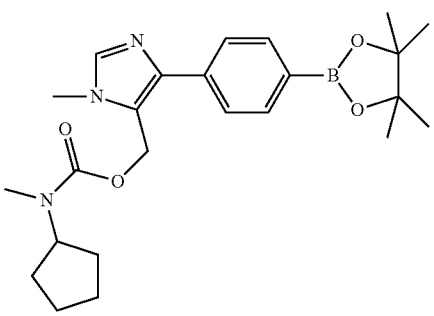
12-9

12-10
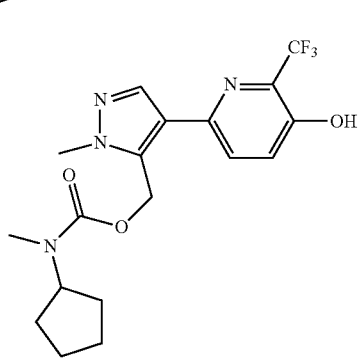
13-6
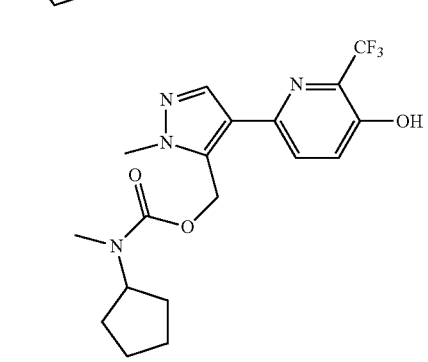
13-7
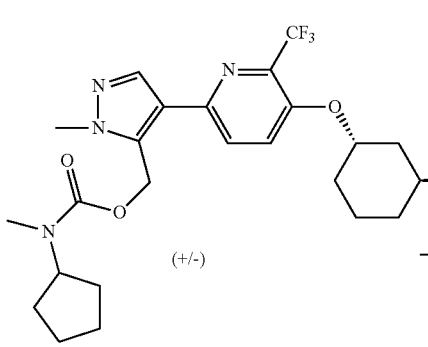

14-5
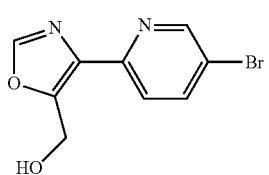
14-6
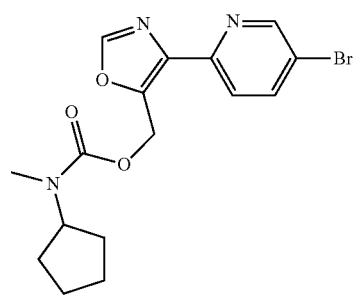
14-7
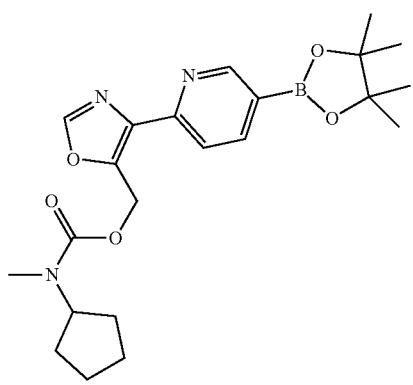
14-8
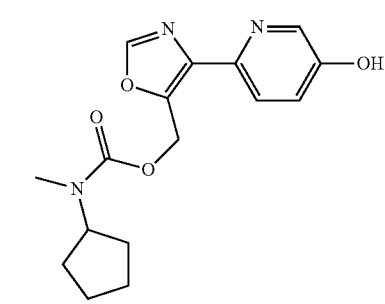
14-10
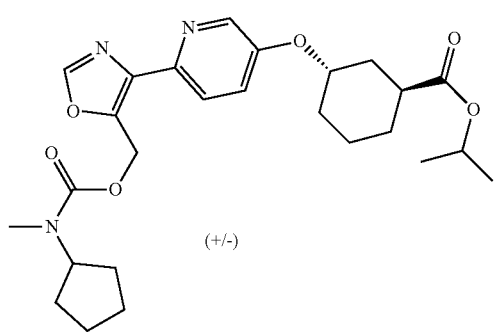
(+/-)
15-5
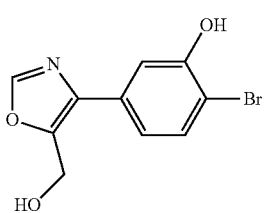
15-7
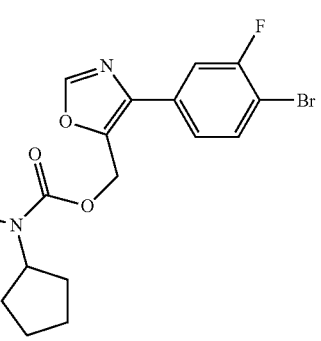
15-8
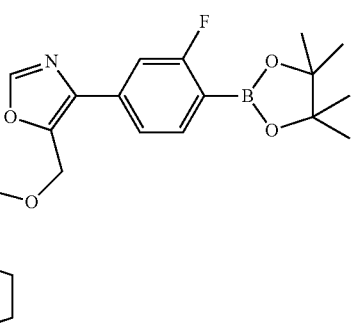
15-9
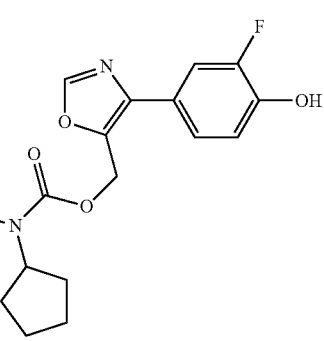
15-10
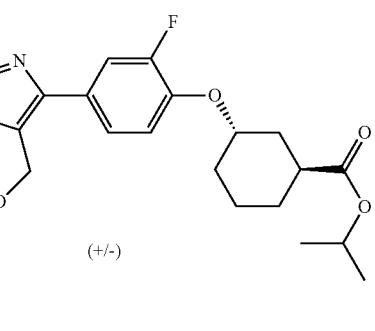
(+/-)

16-6
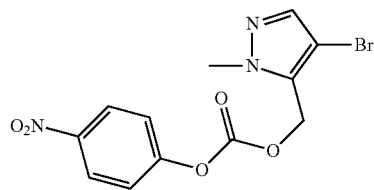
16-7
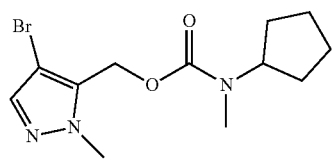
16-8
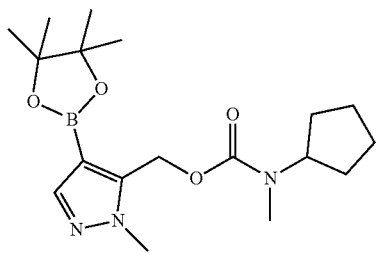
16-9
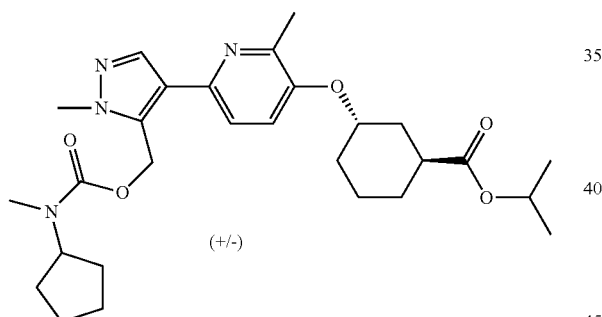
(+/-)
17-6
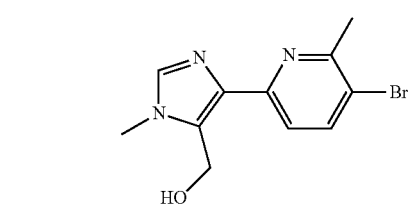
17-7
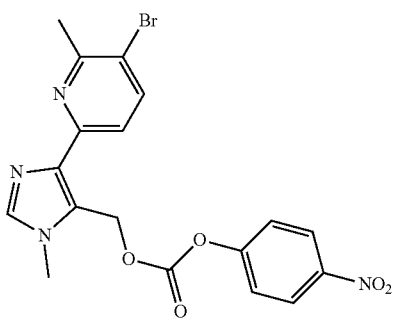
17-8
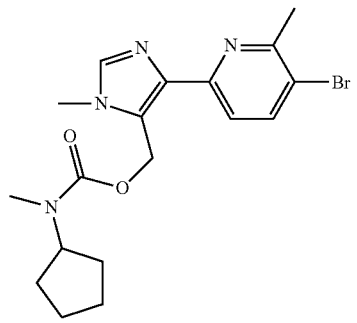
17-9
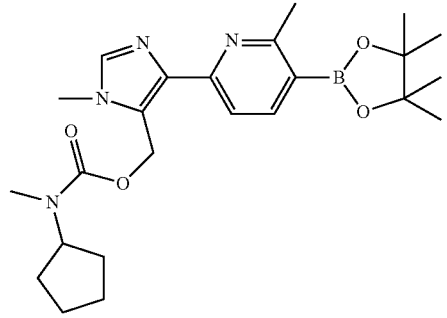
17-10
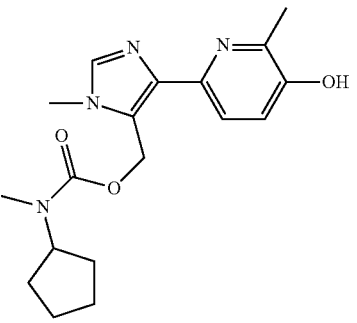
17-11
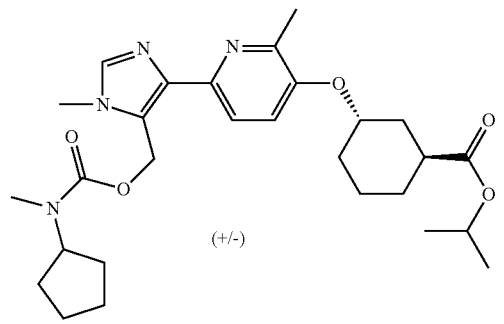
(+/-)
18-2
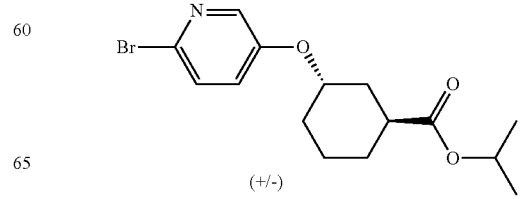
(+/-)

18-3
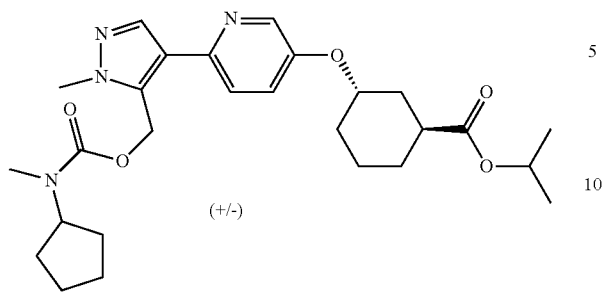
(+/-)
19-5
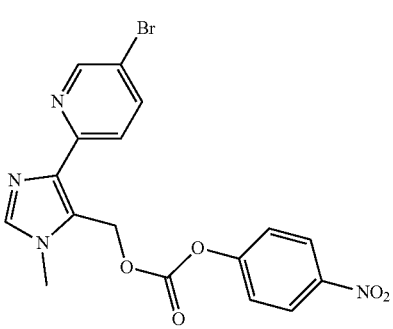
19-6
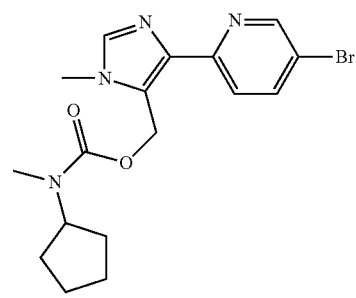
19-7
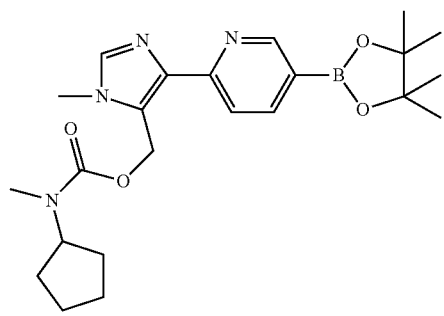
19-8
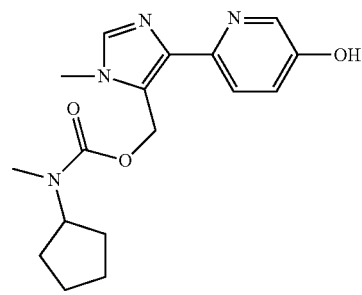
19-9
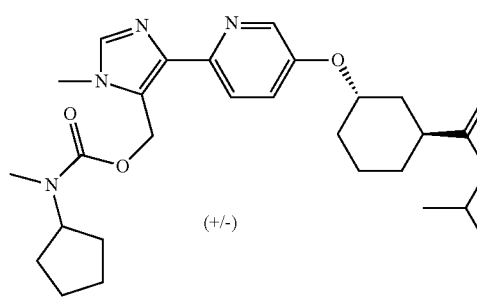
(+/-)
20-2
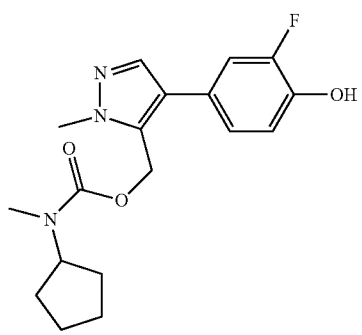
20-3
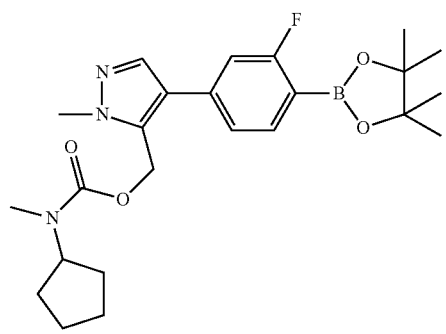
20-4
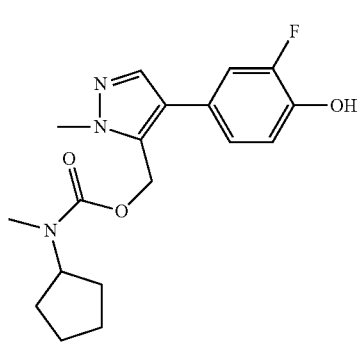
20-5
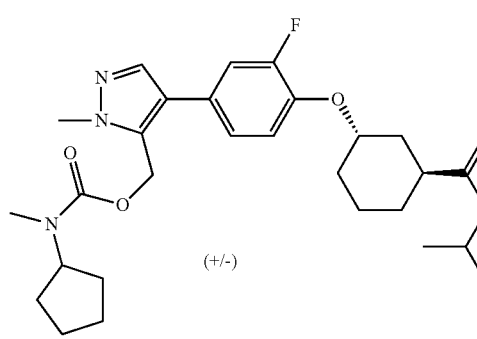
(+/-)

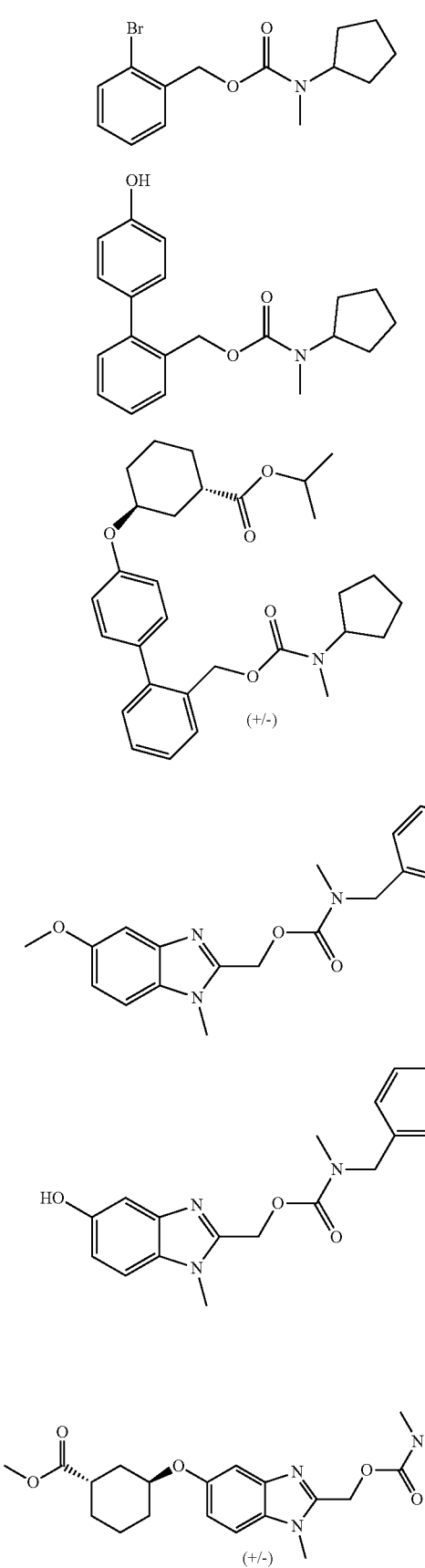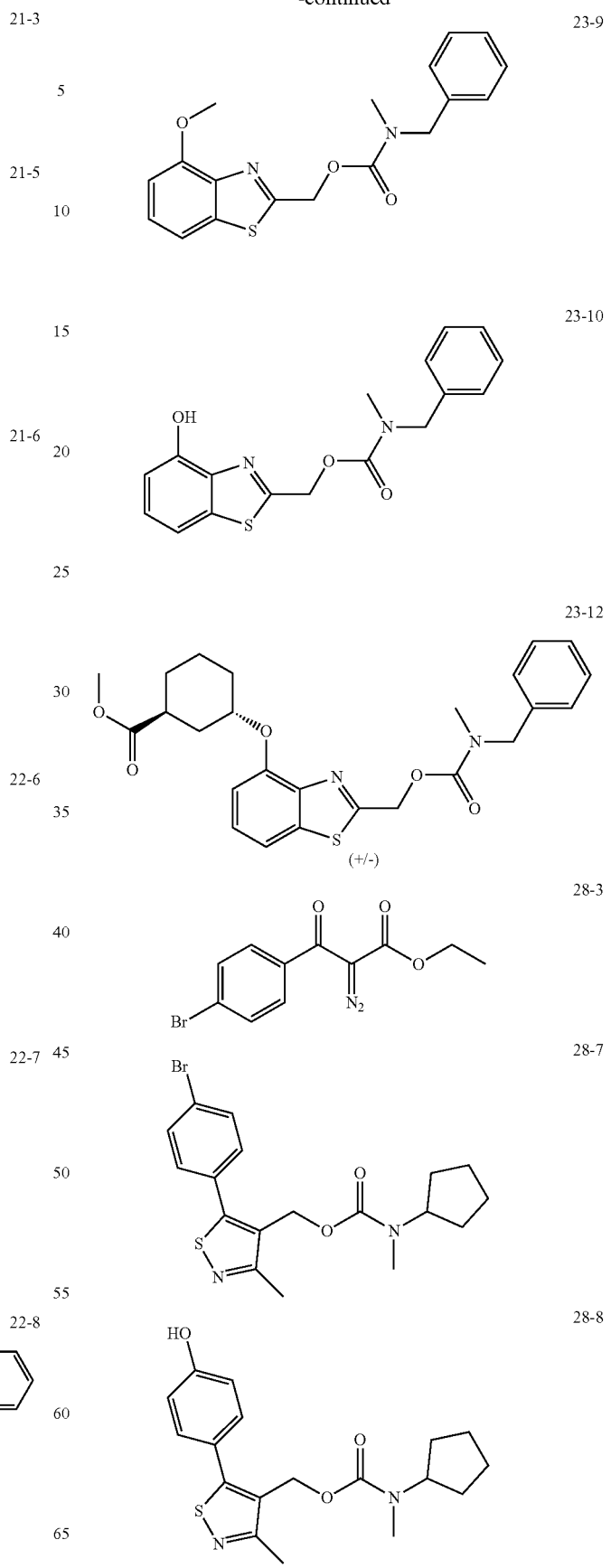

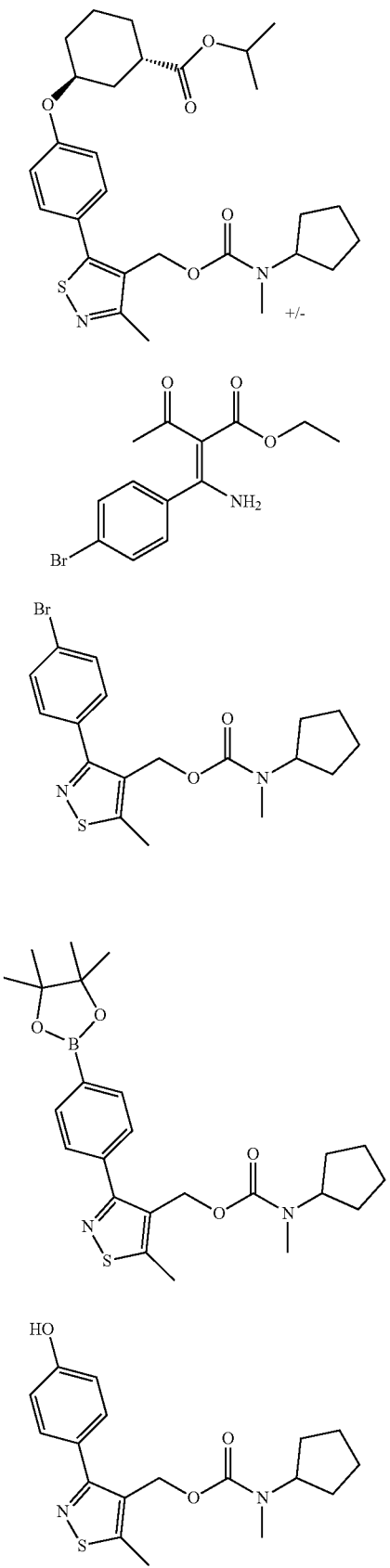
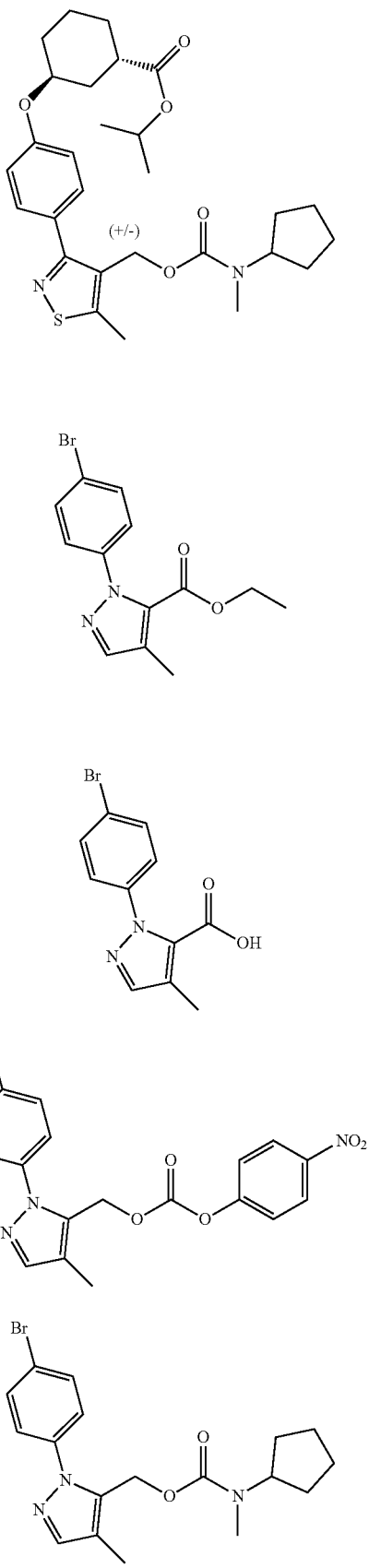

30-6
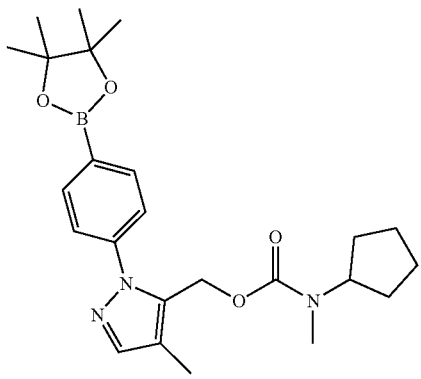
30-7
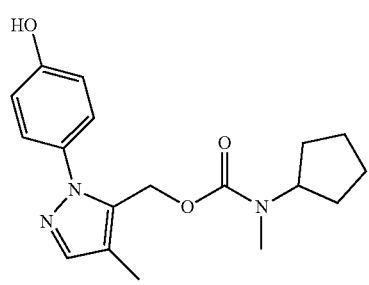
30-8
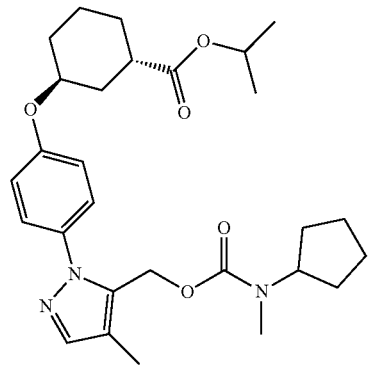
34-5
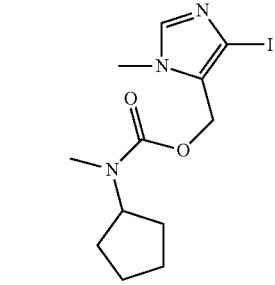
34-7
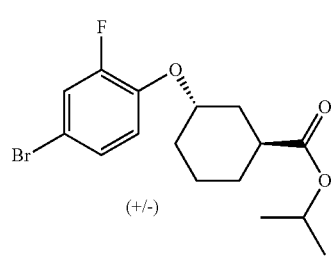
(+/-)
34-8
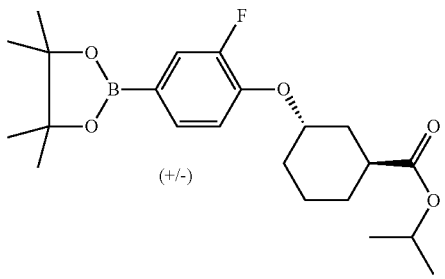
(+/-)
34-9
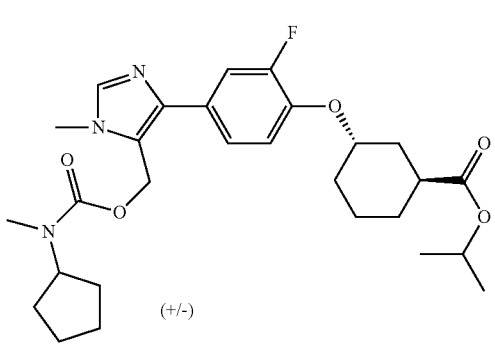
(+/-)
35-7
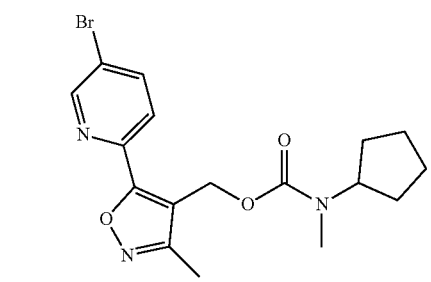
35-8
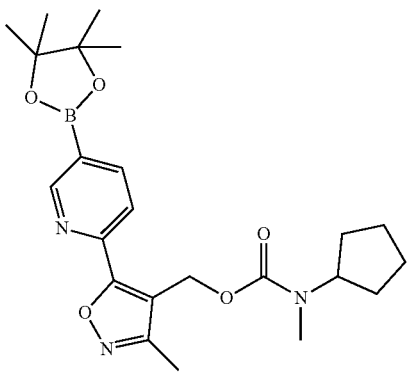
35-9
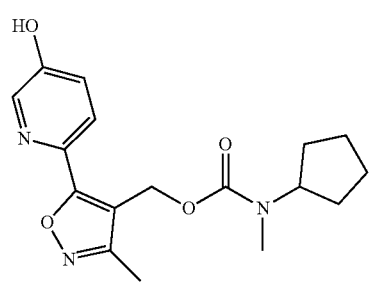

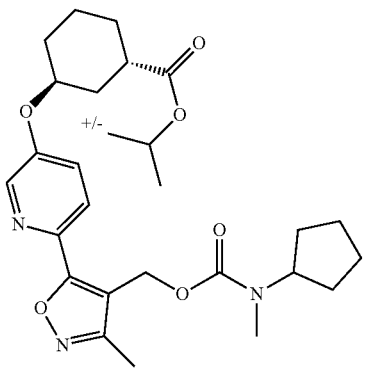
35-10
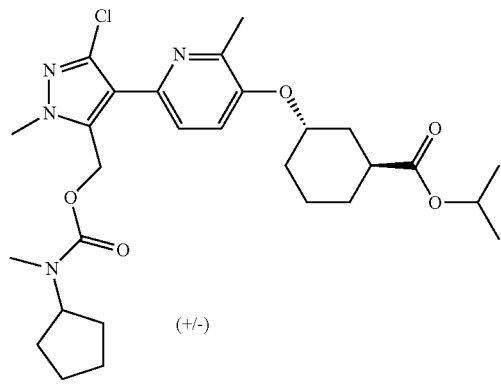
56-4
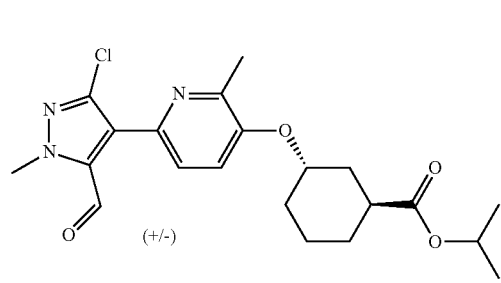
56-1
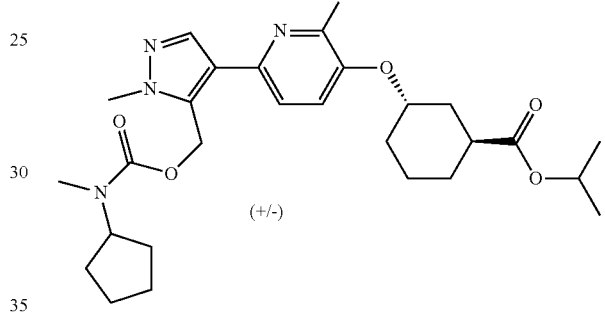
59-6
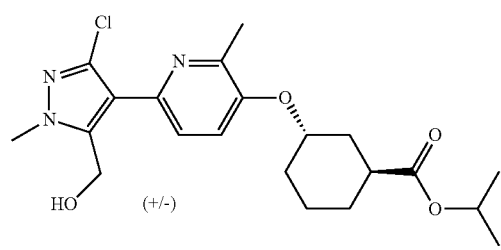
56-2
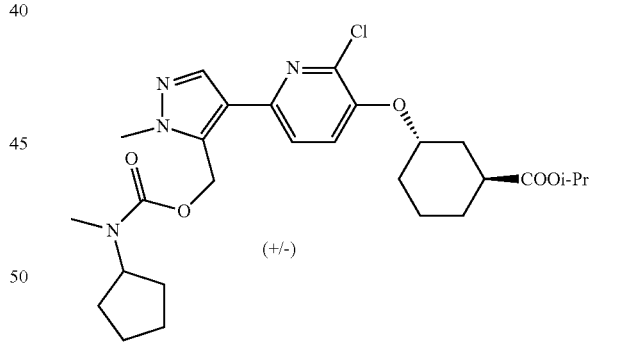
60-3
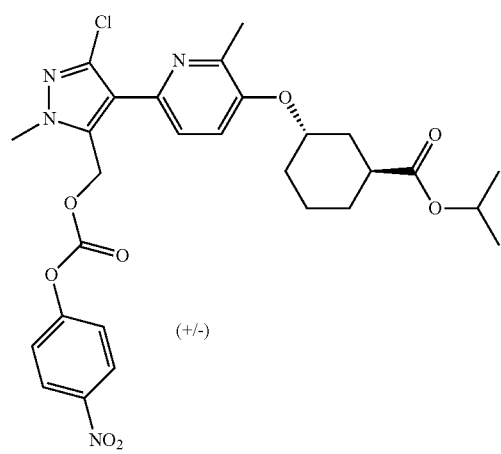
56-3
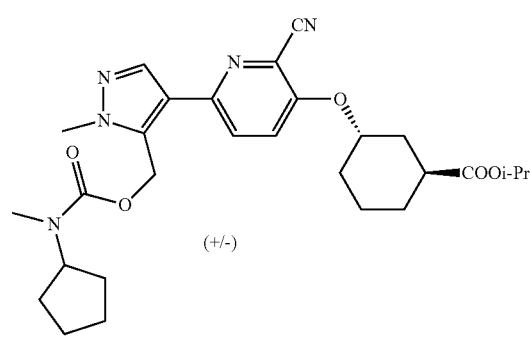
60-4

61-6
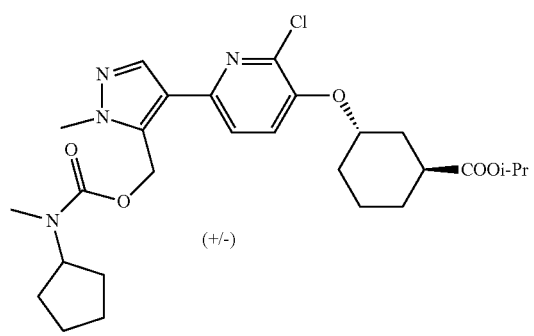
(+/-)
62-6
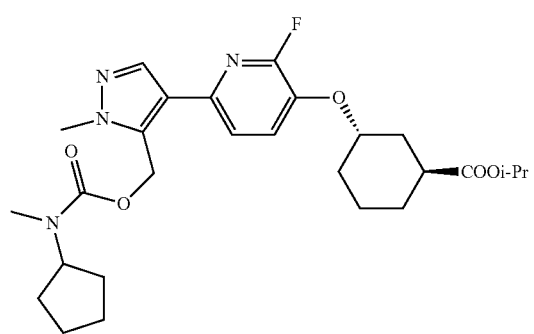
(+/-)
63-8
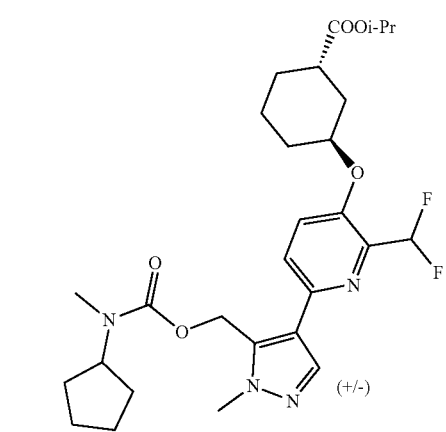
(+/-)
64-2
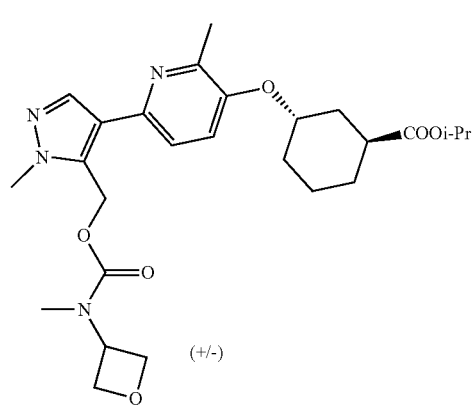
(+/-)
65-4
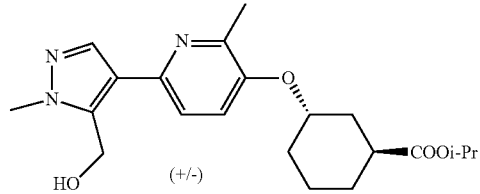
(+/-)
65-5
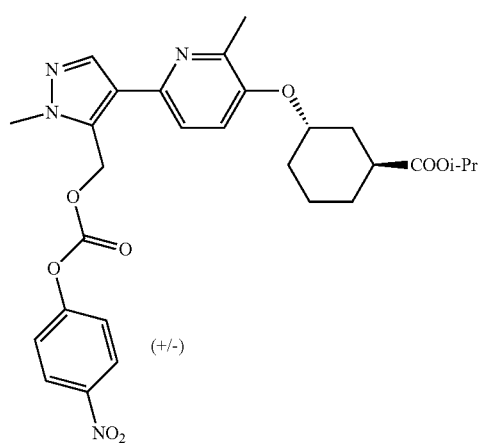
(+/-)
65-7
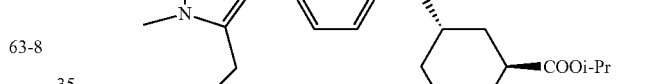
(+/-)
66-5
(+/-)
88-9
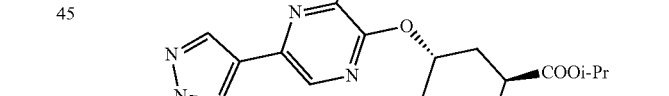

88-10
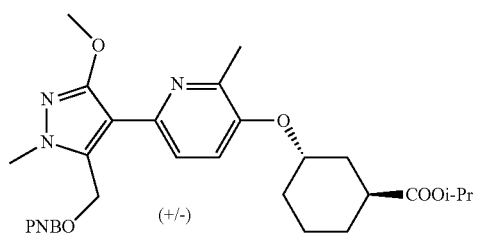
(+/-)
88-11
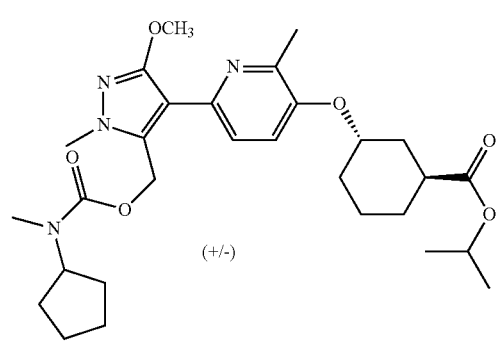
(+/-)
91-8
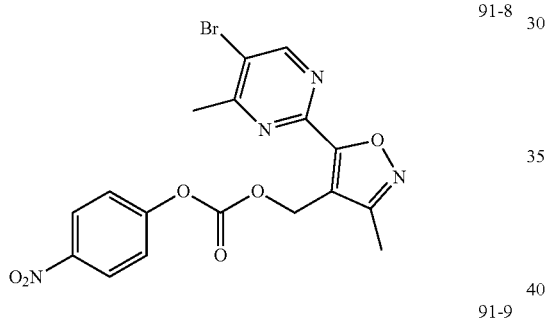
91-9
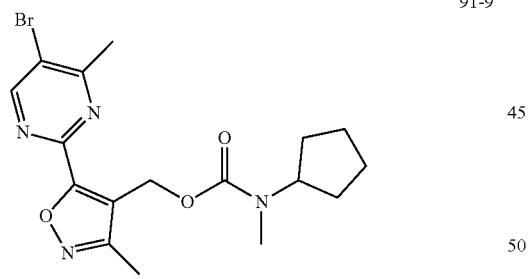
91-10
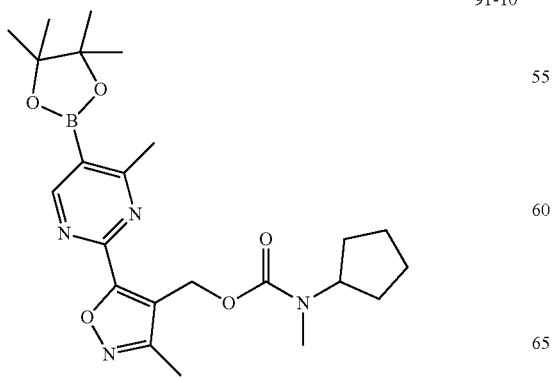
91-11
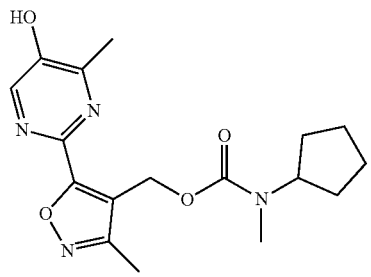
91-12
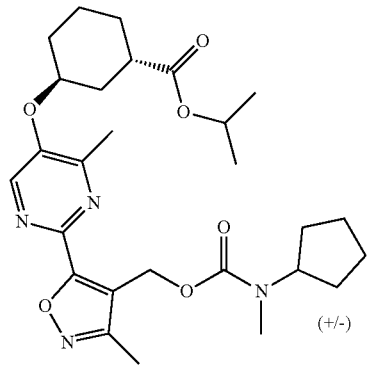
(+/-)
92-9
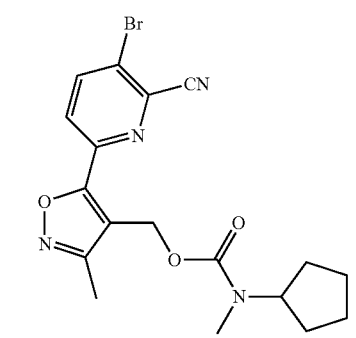
92-10
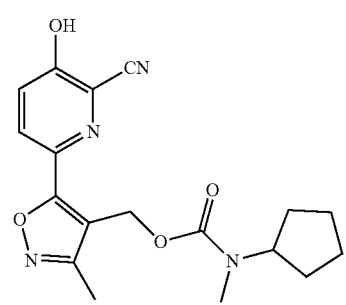
92-11
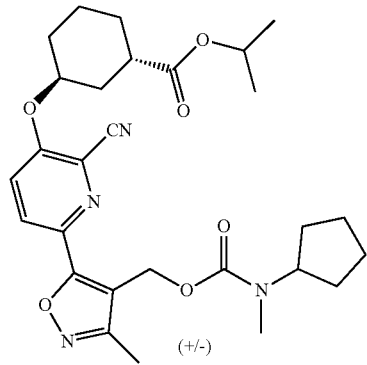
(+/-)

-continued
93-2
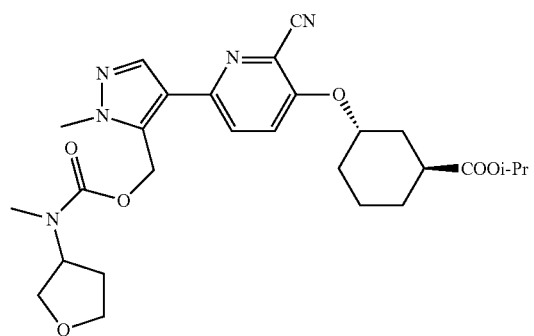
94-5
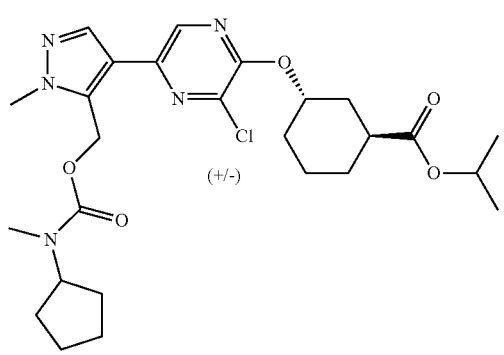
(+/-)
94-6
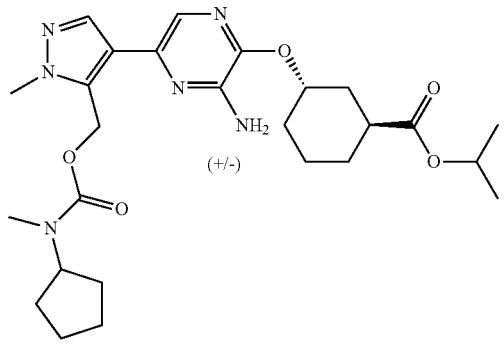
(+/-)
95-2
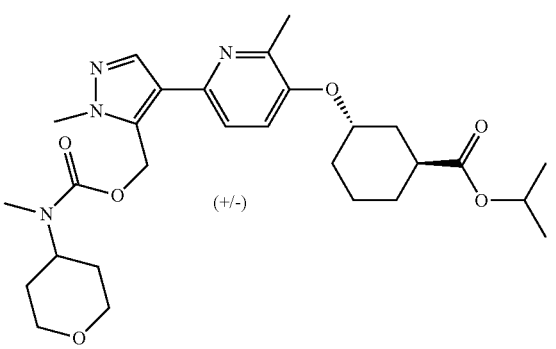
(+/-)
-continued
98-5
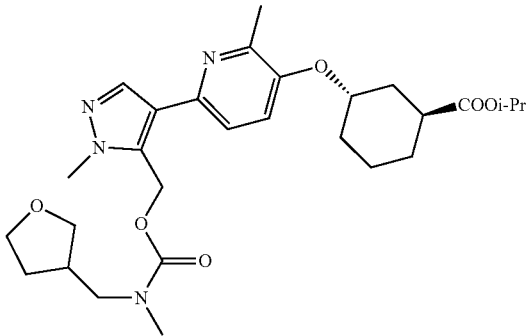
100-3
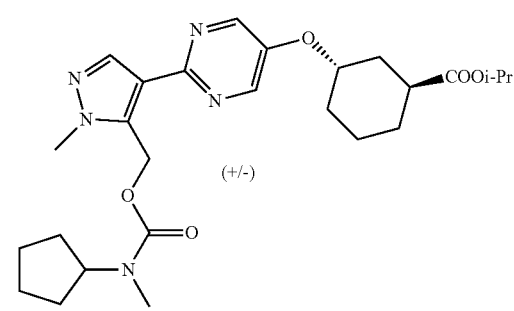
(+/-)
103-5
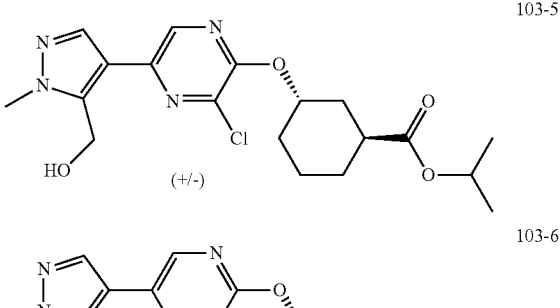
(+/-)
103-6
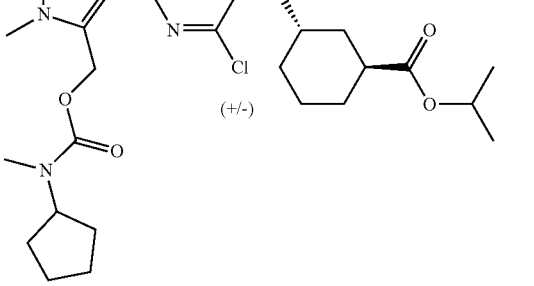
(+/-)
103-7
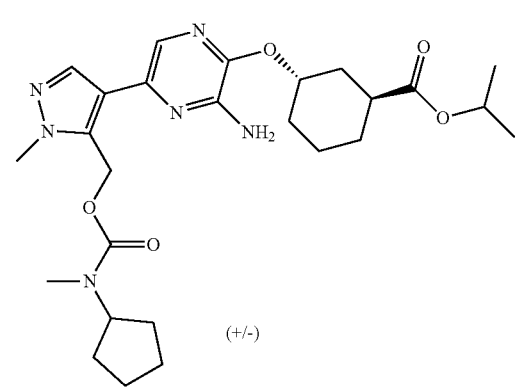
(+/-)

-continued
103-8
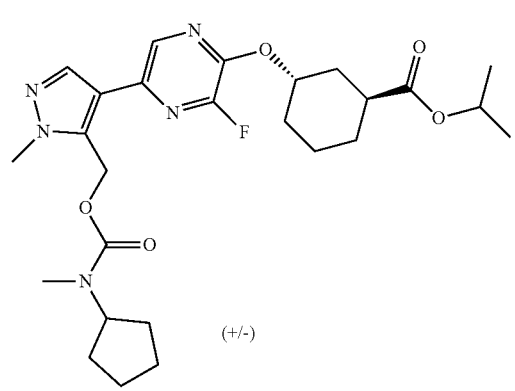
(+/-)
104-1
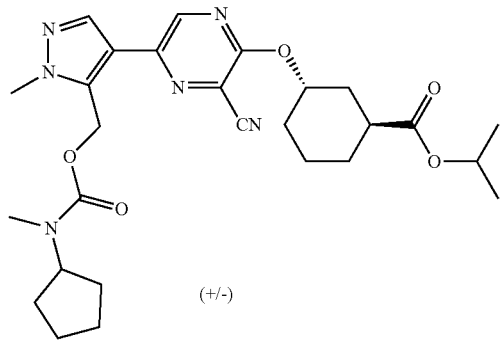
(+/-)
108-3
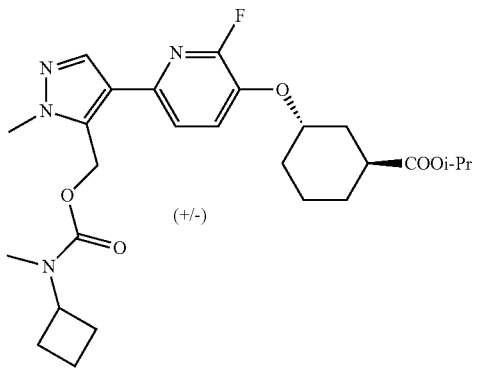
(+/-)
108-4
(+/-)
108-5
(+/-)
-continued
109-1
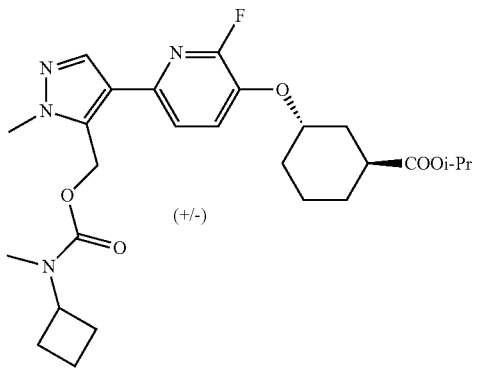
(+/-)
110-1
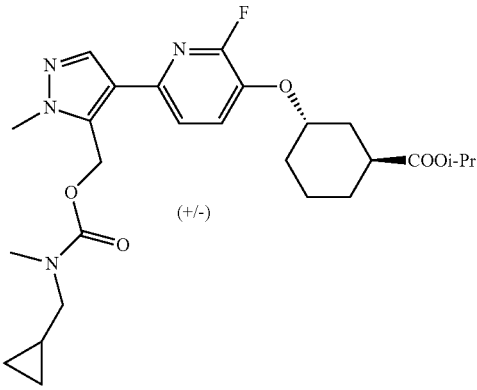
(+/-)
112-3
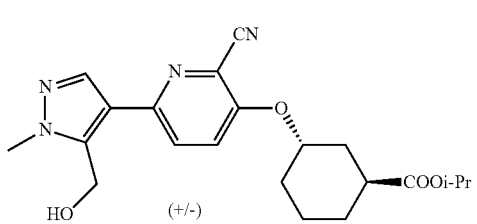
(+/-)
112-4
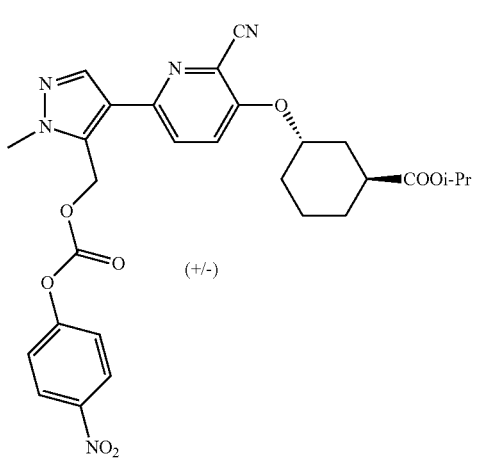
(+/-)

-continued
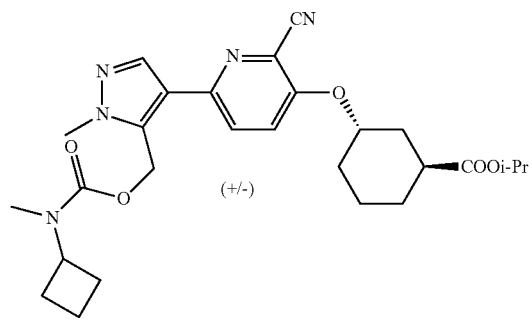
112-5
(+/-)
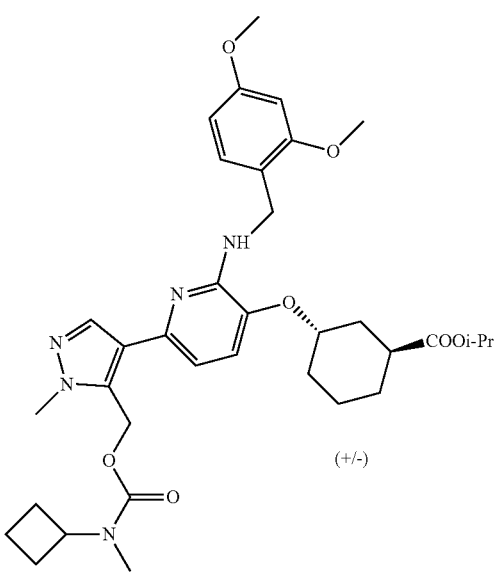
113-2
(+/-)
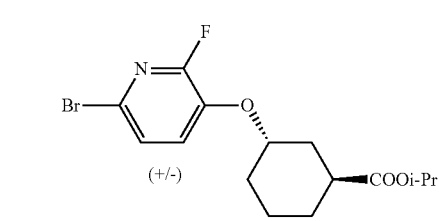
114-2
(+/-)
114-5
-continued
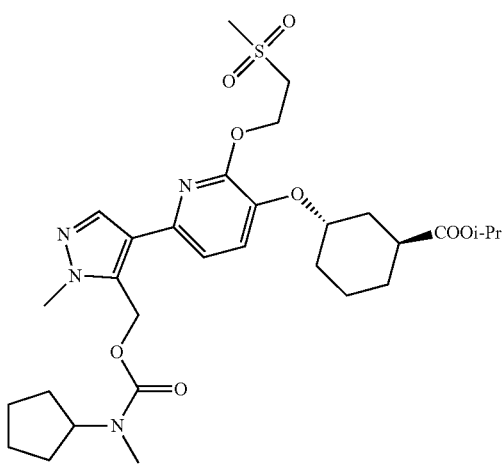
114-6
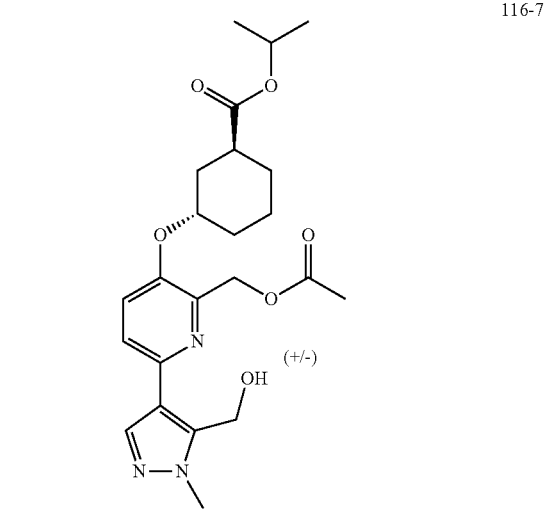
116-7
(+/-)
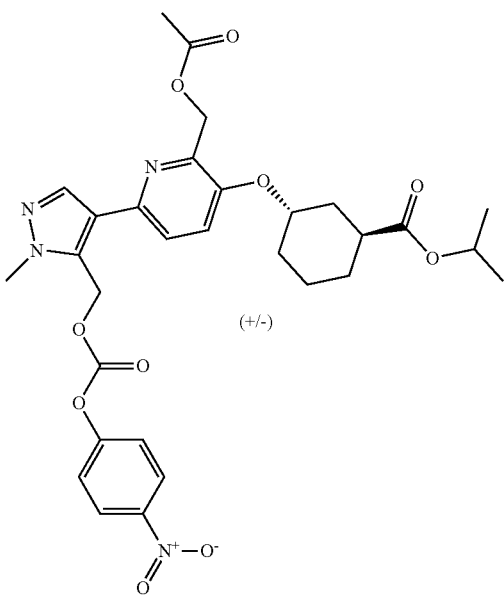
116-8
(+/-)

-continued 116-9

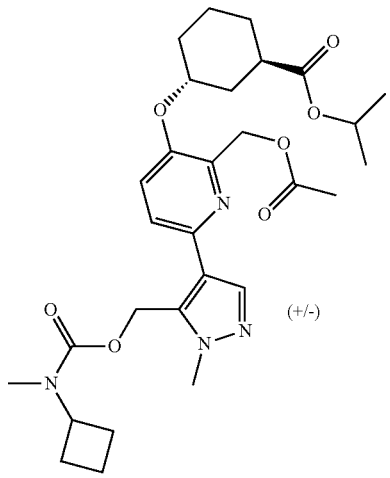

117-1

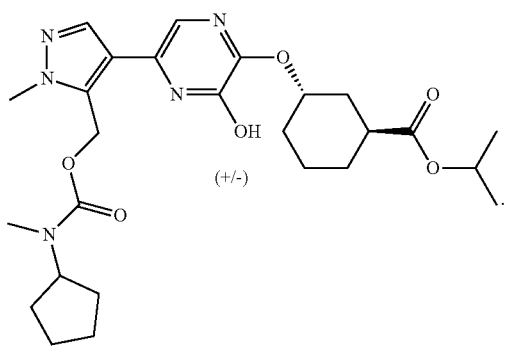

The compound of formula (I) or the stereoisomer, the tautomer, the isotopically labeled compound, the nitrogen oxide, the solvate, the polymorph, the metabolite, the ester, the pharmaceutically acceptable salt or the prodrug thereof disclosed herein can be synthesized by methods similar to those known in the chemical field, with the steps and conditions that can be referred to those of similar reactions in the art, especially according to the description herein. The starting materials are generally from commercial sources (e.g., Aldrich) or can be readily prepared using methods well known to those skilled in the art (obtained by SciFinder and Reaxys online databases).

The other compounds of formula (I) can also be obtained by peripherally modifying the prepared compound of formula (I) disclosed herein using conventional methods known in the art.

Generally, the compounds disclosed herein may be prepared by the methods described herein, wherein the substituents are defined as in formula (I), unless otherwise specified. The following schemes and examples serve to further illustrate the context of the present invention.

In the present invention, after the reaction is completed, conventional post-treatment methods can be adopted for a treatment. In the present invention, if the crude compound of formula (I) is obtained after the treatment, conventional means such as preparative HPLC, preparative TLC or recrystallization can be adopted for separation or purification.

The present invention also provides a pharmaceutical composition comprising one, two or more of the compound of formula (I) and the stereoisomer, the tautomer, the isotopically labeled compound, the nitrogen oxide, the solvate, the polymorph, the metabolite, the ester, the pharmaceutically acceptable salt and the prodrug thereof.

According to the present invention, the pharmaceutical composition may also optionally comprise at least one additional active ingredient; specifically, the pharmaceutical composition may also comprise one or more active ingredients besides the compound of formula (I) and the stereoisomer, the tautomer, the isotopically labeled compound, the nitrogen oxide, the solvate, the polymorph, the metabolite, the ester, the pharmaceutically acceptable salt and the prodrug thereof.

The pharmaceutical composition may comprise a therapeutically effective amount of the compound of formula (I) and the pharmaceutically acceptable salt, the solvate, the polymorph, the metabolite, the stereoisomer, the tautomer, the isotopically labeled compound, the nitrogen oxide, the ester and the prodrug thereof.

According to the present invention, the pharmaceutical composition is an LPAR1 inhibitor.

According to the present invention, the pharmaceutical composition is used for preventing and/or treating organ fibrotic diseases, respiratory diseases, renal diseases, hepatic diseases, inflammatory diseases, neurological diseases, cardiovascular and cerebrovascular diseases, gastrointestinal diseases, pains, urinary system diseases, ophthalmic diseases, metabolic diseases, cancers and rejection of transplanted organs.

According to the present invention, the pharmaceutical composition disclosed herein can be prepared into a dosage form suitable for administration by methods known in the art.

The present invention also provides use of one, two or more of the compound of formula (I) and the pharmaceutically acceptable salt, the solvate, the polymorph, the metabolite, the ester, the stereoisomer, the tautomer, the isotopically labeled compound, the nitrogen oxide and the prodrug thereof in the preparation of a medicament.

According to the present invention, the medicament is an LPAR1 inhibitor.

According to the present invention, the medicament is used for preventing and/or treating LPAR1-mediated diseases.

In some embodiments, the medicament is used for preventing and/or treating organ fibrotic diseases, respiratory diseases, renal diseases, hepatic diseases, inflammatory diseases, neurological diseases, cardiovascular and cerebrovascular diseases, gastrointestinal diseases, pains, urinary system diseases, ophthalmic diseases, metabolic diseases, cancers and rejection of transplanted organs.

The organ fibrotic diseases include, but are not limited to: pulmonary fibrosis (especially idiopathic pulmonary fibrosis), renal fibrosis, liver fibrosis, skin fibrosis, intestinal fibrosis and ocular fibrosis.

The respiratory diseases include, but are not limited to: respiratory disorders, including asthma, chronic obstructive pulmonary disease (COPD), bronchospasm, cough, chronic cough and respiratory failure.

The renal diseases include, but are not limited to: acute kidney injury and chronic kidney disease.

The hepatic diseases include, but are not limited to: alcoholic steatohepatitis, non-alcoholic steatohepatitis, acute and chronic hepatitis, liver cirrhosis, and hypohepatia.

The inflammatory diseases include, but are not limited to: autoimmune disease, inflammation, arthritis, rheumatoid arthritis, scleroderma, Raynaud phenomenon and chronic pruritus.

The neurological diseases include, but are not limited to: Alzheimer's disease, Parkinson's disease, neurodegeneration, traumatic brain injury, epilepsy, mental disease and sleep disorder.

The cardiovascular and cerebrovascular diseases include, but are not limited to: collagen vascular diseases, myocardial infarction, cerebral stroke, thrombosis, atherosclerosis, heart failure and hypertension.

The gastrointestinal diseases include, but are not limited to: colon syndrome, inflammatory bowel disease, gastrointestinal disease and gastrointestinal dysfunction.

The pains include, but are not limited to: cancer pain, neuropathic pain, inflammatory pain, surgical pain, visceral pain, dental pain, premenstrual pain, central pain, pain caused by burns, migraine (or cluster headache) and chronic pain.

The urinary system diseases include urinary incontinence, dysuria, cystitis, prostatic hypertrophy, dysuria accompanied by prostatic hypertrophy, bladder neck sclerosis and underactive bladder.

The ophthalmic diseases include macular degeneration and diabetic retinopathy.

The cancers include, but are not limited to: breast cancer, pancreatic cancer, ovarian cancer, prostate cancer, glioblastoma, bone cancer, colon cancer, intestinal cancer, head and neck cancer, melanoma, multiple myeloma, chronic lymphocytic leukemia and tumor metastasis.

The present invention also provides a method for treating and/or preventing LPAR1-mediated conditions or diseases, comprising administering a therapeutically effective amount of one, two or more of the compound of formula (I) and the pharmaceutically acceptable salt, the solvate, the polymorph, the metabolite, the ester, the stereoisomer, the tautomer, the isotopically labeled compound, the nitrogen oxide and the prodrug thereof to a subject.

According to the present invention, the conditions or diseases are organ fibrotic diseases, respiratory diseases, renal diseases, hepatic diseases, inflammatory diseases, neurological diseases, cardiovascular and cerebrovascular diseases, gastrointestinal diseases, pains, urinary system diseases, ophthalmic diseases, metabolic diseases, cancers and rejection of transplanted organs.

Definitions and General Terms

Unless otherwise stated, all technical and scientific terms used herein have the same meaning as commonly understood by those skilled in the art to which the present invention belongs. All patents and publications referred to herein are incorporated herein by reference in their entirety.

Unless otherwise stated, the following definitions as used herein should be applied. For the purpose of the present invention, the chemical elements are consistent with the Periodic Table of Elements (CAS version) and *Handbook of Chemistry and Physics* (75th Edition, 1994). In addition, general principles of organic chemistry can be found in *Organic Chemistry*, Thomas Sorrell, University Science Books, Sausalito: 1999, and *March's Advanced Organic Chemistry* by Michael B. Smith and Jerry March, John Wiley & Sons, New York: 2007, which are incorporated herein by reference in their entirety.

The term "include", "includes" or "including" is open-ended, i.e. including what is meant by the present invention, but not excluding other aspects.

The term "stereoisomer" refers to compounds having the same chemical structure but different spatial arrangements of the atoms or groups. Stereoisomers include enantiomers, diastereomers, conformers (rotamers), geometric isomers (cis/trans-isomers), atropisomers and the like.

The term "enantiomer" refers to two isomers of a compound that do not overlap but are mirror images of each other.

The term "diastereoisomer" refers to stereoisomers with two or more chiral centers and whose molecules are not mirror images of each other. Diastereoisomers have different physical properties, such as melting points, boiling points, spectral properties and reactivities. Mixtures of diastereoisomers can be separated by high-resolution analytical procedures such as electrophoresis and chromatography, e.g., high-performance liquid chromatography (HPLC).

The stereochemical definitions and rules used in the present invention generally follow S. P. Parker, Ed., *McGraw-Hill Dictionary of Chemical Terms* (1984) McGraw-Hill Book Company, New York; and Eliel, E. and Wilen, S., *Stereo chemistry of Organic Compounds*, John Wiley & Sons, Inc., New York, 1994. Any asymmetric atom (e.g., carbon) of the compounds disclosed herein may exist in a racemate or enantiomer enriched form, for example, the (R)-, (S)- or (R,S)-configuration. In certain embodiments, each asymmetric atom has at least 0% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration.

Any resulting mixture of stereoisomers may be separated into pure or substantially pure geometric isomers, enantiomers and diastereomers depending on differences in the physicochemical properties of the components, for example, by chromatography and/or fractional crystallization.

The term "tautomer" refers to structural isomers having different energies that are interconvertible by a low energy barrier. If a tautomer is possible (e.g., in solution), the chemical equilibrium of the tautomer can be reached. For example, a proton tautomer, also known as a prototropic tautomer, includes the interconversion by proton transfer, such as keto-enol isomerization and imine-enamine isomerization. A valence tautomer includes the interconversion by recombination of some bonding electrons. A specific example of keto-enol tautomerization is the interconversion of the pentan-2,4-dione and 4-hydroxypent-3-en-2-one tautomers. Another example of tautomerization is phenol-keto tautomerization. A specific example of phenol-keto tautomerization is the interconversion of pyridine-4-ol and pyridine-4(1H)-one tautomers. Unless otherwise indicated, all tautomeric forms of the compounds disclosed herein are within the scope of the present invention.

In general, the term "substituted" means that one or more hydrogen atoms in a given structure are substituted with a particular substituent. Further, when the group is substituted with one or more substituents described above, the substituents are independent of each other, that is, the one or more substituents may be different or the same. Unless otherwise indicated, the substitution of a substituent may occur at various substitutable positions of the substituted group. When more than one position in a given structure can be substituted with one or more substituents selected from particular groups, the substitution of the substituents may occur at various positions, identically or differently. The substituents may be, but are not limited to, =O, hydrogen, deuterium, cyano, nitro, halogen, hydroxyl, thiol, amino, alkyl, haloalkyl, alkoxy, carboxyl, cycloalkyl, cycloalkyloxy, heterocyclyl, heterocyclylalkyl, heterocyclyloxy, aryl, arylalkyl, aryloxy, heteroaryl, heteroarylalkyl, heteroaryloxy and the like.

In each part of this specification, substituents for the disclosed compounds are disclosed according to group types or ranges. It is specifically noted that each separate sub-combination of the various members of these group types and ranges is encompassed in the present invention. For example, the term "$C_{1-6}$ alkyl" specifically refers to independently disclosed $C_1$ alkyl, $C_2$ alkyl, $C_3$ alkyl, $C_4$ alkyl, $C_5$ alkyl or $C_6$ alkyl.

In each part of the present invention, connecting substituents are described. When a connecting group is clearly required to a structure, the Markush variables listed for the group should be understood as a connecting group. For example, if a connecting group is required to the structure and "alkyl" or "aryl" are listed for the Markush group definition of the variable, it should be understood that the "alkyl" or "aryl" respectively represents a connected alkylene group or arylene group.

The term "$C_{1-40}$ alkyl" used herein refers to a linear or branched saturated monovalent hydrocarbon group comprising 1-40 carbon atoms, wherein the alkyl group may optionally be substituted with one or more substituents described herein. In some embodiments, the alkyl group contains 1-12 carbon atoms; in other embodiments, the alkyl group contains 1-6 carbon atoms; in still other embodiments, the alkyl group contains 1-4 carbon atoms. Examples of alkyl groups include, but are not limited to, methyl, ethyl, n-propyl and the like.

The term "$C_{2-40}$ alkenyl" refers to a linear or branched monovalent hydrocarbyl containing 2-40 carbon atoms, wherein there is at least one site of unsaturation, that is, there is a carbon-carbon sp$^2$ double bond, and the double bonds can be separated from each other or conjugated; the alkenyl group may be optionally substituted with one or more substituents described herein, which includes the positioning of "cis" and "tans", or the positioning of "E" and "Z". Examples of alkenyl groups include, but are not limited to, vinyl (—CH=CH$_2$), allyl (—CH$_2$CH=CH$_2$), and the like. In some embodiments, the alkenyl contains 2-10 carbon atoms.

The term "$C_{1-40}$ haloalkyl" means that the $C_{1-40}$ alkyl is substituted with one, two or more halogen atoms. Examples of it include, but are not limited to, trifluoromethyl and the like.

The term "$C_{3-20}$ cycloalkyl" refers to a saturated monocyclic or bicyclic hydrocarbon containing 3-20 ring carbon atoms. In some embodiments, the cycloalkyl contains 3-14 carbon atoms. Examples of cycloalkyl groups include, but are not limited to, cyclopropyl, cyclobutyl, and the like. In other embodiments, the cycloalkyl contains 3-6 carbon atoms. The cycloalkyl group may be optionally substituted with one or more substituents described herein.

The term "3-20 membered heterocyclyl" refers to a saturated monocyclic or bicyclic hydrocarbon ring containing 3-20 ring atoms, which contains at least one heteroatom selected from nitrogen, sulfur and oxygen. In some embodiments, the heterocyclyl contains 3-14 ring atoms. According to the present invention, the heterocyclyl is non-aromatic. The heterocyclyl group may be optionally substituted with one or more substituents described herein. Examples of heterocyclyl groups include, but are not limited to: oxiranyl, thietanyl, pyrrolidinyl and the like.

The term "halogen" or "halo" refers to fluorine (F), chlorine (Cl), bromine (Br), or iodine (I).

The term "$C_{6-20}$ aryl" refers to an aromatic or partially aromatic monocyclic, bicyclic or tricyclic monovalent hydrocarbon ring containing 6-20 carbon atoms, and is preferably "$C_{6-14}$ aryl". Examples of aryl groups may include phenyl, naphthyl or anthryl. The aryl group may be optionally substituted with one or more substituents described herein.

The term "5-20 membered heteroaryl" refers to monocyclic, bicyclic or tricyclic systems containing 5-20 ring atoms, or 5-14 ring atoms, or 5-12 ring atoms, wherein at least one ring contains one or more ring heteroatoms selected from nitrogen, oxygen, and sulfur. Unless otherwise stated, the heteroaryl group may be connected to the rest of the molecule (e.g., the host structure in the formula) via any reasonable site (which may be C in CH, or N in NH). Examples include, but are not limited to, furanyl, imidazolyl, and the like, and also include, but are not limited to, bicyclic rings, such as benzimidazolyl and benzofuranyl. The heteroaryl group may be optionally substituted with one or more substituents described herein.

In addition, it should be noted that, unless otherwise explicitly indicated, the description of " . . . is independently selected from" used herein is to be understood broadly and means that each individual group described is independent from the others and may be independently selected from the same or different specific groups. In more detail, the description of " . . . is independently selected from" can mean that the specific options expressed by the same symbols in different groups do not affect each other; it can also mean that the specific options expressed by the same symbols in the same group do not affect each other.

The term "pharmaceutically acceptable" refers to molecular entities and compositions that are physiologically tolerable and generally do not produce an allergic or similar untoward reaction, such as gastrointestinal distress and dizziness, when administered to a human.

The term "carrier" refers to a diluent, adjuvant, excipient, or matrix with which the compound is administered. Such pharmaceutical carriers can be sterile liquid, such as water and oil, including those derived from petroleum, animals, plants or synthesis, such as peanut oil, soybean oil, mineral oil and sesame oil. Water or aqueous saline solutions and aqueous dextrose and glycerol solutions are preferably used as carriers, particularly injectable solutions. Suitable pharmaceutical carriers are described in *Remington's Pharmaceutical Sciences* by E. W. Martin.

The term "prodrug" used herein represents a compound that is converted in vivo to a compound of formula (I). Such conversion is affected by hydrolysis of the prodrug in the blood or by enzymatic conversion of the prodrug into the parent structure in the blood or tissue. The prodrugs disclosed herein can be esters, and in the prior art, the esters that can be used as prodrugs include phenyl esters, aliphatic ($C_{1-24}$) esters, acyloxymethyl esters, carbonates, carbamates and amino acid esters. For example, a compound disclosed herein containing hydroxyl can be acylated to give a prodrug. Other prodrugs include phosphate esters, and those phosphate esters are obtained by phosphorylating via the hydroxyl on the parent structure. For a complete discussion of prodrugs, reference can be made to the following: T. Higuchiand V. Stella, Pro-drugs as Novel Delivery Systems, Vol. 14 of the *A.C.S. Symposium Series*; Edward B. Roche, ed., Bioreversible Carriers in Drug Design, American Pharmaceutical Association and Pergamon Press, 1987; J. Rautio et al., Prodrugs: Design and Clinical Applications, *Nature Review Drug Discovery*, 2008, 7, 255-270; and S. J. Hecker et al., Prodrugs of Phosphate sand Phosphonates, *Journal of Medicinal Chemistry*, 2008, 51, 2328-2345.

The term "metabolite" used herein refers to a product obtained by the metabolism of a particular compound or salt thereof in vivo. Metabolites of a compound can be identified by techniques well known in the art, and their activities can be characterized by assays as described herein. Such products may be obtained by the oxidation, reduction, hydrolysis, amidation, deamidation, esterification, defatting, enzymatic cleavage, and the like of the administered compound. Accordingly, the present invention includes metabolites of the compound, including metabolites produced by contacting the compounds disclosed herein with a mammal for a sufficient period of time.

The term "pharmaceutically acceptable salt" used herein refers to both organic and inorganic salts of the compounds disclosed herein. Pharmaceutically acceptable salts are well known in the art. For example, S. M. Berge et al. describe pharmaceutically acceptable salts in detail in *J. Pharmaceutical Sciences*, 1977, 66: 1-19. Pharmaceutically acceptable salts formed by non-toxic acids include, but are not limited to, inorganic acid salts such as hydrochloride, hydrobromide, phosphate, sulfate, perchlorate; organic acid salts such as acetate, oxalate, maleate, tartrate, citrate, succinate, malonate; or salts obtained by other methods described in the literature, such as ion exchange. Other pharmaceutically acceptable salts include adipate, alginate, ascorbate, aspartate, benzenesulfonate, benzoate, bisulfate, borate, butyrate, camphorate, camphorsulfonate, cyclopentylpropionate, digluconate, dodecylsulfate, ethanesulfonate, formate, fumarate, glucoheptonate, glycerophosphate, gluconate, hemisulfate, heptanoate, hexanoate, hydriodate, 2-hydroxyethanesulfonate, lactobionate, lactate, laurate, lauryl sulfate, malate, methanesulfonate, 2-naphthalenesulfonate, nicotinate, nitrate, oleate, palmitate, pamoate, pectinate, persulfate, 3-phenylpropionate, picrate, pivalate, propionate, stearate, thiocyanate, p-toluenesulfonate, undecanoate, valerate, and the like. Salts formed by appropriate bases include salts of alkali metal, alkaline earth metal, ammonium and $N^+(C_{1-4}$ alkyl$)_4$. The present invention also contemplates quaternary ammonium salts formed by any compound with a N-containing group. Water-soluble or oil-soluble or dispersible products can be obtained by quaternization. Alkali metals or alkaline earth metals that can form salts include sodium, lithium, potassium, calcium, magnesium, and the like. Pharmaceutically acceptable salts further include suitable and non-toxic ammonium, quaternary ammonium salts and amine cations formed by counterions, such as halides, hydroxides, carboxylates, sulfates, phosphates, nitrates, $C_{1-8}$ sulfonates and aromatic sulfonates.

"Solvate" disclosed herein refers to an association compound of one or more solvent molecules with the compounds disclosed herein. Solvents that form the solvate include, but are not limited to, water, isopropanol, ethanol, methanol, dimethyl sulfoxide, ethyl acetate, acetic acid and aminoethanol. The term "hydrate" refers to an association compound in which the solvent molecules are water molecules.

"Ester" disclosed herein refers to an ester that is hydrolyzable in vivo and formed by a compound containing hydroxyl or carboxyl. Such esters are, for example, pharmaceutically acceptable esters that are hydrolyzed in human or animal to produce parent alcohols or acids. The compound of formula (I) disclosed herein contains carboxyl, which can form an ester that is hydrolyzed in vivo with appropriate groups including, but not limited to, alkyl, arylalkyl and the like.

"Nitrogen oxide" disclosed herein refers to an N-oxide formed by oxidizing one or more nitrogen atoms when the compound contains several amine functional groups. Specific examples of N-oxides are N-oxides of tertiary amines or N-oxides of a nitrogen atom of a nitrogen-containing heterocycle. The corresponding amines can be treated with an oxidizing agent such as hydrogen peroxide or peracid (e.g., peroxycarboxylic acid) to form N-oxides (see *Advanced Organic Chemistry*, Wiley Interscience, 4th edition, Jerry March, pages). In particular, N-oxides may be prepared by the method of L. W. Deady (*Syn. Comm.* 1977, 7, 509-514) in which an amine compound is reacted with m-chloroperoxybenzoic acid (MCPBA), for example, in an inert solvent such as dichloromethane.

The term "isotopically labeled compound" includes, but is not limited to, the compounds disclosed herein that are labeled by isotopes of hydrogen, carbon, nitrogen, oxygen, fluorine, sulfur and chlorine (e.g., $^2H$, $^3H$, $^{13}C$, $^{14}C$, $^{15}N$, $^{18}O$, $^{17}O$, $^{18}F$, $^{35}S$ and $^{36}Cl$). Isotopically-labeled compounds disclosed herein can be used for the determination of the tissue distribution of compounds and prodrugs and metabolites thereof; preferred isotopes for such determinations include $^3H$ and $^{14}C$. In addition, in some cases, substitution with heavier isotopes (e.g., deuterium ($^2H$ or D)) may result in greater metabolic stability, which provides therapeutic advantages, for example increased in vivo half-life or reduced dosage requirement. The isotopically-labeled compounds disclosed herein can generally be prepared by substituting isotopically-labeled reagents for non-isotopically-labeled reagents according to the methods described herein.

In some embodiments, the term "treat", "treating" or "treatment" used herein refers to ameliorating a disease or disorder (i.e., slowing or arresting or reducing the progression of the disease or at least one clinical symptom thereof). In other embodiments, "treat", "treating" or "treatment" refers to mitigating or improving at least one physical parameter, including physical parameters that may not be perceived by a patient. In other embodiments, "treat", "treating" or "treatment" refers to modulating a disease or disorder, either physically (e.g., stabilizing a perceptible symptom) or physiologically (e.g., stabilizing a physical parameter), or both. In other embodiments, "treat", "treating" or "treatment" refers to preventing or delaying the onset, occurrence, or deterioration of a disease or disorder.

Unless otherwise indicated, abbreviations for any of protecting groups, amino acids and other compounds used herein are provided based on their commonly used and accepted abbreviations, or by referring to *IUPAC-IUB Commission on Biochemical Nomenclature* (see *Biochem.* 1972, 11:942-944).

The biological activity of the compounds disclosed herein can be assessed by using any conventionally known method. Appropriate detection methods are well known in the art. For example, the compounds disclosed herein can be tested for inhibitory activity against LPAR1, pharmacokinetic activity, and/or liver microsomal stability, etc., by an appropriate conventional method. The detection methods provided by the present invention are presented as examples only and do not limit the present invention. The compounds disclosed herein are active in at least one of the detection methods provided by the present invention.

The pharmaceutical excipients may be those widely used in the field of pharmaceutical production. The excipients are primarily used to provide a safe, stable and functional pharmaceutical composition and may also provide a method for dissolving the active ingredients at a desired rate or for promoting effective absorption of the active ingredients after administration of the composition to a subject. The pharmaceutically acceptable excipients may be inert fillers or provide a function such as stabilizing the overall pH of the composition or preventing degradation of the active ingredients of the composition. The pharmaceutically acceptable excipients may include one or more of the following excipients: binders, suspending agents, emulsifiers, diluents, fillers, granulating agents, gluing agents, disintegrating agents, lubricants, anti-adherents, glidants, wetting agents, gelling agents, absorption retardants, dissolution inhibitors, reinforcing agents, adsorbents, buffering agents, chelating agents, preservatives, colorants, flavoring agents and sweeteners.

Substances which may serve as pharmaceutically acceptable excipients include, but are not limited to, ion exchangers; aluminum; aluminum stearate; lecithin; serum proteins such as human serum protein; buffer substances such as phosphate; glycine; sorbic acid; potassium sorbate; partial glyceride mixture of saturated vegetable fatty acid; water; salts or electrolytes such as protamine sulfate, disodium hydrogen phosphate, potassium hydrogen phosphate, sodium chloride and zinc salt; colloidal silica; magnesium trisilicate; polyvinylpyrrolidone; polyacrylate; waxes; polyethylene-polyoxypropylene-blocking polymer; wool fat; sugars such as lactose, glucose and sucrose; starches such as corn starch and potato starch; cellulose and its derivatives such as sodium carboxymethyl cellulose, ethyl cellulose and cellulose acetate; gum powder; malt; gelatin; talc powder; adjuvants such as cocoa butter and suppository waxes; oils such as peanut oil, cottonseed oil, safflower oil, sesame oil, olive oil, corn oil and soybean oil; glycols such as propylene glycol and polyethylene glycol; esters such as ethyl oleate and ethyl laurate; agar; buffers such as magnesium hydroxide and aluminum hydroxide; alginic acid; pyrogen-free water; isotonic salts; Ringer's solution; ethanol, phosphate buffered solution, and other non-toxic suitable lubricants such as sodium lauryl sulfate and magnesium stearate, coloring agents, releasing agents, coating agents, sweeteners, flavoring agents and perfumes, preservatives and antioxidants.

The pharmaceutical composition disclosed herein may be prepared in accordance with the disclosure using any method known to those skilled in the art, for example, conventional mixing, dissolving, granulating, emulsifying, levigating, encapsulating, embedding or lyophilizing processes.

The dosage form of the drug disclosed herein can be selected according to specific conditions. Pharmaceutical dosage forms often consist of drugs, excipients, and containers/closure systems. One or more excipients (also known as inactive ingredients) may be added to the compounds disclosed herein to improve or facilitate the manufacture, stability, administration and safety of drugs, and may provide a means to obtain a desired drug release profile. Thus, the type of excipient added to a drug may depend on various factors, such as physical and chemical properties of the drug, route of administration and preparation steps. There are pharmaceutical excipients in the art, including those listed in various pharmacopoeias. (See U.S. Pharmacopeia (USP), Japanese Pharmacopoeia (JP), European Pharmacopoeia (EP) and British pharmacopoeia (BP); publications from the Center for Drug Evaluation and Research (CEDR) of U.S. Food and Drug Administration (www.fda.gov), for example, *Inactive Ingredient Guide*, 1996; and *Handbook of Pharmaceutical Additives*, 2002, edited by Ash, Synapse Information Resources, Inc., Endicott NY; etc.).

The pharmaceutical composition disclosed herein may include one or more physiologically acceptable inactive ingredients that facilitate processing of active molecules into preparations for pharmaceutical use. Appropriate preparations will be determined according to the desired route of administration. The route of administration includes intravenous injection, transmucosal or nasal administration, oral administration and the like. For oral administration, the compound may be formulated into liquid or solid dosage forms and used as immediate release or controlled/sustained release preparations. Suitable dosage forms for oral ingestion by an individual include tablets, pills, dragees, hard and soft shell capsules, liquids, gels, syrups, ointments, suspensions and emulsions.

Oral solid dosage forms can be obtained using excipients including fillers, disintegrants, binders (dry and wet), dissolution retardants, lubricants, glidants, anti-adherents, cationic exchange resins, wetting agents, antioxidants, preservatives, colorants and flavoring agents. These excipients may be of synthetic or natural sources. Examples of such excipients include cellulose derivatives, citric acid, dicalcium phosphate, gelatin, magnesium carbonate, magnesium/sodium lauryl sulfate, mannitol, polyethylene glycol, polyvinylpyrrolidone, silicates, silica, sodium benzoate, sorbitol, starches, stearic acid or salts thereof, sugars (i.e., dextrose, sucrose, lactose, etc.), talc, tragacanth mucilage, vegetable oils (hydrogenated) and waxes. Ethanol and water may be used as adjuvants for granulation. In some cases, it is desirable to coat tablets with, for example, a taste-masking film, a gastric acid-resistant film or a sustained release film. Natural and synthetic polymers are often used to coat tablets in combination with colorants, sugars, and organic solvents or water to produce dragees. When capsules are superior to tablets, the pharmaceutical powders, suspensions or solutions may be delivered in the form of compatible hard or soft shell capsules. The therapeutically effective dosage can first be estimated using various methods well known in the art. Initial dosage for animal studies can be based on established effective concentrations in cell culture assays. Dosage ranges suitable for humans can be determined, for example, using data obtained from animal studies and cell culture assays. In certain embodiments, the compounds disclosed herein may be prepared as medicaments for oral administration.

The correct preparation, route of administration, dosage and time interval between administrations can be determined based on methods known in the art while taking the specificity of the individual into account. In this specification, terms such as "some embodiments," "examples," or "a preferred embodiment" mean that a particular feature, structure, material or characteristic described in reference to the embodiment or example is included in at least one embodiment or example of the present invention. In this specification, the schematic descriptions of the terms described above do not necessarily refer to the same embodiment or example. Moreover, the specific features, materials, structures and other characteristics described may be combined in any one or more embodiments or examples in an appropriate manner. Moreover, various embodiments or examples and features of various embodiments or examples described in this specification can be combined by one skilled in the art to the extent that they do not contradict each other.

Beneficial Effects

Surprisingly, it is found that the compounds disclosed herein feature high antagonistic activity against LPAR1, good selectivity, low toxicity and good metabolic stability, showing a good prospect of drug development. The compounds disclosed herein can be used for preventing and/or treating diseases or disorders related to LPAR1. For example, the compound of formula (I) can be used for preventing and/or treating, delaying or arresting organ fibrotic diseases, respiratory diseases, renal diseases, hepatic diseases, inflammatory diseases, neurological diseases, cardiovascular and cerebrovascular diseases, gastrointestinal diseases, pains, urinary system diseases, ophthalmic diseases, metabolic diseases, cancers and rejection of transplanted organs.

Unexpectedly, it is found that $IC_{50}$ values of some of the compounds disclosed herein can be as low as 300 nM or less, or even 50 nM or less. In addition, some of the compounds disclosed herein have an inhibitory rate of 30-50% against A2058 cell migration, some of the compounds even have an inhibitory rate of 50-70%, and cell migration is remarkably inhibited. Moreover, the compounds disclosed herein all have good safety, and the $CC_{50}$ values can be greater than 200 μM. Furthermore, the compounds disclosed herein have relatively good metabolic stability in humans, rats and mice, wherein the $T_{1/2}$ of some compounds in human liver microsome is more than 30 min, or even more than 90 min. In view of such an excellent inhibitory activity, application thereof as LPAR1 inhibitors to the diseases or disorders described above is anticipated.

In addition, the preparation method for the compounds disclosed herein features simple operation, mild reaction conditions and high product yield, and thus is suitable for industrial production.

DETAILED DESCRIPTION

The present invention is further illustrated by the following examples; however, these examples should not be construed as limiting the present invention. Experimental procedures without specified conditions in the following examples are conducted in accordance with conventional procedures and conditions, or in accordance with the manufacturer's manual.

The following abbreviations are used throughout the present invention:

DMF (N,N-dimethylformamide); DCM (dichloromethane); PE (petroleum ether); EA (ethyl acetate); DIPEA (N,N-diisopropylethylamine); THF (tetrahydrofuran); Ac (acetyl); MeOH (methanol); Boc (tert-butoxycarbonyl); B2Pin2 (bis(pinacolato)diboron); rt (room temperature); HATU (2-(7-azabenzotriazol-1-yl)-N,N,N',N'-tetramethyluronium hexafluorophosphate), reflux (refluxing conditions); eq (equivalent); Rf (retardation factor); g (gram); mg (milligram); mol (mole); mmol (millimole); h (hour); min (minute); mL (milliliter); μL (microliter).

Overnight refers to 8-15 h, for example 12 h; the room temperature refers to 10-30° C.; solvent ratio such as PE/EA refers to volume ratio.

Unless otherwise indicated, all temperatures in the examples described below are given in Celsius degrees. Unless otherwise indicated, reagents are purchased from commercial suppliers such as Aldrich Chemical Company, Arco Chemical Company and Alfa Chemical Company, and used without further purification. General reagents are purchased from Shantou Xilong Chemical Plant Co. Ltd., Guangdong Guanghua Sci-Tech Co., Ltd., Guangzhou Chemical Reagent Factory, Tianjin Yuyu Fine Chemical Co., Ltd., Qingdao Tenglong Chemical Reagent Co., Ltd., and Qingdao Haiyang Chemical Co., Ltd. Anhydrous tetrahydrofuran, dioxane, toluene and diethyl ether are obtained by refluxing and drying with sodium metal. Anhydrous dichloromethane and chloroform are obtained by refluxing and drying with calcium hydride. Ethyl acetate, petroleum ether, n-hexane, N,N-dimethylacetamide and N,N-dimethylformamide are pre-dried over anhydrous sodium sulfate.

The following reactions are generally preformed under a positive pressure of nitrogen or argon or by placing a drying tube over an anhydrous solvent (unless otherwise indicated), the reaction vial is stoppered with a suitable rubber stopper and the substrate is driven in by a syringe. Each piece of glassware is dried.

Chromatographic column is a silica gel column. Silica gel (300-400 mesh) is purchased from Qingdao Haiyang Chemical Co., Ltd. NMR spectral data are measured on a Bruker Avance 400 NMR spectrometer or a Bruker Avance IIIHD 600 NMR spectrometer using $CDCl_3$, DMSO-d6, $CD_3OD$ or Acetone-$d_6$ as solvents (reported in ppm) and TMS (0 ppm) or chloroform (7.25 ppm) as reference standards. When multiple peaks are present, the following abbreviations will be used: s (singlet); d (doublet); t (triplet); m (multiplet); br (broadened); dd (doublet of doublets); dt (doublet of triplets); ddd (doublet of doublet of doublets); ddt (doublet of doublet of triplets); dddd (doublet of doublet of doublet of doublets). Coupling constants are expressed in hertz (Hz).

Low-resolution mass spectrometry (MS) data are determined on an Agilent 6320 series LC-MS spectrometer equipped with a G1312A binary pump and an aG1316ATCC (column temperature maintained at 30° C.), with a G1329A autosampler and a G1315BDAD detector applied to the analysis and an ESI source applied to the LC-MS spectrometer.

Example 1

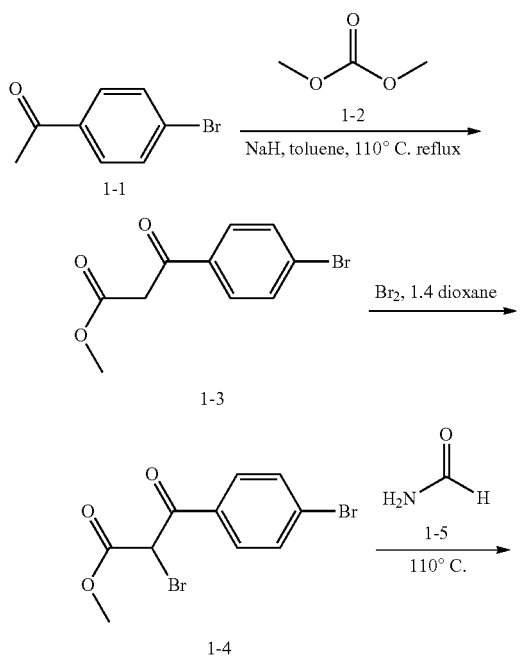

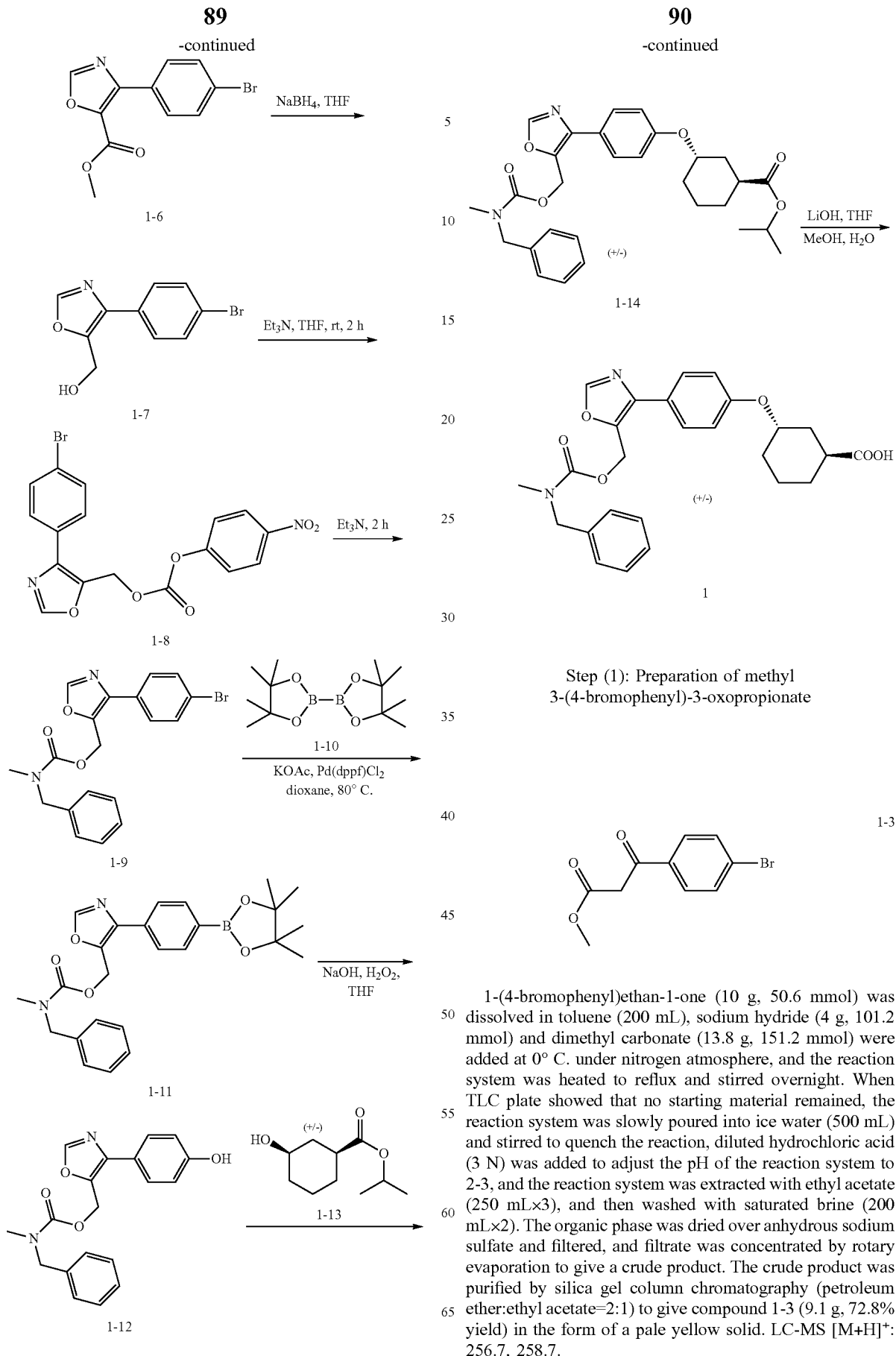

Step (1): Preparation of methyl 3-(4-bromophenyl)-3-oxopropionate 1-(4-bromophenyl)ethan-1-one (10 g, 50.6 mmol) was dissolved in toluene (200 mL), sodium hydride (4 g, 101.2 mmol) and dimethyl carbonate (13.8 g, 151.2 mmol) were added at 0° C. under nitrogen atmosphere, and the reaction system was heated to reflux and stirred overnight. When TLC plate showed that no starting material remained, the reaction system was slowly poured into ice water (500 mL) and stirred to quench the reaction, diluted hydrochloric acid (3 N) was added to adjust the pH of the reaction system to 2-3, and the reaction system was extracted with ethyl acetate (250 mL×3), and then washed with saturated brine (200 mL×2). The organic phase was dried over anhydrous sodium sulfate and filtered, and filtrate was concentrated by rotary evaporation to give a crude product. The crude product was purified by silica gel column chromatography (petroleum ether:ethyl acetate=2:1) to give compound 1-3 (9.1 g, 72.8% yield) in the form of a pale yellow solid. LC-MS [M+H]$^+$: 256.7, 258.7.

Step (2): Preparation of methyl 2-bromo-3-(4-bromophenyl)-3-oxopropionate

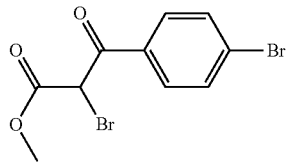

1-4

Compound 1-3 (8 g, 31.2 mmol) was dissolved in 1,4-dioxane (150 mL), and the reaction system was cooled to 0° C., added with bromine (1.9 mL, 37.5 mmol) and stirred overnight. When TLC plate showed that no starting material remained, the reaction system was concentrated by rotary evaporation to give brown-yellow compound 1-4 (12.7 g, crude). LC-MS [M+H]$^+$: 334.6, 336.6, 338.6.

Step (3): Preparation of methyl 4-(4-bromophenyl)oxazole-5-carboxylate

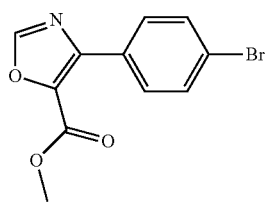

1-6

Compound 1-4 (12.7 g, crude) was added to formamide solution (50 mL). The reaction system was stirred at 110° C. for 1.5 h, cooled to room temperature, added with water (50 mL) to quench the reaction, and extracted with ethyl acetate (35 mL×3). The organic phases were combined, washed with saturated brine (50 mL), dried over anhydrous sodium sulfate and filtered. The filtrate was concentrated by rotary evaporation to give a crude product, and the crude product was purified by silica gel column chromatography (petroleum ether:ethyl acetate=3:1) to give compound 1-6 (2.5 g, 23.11% yield) in the form of a pale yellow solid. LC-MS [M+H]$^+$: 281.7, 283.7.

Step (4): Preparation of (4-(4-bromophenyl)oxazol-5-yl)methanol

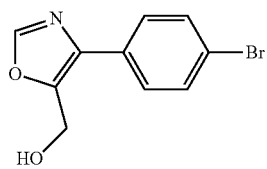

1-7

Compound 1-6 (1.5 g, 5.3 mmol) was dissolved in a mixed solution of tetrahydrofuran (15 mL) and water (1 mL), and sodium borohydride (406 mg, 10.7 mmol) was added at 0° C. The reaction system was warmed to room temperature and reacted for 3 h. When TLC plate showed that no starting material remained, the reaction system was diluted with water (10 mL) and extracted with ethyl acetate (10 mL×3). The organic phase was dried over anhydrous sodium sulfate and filtered. The filtrate was concentrated by rotary evaporation, and the residue was purified by silica gel column chromatography (dichloromethane:methanol=20:1) to give compound 1-7 (550 mg, 42.1% yield) in the form of a brown solid. LC-MS [M+H]$^+$: 253.7, 255.7.

Step (5): Preparation of (4-(4-bromophenyl)oxazol-5-yl)methyl(4-nitrophenyl)carbonate

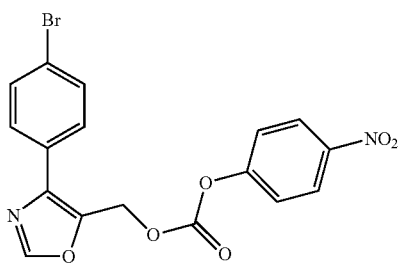

1-8

Compound 1-7 (255 mg, 1 mmol) and pyridine (320 g, 4 mmol) were dissolved in dichloromethane (10 mL), and the reaction system was cooled to 0° C. 4-nitrophenyl chloroformate (600 mg, 3 mmol) was added, and then the reaction system was warmed to room temperature and stirred overnight. The reaction system was washed with saturated brine, the organic phase was dried over anhydrous sodium sulfate and concentrated, and the residue was separated by column chromatography (PE/EA=5/1) to give compound 1-8 (260 mg) in the form of a white solid. LC-MS [M+H]$^+$: 417.8, 419.8.

Step (6): Preparation of (4-(4-bromophenyl)oxazol-5-yl)methylbenzyl(methyl)carbamate

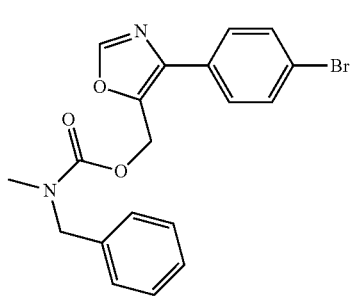

1-9

Compound 1-8 (550 mg, 2.16 mmol) and triethylamine (878 mg, 8.69 mmol) were dissolved in tetrahydrofuran (15 mL), and the reaction system was stirred for 10 min, added with 4-nitrophenylmethyl(phenyl)carbamate (521 mg, 2.61 mmol), warmed to room temperature and reacted for 3 h. The reaction system was added with water (20 mL) to quench the reaction, extracted with ethyl acetate (10 mL×3), and washed with saturated brine (20 mL). The organic phase was dried over anhydrous sodium sulfate and filtered. The filtrate was concentrated by rotary evaporation, and the residue was purified by silica gel column chromatography (dichloromethane:ethyl acetate=10:1) to give compound 1-9 (600 mg, 53.29% yield) in the form of a white solid. LC-MS [M+H]⁺: 400.6, 402.6.

Step (7): Preparation of (4-(4-(4,4,5,5-tetramethyl-1,3,2-dioxaborolan-2-yl)phenyl)oxazol-5-yl) methylbenzyl (methyl)carbamate

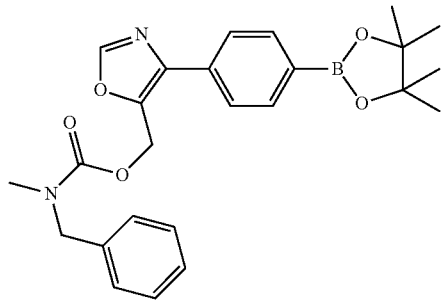

1-11

Compound 1-9 (600 mg, 1.5 mmol) was dissolved in 1,4-dioxane (20 mL), and the reaction system was sequentially added with bis(pinacolato)diboron (762 mg, 3 mmol), potassium acetate (441 mg, 4.5 mmol) and [1,1'-bis(diphenylphosphino)ferrocene]dichloropalladium(II) (110 mg, 0.15 mmol), heated to 80° C. and reacted for 4 h, and filtered. The filtrate was concentrated by rotary evaporation to give compound 1-11 (670 mg, crude) in the form of a brown-black solid. LC-MS [M+H]⁺: 449.1.

Step (8): Preparation of (4-(4-hydroxyphenyl)oxazol-5-yl)methylbenzyl(methyl)carbamate

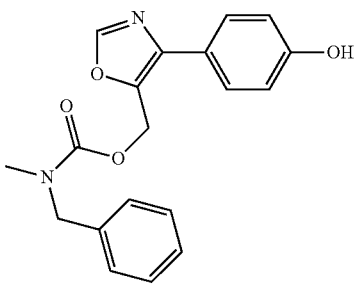

1-12

Compound 1-11 (670 mg, 1.5 mmol) was dissolved in tetrahydrofuran (20 mL), and the reaction system was cooled to 0° C., sequentially added with sodium hydroxide solution (1 N, 0.4 mL, 0.4 mmol) and hydrogen peroxide (20 mL), and stirred at 0° C. Until TLC plate showed that no starting material remained, the reaction system was diluted with water (20 mL), extracted with ethyl acetate (20 mL), and wash with saturated brine (20 mL). The organic phase was dried over anhydrous sodium sulfate and filtered. The filtrate was concentrated by rotary evaporation, and the residue was purified by silica gel column chromatography (dichloromethane:methanol=50:1) to give compound 1-12 (200 mg, 39.45% yield) in the form of a pale yellow solid. LC-MS [M+H]⁺: 339.0.

Step (9): Preparation of (+/−)-isopropyl (1S,3S)-3-(4-(5-(((benzyl(methyl)carbamoyl)oxy)methyl) oxazol-4-yl)phenoxy)cyclohexane-1-carboxylate

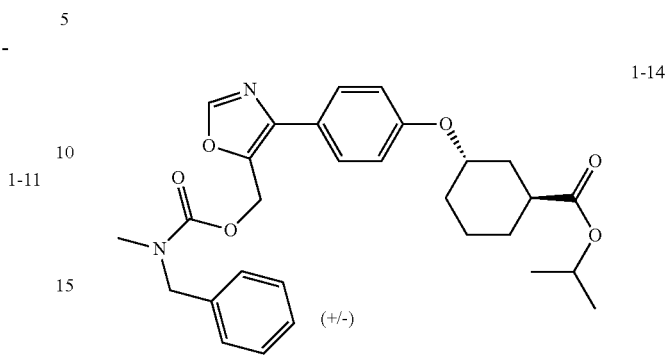

1-14

(+/−)

Compound 1-12 (410 mg, 2.34 mmol), DTAD (498 mg, 2.34 mmol) and triphenylphosphine (686 mg, 2.34 mmol) were dissolved in tetrahydrofuran (10 mL), and the reaction system was stirred overnight at room temperature under nitrogen atmosphere. The reaction system was then purified by silica gel column chromatography (DCM/EA=5/1) to give compound 1-14 (157 mg, 46.29% yield) in the form of a yellow solid. LC-MS [M+H]⁺: 507.6.

Step (10): Preparation of (+/−)-(1S,3S)-3-(4-(5-(((benzyl(methyl)carbamoyl)oxy)methyl)oxazol-4-yl) phenoxy)cyclohexane-1-carboxylic Acid

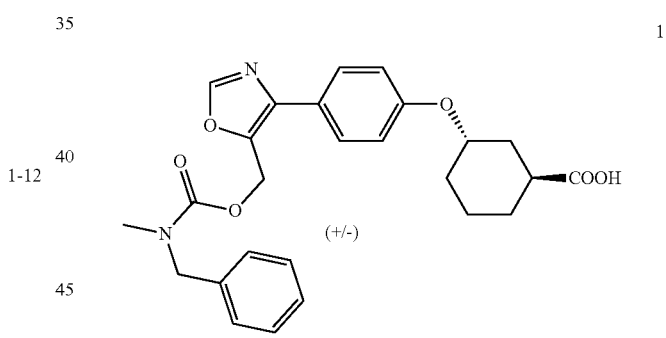

1

(+/−)

Compound 1-14 (157 mg, 0.31 mmol) was dissolved in tetrahydrofuran (3 mL), and the reaction system was added sequentially with methanol (1 mL), water (1 mL) and lithium hydroxide (152 mg, 1.55 mmol), and stirred overnight at room temperature. The reaction system was diluted with water (10 mL), and the organic solvent was removed by rotary evaporation under reduced pressure. The aqueous phase was adjusted to pH 2-3 with hydrochloric acid (1 N), and extracted with dichloromethane (10 mL×2). The organic phase was dried over anhydrous sodium sulfate and filtered, and the filtrate was concentrated by rotary evaporation. The residue was purified by silica gel column chromatography (dichloromethane/methanol=20:1) and then lyophilized to give compound 1 (25 mg) in the form of a white solid.

LC-MS [M+H]⁺: 465.6. ¹H NMR (400 MHz, CDCl₃) δ 7.94 (d, J=6.9 Hz, 1H), 7.66 (dd, J=21.5, 7.6 Hz, 2H), 7.39-7.28 (m, J=17.8, 7.1 Hz, 4H), 7.19 (d, J=7.0 Hz, 1H), 7.00 (m, 2H), 5.37 (d, J=4.1 Hz, 2H), 4.70 (s, 1H), 4.54 (s, 1H), 4.48 (s, 1H), 2.96 (s, 1H), 2.94-2.89 (m, J=8.9, 4.8 Hz,

1H), 2.88 (d, J=12.3 Hz, 1H), 2.18 (d, J=13.2 Hz, 1H), 2.05-1.90 (m, J=23.2, 11.8 Hz, 3H), 1.84-1.75 (m, J=3.2 Hz, 1H), 1.66 (m, 3H).

Example 2

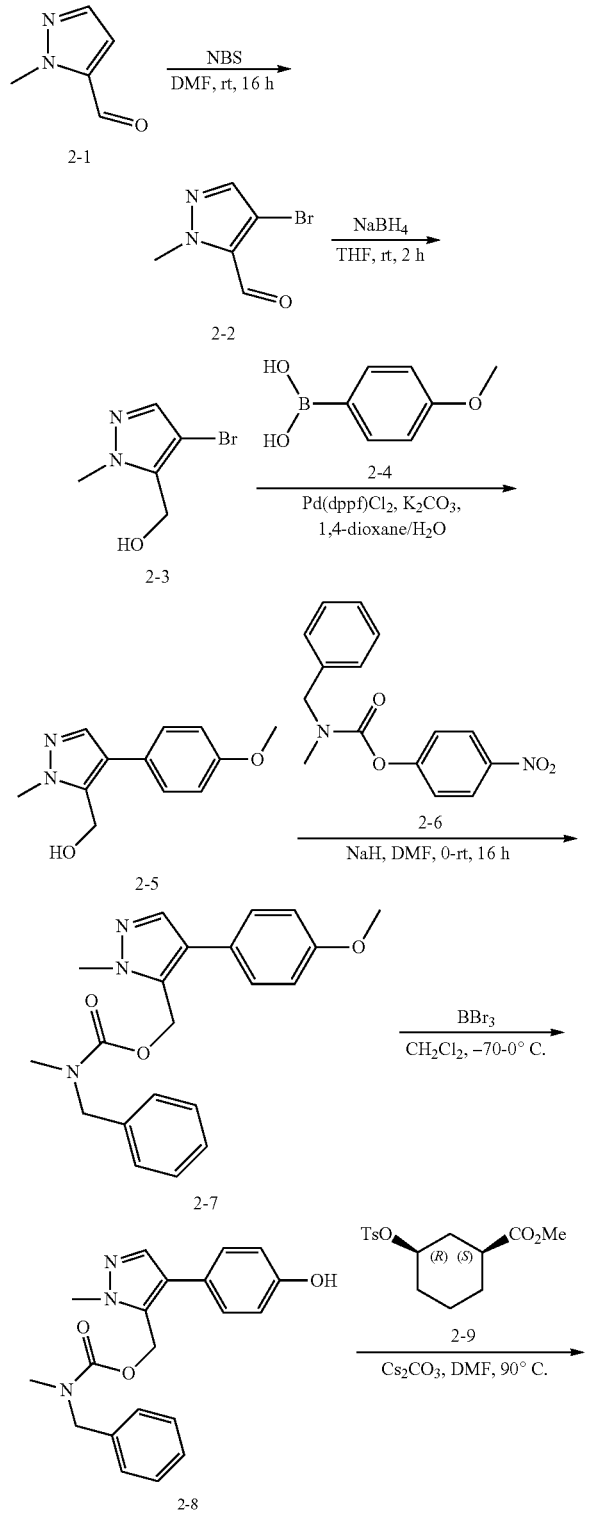

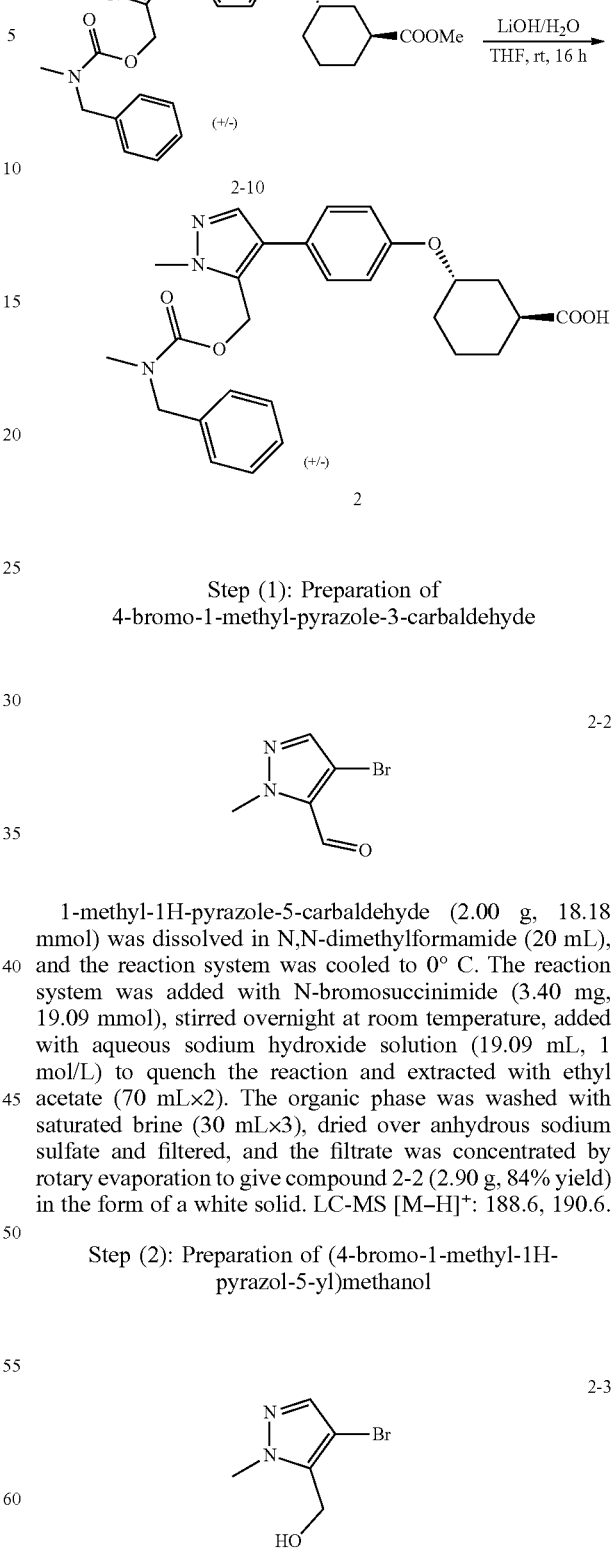

Step (1): Preparation of 4-bromo-1-methyl-pyrazole-3-carbaldehyde 1-methyl-1H-pyrazole-5-carbaldehyde (2.00 g, 18.18 mmol) was dissolved in N,N-dimethylformamide (20 mL), and the reaction system was cooled to 0° C. The reaction system was added with N-bromosuccinimide (3.40 mg, 19.09 mmol), stirred overnight at room temperature, added with aqueous sodium hydroxide solution (19.09 mL, 1 mol/L) to quench the reaction and extracted with ethyl acetate (70 mL×2). The organic phase was washed with saturated brine (30 mL×3), dried over anhydrous sodium sulfate and filtered, and the filtrate was concentrated by rotary evaporation to give compound 2-2 (2.90 g, 84% yield) in the form of a white solid. LC-MS [M−H]⁺: 188.6, 190.6.

Step (2): Preparation of (4-bromo-1-methyl-1H-pyrazol-5-yl)methanol 4-bromo-1-methyl-1H-pyrazol-5-carbaldehyde (2.90 g, 15.34 mmol) was dissolved in tetrahydrofuran (50 mL), and then the reaction system was cooled to 0° C., added with sodium borohydride (408 mg, 10.74 mmol) and stirred at room temperature for 2 h. The reaction system was then added with water (4 mL) to quench the reaction, and concentrated by rotary evaporation, and the residue was separated by column chromatography (ethyl acetate:petroleum ether=1:2) to give compound 2-3 (2.5 g, 85% yield) in the form of a white solid. LC-MS [M+H]$^+$: 190.7, 192.7.

Step (3): Preparation of (4-(4-methoxyphenyl)-1-methyl-1H-pyrazol-5-yl)methanol

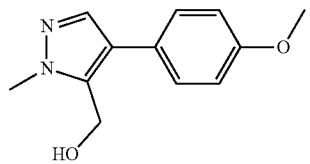

2-5

Compound 2-3 (800 mg, 4.19 mmol), 4-methoxyphenylboronic acid (760 mg, 5.03 mmol), and [1,1'-bis(diphenylphosphino)ferrocene]dichloropalladium(II) (178 mg, 025 mmol) were added to 1,4-dioxane (16 mL), and then the reaction system was added with a solution of potassium carbonate (1.45 g, 10.48 mmol) in water (4 mL) and reacted at 100° C. overnight under nitrogen atmosphere. The reaction system was filtered, and the organic phase was concentrated by rotary evaporation, extracted with ethyl acetate (30 mL×2) and concentrated, and the residue was separated by column chromatography (PE/EA=1/1) to give compound 2-5 (750 g, 82% yield) in the form of a brown solid. LC-MS [M+H]$^+$: 219.2.

Step (4): Preparation of (4-(4-methoxyphenyl)-1-methyl-1H-pyrazol-5-yl)methylbenzyl(methyl)carbamate

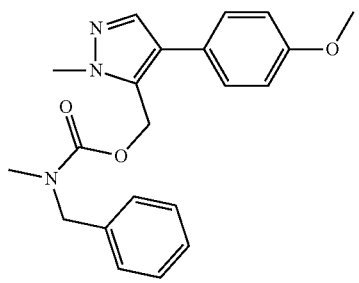

2-7

Compound 2-5 (750 mg, 3.44 mmol) was dissolved in N,N-dimethylformamide (20 mL), and the reaction system (344 mg, 8.60 mmol) was added with sodium hydride at 0° C., reacted at 0° C. for 1 h, and added dropwise with a solution of 4-nitrophenylbenzyl(methyl)carbamate in N,N-dimethylformamide (1.18 g, 4.13 mmol). Then the reaction system was stirred overnight at room temperature, poured into ice water, and extracted with ethyl acetate (40 mL×2). The organic phases were combined, washed with saturated brine (20 mL×2), dried over anhydrous sodium sulfate, filtered and concentrated, and the residue was separated by column chromatography (EA/PE=1/1) to give compound 2-7 (780 mg, 62% yield) in the form of a colorless oily liquid. LC-MS [M+H]$^+$: 366.

Step (5): Preparation of (4-(4-hydroxyphenyl)-1-methyl-1H-pyrazol-5-yl)methylbenzyl(methyl)carbamate

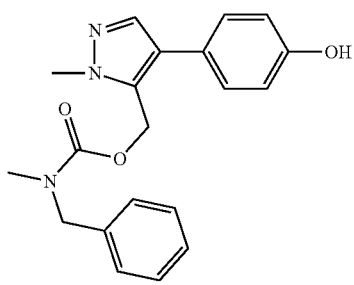

2-8

Compound 2-7 (780 mg, 2.14 mmol) was dissolved in anhydrous dichloromethane (8 mL), and the reaction system was added dropwise with a solution of boron tribromide in dichloromethane (4 mL, 1 mol/L) at −70° C. and reacted at 0° C. for 7 h. Then the reaction system was poured into ice water, and extracted with dichloromethane (30 mL×2). The organic phases were combined, washed with saturated brine (10 mL×2), dried over anhydrous sodium sulfate, filtered and concentrated, and the residue was separated by column chromatography (EA/PE=1/1) to give compound 2-8 (195 mg, 26% yield) in the form of a gray solid. LC-MS [M+H]$^+$: 352.2.

Step (6): Preparation of (+/−)-methyl (1S,3S)-3-(4-(5-(((benzyl(methyl)carbamoyl)oxy)methyl)-1-methyl-1H-pyrazol-4-yl)phenoxy)cyclohexane-1-carboxylate

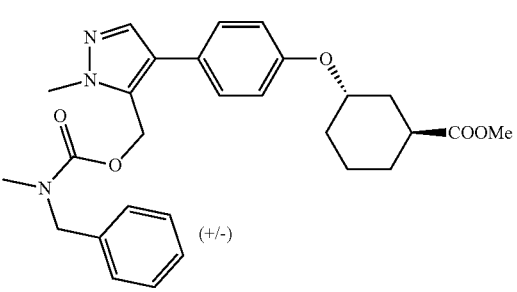

2-10

Compound 2-8 (195 mg, 0.55 mmol) and methyl (1S, 3R)-3-(tosyloxy)cyclohexane-1-carboxylate (343 mg, 1.10 mmol) were added to anhydrous N,N-dimethylformamide (5 mL), and the reaction system was added with cesium carbonate (538 mg, 1.65 mmol), and then reacted at 90° C. for 5 h. The reaction system was extracted with ethyl acetate (40 mL×2). The organic phase was washed with saturated brine (20 mL×2), dried over anhydrous sodium sulfate, filtered and concentrated, and the residue was separated by column chromatography (PE/EA=1/1) to give compound 2-10 (120 mg, 44% yield) in the form of a colorless oily liquid. LC-MS [M+H]$^+$: 492.2.

Step (7): Preparation of (+/−)-(1S,3S)-3-(4-(5-(((benzyl(methyl)carbamoyl)oxy)methyl)-1-methyl-1H-pyrazol-4-yl)phenoxy)cyclohexane-1-carboxylic Acid

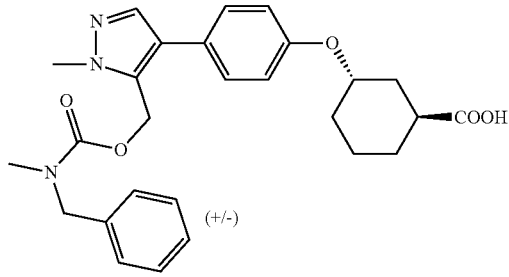

Compound 2-10 (120 mg, 0.24 mmol) was dissolved in tetrahydrofuran (5 mL), and then the reaction system was cooled to 0° C., added dropwise with aqueous lithium hydroxide solution (0.24 mL, 3 mol/L), and stirred overnight at room temperature. The reaction system was then concentrated under reduced pressure, adjusted to pH 3 with diluted hydrochloric acid (0.8 mL, 1 mol/L), extracted with ethyl acetate (20 mL×2), and concentrated, and the residue was separated by preparative reverse phase chromatography to give compound 2 (16 mg, 14% yield) in the form of a white solid.

LC-MS [M+H]$^+$: 478.3. $^1$H NMR (400 MHz, MeOD) δ 7.58 (s, 1H), 7.48-7.18 (m, 6H), 7.15 (d, 1H), 6.98 (d, J=13.4 Hz, 2H), 5.29 (d, J=22.7 Hz, 2H), 4.69 (m, 1H), 4.48 (d, J=18.9 Hz, 2H), 3.92 (d, J=61.1 Hz, 3H), 2.89 (d, J=60.0 Hz, 3H), 2.78 (m, 1H), 2.06 (d, 1H), 2.00-1.54 (m, 7H).

Example 3

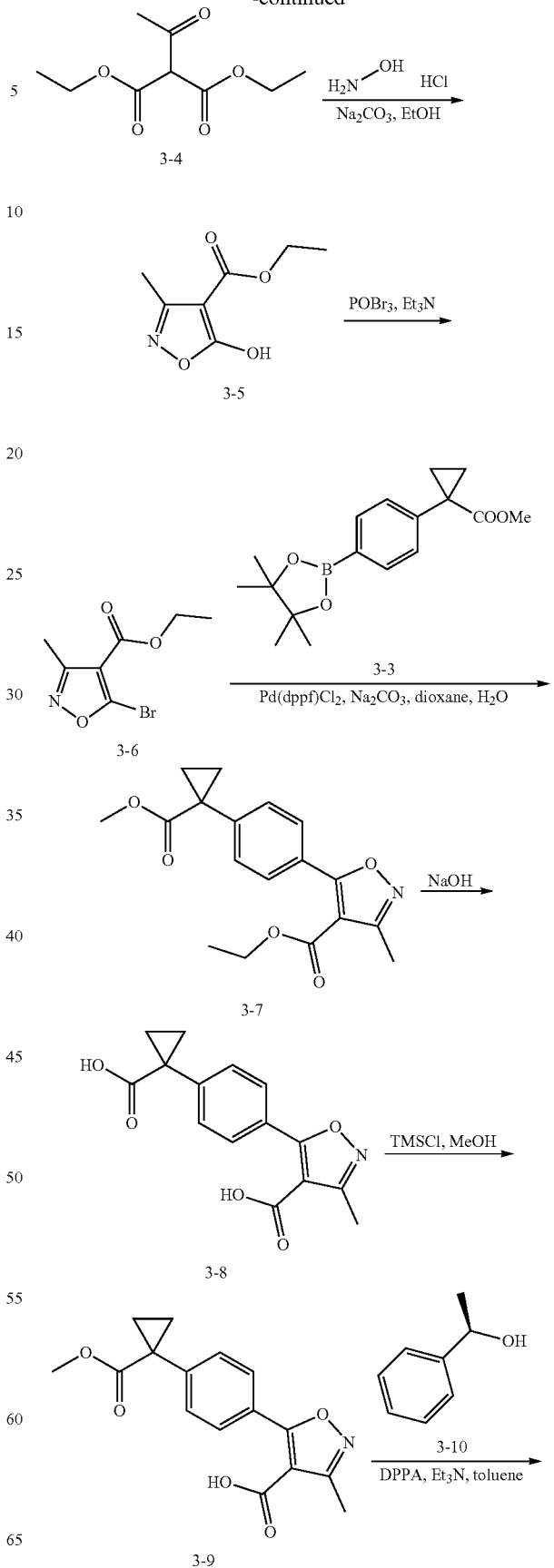

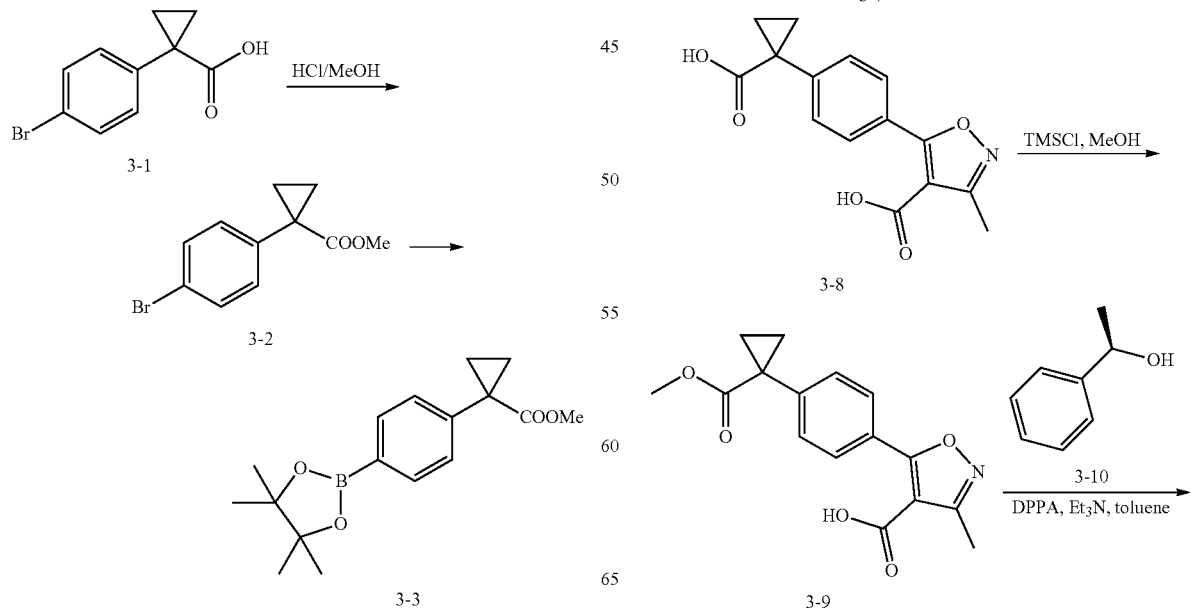

-continued

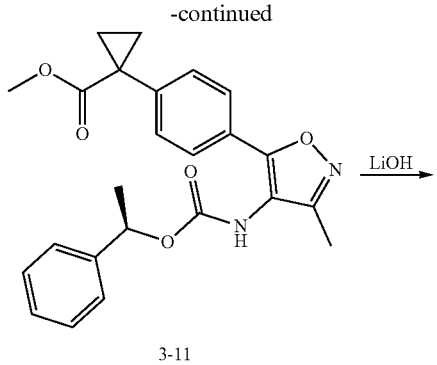

3-11

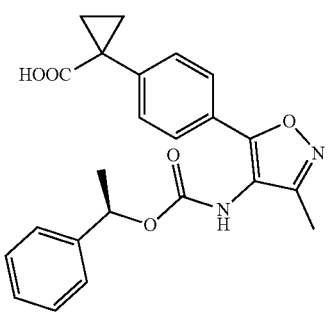

3

Step (1): Preparation of methyl 1-(4-bromophenyl)cyclopropane-1-carboxylate

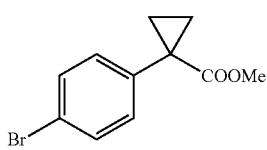

3-2

1-(4-bromophenyl)cyclopropane-1-carboxylic acid (3.5 g, 14.5 mmol) was dissolved in methanol (30 mL), and the reaction system was cooled to 0° C., added dropwise with acetyl chloride (10 mL), and then slowly warmed to room temperature and reacted for 16 h. The reaction system was concentrated, and the residue was diluted with ethyl acetate (50 mL), washed with saturated brine (20 mL×2), dried over anhydrous sodium sulfate, and concentrated. The residue was separated by column chromatography (PE/EA=10/1) to give compound 3-2 (3.7 g, 99% yield) in the form of a white solid. LC-MS [M+H]$^+$: 254.6, 256.6.

Step (2): Preparation of methyl 1-(4-(4,4,5,5-tetramethyl-1,3,2-dioxaborolan-2-yl)phenyl)cyclopropane-1-carboxylate

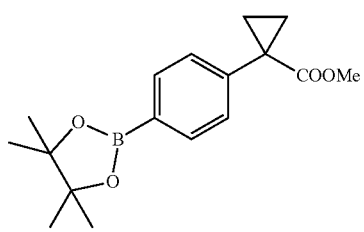

3-3

Compound 3-2 (2.55 g, 10 mmol) was dissolved in dioxane (30 mL), and the reaction system was added with bis(pinacolato)diboron (3.81 g, 15 mmol), [1,1'-bis(diphenylphosphino)ferrocene] dichloropalladium(II) (730 mg, 1 mmol) and potassium acetate (1.96 g, 20 mmol), heated to 100° C. and stirred for 3 h under nitrogen atmosphere to give compound 3-3. The reaction system was directly used in the next step without purification. LC-MS [M+H]$^+$: 303.2.

Step (3): Preparation of ethyl 5-hydroxy-3-methylisothiazole-4-carboxylate

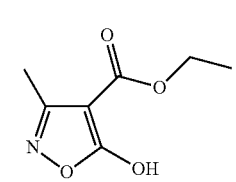

3-5

Compound 3-4 (6.06 g, 30 mmol), hydroxylamine hydrochloride (2.3 g, 33 mmol) and sodium carbonate (1.6 g, 15 mmol) was added to ethanol (50 mL), and the reaction system was heat to reflux for 2 h. The reaction system was concentrated under reduced pressure to remove most of the ethanol. The residue was poured into water (100 mL), filtered, and dried to give compound 3-5 (1.72 g, 35% yield) in the form of a white solid. LC-MS [M+H]$^+$: 172.2.

Step (4): Preparation of ethyl 5-bromo-3-methylisothiazole-4-carboxylate

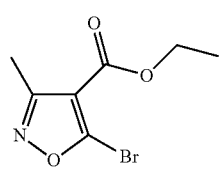

3-6

Compound 3-5 (4.04 g, 23.6 mmol) was dissolved in toluene (50 mL), and the reaction system was added with phosphorus oxybromide (20.3 g, 70.8 mmol) and triethylamine (2.39 g, 23.6 mmol), heated to 80° C. and reacted for 5 h. The reaction system was poured into ice water (100 mL), extracted with ethyl acetate (50 mL×2), and washed with saturated brine (30 mL×2). The organic phase was dried over anhydrous sodium sulfate, and purified by silica gel column chromatography (PE/EA=10/1) to give compound 3-6 (1.86 g, 34% yield) in the form of a white solid. LC-MS [M+H]$^+$: 233.6, 235.6.

Step (5): Preparation of ethyl 5-(4-(1-(carbomethoxy<methoxycarbonyl>)cyclopropyl)phenyl)-3-methylisothiazole-4-carboxylate

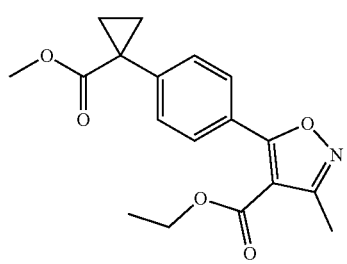

3-7

Compound 3-6 (1.86 g, 8 mmol) was added to the reaction system in step (2), and [1,1'-bis(diphenylphosphino)ferrocene]dichloropalladium(II) (585 mg, 0.8 mmol), sodium carbonate (1.7 g, 16 mmol) and water (5 mL) were added, and the reaction system was heated to 80° C. and stirred overnight under nitrogen atmosphere. The reaction system was filtered to remove the solid, and the filtrate was extracted with ethyl acetate (50 mL×2), and washed with saturated brine (30 mL×2). The organic phase was dried over anhydrous sodium sulfate, and purified by silica gel column chromatography (PE/EA=5/1) to give compound 3-7 (1.2 g, 46% yield) in the form of a white solid. LC-MS [M+H]$^+$: 330.2.

Step (6): Preparation of 5-(4-(1-carboxycyclopropyl)phenyl)-3-methylisothiazole-4-carboxylic Acid

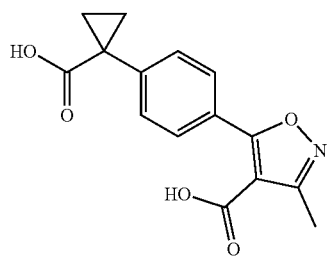

3-8

Compound 3-7 (1.2 g, 3.65 mmol) was dissolved in THF (30 mL), and the reaction system was sequentially added with MeOH (10 mL), H$_2$O (10 mL) and sodium hydroxide (730 mg, 18.2 mmol), and stirred overnight at room temperature. Then water (20 mL) was added for dilution, and the organic solvent was removed by rotary evaporation under reduced pressure. The aqueous phase was adjusted to pH 5-6 with hydrochloric acid (1 N), filtered, and dried to give compound 3-8 (0.87 g, 82% yield) in the form of a white solid. LC-MS [M+H]$^+$: 288.4.

Step (7): Preparation of 5-(4-(1-(carbomethoxy<methoxycarbonyl>)cyclopropyl)phenyl)-3-methylisothiazole-4-carboxylic Acid

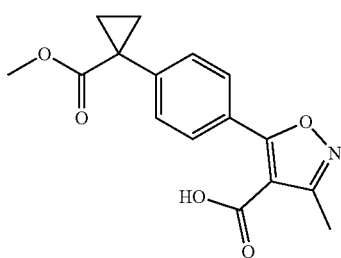

3-9

Compound 3-8 (870 mg, 3.02 mmol) was dissolved in methanol (30 mL), and the reaction system was cooled to 0° C., added with tetramethylchlorosilane (330 mg, 3.02 mmol), and then slowly warmed to room temperature and reacted for 16 h. The reaction system was concentrated, and the residue was separated by column chromatography (DCM/MeOH=10/1) to give compound 3-9 (0.65 g, 71% yield) in the form of a white solid. LC-MS [M+H]$^+$: 302.1.

Step (8): Preparation of methyl (R)-1-(4-(3-methyl-4-(((1-phenylethoxy)carbonyl)amino)isothiazol-5-yl)phenyl)cyclopropane-1-carboxylate

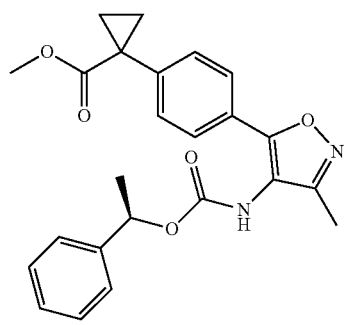

3-11

Compound 3-9 (200 mg, 0.66 mmol) was dissolved in toluene (30 mL), and the reaction system was added with (R)-1-phenylethan-1-ol (162 mg, 1.33 mmol), diphenylphosphoryl azide (218 mg, 0.79 mmol) and triethylamine (133 mg, 1.33 mmol), and heated to reflux for 16 h under nitrogen atmosphere. The reaction system was concentrated, and the residue was separated by column chromatography (DCM/EA=5/1) to give compound 3-11 (0.18 g, 64% yield) in the form of a white solid. LC-MS [M+H]$^+$: 421.3.

Step (9): Preparation of (R)-1-(4-(3-methyl-4-(((1-phenylethoxy)carbonyl)amino)isothiazol-5-yl) phenyl)cyclopropane-1-carboxylic Acid

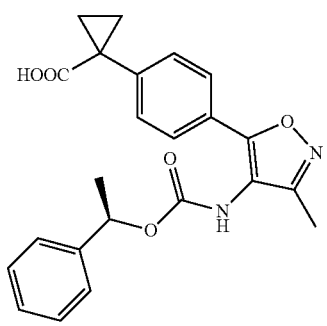

Compound 3-11 (180 mg, 0.44 mmol) was dissolved in THF (9 mL), and the reaction system was sequentially added with MeOH (3 mL), H₂O (3 mL) and lithium hydroxide (100 mg, 2.4 mmol), and stirred overnight at room temperature. Then water (10 mL) was added for dilution, and the organic solvent was removed by rotary evaporation under reduced pressure. The aqueous phase was adjusted to pH 5-6 with hydrochloric acid (1 N), and extracted with dichloromethane (10 mL×2). The organic phase was dried over anhydrous sodium sulfate and filtered, and the filtrate was concentrated by rotary evaporation. The residue was purified by silica gel column chromatography (DCM/MeOH=20/1) and then lyophilized to give compound 3 (108 mg, 54% yield) in the form of a white solid.

LC-MS [M+H]⁺: 407. ¹H NMR (400 MHz, MeOD) δ 7.70 (d, J=7.9 Hz, 2H), 7.63-7.25 (m, 7H), 5.85-5.79 (m, 1H), 2.18 (s, 3H), 1.65-1.56 (m, 5H), 1.25-1.20 (m, 2H).

Example 4

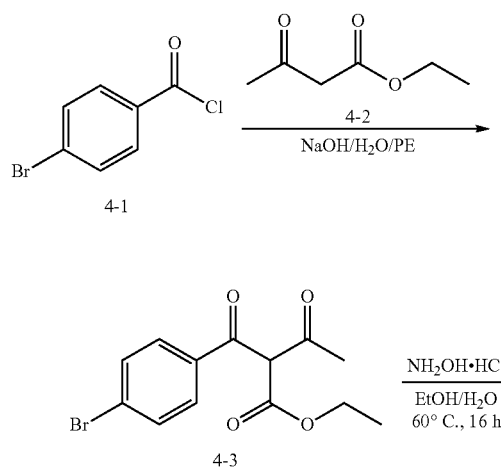

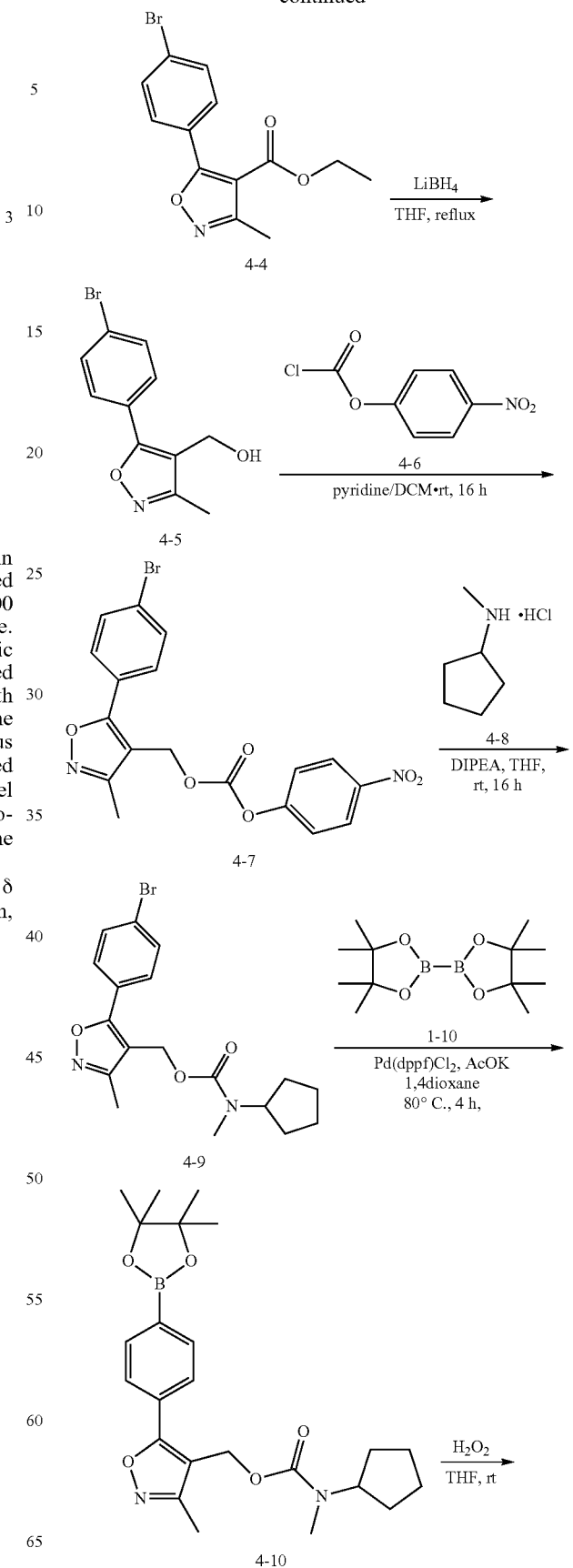

-continued

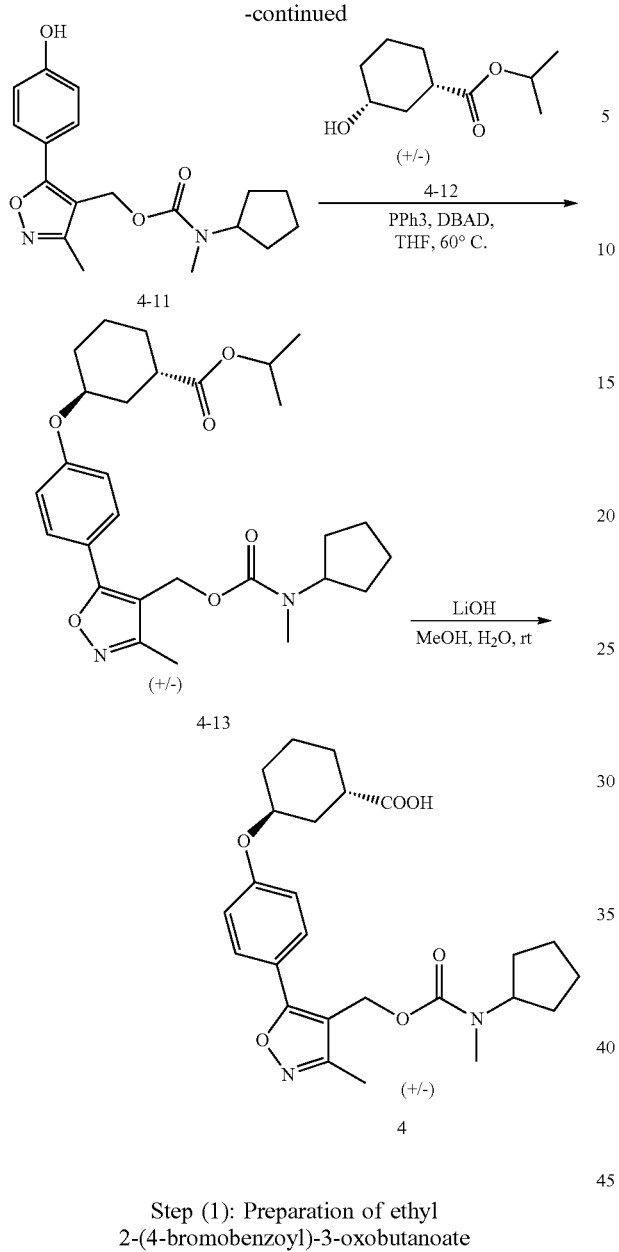

Step (1): Preparation of ethyl 2-(4-bromobenzoyl)-3-oxobutanoate

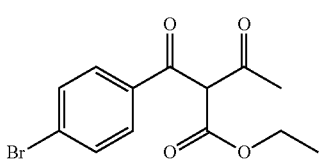

Ethyl acetoacetate (10.0 g, 77 mmol) was dissolved in petroleum ether (25 mL), and aqueous sodium hydroxide solution (4 N, 8 mL) was added. The reaction system was stirred for 30 min at 0° C., slowly added dropwise with 4-bromobenzoyl chloride (16.8 g, 77 mmol) and aqueous sodium hydroxide solution (4 N, 30 mL), and filtered, and the filtrate was washed with water and petroleum ether, and dried to give compound 4-3 (19 g, 79% yield) in the form of a white solid. MS $[M+H]^+$=313.7, 315.7.

Step (2): Preparation of ethyl 5-(4-bromophenyl)-3-methylisoxazole-4-carboxylate

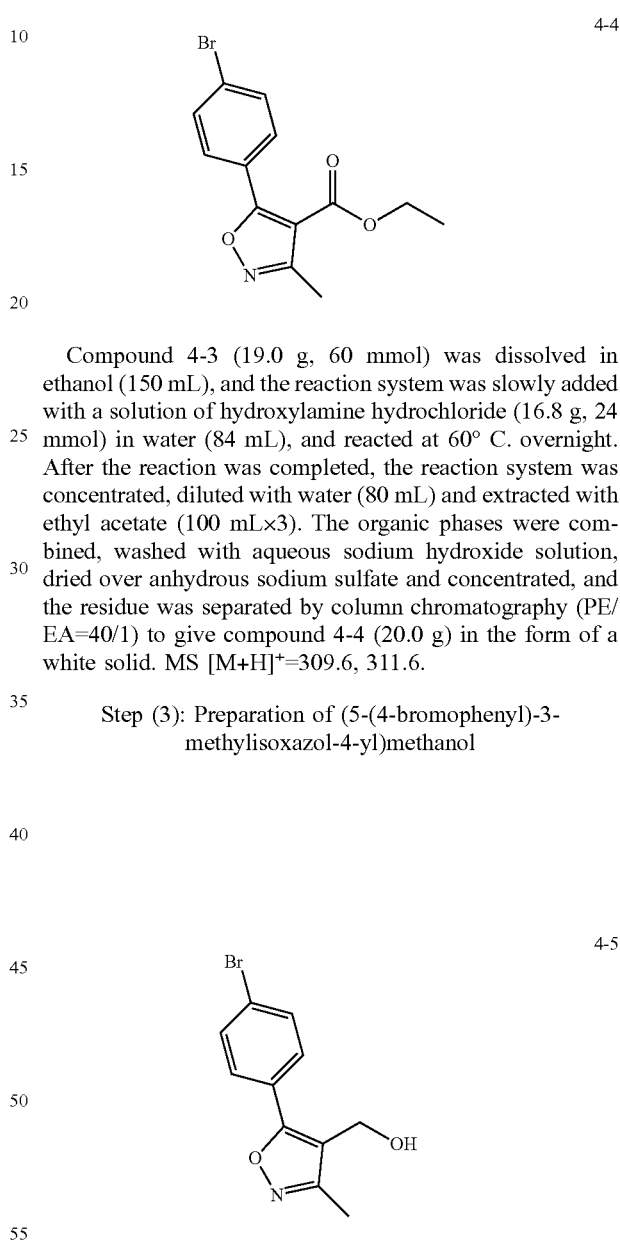

Compound 4-3 (19.0 g, 60 mmol) was dissolved in ethanol (150 mL), and the reaction system was slowly added with a solution of hydroxylamine hydrochloride (16.8 g, 24 mmol) in water (84 mL), and reacted at 60° C. overnight. After the reaction was completed, the reaction system was concentrated, diluted with water (80 mL) and extracted with ethyl acetate (100 mL×3). The organic phases were combined, washed with aqueous sodium hydroxide solution, dried over anhydrous sodium sulfate and concentrated, and the residue was separated by column chromatography (PE/EA=40/1) to give compound 4-4 (20.0 g) in the form of a white solid. MS $[M+H]^+$=309.6, 311.6.

Step (3): Preparation of (5-(4-bromophenyl)-3-methylisoxazol-4-yl)methanol

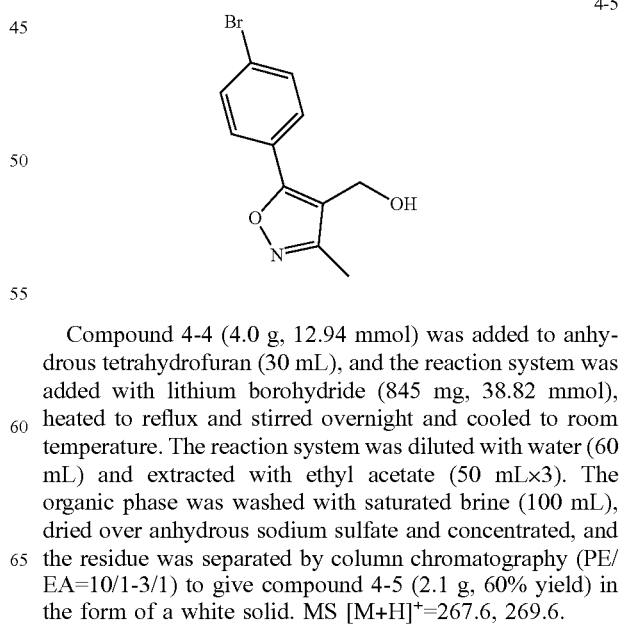

Compound 4-4 (4.0 g, 12.94 mmol) was added to anhydrous tetrahydrofuran (30 mL), and the reaction system was added with lithium borohydride (845 mg, 38.82 mmol), heated to reflux and stirred overnight and cooled to room temperature. The reaction system was diluted with water (60 mL) and extracted with ethyl acetate (50 mL×3). The organic phase was washed with saturated brine (100 mL), dried over anhydrous sodium sulfate and concentrated, and the residue was separated by column chromatography (PE/EA=10/1-3/1) to give compound 4-5 (2.1 g, 60% yield) in the form of a white solid. MS $[M+H]^+$=267.6, 269.6.

Step (4): Preparation of (5-(4-bromophenyl)-3-methylisoxazol-4-yl)methyl(4-nitrophenyl)carbonate

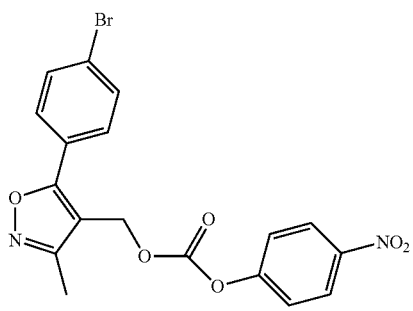

4-7

Compound 4-5 (1.0 g, 3.73 mmol) and pyridine (1.1 g, 14.92 mmol) were dissolved in dichloromethane (10 mL), and the reaction system was cooled to 0° C. 4-nitrophenyl chloroformate (1.87 g, 9.30 mmol) was added, and then the reaction system was warmed to room temperature and stirred overnight. The reaction system was washed with saturated brine, the organic phase was dried over anhydrous sodium sulfate and concentrated, and the residue was separated by column chromatography (PE/EA=5/1) to give compound 4-7 (1.6 g) in the form of a white solid. LC-MS [M+H]$^+$: 432.5, 434.5.

Step (5): Preparation of (5-(4-bromophenyl)-3-methylisoxazol-4-yl)methylcyclopentyl(methyl)carbamate

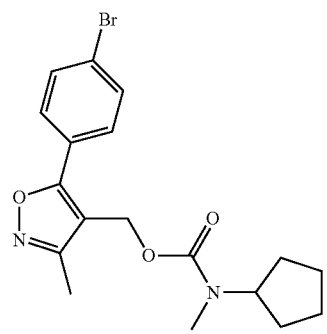

4-9

Compound 4-7 (1.6 g, 3.69 mmol) and diisopropylethylamine (1.9 g, 14.73 mmol) were dissolved in anhydrous tetrahydrofuran (20 mL), and N-methylcyclopentanamine (0.6 g, 4.41 mmol) was added to the reaction system. The reaction system was stirred overnight at room temperature under nitrogen atmosphere and washed with saturated brine (20 mL). The organic phase was dried over anhydrous sodium sulfate, filtered and concentrated, and the residue was separated by column chromatography (PE/EA=10/1) to give compound 4-9 (1.05 g, 72% yield) in the form of a white solid. LC-MS [M+H]$^+$: 392.6, 394.6.

Step (6): Preparation of (3-methyl-5-(4-(4,4,5,5-tetramethyl-1,3,2-dioxaborolan-2-yl)phenyl)isoxazol-4-yl)methylcyclopentyl(methyl)carbamate

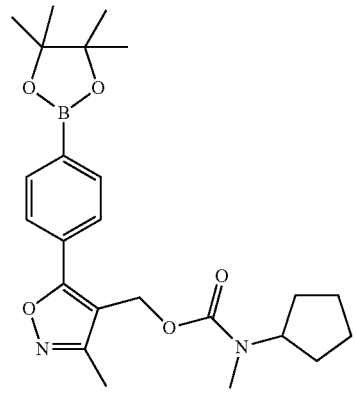

4-10

Compound 4-9 (1.05 g, 2.67 mmol) and compound 1-10 (1.02 g, 4.02 mmol) were dissolved in dioxane (15 mL), and the reaction system was added with [1,1'-bis(diphenylphosphino)ferrocene]dichloropalladium (II) (98 mg, 0.13 mmol) and potassium acetate (790 mg, 8.06 mmol), and stirred at 80° C. for 5 h under nitrogen atmosphere. The reaction system was filtered, and the filtrate was concentrated to give compound 4-10 (1.2 g). LC-MS [M+H]$^+$: 441.8.

Step (7): Preparation of (5-(4-hydroxyphenyl)-3-methylisoxazol-4-yl)methylcyclopentyl(methyl) carbamate

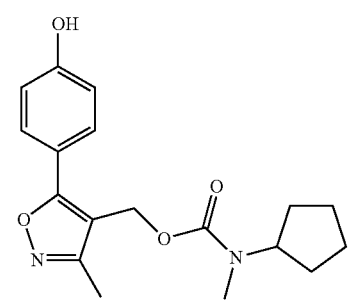

4-11

Compound 4-10 (1.2 g, crude) was dissolved in tetrahydrofuran (15 mL), and the reaction system was added with hydrogen peroxide (7 mL), and reacted at room temperature for 5 h. The reaction system was diluted with water (30 mL), and extracted with ethyl acetate (20 mL×3). The organic phases were combined, washed with saturated brine (60 mL), dried over anhydrous sodium sulfate, filtered and concentrated, and the residue was separated by column chromatography (PE/EA=5/1) to give compound 4-11 (0.7 g, 78% yield over two steps) in the form of a white solid. LC-MS [M+H]$^+$: 331.0.

Step (8): Preparation of (+/−)-isopropyl (1S,3S)-3-(4-(4-(((cyclopentyl(methyl)carbamoyl)oxy)methyl)-3-methylisoxazol-5-yl)phenoxy)cyclohexanecarboxylate

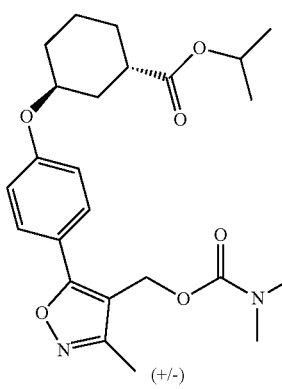

4-13

Compound 4-11 (200 mg, 0.61 mmol) and isopropyl (1S,3R)-3-hydroxycyclohexanecarboxylate (450 mg, 2.42 mmol) were dissolved in anhydrous tetrahydrofuran (10 mL), and the reaction system was added with triphenylphosphine (635 mg, 2.42 mmol) and di-tert-butyl azodicarboxylate (557 mg, 2.42 mmol), reacted at 60° C. for 15 h under nitrogen atmosphere, filtered, diluted with water (50 mL), and then extracted with ethyl acetate (30 mL×3). The organic phases were combined, dried over anhydrous sodium sulfate and concentrated, and the residue was separated by column chromatography (PE/EA=8/1) to give compound 4-13 (300 mg) in the form of a white solid. LC-MS [M+H]⁺: 499.2.

Step (9): Preparation of (+/−)-(1S,3S)-3-(4-(4-(((cyclopentyl(methyl)carbamoyl)oxy)methyl)-3-methyl-isoxazol-5-yl)phenoxy)cyclohexane-1-carboxylic Acid

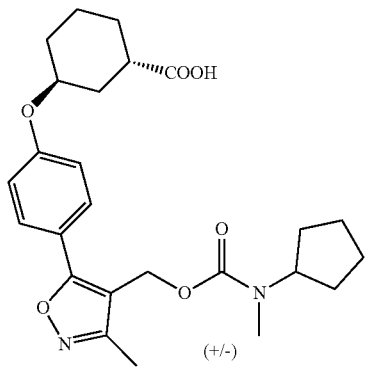

4

Compound 4-13 (300 mg, crude) and lithium hydroxide (69 mg, 1.63 mmol) were dissolved in methanol (3 mL) and water (3 mL), and the reaction system was reacted at room temperature for 10 h, concentrated, adjusted to pH 5 with diluted hydrochloric acid (1 N), and then extracted with ethyl acetate (10 mL×3). The organic phases were combined, dried over anhydrous sodium sulfate and concentrated, and the residue was separated by thin layer chromatography to give compound 4 (57 mg, 20.7% yield over two steps) in the form of a white solid.

LC-MS [M+H]⁺: 457.2. ¹H NMR (400 MHz, CDCl₃) δ 7.72 (d, J=8.8 Hz, 2H), 7.01 (d, J=8.8 Hz, 2H), 5.08 (s, 2H), 4.75-7.71 (m, 1H), 4.65-4.45 (m, 1H), 2.90 (m, 1H), 2.78 (s, 3H), 2.38 (s, 3H), 2.15 (m, 1H), 2.03-1.90 (m, 3H), 1.83-1.49 (m, 12H).

Example 5

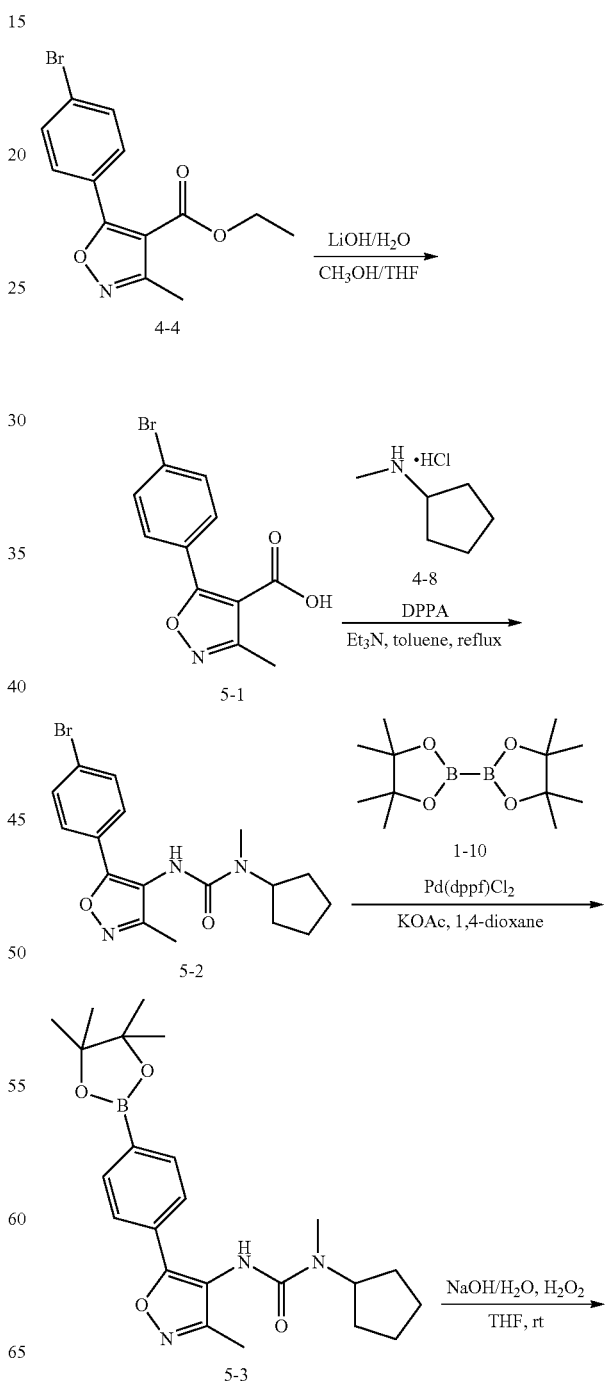

-continued

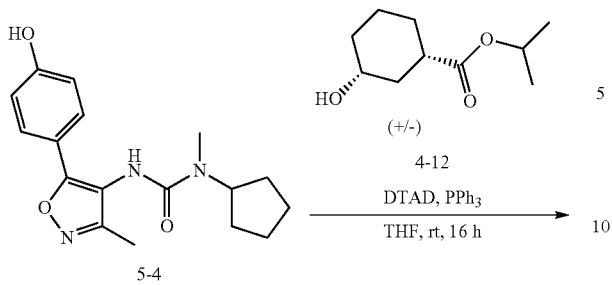

5-4

4-12
DTAD, PPh₃
THF, rt, 16 h

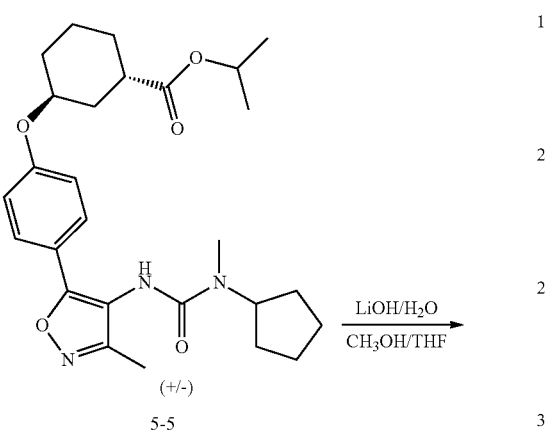

5-5

LiOH/H₂O
CH₃OH/THF

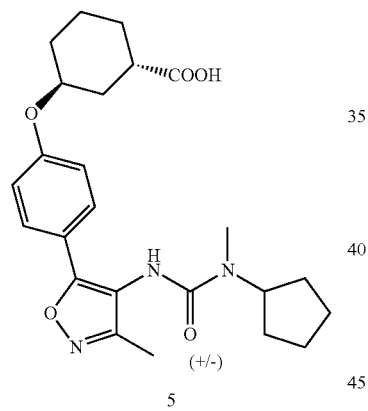

5

Step (1): Preparation of 5-(4-bromophenyl)-3-methylisothiazole-4-carboxylic Acid Compound 4-4 (2 g, 6.45 mmol) was dissolved in methanol (10 mL) and tetrahydrofuran (10 mL), and then the reaction system was cooled to 0° C., added dropwise with aqueous lithium hydroxide solution (0.65 mL, 3 mol/L), and stirred overnight at room temperature. The reaction system was then concentrated under reduced pressure, adjusted to pH 3 with diluted hydrochloric acid (2.2 mL, 1 mol/L) and extracted with ethyl acetate (60 mL×2). The organic phase was washed with saturated brine (30 mL×2), dried over anhydrous sodium sulfate and filtered, and the filtrate was concentrated by rotary evaporation to give compound 5-1 (1.4 g, 77% yield) in the form of a white solid. LC-MS [M+H]⁺: 281.6, 283.6.

Step (2): Preparation of 3-(5-(4-bromophenyl)-3-methylisothiazol-4-yl)-1-cyclopentyl-1-methylurea 5-2

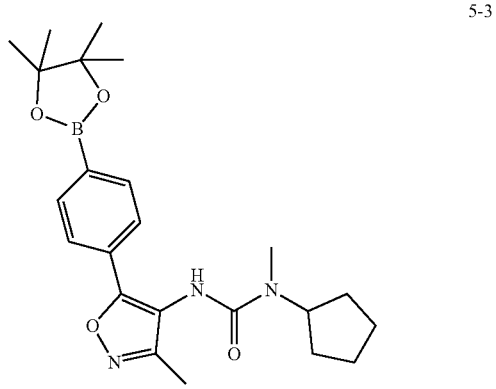 [SMILES: Cc1noc(-c2ccc(B3OC(C)(C)C(C)(C)O3)cc2)c1NC(=O)N(C)C1CCCC1]

Compound 5-1 (1 g, 3.55 mmol) and triethylamine (1.08 g, 10.65 mmol) were dissolved in toluene (15 mL), and then the reaction system was added with diphenylphosphoryl azide, and stirred at room temperature for 1 h. N-methyl-cyclopentanamine The reaction system was added with hydrochloride, and reacted at 110° C. overnight. The reaction system was concentrated by rotary evaporation, and the residue was separated by column chromatography (ethyl acetate:petroleum ether=1:2) to give compound 5-2 (580 mg, 43% yield) in the form of a gray solid. LC-MS [M+H]⁺: 377.6, 379.6.

Step (3): Preparation of 3-(3-methyl-5-(4-(4,4,5,5-tetramethyl-1,3,2-dioxaborolan-2-yl)phenyl) isothiazol-4-yl)-1-cyclopentyl-1-methyl-urea 5-3

Compound 5-2 (580 mg, 1.53 mmol), bis(pinacolato)diboron (585 mg, 2.30 mmol), potassium acetate (225 mg, 2.30 mmol) and [1,1'-bis(diphenylphosphino)ferrocene]dichloropalladium(II) (87 mg, 0.12 mmol) were added to 1,4-dioxane (12 mL), and the reaction system was reacted at 80° C. overnight under nitrogen atmosphere. The reaction system was filtered, and the organic phase was concentrated by rotary evaporation to give compound 5-3 (660 mg, crude) in the form of a black oil. LC-MS [M+H]⁺: 426.2.

Step (4): Preparation of 3-(5-(4-hydroxyphenyl)-3-methylisothiazol-4-yl)-1-cyclopentyl-1-methylurea

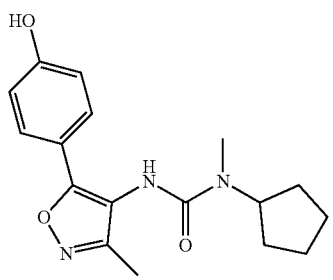

5-4

Compound 5-3 (660 mg, 1.55 mmol) was dissolved in tetrahydrofuran (10 mL), and the reaction system was added with aqueous sodium hydroxide solution (1.6 mL, 1 mol/L), and then added dropwise with hydrogen peroxide (1 mL, 33%). The reaction system was stirred at room temperature for 2 h, and quenched with saturated aqueous sodium thiosulfate solution (2 mL). Then the reaction system was extracted with ethyl acetate (40 mL×2). The organic phases were combined, washed with saturated brine (20 mL×2), dried over anhydrous sodium sulfate, filtered and concentrated, and the residue was separated by column chromatography (EA/PE=1/1) to give compound 5-4 (160 mg, 33% yield) in the form of a colorless oily liquid. LC-MS [M+H]$^+$: 316.2.

Step (5): Preparation of (+/−)-isopropyl (1S,3S)-3-(4-(4-(3-cyclopentyl-3-methylureido)-3-methylisothiazol-5-yl)phenoxy)cyclohexane-1-carboxylate

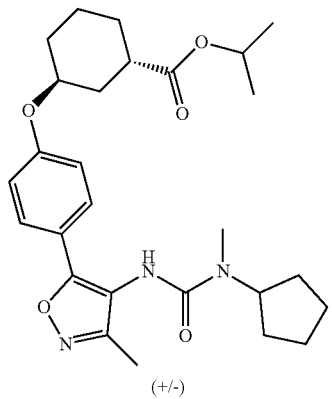

5-5

Compound 5-4 (240 mg, 0.76 mmol), compound 4-12 (567 mg, 3.05 mmol), triphenylphosphine (799 mg, 3.05 mmol) and di-tert-butyl azodicarboxylate (701 mg, 3.05 mmol) were dissolved in anhydrous tetrahydrofuran (10 mL), and the reaction system was reacted at room temperature overnight. The reaction system was concentrated by rotary evaporation, added with water, and extracted with ethyl acetate (30 mL×2). The organic phases were combined, washed with saturated brine (10 mL×2), dried over anhydrous sodium sulfate, filtered and concentrated, and the residue was separated by column chromatography (EA/PE=1/1) to give compound 5-5 (170 mg, 43% yield) in the form of a colorless oil. LC-MS [M+H]$^+$: 484.2.

Step (6): Preparation of (+/−)-(1S,3S)-3-(4-(4-(3-cyclopentyl-3-methylureido)-3-methylisothiazol-5-yl) phenoxy)cyclohexane-1-carboxylic Acid

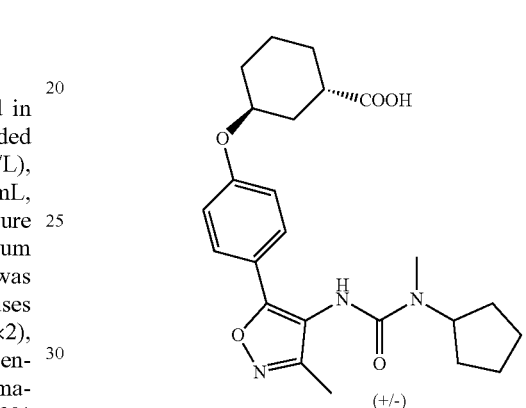

5

Compound 5-5 (170 mg, 0.35 mmol) was dissolved in methanol (3 mL) and tetrahydrofuran (2 mL), and then the reaction system was cooled to 0° C., added dropwise with aqueous lithium hydroxide solution (0.35 mL, 3 mol/L), and stirred overnight at room temperature. The reaction system was then concentrated under reduced pressure, adjusted to pH 3 with diluted hydrochloric acid (1 N), extracted with ethyl acetate (20 mL×2) and concentrated, and the residue was separated by preparative reverse phase chromatography to give compound 5 (70 mg, 45% yield) in the form of a white solid.

LC-MS [M+H]$^+$: 442.1. $^1$H NMR (400 MHz, MeOD) δ 7.76 (d, J=9.0 Hz, 2H), 7.09 (d, J=9.0 Hz, 2H), 4.79-4.75 (m, 1H), 4.65-4.56 (m, 1H), 2.95 (s, 3H), 2.85-2.74 (m, 1H), 2.21 (s, 3H), 2.07-2.03 (m, 1H), 2.00-1.85 (m, 5H), 1.80-1.65 (m, 10H).

Example 6

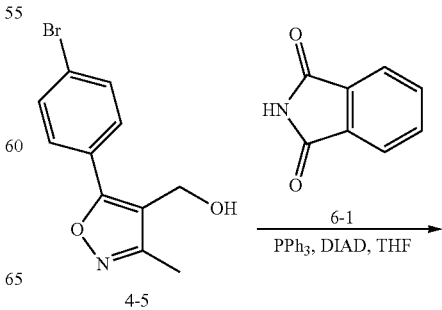

4-5

-continued
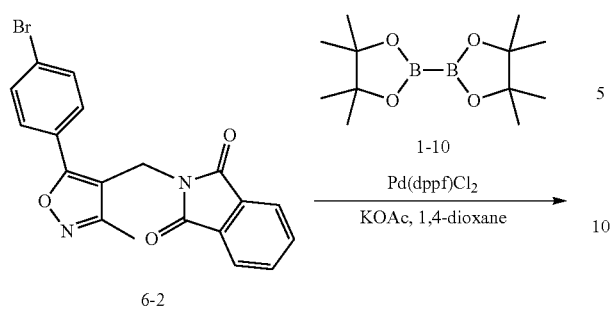
6-2
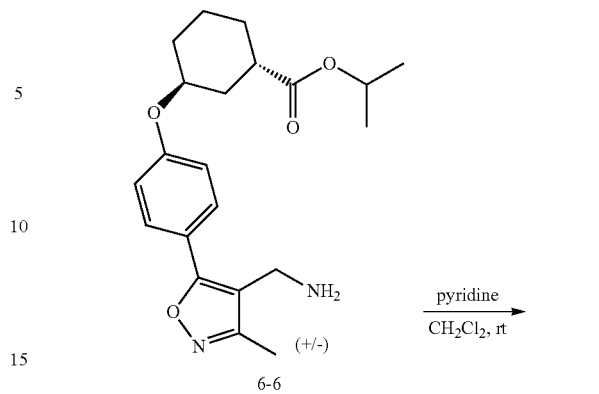
6-6
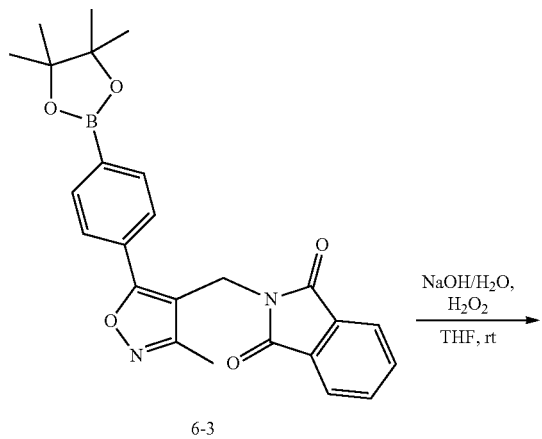
6-3
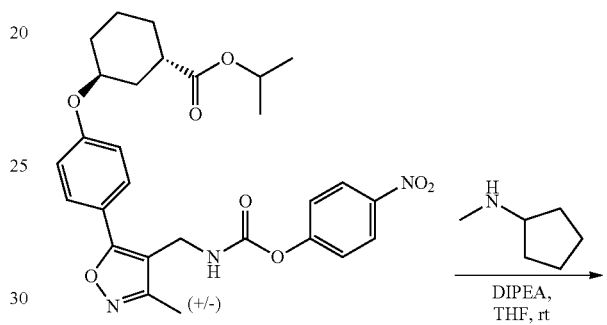
6-7
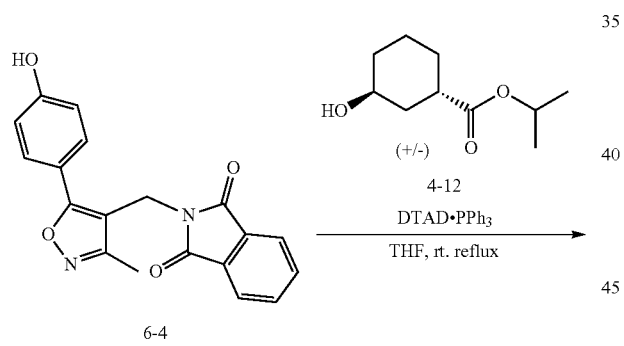
6-4
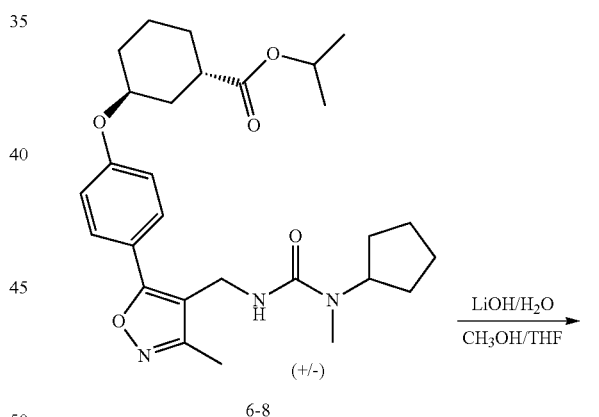
6-8
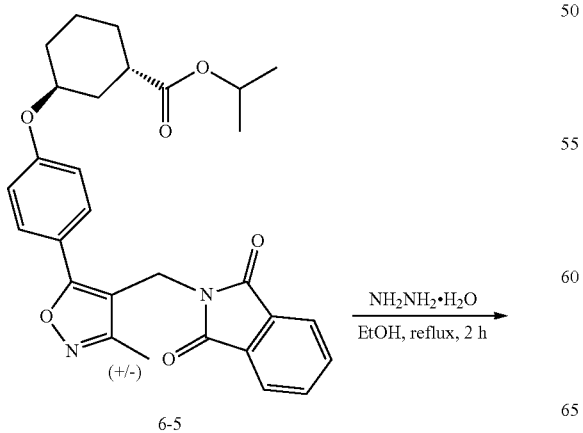
6-5
6

Step (1): Preparation of 2-((5-(4-bromophenyl)-3-methylisothiazol-4-yl)methyl)isoindoline-1,3-dione

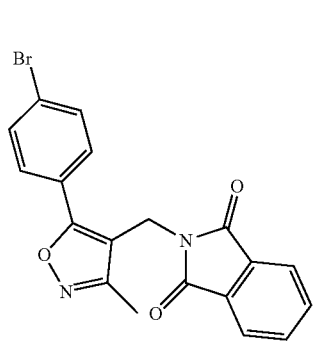

6-2

Compound 4-5 (800 mg, 2.98 mmol), phthalimide (658 mg, 4.48 mmol), triphenylphosphine (2.34 g, 8.94 mmol) and diisopropyl azodicarboxylate (1.81 g, 8.94 mmol) were dissolved in anhydrous tetrahydrofuran (25 mL), and the reaction system was reacted at room temperature overnight. The reaction system was concentrated by rotary evaporation, and diluted with ethyl acetate (50 mL). The organic phase was washed with saturated brine (20 mL×2), dried over anhydrous sodium sulfate, filtered and concentrated, and the residue was separated by column chromatography (EA/PE=1/5) to give compound 6-2 (1 g, 68% yield) in the form of a white solid. LC-MS [M+H]$^+$: 397.2.

Step (2): Preparation of 2-((3-methyl-5-(4-(4,4,5,5-tetramethyl-1,3,2-dioxaborolan-2-yl)phenyl) isothiazol-4-yl)methyl)isoindoline-1,3-dione

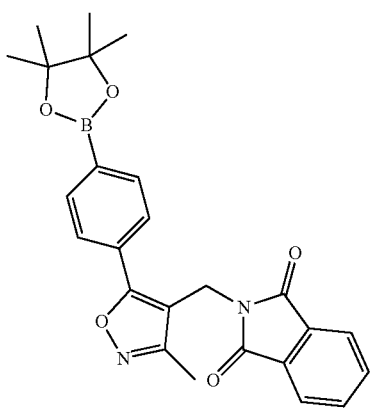

6-3

Compound 6-2 (1 g, 2.52 mmol), bis(pinacolato)diboron (960 mg, 3.78 mmol), potassium acetate (370 mg, 3.78 mmol) and [1,1'-bis(diphenylphosphino)ferrocene]dichloropalladium(II) (215 mg, 0.30 mmol) were added to 1,4-dioxane (16 mL), and the reaction system was reacted at 80° C. overnight under nitrogen atmosphere. The reaction system was filtered, and the organic phase was concentrated by rotary evaporation to give compound 6-3 (1.2 g, crude) in the form of a black oil. LC-MS [M+H]$^+$: 445.2.

Step (3): Preparation of 2-((5-(4-hydroxyphenyl)-3-methylisothiazol-4-yl)methyl)isoindoline-1,3-dione

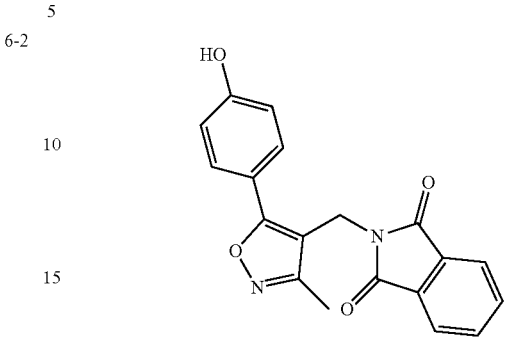

6-4

Compound 6-3 (1.2 g, 2.70 mmol) was dissolved in tetrahydrofuran (20 mL), and the reaction system was added with aqueous sodium hydroxide solution (2.7 mL, 1 mol/L), and then added dropwise with hydrogen peroxide (2 mL, 33%). The reaction system was stirred at room temperature for 2 h, and quenched with saturated aqueous sodium thiosulfate solution (3 mL). Then the reaction system was extracted with ethyl acetate (40 mL×2). The organic phases were combined, washed with saturated brine (20 mL×2), dried over anhydrous sodium sulfate, filtered and concentrated, and the residue was separated by column chromatography (EA/PE=1/1) to give compound 6-4 (800 mg, 88% yield) in the form of a white solid. LC-MS [M+H]$^+$: 335.1.

Step (4): Preparation of (+/−)-isopropyl (1S,3S)-3-(4-(4-((1,3-dioxoisoindolin-2-yl)methyl)-3-methylisothiazol-5-yl)phenoxy)cyclohexane-1-carboxylate

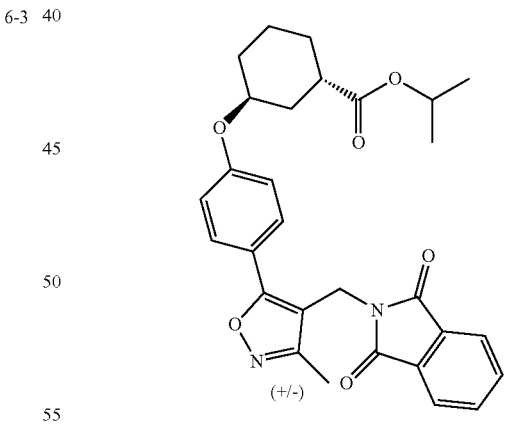

6-5

Compound 6-4 (400 mg, 1.20 mmol), compound 4-12 (670 mg, 3.60 mmol), triphenylphosphine (943 mg, 3.60 mmol) and di-tert-butyl azodicarboxylate (828 mg, 3.60 mmol) were dissolved in anhydrous tetrahydrofuran (15 mL), and the reaction system was reacted at room temperature overnight. The reaction system was concentrated by rotary evaporation, added with water, and extracted with ethyl acetate (40 mL×2). The organic phases were combined, washed with saturated brine (10 mL×2), dried over anhydrous sodium sulfate, filtered and concentrated, and the residue was separated by column chromatography (EA/

PE=1/3) to give compound 6-5 (350 mg, 58% yield) in the form of a colorless oil. LC-MS [M+H]⁺: 503.1.

Step (5): Preparation of (+/−)-isopropyl (1S,3S)-3-(4-(4-(aminomethyl)-3-methylisothiazol-5-yl) phenoxy)cyclohexane-1-carboxylate

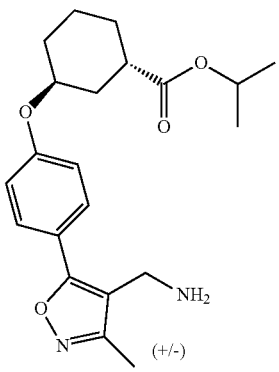

6-6

Compound 6-5 (350 mg, 0.70 mmol) was dissolved in ethanol (10 mL), and the reaction system was added with hydrazine hydrate (2 mL) at room temperature, refluxed for 2 h, concentrated and extracted with ethyl acetate (30 mL×2). The organic phases were combined, washed with saturated brine (10 mL×2), dried over anhydrous sodium sulfate, filtered and concentrated, and the residue was separated by column chromatography (EA/PE=1/1) to give compound 6-6 (200 mg, 77% yield) in the form of a gray solid. LC-MS [M+H]⁺: 373.1.

Step (6): Preparation of (+/−)-isopropyl (1S,3S)-3-(4-(3-methyl-4-((((4-nitrophenoxy)carbonyl)amino)methyl)isothiazol-5-yl)phenoxy)cyclohexane-1-carboxylate

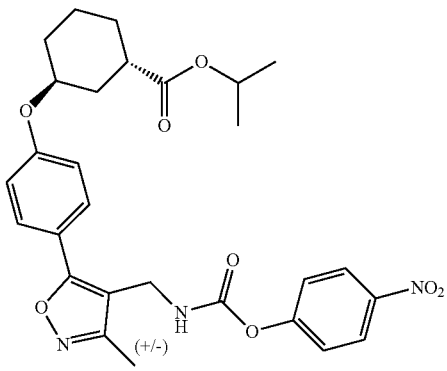

6-7

Compound 6-6 (200 mg, 0.54 mmol) and pyridine (118 mg, 1.62 mmol) were dissolved in dichloromethane (10 mL), and 4-nitrophenyl chloroformate (163 mg, 0.81 mmol) was added at 0° C., and the reaction system was stirred overnight at room temperature. The reaction system was then extracted with dichloromethane (30 mL×2), and the organic phases were combined, washed with saturated brine (20 mL) and concentrated, and the residue was separated by column chromatography (wet loading, petroleum ether/ethyl acetate=5/1) to give compound 6-7 (230 mg, 80% yield) in the form of a pale yellow solid. LC-MS [M+H]⁺: 538.3.

Step (7): Preparation of (+/−)-isopropyl (1S,3S)-3-(4-(4-((3-cyclopentyl-3-methylureido)methyl)-3-methylisothiazol-5-yl)phenoxy)cyclohexane-1-carboxylate

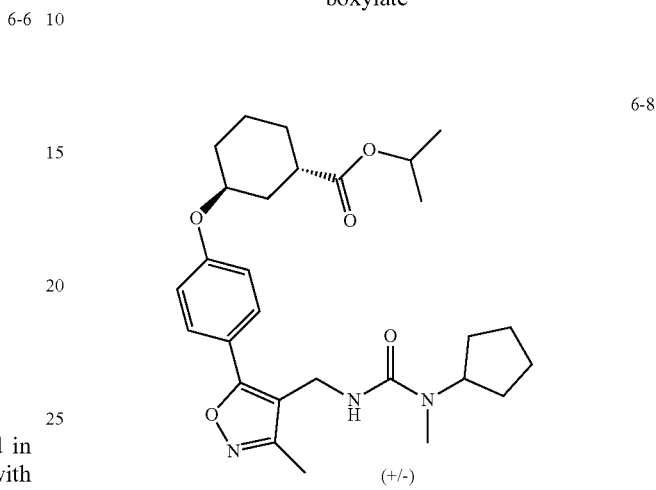

6-8

Compound 6-7 (230 mg, 0.43 mmol) and N,N-diisopropylethylamine (166 mg, 1.29 mmol) were added to anhydrous tetrahydrofuran (10 mL), and then N-methylcyclopentanamine hydrochloride (70 mg, 0.52 mmol) was added. The reaction system was reacted at room temperature overnight and extracted with ethyl acetate (30 mL×2). The organic phase was washed with saturated brine (20 mL), dried over anhydrous sodium sulfate and concentrated, and the residue was separated by column chromatography (PE/EA=1/1) to give compound 6-8 (150 mg, 70% yield) in the form of a colorless oil. LC-MS [M+H]⁺: 498.4.

Step (8): Preparation of (+/−)-(1S,3S)-3-(4-(4-((3-cyclopentyl-3-methylureido)methyl)-3-methylisothiazol-5-yl)phenoxy)cyclohexane-1-carboxylic Acid

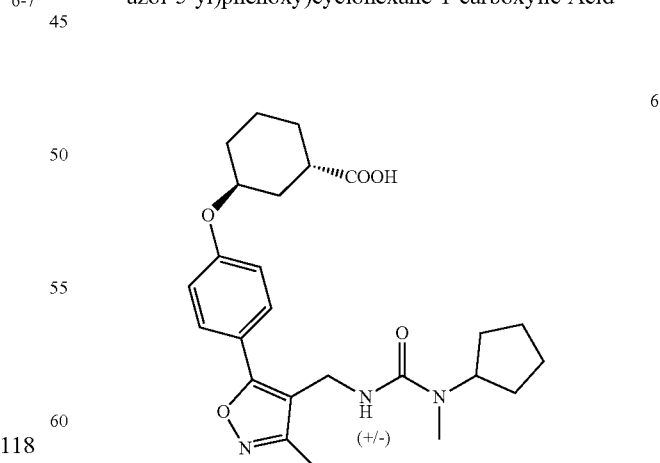

6

Compound 6-8 (150 mg, 0.30 mmol) was dissolved in methanol (3 mL) and tetrahydrofuran (3 mL), and then the reaction system was cooled to 0° C., added dropwise with aqueous lithium hydroxide solution (0.3 mL, 3 mol/L), and stirred overnight at room temperature. The reaction system was then concentrated under reduced pressure, adjusted to pH 3 with diluted hydrochloric acid (1 mL, 1 mol/L), extracted with ethyl acetate (20 mL×2), and concentrated, and the residue was separated by preparative reverse phase chromatography to give compound 6 (45 mg, 33% yield) in the form of a white solid.

LC-MS [M+H]$^+$: 456.2. $^1$H NMR (400 MHz, MeOD) δ 7.70 (d, J=8.9 Hz, 2H), 7.11 (d, J=8.9 Hz, 2H), 4.50-4.44 (m, 1H), 4.54-4.42 (m, 1H), 4.38 (s, 2H), 2.84-2.77 (m, 1H), 2.69 (s, 3H), 2.34 (s, 3H), 2.12-2.05 (m, 1H), 2.01-1.86 (m, 3H), 1.85-1.41 (m, 12H).

Example 7

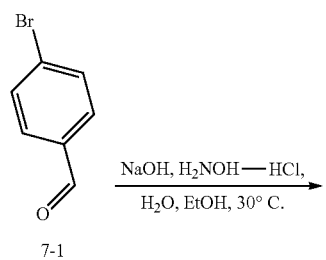

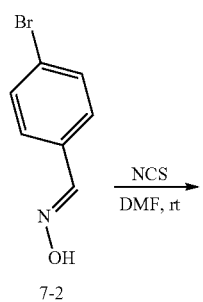

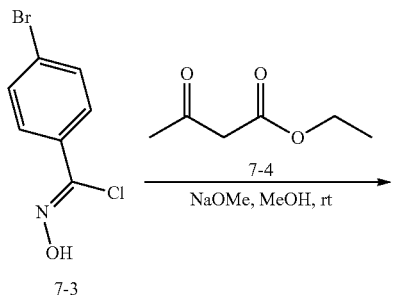

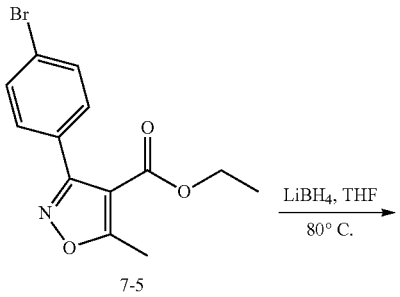

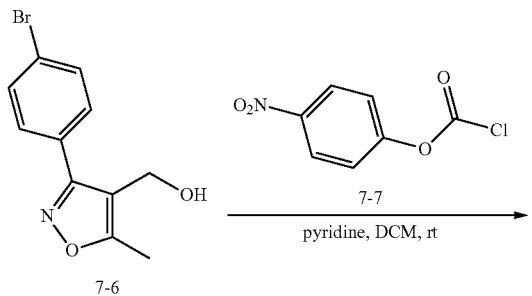

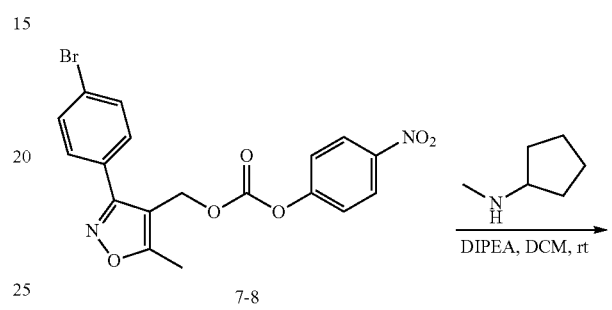

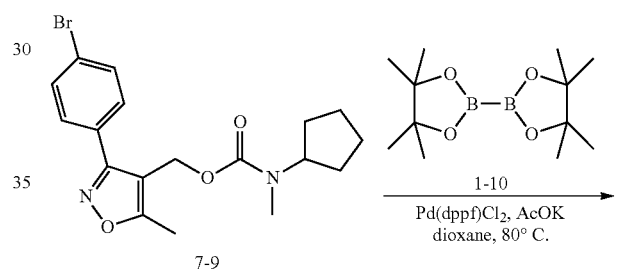

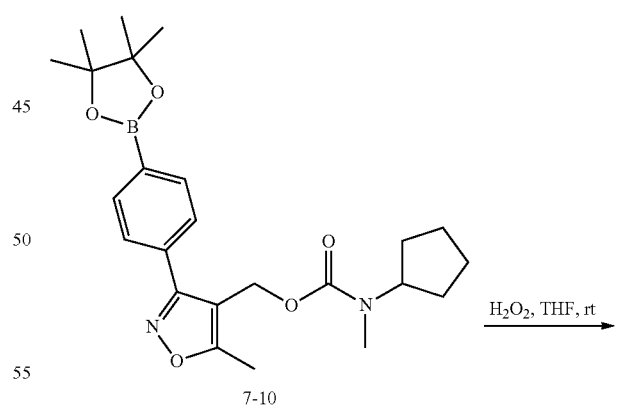

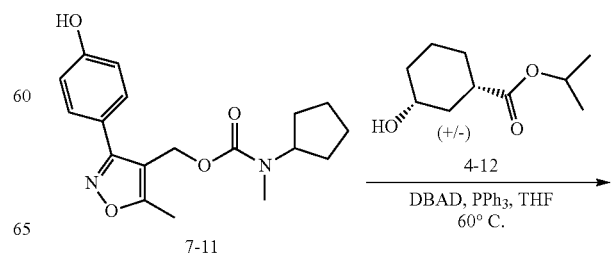

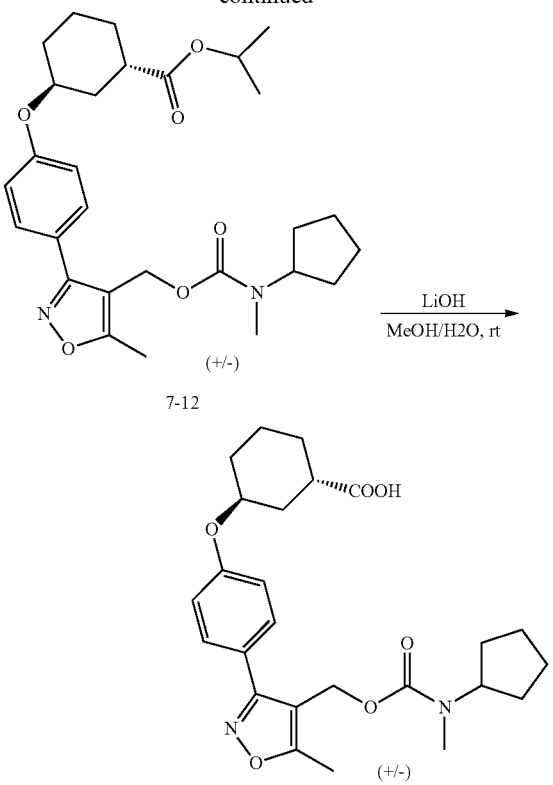

(+/-)
7-12

↓ LiOH, MeOH/H2O, rt

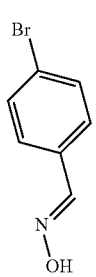

(+/-)
7

Step (1): Preparation of (E)-4-bromobenzaldehyde Oxime

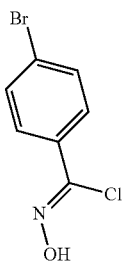
7-2

4-bromobenzaldehyde (10 g, 54.05 mmol) was dissolved in ethanol (60 mL), and the reaction system was added with hydroxylamine hydrochloride (11.3 g, 162.6 mmol) and sodium hydroxide (7.8 g, 18 wt %), and reacted overnight at 30° C. After the reaction was completed, the reaction system was added with water (100 mL) and extracted with ethyl acetate (150 mL×3). The organic phases were combined, washed with saturated brine (100 mL×1), dried over anhydrous sodium sulfate, and filtered, and the filtrate was concentrated by rotary evaporation to give a crude product. The crude product was purified by silica gel column chromatography (80 g of silica gel) to give compound 7-2 (6 g, 51% yield) in the form of a white solid. MS [M+H]⁺=199.6, 201.6.

Step (2): Preparation of (Z)-4-bromo-N-hydroxybenzimidoyl Chloride

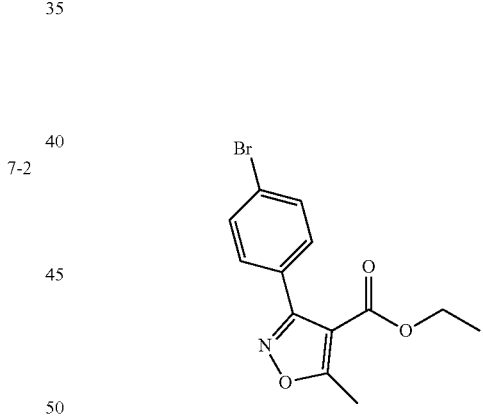

Compound 7-2 (6 g, 30.00 mmol) was dissolved in N,N-dimethylformamide (50 mL) under nitrogen atmosphere, and the reaction system was slowly added with N-chlorosuccinimide (4.8 g, 35.95 mmol), and reacted at room temperature for 2 h. After the reaction was completed, ice water (100 mL) was added to quench the reaction, then the reaction system was filtered. The filter cake was washed with ethyl acetate, the filtrate was washed with saturated brine (100 mL×3) and then concentrated by rotary evaporation to give compound 7-3 (5.4 g) in the form of a yellow oil, MS [M+H]⁺: 233.6, 235.6.

Step (3): Preparation of ethyl 3-(4-bromophenyl)-5-methylisoxazole-4-carboxylate Ethyl acetoacetate (3.9 g, 29.97 mmol) was dissolved in anhydrous methanol (50 mL), and the reaction system was added with compound 7-3 (5.4 g, 23.03 mmol) and sodium methoxide (1.4 g, 25.92 mmol) at 0° C., and reacted at room temperature for 10 min. Then the reaction system was added with sodium methoxide (1.4 g, 25.92 mmol) and reacted at room temperature for 30 min. After the reaction was completed, the reaction system was added with water (100 mL) and extracted with ethyl acetate (150 mL×3). The organic phases were combined, washed with saturated brine (100 mL×1), dried over anhydrous sodium sulfate, and filtered, and the filtrate was concentrated by rotary evaporation to give a crude product. The crude product was purified by silica gel column chromatography to give compound 7-5 (1.8 g) in the form of a white solid. MS [M+H]⁺=309.7, 311.7.

Step (4): Preparation of (3-(4-bromophenyl)-5-methylisoxazol-4-yl)methanol

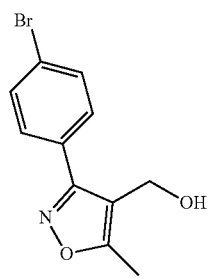

7-6

Compound 7-5 (1.8 g, 5.8 mmol) was added to anhydrous tetrahydrofuran (25 mL), and the reaction system was added with lithium borohydride (463 mg, 21.28 mmol), heated to reflux and stirred overnight and cooled to room temperature. The reaction system was diluted with water (50 mL) and extracted with ethyl acetate (25 mL×3). The organic phase was washed with saturated brine (100 mL), dried over anhydrous sodium sulfate and concentrated, and the residue was separated by column chromatography (PE/EA=10/1-3/1) to give compound 7-6 (1.39 g, 89% yield) in the form of a white solid. LC-MS [M+H]$^+$: 267.7, 269.7.

Step (5): Preparation of (3-(4-bromophenyl)-5-methylisoxazol-4-yl)methyl(4-nitrophenyl)carbonate

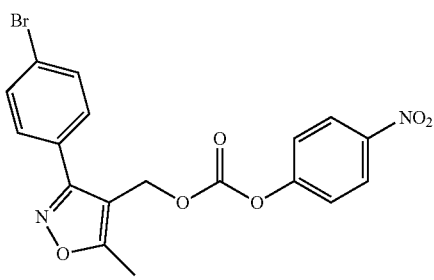

7-8

Compound 7-6 (1.39 g, 5.18 mmol) and pyridine (2 g, 25.36 mmol) were dissolved in dichloromethane (30 mL), and the reaction system was cooled to 0° C. 4-nitrophenyl chloroformate (2.56 g, 12.68 mmol) was added, and then the reaction system was warmed to room temperature and stirred overnight. The reaction system was washed with saturated brine, the organic phase was dried over anhydrous sodium sulfate and concentrated, and the residue was separated by column chromatography (PE/EA=20/1-5/1) to give compound 7-8 (1.4 g) in the form of a white solid. LC-MS [M+H]$^+$: 432.5, 434.5.

Step (6): Preparation of (3-(4-bromophenyl)-5-methylisoxazol-4-yl)methylcyclopentyl(methyl)carbamate

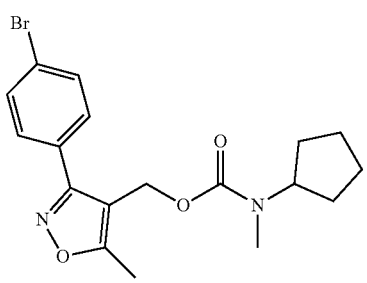

7-9

Compound 7-8 (300 mg, 0.6925 mmol) and diisopropylethylamine (358 mg, 2.77 mmol) were dissolved in anhydrous dichloromethane (10 mL), and N-methylcyclopentanamine (113 mg, 0.831 mmol) was added to the reaction system. The reaction system was stirred overnight at room temperature under nitrogen atmosphere and washed with saturated brine (20 mL). The organic phase was dried over anhydrous sodium sulfate, filtered and concentrated, and the residue was separated by column chromatography (PE/EA=20/1-10/1) to give compound 7-9 (250 mg, 85% purity, 78% yield) in the form of a yellow solid. LC-MS [M+H]$^+$: 392.6, 394.6.

Step (7): Preparation of (5-methyl-3-(4-(4,4,5,5-tetramethyl-1,3,2-dioxaborolan-2-yl)phenyl)isoxazol-4-yl)methylcyclopentyl(methyl)carbamate

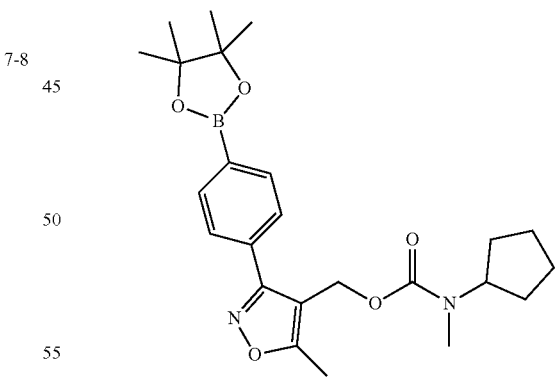

7-10

Compound 7-9 (250 mg, 0.6357 mmol) and 4,4,4',4',5,5,5',5'-octamethyl-2,2'-bis(1,3,2-dioxaborolane) (178 mg, 0.6993 mmol) were dissolved in dioxane (15 mL), and the reaction system was added with [1,1'-bis(diphenylphosphino)ferrocene]dichloropalladium(II) (24 mg, 0.0318 mmol) and potassium acetate (187 mg, 1.9 mmol), and stirred at 80° C. for 5 h under nitrogen atmosphere. The reaction system was filtered, and the filtrate was concentrated to give compound 7-10 (550 mg, crude). LC-MS [M+1]$^+$: 441.2.

Step (8): Preparation of (3-(4-hydroxyphenyl)-5-methylisoxazol-4-yl)methylcyclopentyl(methyl) carbamate

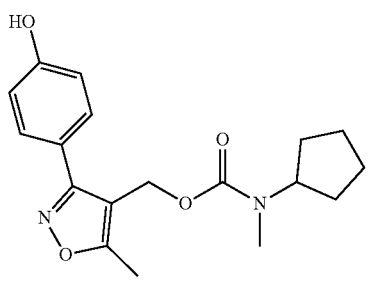

7-11

Compound 7-10 (550 mg, crude) was dissolved in tetrahydrofuran (10 mL), and the reaction system was added with hydrogen peroxide (2 mL), and reacted at room temperature for 5 h. The reaction system was diluted with water (20 mL), and extracted with ethyl acetate (10 mL×3). The organic phases were combined, washed with saturated brine (40 mL), dried over anhydrous sodium sulfate, filtered and concentrated, and the residue was separated by column chromatography (PE/EA=10/1-3/1) to give compound 7-11 (180 mg, 85% yield over two steps) in the form of a yellow oily liquid. LC-MS [M+H]$^+$: 331.4.

Step (9): Preparation of (+/−)-isopropyl (1S,3S)-3-(4-(4-(((cyclopentyl(methyl)carbamoyl)oxy)methyl)-5-methylisoxazol-3-yl)phenoxy)cyclohexanecarboxylate

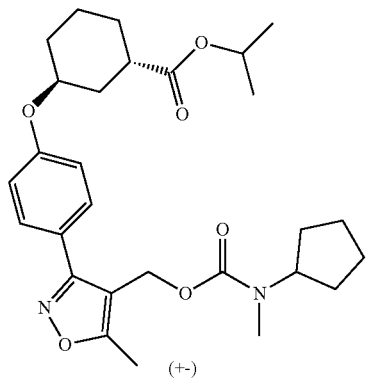

7-12

Compound 7-11 (180 mg, 0.5448 mmol) and isopropyl (1S,3R)-3-hydroxycyclohexanecarboxylate (406 mg, 2.1793 mmol) were dissolved in anhydrous tetrahydrofuran (10 mL), and the reaction system was added with triphenylphosphine (572 mg, 2.1793 mmol) and di-tert-butyl azodicarboxylate (502 mg, 2.1793 mmol), reacted at 60° C. for 15 h under nitrogen atmosphere, filtered, diluted with water (50 mL), and then extracted with ethyl acetate (30 mL×3). The organic phases were combined, dried over anhydrous sodium sulfate and concentrated, and the residue was separated by column chromatography (PE/EA=1/1) to give compound 7-12 (450 mg, 35% purity) in the form of a white solid. LC-MS [M+H]$^+$: 499.7.

Step (10): Preparation of (+/−)-(1S,3S)-3-(4-(4-(((cyclopentyl(methyl)carbamoyl)oxy)methyl)-5-methylisoxazol-3-yl)phenoxy)cyclohexane-1-carboxylic Acid

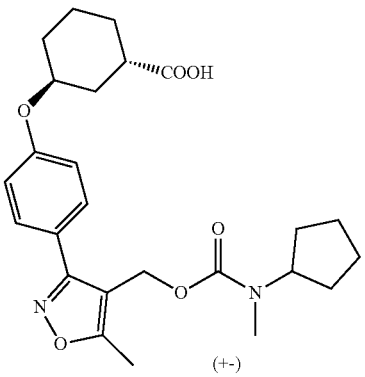

7

Compound 7-12 (450 mg, crude) and lithium hydroxide (69 mg, 1.6344 mmol) were dissolved in methanol (3 mL) and water (3 mL), and the reaction system was reacted at room temperature for 10 h, concentrated, adjusted to pH 5 with diluted hydrochloric acid (1 N), and then extracted with ethyl acetate (10 mL×3). The organic phases were combined, dried over anhydrous sodium sulfate and concentrated, and the residue was separated by preparative HPLC to give compound 7 (105 mg, 24% yield over two steps) in the form of a white solid.

LC-MS [M+H]$^+$: 457.7. $^1$H NMR (400 MHz, CDCl$_3$) δ 7.70 (d, J=8.7 Hz, 2H), 7.01 (d, J=8.7 Hz, 2H), 5.03 (s, 2H), 4.72 (s, 1H), 4.54 (s, 1H), 2.99-2.85 (m, 1H), 2.76 (s, 3H), 2.55 (s, 3H), 2.18 (m, 1H), 1.96 (m, 3H), 1.80 (m, 2H), 1.66 (m, 5H), 1.48 (m, 5H).

Example 8

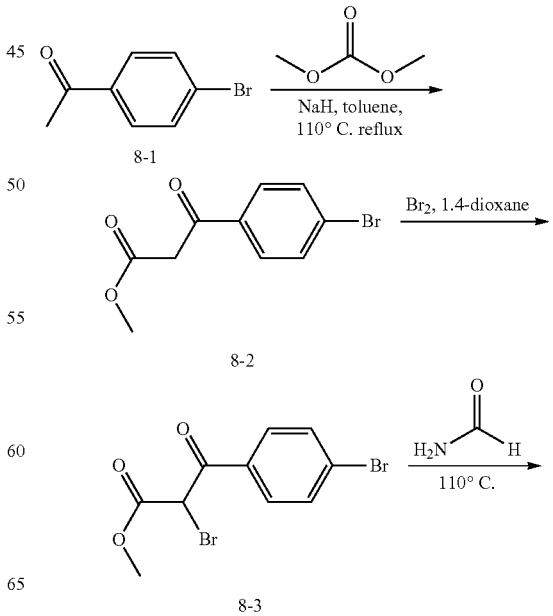

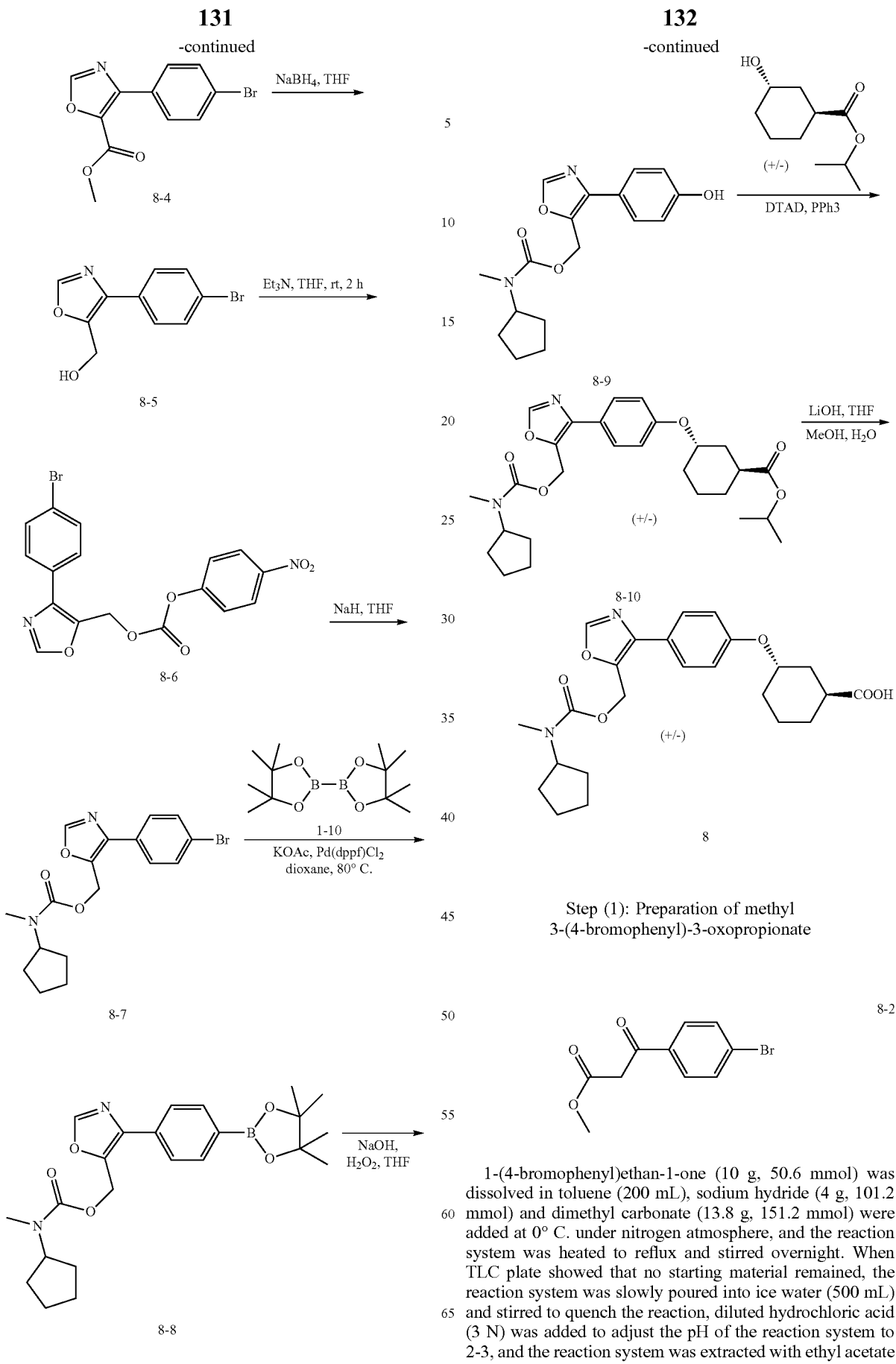

Step (1): Preparation of methyl 3-(4-bromophenyl)-3-oxopropionate 1-(4-bromophenyl)ethan-1-one (10 g, 50.6 mmol) was dissolved in toluene (200 mL), sodium hydride (4 g, 101.2 mmol) and dimethyl carbonate (13.8 g, 151.2 mmol) were added at 0° C. under nitrogen atmosphere, and the reaction system was heated to reflux and stirred overnight. When TLC plate showed that no starting material remained, the reaction system was slowly poured into ice water (500 mL) and stirred to quench the reaction, diluted hydrochloric acid (3 N) was added to adjust the pH of the reaction system to 2-3, and the reaction system was extracted with ethyl acetate (250 mL×3), and then washed with saturated brine (200 mL×2). The organic phase was dried over anhydrous sodium sulfate and filtered. The filtrate was concentrated by rotary evaporation to give a crude production, and the crude product was purified by silica gel column chromatography (petroleum ether:ethyl acetate=2:1) to give compound 8-2 (11.2 g, 86.46% yield) in the form of a pale yellow solid. LC-MS [M+H]⁺: 256.8, 258.8.

Step (2): Preparation of methyl 2-bromo-3-(4-bromophenyl)-3-oxopropionate

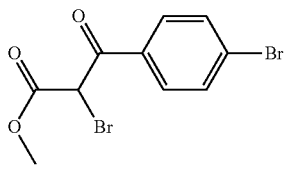

8-3

Compound 8-2 (8 g, 31.2 mmol) was dissolved in 1,4-dioxane (150 mL), and the reaction system was cooled to 0° C., added with bromine (1.9 mL, 37.5 mmol) and stirred overnight. When TLC plate showed that no starting material remained, the reaction system was concentrated by rotary evaporation to give brown-yellow compound 8-3 (12.8 g, crude) for use in next step. LC-MS [M+H]⁺: 334.5, 336.5, 338.5.

Step (3): Preparation of methyl 4-(4-bromophenyl)oxazole-5-carboxylate

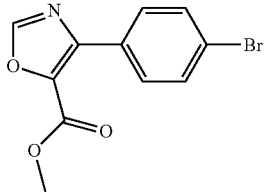

8-4

Compound 8-3 (12.8 g, crude) was added to formamide solution (50 mL). The reaction system was stirred at 110° C. for 1.5 h, cooled to room temperature, quenched with water (50 mL), and extracted with ethyl acetate (35 mL×3). The organic phases were combined, washed with saturated brine (50 mL), dried over anhydrous sodium sulfate and filtered. The filtrate was concentrated by rotary evaporation to give a crude product, and the crude product was purified by silica gel column chromatography (petroleum ether:ethyl acetate=3:1) to give compound 8-4 (2.6 g, 24.01% yield) in the form of a pale yellow solid. LC-MS [M+H]⁺: 281.6, 283.6.

Step (4): Preparation of (4-(4-bromophenyl)oxazol-5-yl)methanol

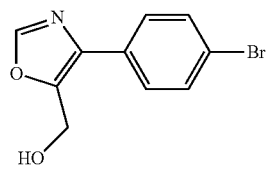

8-5

Compound 8-4 (2.6 g, 9.22 mmol) was dissolved in a mixed solution of tetrahydrofuran (20 mL) and water (1 mL), and sodium borohydride (700 mg, 18.44 mmol) was added at 0° C. The reaction system was warmed to room temperature and reacted for 3 h. When TLC plate showed that no starting material remained, the reaction system was diluted with water (15 mL) and extracted with ethyl acetate (15 mL×3). The organic phase was dried over anhydrous sodium sulfate and filtered. The filtrate was concentrated by rotary evaporation, and the residue was purified by silica gel column chromatography (dichloromethane:methanol=20:1) to give compound 8-5 (1 g, 42.70% yield) in the form of a brown solid. LC-MS [M+H]⁺: 253.7, 255.7.

Step (5)

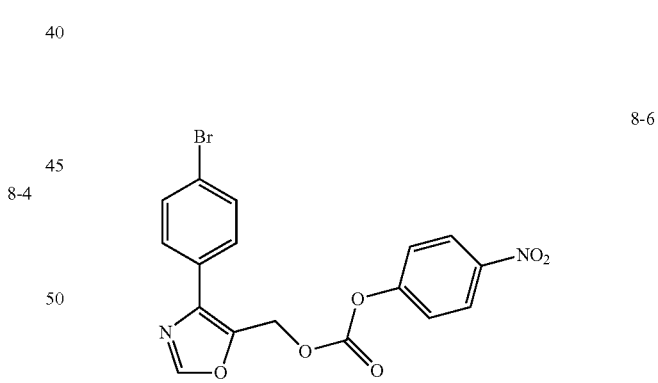

8-6

Compound 8-5 (255 mg, 1 mmol) and pyridine (320 g, 4 mmol) were dissolved in dichloromethane (10 mL), and the reaction system was cooled to 0° C. 4-nitrophenyl chloroformate (600 mg, 3 mmol) was added, and then the reaction system was warmed to room temperature and stirred overnight. The reaction system was washed with saturated brine, the organic phase was dried over anhydrous sodium sulfate and concentrated, and the residue was separated by column chromatography (PE/EA=5/1) to give compound 8-6 (260 mg) in the form of a white solid. LC-MS [M+H]⁺: 418.6, 420.6.

Step (6): Preparation of (4-(5-bromophenyl-2-yl)oxazol-5-yl)methylcyclopentyl(methyl)carbamate

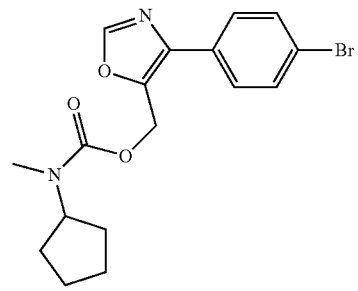

8-7

Compound 8-6 (273 mg, 1.1 mmol), sodium hydride (66 mg, 1.65 mmol) were dissolved in tetrahydrofuran (10 mL), and the reaction system was stirred for 10 min, added with 4-nitrophenylcyclopentyl(methyl)carbamate (435 mg, 1.65 mmol), warmed to room temperature and reacted for 3 h. The reaction system was quenched with saturated aqueous ammonium chloride (10 mL), extracted with ethyl acetate (10 mL×3), and washed with saturated brine (20 mL). The organic phase was dried over anhydrous sodium sulfate and filtered. The filtrate was concentrated by rotary evaporation, and the residue was purified by silica gel column chromatography (dichloromethane:ethyl acetate=10:1) to give compound 8-7 (340 mg, 81.55% yield) in the form of a white solid. LC-MS [M+H]$^+$: 378.7, 380.7.

Step (7): Preparation of (4-(4-(4,4,5,5-tetramethyl-1,3,2-dioxaborolan-2-yl)phenyl)oxazol-5-yl) methylcyclopentyl(methyl)carbamate

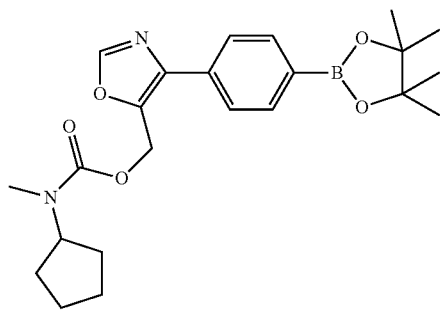

8-8

Compound 8-7 (300 mg, 0.79 mmol) was dissolved in 1,4-dioxane (20 mL), and the reaction system was sequentially added with bis(pinacolato)diboron (403 mg, 1.59 mmol), potassium acetate (232 mg, 2.38 mmol) and [1,1'-bis(diphenylphosphino)ferrocene]dichloropalladium(II) (73 mg, 0.1 mmol), heated at 80° C. for 4 h and filtered. The filtrate was concentrated by rotary evaporation to give compound 8-8 (1 g, crude) in the form of a brown-black solid. LC-MS [M+H]$^+$: 427.8.

Step (8): Preparation of (4-(4-hydroxyphenyl)oxazol-5-yl)methylbenzyl(methyl)carbamate

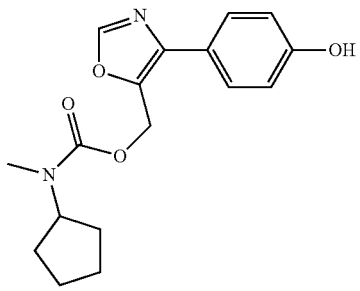

8-9

Compound 8-8 (1 g, crude) was dissolved in tetrahydrofuran (15 mL), and the reaction system was cooled to 0° C., sequentially added with sodium hydroxide solution (1 N, 2.5 mL) and hydrogen peroxide (15 mL), and stirred at 0° C. When TLC plate showed that no starting material remained, the reaction system was diluted with water (20 mL), extracted with ethyl acetate (15 mL×3), and wash with saturated brine (20 mL). The organic phase was dried over anhydrous sodium sulfate and filtered. The filtrate was concentrated by rotary evaporation, and the residue was purified by silica gel column chromatography (dichloromethane:methanol=50:1) to give compound 8-9 (300 mg) in the form of a white solid. LC-MS [M+H]$^+$: 316.9.

Step (9): Preparation of (+/−)-isopropyl (1S,3S)-3-(4-(5-(((cyclopentyl(methyl)carbamoyl)oxy)methyl)oxazol-4-yl)phenoxy)cyclohexane-1-carboxylate

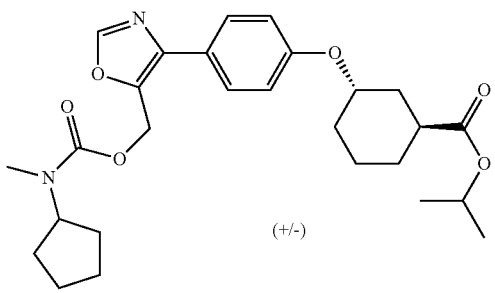

8-10

Compound 8-9 (340 mg, 1.1 mmol), isopropyl (3S)-3-hydroxycyclohexane-1-carboxylate (827 mg, 4.4 mmol), DTAD (1 g, 4.4 mmol) and PPh$_3$ (1.2 mg, 4.4 mmol) were dissolved in THF (30 mL), and then the reaction system was stirred overnight at room temperature under nitrogen atmosphere, diluted with water (20 mL), extracted with ethyl acetate (15 mL×3), and washed with saturated brine (20 mL). The reaction system was then purified by silica gel column chromatography (DCM/EA=5/1) to give compound 8-10 (270 mg, 50.71% yield) in the form of a white solid. LC-MS [M+H]$^+$: 485.7.

Step (10): Preparation of (+/−)-(1S,3S)-3-(4-(5-((((cyclopentyl(methyl)carbamoyl)oxy)methyl)oxazol-4-yl)phenoxy)cyclohexane-1-carboxylic Acid

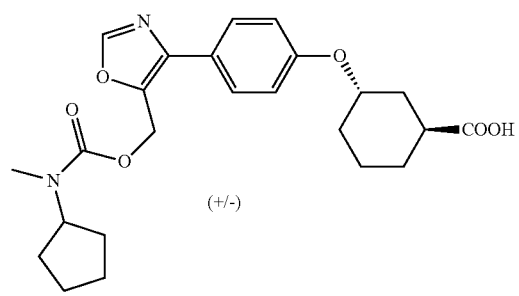

(+/−)

Compound 8-10 (130 mg, 0.27 mmol) was dissolved in THF (3 mL), and the reaction system was sequentially added with MeOH (1 mL), H$_2$O (1 mL) and lithium hydroxide (131 mg, 1.34 mmol), and stirred overnight at room temperature. Then water (10 mL) was added for dilution, and the organic solvent was removed by rotary evaporation under reduced pressure. The aqueous phase was adjusted to pH 2-3 with hydrochloric acid (1 N), and extracted with dichloromethane (10 mL×2). The organic phase was dried over anhydrous sodium sulfate and filtered, and the filtrate was concentrated by rotary evaporation. The residue was purified by silica gel column chromatography (DCM/MeOH=20/1) and then lyophilized to give compound 8 (10 mg) in the form of a white solid.

LC-MS [M+H]$^+$: 443.7. $^1$H NMR (400 MHz, CDCl3) δ 7.93 (s, 1H), 7.72-7.65 (m, 2H), 7.05-6.99 (m, 2H), 5.31 (s, 2H), 4.71 (s, 1H), 4.61 (s, 1H), 2.93 (s, 1H), 2.81 (s, 3H), 2.23-2.16 (m, J=13.6 Hz, 1H), 1.97-1.51 (m, 15H).

Example 9

9-1

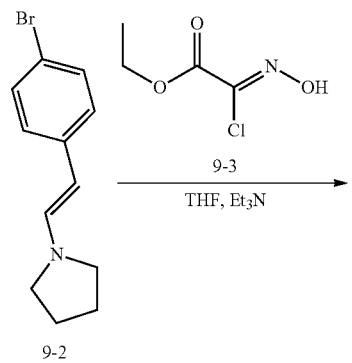

9-2

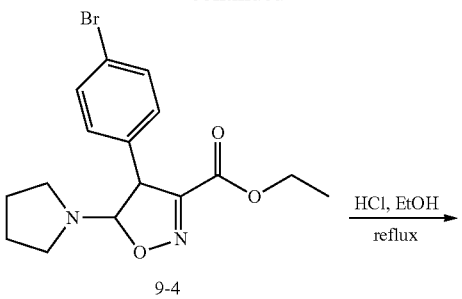

9-4

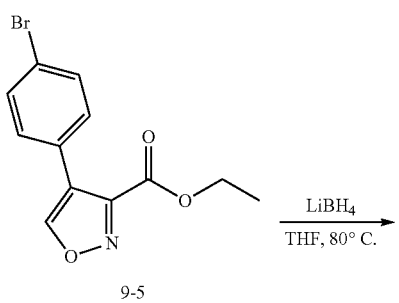

9-5

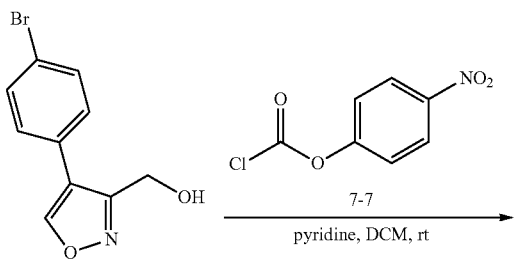

9-6

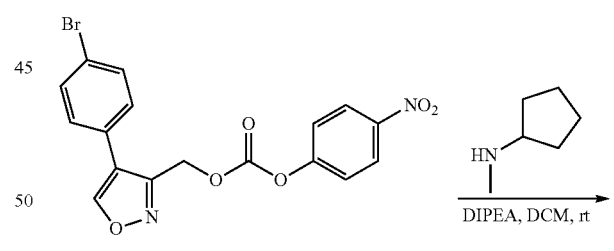

9-7

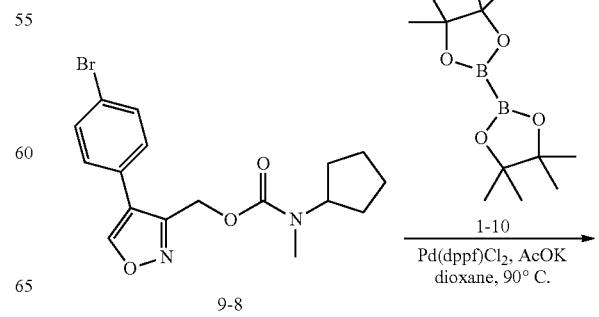

9-8

-continued

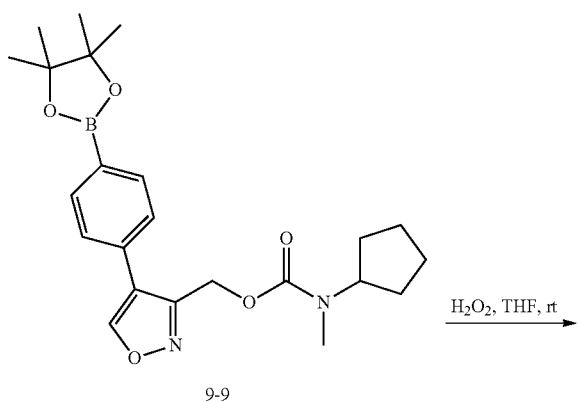

9-9

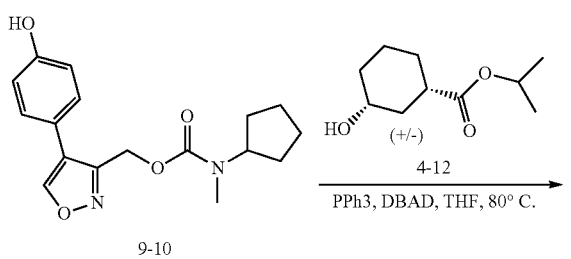

9-10

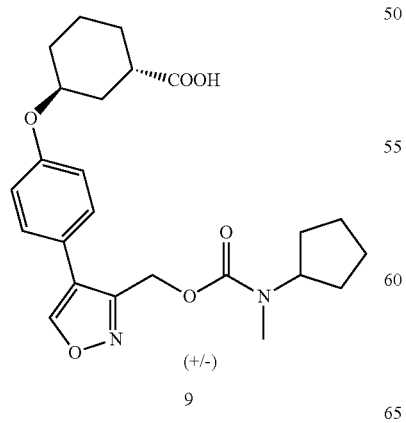

9-11

9

Step (1): Preparation of (E)-1-(4-bromostyryl)pyrrolidine

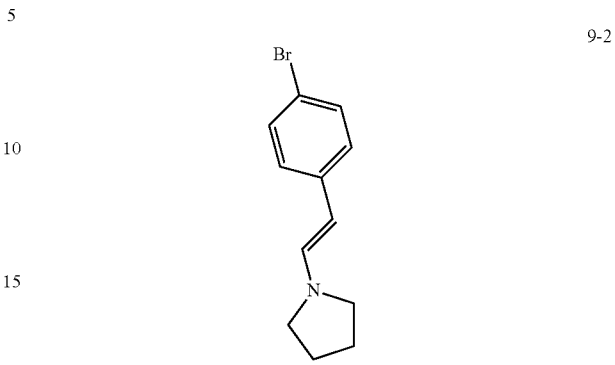

9-2

2-(4-bromophenyl)acetaldehyde (1.5 g, 7.54 mmol) was dissolved in toluene (15 mL), and the reaction system was added with pyrrolidine (640 mg, 9.01 mmol), and stirred at room temperature for 1 h under nitrogen atmosphere to give compound 9-2. The reaction system was directly used in the next step.

Step (2): Preparation of ethyl 4-(4-bromophenyl)-5-(pyrrolidin-1-yl)-4,5-dihydroisoxazole-3-carboxylate

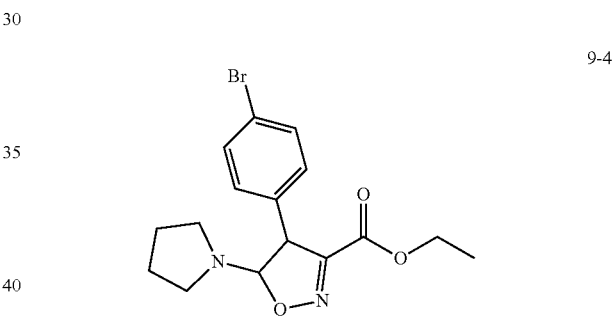

9-4

Triethylamine (1.52 g, 15.10 mmol) and tetrahydrofuran (3 mL) were added to the reaction system in the step (1), and the reaction system was slowly added dropwise with a solution of compound 9-2 (2.28 g, 15.10 mmol) in tetrahydrofuran, stirred overnight at room temperature and filtered. The filtrate was concentrated to give compound 9-4 (2.8 g, crude), which was directly used in the next step.

Step (3): Preparation of ethyl 4-(4-bromophenyl)isoxazole-3-carboxylate

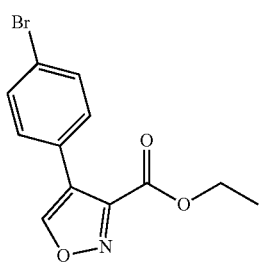

9-5

Compound 9-4 (2.8 g, crude) was dissolved in ethanol (20 mL), and the reaction system was added with concentrated hydrochloric acid (3 mL), and stirred at 50° C. for 2 h under nitrogen atmosphere. The reaction system was then diluted with water (100 mL) and extracted with ethyl acetate (30 mL×3). The organic phases were combined, dried over anhydrous sodium sulfate and concentrated, and the residue was purified by column chromatography (PE/EA=50/1) to give compound 9-5 (2.1 g, 94% yield over three steps) in the form of a yellow solid. LC-MS [M+H]$^+$: 295.8, 297.8.

Step (4): Preparation of (4-(4-bromophenyl)isoxazol-3-yl)methanol

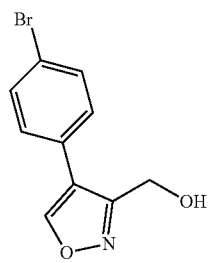

9-6

Compound 9-5 (2.1 g, 7.09 mmol) was added to anhydrous tetrahydrofuran (20 mL), and the reaction system was added with lithium borohydride (774 mg, 42.11 mmol), heated to reflux and stirred overnight and cooled to room temperature. The reaction system was diluted with water (50 mL) and extracted with ethyl acetate (50 mL×3). The organic phase was washed with saturated brine (100 mL), dried over anhydrous sodium sulfate and concentrated, and the residue was separated by column chromatography (PE/EA=15/1-3/1) to give compound 9-6 (1.2 g, 66% yield) in the form of a white solid. LC-MS [M+H]$^+$: 253.5, 255.5.

Step (5): Preparation of (4-(4-bromophenyl)isoxazol-3-yl)methyl(4-nitrophenyl)carbonate

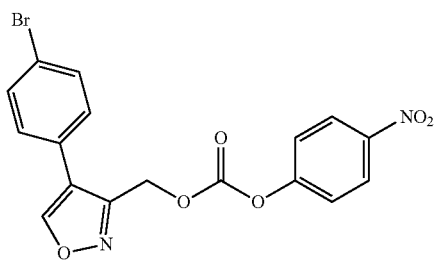

9-7

Compound 9-6 (254 mg, 1 mmol) and pyridine (316 mg, 4 mmol) were dissolved in dichloromethane (10 mL), and the reaction system was cooled to 0° C. 4-nitrophenyl chloroformate (403 mg, 2 mmol) was added, and then the reaction system was warmed to room temperature and stirred overnight. The reaction system was washed with saturated brine, the organic phase was dried over anhydrous sodium sulfate and concentrated, and the residue was separated by column chromatography (PE/EA=15/1-5/1) to give compound 9-7 (420 mg) in the form of a yellow oily liquid. LC-MS [M+H]$^+$: 418.5, 420.5.

Step (6): Preparation of (4-(4-bromophenyl)isoxazol-3-yl)methylcyclopentyl(methyl)carbamate

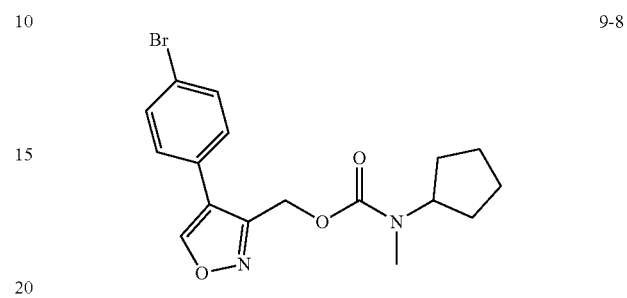

9-8

Compound 9-7 (420 mg, 1.0 mmol) and diisopropylethylamine (517 mg, 4.0 mmol) were dissolved in anhydrous dichloromethane (10 mL), and N-methylcyclopentanamine (163 mg, 1.2 mmol) was added to the reaction system. The reaction system was stirred overnight at room temperature under nitrogen atmosphere and washed with saturated brine (20 mL). The organic phase was dried over anhydrous sodium sulfate, filtered and concentrated, and the residue was separated by column chromatography (PE/EA=10/1) to give compound 9-8 (269 mg, 70.9% yield over two steps) in the form of a yellow oily liquid. LC-MS [M+H]$^+$: 378.7, 380.7.

Step (7): Preparation of (4-(4-(4,4,5,5-tetramethyl-1,3,2-dioxaborolan-2-yl)phenyl)isoxazol-3-yl) methylcyclopentyl(methyl)carbamate

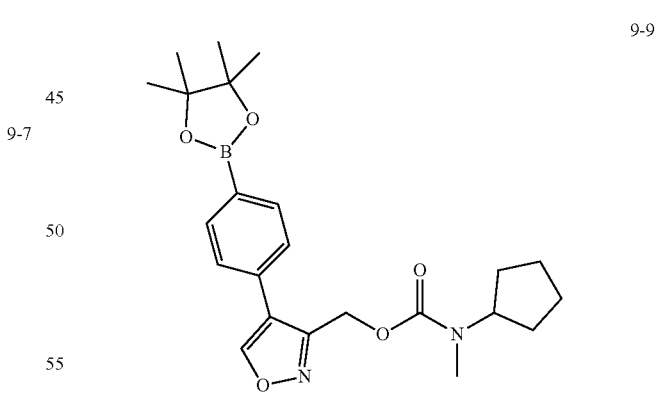

9-9

Compound 9-8 (269 mg, 0.71 mmol) and 4,4,4',4',5,5,5',5'-octamethyl-2,2'-bi(1,3,2-dioxaborolane) (198 mg, 0.78 mmol) were dissolved in dioxane (10 mL), and the reaction system was added with [1,1'-bis(diphenylphosphino)ferrocene]dichloropalladium(II) (26 mg, 0.035 mmol) and potassium acetate (209 mg, 2.13 mmol), and stirred at 80° C. for 5 h under nitrogen atmosphere. The reaction system was filtered, and the filtrate was concentrated to give compound 9-9 (400 mg, crude). LC-MS [M+H]$^+$: 427.2.

Step (8): Preparation of (4-(4-hydroxyphenyl)isoxazol-3-yl)methylcyclopentyl(methyl)carbamate

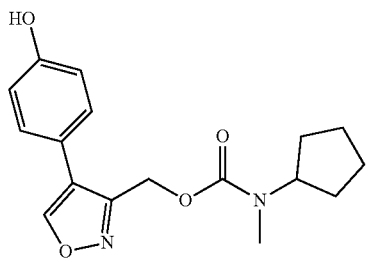

9-10

Compound 9-9 (400 mg, crude) was dissolved in tetrahydrofuran (15 mL), and the reaction system was added with hydrogen peroxide (7 mL), and reacted at room temperature for 5 h. The reaction system was diluted with water (30 mL), and extracted with ethyl acetate (20 mL×3). The organic phases were combined, washed with saturated brine (60 mL), dried over anhydrous sodium sulfate, filtered and concentrated, and the residue was separated by column chromatography (PE/EA=10/1-3/1) to give compound 9-10 (196 mg, 87% yield over two steps) in the form of a yellow oily liquid. LC-MS [M+H]⁺: 317.4.

Step (9): Preparation of (+/−)-isopropyl (1S,3S)-3-(4-(3-(((cyclopentyl(methyl)carbamoyl)oxy)methyl)isoxazol-4-yl)phenoxy)cyclohexane-1-carboxylate

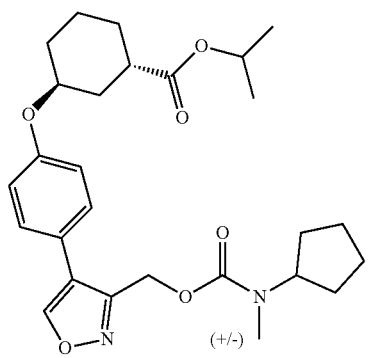

9-11

Compound 9-10 (196 mg, 0.6195 mmol) and isopropyl (1S,3R)3-hydroxycyclohexanecarboxylate (452 mg, 2.4782 mmol) were dissolved in anhydrous tetrahydrofuran (10 mL), and the reaction system was added with triphenylphosphine (650 mg, 2.4782 mmol) and di-tert-butyl azodicarboxylate (571 mg, 2.4782 mmol), reacted at 60° C. for 15 h under nitrogen atmosphere, filtered, diluted with water (50 mL), and then extracted with ethyl acetate (30 mL×3). The organic phases were combined, dried over anhydrous sodium sulfate and concentrated, and the residue was separated by column chromatography (PE/EA=15/1-10/1) to give compound 9-11 (500 mg, 50-60% purity) in the form of a white solid. LC-MS [M+H]⁺: 485.3.

Step (10): Preparation of (+/−)-(1S,3S)-3-(4-(3-(((cyclopentyl(methyl)carbamoyl)oxy)methyl)isoxazol-4-yl)phenoxy)cyclohexane-1-carboxylic Acid

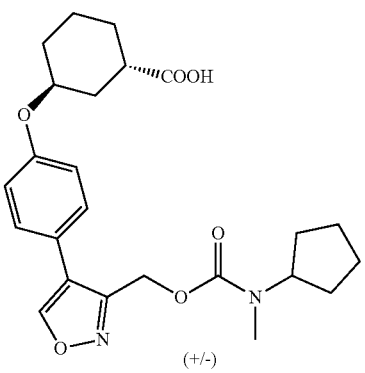

9

Compound 9-11 (500 mg, crude) and lithium hydroxide (130 mg, 3.0975 mmol) were dissolved in methanol (5 mL) and water (5 mL), and the reaction system was reacted at room temperature for 10 h, concentrated, adjusted to pH 5 with diluted hydrochloric acid (1 N), and then extracted with ethyl acetate (10 mL×3). The organic phases were combined, dried over anhydrous sodium sulfate and concentrated, and the residue was separated by preparative HPLC to give compound 9 (82 mg, 29.9% yield over two steps) in the form of a white solid.

LC-MS [M+H]⁺: 443.1. ¹H NMR (400 MHz, CDCl3) δ 8.47 (s, 1H), 7.32 (d, J=8.7 Hz, 2H), 6.97 (d, J=8.7 Hz, 2H), 5.32 (s, 2H), 4.70-4.66 (m, 1H), 4.62-4.05 (m, 1H), 2.96-2.87 (m, 1H), 2.65 (brs, 3H), 2.20-2.12 (m, 1H), 2.08-1.84 (m, 3H), 1.89-1.25 (m, 12H).

Example 10

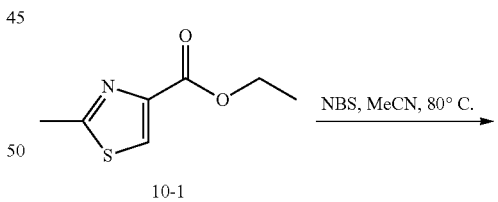

10-1

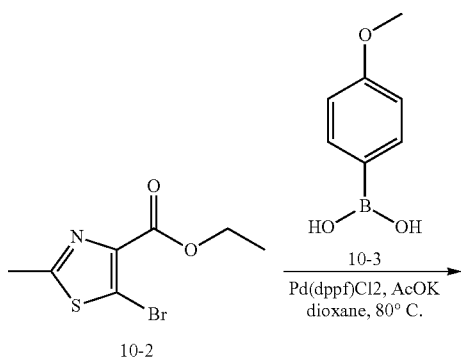

10-2

10-3

Pd(dppf)Cl2, AcOK
dioxane, 80° C.

-continued

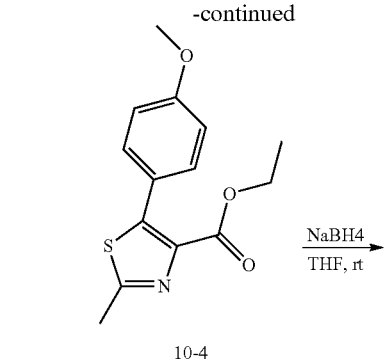

10-4

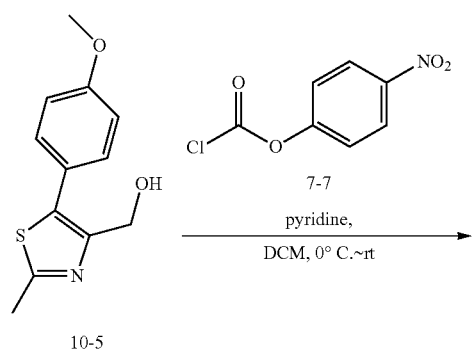

10-5

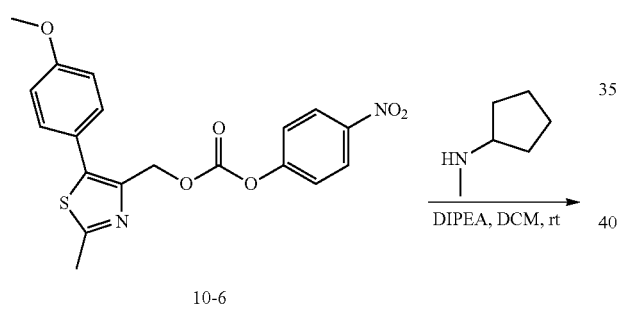

10-6

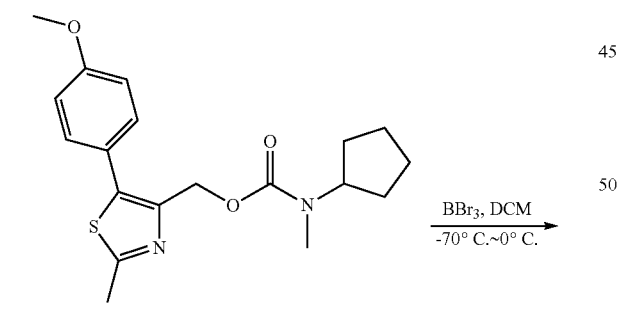

10-7

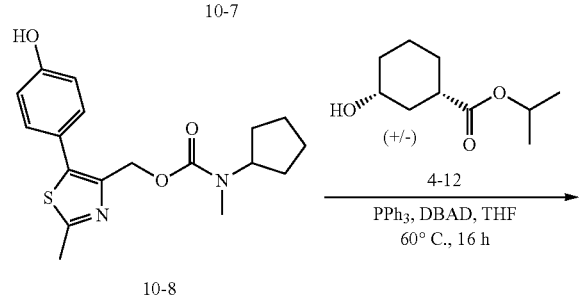

10-8

-continued

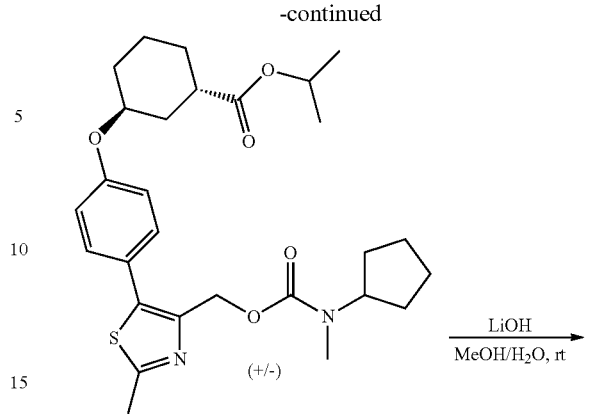

10-9

10

Step (1): Preparation of ethyl 5-bromo-2-methylthiazole-4-carboxylate 10-2

Ethyl 2-methylthiazole-4-carboxylate (2.0 g, 11.68 mmol) was dissolved in acetonitrile (30 mL), and the reaction system was added with NBS (2.287 g, 12.85 mmol), and refluxed overnight. The reaction system was cooled to room temperature, added with water (60 mL), and extracted with ethyl acetate (40 mL×3). The organic phases were combined, washed with saturated brine (150 mL), dried over anhydrous magnesium sulfate, filtered and concentrated. The residue was separated by column chromatography (PE/EA=20/1-10/1) to give compound 10-2 (1.8 g) in the form of a white solid. LC-MS [M+H]⁻: 249.7, 251.7.

Step (2): Preparation of ethyl 5-(4-methoxyphenyl)-2-methylthiazole-4-carboxylate

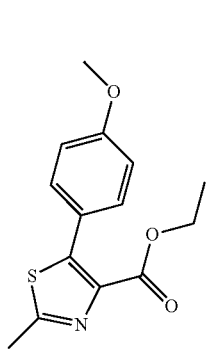

10-4

Compound 10-2 (1.55 g, 6.20 mmol) and 4-methoxyphenylboronic acid (1.036 g, 6.82 mmol) were dissolved in dioxane (30 mL), and the reaction system was added with [1,1'-bis(diphenylphosphino)ferrocene]dichloropalladium (II) (227 mg, 0.31 mmol) and potassium acetate (1.82 g, 18.06 mmol), and stirred at 80° C. overnight under nitrogen atmosphere. The reaction system was filtered, and the filtrate was diluted with water (60 mL), and extracted with ethyl acetate (40 mL×3). The organic phases were combined, washed with saturated brine (150 mL), dried over anhydrous sodium sulfate, and concentrated, and the residue was separated by column chromatography (PE/EA=10/1) to give compound 10-4 (700 mg, 40% yield over two steps) in the form of a yellow oily liquid. LC-MS [M+H]$^+$: 278.8.

Step (3): Preparation of (5-(4-methoxyphenyl)-2-methylthiazol-4-yl)methanol

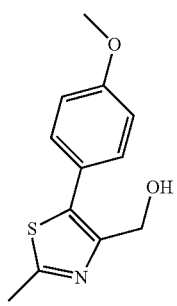

10-5

Compound 10-4 (700 mg, 2.52 mmol) was added to anhydrous tetrahydrofuran (15 mL), and the reaction system was added with sodium borohydride (958 mg, 25.24 mmol), and stirred overnight at room temperature. The reaction system was diluted with water (50 mL) and extracted with ethyl acetate (25 mL×3). The organic phase was washed with saturated brine (100 mL), dried over anhydrous sodium sulfate and concentrated, and the residue was separated by column chromatography (PE/EA=5/1) to give compound 10-5 (340 mg, 57% yield) in the form of a colorless oily liquid. LC-MS [M+H]$^+$: 236.8.

Step (4): Preparation of (5-(4-methoxyphenyl)-2-methylthiazol-4-yl)methyl(4-nitrophenyl)carbonate

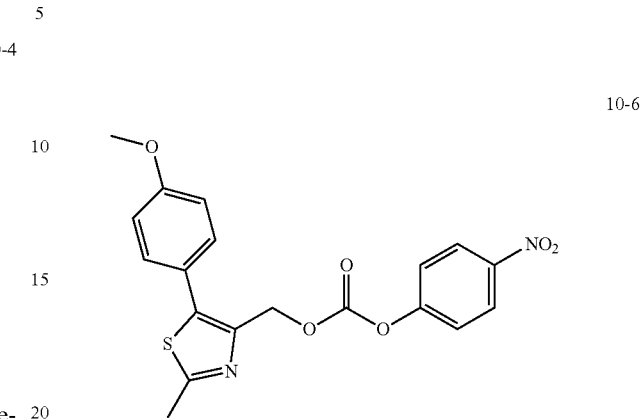

10-6

Compound 10-5 (340 mg, 1.45 mmol) and pyridine (363 mg, 4.59 mmol) were dissolved in dichloromethane (10 mL), and the reaction system was cooled to 0° C. 4-nitrophenyl chloroformate (463 mg, 2.30 mmol) was added, and then the reaction system was warmed to room temperature and stirred overnight. The reaction system was washed with saturated brine, the organic phase was dried over anhydrous sodium sulfate and concentrated, and the residue was separated by column chromatography (PE/EA=15/1-5/1) to give compound 10-6 (620 mg) in the form of a yellow oily liquid. LC-MS [M+H]$^+$: 401.8.

Step (5): Preparation of (5-(4-methoxyphenyl)-2-methylthiazol-4-yl)methylcyclopentyl(methyl)carbamate

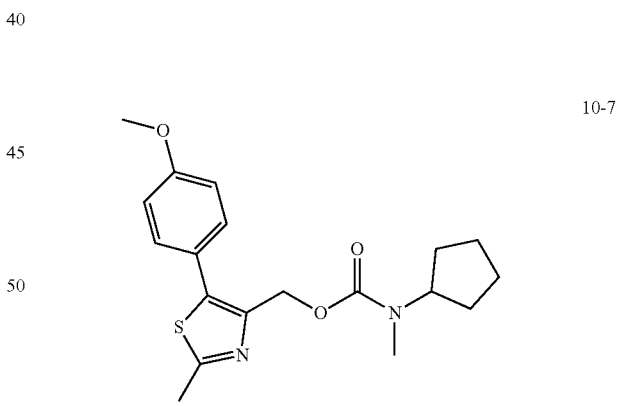

10-7

Compound 10-6 (620 mg, 1.45 mmol) and diisopropylethylamine (593 mg, 4.59 mmol) were dissolved in anhydrous dichloromethane (10 mL), and N-methylcyclopentanamine (252 mg, 1.86 mmol) was added to the reaction system. The reaction system was stirred overnight at room temperature under nitrogen atmosphere and washed with saturated brine (20 mL). The organic phase was dried over anhydrous sodium sulfate, filtered and concentrated, and the residue was separated by column chromatography (PE/EA=15/1) to give compound 10-7 (470 mg, 83% yield) in the form of a yellow oily liquid. LC-MS [M+H]$^+$: 361.8.

Step (6): Preparation of (5-(4-hydroxyphenyl)-2-methylthiazol-4-yl)methylcyclopentyl(methyl)carbamate

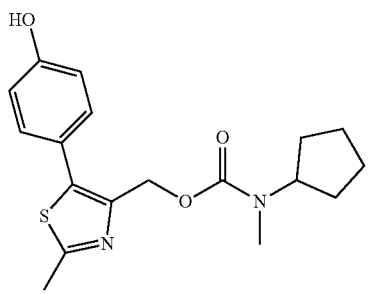

10-8

Compound 10-7 (470 mg, 1.30 mmol) was dissolved in anhydrous dichloromethane (10 mL), and the reaction system was cooled to −78° C. under nitrogen atmosphere, and added dropwise with a solution of boron tribromide in dichloromethane solution (1 N, 4.2 mL). After the addition was completed, the reaction system was stirred in an ice bath for 7 h, poured into ice water, and extracted with dichloromethane (10 mL×3). The organic phase was washed with saturated sodium bicarbonate solution (30 mL×2), dried over anhydrous sodium sulfate, and concentrated, and the residue was separated by column chromatography (PE/EA=5/1) to give compound 10-8 (215 mg, 47.5% yield) in the form of a yellow oily liquid. LC-MS [M+H]⁺: 347.1.

Step (7): Preparation of (+/−)-isopropyl (1S,3S)-3-(4-(4-(((cyclopentyl(methyl)carbamoyl)oxy)methyl)-2-methylthiazol-5-yl)phenoxy)cyclohexane-1-carboxylate

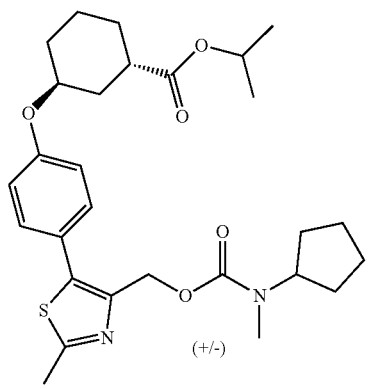

10-9

Compound 10-8 (215 mg, 0.62 mmol) and triphenylphosphine (650 mg, 2.48 mmol) were dissolved in anhydrous tetrahydrofuran (15 mL), and the reaction system was added with di-tert-butyl azodicarboxylate (570 mg, 2.48 mmol) and isopropyl (1S,3R)-3-hydroxycyclohexane-1-carboxylate (464 mg, 2.48 mmol), reacted at 60° C. for 12 h, cooled to room temperature, diluted with water (40 mL), and extracted with ethyl acetate (25 mL×3). The organic phases were combined, dried over anhydrous sodium sulfate, and concentrated, and the residue was separated by column chromatography (PE/EA=1/1) to give compound 10-9 in the form of a yellow oily liquid (250 mg, 78% yield). LC-MS [M+H]⁺: 515.7.

Step (8): Preparation of (+/−)-(1S,3S)-3-(4-(4-(((cyclopentyl(methyl)carbamoyl)oxy)methyl)-2-methylthiazol-5-yl)phenoxy)cyclohexane-1-carboxylic Acid

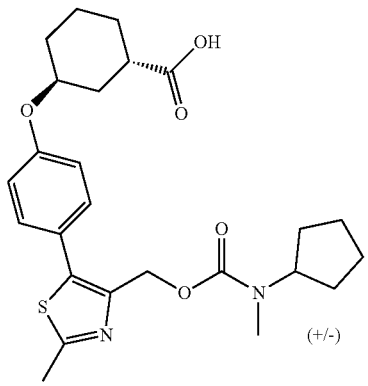

10

Compound 10-9 (250 mg, 0.49 mmol) and lithium hydroxide (42 mg, 1.00 mmol) were dissolved in methanol (4 mL) and water (2 mL), and the reaction system was stirred overnight at room temperature, concentrated to remove the methanol, adjusted to pH 5 with diluted hydrochloric acid (1 N), and extracted with ethyl acetate (10 mL×3). The organic phases were combined, dried over anhydrous sodium sulfate, concentrated, and the residue was purified by preparative HPLC to give compound 10 (105 mg, 45% yield) in the form of a white solid.

LC-MS [M+H]⁺: 473.7. ¹H NMR (400 MHz, CDCl₃) δ 7.37 (d, J=8.7 Hz, 2H), 6.96 (d, J=8.7 Hz, 2H), 5.15 (s, 2H), 4.69 (m, J=2.3 Hz, 1H), 4.54 (s, 1H), 2.91 (m, J=13.8, 4.9 Hz, 1H), 2.77 (s, 3H), 2.74 (s, 3H), 2.16 (m, J=13.3 Hz, 1H), 2.05-1.89 (m, 3H), 1.88-1.74 (m, 3H), 1.73-1.58 (m, 5H), 1.59-1.42 (m, 4H).

Example 11

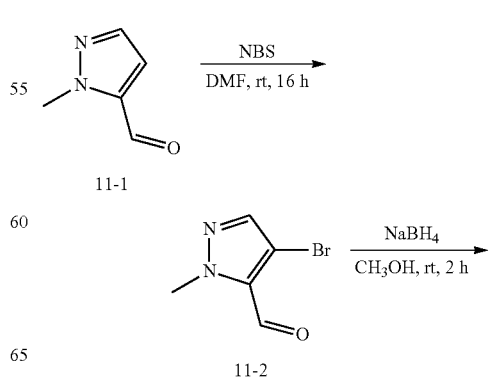

-continued

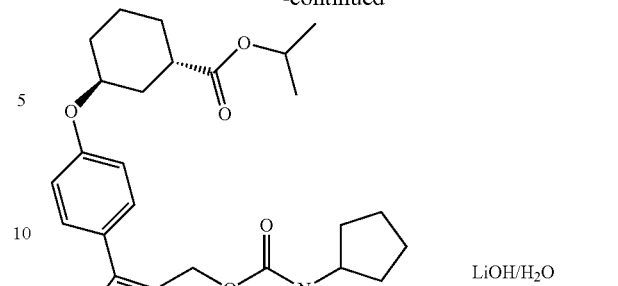

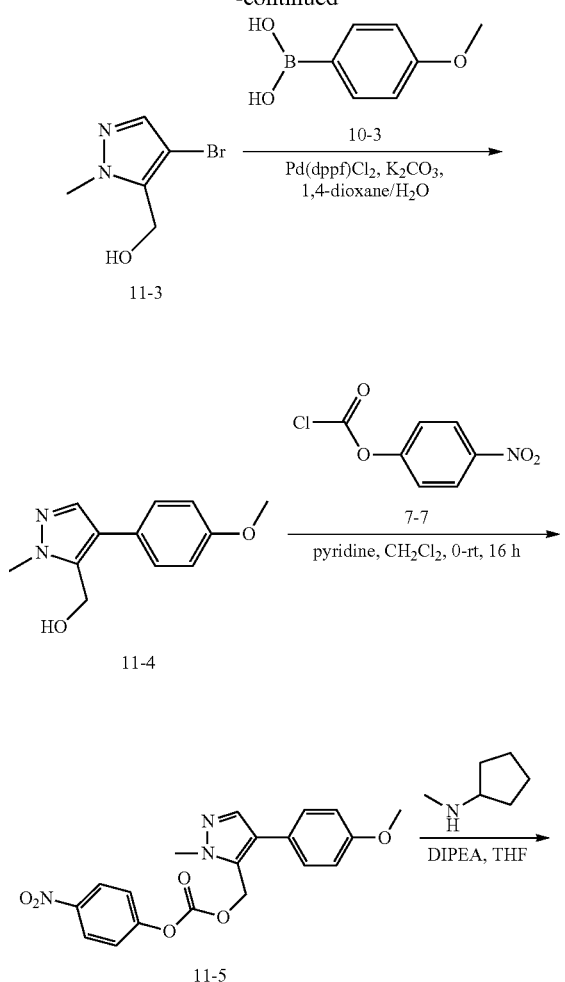

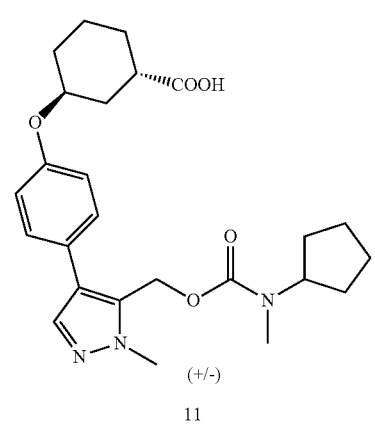

Step (1): Preparation of 4-bromo-1-methyl-pyrazole-3-carbaldehyde

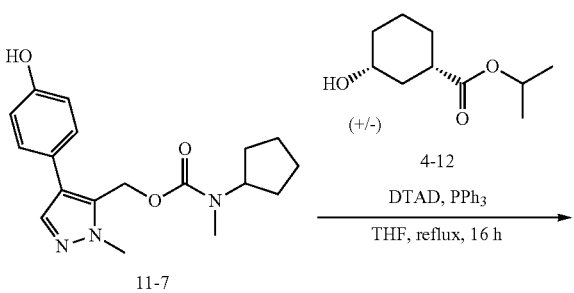

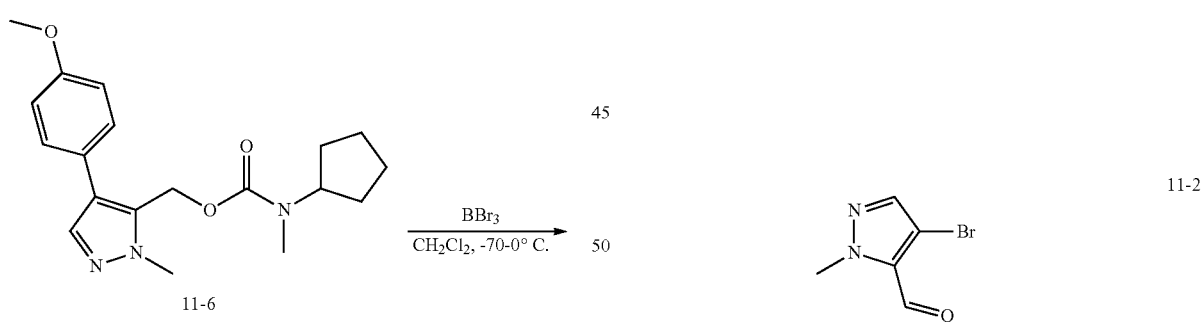

1-methyl-1H-pyrazole-5-carbaldehyde (2.00 g, 18.18 mmol) was dissolved in N,N-dimethylformamide (20 mL), and the reaction system was cooled to 0° C. The reaction system was added with N-bromosuccinimide (3.40 mg, 19.09 mmol), stirred overnight at room temperature, quenched with aqueous sodium hydroxide solution (19.09 mL, 1 mol/L) and extracted with ethyl acetate (70 mL×2). The organic phase was washed with saturated brine (30 mL×3), dried over anhydrous sodium sulfate and filtered, and the filtrate was concentrated by rotary evaporation to give compound 11-2 (2.90 g, 84% yield) in the form of a white solid. LC-MS [M−H]$^+$: 188.6, 190.6.

Step (2): Preparation of (4-bromo-1-methyl-1H-pyrazol-5-yl)methanol

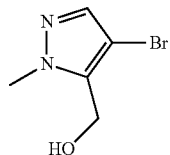

11-3

Compound 11-2 (2.90 g, 15.34 mmol) was dissolved in tetrahydrofuran (50 mL), and then the reaction system was cooled to 0° C., added with sodium borohydride (408 mg, 10.74 mmol) and stirred at room temperature for 2 h. The reaction system was then quenched with water (4 mL), and concentrated by rotary evaporation, and the residue was separated by column chromatography (ethyl acetate:petroleum ether=1:2) to give compound 11-3 (2.5 g, 85% yield) in the form of a white solid. LC-MS [M+H]$^+$: 190.7, 192.7.

Step (3): Preparation of (4-(4-methoxyphenyl)-1-methyl-1H-pyrazol-5-yl)methanol

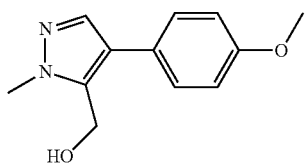

11-4

Compound 11-3 (800 mg, 4.19 mmol), 4-methoxyphenylboronic acid (760 mg, 5.03 mmol), and [1,1'-bis(diphenylphosphino)ferrocene]dichloropalladium(II) (178 mg, 025 mmol) were added to 1,4-dioxane (16 mL), and then the reaction system was added with a solution of potassium carbonate (1.45 g, 10.48 mmol) in water (4 mL) and reacted at 100° C. overnight under nitrogen atmosphere. The reaction system was filtered, and the organic phase was concentrated by rotary evaporation. The reaction system was extracted with ethyl acetate (30 mL×2) and concentrated, and the residue was separated by column chromatography (PE/EA=1/1) to give compound 11-4 (750 g, 82% yield) in the form of a brown solid. LC-MS [M+H]$^+$: 219.1.

Step (4): Preparation of (4-(4-methoxyphenyl)-1-methyl-1H-pyrazol-5-yl)methyl(4-nitrophenyl)carbonate

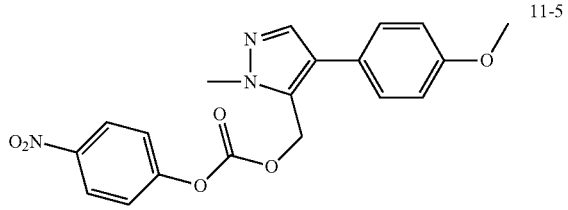 [SMILES: COc1ccc(-c2cnn(C)c2COC(=O)Oc2ccc([N+](=O)[O-])cc2)cc1]

11-5

Compound 11-4 (984 mg, 4.51 mmol) and pyridine (988 mg, 13.53 mmol) were dissolved in dichloromethane (20 mL), and 4-nitrophenyl chloroformate (1.36 g, 6.77 mmol) was added at 0° C., and the reaction system was stirred overnight at room temperature. The reaction system was then extracted with dichloromethane (50 mL×2), and the organic phases were combined, washed with saturated brine (20 mL) and concentrated, and the residue was separated by column chromatography (wet loading, petroleum ether/ethyl acetate=5/1) to give compound 11-5 (1.4 g, 81% yield) in the form of a pale yellow solid. LC-MS [M+H]$^+$: 384.5.

Step (5): Preparation of (4-(4-methoxyphenyl)-1-methyl-1H-pyrazol-5-yl)methylcyclopentyl(methyl)carbamate

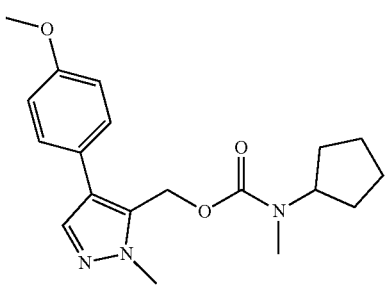

11-6

Compound 11-5 (1.4 g, 3.65 mmol) and N,N-diisopropylethylamine (1.41 g, 10.95 mmol) were added to anhydrous tetrahydrofuran (20 mL), and then N-methylcyclopentanamine hydrochloride (596 mg, 4.38 mmol) was added. The reaction system was reacted at room temperature overnight and extracted with ethyl acetate (50 mL×2). The organic phase was washed with saturated brine (20 mL), dried over anhydrous sodium sulfate and concentrated, and the residue was separated by column chromatography (PE/EA=1/1) to give compound 11-6 (900 mg, 72% yield) in the form of a colorless oil. LC-MS [M+H]$^+$: 344.1.

Step (6): Preparation of (4-(4-hydroxyphenyl)-1-methyl-1H-pyrazol-5-yl)methylcyclopentyl(methyl)carbamate

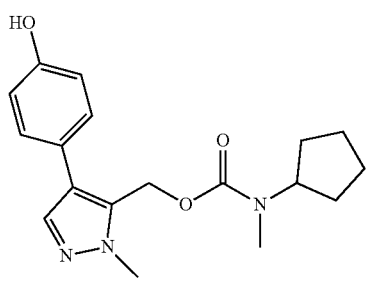

11-7

Compound 11-6 (900 mg, 2.62 mmol) was dissolved in anhydrous dichloromethane (12 mL), and a solution of boron tribromide in dichloromethane (4 mL, 1 mol/L) was added dropwise at −70° C. and reacted at 0° C. for 7 h. The reaction system was poured into ice water, and extracted with dichloromethane (50 mL×2). The organic phases were combined, washed with saturated brine (10 mL×2), dried over anhydrous sodium sulfate, filtered and concentrated, and the residue was separated by column chromatography (EA/PE=1/1) to give compound 11-7 (80 mg, 9% yield) in the form of a gray solid. LC-MS [M+H]⁺: 330.5.

Step (7): Preparation of (+/−)-isopropyl (1S,3S)-3-(4-(5-(((cyclopentyl(methyl)carbamoyl)oxy)methyl)-1-methyl-1H-pyrazol-4-yl)phenoxy)cyclohexane-1-carboxylate

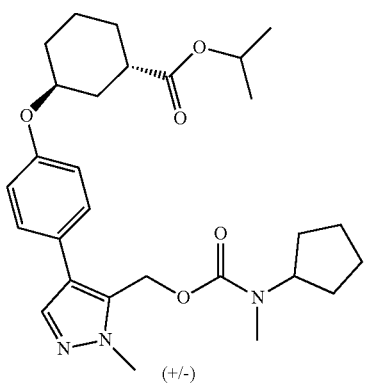

11-8

Compound 11-7 (80 mg, 0.24 mmol), (+/−)-isopropyl (1S,3S)-3-hydroxycyclohexane-1-carboxylate (178 mg, 0.96 mmol), triphenylphosphine (251 mg, 0.96 mmol) and di-tert-butyl azodicarboxylate (221 mg, 0.96 mmol) were dissolved in anhydrous tetrahydrofuran (8 mL), and the reaction system was reacted at 70° C. overnight. The reaction system was concentrated by rotary evaporation, added with water, and extracted with ethyl acetate (30 mL×2). The organic phases were combined, washed with saturated brine (10 mL×2), dried over anhydrous sodium sulfate, filtered and concentrated, and the residue was separated by column chromatography (EA/PE=1/1) to give compound 11-8 (60 mg, 49% yield) in the form of a colorless oil. LC-MS [M+H]⁺: 498.7.

Step (8): Preparation of (+/−)-(1S,3S)-3-(4-(5-(((cyclopentyl(methyl)carbamoyl)oxy)methyl)-1-methyl-1H-pyrazol-4-yl)phenoxy)cyclohexane-1-carboxylate

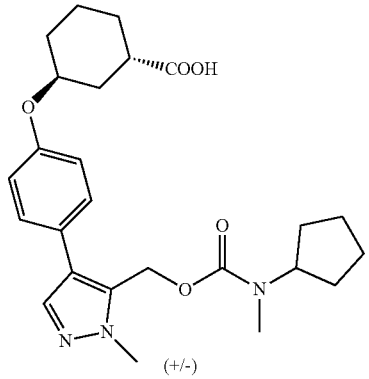

11

Compound 11-8 (60 mg, 0.12 mmol) was dissolved in methanol (3 mL) and tetrahydrofuran (3 mL), and then the reaction system was cooled to 0° C., added dropwise with aqueous lithium hydroxide solution (0.12 mL, 3 mol/L), and stirred overnight at room temperature. The reaction system was then concentrated under reduced pressure, adjusted to pH 3 with diluted hydrochloric acid (1 N), extracted with ethyl acetate (20 mL×2), and concentrated, and the residue was separated by preparative reverse phase chromatography to give compound 11 (9.0 mg, 16% yield) in the form of a white solid.

LC-MS [M+H]⁺: 456.2. ¹H NMR (400 MHz, CDCl₃) δ 7.59 (s, 1H), 7.34 (d, J=8.6 Hz, 2H), 6.97 (d, J=8.7 Hz, 2H), 5.21 (s, 2H), 4.71-4.65 (m, 1H), 4.65-4.30 (m, 1H), 3.99 (s, 3H), 2.97-2.90 (m, 1H), 2.80 (brs, 3H), 2.22-2.14 (m, 1H), 2.06-1.46 (m, 15H).

Example 12

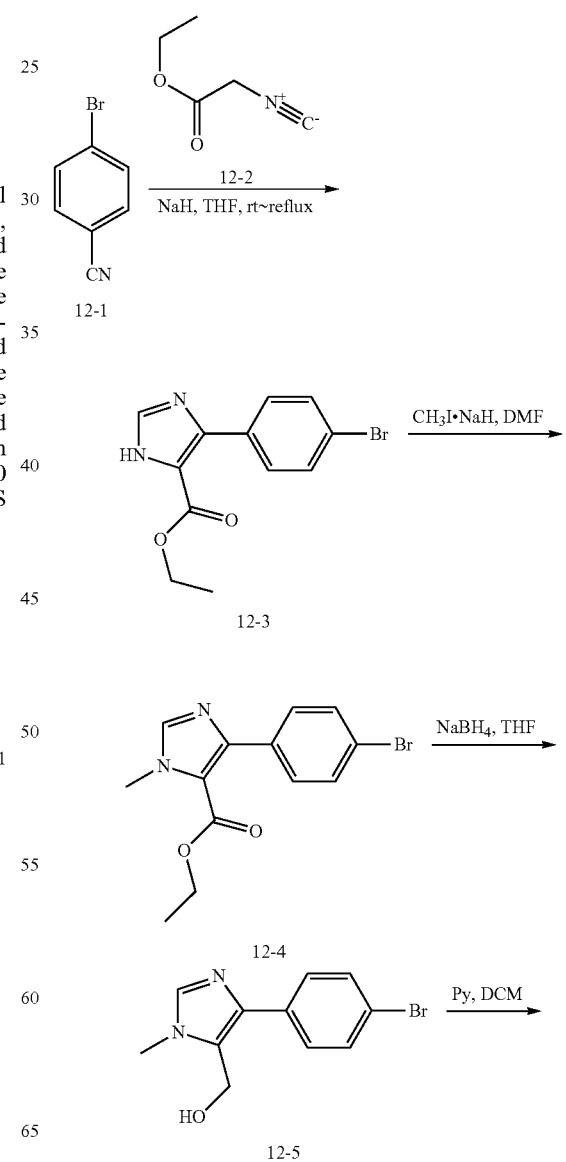

157

-continued

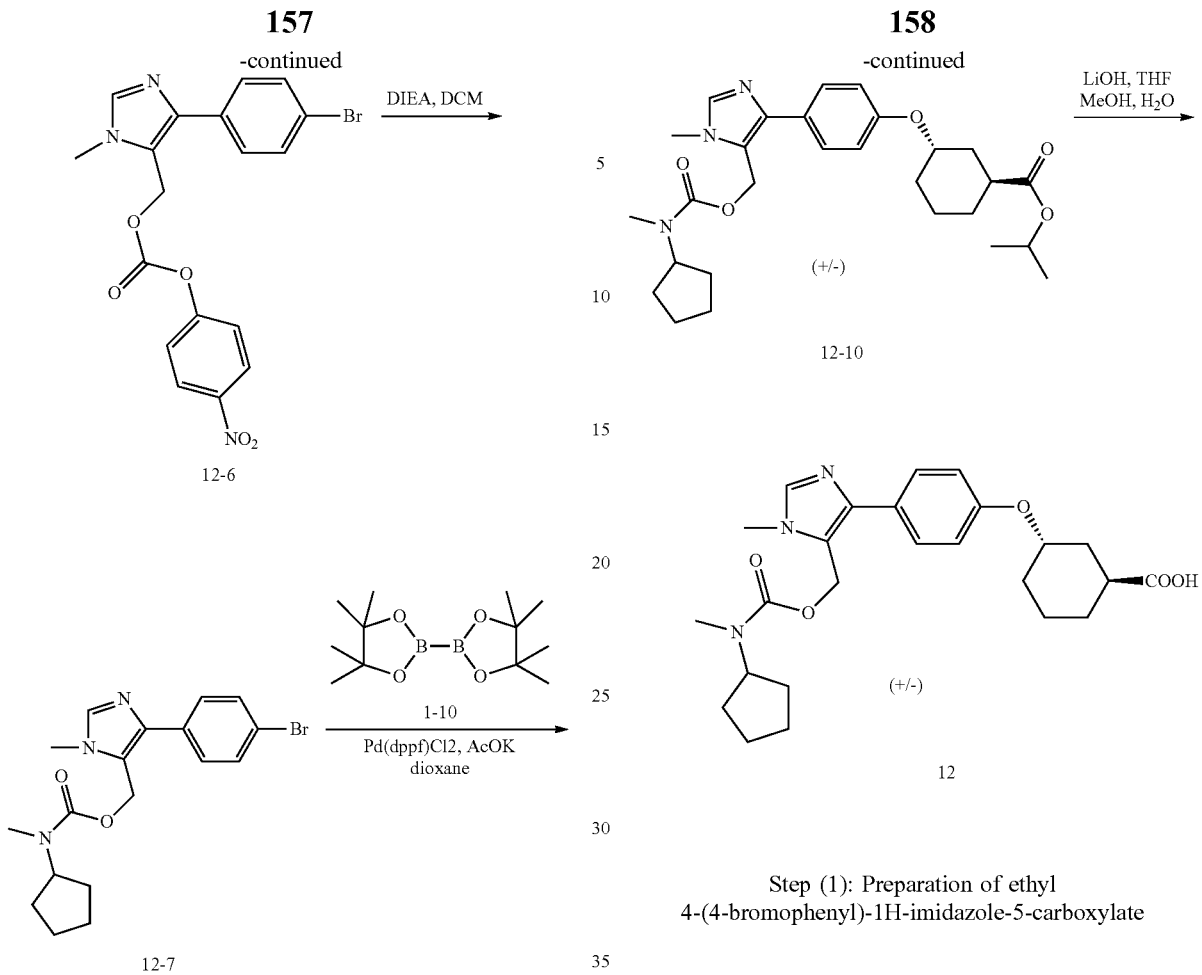

12-6

12-7

12-8

12-9

158

-continued 12-10

12

Step (1): Preparation of ethyl 4-(4-bromophenyl)-1H-imidazole-5-carboxylate

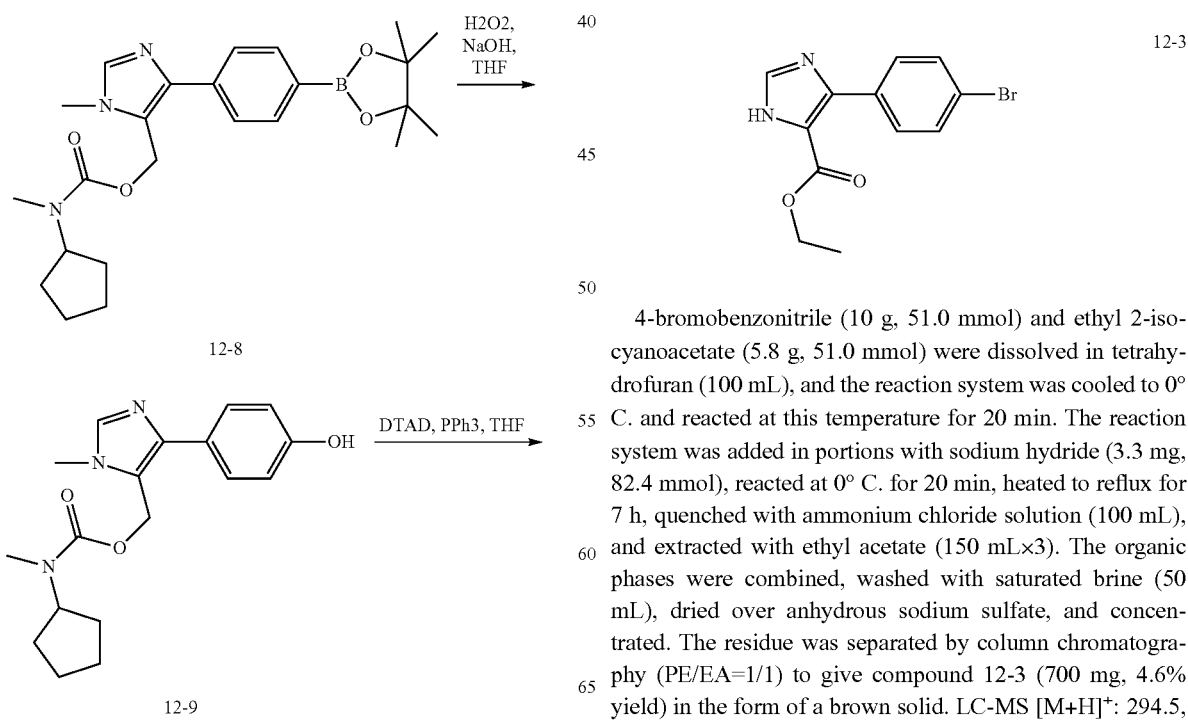

12-3

4-bromobenzonitrile (10 g, 51.0 mmol) and ethyl 2-isocyanoacetate (5.8 g, 51.0 mmol) were dissolved in tetrahydrofuran (100 mL), and the reaction system was cooled to 0° C. and reacted at this temperature for 20 min. The reaction system was added in portions with sodium hydride (3.3 mg, 82.4 mmol), reacted at 0° C. for 20 min, heated to reflux for 7 h, quenched with ammonium chloride solution (100 mL), and extracted with ethyl acetate (150 mL×3). The organic phases were combined, washed with saturated brine (50 mL), dried over anhydrous sodium sulfate, and concentrated. The residue was separated by column chromatography (PE/EA=1/1) to give compound 12-3 (700 mg, 4.6% yield) in the form of a brown solid. LC-MS [M+H]$^+$: 294.5, 296.5.

Step (2): Preparation of ethyl 4-(4-bromophenyl)-1-methyl-1H-imidazole-5-carboxylate

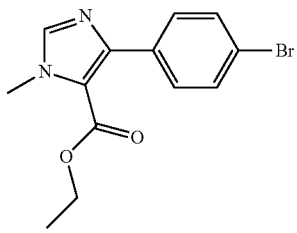

12-4

Compound 12-3 (700 g, 2.4 mmol) and sodium hydride (96 mg, 2.4 mmol) were dissolved in tetrahydrofuran (10 mL), and the reaction system was reacted at room temperature for 30 min. The reaction system was added with methyl iodide (412 mg, 2.88 mmol), reacted at room temperature for 2 h, quenched with water (20 mL), and extracted with ethyl acetate (30 mL×3). The organic phases were combined, washed with saturated brine (20 mL), dried over anhydrous sodium sulfate and concentrated, and the residue was separated by column chromatography (PE/EA=1/1) to give compound 12-4 (500 mg) in the form of a yellow oily liquid. LC-MS [M+H]$^+$: 308.7, 310.7.

Step (3): Preparation of (4-(4-bromophenyl)-1-methyl-1H-imidazol-5-yl)methanol

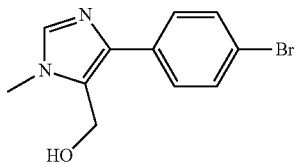

12-5

Compound 12-4 (500 g, 1.64 mmol) and sodium borohydride (3.1 g, 8.2 mmol) were dissolved in tetrahydrofuran (10 mL). The reaction system was heated to reflux overnight, quenched with ammonium chloride solution (10 mL), and extracted with ethyl acetate (30 mL×3). The organic phases were combined, washed with saturated brine (20 mL), dried over anhydrous sodium sulfate and concentrated to give compound 12-5 (50 mg) in the form of a yellow solid. LC-MS [M+H]$^+$: 266.5, 268.5.

Step (4): Preparation of (4-(4-bromophenyl)-1-methyl-1H-imidazol-5-yl)methylcyclopentyl(methyl) carbamate

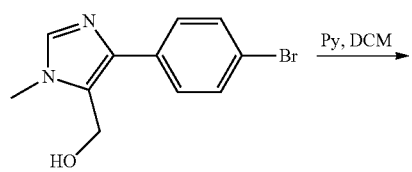

12-5

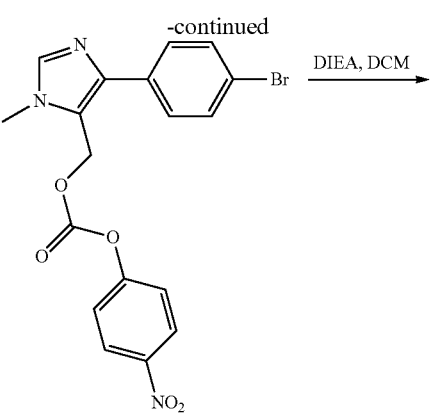

12-6

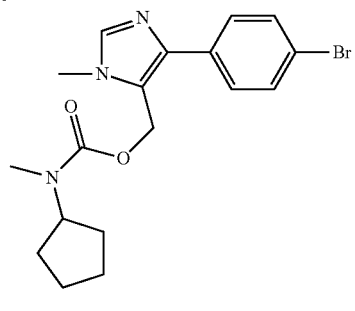

12-7

Compound 12-5 (250 mg, 0.94 mmol), pyridine (367 mg, 4.65 mmol) and p-nitrophenyl chloroformate (602 mg, 2.79 mmol) were dissolved in dichloromethane (5 mL), and the reaction system was reacted at room temperature overnight. The reaction system was quenched with water and extracted with ethyl acetate (15 mL×3). The organic phase was washed with saturated brine (15 mL), dried over anhydrous sodium sulfate, and concentrated. The residue was dissolved in dichloromethane, and the reaction system was added with DIEA (220 mg, 1.72 mmol) and N-methylcyclopentylamine hydrochloride (122 mg, 0.84 mmol), reacted at room temperature overnight, quenched with water, extracted with ethyl acetate (15 mL×3), and washed with saturated brine (15 mL). The organic phase was dried over anhydrous sodium sulfate and concentrated. The residue was separated by column chromatography (PE/EA=1/1) to give compound 12-7 (200 mg, 54.5% yield over two steps) in the form of a yellow solid. LC-MS [M+H]$^+$: 391.5, 393.5.

Step (5): Preparation of (4-(4-hydroxyphenyl)-1-methyl-1H-imidazol-5-yl)methylcyclopentyl(methyl) carbamate

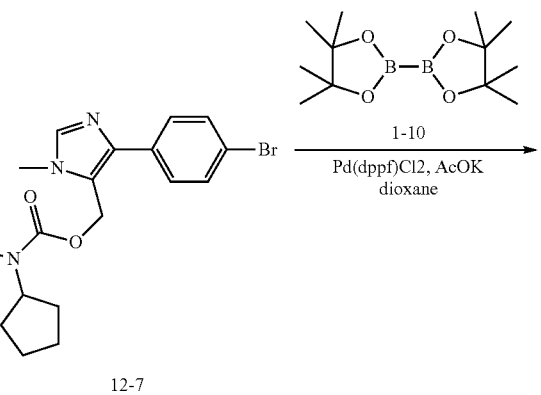

12-7

-continued

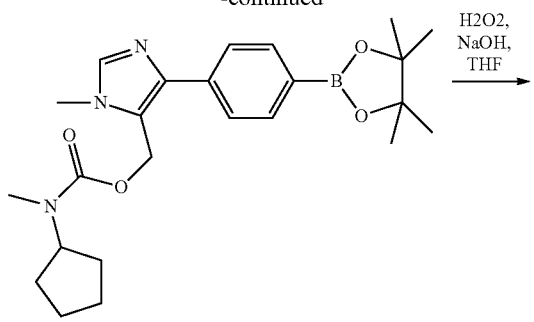

12-8

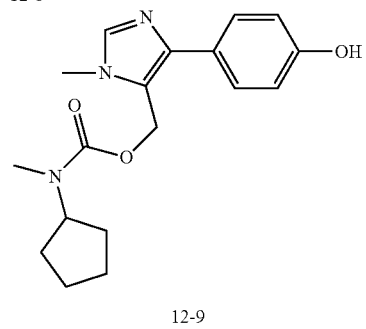

12-9

Compound 12-7 (200 mg, 0.51 mmol), 4,4,4',4',5,5,5',5'-octamethyl-2,2'-bi(1,3,2-dioxaborolane) (259 mg, 1.02 mmol), potassium acetate (150 mg, 1.53 mmol) and Pd(dppf)Cl$_2$ (37 mg, 0.051 mmol) were dissolved in anhydrous dioxane (5 mL), and the reaction system was stirred at 80° C. for 3 h, filtered, and concentrated. The residue was dissolved in tetrahydrofuran. The reaction system was cooled to 0° C., added with NaOH solution (1 mL, 1 N) and hydrogen peroxide (0.5 mL), reacted at 0° C. for 1 h, quenched with water and extracted with ethyl acetate (15 mL×3). The organic phases were washed with saturated brine (15 mL), dried over anhydrous sodium sulfate and concentrated, and the residue was separated by column chromatography (PE/EA=1/1) to give compound 12-9 (150 mg, 89.3% yield) in the form of a yellow oily liquid. LC-MS [M+H]$^+$: 330.2.

Step (6): Preparation of (+/−)-isopropyl (1S,3S)-3-(4-(5-(((cyclopentyl(methyl)carbamoyl)oxy)methyl)-1-methyl-1H-imidazol-4-yl)phenoxy)cyclohexane-1-carboxylate

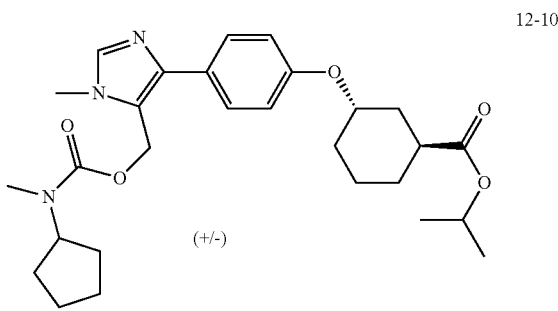 [SMILES: CC(C)OC(=O)[C@H]1CCC[C@H](Oc2ccc(-c3ncn(C)c3COC(=O)N(C)C3CCCC3)cc2)C1]

12-10

Compound 12-9 (150 mg, 0.3 mmol), isopropyl (1S,3R)-3-hydroxycyclohexane-1-carboxylate (223 mg, 1.2 mmol), di-tert-butyl azodicarboxylate (276 mg, 1.2 mmol) and triphenylphosphine (314 mg, 1.2 mmol) were dissolved in tetrahydrofuran (5 mL), and then the reaction system was reacted at 60° C. for 12 h under nitrogen atmosphere, quenched with water, and extracted with ethyl acetate (15 mL×3). The organic phases were combined, washed with saturated brine (15 mL), dried over anhydrous sodium sulfate and concentrated, and the residue was separated by column chromatography (PE/EA=2/1) to give compound 12-10 (100 mg) in the form of a yellow oily liquid. LC-MS [M+H]$^+$: 498.6.

Step (7): Preparation of (+/−)-(1S,3S)-3-(4-(5-(((cyclopentyl(methyl)carbamoyl)oxy)methyl)-1-methyl-1H-imidazol-4-yl)phenoxy)cyclohexane-1-carboxylate

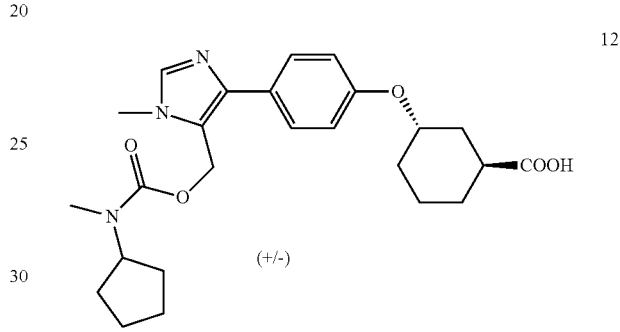

12

Compound 12-10 (100 mg, 0.2 mmol) and lithium hydroxide (24 mg, 1.0 mmol) were dissolved in a mixed solvent of THF (3 mL), MeOH (1 mL) and H$_2$O (1 mL), and then the reaction system was stirred overnight at room temperature, quenched with water (10 mL), and extracted with ethyl acetate (5 mL×3). The organic phase was dried over Na$_2$SO$_4$ and filtered, and the filtrate was concentrated by rotary evaporation. The residue was separated by column chromatography (DCM/MeOH=40/1) and lyophilized to give compound 12 (15 mg, 6% yield) in the form of a white solid.

$^1$H NMR (400 MHz, DMSO) δ 7.69 (s, 1H), 7.56 (d, J=8.7 Hz, 2H), 7.00 (d, J=8.7 Hz, 2H), 5.17 (s, 2H), 4.67 (s, 1H), 4.41 (s, 1H), 3.68 (s, 3H), 2.71 (s, 3H), 2.63 (s, 1H), 1.87-1.77 (m, 4H), 1.68-1.45 (m, 12H).

Example 13

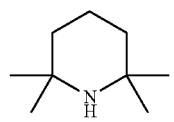

13-2

13-1 i: n-BuLi, THF, -40° C., 30 min
ii: B(OMe)$_3$, -78° C., 3 h
iii: H$_2$O$_2$, 0° C., 1 h

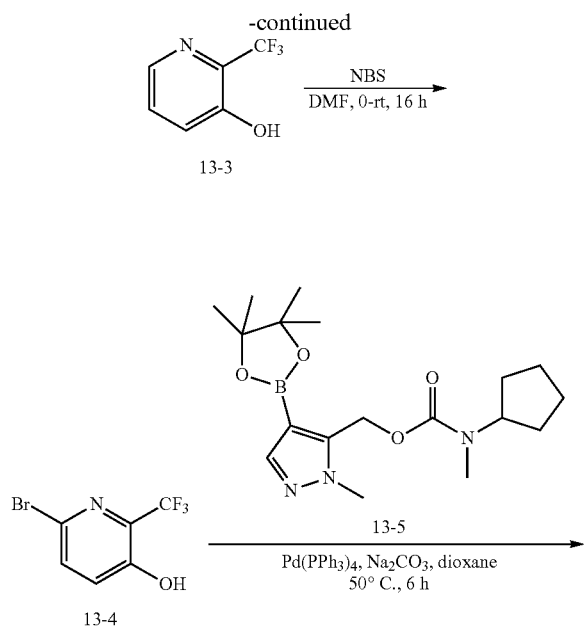

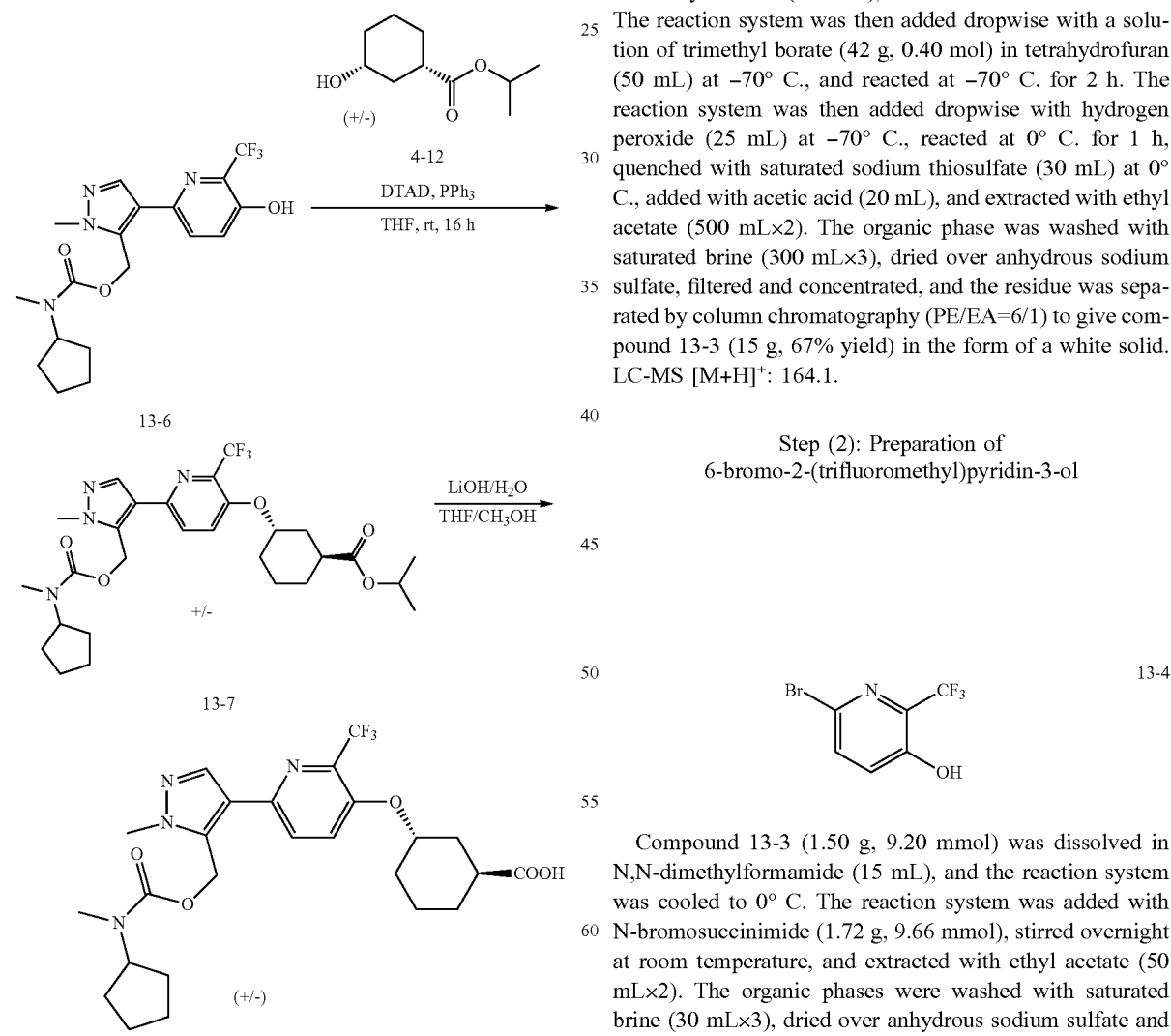

Step (1): Preparation of 2-(trifluoromethyl)pyridin-3-ol 2,2,6,6-tetramethylpiperidine (28.20 g, 0.20 mol) was dissolved in anhydrous tetrahydrofuran (500 mL), and the reaction system was added dropwise with n-butyllithium (70 mL, 2.4 mol/L) at −40° C., and reacted at 0° C. for 0.5 h. The reaction system was cooled to −78° C., added dropwise with a solution of 2-trifluoromethylpyridine (20.00 g, 0.14 mol) in tetrahydrofuran (100 mL), and reacted at −70° C. for 2 h. The reaction system was then added dropwise with a solution of trimethyl borate (42 g, 0.40 mol) in tetrahydrofuran (50 mL) at −70° C., and reacted at −70° C. for 2 h. The reaction system was then added dropwise with hydrogen peroxide (25 mL) at −70° C., reacted at 0° C. for 1 h, quenched with saturated sodium thiosulfate (30 mL) at 0° C., added with acetic acid (20 mL), and extracted with ethyl acetate (500 mL×2). The organic phase was washed with saturated brine (300 mL×3), dried over anhydrous sodium sulfate, filtered and concentrated, and the residue was separated by column chromatography (PE/EA=6/1) to give compound 13-3 (15 g, 67% yield) in the form of a white solid. LC-MS [M+H]$^+$: 164.1.

Step (2): Preparation of 6-bromo-2-(trifluoromethyl)pyridin-3-ol

Compound 13-3 (1.50 g, 9.20 mmol) was dissolved in N,N-dimethylformamide (15 mL), and the reaction system was cooled to 0° C. The reaction system was added with N-bromosuccinimide (1.72 g, 9.66 mmol), stirred overnight at room temperature, and extracted with ethyl acetate (50 mL×2). The organic phases were washed with saturated brine (30 mL×3), dried over anhydrous sodium sulfate and filtered, and the filtrate was concentrated by rotary evaporation to give compound 13-4 (1 g, 45% yield) in the form of a white solid. LC-MS [M+H]$^+$: 241.6, 243.6.

Step (3): Preparation of (4-(5-hydroxy-6-(trifluoromethyl)pyridin-2-yl)-1-methyl-1H-pyrazol-5-yl)methylcyclopentyl(methyl)carbamate

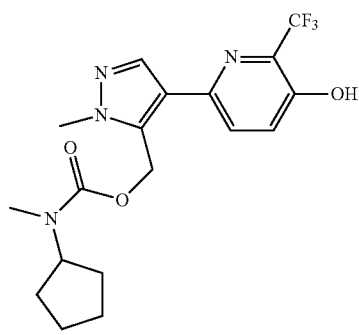

13-6

Compound 13-4 (500 mg, 2.07 mmol), compound 13-5 (1.13 g, 3.11 mmol), and tetrakis(triphenylphosphine)palladium(0) (191 mg, 0.17 mmol) were added to 1,4-dioxane (16 mL), and then the reaction system was added with a solution of sodium carbonate (439 mg, 4.14 mmol) in water (4 mL) and reacted at 85° C. overnight under nitrogen atmosphere. The reaction system was filtered, and the organic phase was concentrated by rotary evaporation. The reaction system was extracted with ethyl acetate (50 mL×2) and concentrated, and the residue was separated by column chromatography (PE/EA=5/1) to give compound 13-6 (210 mg, 26% yield) in the form of a colorless oil. LC-MS [M+H]$^+$: 399.5.

Step (4): Preparation of (+/−)-isopropyl (1S,3S)-3-((6-(5-(((cyclopentyl(methyl)carbamoyl)oxy)methyl)-1-methyl-1H-pyrazol-4-yl)-2-(trifluoromethyl)pyridin-3-yl)oxo)cyclohexane-1-carboxylate

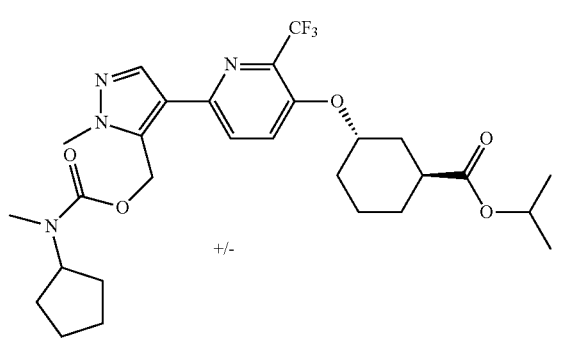

13-7

Compound 13-6 (210 mg, 0.53 mmol), isopropyl (1S,3R)-3-hydroxycyclohexane-1-carboxylate (394 mg, 2.12 mmol), triphenylphosphine (555 mg, 2.12 mmol) and Di-tert-butyl azodicarboxylate (488 mg, 2.12 mmol) were dissolved in anhydrous tetrahydrofuran (10 mL), and the reaction system was reacted at room temperature overnight. The reaction system was concentrated by rotary evaporation, added with water, and extracted with ethyl acetate (30 mL×2). The organic phases were combined, washed with saturated brine (10 mL×2), dried over anhydrous sodium sulfate, filtered and concentrated, and the residue was separated by column chromatography (EA/PE=1/1) to give compound 13-7 (120 mg, 40% yield) in the form of a colorless oil. LC-MS [M+H]$^+$: 567.3.

Step (5): Preparation of (+/−)-(1S,3S)-3-((6-(5-(((cyclopentyl(methyl)carbamoyl)oxy)methyl)-1-methyl-1H-pyrazol-4-yl)-2-(trifluoromethyl)pyridin-3-yl)oxy)cyclohexane-1-carboxylic Acid

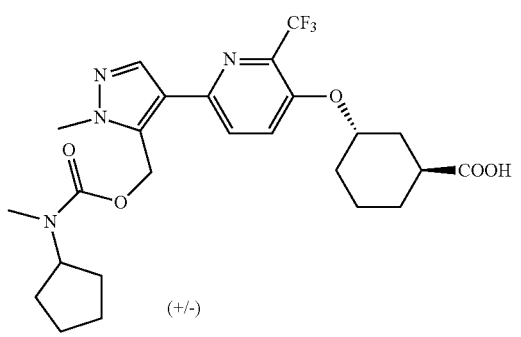

13

Compound 13-7 (120 mg, 0.21 mmol) was dissolved in methanol (3 mL) and tetrahydrofuran (3 mL), and then the reaction system was cooled to 0° C., added dropwise with aqueous lithium hydroxide solution (0.21 mL, 3 mol/L), and stirred overnight at room temperature. The reaction system was then concentrated under reduced pressure, adjusted to pH 3 with diluted hydrochloric acid (0.7 mL, 1 mol/L), extracted with ethyl acetate (20 mL×2), and concentrated, and the residue was separated by preparative reverse phase chromatography to give compound 13 (24 mg, 22% yield) in the form of a white solid.

LC-MS [M+H]$^+$: 525.2. $^1$H NMR (400 MHz, MeOD) δ 7.93 (s, 1H), 7.86 (d, J=8.8 Hz, 1H), 7.72 (d, J=8.9 Hz, 1H), 5.62 (s, 2H), 4.95-4.91 (m, 1H), 4.57-4.15 (m, 1H), 3.99 (s, 3H), 2.82-2.74 (m, 1H), 2.74 (s, 3H), 2.18-2.10 (m, 1H), 2.03-1.88 (m, 3H), 1.85-1.51 (m, 12H).

Example 14

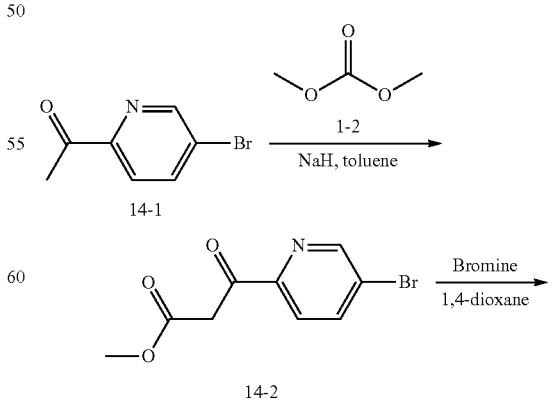

-continued

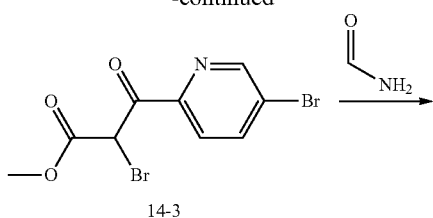
14-3

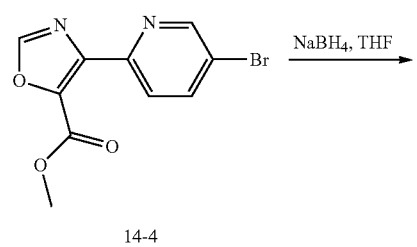
14-4

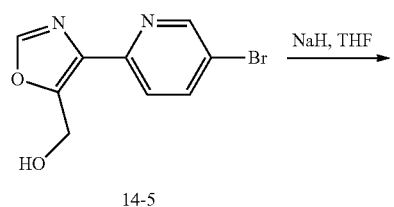
14-5

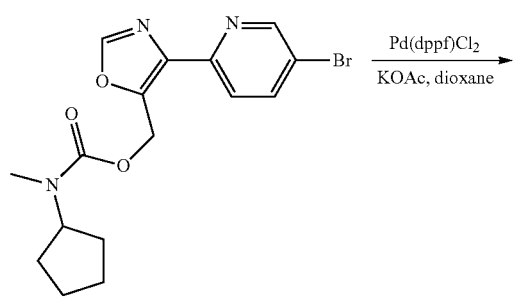
14-6

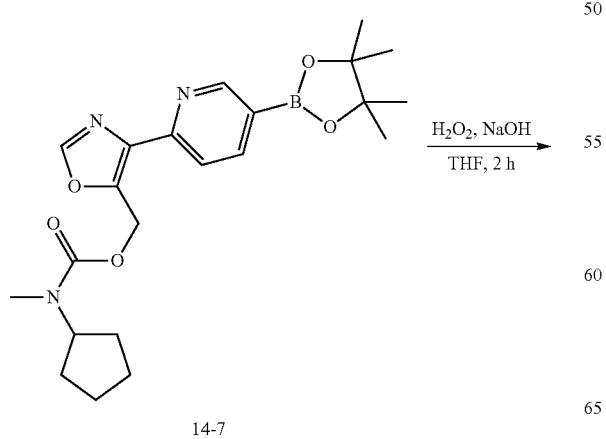
14-7

-continued

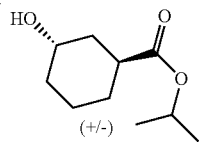
14-9

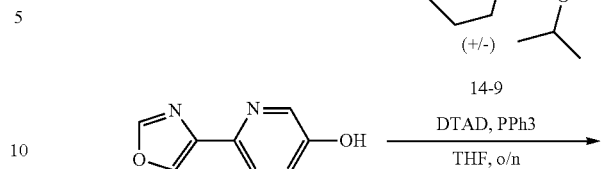
14-8

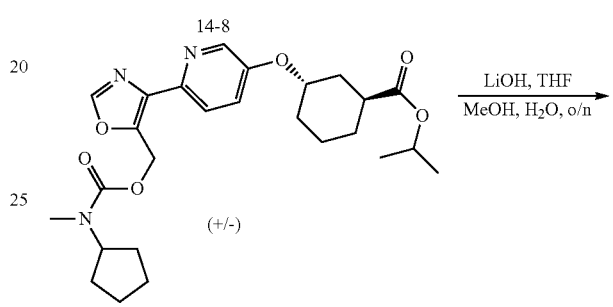
14-10

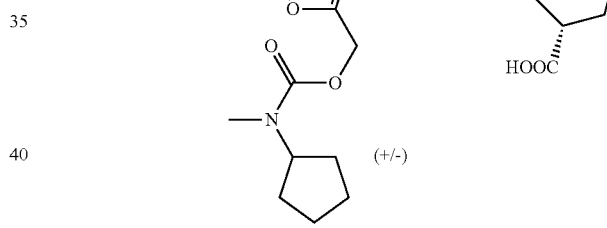
14

Step (1): Preparation of methyl 3-(5-bromopyridin-2-yl)-3-oxopropionate

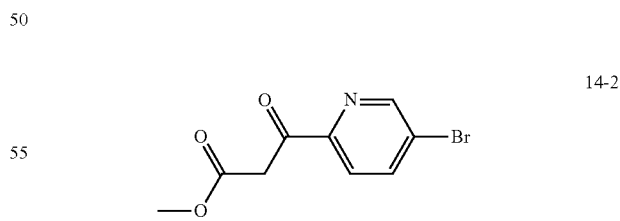
14-2

1-(5-bromopyridin-2-yl)ethan-1-one (15 g, 75.9 mmol) was dissolved in toluene (250 mL), sodium hydride (6 g, 151.8 mmol) and dimethyl carbonate (20.7 g, 226.8 mmol) were added at 0° C. under nitrogen atmosphere, and the reaction system was heated to reflux and stirred overnight. When TLC plate showed that no starting material remained, the reaction system was slowly poured into ice water (500 mL) and stirred to quench the reaction, diluted hydrochloric acid (3 N) was added to adjust the pH of the reaction system to 2-3, and the reaction system was extracted with ethyl acetate (250 mL×3), and then washed with saturated brine (200 mL×2). The organic phase was dried over anhydrous sodium sulfate and filtered. The filtrate was concentrated by rotary evaporation to give a crude production, and the crude product was purified by silica gel column chromatography (petroleum ether:ethyl acetate=2:1) to give compound 14-2 (5 g, 33.23% yield) in the form of a pale yellow solid. LC-MS [M+H]$^+$: 257.6, 259.6.

Step (2): Preparation of methyl 2-bromo-3-(5-bromopyridin-2-yl)-3-oxopropionate

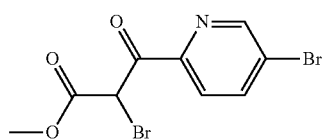

14-3

Compound 14-2 (5 g, 31.2 mmol) was dissolved in 1,4-dioxane (150 mL), and the reaction system was cooled to 0° C., added with bromine (1.2 mL, 22.5 mmol) and stirred overnight. When TLC plate showed that no starting material remained, the reaction system was concentrated by rotary evaporation to give brown-yellow compound 14-3 (7 g, crude) for use in next step. LC-MS [M+H]$^+$: 335.6, 337.5, 339.6.

Step (3): Preparation of methyl 4-(5-bromopyridin-2-yl)oxazole-5-carboxylate

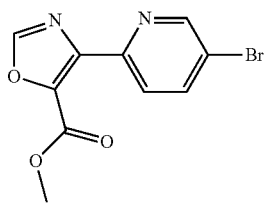

14-4

Compound 14-3 (7 g, crude) was added to formamide solution (50 mL). The reaction system was stirred at 110° C. for 1.5 h, cooled to room temperature, added with water (50 mL) to quench the reaction, and extracted with ethyl acetate (35 mL×3). The organic phases were combined, washed with saturated brine (50 mL), dried over anhydrous sodium sulfate and filtered. The filtrate was concentrated by rotary evaporation to give a crude product, and the crude product was purified by silica gel column chromatography (petroleum ether:ethyl acetate=3:1) to give compound 14-4 (2.6 g, 29.65% yield) in the form of a pale yellow solid. LC-MS [M+H]$^+$: 282.6, 284.6.

Step (4): Preparation of (4-(5-bromopyridine)oxazol-5-yl)methanol

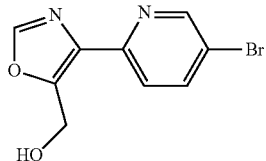

14-5

Compound 14-4 (600 mg, 2.13 mmol) was dissolved in a mixed solution of tetrahydrofuran (15 mL) and water (0.2 mL), and sodium borohydride (162 mg, 4.27 mmol) was added at 0° C. The reaction system was warmed to room temperature and reacted for 3 h. When TLC plate showed that no starting material remained, the reaction system was diluted with water (20 mL) and extracted with ethyl acetate (10 mL×3). The organic phase was dried over anhydrous sodium sulfate and filtered. The filtrate was concentrated by rotary evaporation, and the residue was purified by silica gel column chromatography (dichloromethane:methanol=20:1) to give compound 14-5 (100 mg, 18.48% yield) in the form of a brown solid. LC-MS [M+H]$^+$: 254.7, 256.7.

Step (5): Preparation of (4-(5-bromopyridin-2-yl)oxazol-5-yl)methylcyclopentyl(methyl)carbamate

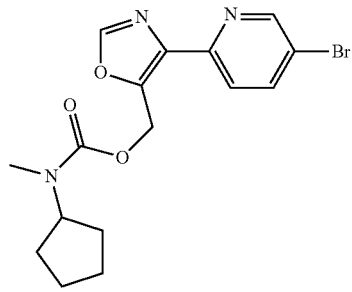

14-6

Compound 14-5 (100 mg, 0.39 mmol) and sodium hydride (47 mg, 1.18 mmol) were dissolved in tetrahydrofuran (5 mL), and the reaction system was stirred for 10 min, added with 4-nitrophenylcyclopentyl(methyl)carbamate (125 mg, 0.47 mmol), warmed to room temperature and reacted for 3 h. The reaction system was added with water (10 mL) to quench the reaction, extracted with ethyl acetate (5 mL×3), and washed with saturated brine (5 mL). The organic phase was dried over anhydrous sodium sulfate and filtered. The filtrate was concentrated by rotary evaporation, and the residue was purified by silica gel column chromatography (dichloromethane:ethyl acetate=10:1) to give compound 14-6 (95 mg, 64.27% yield) in the form of a white solid. LC-MS [M+H]$^+$: 379.9, 381.9.

Step (6): Preparation of (4-(4-(4,4,5,5-tetramethyl-1,3,2-dioxaborolan-2-yl)pyridine)oxazol-5-yl) methylbenzyl(methyl)carbamate

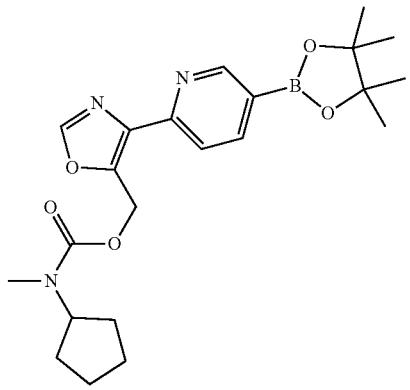

14-7

Compound 14-6 (95 mg, 0.25 mmol) was dissolved in 1,4-dioxane (10 mL), and the reaction system was sequentially added with bis(pinacolato)diboron (126 mg, 0.50 mmol), potassium acetate (73 mg, 0.75 mmol) and [1,1'-bis(diphenylphosphino)ferrocene]dichloropalladium(II) (18 mg, 0.03 mmol), heated at 80° C. for 4 h and filtered. The filtrate was concentrated by rotary evaporation to give compound 14-7 (400 mg, crude) in the form of a brown-black solid. LC-MS [M+H]$^+$: 428.7.

Step (7): Preparation of (4-(4-hydroxypyridine)oxazol-5-yl)methylbenzyl(methyl)carbamate

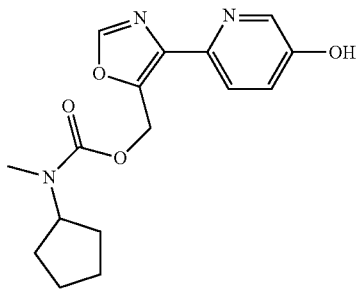

14-8

Compound 14-7 (400 mg, crude) was dissolved in tetrahydrofuran (10 mL), and the reaction system was cooled to 0° C., sequentially added with sodium hydroxide solution (1 N, 0.4 mL, 0.4 mmol) and hydrogen peroxide (20 mL), and stirred at 0° C. for 2 h. When TLC plate showed that no starting material remained, the reaction system was diluted with water (20 mL), extracted with ethyl acetate (20 mL), and wash with saturated brine (20 mL). The organic phase was dried over anhydrous sodium sulfate and filtered. The filtrate was concentrated by rotary evaporation, and the residue was purified by silica gel column chromatography (dichloromethane:methanol=50:1) to give compound 14-8 (30 mg, 37.85% yield) in the form of a white solid. LC-MS [M+H]$^+$: 318.9.

Step (8): Preparation of (+/−)-isopropyl (1S,3S)-3-((6-(5-(((cyclopentyl(methyl)carbamoyl)oxy)methyl)oxazol-4-yl)pyridin-3-yl)oxy)cyclohexane-1-carboxylate

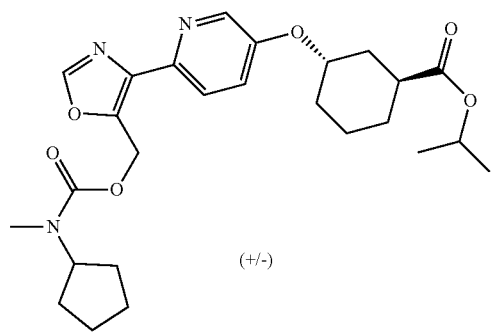

14-10
(+/−)

Compound 14-8 (30 mg, 0.09 mmol) and isopropyl (3S)-3-hydroxycyclohexane-1-carboxylate (64 mg, 0.38 mmol), DTAD (87 mg, 0.38 mmol) and PPh$_3$ (99 mg, 0.38 mmol) were dissolved in tetrahydrofuran (10 mL), and the reaction system was stirred overnight at room temperature under nitrogen atmosphere. The reaction system was purified by silica gel column chromatography (dichloromethane/ethyl acetate=5/1) to give compound 14-10 (30 mg, 65.38% yield) in the form of a white solid. LC-MS [M+H]$^+$: 486.7.

Step (9): Preparation of (+/−)-(1S,3S)-3-(4-(5-(((benzyl(methyl)carbamoyl)oxy)methyl)oxazol-4-yl) phenoxy)cyclohexane-1-carboxylic Acid

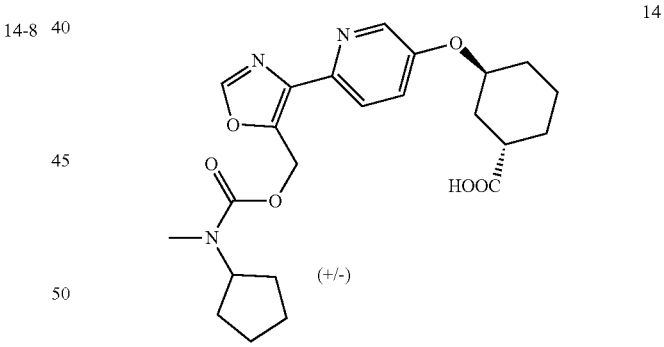

14
(+/−)

Compound 14-10 (30 mg, 0.06 mmol) was dissolved in tetrahydrofuran (3 mL), and the reaction system was added sequentially with methanol (1 mL), water (1 mL) and lithium hydroxide (30 mg, 0.31 mmol), and stirred overnight at room temperature. Then water (10 mL) was added for dilution, and the organic solvent was removed by rotary evaporation under reduced pressure. The aqueous phase was adjusted to pH 2-3 with hydrochloric acid (1 N), and extracted with dichloromethane (10 mL×2). The organic phase was dried over anhydrous sodium sulfate and filtered, and the filtrate was concentrated by rotary evaporation. The residue was purified by silica gel column chromatography (DCM/MeOH=20/1) and then lyophilized to give compound 14 (9 mg) in the form of a white solid.

LC-MS [M+H]⁺: 444.7. ¹H NMR (400 MHz, MeOD) δ 8.30 (s, 2H), 8.00 (s, 1H), 7.56 (s, 1H), 5.71 (s, 2H), 4.83 (s, 2H), 4.46 (s, 1H), 2.79 (s, 4H), 2.16-1.87 (m, 4H), 1.74 (d, J=24.0 Hz, 8H), 1.57 (s, 4H).
Example 15
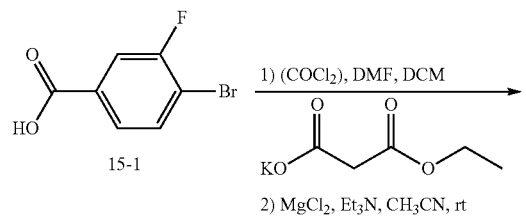
15-1
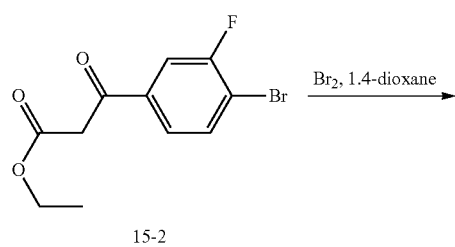
15-2
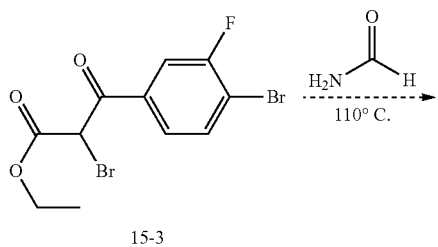
15-3
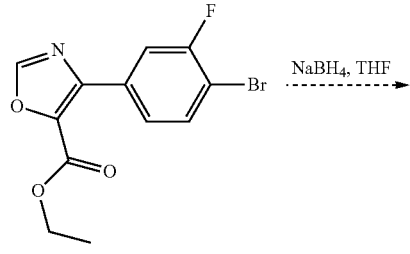
15-4
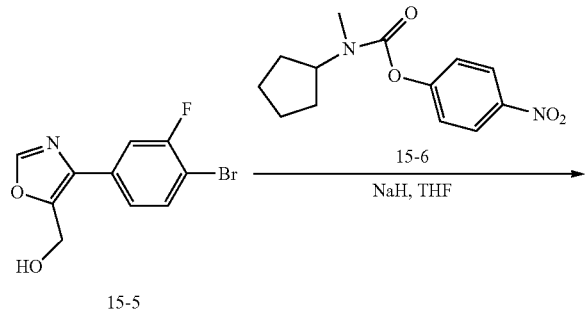
15-5
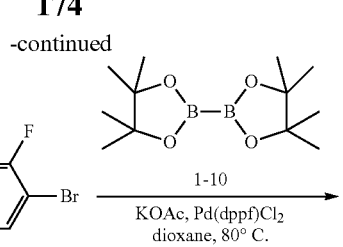
15-7
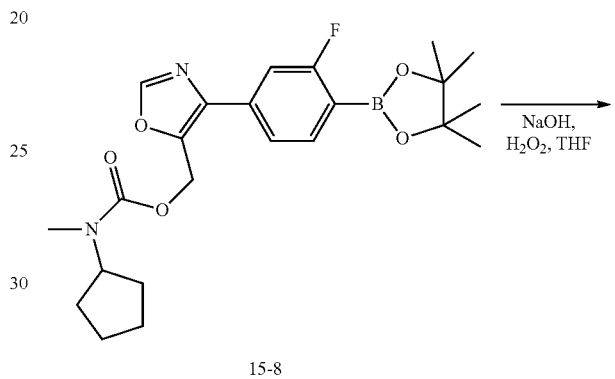
15-8
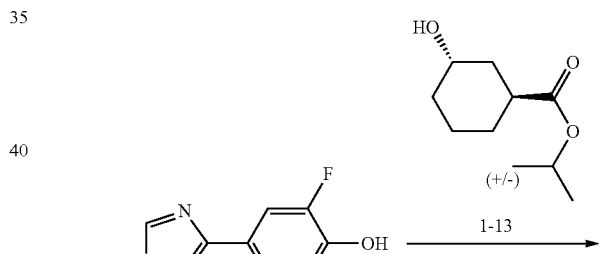
15-9
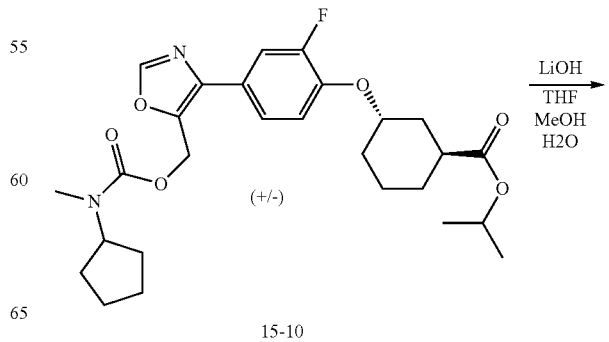
15-10

-continued

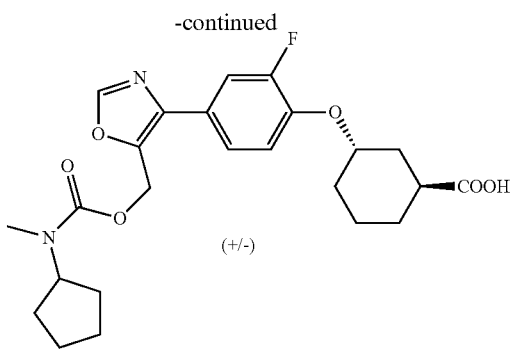

15 (+/-)

Step (1): Preparation of methyl 4-(((cyclopropylmethyl)amino)methyl)benzoate

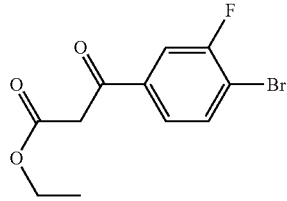

15-2

4-bromo-3-fluorobenzoic acid (14.5 g, 66.0 mmol) was dissolved in anhydrous dichloromethane (90 mL), and the reaction system was added dropwise with oxalyl chloride (13.3 g, 105.1 mmol) and N,N-dimethylformamide (0.2 mL) in an ice water bath, and stirred at room temperature for 2 h. Potassium 3-ethoxy-3-oxopropionate (13.7 g, 78.2 mmol) was dissolved in anhydrous acetonitrile (164 mL), and the reaction system was added with triethylamine (25 mL), reacted in an ice water bath for 10 min, added with anhydrous magnesium chloride (9.0 g, 94.0 mmol), and reacted for 3 h. 4-bromo-3-fluorobenzoic acid reaction system was concentrated and then added dropwise with potassium 3-ethoxy-3-oxopropionate and stirred overnight. The reaction system was reacted in an ice bath, added dropwise with hydrochloric acid (200 mL, 2 N), and stirred for 1.5 h. The reaction system was extracted with ethyl acetate (300 mL×2). The organic phases were combined, washed with saturated sodium bicarbonate (200 mL) and saturated brine (200 mL), and dried over anhydrous sodium sulfate to give compound 15-2 (17.0 g, 90% yield) in the form of a pale yellow oily liquid. LC-MS [M+H]⁺: 288.6, 290.6.

Step (2): Preparation of ethyl 2-bromo-3-(4-bromo-3-fluorophenyl)-3-oxopropionate

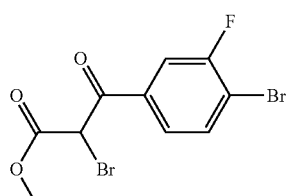

15-3

Compound 15-2 (17.0 g, 60 mmol) was dissolved in dioxane (180 mL), and the reaction system was stirred under an ice water bath, cooled to 0° C., added dropwise with bromine (10.4 g, 65 mmol), and stirred overnight at room temperature. Then the reaction system was added with saturated aqueous sodium thiosulfate solution (30 mL) to quench the reaction, diluted with water (300 mL), and extracted with ethyl acetate (250 mL×2). The organic phases were combined, washed with saturated brine (200 mL), dried over anhydrous sodium sulfate, filtered and concentrated to give compound 15-3 (17.4 g, 71% yield) in the form of a yellow oily liquid. LC-MS [M+H]⁺: 366.6, 368.5, 370.6.

Step (3): Preparation of ethyl 4-(4-bromo-3-fluorophenyl)oxazole-5-carboxylate

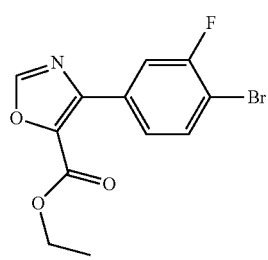

15-4

Compound 15-3 (17.4 g, 48.9 mmol) was dissolved in formamide (100 mL), and the reaction system was warmed to 110° C. and stirred overnight. Then the reaction system was cooled to room temperature, diluted with H₂O (300 mL) and extracted with ethyl acetate (150 mL×2). The organic phases were combined, washed with saturated brine (150 mL), dried over anhydrous sodium sulfate, filtered and concentrated, and the residue was separated by column chromatography (PE/EA=20/1) to give compound 15-4 (2.2 g, 15% yield) in the form of a colorless oily liquid. LC-MS [M+H]⁺: 313.2, 315.2.

Step (4): Preparation of (4-(4-bromo-3-fluorophenyl)oxazol-5-yl)methanol

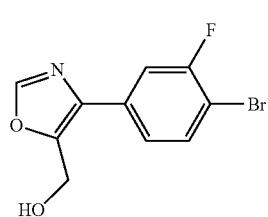

15-5

Compound 15-4 (950 mg, 3.1 mmol) was dissolved in tetrahydrofuran (15 mL), and the reaction system was added with sodium borohydride (470 mg, 12.4 mmol), warmed to 40° C. and reacted overnight. Then the reaction system was cooled to room temperature, quenched with saturated aqueous ammonium chloride solution (10 mL), diluted with water (40 mL), and extracted with ethyl acetate (20 mL×2). The organic phases were combined, washed with saturated brine (20 mL), dried over anhydrous sodium sulfate, filtered and concentrated, and the residue was separated by column chromatography (PE/EA=1/1) to give compound 15-5 (424 mg, 53% yield) in the form of a white solid. LC-MS [M+H]+: 271.1, 273.1.

Step (5): Preparation of (4-(4-bromo-3-fluorophenyl)oxazol-5-yl)methylcyclopentyl(methyl)carbamate

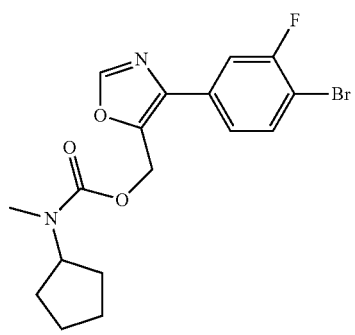

15-7

Compound 15-5 (424 mg, 1.56 mmol) was dissolved in tetrahydrofuran (10 mL), and the reaction system was added in portions with sodium hydride (93 mg, 2.34 mmol) in an ice water bath, and stirred for 15 min. The reaction system was added with 4-nitrophenylcyclopentyl(methyl)carbamate (479 mg, 1.87 mmol), and stirred overnight at room temperature. The reaction system was added with saturated aqueous ammonium chloride solution (10 mL) to quench the reaction, diluted with water (40 mL), and extracted with ethyl acetate (20 mL×2). The organic phases were combined, washed with saturated brine (20 mL), dried over anhydrous sodium sulfate, filtered and concentrated, and the residue was separated by column chromatography (PE/EA=8/1) to give compound 15-7 (322 mg, 98% purity, 51% yield) in the form of a white solid. LC-MS [M+H]+: 396.2, 398.2.

Step (6): Preparation of (4-(3-fluoro-4-(4,4,5,5-tetramethyl-1,3,2-dioxaborolan-2-yl)phenyl)oxazol-5-yl)methylcyclopentyl(methyl)carbamate

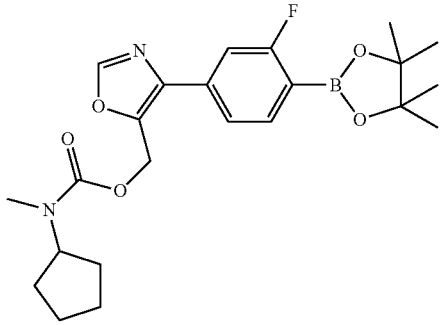

15-8

Compound 15-7 (200 mg, 0.5 mmol), compound 1-10 (190 mg, 0.75 mmol), potassium acetate (98 mg, 1.0 mmol) and [1,1'-bis(diphenylphosphino)ferrocene]dichloropalladium(II) (37 mg, 0.05 mmol) were added to anhydrous dioxane (5 mL), and the reaction system was warmed to 100° C. and reacted for 4 h under nitrogen atmosphere. The reaction system was cooled to room temperature and filtered, and the filtrate was concentrated by rotary evaporation to give compound 15-8 (200 mg) in the form of a black-brown solid. LC-MS [M+H]+: 444.7.

Step (7): Preparation of (4-(3-fluoro-4-hydroxyphenyl)oxazol-5-yl)methylcyclopentyl(methyl)carbamate

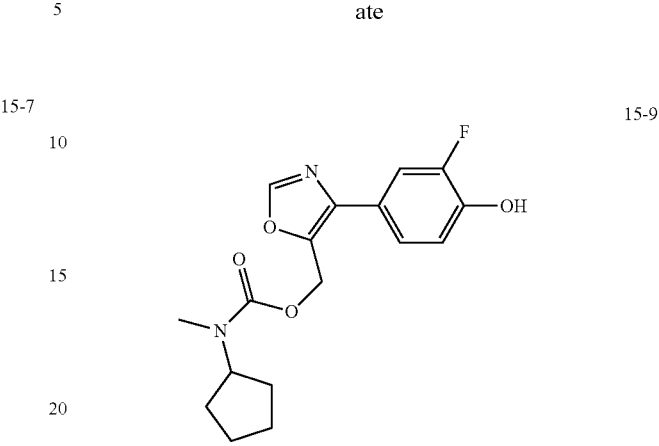

15-9

Compound 15-8 (200 mg, 0.45 mmol) was dissolved in tetrahydrofuran (5 mL), and the reaction system was added dropwise with hydrogen peroxide (0.5 mL) and sodium hydroxide (0.2 mL, 1 N) in an ice water bath, reacted at room temperature for 4 h, and added with saturated sodium thiosulfate solution (2 mL) to quench the reaction. The reaction system was diluted with water (10 mL). Then the reaction system was extracted with ethyl acetate (15 mL×2). The organic phases were washed with saturated brine (15 mL×2), dried over anhydrous sodium sulfate, filtered and concentrated, and the residue was separated by column chromatography (DCM/CH$_3$OH=50/1) to give compound 15-9 (142 mg, 85% yield over two steps) in the form of a white solid. LC-MS [M+H]+: 335.1.

Step (8): Preparation of (+/−)-isopropyl (1S,3S)-3-(4-(5-(((cyclopentyl(methyl)carbamoyl)oxy)methyl)oxazol-4-yl)-2-fluorophenoxy)cyclohexane-1-carboxylate

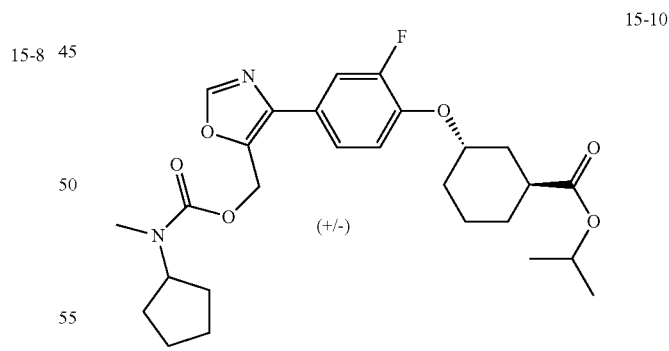

15-10

Compound 15-9 (142 mg, 0.43 mmol) was dissolved in tetrahydrofuran (10 mL), added with triphenylphosphonium (445 mg, 1.7 mmol), di-tert-butyl azodicarboxylate (391 mg, 1.7 mmol) and isopropyl (1S,3R)-3-hydroxycyclohexane-1-carboxylate (316.2 mg, 1.7 mmol) under nitrogen atmosphere, and then the reaction system was warmed to 60° C. and stirred overnight. The reaction system was then added with H$_2$O (20 mL) to quench the reaction, and extracted with ethyl acetate (15 mL×2). The organic phases were combined, washed with saturated brine (15 mL), dried over anhydrous sodium sulfate, filtered and concentrated, and the residue was separated by column chromatography (PE/EA=10/1) to give compound 15-10 (435 mg) in the form of a pale yellow oily liquid. LC-MS [M+Na]: 524.8.

Step (9): Preparation of (+/−)-(1S,3S)-3-(4-(5-(((cyclopentyl(methyl)carbamoyl)oxy)methyl)oxazol-4-yl)-2-fluorophenoxy)cyclohexane-1-carboxylic Acid

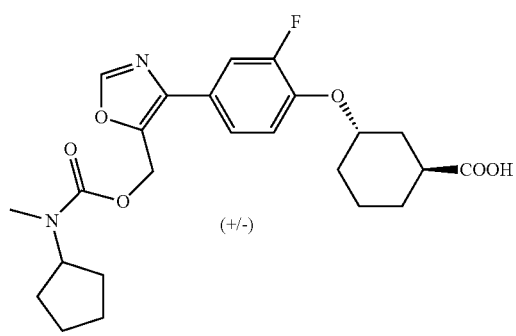

Compound 15-10 (435 mg, 0.87 mmol) was dissolved in tetrahydrofuran (6 mL)/methanol (2 mL)/water (2 mL), and then lithium hydroxide hydrate (146 mg, 3.48 mmol) was added, and the reaction system was stirred at room temperature for 5 h. Then the reaction system was concentrated, diluted with $H_2O$ (15 mL), adjusted to pH 2-3 with diluted hydrochloric acid (1 N), and then extracted with ethyl acetate (20 mL×2). The organic phases were combined, washed with saturated brine (20 mL), dried over anhydrous sodium sulfate, filtered and concentrated to give a crude product, and the crude product was purified by preparative reverse phase chromatography and lyophilized to give compound 15 (43 mg, 22% yield over two steps) in the form of a white solid. LC-MS [M+Na]: 483.2. $^1$H NMR (400 MHz, MeOD) δ 8.24 (s, 1H), 7.53 (dd, J=12.3, 2.1 Hz, 1H), 7.49 (dd, J=8.5, 2.1 Hz, 1H), 7.25 (t, J=8.6 Hz, 1H), 5.34 (s, 2H), 4.84-4.66 (m, 1H), 4.55-4.35 (m, 1H), 2.93-2.74 (m, 4H), 2.18-2.06 (m, 1H), 1.99-1.87 (m, 3H), 1.85-1.51 (m, 12H).

Example 16

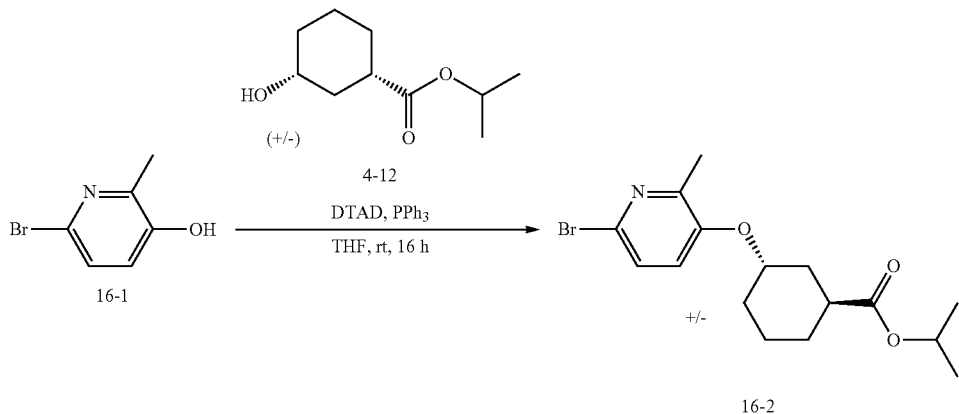

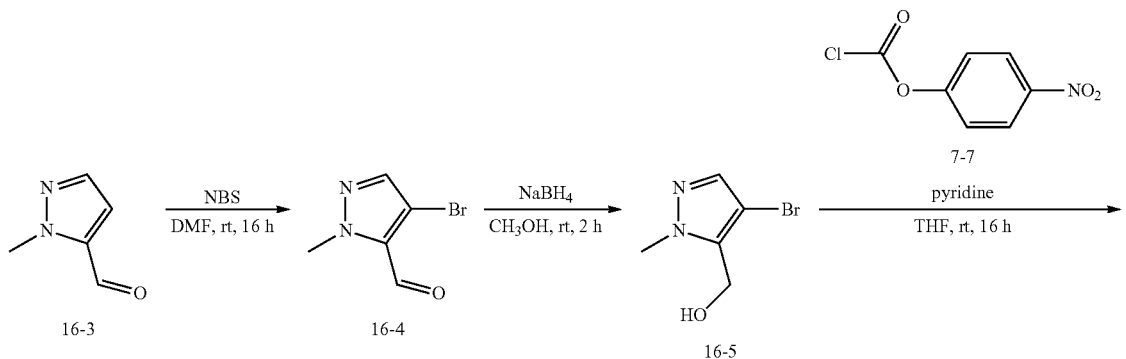

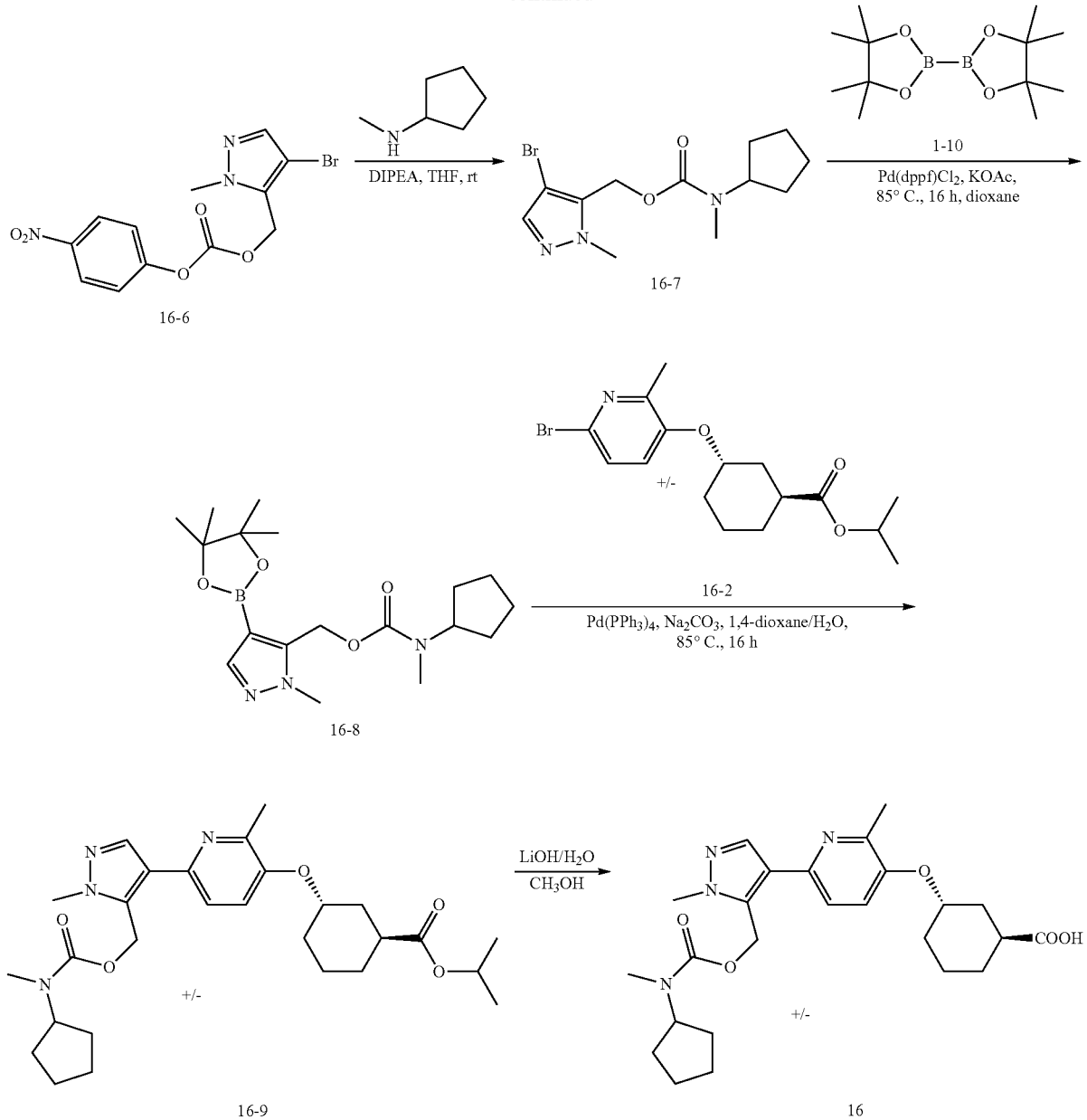

Step (1): Preparation of (+/−)-isopropyl (1S,3S)-3-((6-bromo-2-methylpyridin-3-yl)oxy)cyclohexane-1-carboxylate 6-bromo-3-hydroxy-2-methylpyridine (400 mg, 2.13 mmol), compound 4-12 (1.58 g, 8.52 mmol), triphenylphosphine (2.23 g, 8.52 mmol) and di-tert-butyl azodicarboxylate (1.96 g, 8.52 mmol) were dissolved in anhydrous tetrahydrofuran (20 mL), and the reaction system was reacted at 50° C. overnight. The reaction system was concentrated by rotary evaporation, added with water, and extracted with ethyl acetate (50 mL×2). The organic phases were combined, washed with saturated brine (10 mL×2), dried over anhydrous sodium sulfate, filtered and concentrated, and the residue was separated by column chromatography (EA/PE=1/20) to give compound 16-2 (700 mg, 92% yield) in the form of a colorless oil. LC-MS [M+H]⁺: 355.6, 357.7.

Step (2): Preparation of 4-bromo-1-methyl-pyrazole-3-carbaldehyde

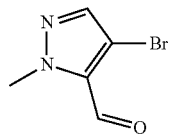

16-4

Compound 16-3 (2.00 g, 18.18 mmol) was dissolved in N,N-dimethylformamide (20 mL), and the reaction system was cooled to 0° C. The reaction system was added with N-bromosuccinimide (3.40 g, 19.09 mmol), stirred overnight at room temperature, added with aqueous sodium hydroxide solution (19.09 mL, 1 mol/L) to quench the reaction, diluted with water (100 mL), and extracted with ethyl acetate (70 mL×2). The organic phase was washed with saturated brine (30 mL×3), dried over anhydrous sodium sulfate and filtered, and the filtrate was concentrated by rotary evaporation to give compound 16-4 (2.90 g, 84% yield) in the form of a white solid. LC-MS [M+H]$^+$: 188.6, 190.6.

Step (3): Preparation of (4-bromo-1-methyl-1H-pyrazol-5-yl)methanol

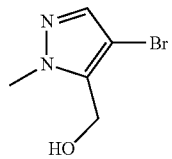

16-5

Compound 16-4 (2.90 g, 15.34 mmol) was dissolved in tetrahydrofuran (50 mL), and then the reaction system was cooled to 0° C., added with sodium borohydride (408 mg, 10.74 mmol) and stirred at room temperature for 2 h. The reaction system was then added with water (4 mL) to quench the reaction, and concentrated by rotary evaporation, and the residue was separated by column chromatography (ethyl acetate:petroleum ether=1:2) to give compound 16-5 (2.5 g, 85% yield) in the form of a white solid. LC-MS [M+H]$^+$: 190.7, 192.7.

Step (3): Preparation of (4-bromo-1-methyl-1H-pyrazol-5-yl)methyl(4-nitrophenyl)carbonate

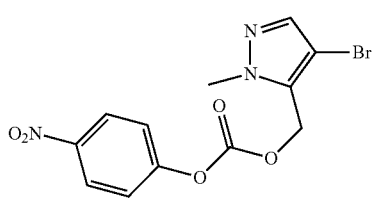

16-6

Compound 16-5 (3 g, 15.71 mmol) and pyridine (3.44 g, 47.13 mmol) were dissolved in dichloromethane (50 mL), and 4-nitrophenyl chloroformate (4.76 g, 23.56 mmol) was added at 0° C., and the reaction system was stirred overnight at room temperature. The reaction system was then extracted with dichloromethane (60 mL×2), and the organic phases were combined, washed with saturated brine (40 mL) and concentrated, and the residue was separated by column chromatography (wet loading, petroleum ether/ethyl acetate=5/1) to give compound 16-6 (4.2 g, 75% yield) in the form of a pale yellow solid. LC-MS [M+H]$^+$: 355.6, 357.6.

Step (5): Preparation of (4-bromo-1-methyl-1H-pyrazol-5-yl)methylcyclopentyl(methyl)carbamate

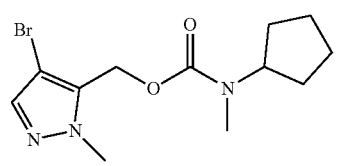

16-7

Compound 16-6 (4.00 g, 14.04 mmol) and N,N-diisopropylethylamine (7.24 g, 56.16 mmol) were added to anhydrous tetrahydrofuran (70 mL), and then N-methylcyclopentanamine hydrochloride (2.29 g, 16.85 mmol) was added. The reaction system was reacted at room temperature overnight, concentrated, and extracted with ethyl acetate (50 mL×2). The organic phases were washed with saturated brine (30 mL), dried over anhydrous sodium sulfate and concentrated, and the residue was separated by column chromatography (PE/EA=1/1) to give compound 16-7 (2.2 g, 62% yield) in the form of a colorless oil. LC-MS [M+H]$^+$: 315.6, 317.6.

Step (6): Preparation of (1-methyl-4-(4,4,5,5-tetramethyl-1,3,2-dioxaborolan-2-yl)-1H-pyrazol-5-yl)methylcyclopentyl(methyl)carbamate

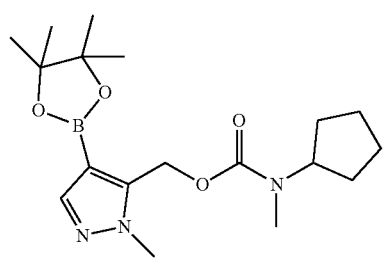

16-8

Compound 16-7 (2.2 g, 6.96 mmol), bis(pinacolato)diboron (2.65 g, 10.44 mmol), potassium acetate (1.02 g, 10.44 mmol) and [1,1'-bis(diphenylphosphino)ferrocene]dichloropalladium(II) (398 mg, 0.56 mmol) were added to 1,4-dioxane (30 mL), and the reaction system was reacted at 90° C. overnight under nitrogen atmosphere. The reaction was filtered and concentrated. The residue was separated by column chromatography (EA/PE=1/2) to give compound 16-8 (1.6 g, 63% yield) in the form of a black oil. LC-MS [M+H]$^+$: 364.3.

Step (7): Preparation of (+/−)-isopropyl (1S,3S)-3-((6-(5-(((cyclopentyl(methyl)carbamoyl)oxy)methyl)-1-methyl-1H-pyrazol-4-yl)-2-methylpyridin-3-yl)oxy)cyclohexane-1-carboxylate 16-9

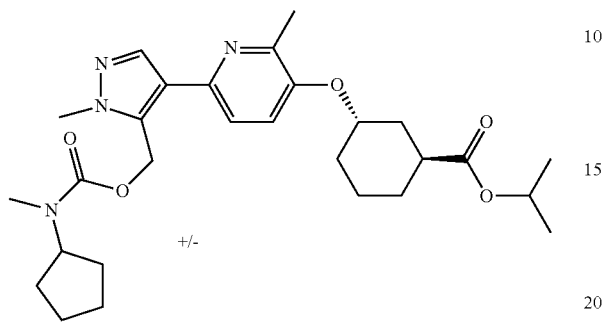

Compound 16-2 (700 mg, 1.97 mmol), compound 16-8 (800 mg, 2.20 mmol), and tetrakis(triphenylphosphine)palladium(0) (182 mg, 0.16 mmol) were added to 1,4-dioxane (16 mL), and then the reaction system was added with a solution of sodium carbonate (418 mg, 3.94 mmol) in water (4 mL) and reacted at 85° C. overnight under nitrogen atmosphere. The reaction system was filtered, and the organic phase was concentrated by rotary evaporation. The reaction system was extracted with ethyl acetate (50 mL×2) and concentrated, and the residue was separated by column chromatography (PE/EA=5/1) to give compound 16-9 (420 mg, 42% yield) in the form of a colorless oil. LC-MS [M+H]$^+$: 513.6.

Step (8): Preparation of (+/−)-(1S,3S)-3-((6-(5-(((cyclopentyl(methyl)carbamoyl)oxy)methyl)-1-methyl-1H-pyrazol-4-yl)-2-methylpyridin-3-yl)oxy)cyclohexane-1-carboxylic Acid

16

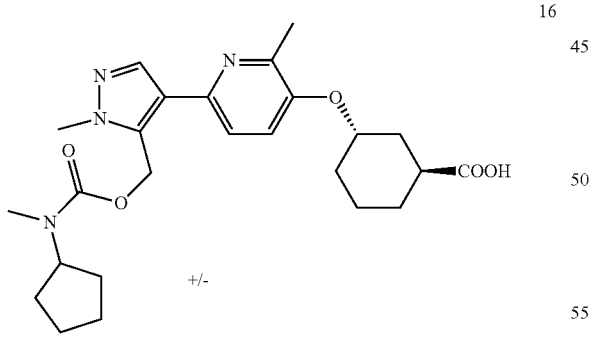

Compound 16-9 (420 mg, 0.82 mmol) was dissolved in methanol (10 mL), and then the reaction system was cooled to 0° C., added dropwise with aqueous lithium hydroxide solution (0.8 mL, 3 mol/L), and stirred overnight at room temperature. The reaction system was then concentrated under reduced pressure, adjusted to pH 3 with diluted hydrochloric acid (1 N), extracted with ethyl acetate (30 mL×2), and concentrated, and the residue was separated by preparative reverse phase chromatography to give compound 16 (150 mg) in the form of a white solid. The reaction system was then subjected to chiral resolution (ethanol-ethylenediamine), the resulting solutions were respectively adjusted with an acid, extracted, and concentrated by rotary evaporation, and the residue was lyophilized to give compound 16-A (35 mg, 23% yield) and compound 16-B (55.5 mg).

Compound 16-A LC-MS [M+H]$^+$: 471.5. $^1$H NMR (400 MHz, MeOD) δ 7.95 (brs, 1H), 7.88 (s, 1H), 7.77 (brs, 1H), 5.46 (s, 2H), 4.97-4.93 (m, 1H), 4.60-4.35 (m, 1H), 4.04 (s, 3H), 2.84 (s, 3H), 2.84-2.77 (m, 1H), 2.69 (s, 3H), 2.13-2.09 (m, 1H), 2.07-1.88 (m, 3H), 1.73 (m, 12H).

16-A

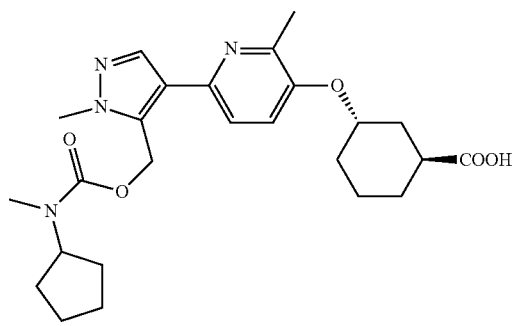

16-B

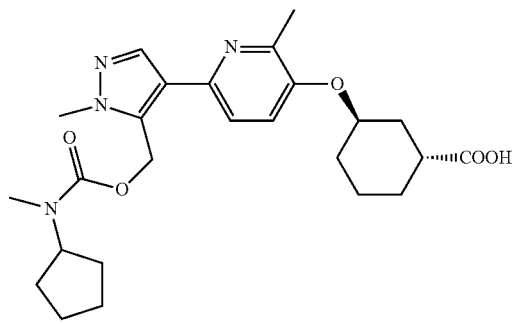

Example 17

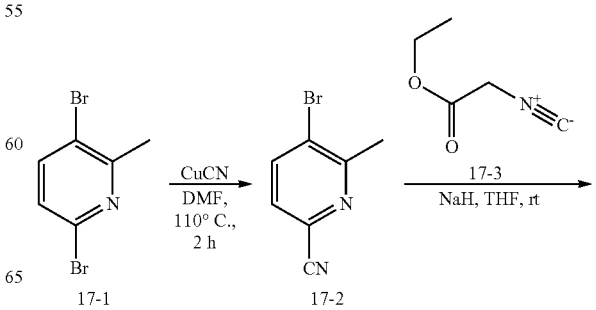

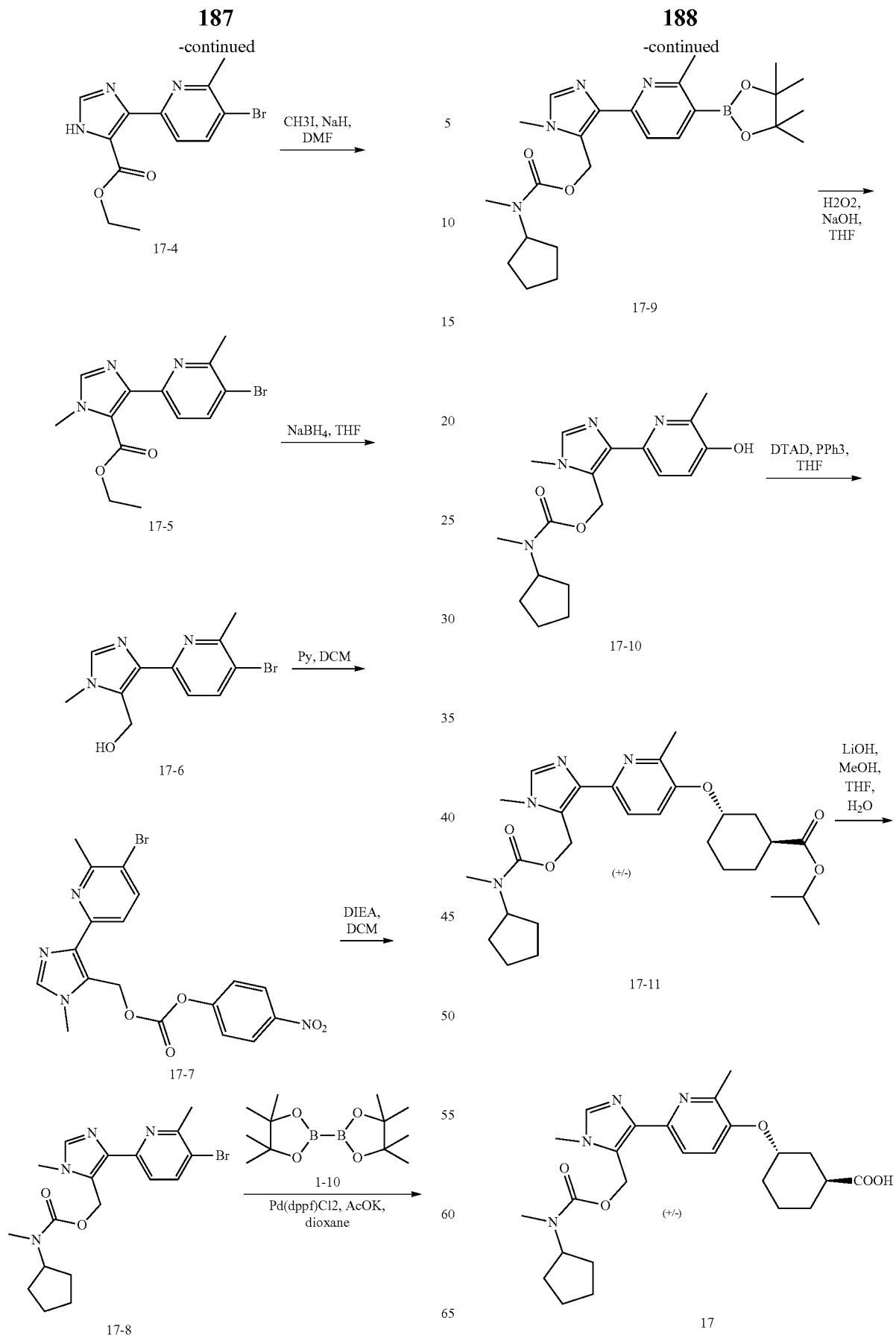

Step (1): Preparation of 5-bromo-6-methylcyanopyridine

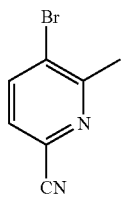

17-2

3,6-dibromo-2-methylpyridine (20 g, 80 mmol) and copper(I) cyanide (7.2 g, 80 mmol) was dissolved in DMF (200 mL), and the reaction system was warmed to 110° C., reacted at this temperature for 2 h, quenched with water, and extracted with ethyl acetate (150 mL×3). The organic phases were combined, washed with saturated brine (150 mL), dried over anhydrous sodium sulfate, and concentrated. The residue was separated by column chromatography (PE/EA=1/1) to give compound 17-2 (6.0 g, 77.0% yield) in the form of a brown solid. LC-MS [M+H]$^+$: 196.4, 198.4.

Step (2): Preparation of ethyl 4-(5-bromo-6-methylpyridin-2-yl)-1H-imidazole-5-carboxylate

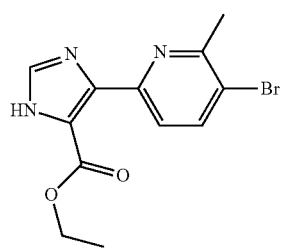

17-4

Compound 17-2 (6.0 g, 30.6 mmol) and ethyl 2-isocyanoacetate (3.5 g, 30.6 mmol) were dissolved in tetrahydrofuran (100 mL), and the reaction system was cooled to 0° C. and reacted at this temperature for 20 min. The reaction system was added in portions with sodium hydride (1.2 g, 30.6 mmol), reacted 0° C. for 20 min, quenched with ammonium chloride solution (100 mL), and extracted with ethyl acetate (150 mL×3). The organic phases were combined, washed with saturated brine (50 mL), dried over anhydrous sodium sulfate, and concentrated. The residue was separated by column chromatography (PE/EA=1/1) to give compound 17-4 (3.0 g, 31.6% yield) in the form of a brown solid. LC-MS [M+H]$^+$: 309.6, 311.6.

Step (3): Preparation of ethyl 4-(5-bromo-6-methylpyridin-2-yl)-1-methyl-1H-imidazole-5-carboxylate

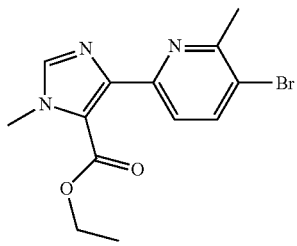

17-5

Compound 17-4 (3.0 g, 9.67 mmol) and sodium hydride (232 mg, 9.67 mmol) were dissolved in tetrahydrofuran (20 mL), and the reaction system was reacted at room temperature for 30 min. The reaction system was added with methyl iodide (16 g, 11.6 mmol), reacted at room temperature for 2 h, added with water (20 mL), and extracted with ethyl acetate (30 mL×3). The organic phases were combined, washed with saturated brine (20 mL), dried over anhydrous sodium sulfate and concentrated, and the residue was separated by column chromatography (PE/EA=1/1) to give compound 17-5 (700 mg, crude) in the form of a yellow oily liquid. LC-MS [M+H]$^+$: 323.6, 325.7.

Step (4): Preparation of (4-(5-bromo-6-methylpyridin-2-yl)-1-methyl-1H-imidazol-5-yl)methanol

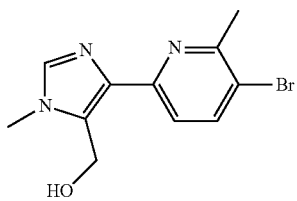

17-6

Compound 17-5 (700 g, 2.1 mmol) and sodium borohydride (400 mg, 10.5 mmol) were dissolved in tetrahydrofuran (10 mL). The reaction system was heated to reflux overnight, added with ammonium chloride solution (10 mL) to quench the reaction, and extracted with ethyl acetate (30 mL×3). The organic phases were combined, washed with saturated brine (20 mL), dried over anhydrous sodium sulfate and concentrated to give compound 17-6 (250 mg, crude) in the form of a yellow solid. LC-MS [M+H]$^+$: 281.6, 283.6.

Step (5): Preparation of (4-(5-bromo-6-methylpyridin-2-yl)-1-methyl-1H-imidazol-5-yl)methylcyclopentyl (methyl)carbamate

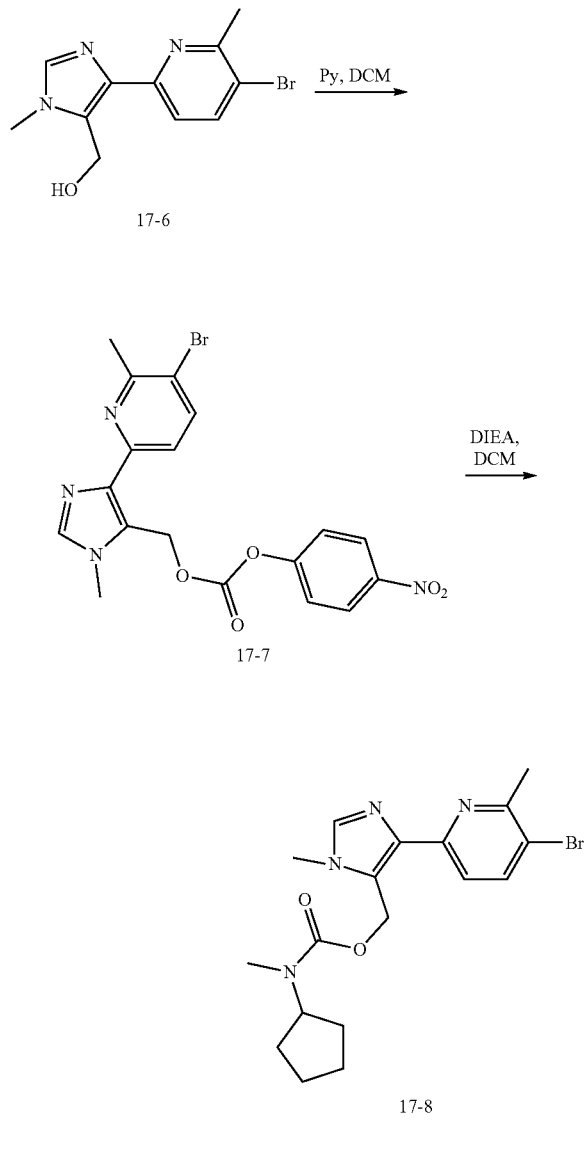

Step (6): Preparation of (4-(5-hydroxy-6-methylpyridin-2-yl)-1-methyl-1H-imidazol-5-yl)methylcyclopentyl (methyl)carbamate

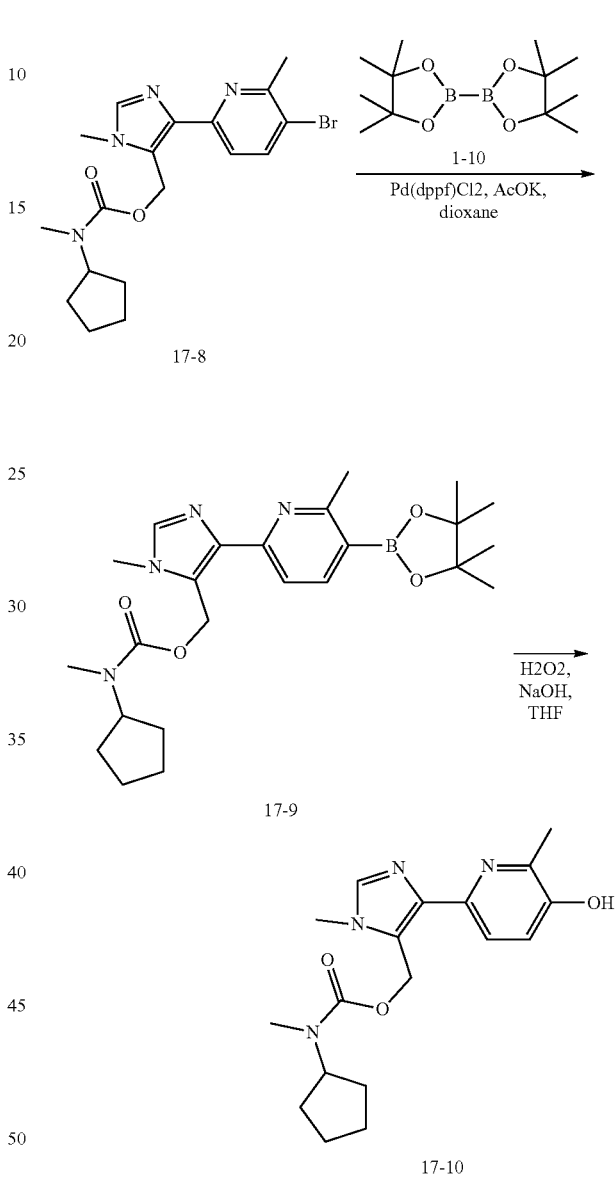

Compound 17-6 (250 mg, 0.71 mmol), pyridine (276 mg, 3.5 mmol) and p-nitrophenyl chloroformate (453 mg, 2.1 mmol) were dissolved in dichloromethane (5 mL), and the reaction system was reacted at room temperature overnight. The reaction system was added with water to quench the reaction and extracted with ethyl acetate (15 mL×3). The organic phase was washed with saturated brine (15 mL), dried over anhydrous sodium sulfate, and concentrated. The residue was dissolved in dichloromethane, and the reaction system was added with DIEA (166 mg, 1.29 mmol) and N-methylcyclopentylamine hydrochloride (92 mg, 0.63 mmol), reacted at room temperature overnight, added with water to quench the reaction, extracted with ethyl acetate (15 mL×3), and washed with saturated brine (15 mL). The organic phase was dried over anhydrous sodium sulfate and concentrated. The residue was separated by column chromatography (PE/EA=1/1) to give compound 17-8 (200 mg, 69.4% yield over two steps) in the form of a yellow solid. LC-MS [M−55]+: 406.7, 408.7.

Compound 17-8 (200 mg, 0.49 mmol), compound 1-10 (248 mg, 0.98 mmol), potassium acetate (144 mg, 1.47 mmol) and Pd(dppf)Cl$_2$ (35 mg, 0.049 mmol) were dissolved in anhydrous dioxane (5 mL), and the reaction system was stirred at 80° C. for 3 h, filtered, and concentrated. The residue was dissolved in tetrahydrofuran. The reaction system was cooled to 0° C., added with NaOH solution (1 mL, 1 N) and hydrogen peroxide (0.5 mL), reacted at 0° C. for 1 h, added with water to quench the reaction, and extracted with ethyl acetate (15 mL×3). The organic phase was washed with saturated brine (15 mL), dried over anhydrous sodium sulfate and concentrated, and the residue was separated by column chromatography (PE/EA=1/1) to give compound 17-10 (150 mg, 89.3% yield) in the form of a yellow oily liquid. LC-MS [M+H]+: 345.2.

Step (7): Preparation of (+/−)-isopropyl (1S,3S)-3-((6-(5-(((cyclopentyl(methyl)carbamoyl)oxy)methyl)-1-methyl-1H-imidazol-4-yl)-2-methylpyridin-3-yl)oxy)cyclohexane-1-carboxylate

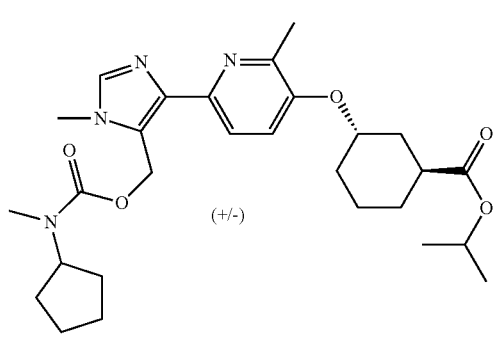

17-11

(+/-)

Compound 17-10 (150 mg, 0.44 mmol), isopropyl (1S, 3R)-3-hydroxycyclohexane-1-carboxylate (216 mg, 1.16 mmol), di-tert-butyl azodicarboxylate (267 mg, 1.16 mmol) and triphenylphosphine (304 mg, 1.16 mmol) were dissolved in tetrahydrofuran (5 mL), and then the reaction system was reacted at 60° C. for 12 h under nitrogen atmosphere, added with water to quench the reaction, and extracted with ethyl acetate (15 mL×3). The organic phases were combined, washed with saturated brine (15 mL), dried over anhydrous sodium sulfate and concentrated, and the residue was separated by column chromatography (PE/EA=2/1) to give compound 17-11 (150 mg) in the form of a yellow oily liquid. LC-MS [M+H]$^+$: 513.1.

Step (8): Preparation of (+/−)-(1S,3S)-3-((6-(5-(((cyclopentyl(methyl)carbamoyl)oxy)methyl)-1-methyl-1H-imidazol-4-yl)-2-methylpyridin-3-yl)oxy)cyclohexane-1-carboxylic Acid

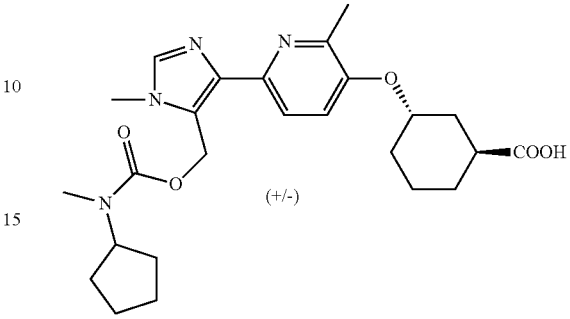

17

(+/-)

Compound 17-11 (150 mg, 0.19 mmol) and lithium hydroxide (23 mg, 0.95 mmol) were dissolved in a mixture of THF (3 mL), MeOH (1 mL) and H$_2$O (1 mL), and then the reaction system was stirred overnight at room temperature, added with water (10 mL) to quench the reaction, and extracted with ethyl acetate (5 mL×3). The organic phase was dried over Na$_2$SO$_4$ and filtered, and the filtrate was concentrated by rotary evaporation. The residue was separated by column chromatography (DCM/MeOH=40/1) and lyophilized to give compound 17 (18 mg, 43.8% yield) in the form of a white solid.

$^1$H NMR (400 MHz, DMSO) δ 12.25 (s, 1H), 8.18 (s, 1H), 7.52 (d, J=8.6 Hz, 1H), 7.44 (d, J=8.4 Hz, 1H), 5.01 (s, 2H), 4.81 (s, 1H), 4.41 (s, 1H), 3.77 (s, 3H), 2.64 (s, 4H), 2.44 (s, 3H), 2.02 (d, J=12.8 Hz, 1H), 1.78-1.84 (m, 3H), 1.44-1.66 (m, 12H).

Example 18

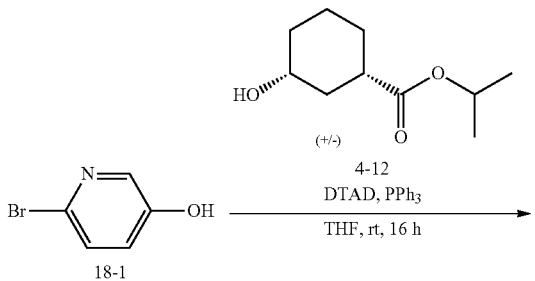

18-1

4-12
DTAD, PPh$_3$
THF, rt, 16 h

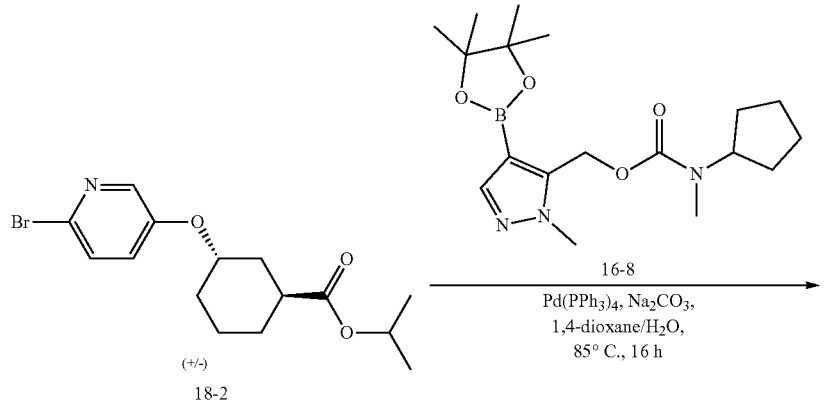

18-2

16-8
Pd(PPh$_3$)$_4$, Na$_2$CO$_3$,
1,4-dioxane/H$_2$O,
85° C., 16 h

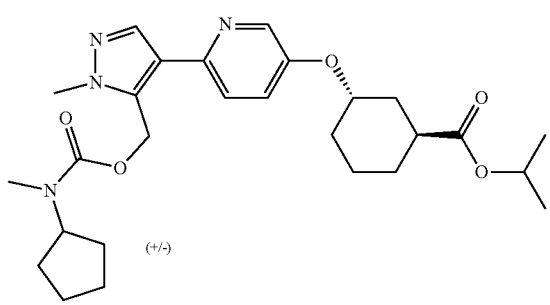

18-3

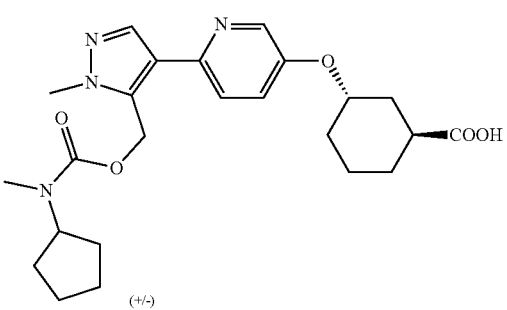

18

-continued

Step (1): Preparation of (+/−)-isopropyl (1S,3S)-3-((6-bromopyridin-3-yl)oxy)cyclohexane-1-carboxylate

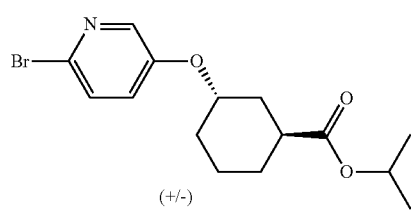

18-2

2-bromo-5-hydroxypyridine (500 mg, 2.87 mmol), compound 4-12 (2.14 g, 11.49 mmol), triphenylphosphine (3.01 g, 11.49 mmol) and di-tert-butyl azodicarboxylate (2.64 g, 11.49 mmol) were dissolved in anhydrous tetrahydrofuran (20 mL), and the reaction system was reacted at 50° C. overnight. The reaction system was concentrated by rotary evaporation, added with water, and extracted with ethyl acetate (50 mL×2). The organic phases were combined, washed with saturated brine (10 mL×2), dried over anhydrous sodium sulfate, filtered and concentrated, and the residue was separated by column chromatography (EA/PE=1/20) to give compound 18-2 (600 mg, 61% yield) in the form of a colorless oil. LC-MS [M+H]+: 341.5, 343.5.

Step (2): Preparation of (+/−)-isopropyl (1S,3S)-3-((6-(5-((((cyclopentyl(methyl)carbamoyl)oxy)methyl)-1-methyl-1H-pyrazol-4-yl)pyridin-3-yl)oxy)cyclohexane-1-carboxylate

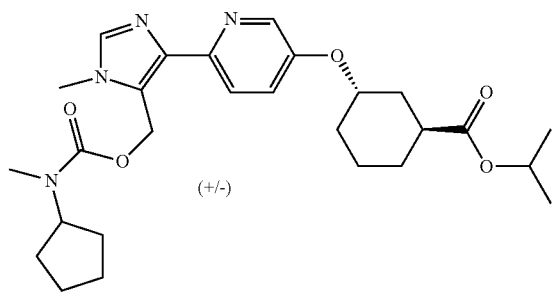

18-3

Compound 18-2 (600 mg, 1.75 mmol), compound 16-8 (951 mg, 2.62 mmol), and tetrakis(triphenylphosphine)palladium(0) (162 mg, 0.14 mmol) were added to 1,4-dioxane (16 mL)/water (4 mL), and then the reaction system was added with sodium carbonate (371 mg, 3.50 mmol) and reacted at 85° C. overnight under nitrogen atmosphere. The reaction system was filtered, and the organic phase was concentrated by rotary evaporation. The reaction system was extracted with ethyl acetate (50 mL×2) and concentrated, and the residue was separated by column chromatography (PE/EA=5/1) to give compound 18-3 (300 mg, 34% yield) in the form of a colorless oil. LC-MS [M+H]+: 499.3.

Step (3): Preparation of (+/−)-(1S,3S)-3-(((6-(5-((((cyclopentyl(methyl)carbamoyl)oxy)methyl)-1-methyl-1H-pyrazol-4-yl)pyridin-3-yl)oxy)cyclohexane-1-carboxylic Acid

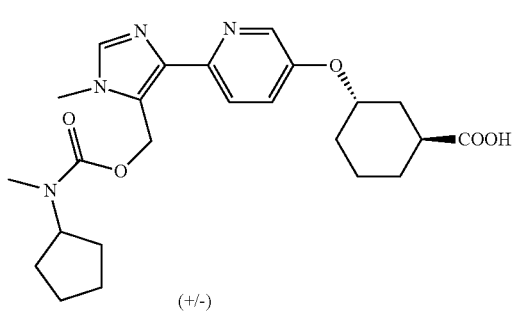

18

Compound 18-3 (300 mg, 0.60 mmol) was dissolved in methanol (8 mL), and then the reaction system was cooled to 0° C., added dropwise with aqueous lithium hydroxide solution (0.9 mL, 2 N), and stirred overnight at room temperature. The reaction system was then concentrated under reduced pressure, adjusted to pH 3 with diluted hydrochloric acid (1 N), extracted with ethyl acetate (20 mL×2), and concentrated, and the residue was separated by preparative reverse phase chromatography to give compound 18 (38 mg, 14% yield) in the form of a white solid.

LC-MS [M+H]+: 457.2. 1H NMR (400 MHz, MeOD) δ 8.30 (d, J=2.8 Hz, 1H), 7.81 (s, 1H), 7.58 (d, J=8.7 Hz, 1H), 7.48 (dd, J=8.8, 3.0 Hz, 1H), 5.53 (s, 2H), 4.80-4.74 (m, 1H), 4.55-4.20 (m, 1H), 3.98 (s, 3H), 2.86-2.78 (m, 1H), 2.75 (s, 3H), 2.15-1.47 (m, 16H).

Example 19
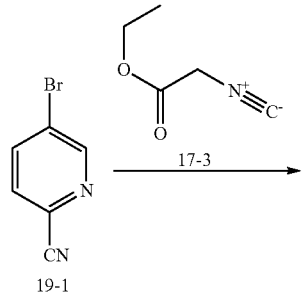
19-1
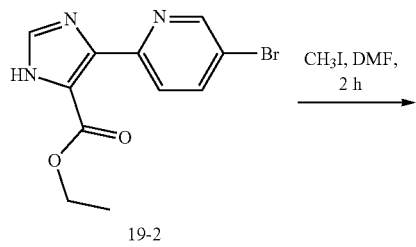
19-2
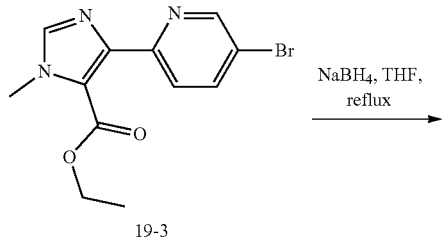
19-3
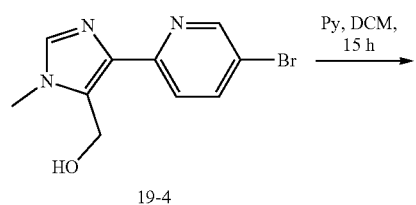
19-4
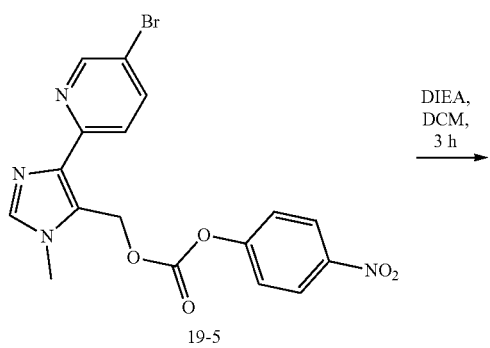
19-5
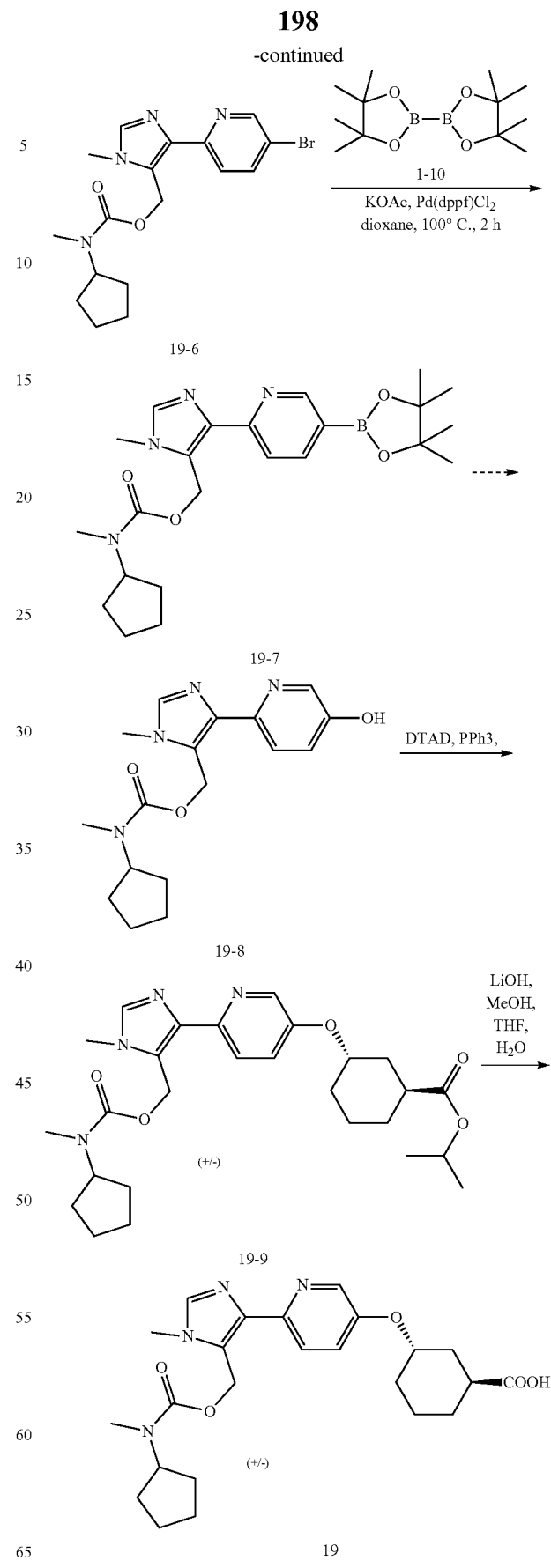

Step (1): Preparation of ethyl 4-(5-bromopyridin-2-yl)-1H-imidazole-5-carboxylate

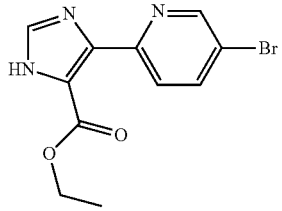

19-2

(Isocyanatomethyl)benzene (10 g, 54.9 mmol) and ethyl 2-isocyanoacetate (6.2 g, 54.9 mmol) were dissolved in tetrahydrofuran (100 mL), and the reaction system was cooled to 0° C. and reacted at this temperature for 20 min. The reaction system was added in portions with sodium hydride (3.3 mg, 82.4 mmol), reacted at 0° C. for 20 min, added with ammonium chloride solution (100 mL) to quench the reaction, and extracted with ethyl acetate (150 mL×3). The organic phases were combined, washed with saturated brine (50 mL), dried over anhydrous sodium sulfate, and concentrated. The residue was separated by column chromatography (PE/EA=1/1) to give compound 19-2 (1.5 g, 9.4% yield) in the form of a brown solid. LC-MS [M+H]$^+$: 295.6, 297.6.

Step (2): Preparation of ethyl 4-(5-bromopyridin-2-yl)-1-methyl-1H-imidazole-5-carboxylate

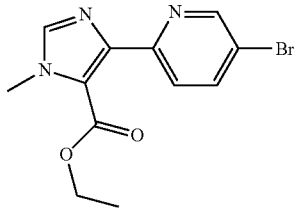

19-3

Compound 19-2 (1.5 g, 5.1 mmol) and sodium hydride (204 mg, 5.1 mmol) were dissolved in tetrahydrofuran (20 mL), and the reaction system was reacted at room temperature for 30 min. The reaction system was added with methyl iodide (866 mg, 6.1 mmol), reacted at room temperature for 2 h, quenched with water (20 mL), and extracted with ethyl acetate (30 mL×3). The organic phases were combined, washed with saturated brine (20 mL), dried over anhydrous sodium sulfate and concentrated, and the residue was separated by column chromatography (PE/EA=1/1) to give compound 19-3 (800 mg, crude) in the form of a yellow oily liquid. LC-MS [M+H]$^+$: 309.6, 311.6.

Step (3): Preparation of (4-(5-bromopyridin-2-yl)-1-methyl-1H-imidazol-5-yl)methanol

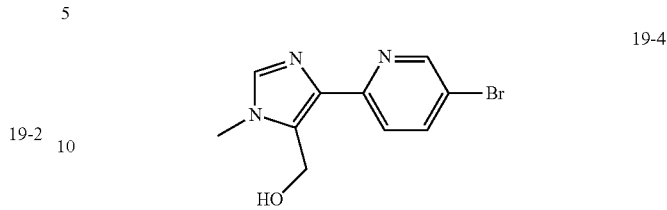

19-4

Compound 19-3 (700 g, 2.26 mmol) and sodium borohydride (172 mg, 4.52 mmol) were dissolved in tetrahydrofuran (10 mL). The reaction system was heated to reflux overnight, quenched with ammonium chloride solution (10 mL), and extracted with ethyl acetate (30 mL×3). The organic phases were combined, washed with saturated brine (20 mL), dried over anhydrous sodium sulfate and concentrated to give compound 19-4 (350 mg, crude) in the form of a yellow solid. LC-MS [M+H]$^+$: 267.4, 269.4.

Step (4): Preparation of (4-(5-bromopyridin-2-yl)-1-methyl-1H-imidazol-5-yl)methylcyclopentyl (methyl)carbamate

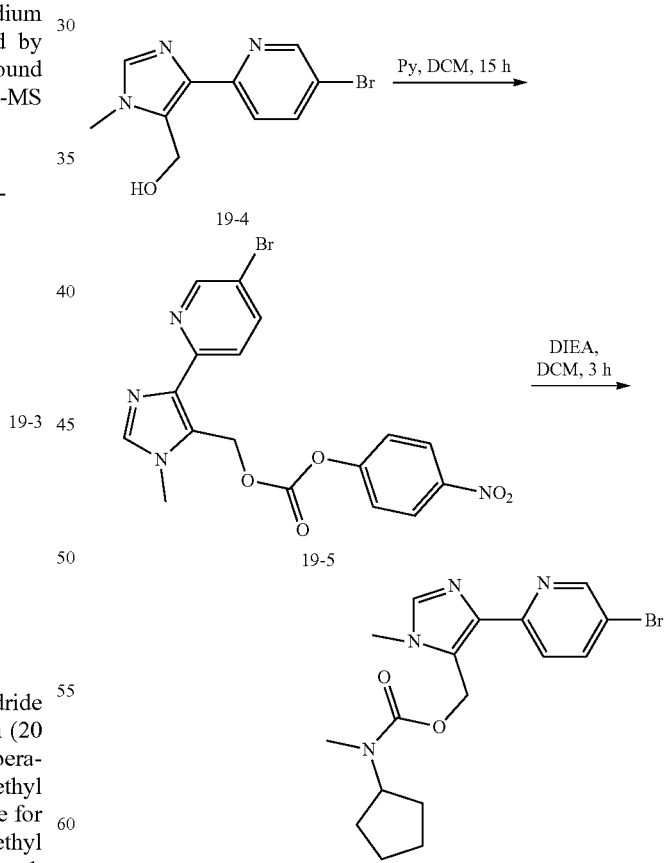

Compound 19-4 (350 mg, 1.33 mmol), pyridine (525 mg, 6.65 mmol) and p-nitrophenyl chloroformate (861 mg, 3.99 mmol) were dissolved in dichloromethane (5 mL), and the reaction system was reacted at room temperature overnight. The reaction system was added with water and extracted with ethyl acetate (15 mL×3). The organic phase was washed with saturated brine (15 mL), dried over anhydrous sodium sulfate, and concentrated. The residue was dissolved in dichloromethane, and the reaction system was added with DIEA (315 mg, 2.45 mmol) and N-methylcyclopentylamine hydrochloride (175 mg, 1.2 mmol), reacted at room temperature overnight, added with water to quench the reaction, extracted with ethyl acetate (15 mL×3), and washed with saturated brine (15 mL). The organic phase was dried over anhydrous sodium sulfate and concentrated. The residue was separated by column chromatography (PE/EA=1/1) to give compound 19-6 (300 mg, 57.5% yield over two steps) in the form of a yellow solid. LC-MS [M+H]$^+$: 392.6, 394.6.

Step (5): Preparation of (4-(5-hydroxypyridin-2-yl)-1-methyl-1H-imidazol-5-yl)methylcyclopentyl (methyl)carbamate

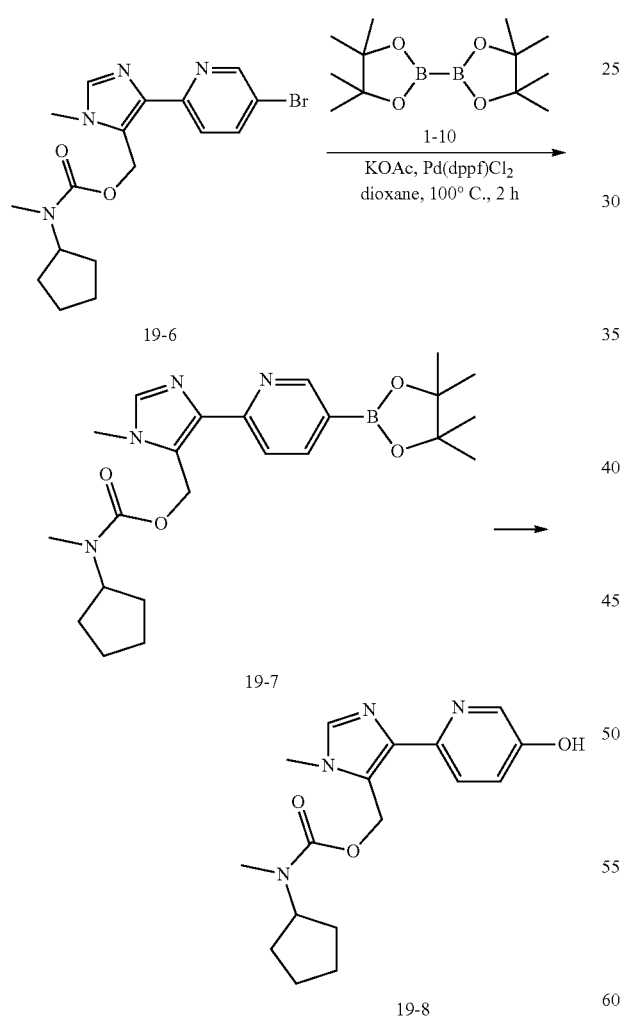

Compound 19-6 (300 mg, 0.76 mmol), compound 1-10 (390 mg, 1.52 mmol), potassium acetate (220 mg, 2.28 mmol) and Pd(dppf)Cl$_2$ (50 mg, 0.076 mmol) were dissolved in anhydrous dioxane (5 mL), and the reaction system was stirred at 80° C. for 3 h, filtered, and concentrated. The residue was dissolved in tetrahydrofuran. The reaction system was cooled to 0° C., added with NaOH solution (1 mL, 1 N) and hydrogen peroxide (0.5 mL), reacted at 0° C. for 1 h, added with water to quench the reaction and extracted with ethyl acetate (15 mL×3). The organic phase was washed with saturated brine (15 mL), dried over anhydrous sodium sulfate and concentrated, and the residue was separated by column chromatography (PE/EA=1/1) to give compound 19-8 (100 mg, 40.0% yield) in the form of a yellow oily liquid. LC-MS [M+H]$^+$: 331.4.

Step (6): Preparation of (+/−)-isopropyl (1S,3S)-3-((6-(5-(((cyclopentyl(methyl)carbamoyl)oxy) methyl)-1-methyl-1H-imidazol-4-yl)pyridin-3-yl) oxy)cyclohexane-1-carboxylate

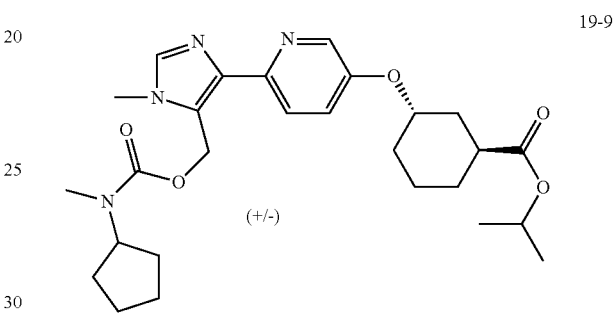

Compound 19-8 (100 mg, 0.6 mmol), isopropyl (1S,3R)-3-hydroxycyclohexane-1-carboxylate (230 mg, 1.2 mmol), di-tert-butyl azodicarboxylate (285 mg, 1.2 mmol) and triphenylphosphine (325 mg, 1.2 mmol) were dissolved in tetrahydrofuran (5 mL), and then the reaction system was reacted at 60° C. for 12 h under nitrogen atmosphere, added with water to quench the reaction, and extracted with ethyl acetate (15 mL×3). The organic phases were combined, washed with saturated brine (15 mL), dried over anhydrous sodium sulfate and concentrated, and the residue was separated by column chromatography (PE/EA=2/1) to give compound 19-9 (100 mg, crude) in the form of a yellow oily liquid. LC-MS [M+H]$^+$: 499.6.

Step (7): Preparation of (+/−)-(1S,3S)-3-((6-(5-(((cyclopentyl(methyl)carbamoyl)oxy)methyl)-1-methyl-1H-imidazol-4-yl)pyridin-3-yl)oxy)cyclohexane-1-carboxylic Acid

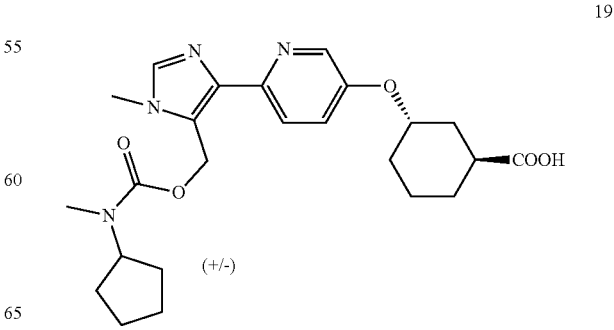

Compound 19-9 (100 mg, 0.1 mmol) and lithium hydroxide (21 mg, 0.5 mmol) were dissolved in a mixed solvent of THF (3 mL), MeOH (1 mL) and H₂O (1 mL), and then the reaction system was stirred overnight at room temperature, quenched with water (10 mL), and extracted with ethyl acetate (5 mL×3). The organic phase was dried over Na₂SO₄ and filtered, and the filtrate was concentrated by rotary evaporation. The residue was separated and lyophilized to give compound 19 (20 mg, 43.8% yield) in the form of a white solid.

¹H NMR (400 MHz, DMSO) δ 8.98 (s, 1H), 8.44 (s, 1H), 7.91 (d, J=7.9 Hz, 1H), 7.66 (d, J=8.4 Hz, 1H), 5.52 (s, 2H), 4.83 (s, 1H), 4.38 (s, 1H), 3.89 (s, 3H), 2.68 (s, 4H), 1.77-1.96 (m, 4H), 1.47-1.70 (m, 12H).

Example 20

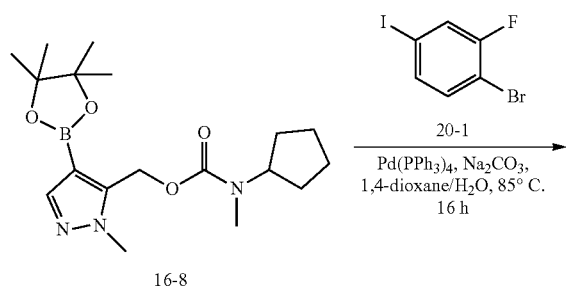

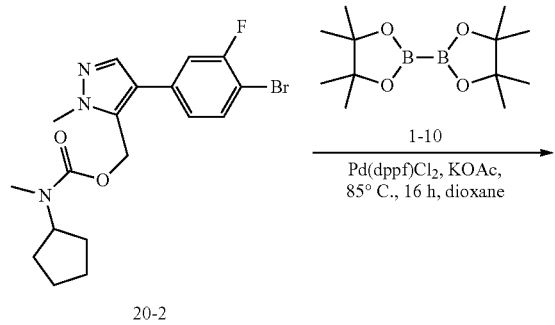

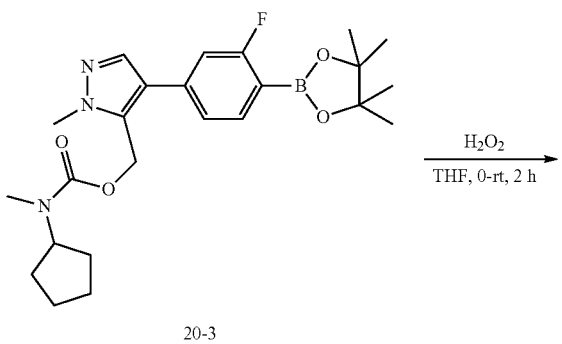

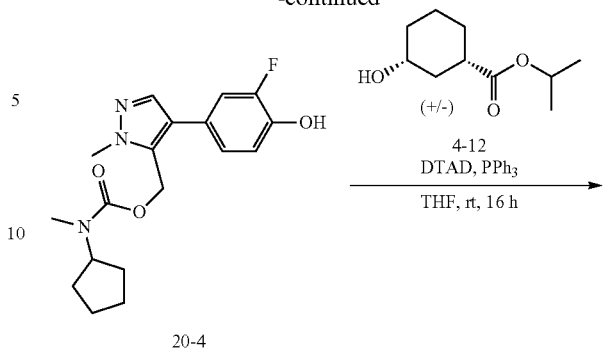

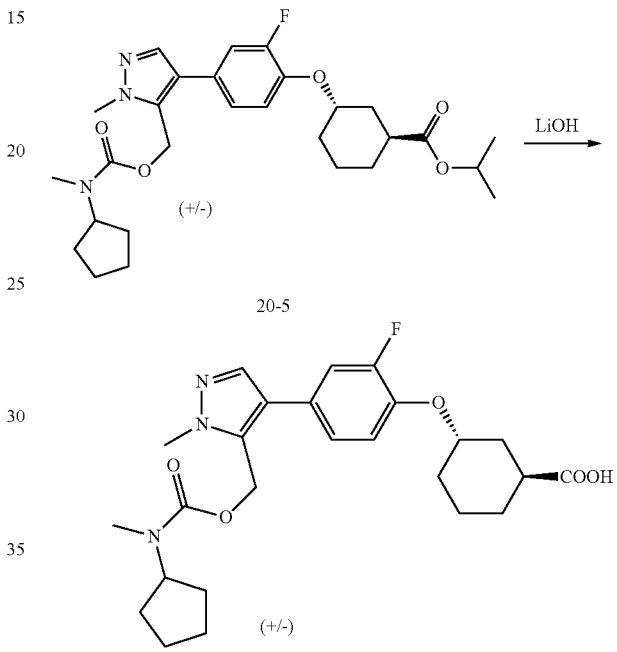

Step (1): Preparation of (4-(4-bromo-3-fluorophenyl)-1-methyl-1H-pyrazol-5-yl)methylcyclopentyl (methyl)carbamate

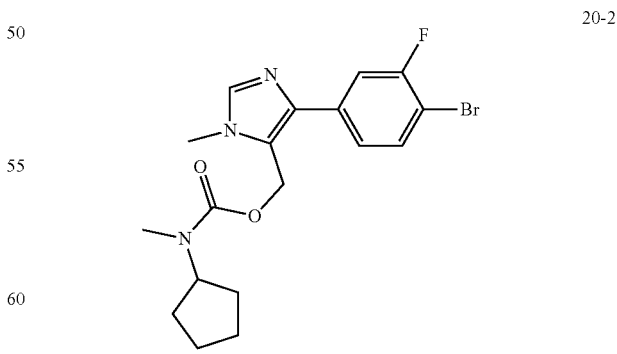

Compound 16-8 (248 mg, 0.68 mmol) was dissolved in dioxane (15 mL), and the reaction system was added with 1-bromo-2-fluoro-4-iodobenzene (205 mg, 0.68 mmol), tetrakis(triphenylphosphine)palladium(0) (79 mg, 0.068 mmol), sodium carbonate (144 mg, 1.36 mmol) and water (5 mL), heated to 80° C. under nitrogen atmosphere and stirred overnight. The reaction system was filtered to remove the solid, and the filtrate was extracted with ethyl acetate (50 mL×2), and washed with saturated brine (30 mL×2). The organic phase was dried over anhydrous sodium sulfate, and purified by silica gel column (PE/EA=4/1) to give compound 20-2 (100 mg, 35% yield) in the form of a white solid. LC-MS [M+H]⁺: 409.6, 411.6.

Step (2): Preparation of (4-(3-fluoro-4-(4,4,5,5-tetramethyl-1,3,2-dioxaborolan-2-yl)phenyl)-1-methyl-1H-pyrazol-5-yl)methylcyclopentyl(methyl)carbamate

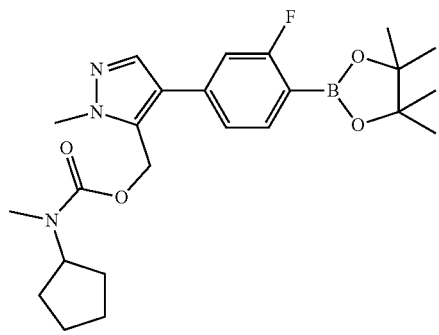

Compound 20-2 (100 mg, 0.24 mmol) was dissolved in dioxane (10 mL), and the reaction system was added with bis(pinacolato)diboron (93 mg, 0.36 mmol), [1,1'-bis(diphenylphosphino)ferrocene] dichloropalladium(II) (18 mg, 0.024 mmol) and potassium acetate (48 mg, 0.48 mmol), heated to 100° C. and stirred for 3 h under nitrogen atmosphere. The reaction system was filtered to remove the solid, and the filtrate was concentrated by rotary evaporation to give compound 20-3. The residue was directly used in the next step without purification. LC-MS [M+H]⁺: 458.3.

Step (3): Preparation of (4-(3-fluoro-4-hydroxyphenyl)-1-methyl-1H-pyrazol-5-yl)methylcyclopentyl(methyl)carbamate

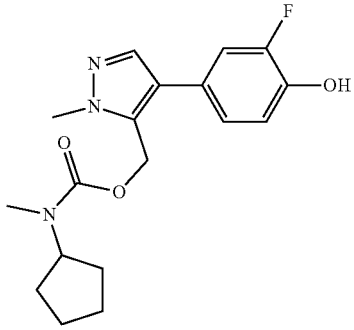

Compound 20-3 was dissolved in tetrahydrofuran (10 mL), and the reaction system was cooled to 0° C., added with hydrogen peroxide (0.5 mL) and sodium hydroxide (0.2 mL, 1 N), and reacted at 0° C. for 1 h. The reaction system was added with saturated sodium thiosulfate solution (2 mL) to quench the reaction, extracted with ethyl acetate (10 mL×2) and washed with saturated brine (10 mL×2). The organic phase was dried over anhydrous sodium sulfate and purified by silica gel column chromatography (DCM/MeOH=20/1) to give compound 20-4 (70 mg, 83% yield over two steps) in the form of a yellow solid. LC-MS [M+H]⁺: 348.4.

Step (4): Preparation of (+/−)-isopropyl (1S,3S)-3-(4-(5-((((cyclopentyl(methyl)carbamoyl)oxy)methyl)-1-methyl-1H-pyrazol-4-yl)-2-fluorophenoxy)cyclohexane-1-carboxylate

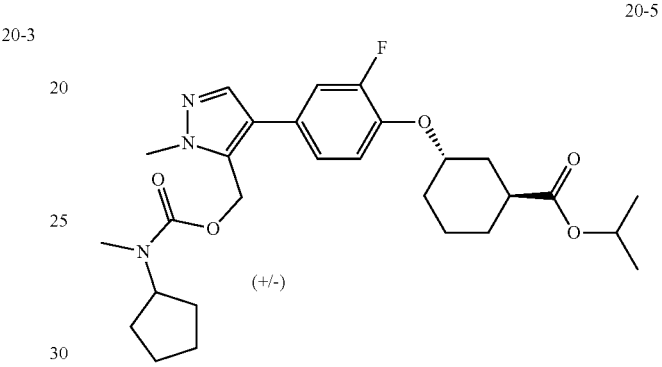

Compound 20-4 (70 mg, 0.2 mmol), (+/−)-isopropyl 3-hydroxycyclohexane-1-carboxylate (150 mg, 0.8 mmol), DTAD (186 mg, 0.8 mmol) and PPh₃ (210 mg, 0.8 mmol) were dissolved in THF (10 mL), and the reaction system was stirred overnight at 60° C. under nitrogen atmosphere. The reaction system was purified by silica gel column (DCM/EA=50/1) to give compound 20-5 (170 mg, crude) in the form of a yellow solid. LC-MS [M+H]⁺: 516.6.

Step (5): Preparation of (+/−)-(1S,3S)-3-(4-(5-(((cyclopentyl(methyl)carbamoyl)oxy)methyl)-1-methyl-1H-pyrazol-4-yl)-2-fluorophenoxy)cyclohexane-1-carboxylic Acid

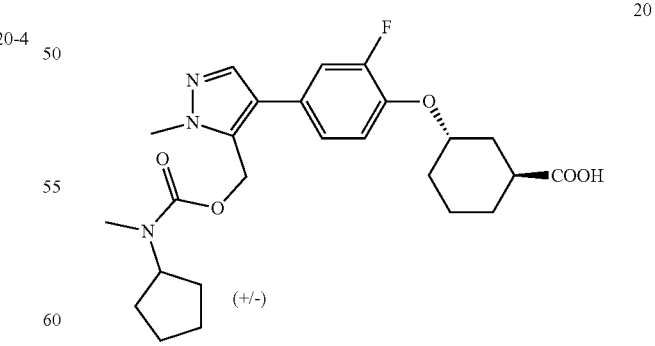

Compound 20-5 (170 mg, crude) was dissolved in THF (9 mL), and the reaction system was sequentially added with MeOH (3 mL), H₂O (3 mL) and lithium hydroxide (100 mg, 2.4 mmol), and stirred overnight at room temperature. Then water (10 mL) was added for dilution, and the organic solvent was removed by rotary evaporation under reduced pressure. The aqueous phase was adjusted to pH 5-6 with hydrochloric acid (1 N), and extracted with dichloromethane (10 mL×2). The organic phase was dried over anhydrous sodium sulfate and filtered, and the filtrate was concentrated by rotary evaporation. The residue was purified by silica gel column chromatography (DCM/MeOH=20/1) and then lyophilized to give compound 20 (14.5 mg, 15% yield) in the form of a white solid. LC-MS [M+H]$^+$: 474.5.

$^1$H NMR (400 MHz, MeOD) δ 7.60 (s, 1H), 7.26-7.17 (m, 3H), 5.25 (s, 2H), 4.71-4.69 (m, 1H), 4.60-4.25 (m, 1H), 3.96 (s, 3H), 2.82-2.77 (m, 4H), 2.11-2.08 (m, 1H), 1.91-1.56 (m, 15H).

Example 21

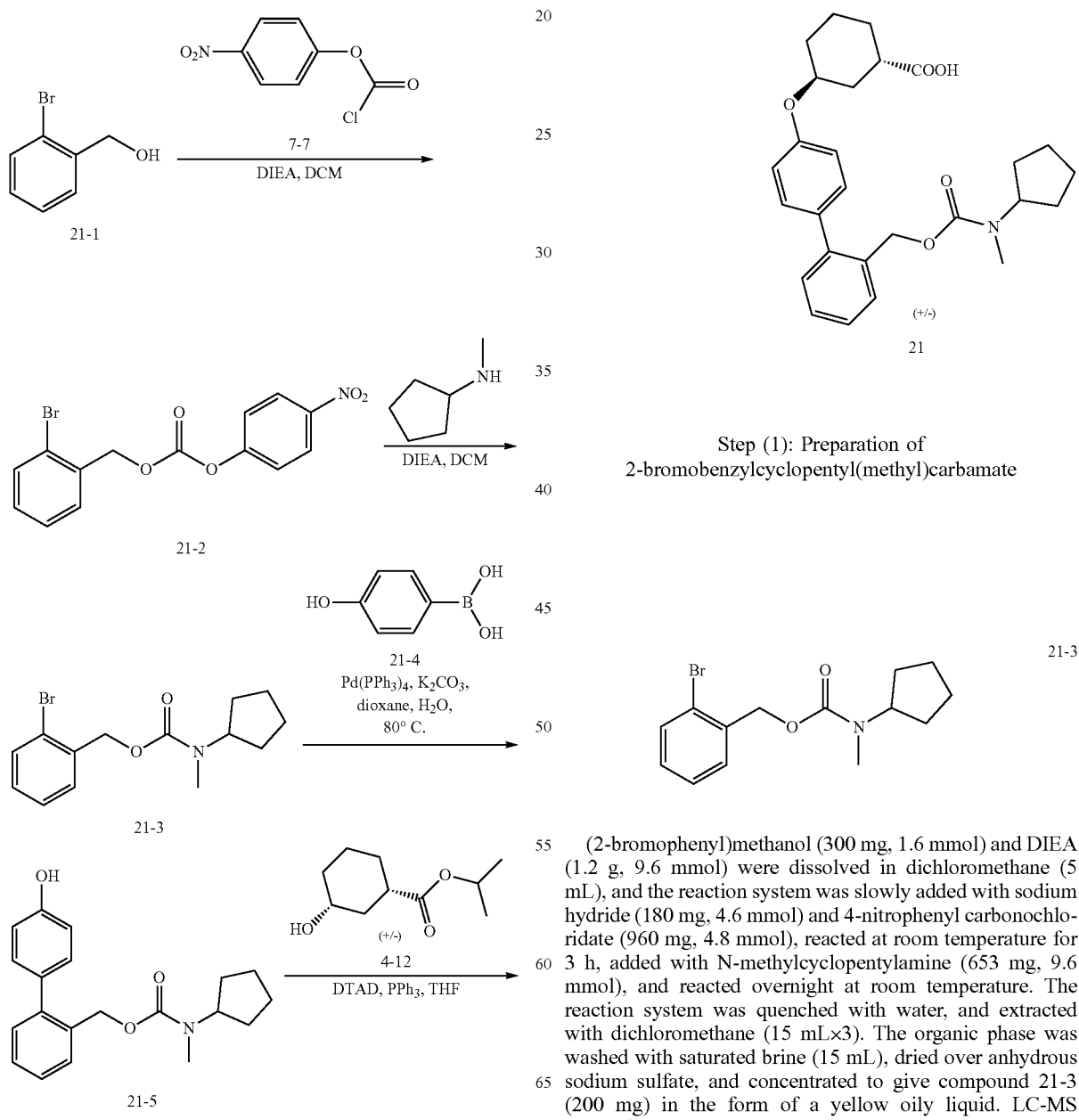

Step (1): Preparation of 2-bromobenzylcyclopentyl(methyl)carbamate (2-bromophenyl)methanol (300 mg, 1.6 mmol) and DIEA (1.2 g, 9.6 mmol) were dissolved in dichloromethane (5 mL), and the reaction system was slowly added with sodium hydride (180 mg, 4.6 mmol) and 4-nitrophenyl carbonochloridate (960 mg, 4.8 mmol), reacted at room temperature for 3 h, added with N-methylcyclopentylamine (653 mg, 9.6 mmol), and reacted overnight at room temperature. The reaction system was quenched with water, and extracted with dichloromethane (15 mL×3). The organic phase was washed with saturated brine (15 mL), dried over anhydrous sodium sulfate, and concentrated to give compound 21-3 (200 mg) in the form of a yellow oily liquid. LC-MS [M+H]$^+$: 311.6, 313.6.

Step (2): Preparation of (4'-hydroxy-[1,1'-biphenyl]-2-yl)methylcyclopentyl(methyl)carbamate

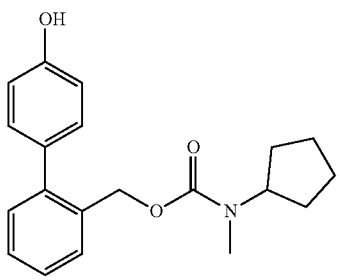

21-5

Compound 21-3 (200 mg, 0.64 mmol), (4-hydroxyphenyl)boronic acid (106 mg, 0.77 mmol), Pd(PPh$_3$)$_4$ (22 mg, 0.03 mmol) and potassium carbonate (265 mg, 1.92 mmol) were dissolved in dioxane/water (6/2, 8 mL). The resulted reaction solution was warmed to 100° C., reacted for 1 h, quenched with water, and extracted with ethyl acetate (30 mL×3). The organic phase was combined, washed with saturated brine (20 mL), dried over anhydrous sodium sulfate and concentrated to give compound 21-5 (120 mg) in the form of a yellow oily liquid. LC-MS [M+H]$^+$: 326.4.

Step (3): Preparation of (+/−)-isopropyl (1S,3S)-3-((2'-(((cyclopentyl(methyl)carbamoyl)oxy)methyl)-[1,1'-biphenyl]-4-yl)oxy)cyclohexane-1-carboxylate

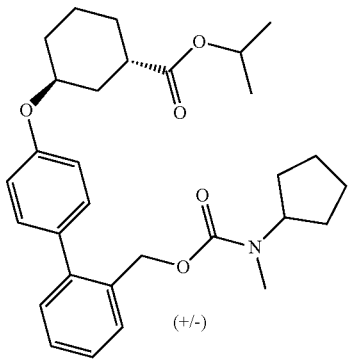

21-6

Compound 21-5 (120 mg, 0.3 mmol), compound 4-12 (220 mg, 1.2 mmol), di-tert-butyl azodicarboxylate (275 mg, 1.2 mmol) and triphenylphosphine (315 mg, 1.2 mmol) were dissolved in tetrahydrofuran (5 mL), and then the reaction system was reacted at 60° C. for 12 h under nitrogen atmosphere, quenched with water, and extracted with ethyl acetate (15 mL×3). The organic phases were combined, washed with saturated brine (15 mL), dried over anhydrous sodium sulfate and concentrated, and the residue was separated by column chromatography (PE/EA=2/1) to give compound 21-6 (200 mg, crude) in the form of a yellow oily liquid. LC-MS [M+H]$^+$: 494.3.

Step (4): Preparation of (+/−)-(1S,3S)-3-((2'-(((cyclopentyl(methyl)carbamoyl)oxy)methyl)-[1,1'-biphenyl]-4-yl)oxy)cyclohexane-1-carboxylate

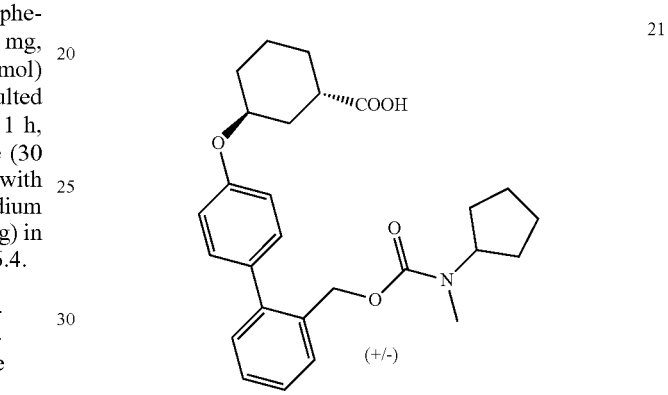

21

Compound 21-6 (200 mg, 0.4 mmol) and lithium hydroxide (84 mg, 2.0 mmol) were dissolved in a mixed solvent of THF (3 mL), MeOH (1 mL) and H$_2$O (1 mL), and then the reaction system was stirred overnight at room temperature, added with water (10 mL) to quench the reaction, and extracted with ethyl acetate (5 mL×3). The organic phase was dried over Na$_2$SO$_4$ and filtered, and the filtrate was concentrated by rotary evaporation. The residue was separated and lyophilized to give compound 21 (30 mg, 16.7% yield) in the form of a white solid.

$^1$H NMR (400 MHz, MeOD) δ 7.49-7.45 (m, 1H), 7.37 (td, J=6.7, 1.7 Hz, 2H), 7.31-7.25 (m, 3H), 7.05-6.99 (m, 2H), 5.08 (s, 2H), 4.72-4.74 (m, 1H), 4.38 (s, 1H), 2.86-2.78 (m, 1H), 2.74 (s, 3H), 2.06-2.13 (m, 1H), 1.93-1.98 (m, 3H), 1.83-1.50 (m, 12H).

Example 22

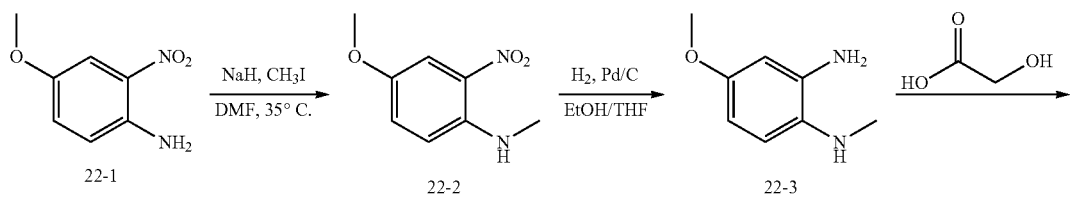

-continued
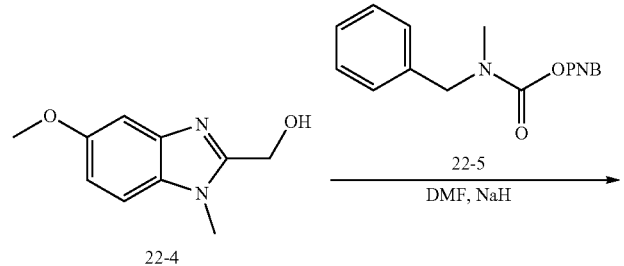
22-4
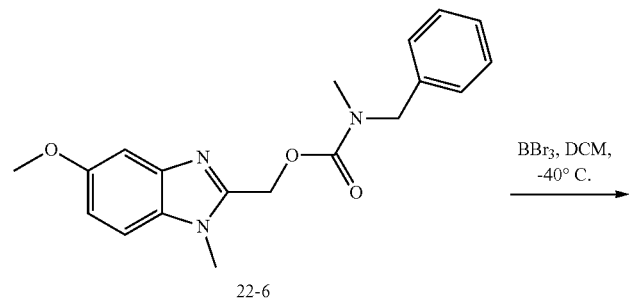
22-6
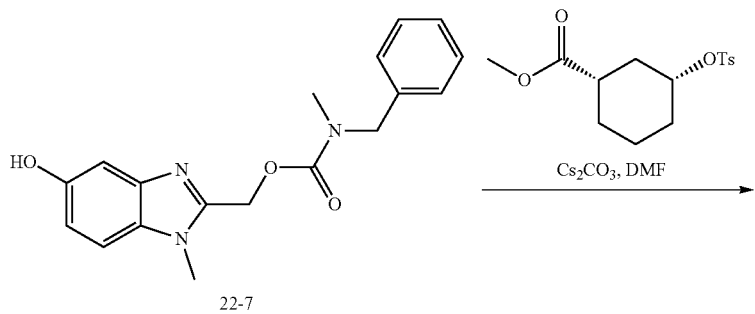
22-7
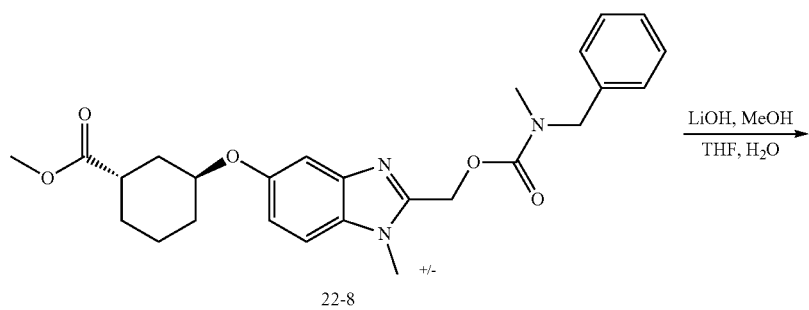
22-8
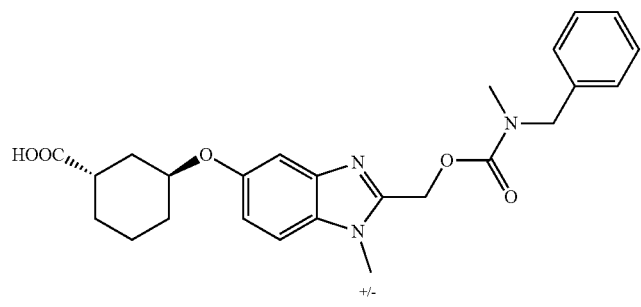
22

Step (1): Preparation of 4-methoxy-N-methyl-2-nitroaniline

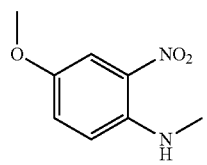

22-2

4-methoxy-2-nitroaniline (5.0 g, 29.8 mmol) and sodium hydride (1.3 g, 32.27 mmol) were dissolved in N,N-dimethylformamide (50 mL) at 0° C., and the reaction system was stirred for 10 min, added with methyl iodide (2.46 mL, 39.2 mmol), heated to 35° C., and reacted for 2 h. The reaction system was added with water (100 mL) to quench the reaction, and extracted with ethyl acetate (40 mL×3). The organic phases were combined, washed with saturated brine (40 mL×2), dried over anhydrous sodium sulfate and filtered. The filtrate was concentrated by rotary evaporation, and the residue was purified by silica gel column chromatography (dichloromethane:ethyl acetate=10:1) to give compound 22-2 (5 g, 92% yield) in the form of a yellow solid. LC-MS [M+H]$^+$: 183.1.

Step (2): Preparation of 4-methoxy-N$^1$-methylbenzene-1,2-diamine

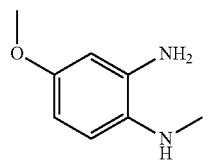

22-3

Compound 22-2 (3.8 g, 20.87 mmol) was dissolved in a mixed solution of ethanol (75 mL) and tetrahydrofuran (15 mL), and the reaction system was added with palladium on carbon catalyst (10%, 500 mg), purged with hydrogen, and stirred overnight at room temperature. The palladium on carbon was filtered, and the filtrate was concentrated by rotary evaporation. The crude product was purified by silica gel column chromatography (dichloromethane:ethyl acetate=10:1) to give compound 22-3 (2.9 g, 91% yield) in the form of a yellow solid. LC-MS [M+H]$^+$: 153.0.

Step (3): Preparation of (5-methoxy-1-methyl-1H-benzo[d]imidazol-2-yl)methanol

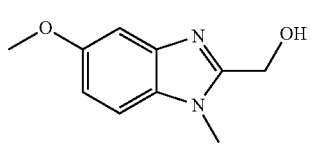

22-4

4-methoxy-N$^1$-methylbenzene-1,2-diamine (2.0 g, 13.2 mmol) and 2-hydroxyacetic acid (3.5 g, 46.1 mmol) were dissolved in a mixed solution of concentrated hydrochloric acid (5 mL) and water (10 mL). The reaction system was reacted at 100° C. for 4 h under nitrogen atmosphere. The reaction system was cooled to room temperature, slowly added with saturated sodium bicarbonate solution (50 mL), and extracted with ethyl acetate (30 mL×3). The organic phases were combined, washed with saturated brine (20 mL), dried over anhydrous sodium sulfate, and filtered. The filtrate was concentrated by rotary evaporation to give a crude product. The crude product was purified by silica gel column chromatography (dichloromethane:methanol=20:1) to give compound 22-4 (1.0 g, 39% yield) in the form of a white solid. LC-MS [M+H]$^+$: 193.9.

Step (4): Preparation of (5-methoxy-1-methyl-1H-benzo[d]imidazol-2-yl)methylbenzyl(methyl)carbamate

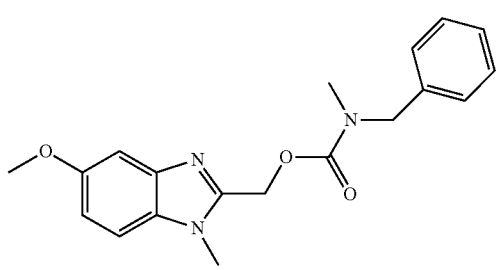

22-6

Compound 22-4 (500 mg, 2.6 mmol) was dissolved in N,N-dimethylformamide (10 mL), and the reaction system was added in portions with sodium hydride (156 mg, 32.3 mmol) in an ice water bath, stirred for 10 min, added with benzyl(methyl)aminomethyl 4-nitrobenzoic anhydride (900 mg, 3.4 mmol), warmed to room temperature, and reacted for 3 h. The reaction system was added with water (50 mL) to quench the reaction and extracted with ethyl acetate (20 mL×3). The organic phases were combined, washed with saturated brine (20 mL×2), dried over anhydrous sodium sulfate and filtered. The filtrate was concentrated by rotary evaporation, and the residue was purified by silica gel column chromatography (dichloromethane:ethyl acetate=10:1) to give compound 22-6 (470 mg, 53% yield) in the form of a white solid. LC-MS [M+H]$^+$: 340.8.

Step (5): Preparation of (5-hydroxy-1-methyl-1H-benzo[d]imidazol-2-yl)methylbenzyl(methyl)carbamate

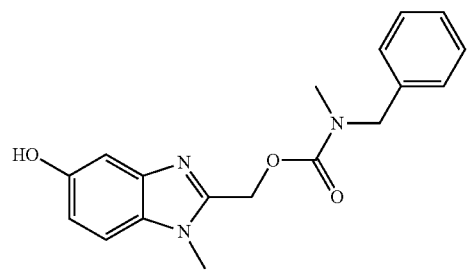

22-7

Compound 22-6 (1.3 g, 3.8 mmol) was dissolved in dichloromethane (20 mL), and the reaction system was cooled to −40° C. under nitrogen atmosphere, and added with boron tribromide (1.1 mL, 11.5 mmol). The reaction system was warmed to 0° C. and reacted for 3 h. The reaction system was added with water (30 mL) to quench the reaction, extracted with ethyl acetate (20 mL×3), and washed with saturated brine (20 mL). The organic phase was dried over anhydrous sodium sulfate and filtered. The filtrate was concentrated by rotary evaporation, and the residue was purified by silica gel column chromatography (dichloromethane:methanol=50:1) to give compound 22-7 (0.72 g, 58% yield) in the form of a white solid. LC-MS [M+H]⁺: 326.8.

Step (6): Preparation of (+/−)-methyl (1S,3S)-3-((2-(((benzyl(methyl)carbamoyl)oxy)methyl)-1-methyl-1H-benzo[d]imidazol-5-yl)oxy)cyclohexane-1-carboxylate

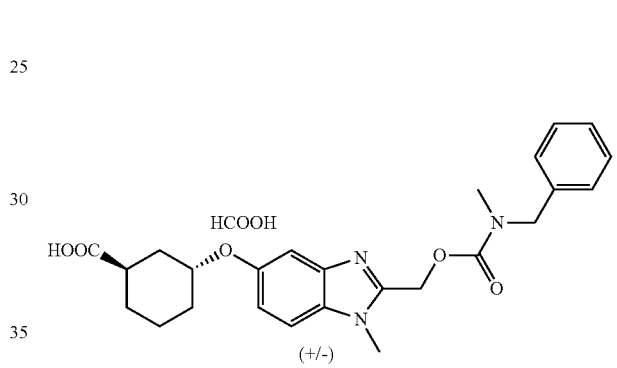

Compound 22-7 (100 mg, 0.31 mmol), methyl (1S,3R)-3-(tosyloxy)cyclohexane-1-carboxylate (100 mg, 0.36 mmol) and Cs₂CO₃ (200 mg, 0.62 mmol) were dissolved in DMF (10 mL), and the reaction system was stirred at 100° C. overnight, cooled to room temperature, quenched with water (50 mL), and extracted with ethyl acetate (15 mL×3). The organic phases were combined, washed with saturated brine (20 mL), dried over anhydrous sodium sulfate and filtered. The filtrate was concentrated by rotary evaporation, and the residue was purified by silica gel column chromatography (dichloromethane:ethyl acetate=5:1) to give compound 22-8 (30 mg, 21% yield) in the form of a white solid. LC-MS [M+H]⁺: 466.7.

Step (7): Preparation of (+/−)-(1S,3S)-3-(((benzyl(methyl)carbamoyl)oxy)methyl)-1-methyl-1H-benzo[d]imidazol-5-yl)oxy)cyclohexane-1-carboxylate Compound 22-8 (30 mg, 0.07 mmol) was dissolved in a mixed solution of tetrahydrofuran (3 mL), methanol (1 mL) and water (1 mL), and the reaction system was stirred overnight at room temperature. After the organic solvent was removed by rotary evaporation, the reaction system was diluted with water (10 mL), then adjusted to pH 2-3 with diluted hydrochloric acid (1 N) and extracted with ethyl acetate (20 mL×3). The organic phase was dried over anhydrous sodium sulfate and filtered, and the filtrate was concentrated by rotary evaporation. The residue was purified by silica gel column chromatography (dichloromethane:ethyl acetate=1/1), subjected to chiral resolution, and lyophilized to give compound 22-A (3 mg) and compound 22-B (2.5 mg) both in the form of a white solid. LC-MS [M+H]⁺: 451.7.

Compound 22-A

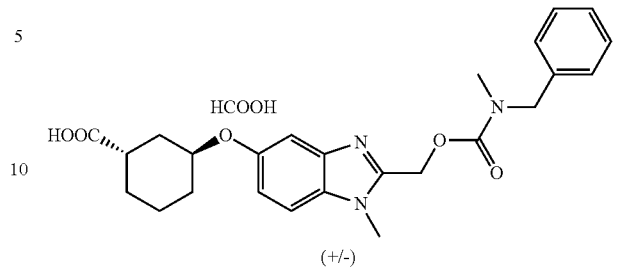

¹H NMR (400 MHz, MeOD) δ 7.40-7.17 (m, 7H), 7.02 (d, J=8.5 Hz, 1H), 5.43 (s, 2H), 4.52 (s, 2H), 4.35-4.29 (m, 1H), 3.91 (s, 1.5H), 3.70 (s, 1.5H), 2.93 (d, 3H), 2.47-2.37 (m, 2H), 2.22-2.16 (m, 1H), 2.03-1.91 (m, 2H), 1.38-1.44 (m, 4H).

Compound 22-B

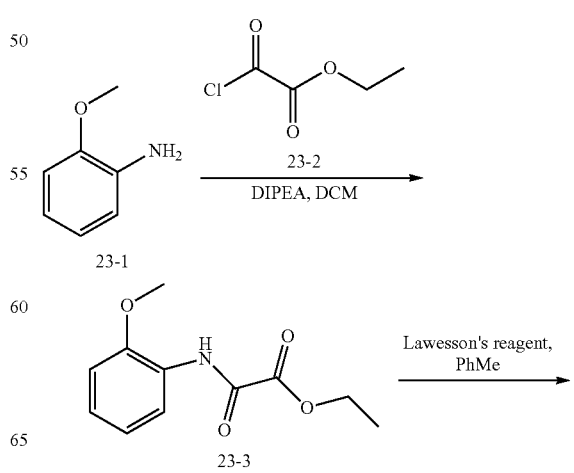

¹H NMR (400 MHz, MeOD) δ 7.45-7.15 (m, 7H), 7.05 (d, J=9.1 Hz, 1H), 5.43 (s, 2H), 4.72-4.67 (m, 1H), 4.52 (s, 2H), 3.91 (s, 1.5H), 3.70 (s, 1.5H), 2.93 (d, 3H), 2.87-2.79 (m, 1H), 2.15-2.09 (m, 1H), 1.98-1.88 (m, 2H), 1.84-1.78 (m, 2H), 1.71-1.59 (m, 3H).

Example 23

217
-continued

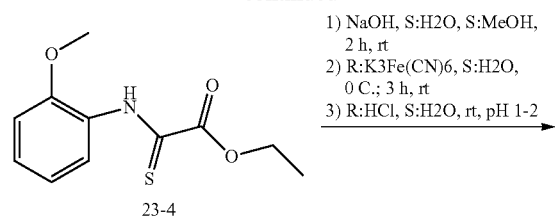

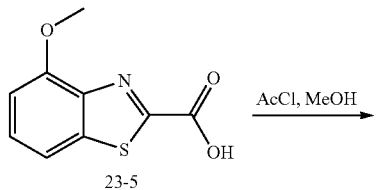

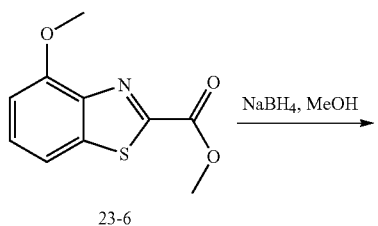

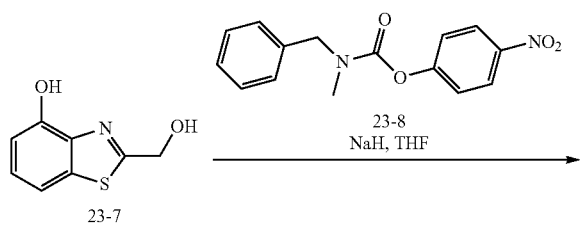

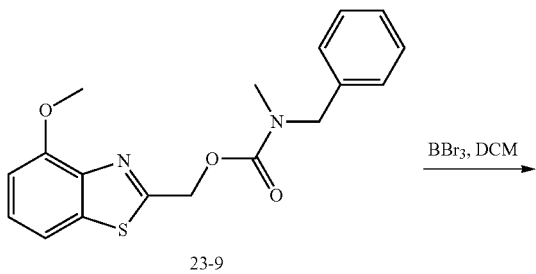

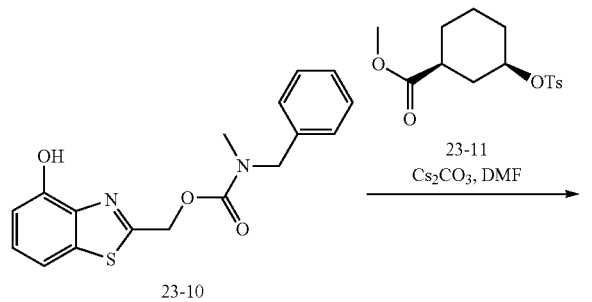

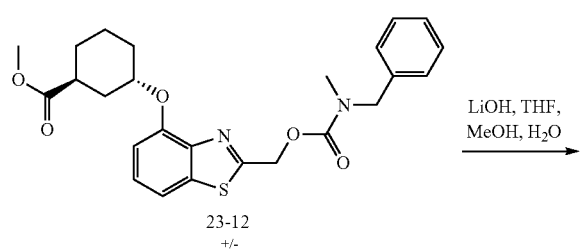

218
-continued

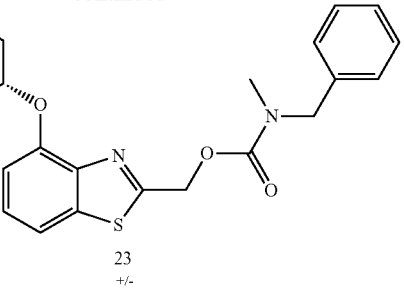

Step (1): Preparation of ethyl 2-((2-methoxyphenyl)amino)-2-oxoacetate

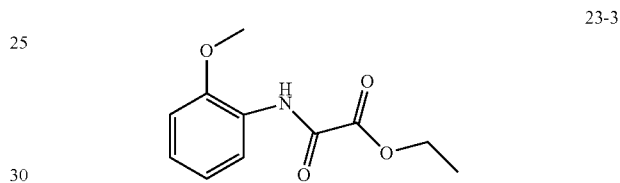

2-methoxyaniline (6.04 g, 49 mmol) and triethylamine (7.42 g, 73.5 mmol) were dissolved in dichloromethane (50 mL), and the reaction system was cooled to 0° C., added dropwise with ethyl 2-chloro-2-oxoacetate (7.03 g, 51.5 mmol), and reacted at room temperature for 2 h. The reaction system was washed sequentially with water (20 mL), saturated sodium carbonate (20 mL) and saturated brine (20 mL), dried over anhydrous sodium sulfate, and concentrated to give compound 23-3 (10.2 g, 92% yield) in the form of a yellow solid. LC-MS [M+H]⁺: 224.4.

Step (2): Preparation of ethyl 2-((2-methoxyphenyl)amino)-2-thioacetate

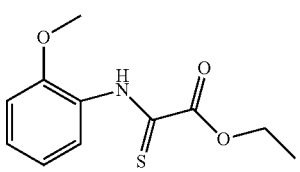

Compound 23-3 (5.0 g, 22.4 mmol) was dissolved in toluene (50 mL), and the reaction system was added with Lawesson reagent (4.5 g, 11.2 mmol), heated to 70° C. and reacted for 3 h. The reaction system was concentrated, and the residue was separated by column chromatography (PM/EA=5/1) to give compound 23-4 (4.2 g, 78.6% yield) in the form of a yellow solid. LC-MS [M+H]⁺: 240.1.

Step (3): Preparation of 4-methoxybenzo[d]thiazole-2-carboxylic Acid

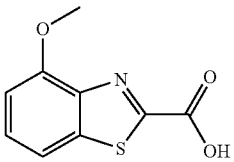

23-5

Compound 23-4 (2.0 g, 8.3 mmol) was dissolved in ethanol (25 mL), and the reaction system was added with sodium hydroxide (30 mL, 2 N), and reacted at room temperature for 2 h. After the reaction was completed, the ethanol was removed by rotary evaporation under reduced pressure, and the reaction system was cooled to 0° C., added dropwise with and a solution of potassium ferricyanide (8.25 g, 25.1 mmol) in water (15 mL), and reacted at room temperature for 3 h. The reaction system was adjusted to pH 1-2 with hydrochloric acid (2 N), and the solid was collected by filtration and dried to give compound 23-5 (2.7 g, crude) in the form of a yellow solid. LC-MS [M+H]$^+$: 210.2.

Step (4): Preparation of methyl 4-methoxybenzo[d]thiazole-2-carboxylate

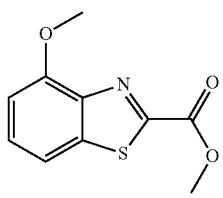

23-6

Compound 23-5 (2.7 g, crude) was dissolved in methanol (20 mL). The reaction system was cooled to 0° C., added with acetyl chloride (2 mL), and then slowly warmed to room temperature and reacted for 16 h. The reaction system was concentrated, and the residue was diluted with ethyl acetate (50 mL), washed with saturated brine (20 mL×2), dried over anhydrous sodium sulfate, and concentrated. The residue was separated by column chromatography (DCM/EA=20/1) to give compound 23-6 (230 mg) in the form of a yellow solid. LC-MS [M+H]$^+$: 224.2.

Step (5): Preparation of (4-methoxybenzo[d]thiazol-2-yl)methanol

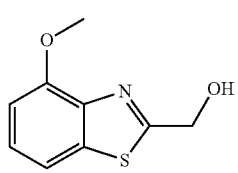

23-7

Compound 23-6 (100 mg, 0.45 mmol) was dissolved in methanol (5 mL). The reaction system was cooled to 0° C., added with sodium borohydride (38 mg, 0.90 mmol), and then reacted at room temperature for 16 h. The reaction system was concentrated, and the residue was separated by column chromatography (DCM/MeOH=30/1) to give compound 23-7 (74 mg, 84% yield) in the form of a yellow solid. LC-MS [M+H]$^+$: 196.2.

Step (6): Preparation of (4-methoxybenzo[d]thiazol-2-yl)methylbenzyl(methyl)carbamate

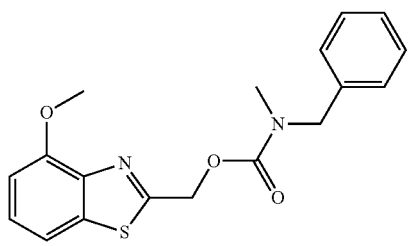

23-9

Compound 23-7 (74 mg, 0.38 mmol) was dissolved in tetrahydrofuran (10 mL), and the reaction system was added with sodium hydride (46 mg, 0.114 mmol) in an ice bath. The reaction system was reacted for 0.5 h, added with compound 23-8 (120 mg, 0.44 mmol), and reacted at room temperature for 16 h. The reaction system was poured into ice water (10 mL), extracted with ethyl acetate (10 mL×2), and washed with saturated brine (10 mL). The organic phase was dried over anhydrous sodium sulfate and filtered, and the filtrate was concentrated by rotary evaporation. The residue was purified by silica gel column chromatography (DCM/MeOH=30/1) to give compound 23-9 (72 mg, 54% yield) in the form of a yellow solid. LC-MS [M+H]$^+$: 343.1.

Step (7): Preparation of (4-hydroxybenzo[d]thiazol-2-yl)methylbenzyl(methyl)carbamate

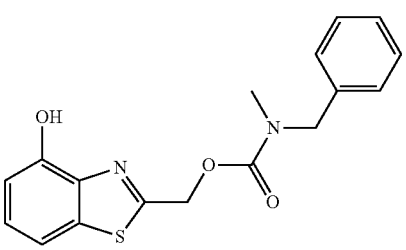

23-10

Compound 23-9 (75 mg, 0.22 mmol) was dissolved in dichloromethane (10 mL), and the reaction system was added with a solution of boron tribromide in dichloromethane (1.1 mL, 1.1 mmol) at −40° C., warmed to 0° C. and reacted for 2 h. The reaction system was quenched with methanol to, diluted with dichloromethane (10 mL), adjusted to pH 9-10 with saturated sodium carbonate, extracted with dichloromethane (10 mL×2), and washed with saturated brine (10 mL). The organic phase was dried over anhydrous sodium sulfate and filtered, and the filtrate was concentrated by rotary evaporation. The residue was purified by silica gel column chromatography (DCM/

MeOH=30/1) to give compound 23-10 (56 mg, 78% yield) in the form of a yellow solid. LC-MS [M+H]⁺: 329.4.

Step (8): Preparation of (+/−)-methyl (1S,3S)-3-((2-(((benzyl(methyl)carbamoyl)oxy)methyl)benzo[d]thiazol-4-yl)oxy)cyclohexane-1-carboxylate

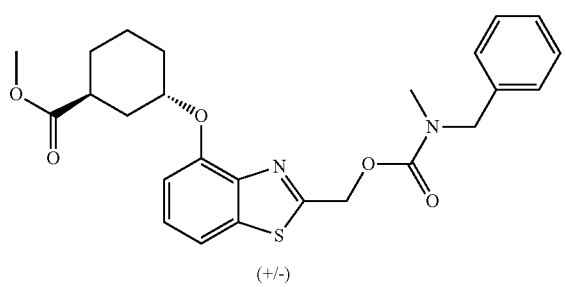

23-12
(+/−)

Compound 23-10 (76 mg, 0.23 mmol), methyl (1S,3R)-3-(tosyloxy)cyclohexane-1-carboxylate (144 mg, 0.46 mmol) and cesium carbonate (150 mg, 0.46 mmol) were dissolved in DMF (10 mL), and the reaction system was heated to 100° C. and reacted for 7 h under nitrogen atmosphere. Then the reaction system was diluted with ethyl acetate (20 mL), washed sequentially with water (10 mL×2) and saturated brine (10 mL), dried over anhydrous sodium sulfate and concentrated, and the residue was separated by column chromatography (DCM/MeOH=50/1) to give compound 23-12 (75 mg, 70% yield) in the form of a yellow solid. LC-MS [M+H]⁺: 469.2.

Step (9): Preparation of (+/−)-(1S,3S)-3-((2-(((benzyl(methyl)carbamoyl)oxy)methyl)benzo[d]thiazole-4-yl) oxy)cyclohexane-1-carboxylic Acid

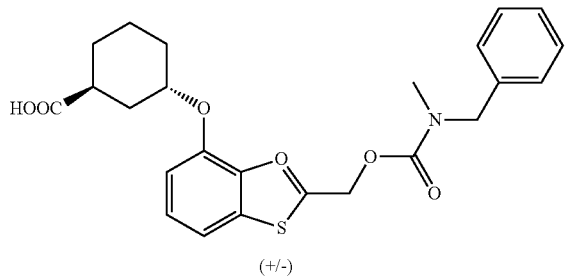

23
(+/−)

Compound 23-12 (75 mg, 0.16 mmol) was dissolved in THF (9 mL), and the reaction system was sequentially added with MeOH (3 mL), H₂O (3 mL) and lithium hydroxide (20 mg, 0.5 mmol), and stirred overnight at room temperature. Then water (10 mL) was added for dilution, and the organic solvent was removed by rotary evaporation under reduced pressure. The aqueous phase was adjusted to pH 5-6 with hydrochloric acid (1 N), and extracted with dichloromethane (10 mL×2). The organic phase was dried over anhydrous sodium sulfate and filtered, and the filtrate was concentrated by rotary evaporation. The residue was purified by silica gel column chromatography (DCM/MeOH=20/1) and then lyophilized to give compound 23 (30 mg, 41% yield) in the form of a white solid. LC-MS [M+H]⁺: 455.3.

¹H NMR (400 MHz, MeOD) δ 7.55 (t, J=9.0 Hz, 1H), 7.46-7.23 (m, 6H), 7.13 (d, J=8.0 Hz, 1H), 5.59-5.58 (d, 2H), 5.00-4.98 (m, 1H), 4.61-4.55 (d, 2H), 2.98-2.95 (m, 4H), 2.19-2.16 (m, 1H), 2.07-1.83 (m, 4H), 1.80-1.54 (m, 3H).

Examples 24-55

The compounds were prepared using the corresponding starting materials with reference to the method described in Example 4.

| No. | Compound structure | LCMC (RT, m/z) |
|---|---|---|
| Example 24 | 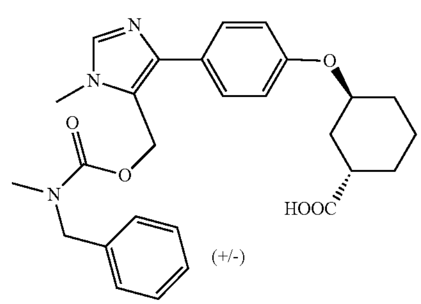 | 478.4 |

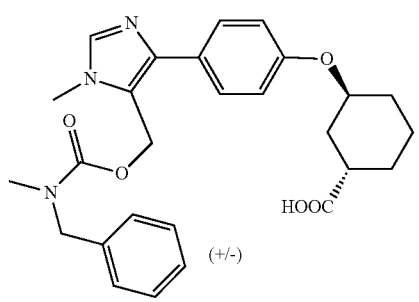

24
(+/−)

| No. | Compound structure | LCMC (RT, m/z) |
|---|---|---|
| Example 25 | 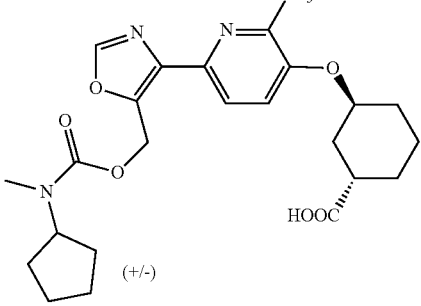<br>(+/-)<br>25 | 512.2 |
| Example 26 | 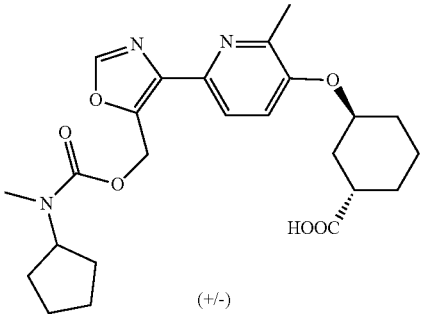<br>(+/-)<br>26 | 458.3 |
| Example 27 | 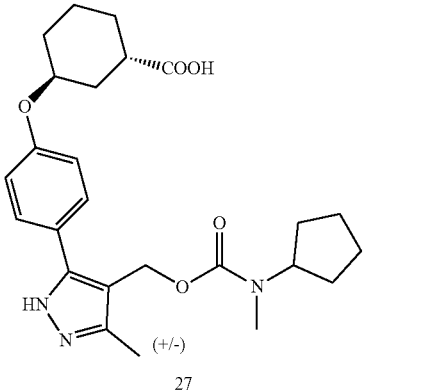 [SMILES: Cc1n[nH]c(-c2ccc(O[C@H]3CCC[C@H](C(=O)O)C3)cc2)c1COC(=O)N(C)C1CCCC1]<br>(+/-)<br>27 | 456.5 |
| Example 31 | 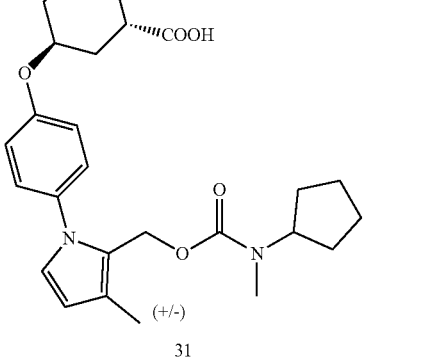<br>(+/-)<br>31 | 455.5 |

-continued

| No. | Compound structure | LCMC (RT, m/z) |
|---|---|---|
| Example 32 | 32 (+/-) | 525.2 |
| Example 33 | 33 (+/-) | 539.4 |
| Example 36 | 36 (+/-) | 472.6 |
| Example 37 | 37 (+/-) | 526.4 |

-continued
| No. | Compound structure | LCMC (RT, m/z) |
|---|---|---|
| Example 38 | 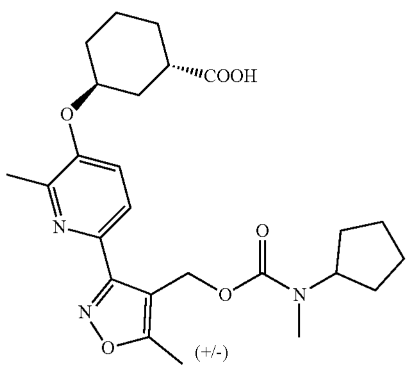 | 472.4 |
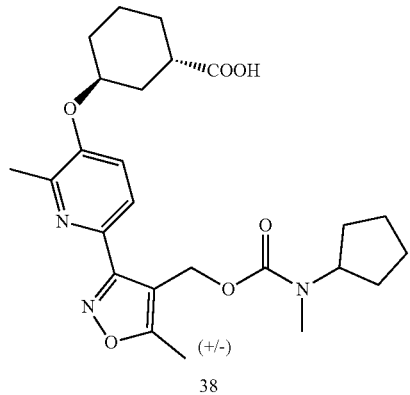
38
| | | |
|---|---|---|
| Example 39 | | 488.1 |
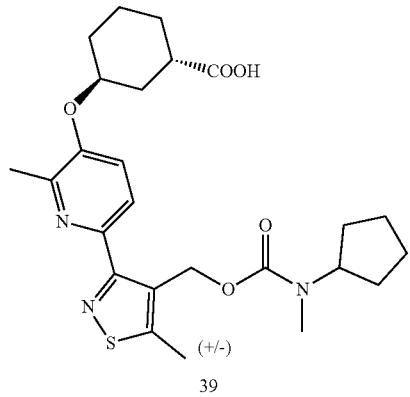
39
| | | |
|---|---|---|
| Example 40 | | 488.4 |
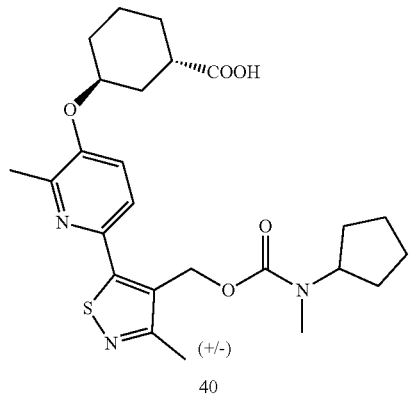 [SMILES: Cc1nc(-c2onc(C)c2COC(=O)N(C)C2CCCC2)ccc1O[C@H]1CCC[C@H](C(=O)O)C1]
40

-continued
| No. | Compound structure | LCMC (RT, m/z) |
|---|---|---|
| Example 41 | 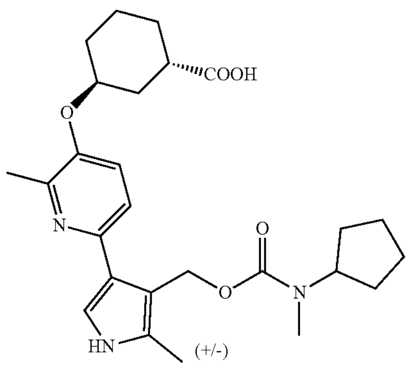 | 470.2 |
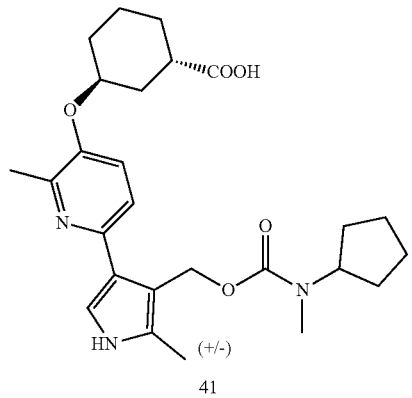 [SMILES: Cc1nc(-c2c[nH]c(C)c2COC(=O)N(C)C2CCCC2)ccc1O[C@H]1CCC[C@H](C(=O)O)C1]
41
| Example 42 | | 471.4 |
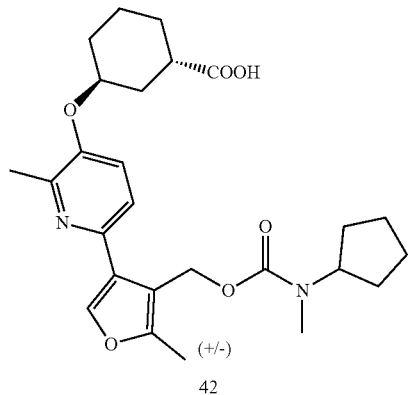
42
| Example 43 | | 487.4 |
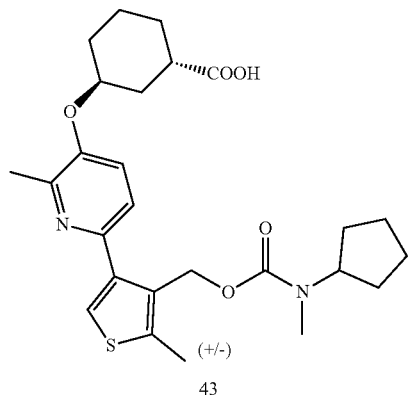 [SMILES: Cc1nc(-c2coc(C)c2COC(=O)N(C)C2CCCC2)ccc1O[C@H]1CCC[C@H](C(=O)O)C1]
43

| No. | Compound structure | LCMC (RT, m/z) |
|---|---|---|
| Example 44 | 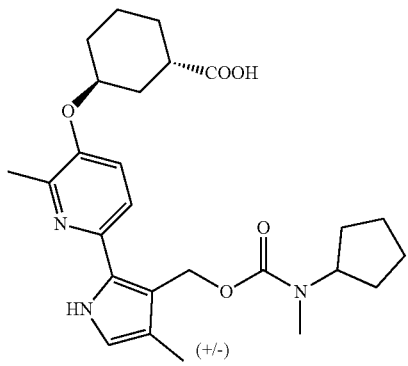<br>(+/-)<br>44 | 470.4 |
| Example 45 | 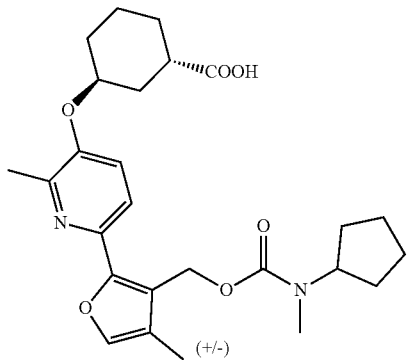<br>(+/-)<br>45 | 471.2 |
| Example 46 | 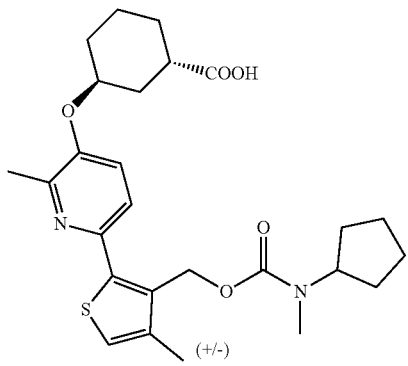<br>(+/-)<br>46 | 487.4 |
| Example 47 | 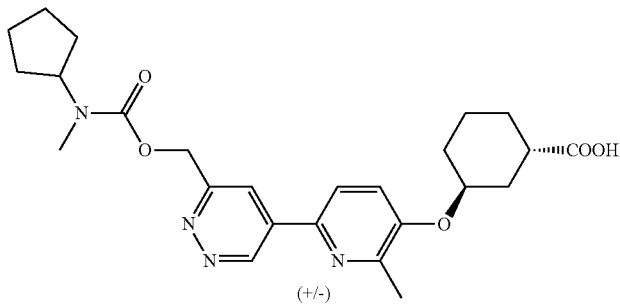<br>(+/-)<br>47 | 469.4 |

-continued
| No. | Compound structure | LCMC (RT, m/z) |
|---|---|---|
| Example 48 | 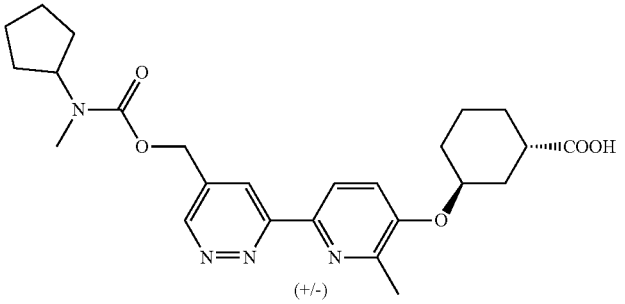<br>(+/−)<br>48 | 483.6 |
| Example 49 | 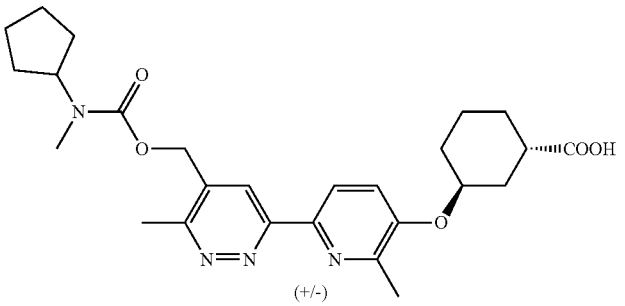<br>(+/−)<br>49 | 483.4 |
| Example 50 | 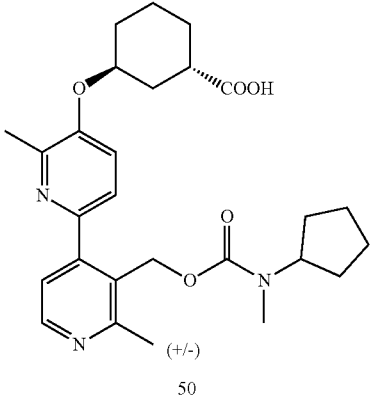<br>(+/−)<br>50 | 469.2 |
| Example 51 | 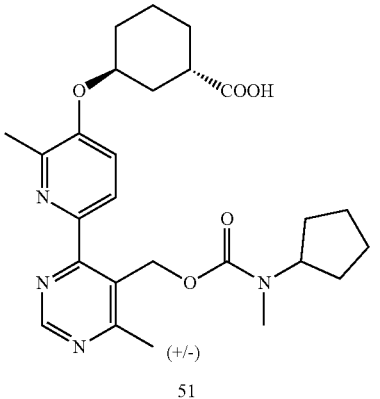 [SMILES: Cc1nc(-c2ncnc(C)c2COC(=O)N(C)C2CCCC2)ccc1O[C@H]1CCC[C@H](C(=O)O)C1]<br>(+/−)<br>51 | 483.2 |

| No. | Compound structure | LCMC (RT, m/z) |
|---|---|---|
| Example 52 | 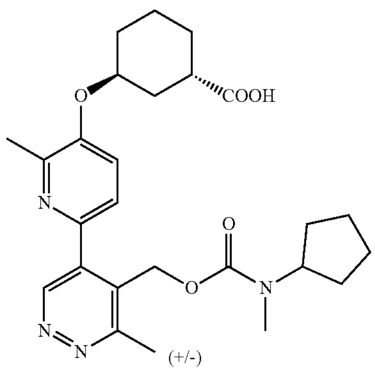 | 483.2 |
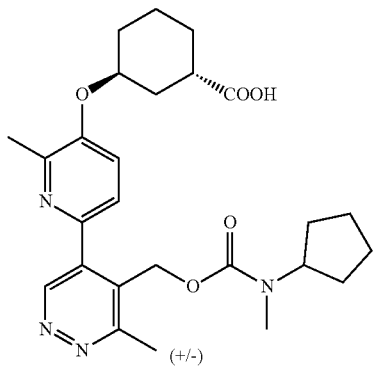
52 (+/-)
| | | |
|---|---|---|
| Example 53 | | 471.2 |
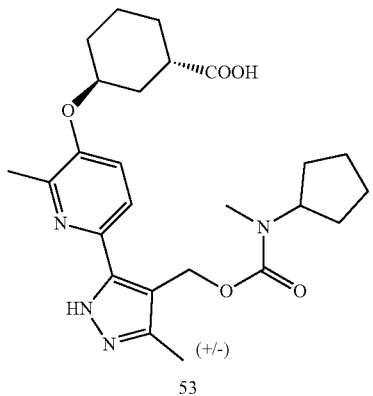 [SMILES: Cc1nc(-c2[nH]nc(C)c2COC(=O)N(C)C2CCCC2)ccc1O[C@H]1CCC[C@H](C(=O)O)C1]
53 (+/-)
| | | |
|---|---|---|
| Example 54 | | 471.4 |
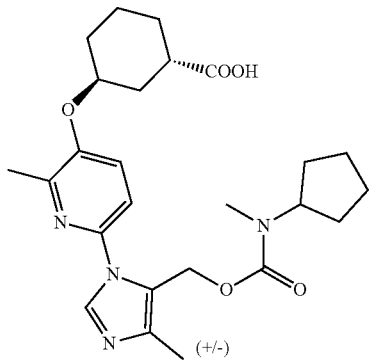
54 (+/-)

-continued
| No. | Compound structure | LCMC (RT, m/z) |
|---|---|---|
| Example 55 | 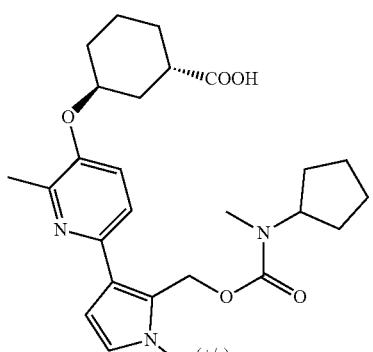<br>(+/-)<br>55 | 470.3 |
| Example 56 | 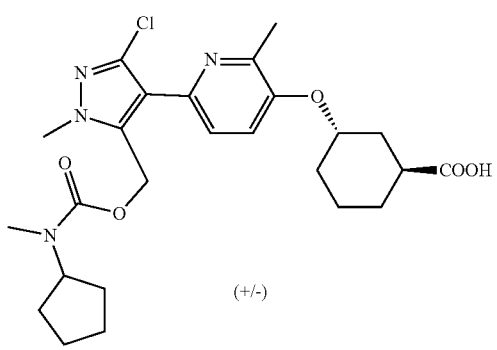<br>(+/-)<br>56 | 505.2 |
| Example 57 | 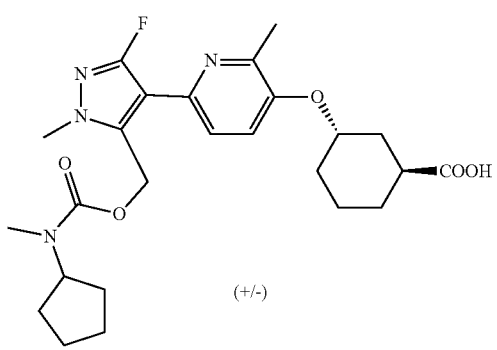<br>(+/-)<br>57 | 489.3 |
| Example 58 | 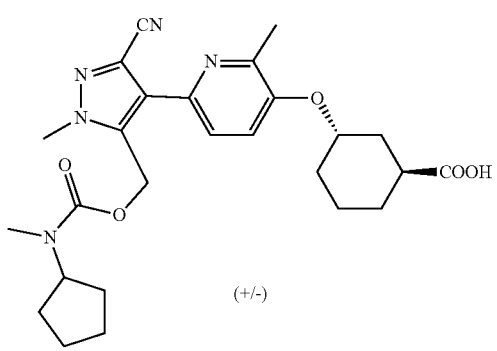<br>(+/-)<br>58 | 496.4 |

Example 28

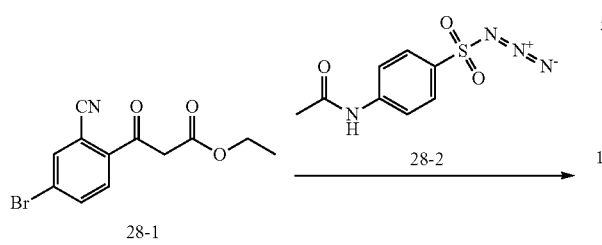

28-1

28-2

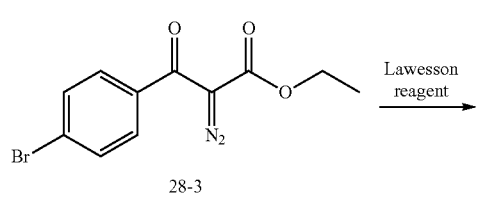

28-3

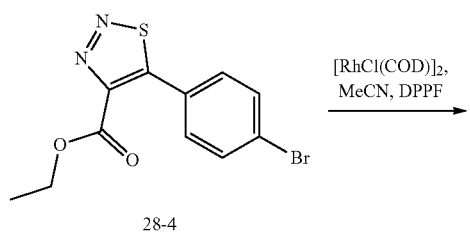

28-4

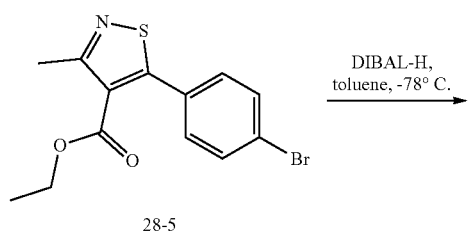

28-5

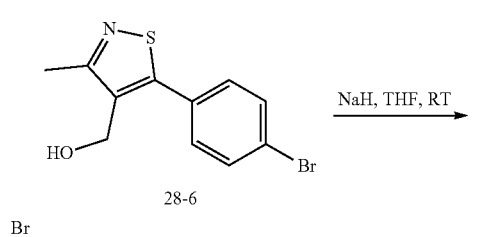

28-6

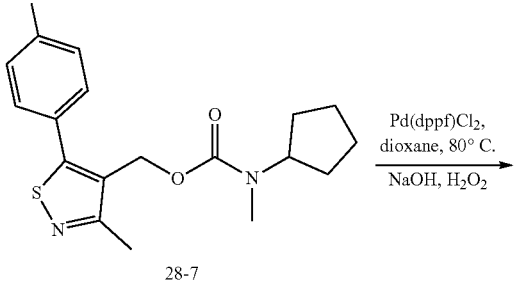

28-7

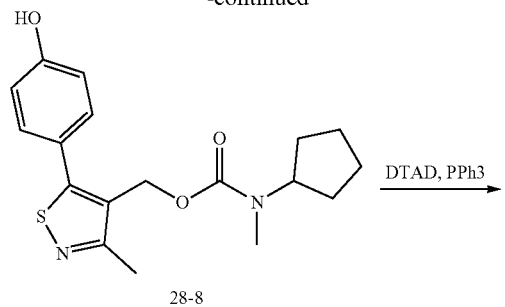

28-8

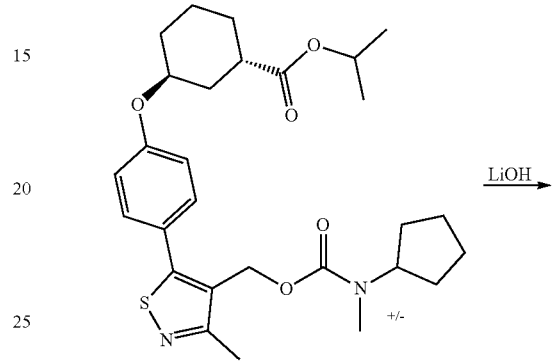

28-9

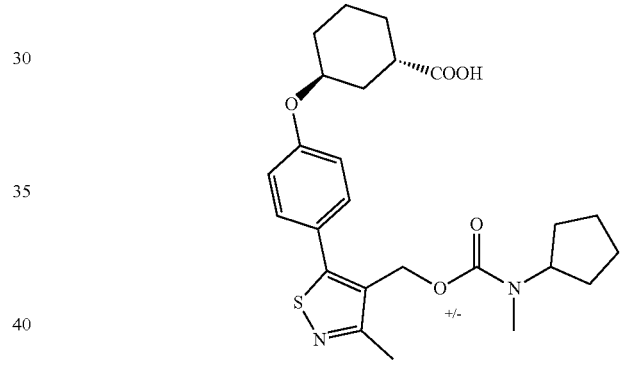

28

Step (1): Preparation of ethyl 3-(4-bromophenyl)-2-diazo-3-oxopropionate 28-3

Ethyl 3-(4-bromophenyl)-3-oxopropionate (1 g, 3.7 mmol) was dissolved in acetonitrile (10 mL), and the reaction system was added with 4-acetamidobenzenesulfonyl azide (803 mg, 4.07 mmol) and triethylamine (1.12 g, 11.1 mmol), reacted at room temperature for 3 h, added with water (20 mL) to quench the reaction, and extracted with ethyl acetate (20 mL×3). The organic phases were combined, washed with saturated brine (15 mL), dried over anhydrous sodium sulfate, filtered and concentrated, and the residue was separated and purified by silica gel column chromatography to give compound 28-3 (900 mg, 65.41% yield) in the form of a white solid. LC-MS [M+Na]⁺: 319.

Step (2): Preparation of ethyl 5-(4-bromophenyl)-1,2,3-thiadiazole-4-carboxylate

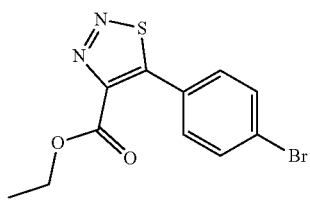

28-4

Compound 28-3 (900 mg, 3.00 mmol) and Lawesson reagent (1.5 g, 3.75 mmol) were dissolved in toluene (10 mL) under nitrogen atmosphere, heated to reflux for 3 h and concentrated, and the residue was separated by column chromatography to give compound 28-4 (800 mg, crude, 68% yield) in the form of a yellow oily liquid. LC-MS [M+Na]⁺: 335.

Step (3): Preparation of ethyl 5-(4-bromophenyl)-3-methylisothiazole-4-carboxylate

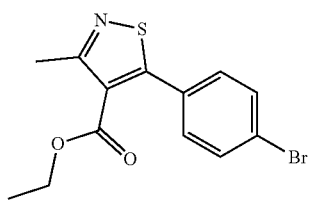

28-5

Compound 28-4 (800 mg, 2.58 mmol) was dissolved in chlorobenzene (10 mL), and the reaction system was added with DPPF (143 mg, 0.26 mmol), acetonitrile (1.06 g, 25.8 mmol), and (1,5-cyclooctadiene)chlororhodium (I) dimer (64 mg, 0.13 mmol), heated to 130° C., reacted for 1 h and concentrated. The residue was separated by column chromatography to give compound 28-5 (500 mg, crude, 47.67% yield) in the form of a yellow oily liquid. LC-MS [M+H]⁺: 326.

Step (4): Preparation of (5-(4-bromophenyl)-3-methylisothiazol-4-yl)methanol

28-6

Compound 28-5 (500 mg, 1.5 mmol) was dissolved in tetrahydrofuran (5 mL) under nitrogen atmosphere, and the reaction system was cooled to −78° C., added dropwise with DIBAL-H (6.0 mL, 6.0 mmol), reacted for 4 h, added with ammonium chloride solution (20 mL) to quench the reaction, and extracted with ethyl acetate (30 mL×3). The organic phases were combined, washed with saturated brine (20 mL), dried over anhydrous sodium sulfate, filtered and concentrated, and the residue was separated by silica gel column chromatography to give compound 28-6 (300 mg, 56.00% yield) in the form of a white solid. LC-MS [M+H]⁺: 286.

Step (5): Preparation of (5-(4-bromophenyl)-3-methylisothiazol-4-yl)methylcyclopentyl(methyl)carbamate

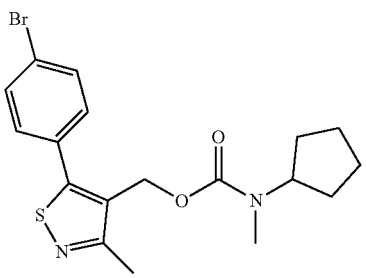

28-7

Compound 28-6 (300 mg, 1.08 mmol) was dissolved in tetrahydrofuran (10 mL), and the reaction system was added with sodium hydride (39 mg, 1.68 mmol), stirred at room temperature for 30 min, added with 4-nitrophenylcyclopentyl(methyl)carbamate (428 mg, 1.68 mmol), reacted overnight at room temperature, quenched with ice water (20 mL), and extracted with ethyl acetate (20 mL×3). The organic phases were combined, washed with saturated brine (15 mL), dried over anhydrous sodium sulfate, filtered and concentrated. The residue was separated by column chromatography to give compound 28-7 (300 mg, 54.63% yield) in the form of a yellow solid. LC-MS [M+H]⁺: 409.

Step (6): Preparation of (5-(4-hydroxyphenyl)-3-methylisothiazol-4-yl)methylcyclopentyl(methyl)carbamate

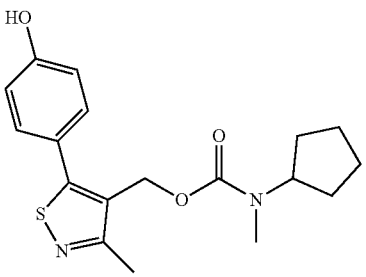

28-8

Compound 28-7 (300 mg, 0.72 mmol), 4,4,4',4',5,5,5',5'-octamethyl-2,2'-bi(1,3,2-dioxaborolane) (366 mg, 1.44 mmol), potassium acetate (213 mg, 2.1 mmol) and Pd(dppf)Cl₂ (54 mg, 0.072 mmol) were dissolved in anhydrous dioxane (5 mL), and the reaction system was stirred at 80° C. for 3 h. The reaction system was cooled to room temperature, filtered and concentrated, and the residue was dissolved in tetrahydrofuran, cooled to 0° C., added with NaOH solution (1 mL, 1 N) and hydrogen peroxide (0.5 mL), reacted for 1 h, diluted with water (10 mL) and extracted with ethyl acetate (15 mL×3). The organic phases were combined, washed with saturated brine (15 mL), dried over anhydrous sodium sulfate, filtered and concentrated. The residue was separated by column chromatography to give compound 28-8 (200 mg, 47.92% yield) in the form of a yellow solid. LC-MS[M+H]$^+$: 347.

Step (7): Preparation of (+/−)-isopropyl (1S,3S)-3-(4-(4-(((cyclopentyl(methyl)carbamoyl)oxy)methyl)-3-methylisothiazol-5-yl)phenoxy)cyclohexane-1-carboxylate

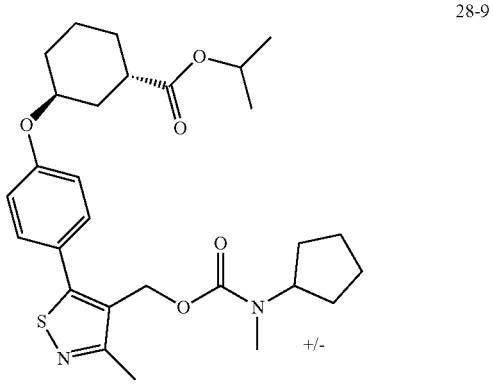 [SMILES: Cc1nsc(-c2ccc(O[C@H]3CCC[C@H](C(=O)OC(C)C)C3)cc2)c1COC(=O)N(C)C1CCCC1]

28-9

Compound 28-8 (200 mg, 0.58 mmol), isopropyl (1S,3R)-3-hydroxycyclohexane-1-carboxylate (432 mg, 2.32 mmol), di-tert-butyl azodicarboxylate (534 mg, 2.32 mmol) and triphenylphosphine (608 mg, 2.32 mmol) were dissolved in tetrahydrofuran (5 mL), and then the reaction system was reacted at 60° C. for 12 h under nitrogen atmosphere, quenched with water (15 mL), and extracted with ethyl acetate (15 mL×3). The organic phases were combined, washed with saturated brine (15 mL), dried over anhydrous sodium sulfate and concentrated, and the residue was separated by column chromatography (EA) to give compound 28-9 (300 mg, 39.66% yield) in the form of a yellow oil. LC-MS [M+H]$^+$: 515.

Step (8): Preparation of (+/−)-(1S,3S)-3-(4-(4-(((cyclopentyl(methyl)carbamoyl)oxy)methyl)-3-methylisothiazol-5-yl)phenoxy)cyclohexane-1-carboxylic Acid

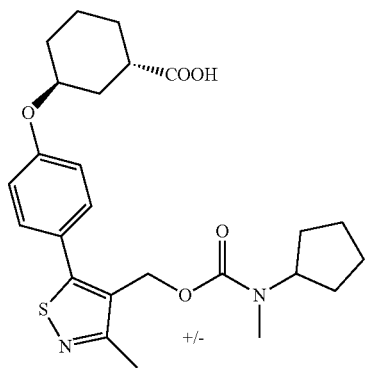

28

Compound 28-9 (300 mg, 0.58 mmol) and lithium hydroxide (122 mg, 2.9 mmol) were dissolved in a mixed solvent of THF (3 mL), MeOH (1 mL) and H$_2$O (1 mL), and the reaction system was stirred overnight at room temperature, diluted with water (10 mL), and washed with ether (10 mL). The aqueous phase was adjusted to pH 4 with diluted hydrochloric acid, and extracted with ethyl acetate (10 mL×3). The organic phase was combined, dried over Na$_2$SO$_4$, filtered and concentrated, and the residue was purified by column chromatography to give compound 28 (100 mg, 36.5% yield) in the form of a white solid.

$^1$H NMR (400 MHz, DMSO-d$_6$) δ 10.63 (bs, 1H), 7.61 (d, J=7.6 Hz, 2H), 6.96 (d, J=7.6 Hz, 2H), 5.05 (s, 2H), 3.64 (m, 1H), 3.61 (m, 1H), 3.27 (s, 3H), 2.42 (s, 3H), 2.31 (m, 1H), 2.17 (m, 1H), 1.95 (m, 1H), 1.92 (m, 1H), 1.86 (m, 2H), 1.73 (m, 2H), 1.72 (m, 1H), 1.70 (m, 1H), 1.63 (m, 2H), 1.61 (m, 2H), 1.53 (m, 1H), 1.47 (m, 1H), 1.43 (m, 1H).

Example 29

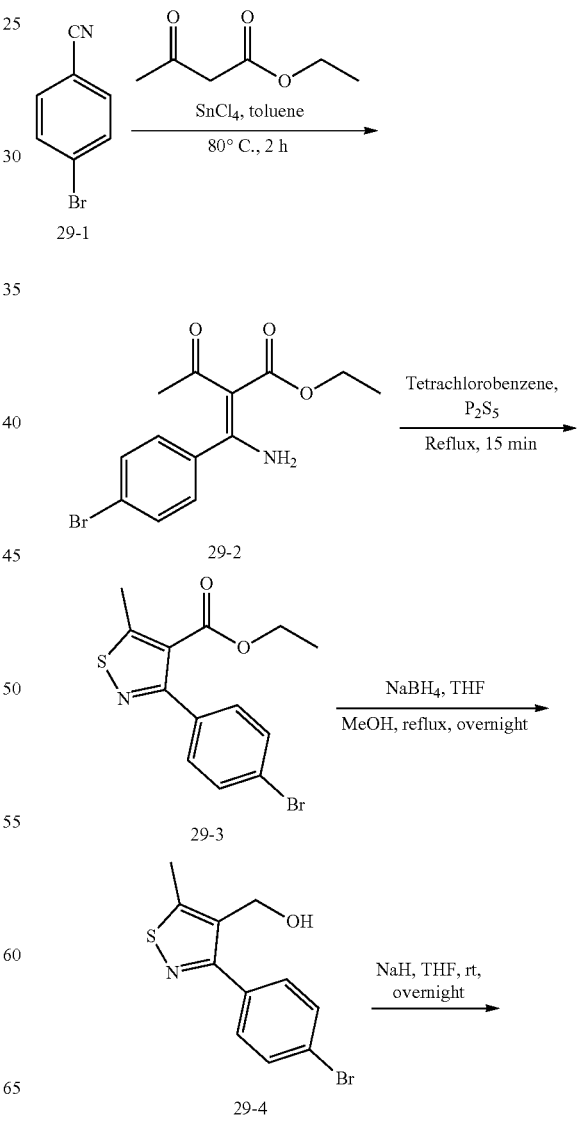

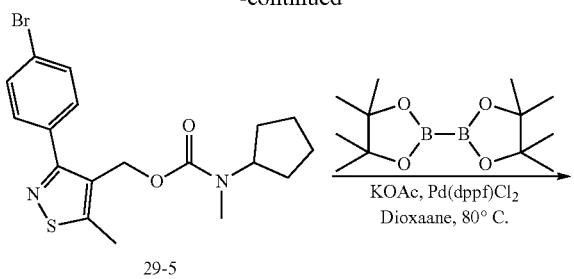

29-5

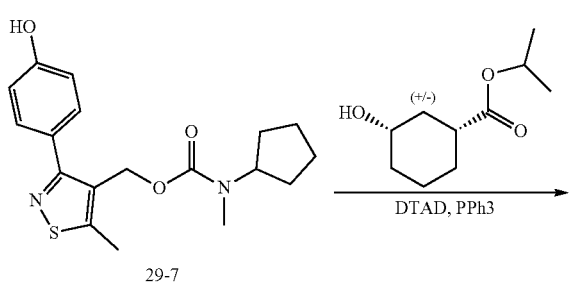

29-6

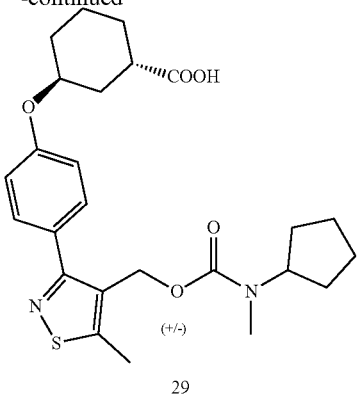

29

Step (1): Preparation of ethyl (Z)-2-(amino(4-bromophenyl)methylene)-3-oxobutanoate

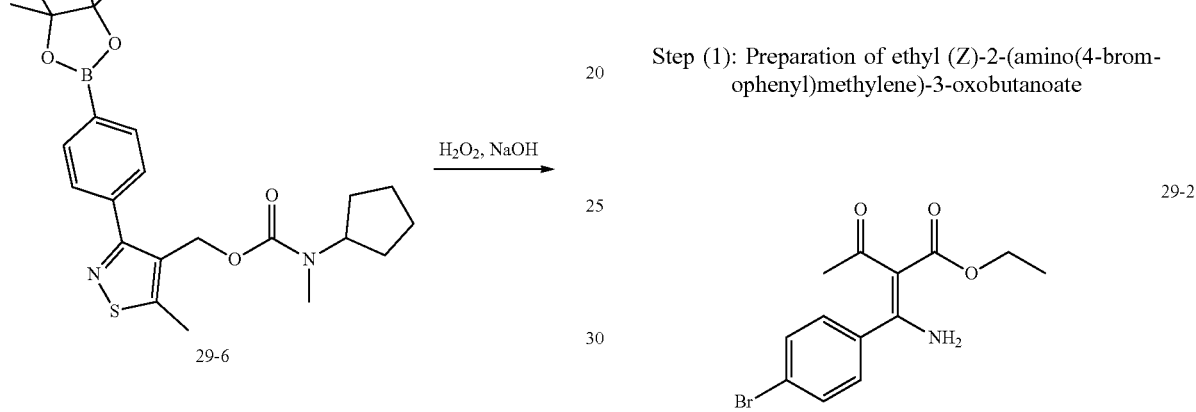

29-2

4-bromobenzonitrile (10 g, 55.3 mmol) and ethyl acetoacetate (7.2 g, 55.3 mmol) were dissolved in toluene (85 mL) under nitrogen atmosphere, and the reaction system was added dropwise with a solution of tin(IV) chloride (1 N, 55 mL) in dichloromethane at 0° C., then heated at room temperature for 40 min, and reacted at 80° C. for 2 h. The reaction system was cooled to room temperature, added with saturated aqueous sodium bicarbonate solution (100 mL), and extracted with ethyl acetate (50 mL×3). The organic phases were combined, washed with saturated brine (40 mL×2), dried over anhydrous sodium sulfate and filtered. The filtrate was concentrated by rotary evaporation, and the residue was purified by silica gel column chromatography to give compound 29-2 (7.8 g, 45.2% yield) in the form of a white solid. LC-MS [M+H]$^+$: 311.7/313.7.

Step (2): Preparation of ethyl 3-(4-bromophenyl)-5-methylisothiazole-4-carboxylate

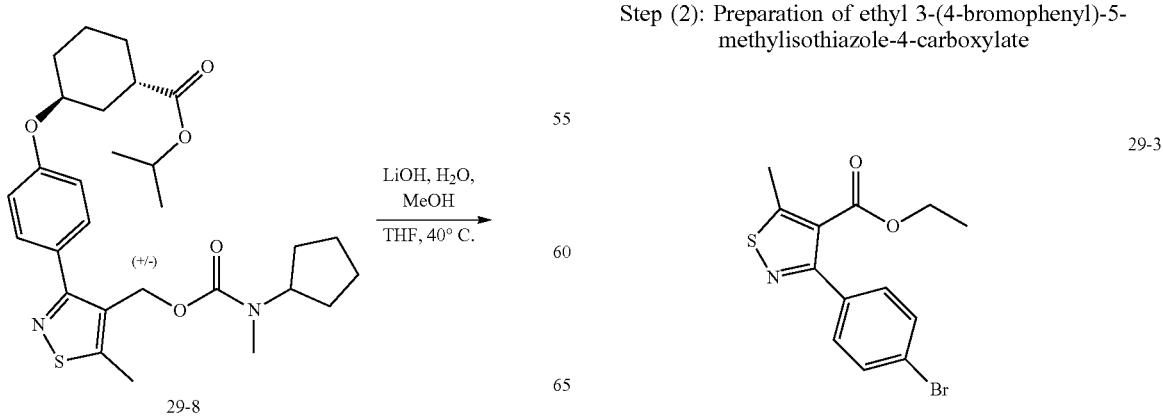

29-3

Compound 29-2 (5.9 g, 19.0 mmol) was dissolved in toluene (100 mL) under nitrogen atmosphere, and the reaction system was added with phosphorus pentasulfide (10.88 g, 56.91 mmol) and tetrachlorobenzoquinone (4.67 g, 18.97 mmol), and refluxed at 110° C. for 15 min. The reaction system was cooled to room temperature and filtered. The filtrate was concentrated by rotary evaporation. The crude product was purified by silica gel column chromatography to give compound 29-3 (2.5 g, 40.4% yield) in the form of a white solid. LC-MS [M+H]$^+$: 325.6/327.6.

Step (3): Preparation of (3-(4-bromophenyl)-5-methylisothiazol-4-yl)methanol

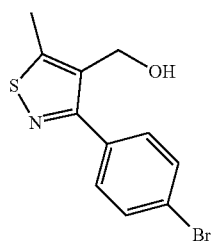

29-4

Compound 29-3 (2.2 g, 6.77 mmol) was dissolved in toluene (20 mL) under nitrogen atmosphere, and the reaction system was cooled to −78° C., added with diisobutylaluminum hydride (1 N, 27.1 mL), and reacted at temperature for 4 h. The reaction system was added with saturated ammonium chloride solution (10 mL) to quench the reaction, diluted with water (10 mL), filtered, and extracted with ethyl acetate (20 mL×3). The organic phases were combined, washed with saturated brine (20 mL×2), dried over anhydrous sodium sulfate and filtered. The filtrate was concentrated by rotary evaporation. The crude product was purified by silica gel column chromatography to give compound 29-4 (1.2 g, 62.4% yield) in the form of a white solid. LC-MS [M+H]$^+$: 283.6/285.6.

Step (4): Preparation of (3-(4-bromophenyl)-5-methylisothiazol-4-yl)methylcyclopentyl(methyl)carbamate

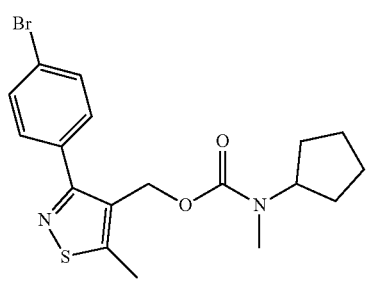

29-5

Compound 29-4 (1.2 g, 4.22 mmol) was dissolved in tetrahydrofuran (30 mL) under nitrogen atmosphere, and the reaction system was added with sodium hydride (338 mg, 8.45 mmol) in an ice water bath, stirred for 10 min, added with benzyl(methyl)aminomethyl 4-nitrobenzoic anhydride (2.23 g, 8.45 mmol), warmed to room temperature, and stirred overnight. The reaction system was added with ice water (30 mL) to quench the reaction and extracted with ethyl acetate (20 mL×3). The organic phases were combined, washed with saturated brine (20 mL×2), dried over anhydrous sodium sulfate and filtered. The filtrate was concentrated by rotary evaporation, and the residue was purified by silica gel column chromatography to give compound 29-5 (1.24 g, 71.8% yield) in the form of a white solid. LC-MS [M+H]$^+$: 408.6/410.6.

Step (5): Preparation of (5-methyl-3-(4-(4,4,5,5-tetramethyl-1,3,2-dioxaborolan-2-yl)phenyl)isothiazol-4-yl)methylcyclopentyl(methyl)carbamate

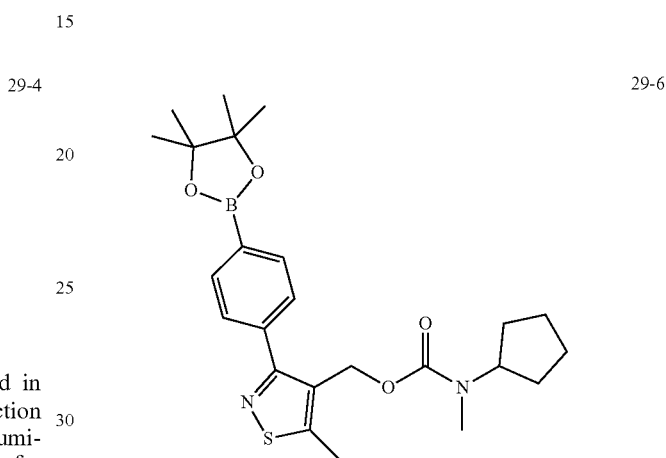

29-6

Compound 29-5 (1.2 g, 3.02 mmol) was dissolved in 1,4-dioxane (30 mL) under nitrogen atmosphere, and the reaction system was sequentially added with bis(pinacolato)diboron (1.15 g, 4.54 mmol), potassium acetate (890 mg, 9.08 mmol) and [1,1'-bis(diphenylphosphino)ferrocene]dichloropalladium(II) (220 mg, 0.31 mmol), reacted at 80° C. for 4 h and filtered. The filtrate was concentrated by rotary evaporation to give compound 29-6 (2.6 g, crude) in the form of a brown-black solid. LC-MS [M+H]$^+$: 456.7.

Step (7): Preparation of (3-(4-hydroxyphenyl)-5-methylisothiazol-4-yl)methylcyclopentyl(methyl)carbamate

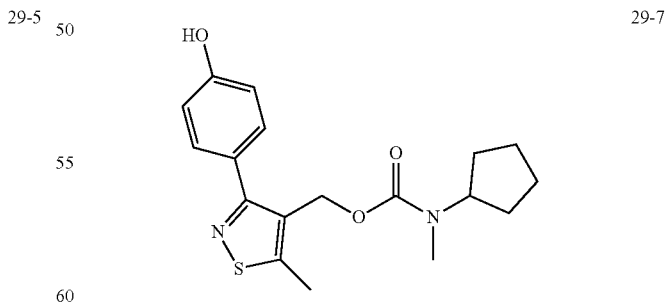

29-7

Compound 29-6 (2.6 g, crude) was dissolved in tetrahydrofuran (20 mL), and the reaction system was cooled to 0° C., sequentially added with sodium hydroxide solution (1 N, 3 mL) and hydrogen peroxide (20 mL), and stirred at 0° C. When TLC plate showed that no starting material remained, the reaction system was diluted by adding water (20 mL), extracted with ethyl acetate (15 mL×3), and wash with saturated brine (20 mL). The organic phase was dried over anhydrous sodium sulfate and filtered. The filtrate was concentrated by rotary evaporation, and the residue was purified by silica gel column chromatography to give compound 29-7 (630 mg, 60.3% yield over two steps) in the form of a white solid. LC-MS [M+H]⁺: 346.8.

Step (8): Preparation of (+/−)-isopropyl (1S,3S)-3-(4-(4-(((cyclopentyl(methyl)carbamoyl)oxy)methyl)-5-methylisothiazol-3-yl)phenoxy)cyclohexane-1-carboxylate

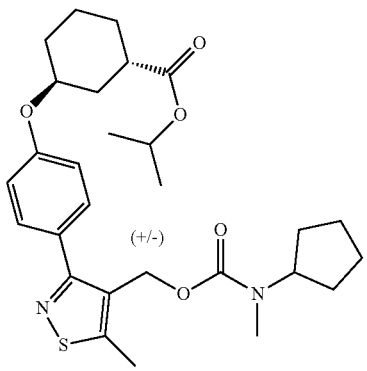

29-8

Compound 29-7 (630 mg, 1.82 mmol), (+/−)-isopropyl (3S)-3-hydroxycyclohexane-1-carboxylate (1.35 g, 7.27 mmol), DTAD (1.67 g, 7.27 mmol) and PPh₃ (1.92 g, 7.27 mmol) were dissolved in THF (30 mL), and then the reaction system was stirred overnight at room temperature under nitrogen atmosphere, diluted with water (20 mL), extracted with ethyl acetate (15 mL×3), and washed with saturated brine (20 mL). The reaction system was then purified by silica gel column chromatography to give compound 29-8 (477 mg. 50.7% yield) in the form of a white solid. LC-MS [M+H]⁺: 514.7.

Step (9): Preparation of (+/−)-(1S,3S)-3-(4-(4-(((cyclopentyl(methyl)carbamoyl)oxy)methyl)-5-methylisothiazol-3-yl)phenoxy)cyclohexane-1-carboxylic Acid

29

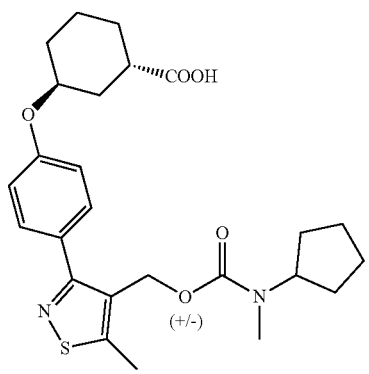

Compound 29-8 (477 mg, 0.93 mmol) was dissolved in THF (6 mL), and the reaction system was sequentially added with MeOH (2 mL), H₂O (2 mL) and lithium hydroxide (194 mg, 4.6 mmol), and stirred overnight at room temperature. Then water (10 mL) was added for dilution, and the organic solvent was removed by rotary evaporation under reduced pressure. The aqueous phase was adjusted to pH 2-3 with hydrochloric acid (1 N), and extracted with dichloromethane (10 mL×2). The organic phases were combined, dried over anhydrous sodium sulfate and filtered, and the filtrate was concentrated by rotary evaporation. The residue was purified by silica gel column chromatography and then lyophilized to give compound 29 (140 mg) in the form of a white solid. LC-MS [M+H]⁺: 472.7.

¹H NMR (400 MHz, DMSO-d₆) δ 10.63 (bs, 1H), 7.55 (d, J=7.6 Hz, 2H), 7.03 (d, J=7.6 Hz, 2H), 5.05 (s, 2H), 3.64 (m, 1H), 3.61 (m, 1H), 3.27 (s, 3H), 2.31 (m, 1H), 2.30 (s, 3H), 2.17 (m, 1H), 1.95 (m, 1H), 1.92 (m, 1H), 1.86 (m, 2H), 1.73 (m, 2H), 1.72 (m, 1H), 1.70 (m, 1H), 1.63 (m, 2H), 1.61 (m, 2H), 1.53 (m, 1H), 1.47 (m, 1H), 1.43 (m, 1H).

Example 30

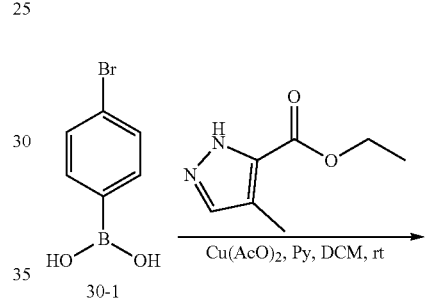

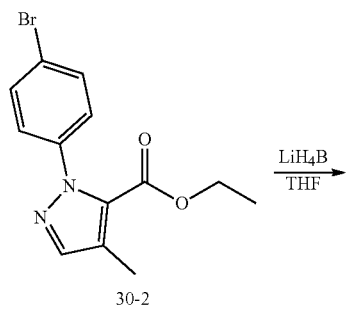

30-2

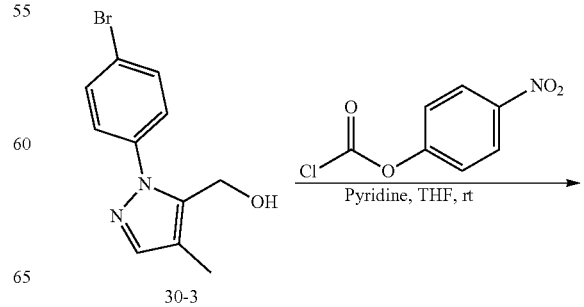

30-3

251
-continued

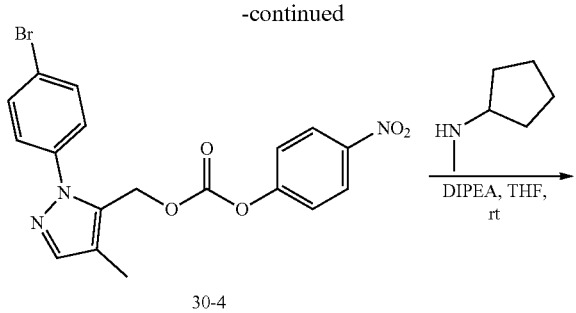

30-4

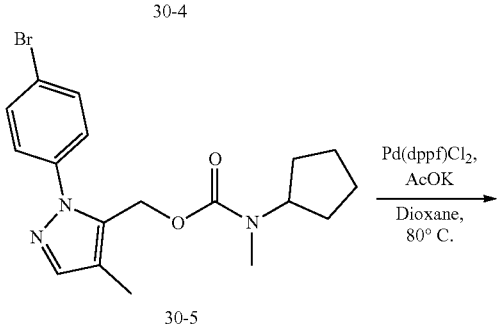

30-5

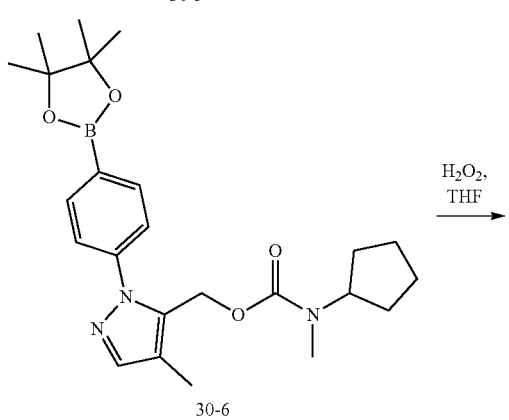

30-6

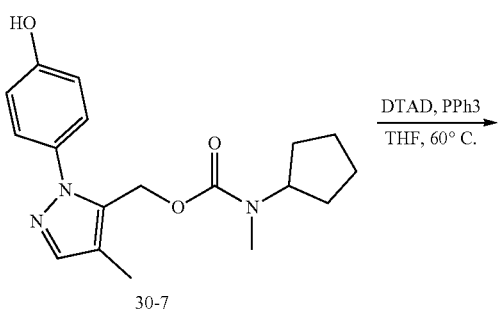

30-7

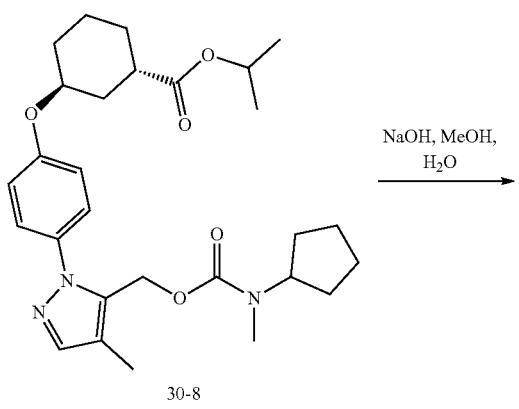

30-8

252
-continued

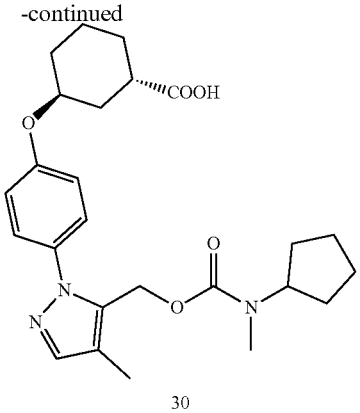

30

Step (1): Preparation of ethyl 1-(4-bromophenyl)-4-methyl-1H-pyrazole-5-carboxylate

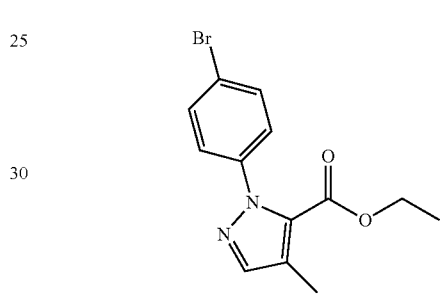

30-2

4-bromophenylboronic acid (2410 mg, 12 mmol) was dissolved in dichloromethane (30 mL), and the reaction system was added with ethyl 4-methyl-1H-pyrazole-5-carboxylate (925 mg, 6.0 mmol), pyridine (949 mg, 12 mmol) and copper(I) iodide (1634 mg, 9.0 mmol), stirred at room temperature for 12 h, and concentrated to give a crude product. The crude product was separated by column chromatography to give compound 30-2 (1.0 g, 51% yield) in the form of a white solid. LC-MS [M+H]$^+$: 309/311.

Step (2): Preparation of (1-(4-bromophenyl)-4-methyl-1H-pyrazol-5-yl)methanol

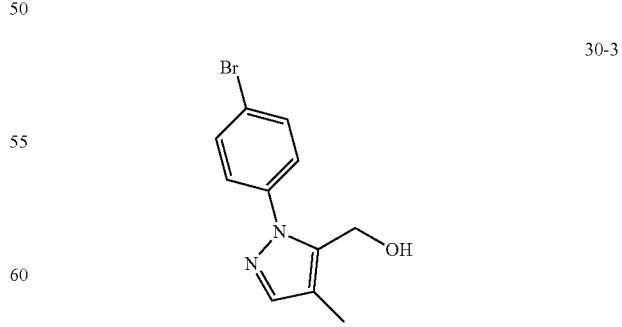

30-3

Compound 30-2 (1.1 g, 3.56 mmol) was dissolved in anhydrous tetrahydrofuran (20 mL), and the reaction system was added with lithium borohydride (388 mg, 17.8 mmol), refluxed and stirred overnight, and concentrated by rotary evaporation, and the residue was separated by column chromatography to give compound 30-3 (1.0 g, 98% yield) in the form of a white solid. LC-MS [M+H]⁺: 267/269.

Step (3): Preparation of (1-(4-bromophenyl)-4-methyl-1H-pyrazol-5-yl)methyl(4-nitrobenzene) carbonate

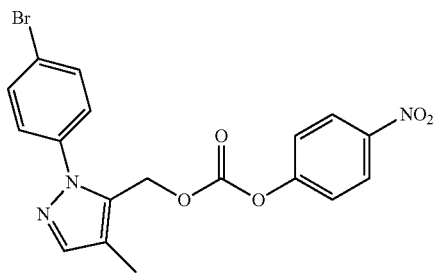

30-4

4-nitrophenyl chloroformate (904 mg, 4.48 mmol) and pyridine (1188 mg, 14.95 mmol) were dissolved in anhydrous tetrahydrofuran (10 mL) under nitrogen atmosphere, and the reaction system was stirred for 10 min, added with compound 30-3 (800 mg, 2.99 mmol), stirred overnight at room temperature, diluted with dichloromethane (50 mL), washed with saturated brine (25 mL), dried over anhydrous sodium sulfate, filtered and concentrated, and the residue was separated by column chromatography to give compound 30-4 (1300 mg, 88% yield) in the form of a white solid. LC-MS [M+H]⁺: 432/434.

Step (4): Preparation of (1-(4-bromophenyl)-4-methyl-1H-pyrazol-5-yl)methylcyclopentyl(methyl) carbamate

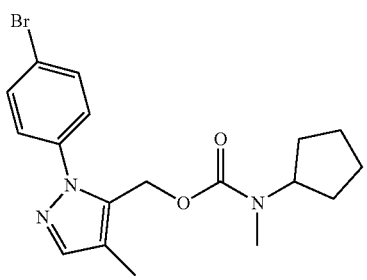

30-5

Compound 30-4 (500 mg, 1.16 mmol) and diisopropylethylamine (450 mg, 3.48 mmol) were dissolved in anhydrous dichloromethane (10 mL) under nitrogen atmosphere, and N-methylcyclopentylamine (138 mg, 1.39 mmol) was added. The reaction system was stirred overnight at room temperature, diluted with dichloromethane (20 mL), washed with sodium hydroxide solution (1 N, 20 mL×2), dried over anhydrous sodium sulfate, filtered and concentrated, and the residue was separated by column chromatography to give compound 30-5 in the form of a white solid (318 mg, 66% yield). LC-MS [M+H]⁺: 392/394.

Step (5): Preparation of (4-methyl-1-(4-(4,4,5,5-tetramethyl-1,3,2-dioxaborolan-2-yl)phenyl)-1H-pyrazol-5-yl)methylcyclopentyl(methyl)carbamate

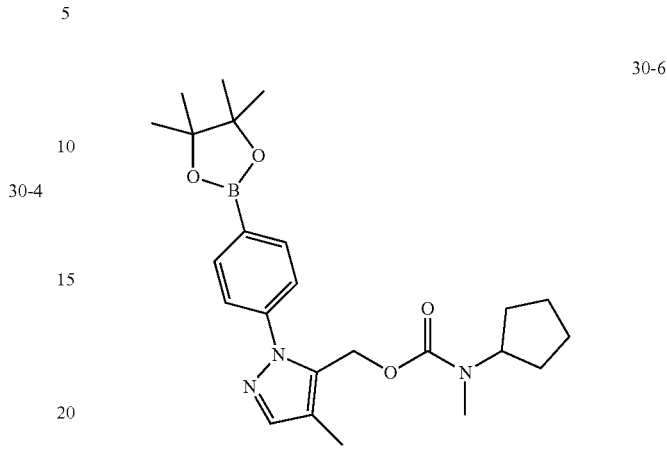

30-6

Compound 30-5 (318 mg, 0.81 mmol) and 4,4,4',4',5,5,5',5'-octamethyl-2,2'-bi(1,3,2-dioxaborolane) (309 mg, 1.22 mmol) were dissolved in 1,4-dioxane (8 mL) under nitrogen atmosphere, and the reaction system was added with [1,1'-bis(diphenylphosphino)ferrocene]dichloropalladium(II) (178 mg, 0.24 mmol) and potassium acetate (238 mg, 2.43 mmol), and reacted at 80° C. for 12 h. The reaction system was filtered and concentrated to give compound 30-6 (400 mg, crude), which was directly used in next step. LC-MS [M+H]⁺: 440.

Step (6): Preparation of (1-(4-hydroxyphenyl)-4-methyl-1H-pyrazol-5-yl)methylcyclopentyl(methyl) carbamate

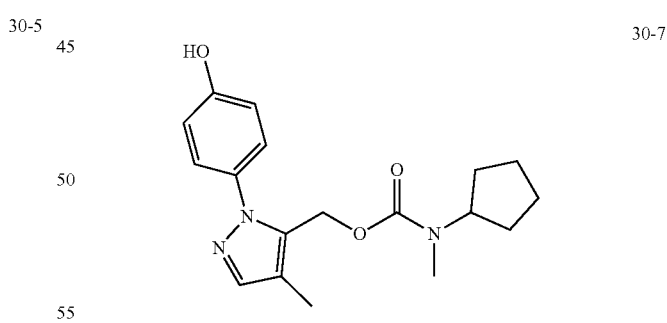

30-7

Compound 30-6 (400 mg, crude) was dissolved in tetrahydrofuran (7 mL). The reaction system was added with hydrogen peroxide (3.5 mL), reacted overnight at room temperature, added with saturated sodium thiosulfate solution (10 mL) to quench the reaction, diluted with water (30 mL), and extracted with ethyl acetate (20 mL×3). The organic phases were combined, dried over anhydrous sodium sulfate, filtered and concentrated, and the residue was separated by column chromatography to give compound 30-7 (260 mg, 84% yield) in the form of a yellow oily liquid. LC-MS [M+H]⁺: 330.

Step (7): Preparation of (+/−)-isopropyl (1S,3S)-3-(4-(5-(((cyclopentyl(methyl)carbamoyl)oxy)methyl)-4-methyl-1H-pyrazol-1-yl)phenoxy)cyclohexane-1-carboxylate

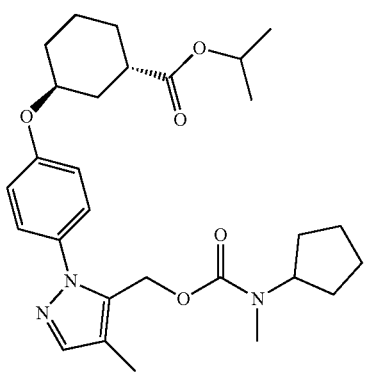

30-8

Compound 30-7 (260 mg, 0.79 mmol) was dissolved in anhydrous tetrahydrofuran (15 mL). The reaction system was added with (+/−)-isopropyl (1S,3S)-3-hydroxycyclohexane-1-carboxylate (589 mg, 3.16) and triphenylphosphine (829 mg, 3.16 mmol), stirred for 10 min, added with di-tert-butyl azodicarboxylate (728 mg, 3.16 mmol), reacted overnight at 40° C. under nitrogen atmosphere, and concentrated, and the residue was separated by column chromatography to give compound 30-8 (400 mg, 35% purity, 35% yield) in the form of an oily liquid. LC-MS [M+H]$^+$: 498.

Step (8): Preparation of (+/−)-(1S,3S)-3-(4-(5-(((cyclopentyl(methyl)carbamoyl)oxy)methyl)-4-methyl-1H-pyrazol-1-yl)phenoxy)cyclohexanoic Acid

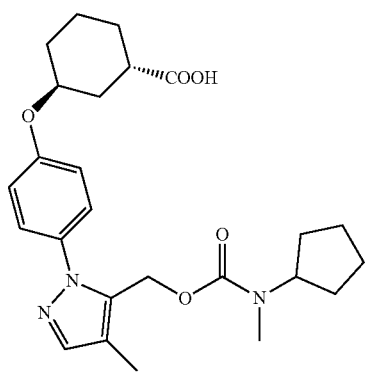

30

Compound 30-8 (400 mg, crude) and sodium hydroxide (34 mg, 0.84 mmol) were dissolved in methanol (6 mL) and water (3 mL). The reaction system was reacted at room temperature for 12 h, concentrated to remove methanol, and adjusted to pH 4 with diluted hydrochloric acid (1 N), and white solid was precipitated. The reaction system was filtered and dried to give compound 30 (110 mg, 82% yield) in the form of a white solid. LC-MS [M+H]$^+$: 456.

$^1$H NMR (400 MHz, DMSO-d$_6$) δ 10.63 (bs, 1H), 7.72 (d, J=7.6 Hz, 2H), 7.53 (s, 1H), 7.03 (d, J=7.6 Hz, 2H), 5.48 (s, 2H), 3.64 (m, 1H), 3.61 (m, 1H), 3.27 (s, 3H), 2.31 (m, 1H), 2.17 (m, 1H), 2.12 (s, 3H), 1.95 (m, 1H), 1.92 (m, 1H), 1.86 (m, 2H), 1.73 (m, 2H), 1.72 (m, 1H), 1.70 (m, 1H), 1.63 (m, 2H), 1.61 (m, 2H), 1.53 (m, 1H), 1.47 (m, 1H), 1.43 (m, 1H).

Example 34

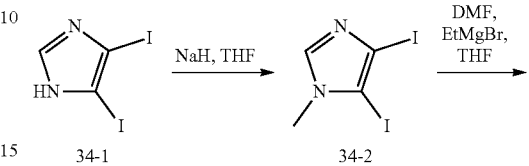

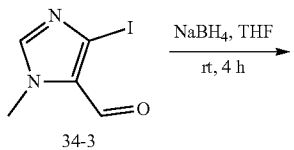

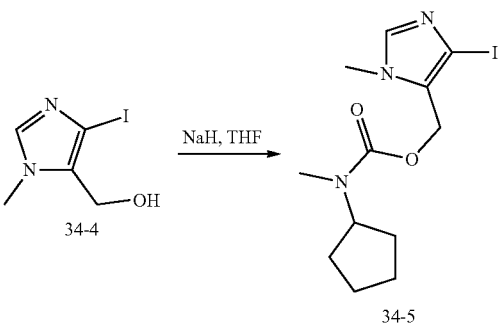

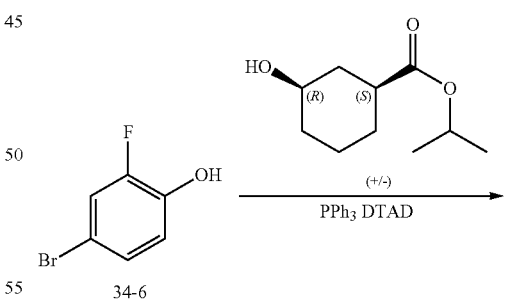

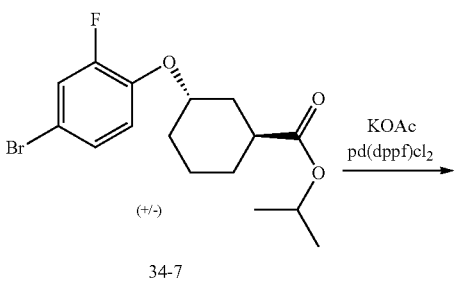

-continued

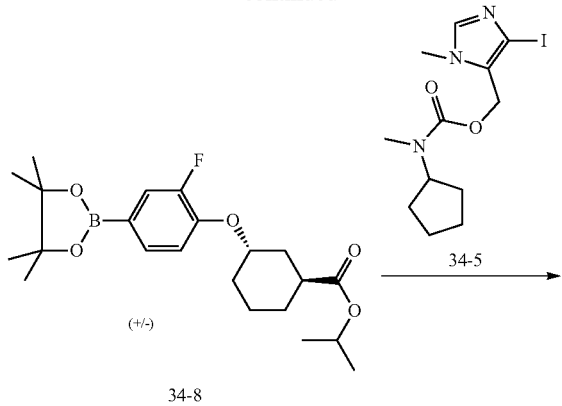

34-8

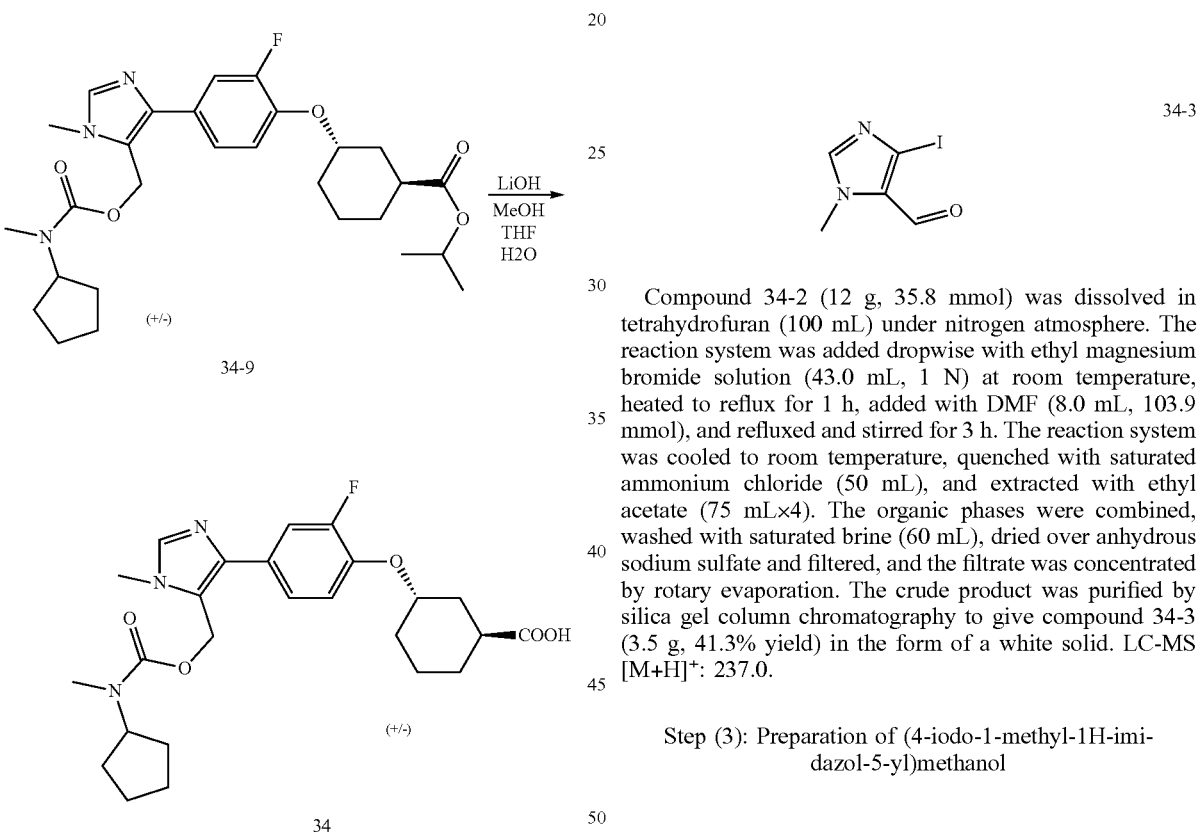

Step (1): Preparation of 4,5-diiodo-1-methyl-1H-imidazole

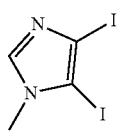

34-2

4,5-diiodo-1H-imidazole (25.0 g, 78.1 mmol) was dissolved in tetrahydrofuran (100 mL) under nitrogen atmosphere. The reaction system was added in portions with sodium hydride (9.3 g, 234.4 mmol) in an ice water bath at 0° C., stirred for 10 min, then added dropwise with methyl iodide (5.3 mL, 85.9 mmol), and reacted at room temperature for 2 h. The reaction system was quenched with ice water (100 mL), and extracted with ethyl acetate (60 mL×3). The organic phases were combined, washed with saturated brine (40 mL×2), dried over anhydrous sodium sulfate and filtered. The filtrate was concentrated by rotary evaporation, and the residue was purified by silica gel column chromatography to give compound 34-2 (13.0 g, 50.1% yield) in the form of a white solid. LC-MS [M+H]$^+$: 334.5.

Step (2): Preparation of 4-iodo-1-methyl-1H-imidazole-5-carbaldehyde

Compound 34-2 (12 g, 35.8 mmol) was dissolved in tetrahydrofuran (100 mL) under nitrogen atmosphere. The reaction system was added dropwise with ethyl magnesium bromide solution (43.0 mL, 1 N) at room temperature, heated to reflux for 1 h, added with DMF (8.0 mL, 103.9 mmol), and refluxed and stirred for 3 h. The reaction system was cooled to room temperature, quenched with saturated ammonium chloride (50 mL), and extracted with ethyl acetate (75 mL×4). The organic phases were combined, washed with saturated brine (60 mL), dried over anhydrous sodium sulfate and filtered, and the filtrate was concentrated by rotary evaporation. The crude product was purified by silica gel column chromatography to give compound 34-3 (3.5 g, 41.3% yield) in the form of a white solid. LC-MS [M+H]$^+$: 237.0.

Step (3): Preparation of (4-iodo-1-methyl-1H-imidazol-5-yl)methanol

Compound 34-3 (3.5 g, 14.8 mmol) was dissolved in tetrahydrofuran (30 mL), and the reaction system was added in portions with sodium borohydride (1.13 g, 29.7 mmol), and reacted at room temperature for 3 h. The reaction system was quenched with saturated ammonium chloride solution (5 mL) with stirring, and concentrated under pressure. The residue was purified by silica gel column chromatography to give compound 34-4 (1.4 g, 39.0% yield) in the form of a white solid. LC-MS [M+H]$^+$: 238.7.

Step (4): Preparation of (4-iodo-1-methyl-1H-imidazol-5-yl)methylcyclopentyl(methyl)carbamate

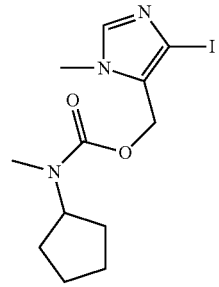

34-5

Compound 34-4 (800 mg, 3.4 mmol) was dissolved in tetrahydrofuran (20 mL) under nitrogen atmosphere, and the reaction system was added in portions with sodium hydride (402 mg, 10.1 mmol) in an ice water bath, stirred for 10 min, added with benzyl(methyl)aminomethyl 4-nitrobenzoic anhydride (970 mg, 3.7 mmol), slowly warmed to room temperature, and reacted for 3 h. The reaction system was quenched with saturated ammonium chloride solution (20 mL), diluted with water (20 mL), and extracted with ethyl acetate (20 mL×3). The organic phases were combined, washed with saturated brine (20 mL×2), dried over anhydrous sodium sulfate and filtered. The filtrate was concentrated by rotary evaporation, and the residue was purified by silica gel column chromatography to give compound 34-5 (400 mg, 32.8% yield) in the form of a white solid. LC-MS $[M+H]^+$: 363.7.

Step (5): Preparation of (+/−)-isopropyl (1S,3S)-3-(4-bromo-2-fluorophenoxy)cyclohexane-1-carboxylate

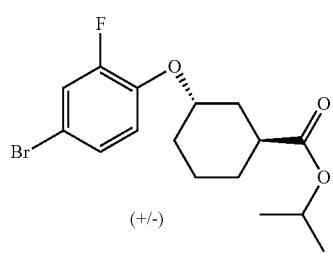

34-7

4-bromo-2-fluorophenol (2 g, 10.5 mmol) and (+/−)-isopropyl (1S,3R)-3-hydroxycyclohexane-1-carboxylate (3.9 g, 21.0 mmol) were dissolved in tetrahydrofuran (20 mL) under nitrogen atmosphere. The reaction system was added with triphenylphosphine (5.5 g, 21.0 mmol) and di-tert-butyl azodicarboxylate (4.8 g, 21.0 mmol), warmed to 60° C. and stirred overnight. The reaction system was cooled to room temperature, quenched with water (30 mL), and extracted with ethyl acetate (40 mL×2). The organic phases were combined, washed with saturated brine (40 mL), dried over anhydrous sodium sulfate, filtered and concentrated. The residue was purified by silica gel column chromatography to give compound 34-7 (3.0 g, 60% purity, 47.6% yield) in the form of a pale yellow oily liquid. LC-MS $[M+Na]^+$: 380.6/382.6.

Step (6): Preparation of (+/−)-isopropyl (1S,3S)-3-(2-fluoro-4-(4,4,5,5-tetramethyl-1,3,2-dioxaborolan-2-yl) phenoxy)cyclohexane-1-carboxylate

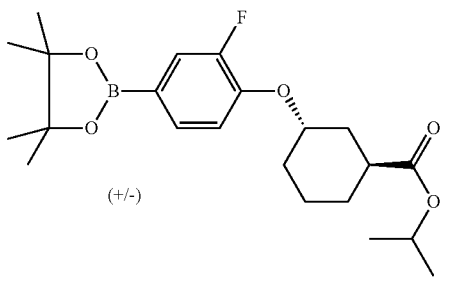

34-8

Compound 34-7 (3.0 g, 8.4 mmol) and 4,4,4',4',5,5,5',5'-octamethyl-2,2'-bi(1,3,2-dioxaborolane) (3.2 g, 12.6 mmol), potassium acetate (1.65 g, 16.8 mmol) and [1,1'-bis(diphenylphosphino)ferrocene] dichloropalladium(II) (307 mg, 0.42 mmol) were dissolved in anhydrous dioxane (30 mL) under nitrogen atmosphere. The reaction system was reacted at 100° C. for 4 h, cooled to room temperature and filtered. The filtrate was concentrated by rotary evaporation to give compound 34-8 (3.6 g, crude) in the form of a brown solid. LC-MS $[M+Na]^+$: 428.8.

Step (7): Preparation of (+/−)-isopropyl (1S,3S)-3-(4-(5-(((cyclopentyl(methyl)carbamoyl)oxy)methyl)-1-methyl-1H-imidazol-4-yl)-2-fluorophenoxy)cyclohexane-1-carboxylate

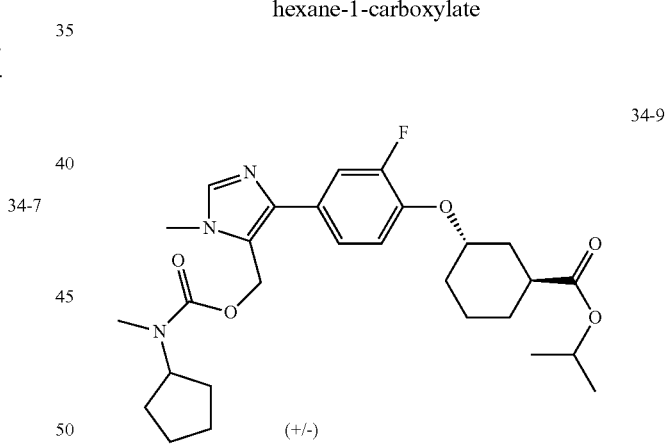

34-9

Compound 34-8 (170 mg, 0.42 mmol) and (4-iodo-1-methyl-1H-imidazol-5-yl)methylcyclopentyl (methyl)carbamate (173 mg, 0.48 mmol) were dissolved in dioxane (3 mL) and water (1 mL) under nitrogen atmosphere. The reaction system was added with potassium carbonate (180 mg, 1.30 mmol) and [1,1'-bis(diphenylphosphino)ferrocene] dichloropalladium(II) (40 mg, 0.057 mmol), reacted at 90° C. for 12 h, cooled to room temperature, diluted with water (20 mL), and extracted with ethyl acetate (15 mL×2). The organic phases were combined, washed with saturated brine (15 mL), dried over anhydrous sodium sulfate, filtered and concentrated. The residue was purified by silica gel column chromatography to give compound 34-9 (40 mg, 18.1% yield) in the form of a colorless oily liquid. LC-MS $[M+Na]^+$: 515.9.

Step (8): Preparation of (+/−)-(1S,3S)-3-(4-(5-(((cyclopentyl(methyl)carbamoyl)oxy)methyl)-1-methyl-1H-imidazol-4-yl)-2-fluorophenoxy)cyclohexane-1-carboxylic Acid

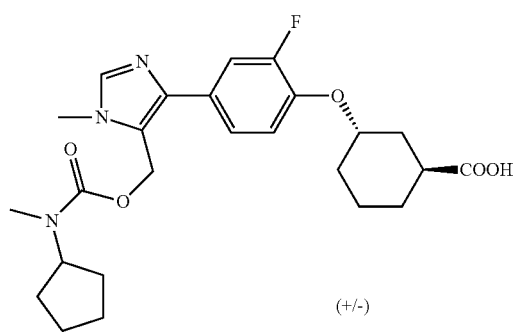

34

(+/−)

Compound 34-9 (40 mg, 0.078 mmol) was dissolved in tetrahydrofuran (2 mL)/methanol (1 mL)/water (1 mL). The reaction system was added with lithium hydroxide monohydrate (13 mg, 0.31 mmol), reacted at room temperature for 10 h, concentrated to 1 mL, adjusted to pH 3-4 with diluted hydrochloric acid (1 N), diluted with water (5 mL) and extracted with dichloromethane (10 mL×2). The organic phases were combined, washed with saturated brine (5 mL), dried over anhydrous sodium sulfate, filtered and concentrated to give a crude product. The crude product was prepared by high performance liquid chromatography and lyophilized to give compound 34 (4 mg, 10.8% yield) in the form of a white solid. LC-MS [M+H]⁺: 473.8. ¹H NMR (400 MHz, MeOD) δ 7.73 (s, 1H), 7.42 (dd, J=12.5, 2.0 Hz, 1H), 7.38 (d, J=8.6 Hz, 1H), 7.21 (t, J=8.5 Hz, 1H), 5.26 (s, 2H), 4.76-4.72 (m, 1H), 4.57-4.40 (m, 1H), 3.81 (s, 3H), 2.86-2.77 (m, 1H), 2.82 (s, 3H), 2.15-2.09 (m, 1H), 1.99-1.55 (m, 15H).

Example 35

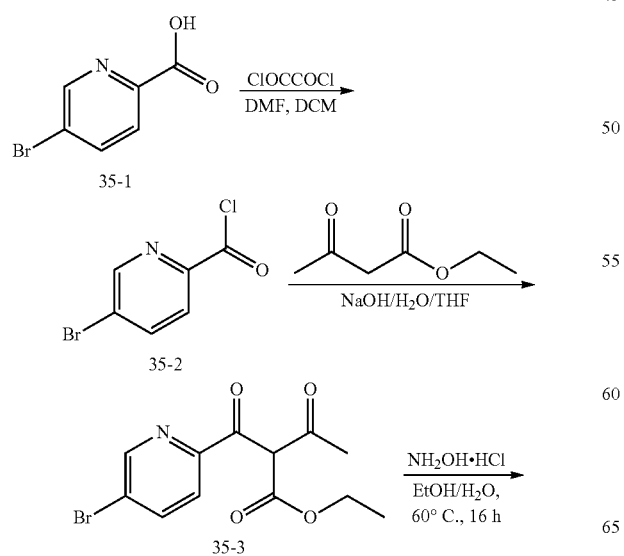

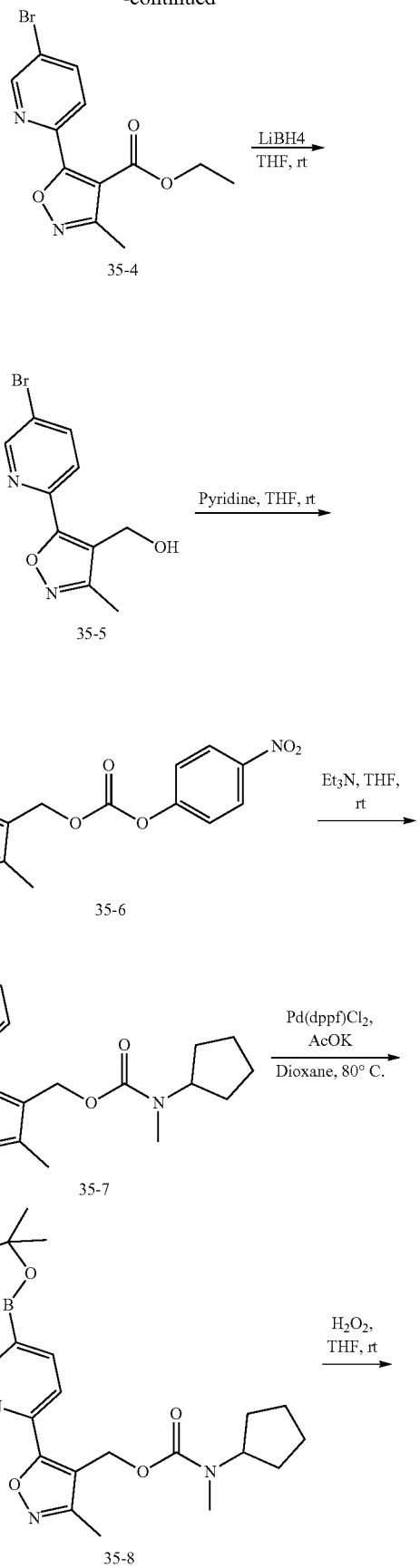

-continued

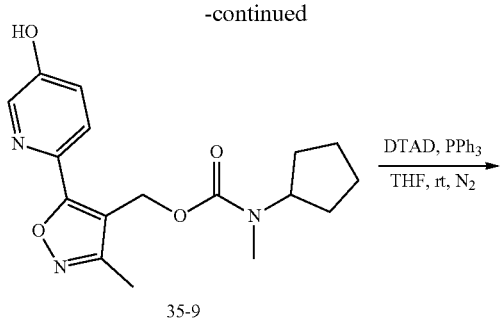

35-9

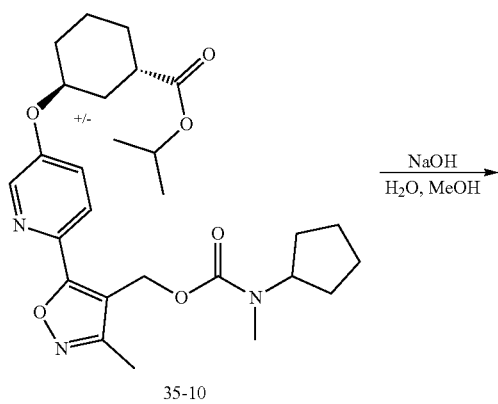

35-10

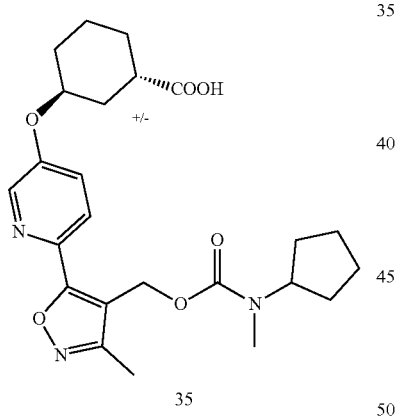

35

Step (1): Preparation of 5-bromopyridine-2-formyl Chloride

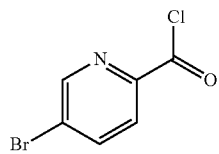

35-2

5-bromopicolinic acid (10.00 g, 49.5 mmol) was dissolved in dichloromethane (100 mL), and the reaction system was cooled to 0° C. The reaction system was added with DMF (0.1 mL) and oxalyl chloride (12.56 g, 99 mmol), stirred at room temperature for 3 h, and concentrated by rotary evaporation to give compound 35-2 (11.00 g, crude) in the form of a red solid, which was directly used in the next step.

Step (2): Preparation of ethyl 2-(5-bromopicolinoyl)-3-oxobutanoate 35-3

Ethyl acetoacetate (12.99 g, 99.8 mmol) was dissolved in tetrahydrofuran (100 mL), and the reaction system was added with sodium hydroxide (11.98 g, 299.4 mmol), then stirred at room temperature for 30 min, and added in portions with compound 35-2 (11.00 g crude). The reaction system was reacted at room temperature for 15 h. The reaction system was concentrated, then adjusted to pH 6 with diluted hydrochloric acid (1 N), and extracted with ethyl acetate (50 mL×3). The organic phases were combined, dried over anhydrous sodium sulfate, filtered and concentrated, and the residue was purified by silica gel column chromatography to give compound 35-3 (12.8 g, 80% purity, 65% yield over two steps) in the form of a yellow oil. LC-MS [M+H]$^+$: 313.6.

Step (3): Preparation of ethyl 5-(5-bromopyridin-2-yl)-3-methylisoxazole-4-carboxylate 35-4

Compound 35-3 (12.8 g, 32.6 mmol) was dissolved in ethanol (120 mL). The reaction system was added with hydroxylamine hydrochloride (12.4 g, ss178.3 mmol) and water (60 mL), and reacted at 60° C. for 12 h. The reaction system was concentrated and filtered to give compound 35-4 (7.0 g, 69% yield) in the form of a white solid. LC-MS [M+H]$^+$: 311.0.

Step (4): Preparation of (5-(5-bromopyridin-2-yl)-3-methylisoxazol-4-yl)methanol

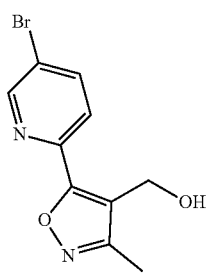
35-5

Compound 35-4 (3.16 g, 10.16 mmol) was added to tetrahydrofuran (40 mL), and the reaction system was added with lithium borohydride (885 mg, 40.64 mmol), and stirred overnight at room temperature. The reaction system was diluted with water (100 mL) and extracted with ethyl acetate (50 mL×2). The organic phases were combined, dried over anhydrous sodium sulfate and concentrated, and the residue was separated by silica gel column chromatography to give compound 35-5 (2.4 g, 87% yield) in the form of a white solid. LC-MS [M+H]$^+$: 268.8.

Step (5): Preparation of (5-(5-bromopyridin-2-yl)-3-methylisoxazol-4-yl)methyl(4-nitrophenyl)carbonate

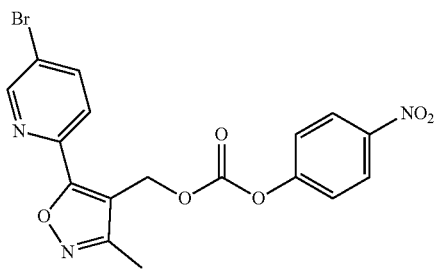
35-6

4-nitrophenyl chloroformate (1.12 g, 5.58 mmol) and pyridine (883 mg, 11.16 mmol) were dissolved in anhydrous tetrahydrofuran (15 mL). The reaction system was stirred at room temperature for 30 min, added with compound 35-5 (1 g, 3.72 mmol), and stirred overnight at room temperature under nitrogen atmosphere. The reaction solution was directly used in the next step without treatment.

Step (6): Preparation of (5-(5-bromopyridin-2-yl)-3-methylisoxazol-4-yl)methylcyclopentyl(methyl) carbamate

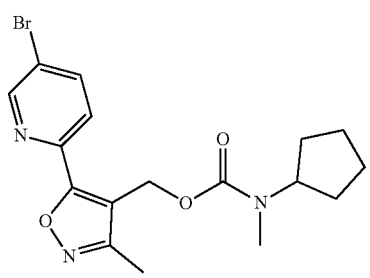
35-7

N-methylcyclopentylamine hydrochloride (812 mg, 8.18 mmol) and triethylamine (1.1 g, 11.16 mmol) were added to the reaction solution in the previous step under nitrogen atmosphere. The reaction system was stirred overnight at room temperature, diluted with ethyl acetate (50 mL), and washed with saturated sodium bicarbonate solution (50 mL×2). The organic phase was dried over anhydrous sodium sulfate, filtered and concentrated, and the residue was separated by silica gel column chromatography to give compound 35-7 (1.5 g, 70% purity, 71% yield over two steps) in the form of a yellow solid. LC-MS [M+H]$^+$: 395.8.

Step (7): Preparation of (3-methyl-5-(5-(4,4,5,5-tetramethyl-1,3,2-dioxaborolan-2-yl)pyridin-2-yl)isoxazol-4-yl)methylcyclopentyl(methyl)carbamate

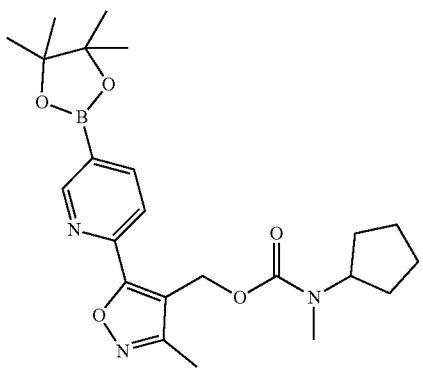
35-8

Compound 35-7 (1.5 g, 70% purity, 2.66 mmol) was dissolved in 1,4-dioxane (20 mL). The reaction system was added with [1,1'-bis(diphenylphosphino)ferrocene]dichloropalladium(II) (295 mg, 0.403 mmol), potassium acetate (1.19 g, 12.09 mmol) and bis(pinacolato)diboron (2.04 g, 8.06 mmol). The reaction system was reacted at 80° C. for 12 h under nitrogen atmosphere. Then the reaction system was filtered and concentrated to give compound 35-8 (4.0 g, crude) in the form of a brown oil, which was directly used in the next step. LC-MS [M+H]$^+$: 360.0.

Step (8): Preparation of (5-(5-hydroxypyridin-2-yl)-3-methylisoxazol-4-yl)methylcyclopentyl(methyl) carbamate

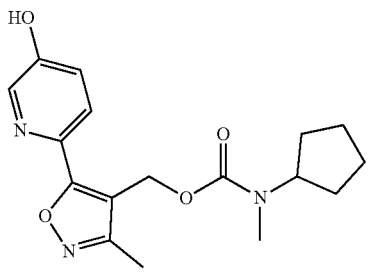

35-9

Compound 35-8 (4.0 g, crude) was dissolved in tetrahydrofuran (30 mL). The reaction system was added with hydrogen peroxide (3 mL, 30% w/w), reacted at room temperature for 8 h, quenched with sodium thiosulfate solution, and extracted with ethyl acetate (50 mL×2). The organic phases were combined, dried with anhydrous sodium sulfate, filtered and concentrated, and the residue was separated by silica gel column chromatography to give compound 35-9 (940 mg, 85% purity, 92% yield over two steps) in the form of a red solid. LC-MS [M+H]$^+$: 331.9.

Step (9): Preparation of (+/−)-isopropyl (1S,3S)-3-((6-(4-(((cyclopentyl(methyl)carbamoyl)oxy)methyl)-3-methylisoxazol-5-yl)pyridin-3-yl)oxy)cyclohexane-1-carboxylate

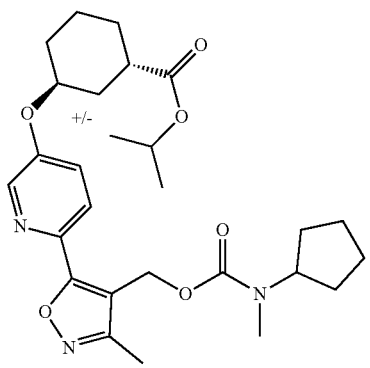

35-10

Compound 35-9 (300 mg, 0.77 mmol) was dissolved in anhydrous tetrahydrofuran (15 mL) under nitrogen atmosphere. The reaction system was added with (+/−)-isopropyl (1S, 3S)-3-hydroxycyclohexane-1-carboxylate (671 mg, 3.60 mmol) and triphenylphosphine (830 mg, 3.60 mmol), stirred for 10 min, added with di-tert-butyl azodicarboxylate (945 mg, 3.60 mmol), reacted overnight at 40° C. under nitrogen atmosphere, and concentrated, and the residue was purified by silica gel column chromatography to give compound 35-10 (480 mg, 35% purity) in the form of a yellow oil. LC-MS [M+H]$^+$: 499.8.

Step (10): Preparation of (+/−)-(1S,3S)-3-((6-(4-(((cyclopentyl(methyl)carbamoyl)oxy)methyl)-3-methylisoxazol-5-yl)pyridin-3-yl)oxy)cyclohexane-1-carboxylic Acid

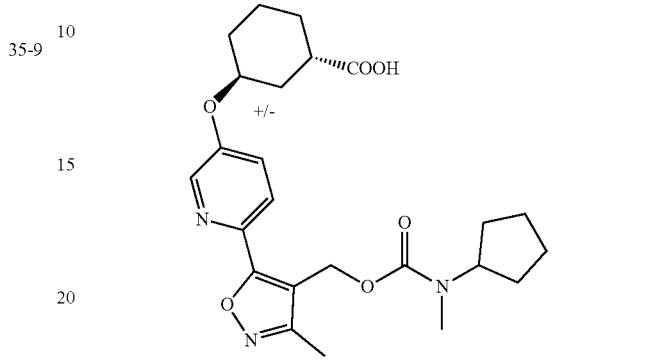

35

Compound 35-10 (480 mg, 35% purity) and sodium hydroxide (48 mg, 1.20 mmol) were dissolved in methanol (5 mL) and water (2.5 mL), and the reaction system was reacted at room temperature for 12 h, concentrated, adjusted to pH 3 with diluted hydrochloric acid (1 N), and then extracted with ethyl acetate (10 mL×3). The organic phases were combined, dried over anhydrous sodium sulfate and concentrated, and the residue was purified by silica gel column chromatography to give compound 35 (128 mg, 36% yield over two steps) in the form of a white solid. LC-MS [M+H]$^+$: 457.8.

$^1$H NMR (400 MHz, CDCl$_3$) δ 8.42 (d, J=2.7 Hz, 1H), 7.87 (d, J=8.7 Hz, 1H), 7.37 (dd, J=8.8, 2.7 Hz, 1H), 5.51 (s, 2H), 4.80-4.76 (m, 1H), 4.65-4.25 (m, 1H), 2.98-2.89 (m, 1H), 2.76 (s, 3H), 2.40 (s, 3H), 2.18-1.41 (m, 16H).

Example 56

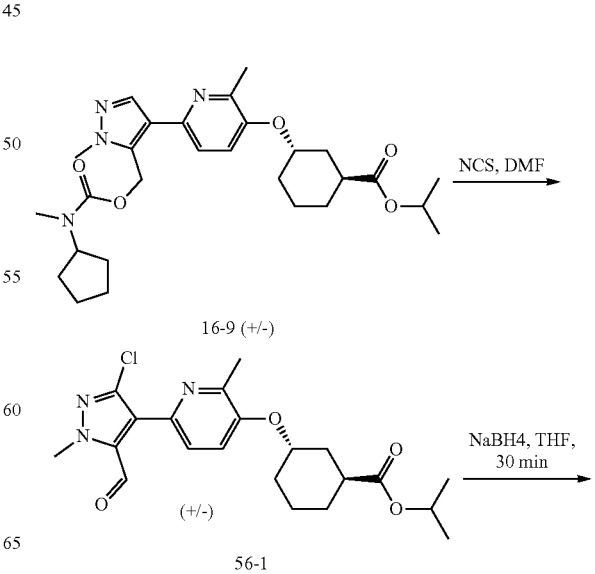

-continued

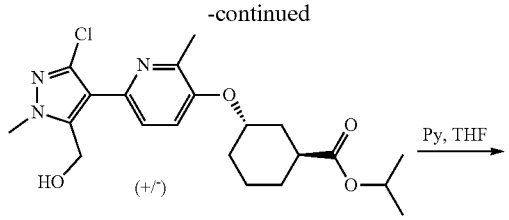

56-2

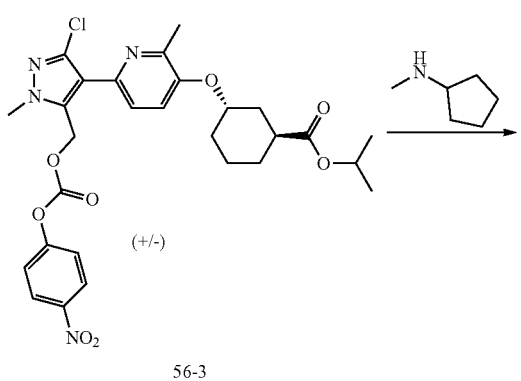

56-3

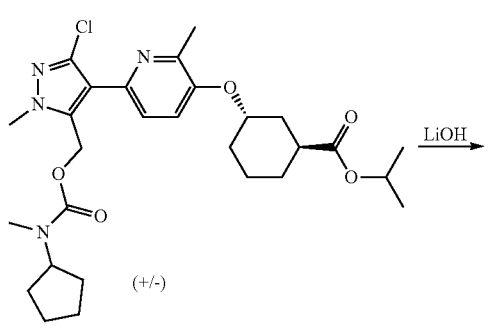

56-4

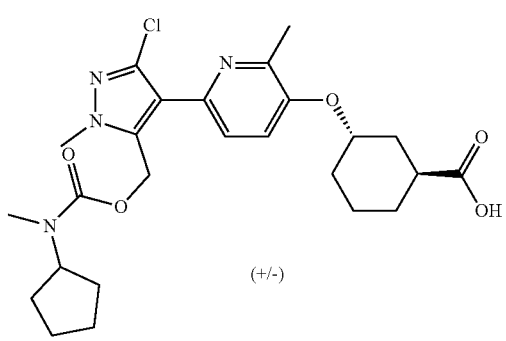

56

Step (1): Preparation of (+/−)-isopropyl (1S,3S)-3-((6-(3-chloro-5-formyl-1-methyl-1H-pyrazol-4-yl)-2-methylpyridin-3-yl)oxy)cyclohexane-1-carboxylate

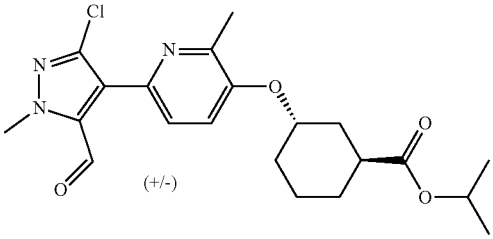

56-1

Compound 16-9 (500 mg, 0.98 mmol) was dissolved in DMF (10 mL). The reaction system was added with bromosuccinimide (654 mg, 4.9 mmol), warmed to 50° C., reacted for 5 h, quenched with water (20 mL), and extracted with ethyl acetate (20 mL×3). The organic phases were combined, washed with saturated brine (15 mL), dried over anhydrous sodium sulfate, filtered and concentrated, and the residue was separated by column chromatography to give compound 56-1 (260 mg, 51.02% yield) in the form of a white solid. LC-MS [M+H]⁺: 419.7.

Step (2): Preparation of (+/−)-isopropyl (1S,3S)-3-((6-(3-chloro-5-(hydroxymethyl)-1-methyl-1H-pyrazol-4-yl)-2-methylpyridin-3-yl)oxy)cyclohexane-1-carboxylate

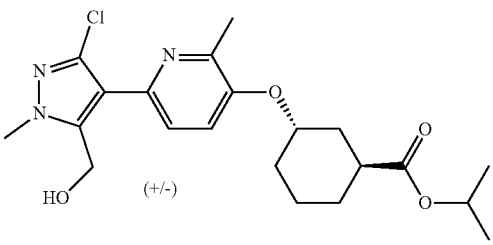

56-2

Compound 56-1 (260 mg, 0.62 mmol) was dissolved in tetrahydrofuran (10 mL), and the reaction system was added with sodium borohydride (24 mg, 0.62 mmol), stirred at room temperature for 30 min, quenched with ice water (20 mL), and extracted with ethyl acetate (20 mL×3). The organic phases were combined, washed with saturated brine (15 mL), dried over anhydrous sodium sulfate, filtered and concentrated. The residue was separated by column chromatography to give compound 56-2 (200 mg, 61.29% yield) in the form of a yellow oily liquid. LC-MS [M+H]⁺: 422.2.

Step (3): Preparation of (+/−)-isopropyl (1S,3S)-3-((6-(3-chloro-5-((((cyclopentyl(methyl)carbamoyl)oxy)methyl)-1-methyl-1H-pyrazol-4-yl)-2-methylpyridin-3-yl)oxy)cyclohexane-1-carboxylate Step (5): Preparation of (+/−)-(1S,3S)-3-((6-(3-chloro-5-((((cyclopentyl(methyl)carbamoyl)oxy)methyl)-1-methyl-1H-pyrazol-4-yl)-2-methylpyridin-3-yl)oxy)cyclohexane-1-carboxylic Acid

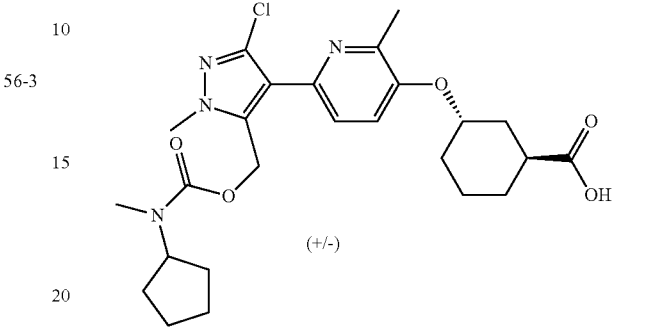

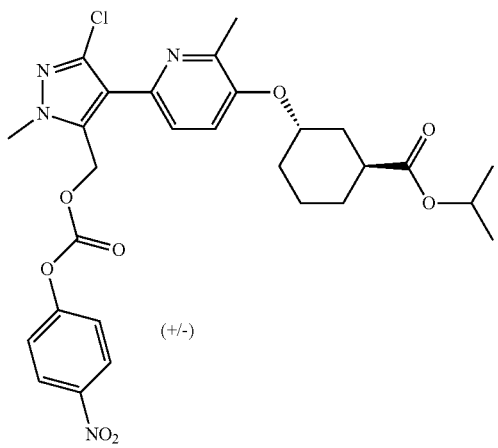

Compound 56-4 (80 mg, 0.15 mmol) was dissolved in methanol/tetrahydrofuran/water (5 mL, 1/3/1), and the reaction system was added with lithium hydroxide monohydrate (32 mg, 0.75 mmol), stirred overnight at room temperature, diluted with water (20 mL), adjusted to pH 5-6 with diluted hydrochloric acid, and extracted with ethyl acetate (20 mL×3). The organic phases were combined, washed with saturated brine (15 mL), dried over anhydrous sodium sulfate, filtered and concentrated. The residue was separated by column chromatography to give compound 56 (60 mg, 79.3% yield) in the form of a yellow oil. LC-MS [M+H]$^+$: 505.

$^1$H NMR (400 MHz, MeOD) δ 7.45 (s, 2H), 5.35 (s, 2H), 4.84-4.78 (m, 1H), 4.55-4.05 (m, 1H), 3.94 (s, 3H), 2.85-2.75 (m, 1H), 2.69 (brs, 3H), 2.50 (s, 3H), 2.16-2.09 (m, 1H), 2.01-1.87 (m, 3H), 1.81-1.46 (m, 12H).

Example 59

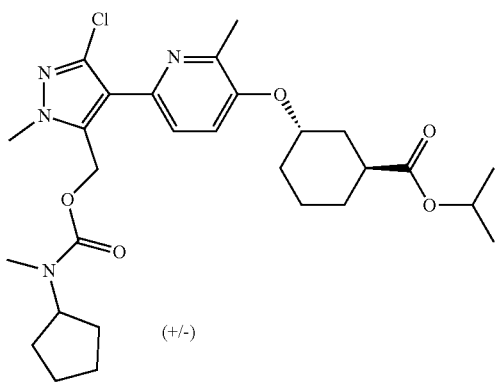

p-nitrophenyl chloroformate (143 mg, 0.71 mmol) was dissolved in dichloromethane (10 mL). The reaction system was added with anhydrous pyridine (225 mg, 2.84 mmol), stirred at room temperature for 10 min, added with compound 56-2 (200 mg, 0.47 mmol), reacted overnight at room temperature, added with N-methylcyclopentylamine hydrochloride (190 mg, 1.41 mmol), then stirred overnight at room temperature, added with water (20 mL), and extracted with ethyl acetate (30 mL×3). The organic phases were combined, washed with saturated brine (20 mL), dried over anhydrous sodium sulfate, filtered and concentrated, and the residue was separated by column chromatography to give compound 56-4 (80 mg, 25.32% yield) in the form of a yellow oily liquid. LC-MS [M+H]$^+$: 546.8.

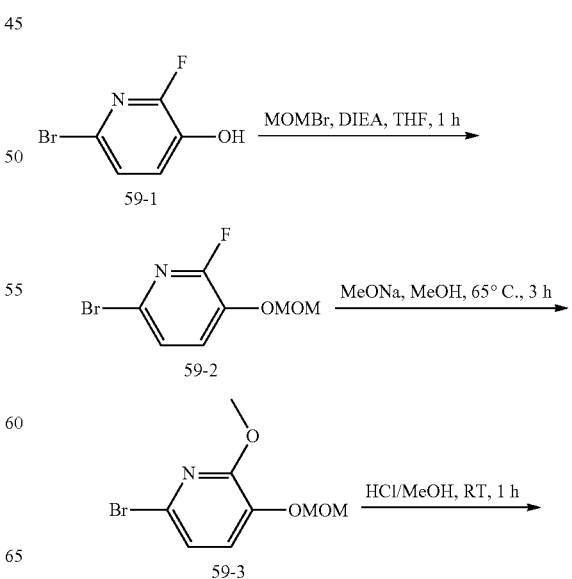

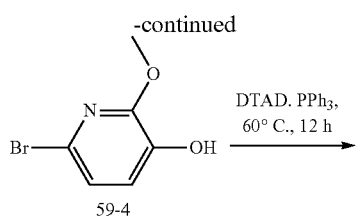

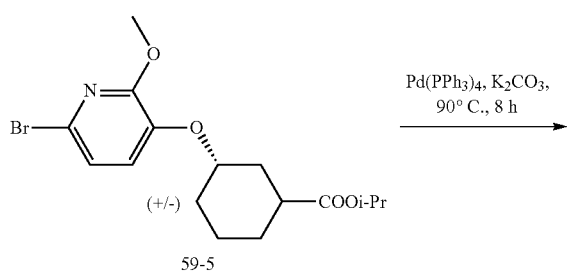

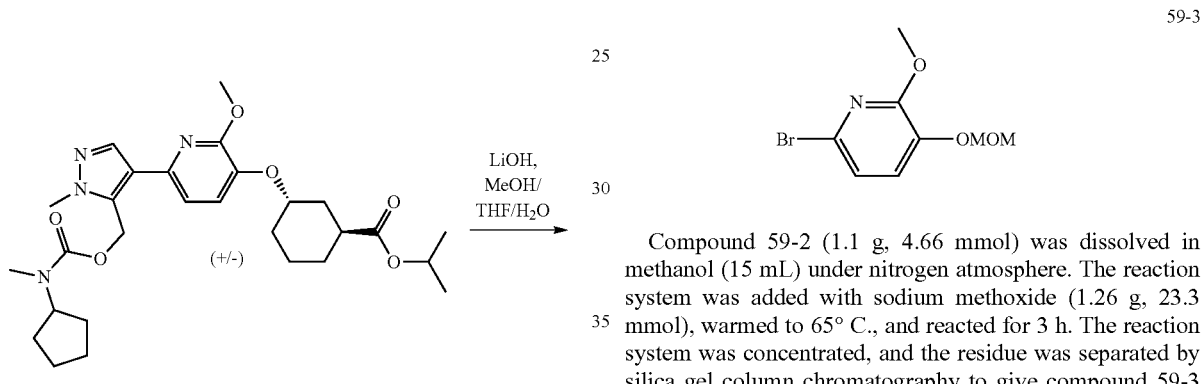

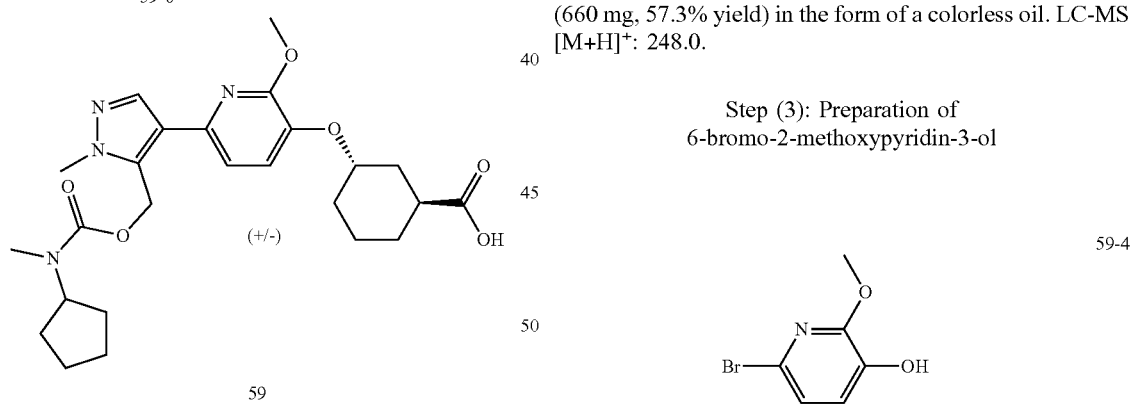

Step (1): Preparation of 6-bromo-2-fluoro-3-(methoxymethoxy)pyridine

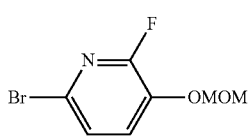

6-bromo-2-fluoropyridin-3-ol (1.0 g, 5.20 mmol) was dissolved in tetrahydrofuran (10 mL) under nitrogen atmosphere. The reaction system was cooled to 0° C., added dropwise with N,N-diisopropylethylamine (2.0 g, 15.60 mmol), reacted at 0° C., stirred for 20 min, then added dropwise with bromomethyl methyl ether (780 mg, 6.24 mmol), and reacted for 2 h after the addition was completed. The reaction system was added with ammonium chloride solution (20 mL) to quench the reaction, and extracted with ethyl acetate (20 mL×3). The organic phases were combined, washed with saturated brine (30 mL), dried over anhydrous sodium sulfate, filtered and concentrated, and the residue was separated by silica gel column chromatography to give compound 59-2 (1.1 g, 90.2% yield) in the form of a colorless oil. LC-MS [M+H]$^+$: 236.0.

Step (2): Preparation of 6-bromo-2-methoxy-3-(methoxymethoxy)pyridine

Compound 59-2 (1.1 g, 4.66 mmol) was dissolved in methanol (15 mL) under nitrogen atmosphere. The reaction system was added with sodium methoxide (1.26 g, 23.3 mmol), warmed to 65° C., and reacted for 3 h. The reaction system was concentrated, and the residue was separated by silica gel column chromatography to give compound 59-3 (660 mg, 57.3% yield) in the form of a colorless oil. LC-MS [M+H]$^+$: 248.0.

Step (3): Preparation of 6-bromo-2-methoxypyridin-3-ol

Compound 59-3 (660 mg, 2.66 mmol) was dissolved in methanol (5 mL). The reaction system was added with a solution of hydrogen chloride in methanol (1 mL, 33%), and stirred at room temperature for 1 h. The reaction system was added with water (20 mL) to quench the reaction, and extracted with ethyl acetate (25 mL×3). The organic phases were combined, washed with saturated brine (20 mL), dried over anhydrous sodium sulfate, filtered and concentrated, and the residue was separated by silica gel column chromatography to give compound 59-4 (370 mg, 68.5% yield) in the form of a colorless oil. LC-MS [M+H]$^+$: 203.9.

Step (4): Preparation of (+/−)-isopropyl (1S,3S)-3-((6-bromo-2-methoxypyridin-3-yl)oxy)cyclohexane-1-carboxylate

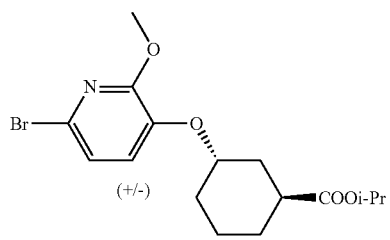

59-5

Compound 59-4 (370 mg, 1.81 mol), triphenylphosphine (950 mg, 3.62 mol), and (+/−)-isopropyl (1S,3S)-3-hydroxycyclohexane-1-carboxylate (674 mg, 3.62 mmol) were dissolved in tetrahydrofuran (10 mL) under nitrogen atmosphere. The reaction system was stirred at room temperature, added dropwise with a solution of di-tert-butyl azodicarboxylate (834 mg, 3.62 mmol) in tetrahydrofuran (2 mL) while stirring at room temperature, and stirred at 60° C. overnight. The reaction system was added with water (50 mL) to quench the reaction, and extracted with ethyl acetate (25 mL×3). The organic phases were combined, washed with saturated brine (30 mL), dried over anhydrous sodium sulfate, filtered and concentrated, and the residue was separated by silica gel column chromatography to give compound 59-5 (500 mg, 74.5% yield) in the form of a colorless oil. LC-MS [M+H]+: 371.8.

Step (5): Preparation of (+/−)-isopropyl (1S,3S)-3-((6-(5-(((cyclopentyl(methyl)carbamoyl)oxy)methyl)-1-methyl-1H-pyrazol-4-yl)-2-methoxypyridin-3-yl)oxy)cyclohexane-1-carboxylate 59-6

Compound 59-5 (500 mg, 1.34 mmol) was dissolved in dioxane/water (10 mL, 4/1) under nitrogen atmosphere. The reaction system was added with (5-(((cyclopentyl(methyl)carbamoyl)oxy)methyl)-1-methyl-1H-pyrazol-4-yl)boronic acid (414 mg, 1.47 mmol), tetrakis(triphenylphosphine)palladium(0) (310 mg, 0.27 mmol) and potassium carbonate (407 mg, 2.95 mmol), and reacted at 90° C. for 8 h. The reaction system was quenched with water (40 mL), and extracted with ethyl acetate (30 mL×3). The organic phases were combined, washed with saturated brine (30 mL), dried over anhydrous sodium sulfate, filtered and concentrated, and the residue was separated by silica gel column chromatography to give compound 59-6 (450 mg, 70% purity, 44.5% yield) in the form of a yellow oil. LC-MS [M+H]+: 528.8.

Step (6): Preparation of (+/−)-(1S,3S)-3-((6-(5-(((cyclopentyl(methyl)carbamoyl)oxy)methyl)-1-methyl-1H-pyrazol-4-yl)-2-methoxypyridin-3-yl)oxy)cyclohexane-1-carboxylic Acid

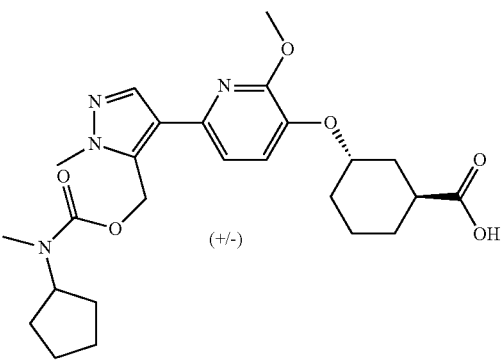

59

Compound 59-6 (450 mg, 0.85 mmol) and lithium hydroxide (178 mg, 4.25 mmol) were dissolved in THF (6 mL)/MeOH (2 mL)/H₂O (2 mL), and the reaction system was stirred overnight at room temperature, diluted with water (10 mL), and adjusted to pH 5-6 with diluted hydrochloric acid, extracted with ethyl acetate (15 mL×3), dried over anhydrous sodium sulfate, filtered and concentrated, and the residue was separated by silica gel column chromatography to give compound 59 (250 mg, 60.5% yield) in the form of a yellow oil. LC-MS [M+H]+: 487.1.

$^1$H NMR (400 MHz, MeOD) δ 7.86 (s, 1H), 7.32 (d, J=8.1 Hz, 1H), 7.19 (d, J=8.0 Hz, 1H), 5.69 (s, 2H), 4.69-4.63 (m, 1H), 4.55-4.20 (m, 1H), 3.99 (s, 3H), 3.98 (s, 3H), 2.90-2.82 (m, 1H), 2.76 (s, 3H), 2.11-2.03 (m, 1H), 1.96-1.47 (m, 15H).

Example 60

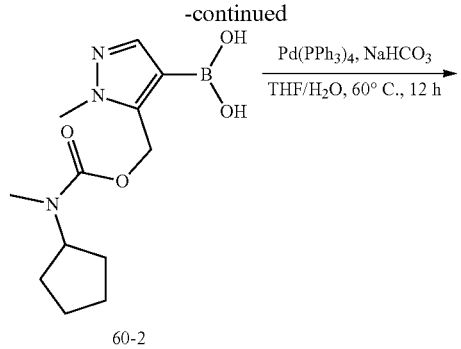

60-2

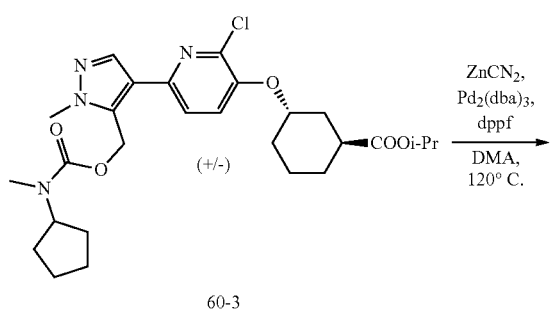

60-3

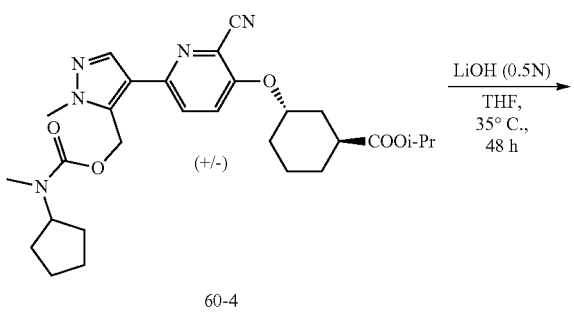

60-4

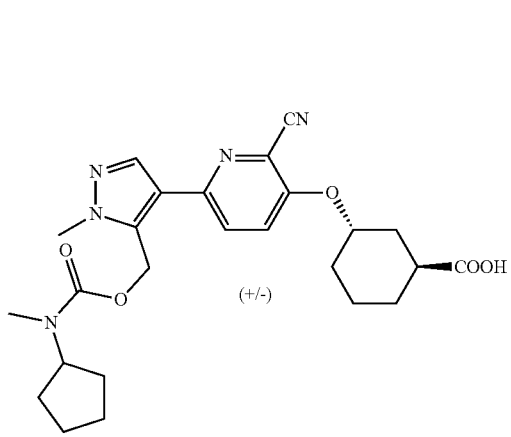

60

Step (1): Preparation of (+/−)-isopropyl (1S,3S)-3-((2-chloro-6-(5-(((cyclopentyl(methyl)carbamoyl)oxy) methyl)-1-methyl-1H-pyrazol-4-yl)pyridin-3-yl)oxy)cyclohexane-1-carboxylate

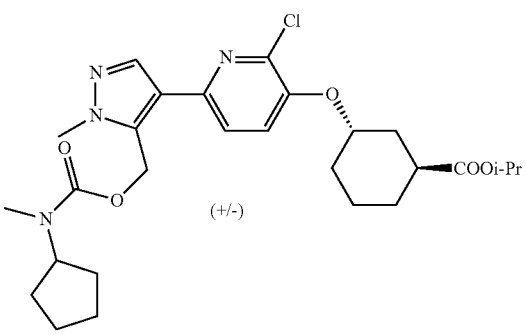

60-3

(+/−)-isopropyl (1S,3S)-3-((6-bromo-2-chloropyridin-3-yl)oxy)cyclohexane-1-carboxylate (300 mg, 0.80 mmol) and (5-((((cyclopentyl(methyl)carbamoyl)oxy)methyl)-1-methyl-1H-pyrazol-4-yl)boronic acid (666 mg, 50% purity, 1.18 mmol) were dissolved in tetrahydrofuran (10 mL)/water (2.5 mL) under nitrogen atmosphere. The reaction system was added with tetrakis(triphenylphosphine)palladium(0) (91 mg, 0.08 mmol) and sodium bicarbonate (166 mg, 1.98 mmol), and reacted at 60° C. for 12 h. Then the reaction system was diluted with water (30 mL), and extracted with ethyl acetate (20 mL×3). The organic phases were combined, dried over anhydrous sodium sulfate, filtered and concentrated, and the residue was purified by silica gel column chromatography (PE/EA=3/1) to give compound 60-3 (180 mg, 42% yield) in the form of a white solid. LC-MS [M+H]$^+$: 533.3.

Step (2): Preparation of (+/−)-isopropyl (1S,3S)-3-((2-cyano-6-(5-(((cyclopentyl(methyl)carbamoyl)oxy) methyl)-1-methyl-1H-pyrazol-4-yl)pyridin-3-yl)oxy)cyclohexane-1-carboxylate

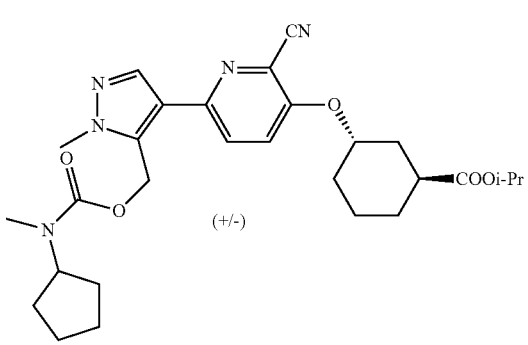

60-4

Compound 60-3 (180 mg, 0.34 mmol) was dissolved in DMA (3 mL) under nitrogen atmosphere. The reaction system was added with zinc cyanide (80 mg, 0.68 mmol), 1,1'-bis(diphenylphosphino) ferrocene (112 mg, 0.20 mmol) and tris(dibenzylideneacetone)dipalladium (58 mg, 0.10 mmol), and reacted at 120° C. for 48 h under nitrogen atmosphere. The reaction system was diluted with ethyl acetate (30 mL), washed with saturated brine (10 mL×3), dried over anhydrous sodium sulfate, filtered, and concentrated to give a crude product. The crude product was purified by silica gel thin layer chromatography (PE/EA=1/6) to give compound 60-4 (120 mg, 60% purity, 40% yield) in the form of a yellow oil. LC-MS [M+H]$^+$: 523.8.

Step (3): Preparation of (+/−)-(1S,3S)-3-((2-cyano-6-(5-((((cyclopentyl(methyl)carbamoyl)oxy)methyl)-1-methyl-1H-pyrazol-4-yl)pyridin-3-yl)oxy)cyclohexane-1-carboxylic Acid

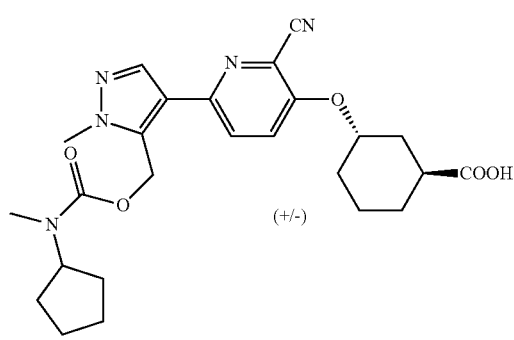

60

Compound 60-4 (120 mg, 0.14 mmol) was dissolved in methanol (4 mL). The reaction system was added with aqueous lithium hydroxide solution (2 mL, 0.5 N), reacted at room temperature for 12 h, concentrated, then adjusted to pH 3 with diluted hydrochloric acid (4 mL, 1 N) and filtered to give compound 60 (100 mg) in the form of a pale yellow solid. LC-MS [M+H]$^+$: 481.8.

$^1$H NMR (400 MHz, CDCl$_3$) δ 7.82 (s, 1H), 7.69 (d, J=8.9 Hz, 1H), 7.45 (d, J=9.1 Hz, 1H), 5.54 (s, 2H), 4.84-4.78 (m, 1H), 4.64-4.28 (m, 1H), 4.01 (s, 3H), 3.05-2.96 (m, 1H), 2.78 (s, 3H), 2.21-1.47 (m, 16H).

Example 61

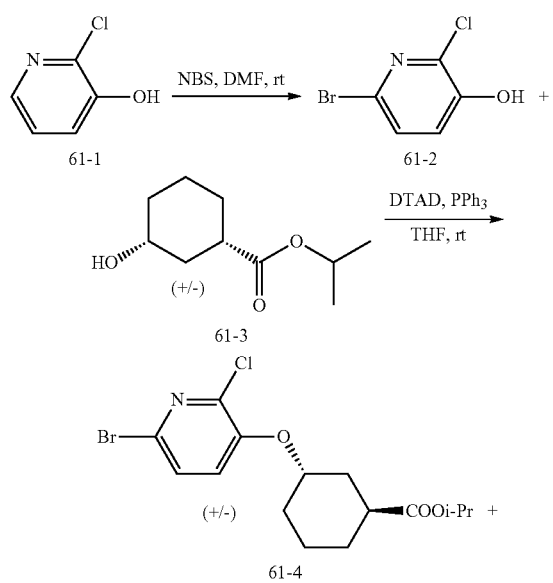

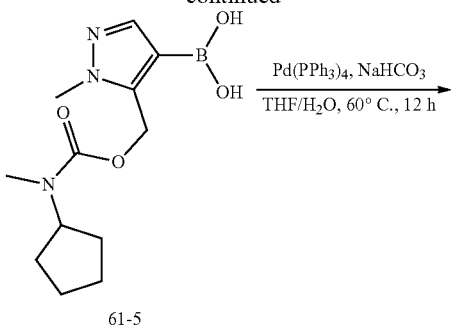

61-5

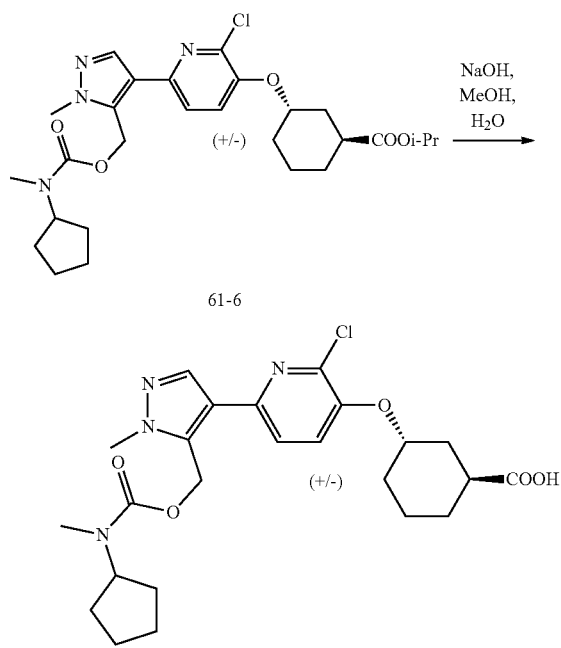

61

Step (1): Preparation of 6-bromo-2-chloropyridin-3-ol

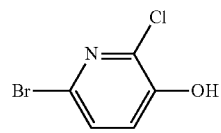

61-2

2-chloropyridin-3-ol (5.00 g, 38.6 mmol) was dissolved in N,N-dimethylformamide (40 mL). The reaction system was cooled to 0° C., added with N-bromosuccinimide (6.87 g, 38.6 mmol), slowly warmed to room temperature, stirred overnight, diluted with ethyl acetate (150 mL), washed with water (60 mL×3) and saturated brine (60 mL), dried over anhydrous sodium sulfate, filtered and concentrated by rotary evaporation. The residue was purified by silica gel column chromatography to give compound 61-2 (1.70 g, 21% yield) in the form of a colorless oil. LC-MS [M−H]$^+$: 207.7.

Step (2): Preparation of (+/−)-isopropyl (1S,3S)-3-((6-bromo-2-chloropyridin-3-yl)oxy)cyclohexane-1-carboxylate

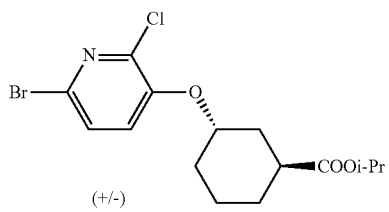

61-4

Compound 61-2 (0.50 g, 2.4 mmol) was dissolved in anhydrous tetrahydrofuran (10 mL) under nitrogen atmosphere. The reaction system was added with compound 61-3 (1.79 g, 9.6 mmol) and triphenylphosphine (2.52 g, 9.6 mmol), then added dropwise with di-tert-butyl azodicarboxylate (2.21 g, 9.6 mmol), stirred overnight at room temperature, and concentrated, and the residue was diluted with water (30 mL), and extracted with ethyl acetate (20 mL×3). The organic phases were combined, washed with saturated brine (30 mL), dried over anhydrous sodium sulfate, filtered and concentrated. The residue was purified by silica gel column chromatography to give compound 61-4 (800 mg, 79% yield) in the form of a colorless oil. LC-MS [M−H]⁺: 375.7.

Step (3): Preparation of (+/−)-isopropyl (1S,3S)-3-((2-chloro-6-(5-(((cyclopentyl(methyl)carbamoyl)oxy) methyl)-1-methyl-1H-pyrazol-4-yl)pyridin-3-yl)oxy)cyclohexane-1-carboxylate

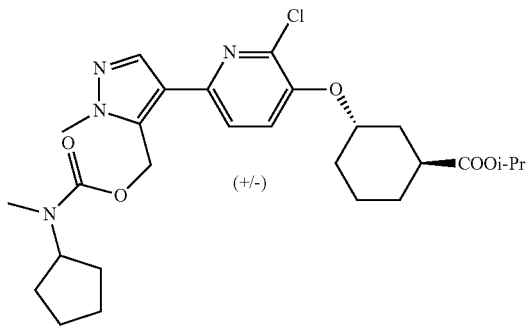

61-6

Compound 61-4 (300 mg, 0.80 mmol) and (5-(((cyclopentyl(methyl)carbamoyl)oxy)methyl)-1-methyl-1H-pyrazol-4-yl)boronic acid (666 mg, 50% purity, 1.18 mmol) were dissolved in tetrahydrofuran (10 mL)/water (2.5 mL) under nitrogen atmosphere. The reaction system was added with tetrakis(triphenylphosphine)palladium(0) (91 mg, 0.08 mmol) and sodium bicarbonate (166 mg, 1.98 mmol), and reacted at 60° C. for 12 h. Then the reaction system was diluted with water (30 mL), and extracted with ethyl acetate (20 mL×3). The organic phases were combined, dried over anhydrous sodium sulfate, filtered and concentrated, and the residue was purified by silica gel column chromatography to give compound 61-6 (180 mg, 42% yield) in the form of a white solid. LC-MS [M+H]⁺: 533.3.

Step (4): Preparation of (+/−)-(1S,3S)-3-((2-chloro-6-(5-((((cyclopentyl(methyl)carbamoyl)oxy)methyl)-1-methyl-1H-pyrazol-4-yl)pyridin-3-yl)oxy)cyclohexane-1-carboxylic Acid

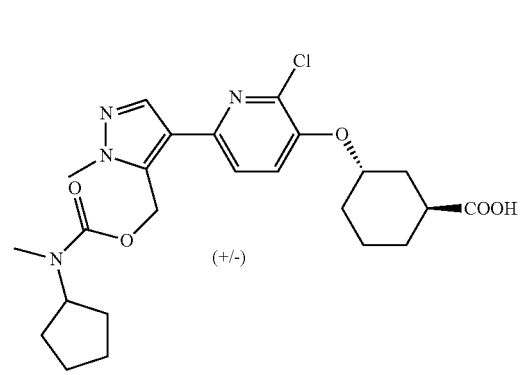

61

Compound 61-6 (180 mg, 0.33 mmol) and sodium hydroxide (31 mg, 0.78 mmol) were dissolved in methanol (4 mL) and water (2 mL), and the reaction system was reacted at room temperature for 12 h, concentrated, adjusted to pH 3 with diluted hydrochloric acid (4 mL, 1 N), and then extracted with ethyl acetate (10 mL×2). The organic phases were combined, dried over anhydrous sodium sulfate, filtered and concentrated, and the residue was separated by silica gel thin layer chromatography to give compound 61-6 (100 mg, 60% yield) in the form of a yellow oil. LC-MS [M−H]⁺: 490.8.

¹H NMR (400 MHz, CDCl3) δ 7.83 (s, 1H), 7.41 (d, J=8.3 Hz, 1H), 7.29 (d, J=8.3 Hz, 1H), 5.54 (s, 2H), 4.76-4.70 (m, 1H), 4.66-4.22 (m, 1H), 4.01 (s, 3H), 3.06-2.90 (m, 1H), 2.77 (s, 3H), 2.30-1.41 (m, 16H).

Example 62

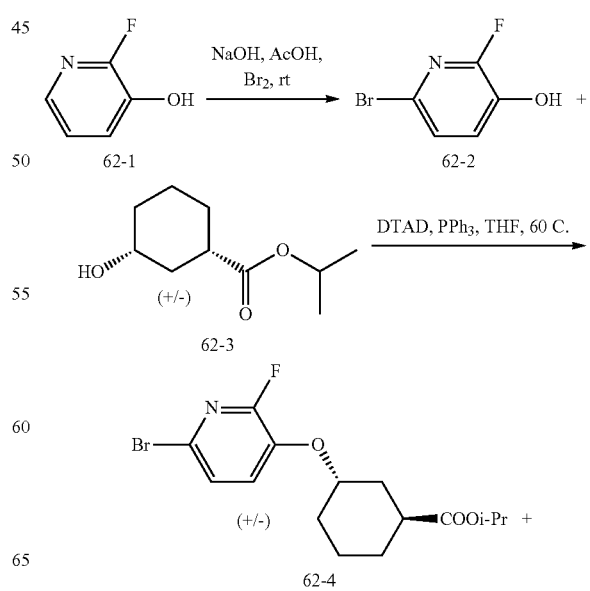

Step (2): Preparation of (+/−)-isopropyl (1S,3S)-3-((6-bromo-2-fluoropyridin-3-yl)oxy)cyclohexane-1-carboxylate

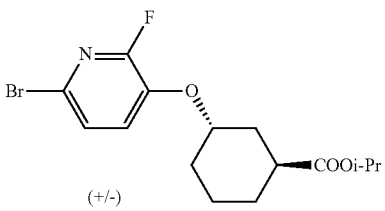

Compound 62-2 (0.58 g, 3.0 mmol), triphenylphosphine (1.57 g, 6.0 mmol) and (+/−)-isopropyl (1S,3R)-3-hydroxy-cyclohexane-1-carboxylate (1.11 g, 6.0 mmol) were dissolved in tetrahydrofuran (30 mL) under nitrogen atmosphere. The reaction system was stirred at room temperature, added dropwise with a solution of di-tert-butyl azodicarboxylate (1.38 g, 6.0 mmol) in tetrahydrofuran (20 mL), then reacted at room temperature for 12 h, quenched with saturated aqueous ammonium chloride solution (40 mL), and extracted with ethyl acetate (30 mL×3). The organic phases were combined, washed with saturated brine (30 mL), dried over anhydrous sodium sulfate, filtered and concentrated. The residue was separated by silica gel column chromatography to give compound 62-4 (610 mg, 55% yield) in the form of a yellow oily liquid. LC-MS [M+H]$^+$: 360, 362.

Step (3): Preparation of (+/−)-isopropyl (1S,3S)-3-((6-(5-(((cyclopentyl(methyl)carbamoyl)oxy)methyl)-1-methyl-1H-pyrazol-4-yl)-2-fluoropyridin-3-yl)oxy)cyclohexane-1-carboxylate

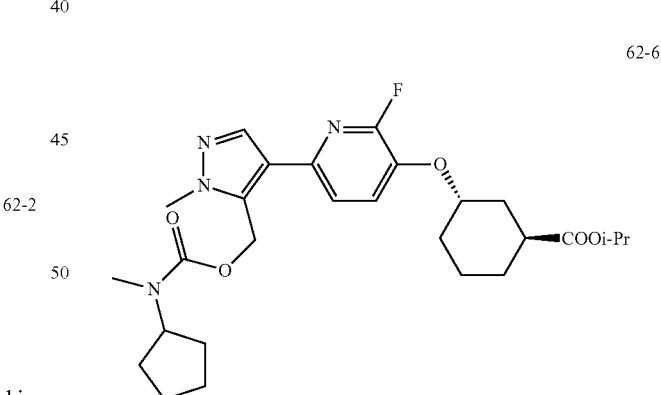

Compound 62-4 (360 mg, 1.0 mmol), compound 62-5 (282 mg, 1.0 mmol) and tetrakis(triphenylphosphine)palladium(0) (116 mg, 0.10 mmol) were dissolved in tetrahydrofuran (20 mL) under nitrogen atmosphere. The reaction system was added with a solution of sodium carbonate (234 mg, 2.2 mmol) in water (4 mL) and reacted at 60° C. overnight under nitrogen atmosphere. The reaction system was quenched with water (50 mL), and extracted with ethyl acetate (25 mL×2). The organic phases were combined, dried over anhydrous sodium sulfate, filtered and concentrated, and the residue was separated by silica gel column

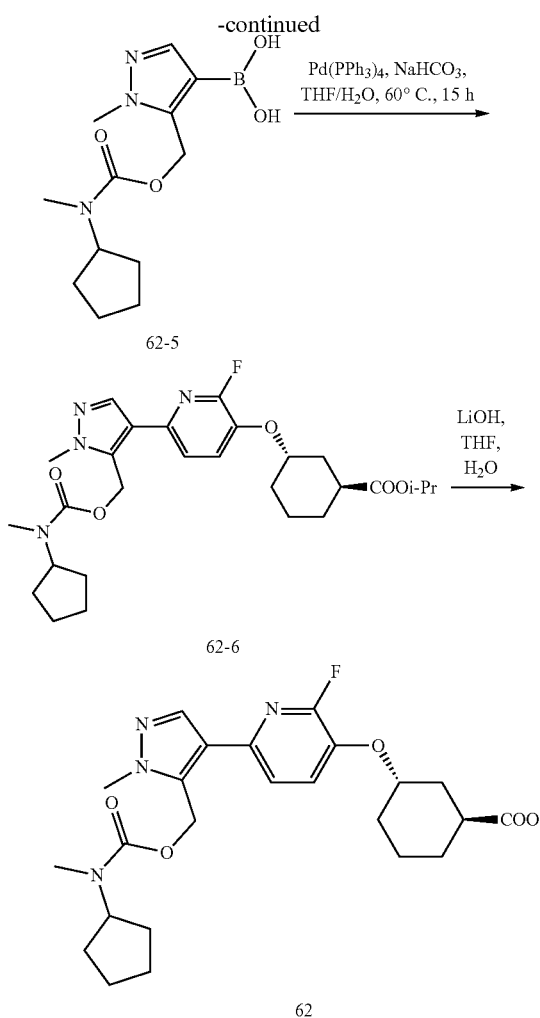

Step (1): Preparation of 6-bromo-2-fluoropyridin-3-ol

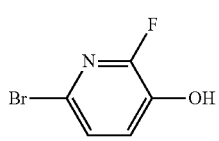

2-fluoropyridin-3-ol (5.65 g, 50.0 mmol) was dissolved in acetic acid (100 mL). The reaction system was added with sodium hydroxide (10 N, 6 mL), stirred at 0° C. for 10 min, slowly added dropwise with bromine (8.39 g, 52.5 mmol), then warmed to room temperature, and reacted for 2 h. The reaction system was quenched with aqueous sodium thiosulfate solution, diluted with water (300 mL), and extracted with ethyl acetate (100 mL×2). The organic phases were combined, washed with saturated brine (100 mL), dried over anhydrous sodium sulfate, filtered and concentrated, and the residue was separated by silica gel column chromatography to give compound 62-2 (7.20 g, 75% yield) in the form of a white solid. LC-MS [M−H]$^+$: 192, 194.

chromatography to give compound 62-6 (250 mg, 39% yield) in the form of a yellow oil. LC-MS [M+H]⁺: 517.

Step (4): Preparation of (+/−)-(1S,3S)-3-((6-(5-((((cyclopentyl(methyl)carbamoyl)oxy)methyl)-1-methyl-1H-pyrazol-4-yl)-2-fluoropyridin-3-yl)oxy)cyclohexane-1-carboxylic Acid

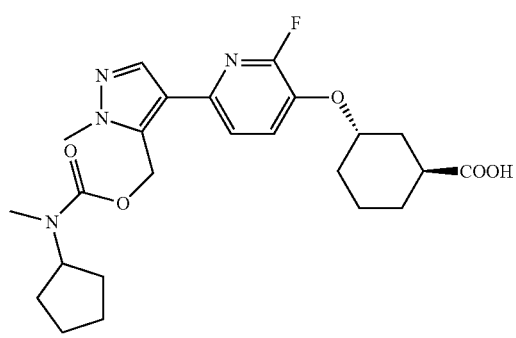

62

Compound 62-6 (230 mg, 0.44 mmol) was dissolved in tetrahydrofuran (6 mL)/methanol (2 mL)/water (2 mL), and the reaction system was added with lithium hydroxide monohydrate (91 mg, 2.2 mmol), and stirred overnight at room temperature. The reaction system was diluted with water (15 mL), adjusted to pH 5 with diluted hydrochloric acid, and extracted with dichloromethane (20 mL×2). The organic phases were combined, washed with saturated brine (15 mL), dried over anhydrous sodium sulfate, filtered and concentrated, and the residue was separated by silica gel column chromatography to give compound 62 (130 mg, 62% yield) in the form of a white solid. LC-MS [M+H]⁺: 475.

¹H NMR (400 MHz, MeOD) δ 7.86 (s, 1H), 7.62 (dd, J=10.3, 8.3 Hz, 1H), 7.49 (d, J=8.1 Hz, 1H), 5.57 (s, 2H), 4.79-4.73 (m, 1H), 4.60-4.25 (m, 1H), 3.98 (s, 3H), 2.88-2.68 (m, 4H), 2.14-2.04 (m, 1H), 1.84-1.46 (m, 15H).

Example 63

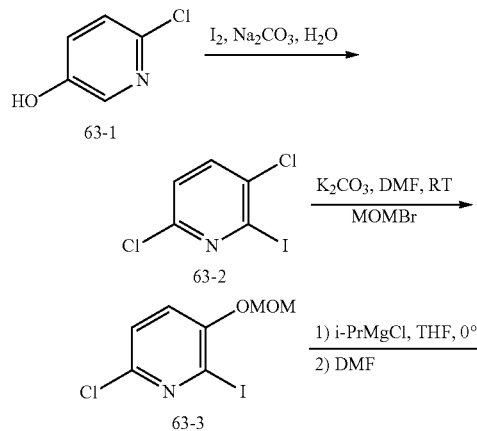

63-4

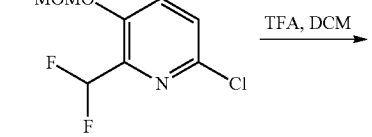

63-5

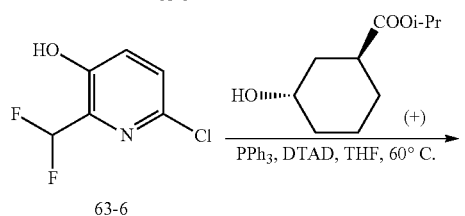

63-6

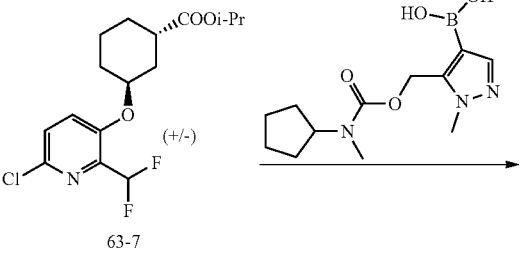

63-7

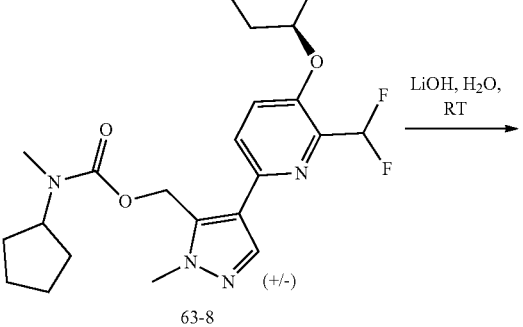

63-8

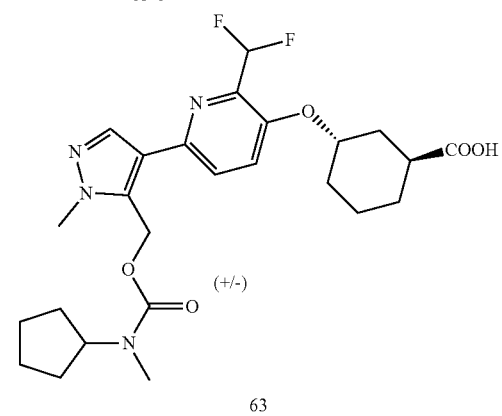

63

Step (1): Preparation of 6-chloro-2-iodopyridin-3-ol

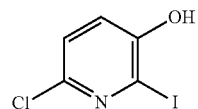
63-2

Iodine (24.37 g, 96 mmol) was added to a solution of 6-chloropyridin-3-ol (10.36 g, 80 mmol) and sodium carbonate (21.20 g, 200 mmol) in water (400 mL), and the reaction system was stirred overnight at room temperature. The reaction system was quenched with saturated sodium bisulfite solution, and extracted with ethyl acetate (100 mL×3). The organic phases were combined, washed with saturated brine (100 mL), dried over anhydrous sodium sulfate, filtered and concentrated to give a crude product, and the crude product was purified by silica gel column chromatography to give compound 63-2 (16.30 g, 80% yield) in the form of a white solid. MS [M+H]$^+$: 255.9.

Step (2): Preparation of 6-chloro-2-iodo-3-(methoxymethoxy)pyridine

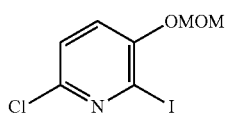
63-3

Potassium carbonate (16.60 g, 120 mmol) was added to a solution of compound 63-2 (10.00 g, 40 mmol) in DMF (100 mL) while stirring at room temperature. The reaction system was stirred for 10 min, added dropwise with a solution of bromomethyl methyl ether (7.50 g, 60 mmol) in DMF (25 mL), and then stirred overnight at room temperature. The reaction system was diluted with water (500 mL) and extracted with ethyl acetate (100 mL×3). The organic phases were combined, washed with saturated brine (150 mL), dried over anhydrous sodium sulfate, filtered and concentrated, and the residue was purified by silica gel column chromatography to give compound 63-3 (10.50 g, 90% yield) in the form of a white solid. MS [M+H]$^+$: 299.7.

Step (3): Preparation of 6-chloro-3-(methoxymethoxy)picolinaldehyde

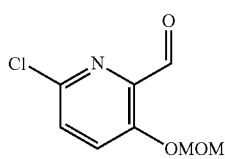
63-4

Isopropylmagnesium chloride (1.3 M, 33 mL) was added dropwise to a solution of compound 63-3 (7.5 g, 30 mmol) in THF (80 mL) in an ice water bath under nitrogen atmosphere. Then the reaction system was stirred at 0° C. for 1 h, added with N,N-dimethylformamide (3.3 g, 45 mmol), stirred at 0° C. for 30 min, slowly warmed to room temperature, quenched with saturated aqueous ammonium chloride (50 mL), diluted with water (200 mL), and extracted with ethyl acetate (100 mL×3). The organic phases were combined, dried over anhydrous sodium sulfate, filtered and concentrated, and the residue was purified by silica gel column chromatography to give compound 63-4 (2.7 g, 33% yield) in the form of a yellow solid. MS [M+H]$^+$=202.1.

Step (4): Preparation of 6-chloro-2-(difluoromethyl)-3-(methoxymethoxy)pyridine

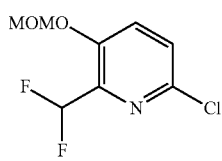
63-5

A solution of compound 63-4 (1.5 g, 10 mmol) in dichloromethane (30 mL) was added dropwise with diethylaminosulfur trifluoride (3.2 g, 20 mmol) at −78° C. under nitrogen atmosphere. Then the reaction system was slowly warmed to room temperature from −78° C. and stirred overnight. The reaction system was quenched with saturated sodium bicarbonate solution (10 mL), diluted with water (50 mL) and extracted with dichloromethane (50 mL×2). The organic phases were combined, washed with saturated brine (30 mL), dried over anhydrous sodium sulfate, filtered and concentrated, and the residue was purified by silica gel column chromatography to give compound 63-5 (1.4 g, 85% yield) in the form of a pale yellow oil. MS [M+H]$^+$: 223.8.

Step (5): Preparation of 6-chloro-2-(difluoromethyl)pyridin-3-ol

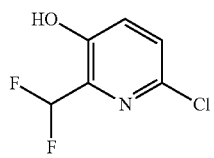
63-6

Trifluoroacetic acid (10 mL) was added to a solution of compound 63-5 (1.3 g, 10 mmol) in dichloromethane (20 mL), and the reaction system was stirred overnight at room temperature. The reaction system was concentrated to give a crude product. The crude product was purified by silica gel column chromatography to give compound 63-6 (0.95 g, 91% yield) in the form of a white solid. MS [M+H]$^+$: 179.9.

Step (6): Preparation of (+/−)-isopropyl (1S,3S)-3-((6-chloro-2-(difluoromethyl)pyridin-3-yl)oxy)cyclohexane-1-carboxylate

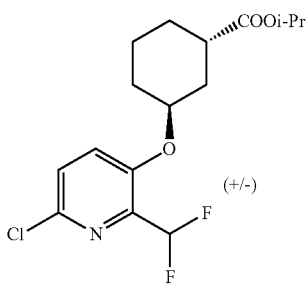

63-7

(+/−)

A solution of DTAD (258 mg, 1.12 mmol) in THF (1 mL) was added dropwise to a solution of compound 63-6 (100 mg, 0.56 mmol), (+/−)-isopropyl (1S,3S)-3-hydroxycyclohexane-1-carboxylate (209 mg, 1.12 mmol) and triphenylphosphine (294 mg, 1.12 mmol) in THF (8 mL) under nitrogen atmosphere, and the reaction system was warmed to 60° C. and stirred overnight. The reaction system was added with methanol (5 mL) to quench the reaction and concentrated by rotary evaporation to give a crude product. The crude product was purified by silica gel column chromatography to give compound 63-7 (180 mg, 93% yield) in the form of a colorless oil. MS [M+H]⁺: 348.2.

Step (7): Preparation of (+/−)-isopropyl (1S,3S)-3-((6-(5-(((cyclopentyl(methyl)carbamoyl)oxy)methyl)-1-methyl-1H-pyrazol-4-yl)-2-(difluoromethyl)pyridin-3-yl)oxy)cyclohexane-1-carboxylate

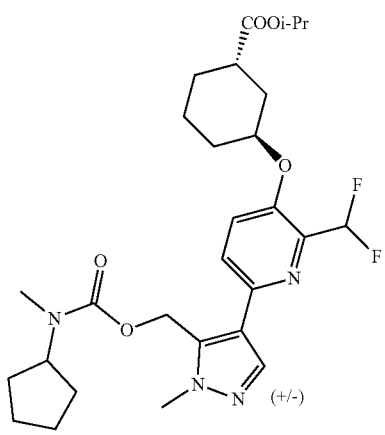

63-8

(+/−)

Potassium carbonate (144 mg, 1.04 mmol) and tetrakis(triphenylphosphine)palladium(0) (60 mg, 0.052 mmol) were added to a solution of compound 63-7 (180 mg, 0.52 mmol) and (4-(dihydroxyboryl)-2-methylpyrazol-3-yl)methyl N-cyclopentyl-N-methylcarbamate (146 mg, 0.52 mmol) in DMF (5 mL) under nitrogen atmosphere. The reaction system was warmed to 80° C. and stirred overnight. The reaction system was diluted with water (50 mL) and extracted with ethyl acetate (15 mL×3). The organic phases were combined, washed with saturated brine (15 mL), dried over anhydrous sodium sulfate, filtered and concentrated to give a crude product, and the crude product was purified by silica gel column chromatography to give compound 63-7 (160 mg, 56% yield) in the form of a yellow solid. MS [M+H]⁺: 548.8.

Step (8): Preparation of (+/−)-(1S,3S)-3-((6-(5-(((cyclopentyl(methyl)carbamoyl)oxy)methyl)-1-methyl-1H-pyrazol-4-yl)-2-(difluoromethyl)pyridin-3-yl)oxy)cyclohexane-1-carboxylic Acid

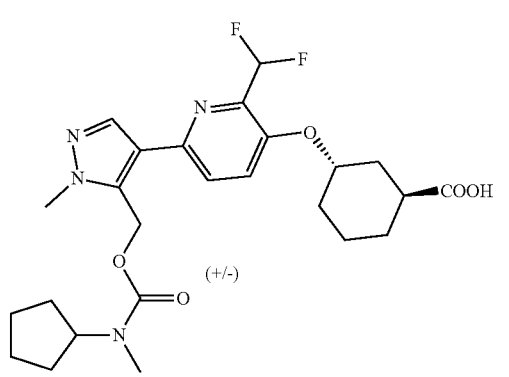

63

(+/−)

Lithium hydroxide solution (0.5 N, 2 mL) was added to a solution of compound 63-7 (160 mg, 0.29 mmol) in THF (2 mL)/MeOH (1 mL), and the reaction system was stirred overnight at room temperature. The reaction system was adjusted to pH 6 with diluted hydrochloric acid, then added with water (20 mL), and extracted with ethyl acetate (20 mL×3). The organic phases were combined, dried over anhydrous sodium sulfate, filtered and concentrated to give a crude product, and the crude product was purified by preparative high performance liquid chromatography to give compound 63 (100 mg, 68% yield) in the form of a white solid. MS [M+H]⁺: 507.3.

¹H NMR (400 MHz, CDCl₃) δ 7.82 (s, 1H), 7.58 (d, J=8.7 Hz, 1H), 7.38 (d, J=8.8 Hz, 1H), 6.84 (t, J=54.4 Hz, 1H), 5.59 (s, 2H), 4.79-4.73 (m, 1H), 4.68-4.24 (m, 1H), 4.00 (s, 3H), 2.96-2.87 (m, 1H), 2.74 (s, 3H), 2.22-2.14 (m, 1H), 2.08-1.90 (m, 3H), 1.89-1.75 (m, 2H), 1.74-1.42 (m, 10H).

Example 64

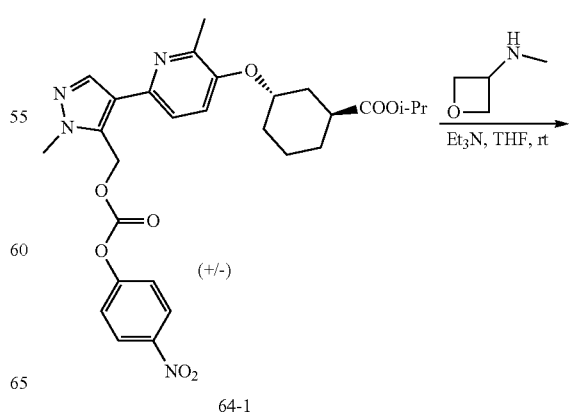

64-1

(+/−)

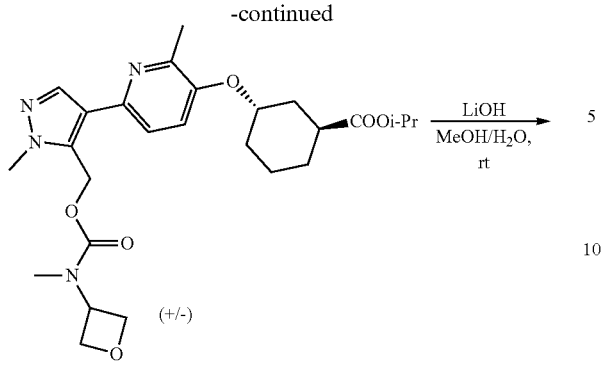

64-2

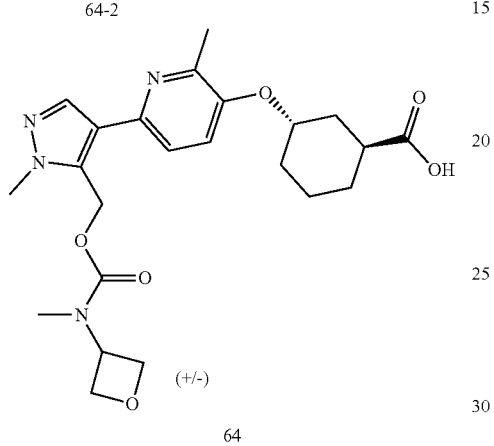

64

Step (1): Preparation of (+/−)-isopropyl (1S,3S)-3-((2-methyl-6-(2-methyl-3-(((methyl(oxetan-3-yl)carbamoyl)oxy)methyl)-2H-pyrrol-4-yl)pyridin-3-yl)oxy)cyclohexane-1-carboxylate

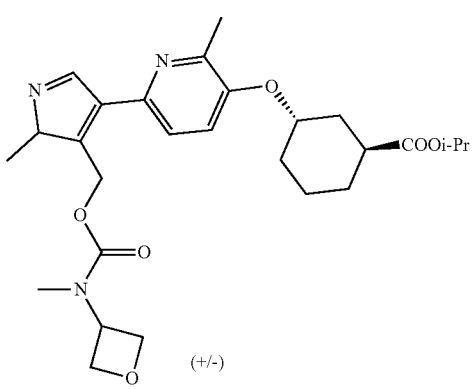

64-1

Compound 64-1 (250 mg, 0.45 mmol) (prepared by referring to Example 12) was dissolved in anhydrous tetrahydrofuran (10 mL) under nitrogen atmosphere. The reaction system was added with N-methyloxetan-3-amine hydrochloride (84 mg, 0.68 mmol) and triethylamine (137 mg, 1.35 mmol), stirred overnight at room temperature and concentrated by rotary evaporation, and the residue was separated by silica gel column chromatography to give compound 64-2 (175 mg, 77% yield) in the form of a yellow oil. LC-MS [M+H]$^+$: 500.8.

Step (2): Preparation of (+/−)-(1S,3S)-3-((2-methyl-6-(1-methyl-5-(((methyl(oxetan-3-yl)carbamoyl)oxy)methyl)-1H-pyrazol-4-yl)pyridin-3-yl)oxy)cyclohexane-1-carboxylic Acid

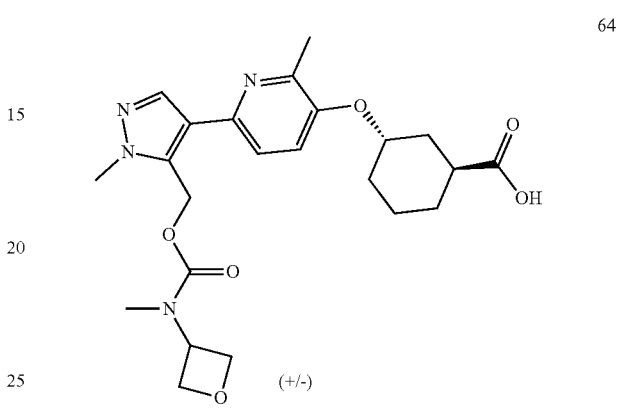

64

Compound 64-2 (175 mg, 0.35 mmol) was dissolved in methanol (6 mL), and the reaction system was added with aqueous lithium hydroxide solution (3 mL, 0.5 N), reacted at room temperature for 12 h, concentrated, adjusted to pH 4 with diluted hydrochloric acid (1 N), and extracted with ethyl acetate (15 mL×2). The organic phases were combined, dried over anhydrous sodium sulfate, filtered and concentrated to give a crude product, and the crude product was separated by preparative high performance liquid chromatography to give compound 64 (60 mg, 37% yield) in the form of a white solid. LC-MS [M+H]$^+$: 458.8.

$^1$H NMR (400 MHz, DMSO-d$_6$) δ 10.63 (bs, 1H), 7.99 (d, J=6.8 Hz, 1H), 7.89 (s, 1H), 7.47 (d, J=6.8 Hz, 1H), 5.46 (s, 2H), 5.08 (m, 2H), 4.83 (m, 2H), 4.82 (m, 1H), 3.64 (m, 1H), 3.63 (s, 3H), 3.27 (s, 3H), 2.51 (s, 3H), 2.31 (m, 1H), 2.17 (m, 1H), 1.95 (m, 1H), 1.92 (m, 1H), 1.72 (m, 1H), 1.70 (m, 1H), 1.53 (m, 1H), 1.47 (m, 1H), 1.43 (m, 1H).

Example 65

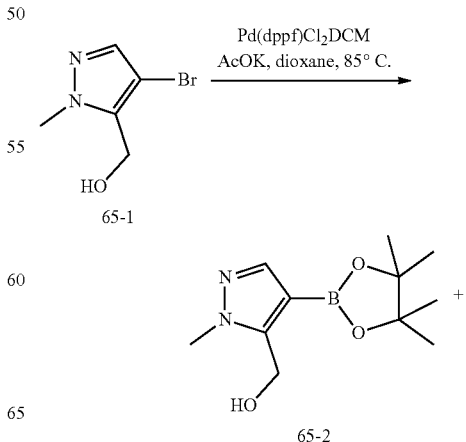

-continued

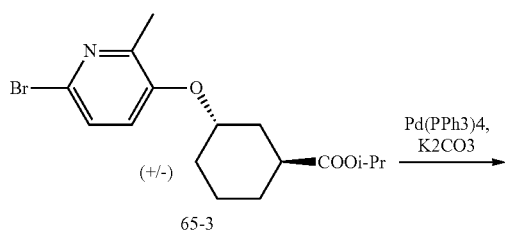

65-3

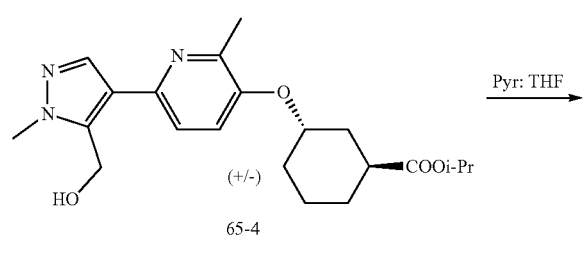

65-4

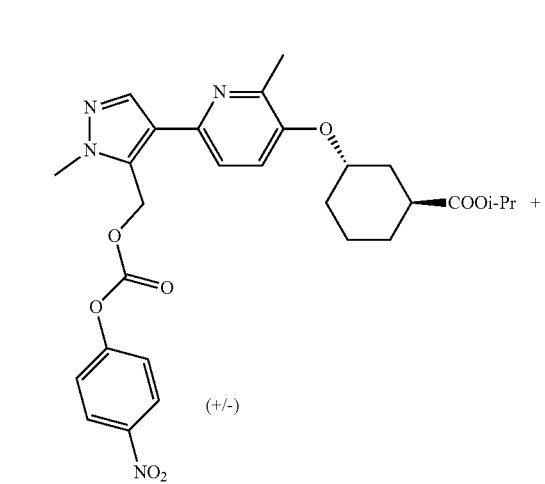

65-5

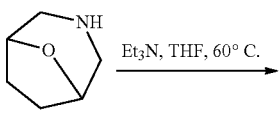

65-6

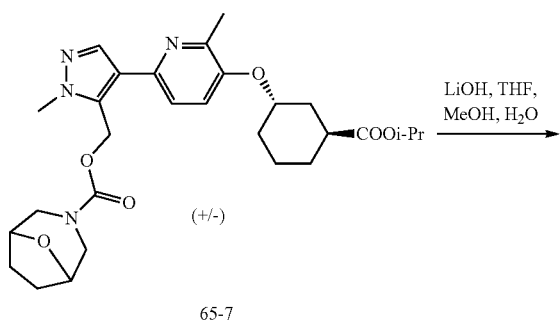

65-7

-continued

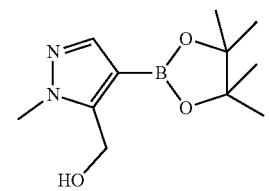

65

Step (1): Preparation of (1-methyl-4-(4,4,5,5-tetramethyl-1,3,2-dioxaborolan-2-yl)-1H-pyrazol-5-yl)methanol

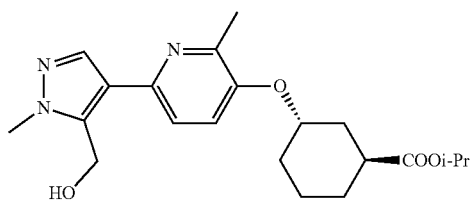

65-2

(4-bromo-1-methyl-1H-pyrazol-5-yl)methanol (3.82 g, 20 mmol), bis(pinacolato)diboron (7.62 g, 30 mmol) and Pd(dppf)Cl$_2$DCM (1.63 g, 2.0 mmol) were dissolved in 1,4-dioxane (60 mL) under nitrogen atmosphere, and the reaction system was added with potassium acetate (3.92 g, 40 mmol), warmed to 85° C. and stirred overnight. The reaction system was concentrated by rotary evaporation to give compound 65-2, which was directly used in the next step. LC-MS [M+H]$^+$: 239.

Step (2): Preparation of (+/−)-isopropyl (1S,3S)-3-((6-(5-(hydroxymethyl)-1-methyl-1H-pyrazol-4-yl)-2-methylpyridin-3-yl)oxy)cyclohexane-1-carboxylate Compound 65-3 (3.56 g, 10 mmol), compound 65-2 (282 mg, 1.0 mmol) and tetrakis(triphenylphosphine)palladium (0) (1.16 g, 1.0 mmol) were dissolved in 1,4-dioxane (60 mL) under nitrogen atmosphere. The reaction system was added with a solution of potassium carbonate (3.04 g, 22 mmol) in water (12 mL), warmed to 80° C. and stirred overnight. The reaction system was diluted with water (100 mL) and extracted with ethyl acetate (80 mL×2). The organic phases were combined, washed with saturated brine (50 mL×2), dried over anhydrous sodium sulfate, filtered and concentrated, and the residue was purified by silica gel column chromatography to give compound 65-4 (5.2 g, 40% yield) in the form of a yellow oily liquid. LC-MS [M+H]+: 388.

Step (3): Preparation of (+/−)-isopropyl (1S,3S)-3-((2-methyl-6-(1-methyl-5-((((4-nitrophenoxy)carbonyl) oxy)methyl)-1H-pyrazol-4-yl)pyridin-3-yl)oxy) cyclohexane-1-carboxylate 65-5

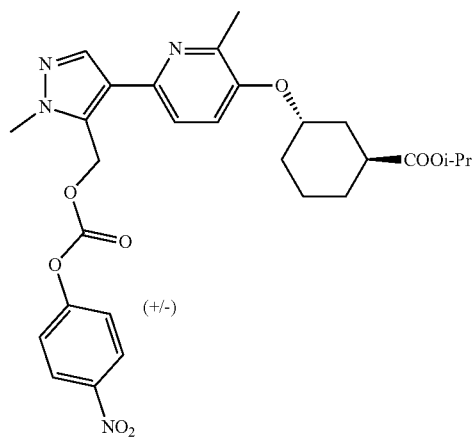

4-nitrophenyl chloroformate (3.61 g, 17.9 mmol) was dissolved in tetrahydrofuran (50 mL) under nitrogen atmosphere, and the reaction system was added dropwise with a solution of compound 65-4 (4.63 g, 12.0 mmol) and pyridine (2.88 g, 35.9 mmol) in tetrahydrofuran (30 mL) at 0° C. and stirred overnight at room temperature. The reaction system was diluted with ethyl acetate (150 mL) and washed with water (50 mL×2) and saturated brine (75 mL). The organic phase was dried over anhydrous sodium sulfate, filtered and concentrated, and the residue was purified by silica gel column chromatography to give compound 65-5 (2.35 g, 32% yield) in the form of a yellow oily liquid. LC-MS [M+H]+: 553.

Step (4): Preparation of (+/−)-(4-(5-(((1S,3S)-3-(isopropoxycarbonyl)cyclohexyl)oxy)-6-methylpyridin-2-yl)-1-methyl-1H-pyrazol-5-yl)methyl 8-oxa-3-azabicyclo[3.2.1]octane-3-carboxylate 65-7

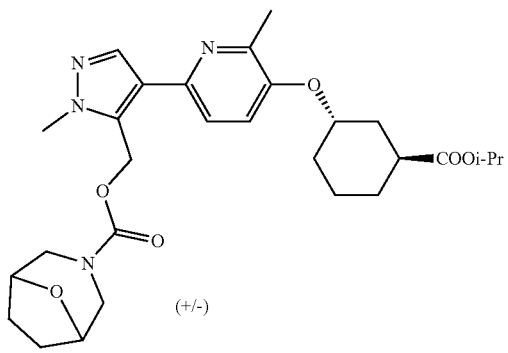

Compound 65-5 (140 mg, 0.25 mmol) and triethylamine (77 mg, 0.76 mmol) were dissolved in anhydrous tetrahydrofuran (10 mL) under nitrogen atmosphere, and the reaction system was added with 8-oxa-3-azabicyclo[3.2.1]octane hydrochloride (44 mg, 0.38 mmol), warmed to 60° C. and stirred overnight. The reaction system was diluted with ethyl acetate (50 mL) and washed with water (20 mL×2), aqueous NaOH solution (10 mL×5, 1 N) and saturated brine (10 mL). The organic phase was dried over anhydrous sodium sulfate, filtered and concentrated, and the residue was separated by silica gel column chromatography to give compound 65-7 (130 mg, 85% yield) in the form of a yellow oily liquid.

LC-MS [M+H]+: 527.

Step (5): Preparation of (+/−)-(1R,3R)-3-((6-(5-(((8-oxa-3-azabicyclo[3.2.1]octane-3-carbonyl)oxy) methyl)-1-methyl-1H-pyrazol-4-yl)-2-methylpyridin-3-yl)oxy)cyclohexane-1-carboxylic Acid

65

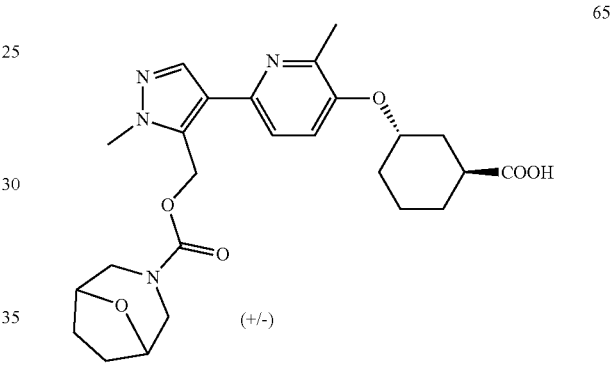

Compound 65-7 (150 mg, 0.28 mmol) was dissolved in tetrahydrofuran (6 mL)/methanol (2 mL), and the reaction system was added with lithium hydroxide solution (2 mL, 1 N), and stirred overnight at room temperature. The reaction system was diluted with water (15 mL), adjusted to pH 5 with diluted hydrochloric acid (1 N), and extracted with dichloromethane (15 mL×2). The organic phases were combined, washed with saturated brine (10 mL), dried over anhydrous sodium sulfate, filtered and concentrated, and the residue was separated by silica gel column chromatography and lyophilized to give compound 65 (110 mg, 71% yield) in the form of a yellow solid. LC-MS [M+H]+: 485.

$^1$H NMR (400 MHz, MeOD) δ 7.80 (s, 1H), 7.40 (s, 2H), 5.57 (q, J=13.9 Hz, 2H), 4.80-4.75 (m, 1H), 4.34-4.31 (m, 1H), 4.24-4.20 (m, 1H), 3.97 (s, 3H), 3.71-3.67 (m, 1H), 3.55-3.51 (m, 1H), 3.10-3.06 (m, 2H), 2.82-2.76 (m, 1H), 2.50 (s, 3H), 2.12-2.08 (m, 1H), 2.02-1.54 (m, 11H).

Example 66

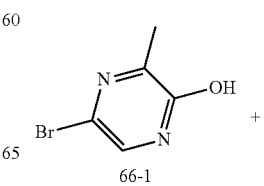

66-1

-continued

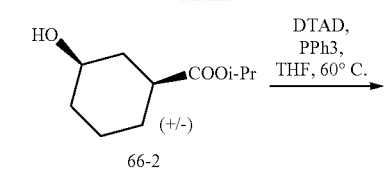
66-2

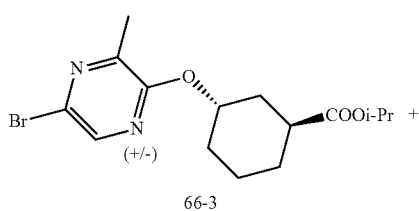
66-3

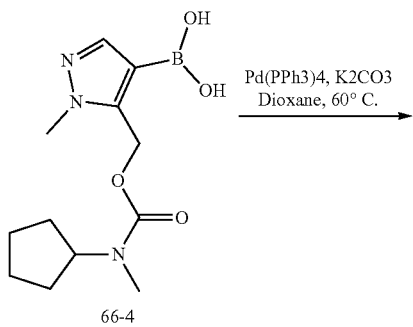
66-4

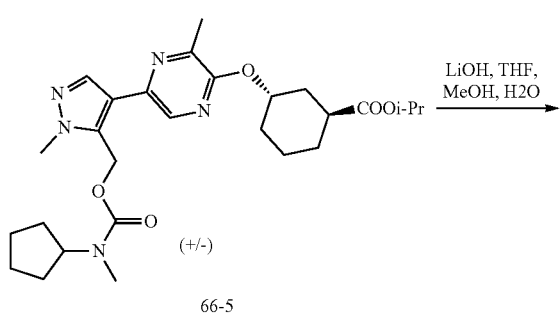
66-5

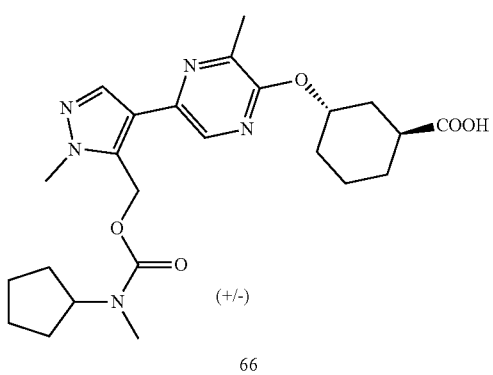
66

Step (1): Preparation of (+/−)-isopropyl (1S,3S)-3-((5-bromo-3-methylpyrazin-2-yl)oxy)cyclohexane-1-carboxylate

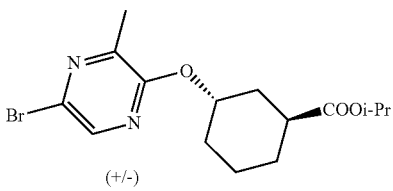
66-3

5-bromo-3-methylpyrazin-2-ol (3.78 g, 20 mmol), (+/−)-isopropyl 3-hydroxycyclohexane-1-carboxylate (5.58 g, 30 mmol) and PPh$_3$ (9.20 g, 35 mmol) were dissolved in THF (50 mL) under nitrogen atmosphere, and the reaction system was slowly added with a solution of DTAD (10.48 g, 40 mmol) in THF (50 mL), warmed to 60° C. and stirred overnight. The reaction system was directly concentrated, and the residue was purified by silica gel column chromatography to give compound 66-3 (4.7 g, 65% yield) in the form of a colorless liquid. LC-MS [M+H]$^+$: 357, 359.

Step (2): Preparation of (+/−)-isopropyl (1S,3S)-3-((5-(5-(((cyclopentyl(methyl)carbamoyl)oxy)methyl)-1-methyl-1H-pyrazol-4-yl)-3-methylpyrazin-2-yl)oxy)cyclohexane-1-carboxylate

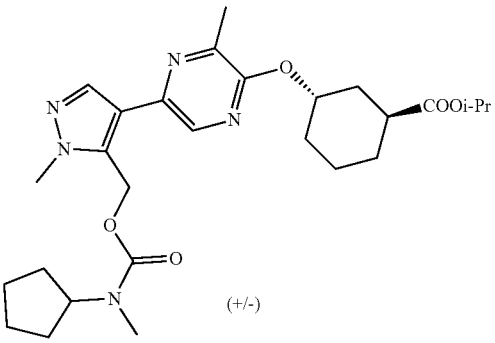
66-5

Compound 66-3 (200 mg, 0.56 mmol), (5-(((cyclopentyl(methyl)carbamoyl)oxy)methyl)-1-methyl-1H-pyrazol-4-yl)boronic acid (157 mg, 0.56 mmol) and tetrakis(triphenylphosphine)palladium(0) (65 mg, 0.056 mmol) were dissolved in 1,4-dioxane (15 mL) under nitrogen atmosphere, and the reaction system was added with potassium carbonate (170 mg, 1.23 mmol) and water (3 mL), warmed to 90° C. and reacted overnight. The reaction system was quenched with water (80 mL) to and extracted with ethyl acetate (30 mL×2). The organic phases were combined, washed with saturated brine (20 mL×2), dried over anhydrous sodium sulfate, filtered and concentrated, and the residue was purified by silica gel column chromatography to give compound 66-5 (160 mg, 53% yield) in the form of a yellow oil. LC-MS [M+H]$^+$: 514.

Step (3): Preparation of (+/−)-(1S,3S)-3-(5-(((cyclopentyl(methyl)carbamoyl)oxy)methyl)-1-methyl-1H-pyrazol-4-yl)-3-methylpyrazin-2-yl)oxy)cyclohexane-1-carboxylic Acid

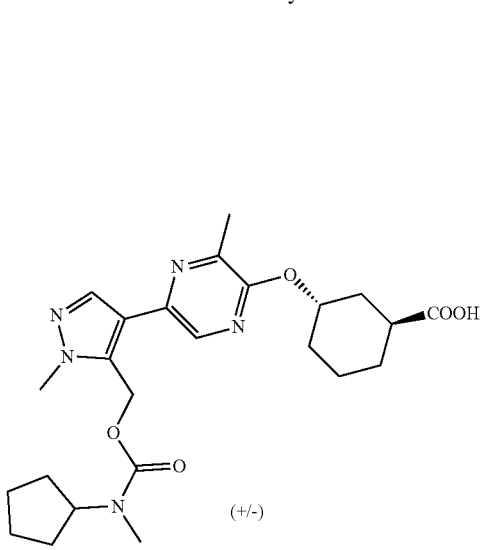

66

Compound 66-5 (160 mg, 0.31 mmol) was dissolved in tetrahydrofuran (6 mL)/methanol (2 mL), and the reaction system was added with lithium hydroxide solution (2 mL, 1 N), and stirred overnight at room temperature. The reaction system was diluted with water (15 mL), adjusted to pH 5 with diluted hydrochloric acid (1 N), extracted with dichloromethane (20 mL×2), washed with saturated brine (15 mL), dried over anhydrous sodium sulfate, filtered and concentrated, and the residue was separated by silica gel column chromatography to give compound 66 (120 mg, 59% yield) in the form of a yellow solid. LC-MS [M+H]$^+$: 472.

$^1$H NMR (400 MHz, MeOD) δ 8.22 (s, 1H), 7.87 (s, 1H), 5.55 (s, 2H), 5.49-5.45 (m, 1H), 4.60-4.15 (m, 1H), 3.99 (s, 3H), 2.79-2.75 (m, 4H), 2.51 (s, 3H), 2.27-2.22 (m, 1H), 2.03-1.53 (m, 15H).

Example 67

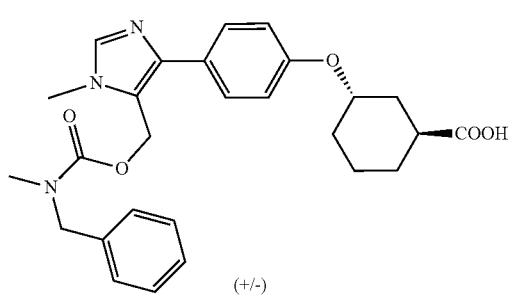

67

Refer to the method in Example 16, LC-MS [M+H]$^+$: 478.15.

Example 68

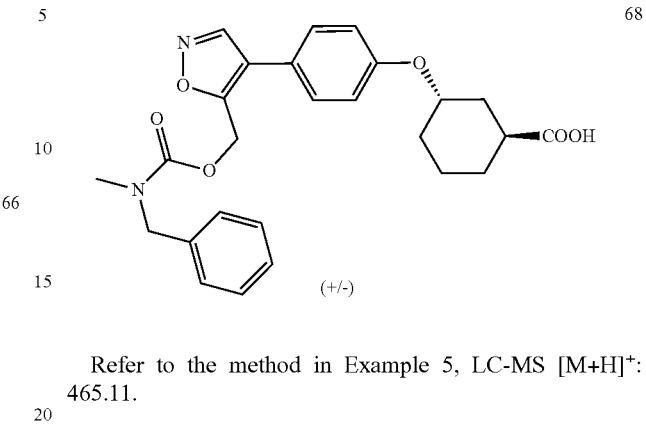

68

Refer to the method in Example 5, LC-MS [M+H]$^+$: 465.11.

Example 69

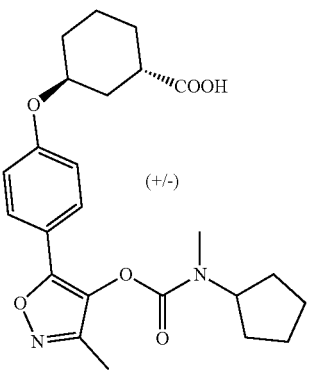

69

Refer to the method in Example 4, LC-MS [M+H]$^+$: 443.18.

Example 70

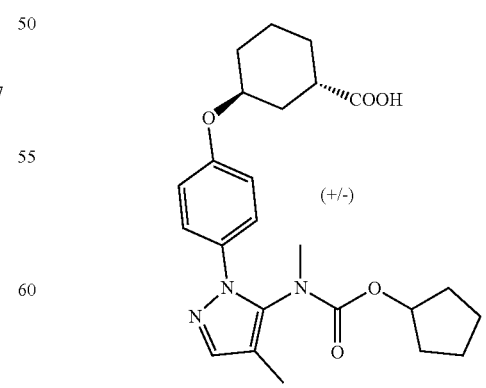

70

Refer to the method in Example 11, LC-MS [M+H]$^+$: 442.21.

Example 71
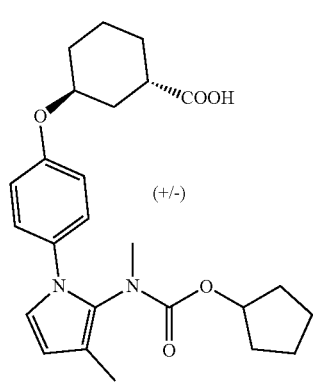
Refer to the method in Example 11, LC-MS [M+H]⁺: 441.18.
Example 72
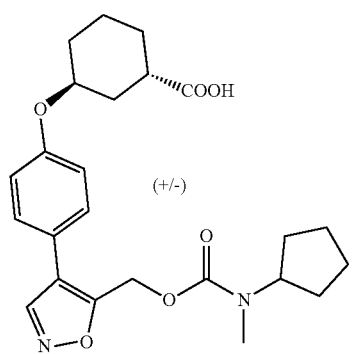
Refer to the method in Example 5, LC-MS [M+H]⁺: 443.18.
Example 73
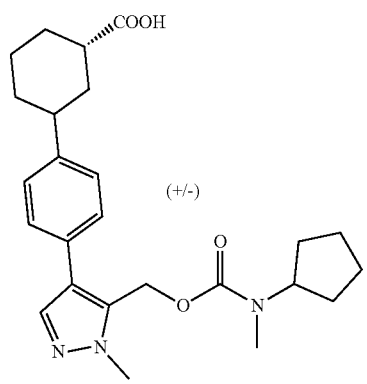
Refer to the method in Example 11, LC-MS [M+H]⁺: 440.17.
Example 74
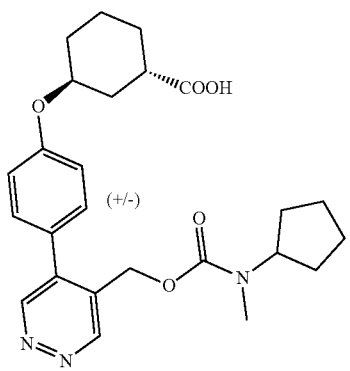
Refer to the method in Example 11, LC-MS [M+H]⁺: 454.21.
Example 75
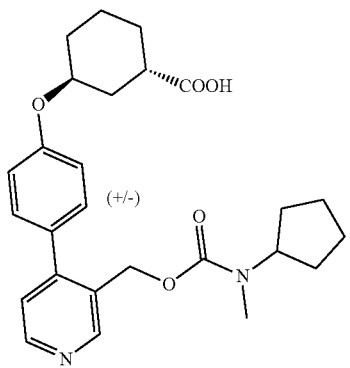
Refer to the method in Example 11, LC-MS [M+H]⁺: 453.16.
Example 76
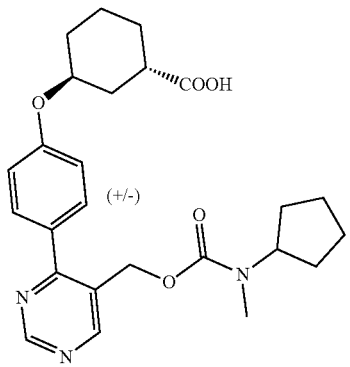
Refer to the method in Example 11, LC-MS [M+H]⁺: 454.24.

Example 77
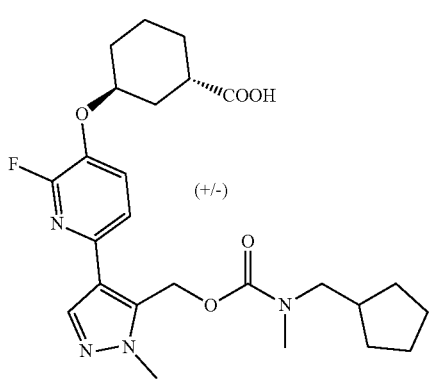
Refer to the method in Example 11, LC-MS [M+H]+: 489.13.
Example 78
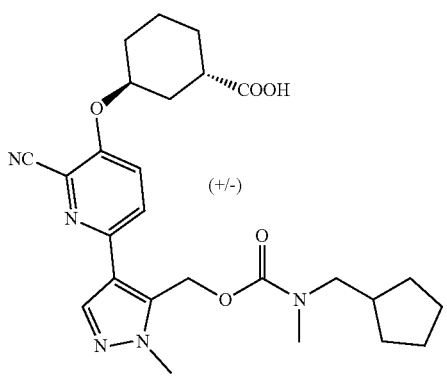
Refer to the method in Example 11, LC-MS [M+H]+: 496.21.
Example 79
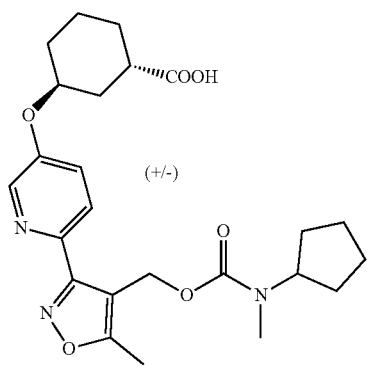
Refer to the method in Example 4, LC-MS [M+H]+: 458.21.
Example 80
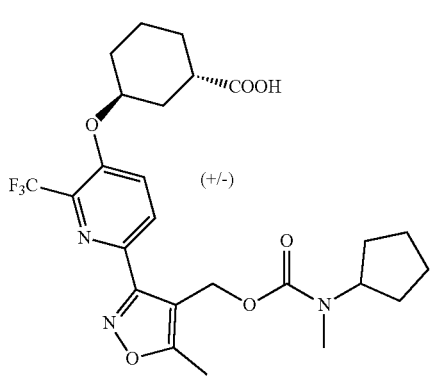
Refer to the method in Example 4, LC-MS [M+H]+: 526.14.
Example 81
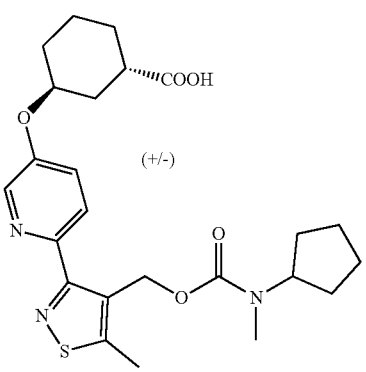
Refer to the method in Example 4, LC-MS [M+H]+: 474.21.
Example 82
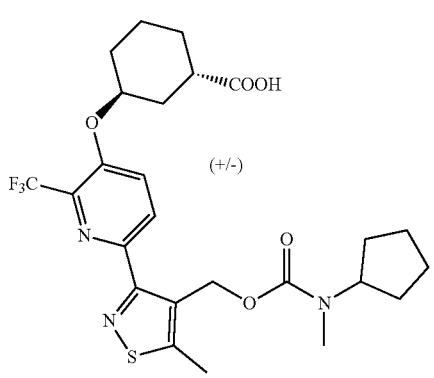
Refer to the method in Example 10, LC-MS [M+H]+: 542.57.

Example 83
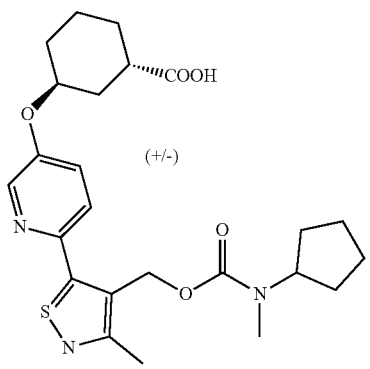
Refer to the method in Example 10, LC-MS [M+H]⁺: 474.20.
Example 84
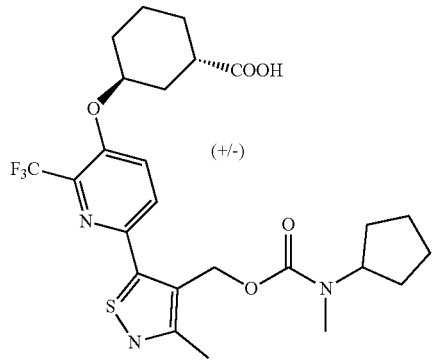
Refer to the method in Example 10, LC-MS [M+H]⁺: 542.18.
Example 85
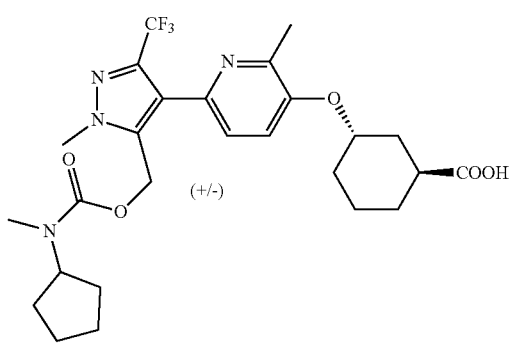
Refer to the method in Example 11, LC-MS [M+H]⁺: 539.23.
Example 86
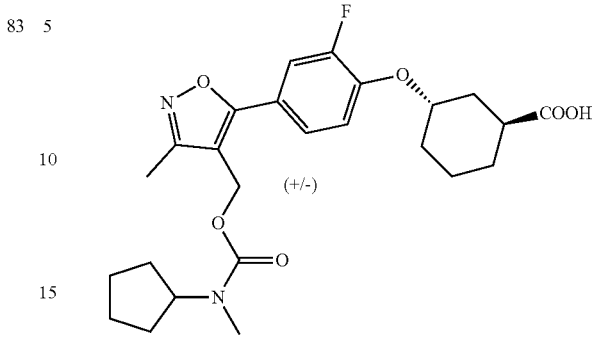
Refer to the method in Example 5, LC-MS [M+H]⁺: 475.21.
Example 87
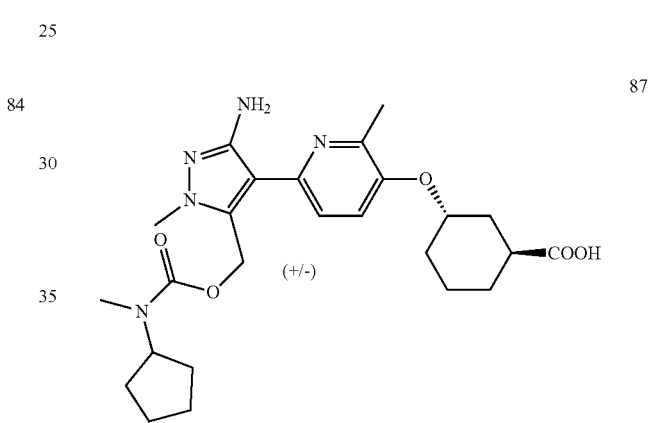
Refer to the method in Example 5, LC-MS [M+H]⁺: 486.21.
Example 88
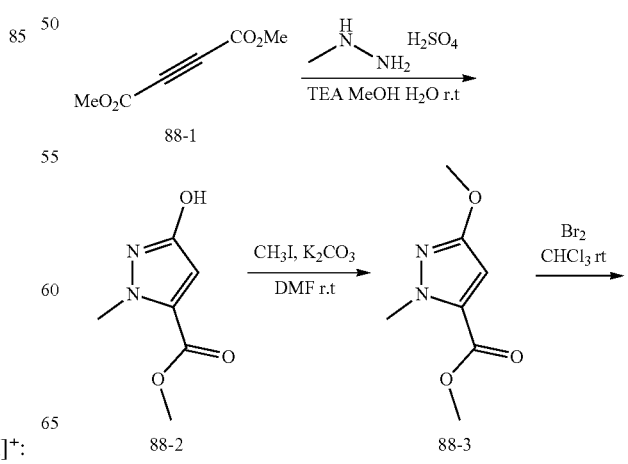

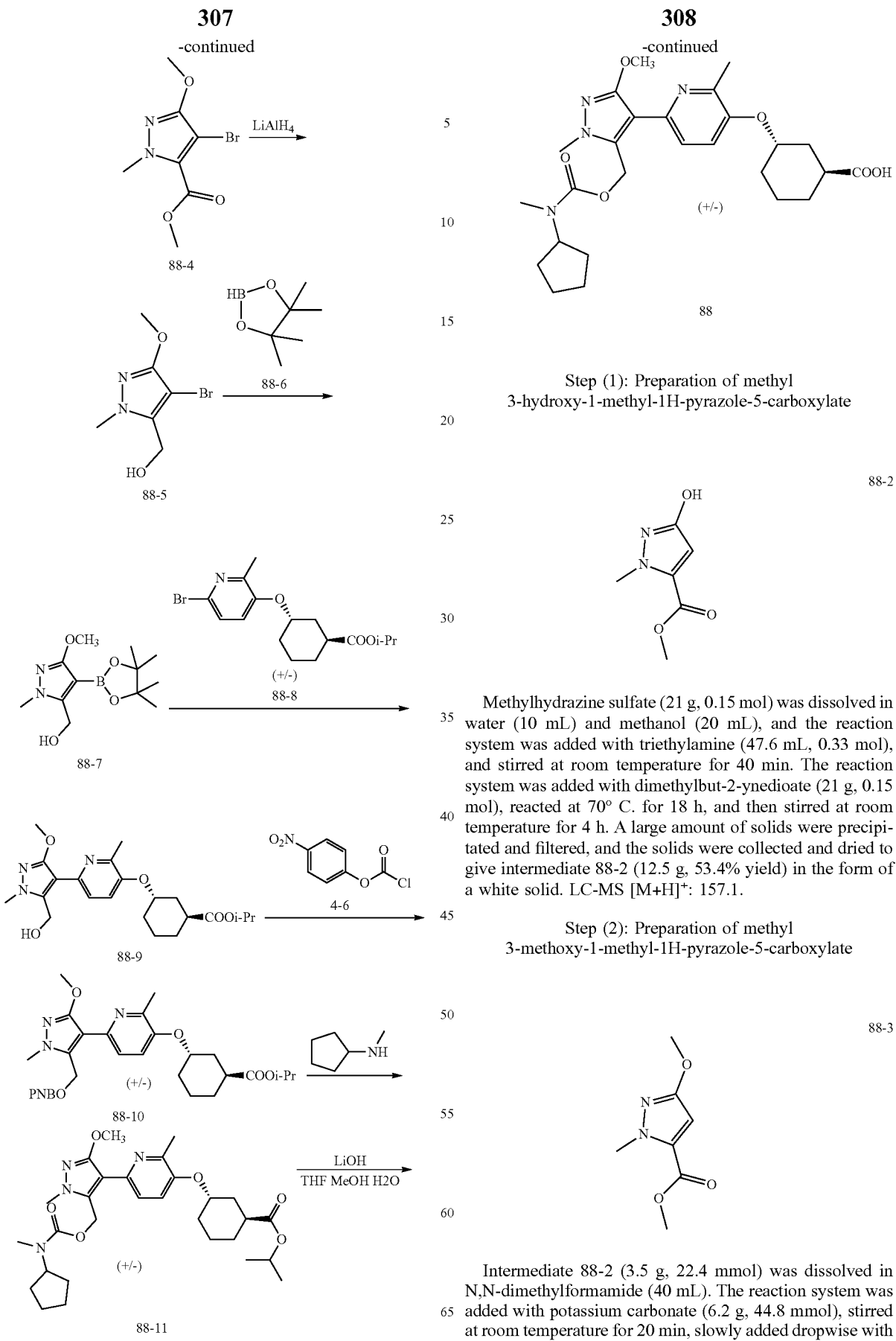

Step (1): Preparation of methyl 3-hydroxy-1-methyl-1H-pyrazole-5-carboxylate

Methylhydrazine sulfate (21 g, 0.15 mol) was dissolved in water (10 mL) and methanol (20 mL), and the reaction system was added with triethylamine (47.6 mL, 0.33 mol), and stirred at room temperature for 40 min. The reaction system was added with dimethylbut-2-ynedioate (21 g, 0.15 mol), reacted at 70° C. for 18 h, and then stirred at room temperature for 4 h. A large amount of solids were precipitated and filtered, and the solids were collected and dried to give intermediate 88-2 (12.5 g, 53.4% yield) in the form of a white solid. LC-MS [M+H]$^+$: 157.1.

Step (2): Preparation of methyl 3-methoxy-1-methyl-1H-pyrazole-5-carboxylate

Intermediate 88-2 (3.5 g, 22.4 mmol) was dissolved in N,N-dimethylformamide (40 mL). The reaction system was added with potassium carbonate (6.2 g, 44.8 mmol), stirred at room temperature for 20 min, slowly added dropwise with methyl iodide (2.1 mL, 33.6 mmol), and reacted overnight at room temperature. Then the reaction system was added with water (100 mL) to quench the reaction and extracted with ethyl acetate (100 mL×2). The organic phases were combined, washed with saturated brine (100 mL), dried over anhydrous sodium sulfate, filtered and concentrated, and the residue was separated by column chromatography to give intermediate 88-3 (2.8 g, 73.6% yield) in the form of a white solid. LC-MS [M+H]$^+$: 170.9.

Step (3): Preparation of methyl 4-bromo-3-methoxy-1-methyl-1H-pyrazole-5-carboxylate

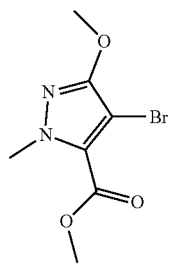

88-4

Intermediate 88-3 (2.8 g, 16.5 mmol) was dissolved in chloroform (30 mL), and the reaction system was slowly added dropwise with bromine (0.94 mL, 18.1 mmol) at room temperature, and reacted overnight at room temperature. After the reaction was completed, the reaction system was quenched with sodium thiosulfate solution (5 mL, 0.65 N), diluted with water (50 mL), and extracted with dichloromethane (50 mL×2). The organic phases were combined, washed with saturated brine (60 mL), dried over anhydrous sodium sulfate, filtered and concentrated, and the residue was separated by column chromatography (PE/EA=9/1) to give intermediate 88-4 (3.4 g, 83% yield) in the form of a white solid. LC-MS [M+H]$^+$: 249.1.

Step (4): Preparation of (4-bromo-3-methoxy-1-methyl-1H-pyrazol-5-yl)methanol

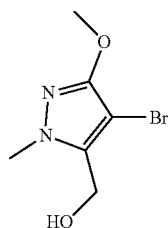

88-5

Intermediate 88-4 (3.4 g, 13.7 mmol) was dissolved in tetrahydrofuran (50 mL), and the reaction system was cooled to 0° C. in an ice water bath, added with lithium aluminum tetrahydrogen (0.62 g, 16.4 mmol) in portions, and reacted at 0° C. for 40 min. After the reaction was completed, the reaction system was added with sodium sulfate decahydrate to quench the reaction and filtered, and the filter cake was washed with ethyl acetate, concentrated and filtered to give intermediate 88-5 (2.0 g, 66% yield) in the form of a yellow oil. LC-MS [M+H]$^+$=221.1.

Step (5): Preparation of (3-methoxy-1-methyl-4-(4,4,5,5-tetramethyl-1,3,2-dioxaborolan-2-yl)-1H-pyrazol-5-yl)methanol

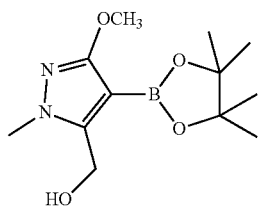

88-7

Intermediate 88-5 (2.0 g, 9.1 mmol) was dissolved in anhydrous dioxane (40 mL). The reaction system was added with palladium acetate (102 mg, 0.46 mmol) and 2-bicyclohexylphosphine-2',6'-dimeoxybiphenyl (373 mg, 0.91 mmol), then added with triethylamine (2.8 g, 27.3 mmol) and pinacolborane (7.0 g, 54.6 mmol) under nitrogen atmosphere, and reacted at 75° C. overnight. After the reaction was completed, the reaction system was filtered, added with water (100 mL), and extracted with ethyl acetate (80 mL×3). The organic phases were combined, washed with saturated brine (100 mL), dried over anhydrous sodium sulfate, filtered and concentrated to give intermediate 88-7 (2.5 g, 30% purity, crude) in the form of a brown solid. LC-MS [M+H]$^+$=269.1.

Step (6): Preparation of (+/−)-isopropyl (1S,3S)-3-((6-(5-(hydroxymethyl)-3-methoxy-1-methyl-1H-pyrazol-4-yl)-2-methylpyridin-3-yl)oxy)cyclohexane-1-carboxylate

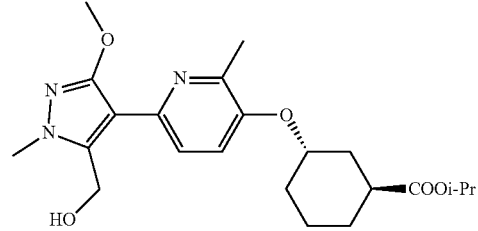

88-9

Intermediate 88-7 (2.5 g, crude) was dissolved in dioxane (20 mL) and water (4 mL), and the reaction system was added with (+/−)-isopropyl (1S,3S)-3-((6-bromo-2-methylpyridin-3-yl)oxy) cyclohexane-1-carboxylate (1.6 g, 4.5 mmol), potassium carbonate (1.2 g, 9.0 mmol) and tetrakis(triphenylphosphine)palladium(0) (520 mg, 0.45 mmol), and stirred at 90° C. overnight under nitrogen atmosphere. The reaction system was cooled to room temperature, diluted with water (40 mL) and extracted with ethyl acetate (30 mL×3). The organic phases were combined, washed with saturated brine (50 mL), dried over anhydrous sodium sulfate, filtered and concentrated, and the residue was separated by silica gel column chromatography to give intermediate 88-9 (500 mg, 80% yield) in the form of a brown oil. LC-MS [M+H]$^+$: 417.9.

Step (7): Preparation of (+/−)-(4-(5-(((1S,3S)-3-(isopropoxycarbonyl)cyclohexyl)oxy)-6-methylpyridin-2-yl)-3-methoxy-1-methyl-1H-pyrazol-5-yl)methyl-4-nitrobenzoate

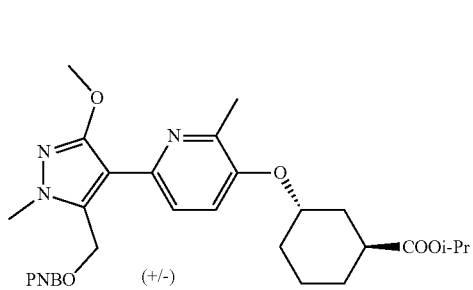

88-10

4-nitrophenyl chloroformate (289 mg, 1.44 mmol) and pyridine (151 mg, 1.92 mmol) were dissolved in tetrahydrofuran (10 mL) under nitrogen atmosphere, and the reaction system was cooled to 0° C., slowly added with a solution of compound 88-9 (500 mg, 0.96 mmol) in tetrahydrofuran (1 mL), warmed to room temperature and stirred overnight. The reaction system was washed with saturated brine (5 mL), dried over anhydrous sodium sulfate, filtered and concentrated to give intermediate 88-10 (600 mg, crude) in the form of a yellow solid. LC-MS [M+H]⁺: 567.2.

Step (8): Preparation of (+/−)-(3-(5-bromo-6-methylpyridin-2-yl)-5-methylisothiazol-4-yl)methylcyclopentyl (methyl)carbamate

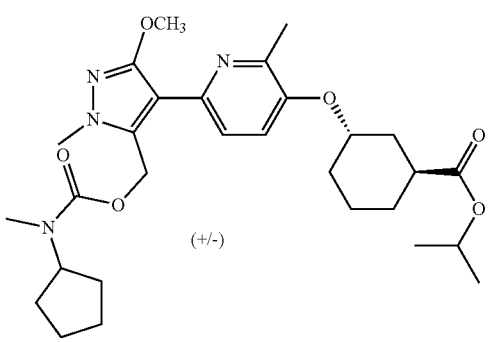

88-11

Intermediate 88-10 (600 mg) was dissolved in anhydrous tetrahydrofuran (10 mL), and the reaction system was added with triethylamine (384 mg, 3.8 mmol), then added with N-methylcyclopentylamine hydrochloride (259 mg, 1.9 mmol), and stirred overnight at room temperature under nitrogen atmosphere. The reaction system was diluted with water (15 mL) and extracted with dichloromethane (30 mL×2). The organic phases were combined, washed with saturated brine (20 mL×2), dried over anhydrous sodium sulfate, filtered and concentrated, and the residue was separated by silica gel column chromatography to give intermediate 88-11 (160 mg, 31% yield over two steps) in the form of a pale yellow oil. LC-MS [M+H]⁺: 542.9.

Step (9): Preparation of (+/−)-(1S,3S)-3-((6-(5-(((cyclopentyl(methyl)carbamoyl)oxy)methyl)-3-methoxy-1-methyl-1H-pyrazol-4-yl)-2-methylpyridin-3-yl)oxy)cyclohexane-1-carboxylic Acid

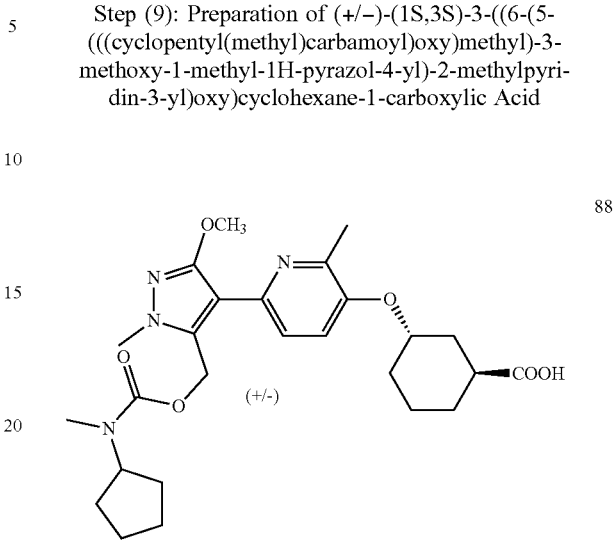

88

Intermediate 88-11 (160 mg, 0.3 mmol) and lithium hydroxide (50 mg, 1.2 mmol) were dissolved in tetrahydrofuran (3 mL), methanol (1 mL) and water (1 mL), and the reaction system was reacted at room temperature for 10 h. The reaction system was concentrated under reduced pressure, and the residue was added with water (10 mL) and extracted with ether (5 mL×3). The aqueous phase was retained, adjusted to pH 4 with diluted hydrochloric acid (1 N), and extracted with dichloromethane (5 mL×3). The organic phases were combined, dried over anhydrous sodium sulfate, filtered and concentrated, and the residue was separated by preparative HPLC to give compound 88 (90 mg, 60% yield) in the form of a white solid. LC-MS [M+H]⁺: 500.8.

$^1$H NMR (400 MHz, MeOD) δ 7.50 (d, J=8.6 Hz, 1H), 7.35 (d, J=8.7 Hz, 1H), 5.49 (s, 2H), 4.78-4.73 (m, 1H), 4.60-4.20 (m, 1H), 3.97 (s, 3H), 3.83 (s, 3H), 2.84-2.67 (m, 4H), 2.46 (s, 3H), 2.14-2.07 (m, 1H), 2.00-1.45 (m, 15H).

Example 89

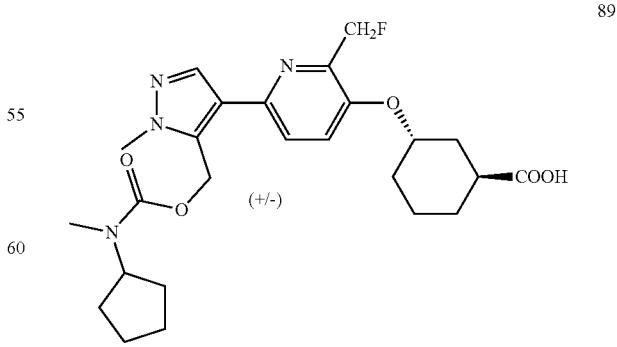

89

Refer to the method in Example 16, LC-MS [M+H]⁺: 489.21.

Example 90
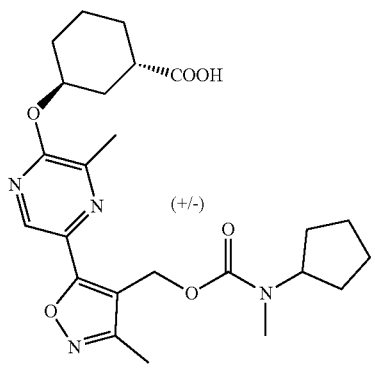
Refer to the method in Example 5, LC-MS [M+H]⁺: 473.21.
Example 91
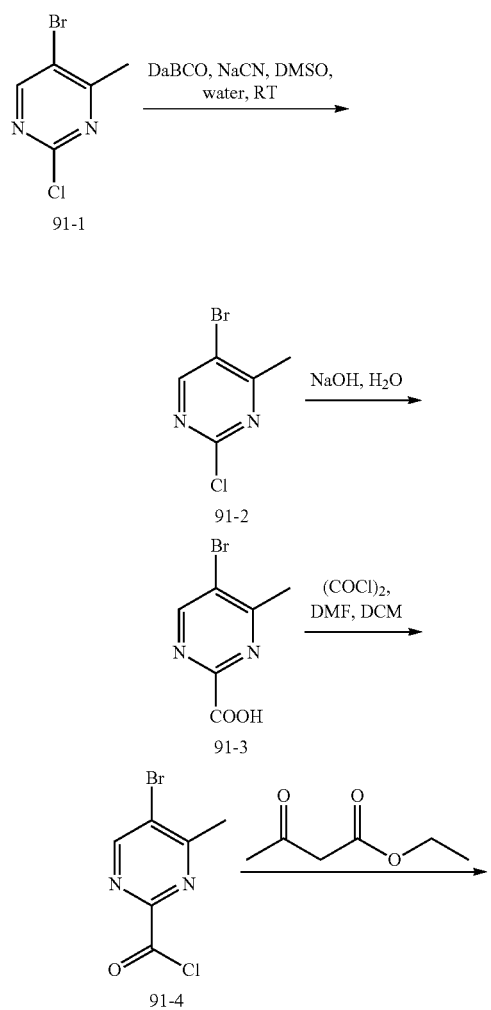
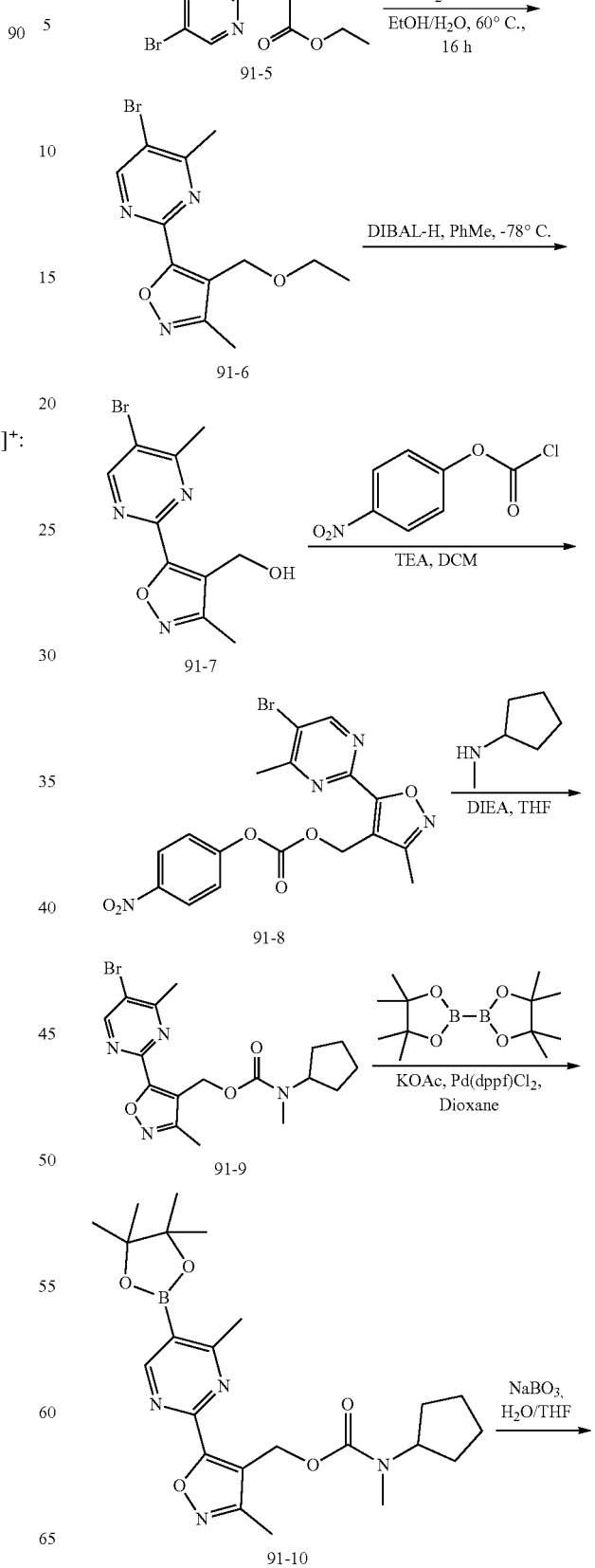

-continued

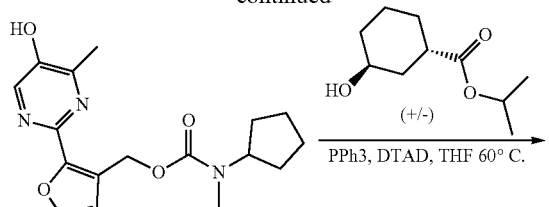

91-11

PPh3, DTAD, THF 60° C.

concentrated to give a crude product, and the crude product was purified by silica gel column chromatography to give intermediate 91-2 (3.0 g, 99% yield) in the form of a yellow solid. MS [M+H]$^+$=198.1.

Step (2): Preparation of 5-bromo-4-methylpyrimidine-2-carboxylic Acid

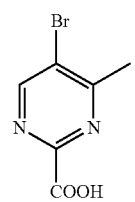

91-3

Sodium hydroxide (270 mg, 6.76 mmol) was added to a suspension of intermediate 91-2 (670 mg, 3.38 mmol) and water (20 mL). The reaction system was warmed to 60° C. and stirred overnight. The reaction system was cooled to room temperature and adjusted to pH 4 with concentrated hydrochloric acid. Water was removed by distillation under reduced pressure, and the residue was resuspended in methanol:ethyl acetate (50 mL, 1:1), and filtered, and the filtrate was concentrated to give intermediate 91-3 (3.6 g, 99% yield) in the form of a yellow solid. MS [M+H]$^+$: 216.8.

91-12

LiOH, MeOH, THF, H$_2$O

Step (3): Preparation of 5-bromo-4-methylpyrimidine-2-carbonyl Chloride

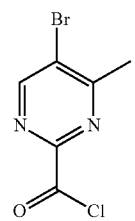

91-4

91

Oxalyl chloride (1.52 g, 12 mmol) and 1 drop of DMF were added to a solution of intermediate 91-3 (2.5 g, 10 mmol) in DCM (45 mL) while stirring at room temperature under nitrogen atmosphere. The reaction system was stirred at room temperature for 1 h, then concentrated, added with anhydrous toluene (100 mL), then concentrated again to give intermediate 91-4 (2.7 g, 99% yield) in the form of a yellow solid. MS [M+H]$^+$=230.8.

Step (1): Preparation of 5-bromo-4-methylpyrimidine-2-carbonitrile

Step (4): Preparation of ethyl 2-(5-bromo-4-methylpyrimidin-2-carbonyl)-3-oxobutanoate

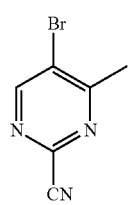

91-2

NaCN (1.2 g, 24 mmol) was added to a solution of triethylenediamine (0.22 g, 2.0 mmol) in DMSO/water (2:1, 45 mL), and then the reaction system was added with a solution of 5-bromo-2-chloro-4-methylpyrimidine (5 g, 20 mmol) in DMSO (40 mL), and stirred overnight at room temperature. The reaction system was diluted with water (200 mL) and extracted with ethyl acetate (100 mL×5). The organic phases were combined, washed with saturated brine (100 mL), dried over anhydrous sodium sulfate, filtered and

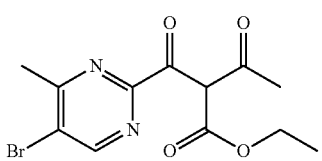

91-5

T-BuOK (1.1 g, 10 mmol) was added in portions to a solution of ethyl 3-oxobutyrate (2.6 g, 20 mmol) in THF (80 mL) while stirring at room temperature under nitrogen atmosphere, and the reaction system was stirred for 30 min, then added with intermediate 91-4 (2.7 g, 10 mmol), and then stirred at room temperature for 1.5 h. The reaction system was diluted with water (200 mL) and extracted with ethyl acetate (100 mL×3). The organic phases were combined, washed with saturated brine (100 mL), dried over anhydrous sodium sulfate, filtered and concentrated to give intermediate 91-5 (3.8 g, 99% yield) in the form of a black oil. MS [M+H]$^+$=328.8.

Step (5): Preparation of ethyl 5-(5-bromo-4-methylpyrimidin-2-yl)-3-methylisoxazole-4-carboxylate

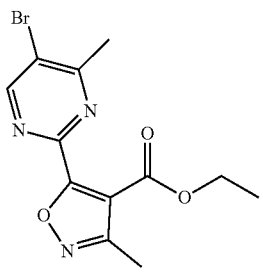

91-6

A solution of hydroxylamine hydrochloride (1.4 g, 20 mmol) in water (10 mL) was added to a solution of intermediate 91-5 (3.8 g, 10 mmol) in EtOH (50 mL), and the reaction system was warmed to 60° C. and stirred overnight. The reaction system was concentrated under reduced pressure to remove ethanol, added with water (20 mL) and extracted with ethyl acetate (50 mL×2). The organic phases were combined, washed with saturated brine (50 mL), dried over anhydrous sodium sulfate, filtered and concentrated to give a crude product, and the crude product was purified by silica gel column chromatography to give intermediate 91-6 (0.54 g, 15% yield) in the form of a green oil. MS [M+H]$^+$=327.9.

Step (6): Preparation of (5-(5-bromo-4-methylpyrimidin-2-yl)-3-methylisoxazol-4-yl)methanol

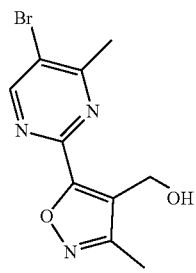

91-7

Diisobutylaluminum hydride (1 M, 3.18 mL) was added dropwise to a solution of intermediate 91-6 (520 mg, 1.59 mmol) in toluene (20 mL) at −78° C. under nitrogen atmosphere in a dry ice acetone bath, and the reaction system was reacted at −78° C. for 2 h. The reaction system was added with saturated aqueous ammonium chloride solution (10 mL) to quench the reaction, diluted with water (50 mL) and extracted with ethyl acetate (30 mL×3). The organic phases were combined, washed with saturated brine (40 mL), dried over anhydrous sodium sulfate, filtered and concentrated to give a crude product, and the crude product was purified by silica gel column chromatography to give intermediate 91-7 (375 mg, 82% yield) in the form of a white solid. MS [M+H]$^+$=286.0.

Step (7): Preparation of (5-(5-bromo-4-methylpyrimidin-2-yl)-3-methylisoxazol-4-yl)methyl(4-nitrophenyl) carbonate

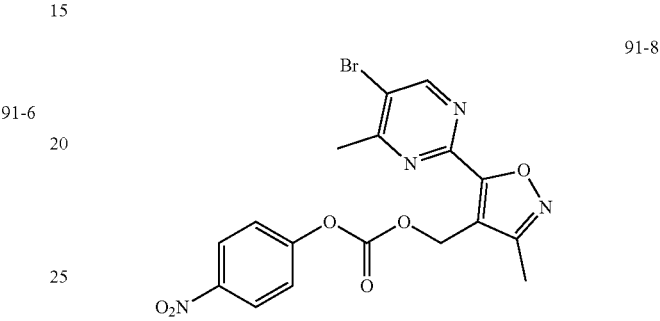

91-8

4-nitrophenyl chloroformate (851 mg, 4.2 mmol) was added to a solution of intermediate 91-7 (300 mg, 1.01 mmol) and triethylamine (534 mg, 5.28 mmol) in dichloromethane (20 mL) while stirring at room temperature under nitrogen atmosphere, and the reaction system was stirred overnight at room temperature. The reaction system was diluted with water (50 mL) and extracted with dichloromethane (30 mL×2). The organic phases were combined, washed with saturated brine, dried over anhydrous sodium sulfate, filtered and concentrated to give a crude product, and the crude product was purified by silica gel column chromatography to give intermediate 91-8 (450 mg, 90% yield) in the form of a yellow solid. MS [M+H]$^+$=451.0.

Step (8): Preparation of (5-(5-bromo-4-methylpyrimidin-2-yl)-3-methylisoxazol-4-yl)methylcyclopentyl (methyl)carbamate

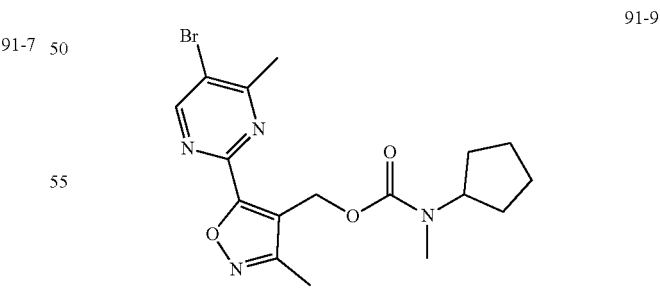

91-9

N-methylcyclopentylamine hydrochloride (260 mg, 1.914 mmol) was added to a solution of intermediate 91-8 (430 mg, 0.957 mmol) and DIEA (494 mg, 3.828 mmol) in tetrahydrofuran (15 mL) while stirring at room temperature, and the reaction system was stirred overnight at room temperature. The reaction system was diluted with water (20 mL) and extracted with ethyl acetate (10 mL×3). The organic phases were combined, washed with saturated brine, dried over anhydrous sodium sulfate, filtered and concentrated to give a crude product, and the crude product was purified by column chromatography to give intermediate 91-9 (420 mg, 86% yield) in the form of a yellow solid. MS [M+H]$^+$=409.1.

Step (9): Preparation of (3-methyl-5-(4-methyl-5-(4,4,5,5-tetramethyl-1,3,2-dioxaborolan-2-yl) pyrimidin-2-yl)isoxazol-4-yl)methylcyclopentyl(methyl) carbamic Acid

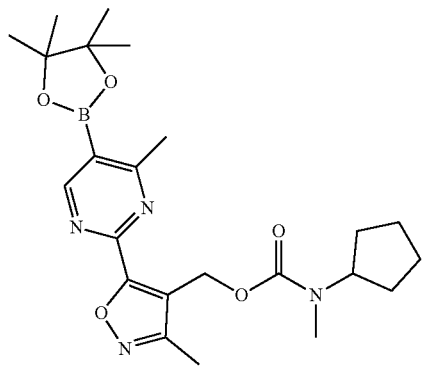

91-10

[1,1'-bis(diphenylphosphino)ferrocene]dichloropalladium(II) (74.37 mg, 0.101 mmol) was added to a solution of intermediate 91-9 (416 mg, 1.016 mmol), 4,4,5,5-tetramethyl-2-(4,4,5,5-tetramethyl-1,3,2-dioxaborolan-2-yl)-1,3,2-dioxaborolane (516.2 mg, 2.032 mmol) and potassium acetate (399 mg, 4.065 mmol) in anhydrous dioxane (20 mL) while stirring at room temperature under nitrogen atmosphere, and the reaction system was stirred at 80° C. for 3 h. The reaction system was filtered, and the filtrate was concentrated to give intermediate 91-10 (500 mg) in the form of a black oil. MS [M+H]$^+$=375.2.

Step (10): Preparation of (5-(5-hydroxy-4-methylpyrimidin-2-yl)-3-methylisoxazol-4-yl)methylcyclopentyl (methyl)carbamate

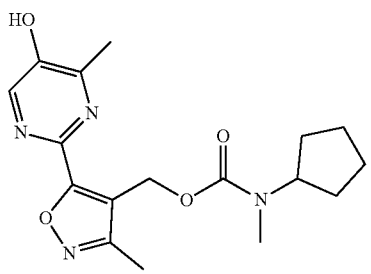

91-11

Sodium perborate tetrahydrate (425 mg, 2.76 mmol) was added to a mixed solution of intermediate 91-10 (420 mg, 0.92 mmol) in tetrahydrofuran and water (1:1, 24 mL) while stirring at room temperature, and the reaction system was stirred overnight at room temperature. The reaction system was quenched with saturated ammonium chloride (10 mL) and extracted with ethyl acetate (20 mL×2). The organic phases were combined, washed with saturated brine, dried over anhydrous sodium sulfate, filtered and concentrated to give a crude product, and the crude product was purified by column chromatography to give intermediate 91-11 (110 mg, 34% yield) in the form of a white solid. MS [M+H]$^+$=347.1.

Step (11): Preparation of (+/−)-isopropyl (1S,3S)-3-((2-(4-(((cyclopentyl(methyl)carbamoyl)oxy)methyl)-3-methylisoxazol-5-yl)-4-methylpyrimidin-5-yl)oxy)cyclohexane-1-carboxylate

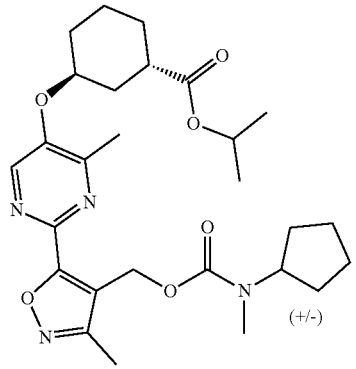

91-12

A solution of DTAD (266 mg, 1.154 mmol) in THF (5 mL) was added dropwise to a solution of intermediate 91-11 (100 mg, 0.288 mmol), (+/−)-isopropyl (1S,3S)-3-hydroxycyclohexane-1-carboxylate (322 mg, 1.732 mmol) and triphenylphosphine (302 mg, 1.154 mmol) in THF (25 mL) while stirring at room temperature under nitrogen atmosphere, and the reaction system was warmed to 60° C. and stirred overnight. The reaction system was directly concentrated under reduced pressure and purified by column chromatography to give intermediate 91-12 (160 mg, 97% yield) in the form of a white solid. MS [M+H]$^+$=515.1.

Step (12): Preparation of (+/−)-(1S,3S)-3-((2-(4-(((cyclopentyl(methyl)carbamoyl)oxy)methyl)-3-methylisoxazol-5-yl)-4-methylpyrimidin-5-yl)ox) cyclohexane-1-carboxylic Acid

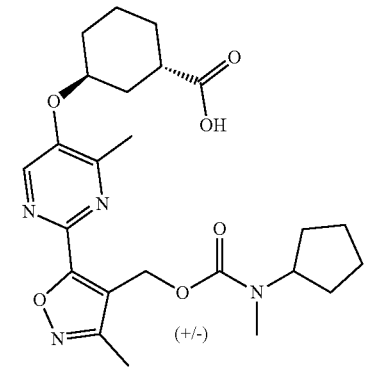

91

Lithium hydroxide solution (1 N, 1 mL) was added to a solution of intermediate 91-12 (160 mg, 0.33 mmol) in methanol and tetrahydrofuran (1:1, 2 mL), and the reaction system was stirred overnight at room temperature. The reaction system was adjusted to pH 6 with diluted hydrochloric acid, diluted with water (10 mL) and extracted with dichloromethane (10 mL×3). The organic phases were combined, washed with saturated brine, dried over anhydrous sodium sulfate, filtered and concentrated to give a crude product, and the crude product was purified by column chromatography to give compound 91 (120 mg, 82% yield) in the form of a white solid. MS [M+H]$^+$=473.2.

$^1$H NMR (400 MHz, CDCl$_3$) δ 8.47 (s, 1H), 5.52 (s, 2H), 4.90-4.85 (m, 1H), 4.62-4.25 (m, 1H), 2.94-2.88 (m, 1H), 2.73 (s, 3H), 2.55 (s, 3H), 2.40 (s, 3H), 2.17-2.10 (m, 1H), 2.08-2.01 (m, 1H), 1.97-1.88 (m, 2H), 1.84-1.73 (m, 4H), 1.71-1.59 (m, 4H), 1.58-1.45 (m, 4H).

Example 92

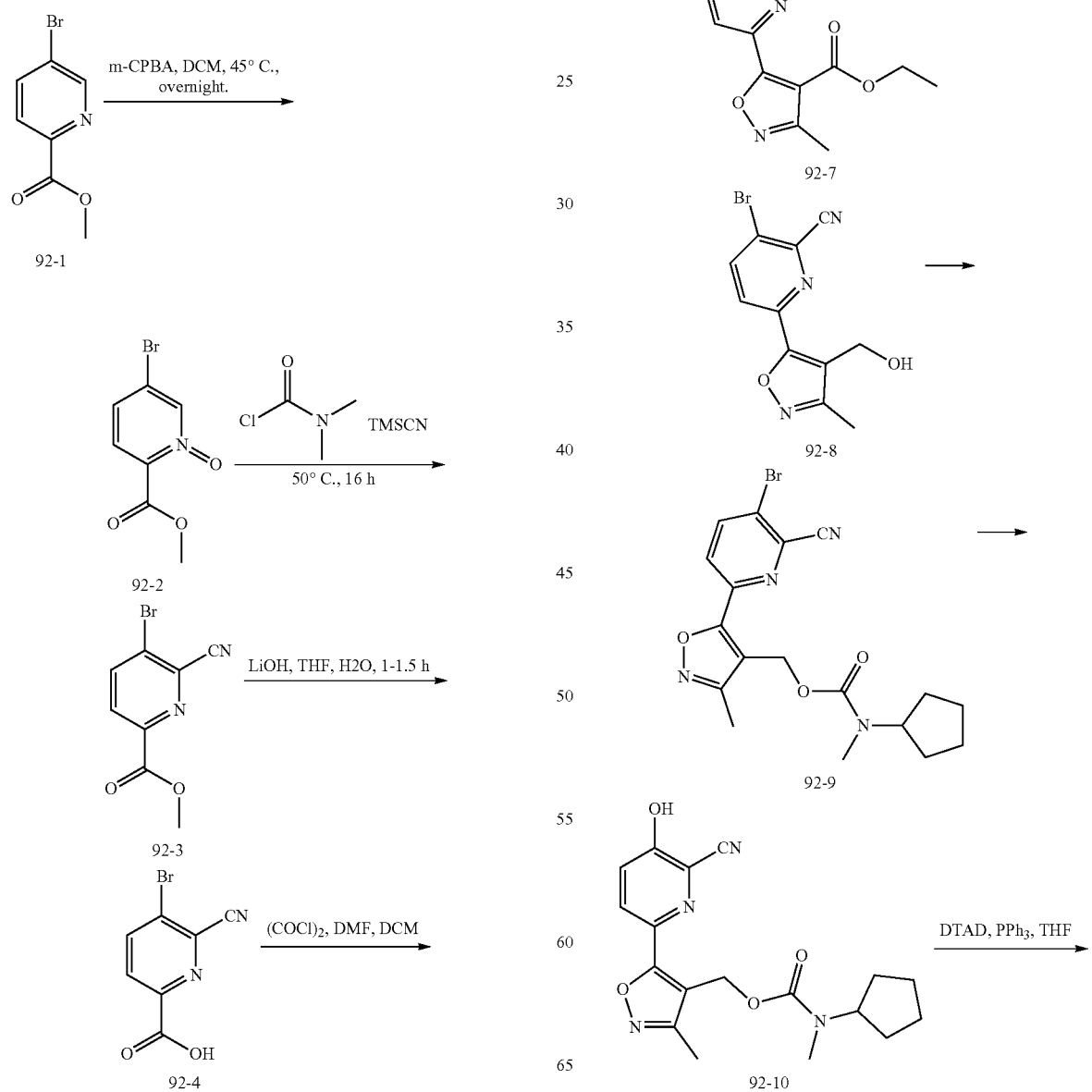

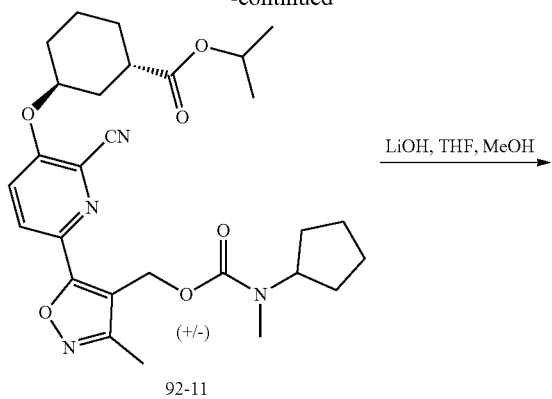

92-11

↓ LiOH, THF, MeOH

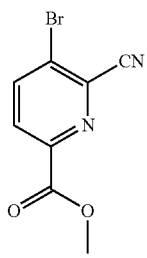

92

Step (1): Preparation of 5-bromo-2-(methoxycarbonyl)pyridine-1-oxide 92-2

Methyl 5-bromopicolinate (20 g, 0.09 mol) was dissolved in anhydrous dichloromethane (200 mL), and the reaction system was cooled to 0° C., added in portions with m-chloroperoxybenzoic acid (47 g, 0.27 mol), and reacted overnight at 45° C. The reaction system was concentrated by rotary evaporation to give a crude product, and the crude product was dissolved in ethyl acetate (50 mL). The reaction system was adjusted to pH 8 with saturated sodium carbonate solution and extracted with ethyl acetate (100 mL×2). The organic phase was washed with saturated brine (200 mL), dried over anhydrous sodium sulfate, filtered and concentrated to give intermediate 92-2 (30 g, crude). LC-MS [M+H]⁺: 232.0.

Step (2): Preparation of methyl 5-bromo-6-cyanopicolinate

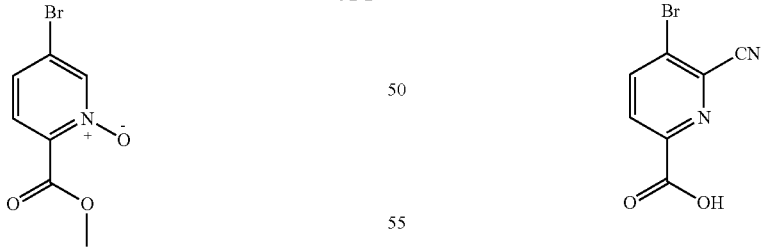

92-3

Intermediate 92-2 (30 g, 0.13 mol) was dissolved in dimethylaminomethyl chloride (125 mL), and the reaction system was added with TMSCN (80 mL) and reacted overnight at 50° C. The reaction system was cooled to 0° C., adjusted to pH 8 with sodium carbonate, and extracted with ethyl acetate (300 mL×2). The organic phases were combined, washed with saturated brine (500 mL), dried over anhydrous sodium sulfate, filtered and concentrated, and the residue was separated by column chromatography to give intermediate 92-3 (8 g) in the form of a yellow oily liquid. LC-MS [M+H]⁺: 243.

Step (3): Preparation of 5-bromo-6-cyanopicolinic Acid 92-4

Intermediate 92-3 (8.0 g, 0.03 mol) was dissolved in tetrahydrofuran (30 mL) and water (10 mL), and the reaction system was added with lithium hydroxide (1.26 g, 0.03 mol) and reacted at room temperature for 1.5 h. Then the reaction system was adjusted to pH 5-6 with diluted hydrochloric acid and extracted with ethyl acetate (100 mL×2). The organic phases were combined, washed with saturated brine (100 mL), dried over anhydrous sodium sulfate, filtered and concentrated, and the residue was separated by column chromatography to give intermediate 92-4 (4.0 g, 59.0% yield) in the form of a white solid. LC-MS [M+H]⁺: 228.0.

Step (4): Preparation of 5-bromo-6-cyanopyridin-2-formyl Chloride

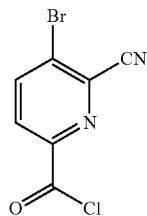

92-5

Intermediate 92-4 (4.0 g, 0.018 mol) was dissolved in anhydrous dichloromethane (40 mL), and the reaction system was added dropwise with oxalyl chloride (2.7 g, 0.021 mol), and reacted at room temperature for 1 h. After the reaction was completed, the reaction system was concentrated by rotary evaporation to give intermediate 92-5 (4 g, crude) in the form of a yellow oil.

Step (5): Preparation of ethyl 2-(5-bromo-6-cyanopicolinoyl)-3-oxobutanoate

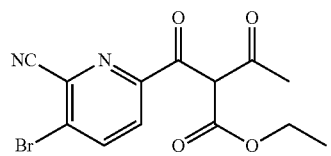

92-6

Ethyl acetoacetate (4.2 g, 32.6 mmol) was dissolved in anhydrous tetrahydrofuran (40 mL), and the reaction system was added with sodium hydroxide (3.9 g, 97.8 mmol), stirred at room temperature for 30 min, added with intermediate 92-5 (4.0 g, 16.3 mmol), and reacted overnight at room temperature. The reaction system was added with water (60 mL) and extracted with ethyl acetate (100 mL×3). The organic phases were combined, washed with saturated brine (100 mL), dried over anhydrous sodium sulfate and concentrated by rotary evaporation to give intermediate 92-6 (7.0 g) in the form of a yellow oily liquid. LC-MS [M+H]$^+$=340.6.

Step (6): Preparation of ethyl 5-(5-bromo-6-cyanopyridin-2-yl)-3-methylisothiazole-4-carboxylate

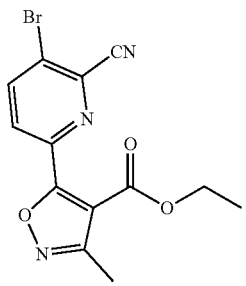

92-7

Hydroxylamine hydrochloride (5.7 g, 82.4 mmol) was dissolved in water (25 mL), and the reaction system was added dropwise with a solution of intermediate 92-6 (7.0 g, 20.6 mmol) in ethanol (50 mL) and stirred overnight at 60° C. The reaction system was diluted with water (75 mL), extracted with ethyl acetate (100 mL×3), washed with saturated brine (150 mL), dried over anhydrous sodium sulfate and concentrated, and the residue was separated by column chromatography to give intermediate 92-7 (800 mg, 13.6% yield over three steps) in the form of a yellow solid. LC-MS [M+H]$^+$: 335.9.

Step (7): Preparation of 3-bromo-6-(4-(hydroxymethyl)-3-methylisothiazol-5-yl)cyanopyridine

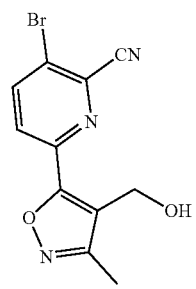

92-8

Intermediate 92-7 (700 mg, 2.1 mmol) was dissolved in anhydrous tetrahydrofuran (10 mL), and the reaction system was added with lithium borohydride (272 mg, 12.5 mmol) and water (10 mg, 0.56 mmol), and the reaction system was stirred at room temperature for 2 h. The reaction system was diluted with water (20 mL), extracted with ethyl acetate (25 mL×3), washed with saturated brine (25 mL), dried over anhydrous sodium sulfate and concentrated, and the residue was separated by column chromatography to give intermediate 92-8 (300 mg, 48.8% yield) in the form of a yellow solid. LC-MS [M+H]$^+$: 295.1.

Step (8): Preparation of (5-(5-bromo-6-cyanopyridin-2-yl)-3-methylisothiazol-4-yl)methylcyclopentyl (methyl)carbamate

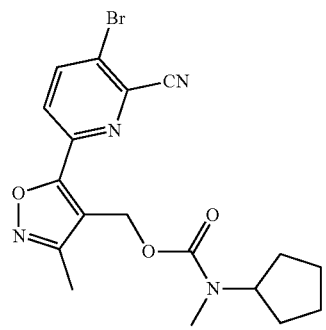

92-9

4-nitrophenyl chloroformate (308 mg, 1.5 mmol) and pyridine (484 mg, 6.12 mmol) were dissolved in dichloromethane (10 mL) under nitrogen atmosphere, and the reaction system was cooled to 0° C., added with intermediate 92-8 (300 mg, 1.0 mmol), warmed to room temperature and stirred overnight. The reaction system was added with triethylamine (618 mg, 6.1 mmol) and N-methylcyclopentylamine (607 mg, 6.1 mmol), and stirred overnight at room temperature. The reaction system was diluted with water (15 mL), extracted with dichloromethane (15 mL×2), washed with saturated brine (20 mL×2), dried over anhydrous sodium sulfate, filtered and concentrated, and the residue was separated by silica gel column chromatography to give intermediate 92-9 (300 mg, 70.1% yield) in the form of a yellow oil. LC-MS [M+H]⁺: 420.7.

Step (10): Preparation of (5-(6-cyano-5-hydroxypyridin-2-yl)-3-methylisothiazol-4-yl)methylcyclopentyl (methyl)carbamate

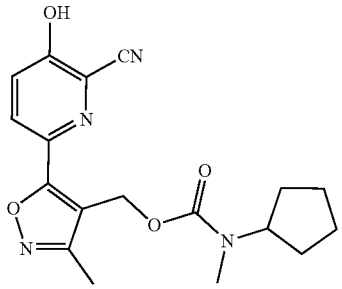

92-10

Intermediate 92-9 (150 mg, 0.36 mmol), potassium carbonate (247 mg, 1.8 mmol) and acetohydroxamic acid (80 mg, 1.1 mmol) were dissolved in dimethyl sulfoxide (5 mL) under nitrogen atmosphere, and the reaction system was stirred overnight at 80° C. Then the reaction system was diluted with water (15 mL) and extracted with ethyl acetate (15 mL×3). The organic phases were combined, washed with saturated brine (15 mL), dried over anhydrous sodium sulfate, filtered and concentrated, and the residue was separated by column chromatography to give intermediate 92-10 (100 mg, 78.1% yield) in the form of a yellow oily liquid. LC-MS [M+H]⁺: 357.2.

Step (11): Preparation of (+/−)-isopropyl (1S,3S)-3-((2-cyano-6-(4-(((cyclopentyl(methyl)carbamoyl)oxy)methyl)-3-methylisothiazol-5-yl)pyridin-3-yl)oxy)cyclohexane-1-carboxylate

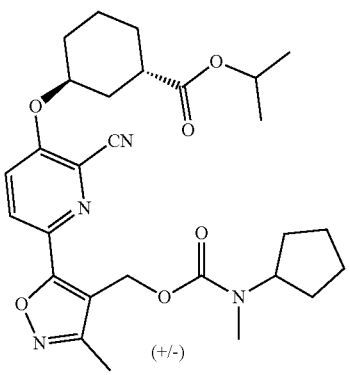

92-11

Intermediate 92-10 (100 mg, 0.28 mmol) and (+/−)-isopropyl (1S,3R)-3-hydroxycyclohexane-1-carboxylate (209 mg, 1.12 mmol) were dissolved in anhydrous tetrahydrofuran (10 mL), and the reaction system was added with triphenylphosphine (294 mg, 1.12 mmol) and di-tert-butyl azodicarboxylate (258.4 mg, 1.12 mmol), and reacted at 60° C. for 15 h under nitrogen atmosphere. The reaction system was concentrated, and the residue was separated by column chromatography to give intermediate 92-11 (80 mg, 54.8% yield) in the form of a white solid. LC-MS [M+H]⁺: 525.3.

Step (12): Preparation of (+/−)-(1S,3S)-3-((2-cyano-6-(4-(((cyclopentyl(methyl)carbamoyl)oxy)methyl)-3-methylisothiazol-5-yl)pyridin-3-yl)oxy)cyclohexane-1-carboxylic Acid

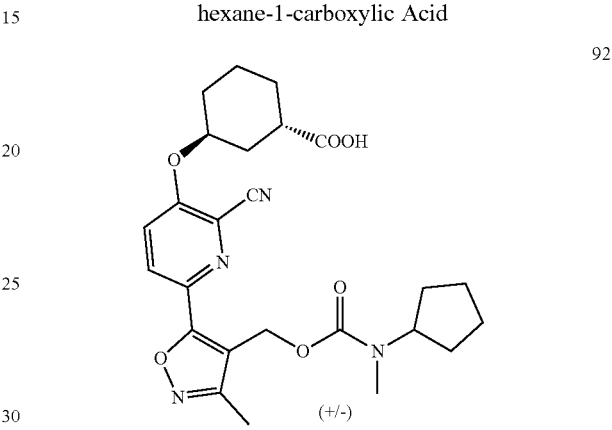

92

Intermediate 92-11 (50 mg, 0.1 mmol) and lithium hydroxide monohydrate (21 mg, 0.5 mmol) were dissolved in tetrahydrofuran (3 mL)/methanol (1 mL)/water (1 mL), and the reaction system was reacted at room temperature for 10 h. The reaction system was concentrated under reduced pressure, and the residue was added with water (10 mL) and extracted with ether (5 mL×3). The aqueous phase was retained, adjusted to pH 4 with diluted hydrochloric acid (1 N), and extracted with dichloromethane (10 mL×3). The organic phases were combined, dried over anhydrous sodium sulfate, and concentrated, and the residue was separated by preparative HPLC to give a white solid (6.5 mg). LC-MS [M+H]⁺: 483.3.

¹H NMR (400 MHz, MeOD) δ 8.16 (d, J=9.1 Hz, 1H), 7.91 (d, J=9.2 Hz, 1H), 5.42 (s, 2H), 5.05 (s, 1H), 4.52-4.31 (m, 1H), 2.90-2.80 (m, 1H), 2.78 (s, 3H), 2.41 (s, 3H), 2.21-2.09 (m, 1H), 2.05-1.94 (m, 3H), 1.87-1.48 (m, 12H).

Example 93

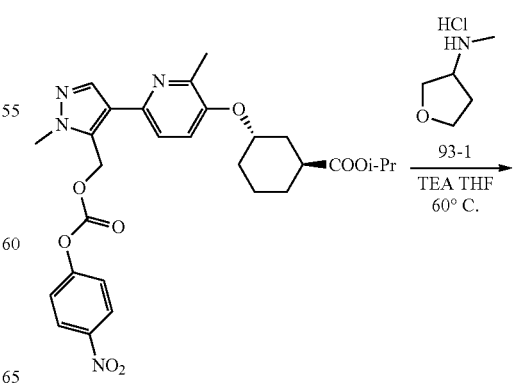

65-5

-continued

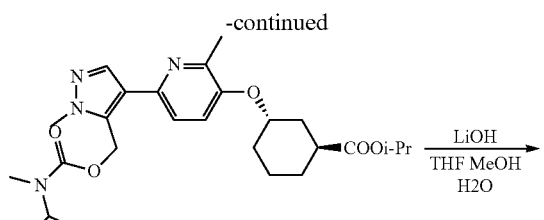

93-2

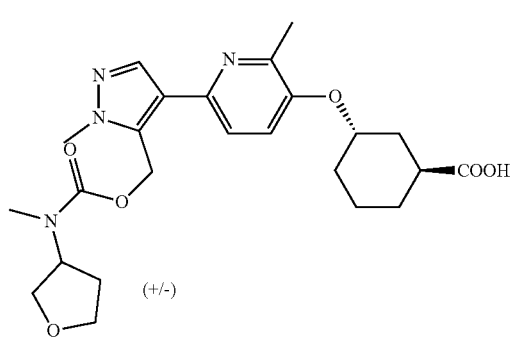

93

Step (4): Preparation of (+/−)-isopropyl (1S,3S)-3-((2-methyl-6-(1-methyl-5-(((methyl(tetrahydrofuran-3-yl) carbamoyl)oxy)methyl)-1H-pyrazol-4-yl)pyridin-3-yl)oxy)cyclohexane-1-carboxylate

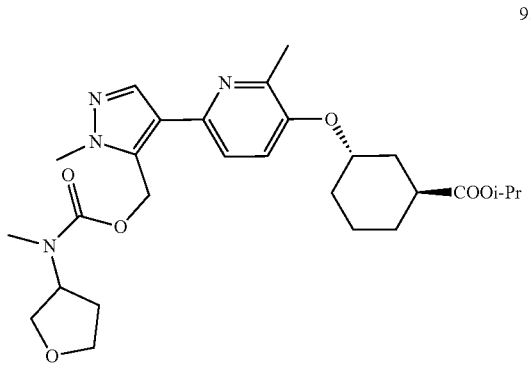

Intermediate 65-5 (200 mg, 0.36 mmol) was dissolved in anhydrous tetrahydrofuran (5 mL). The reaction system was added with N-methyltetrahydrofuran-3-amine hydrochloride (74 mg, 0.54 mmol) and triethylamine (109 mg, 1.08 mmol), stirred overnight at room temperature and under nitrogen atmosphere, and then concentrated by rotary evaporation, and the residue was purified by silica gel column chromatography to give intermediate 93-2 (150 mg, 81% yield) in the form of a yellow oil. LC-MS [M+H]⁺: 515.2.

Step (5): Preparation of (+/−)-isopropyl (1S,3S)-3-((2-methyl-6-(1-methyl-5-(((methyl(tetrahydrofuran-3-yl) carbamoyl)oxy)methyl)-1H-pyrazol-4-yl)pyridin-3-yl)oxy)cyclohexane-1-carboxylate

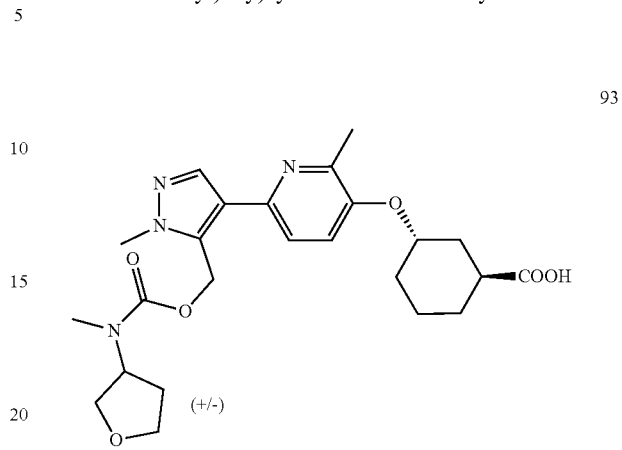

Intermediate 93-2 (150 mg, 0.29 mmol) was dissolved in tetrahydrofuran/methanol/water (2/1/1, 3 mL), and the reaction system was added with lithium hydroxide (49 mg, 1.16 mmol), reacted at room temperature for 12 h, and concentrated, and the residue was diluted with water (10 mL) and extracted with ether (5 mL×3). The aqueous phase was retained, adjusted to pH 4 with diluted hydrochloric acid (1 N), and extracted with dichloromethane (10 mL×3). The organic phases were combined, dried over anhydrous sodium sulfate and concentrated, and the residue was separated by preparative HPLC to give compound 93 (63.5 mg, 46% yield) in the form of a white solid. LC-MS [M+H]⁺: 472.8.

¹H NMR (400 MHz, MeOD) δ 7.81 (s, 1H), 7.47 (brs, 2H), 5.54 (s, 2H), 4.78-4.82 (m, 1H), 4.67-4.49 (m, 1H), 3.99 (s, 3H), 3.91-3.56 (m, 4H), 2.87-2.77 (m, 4H), 2.52 (s, 3H), 2.13-1.65 (m, 10H).

Example 94

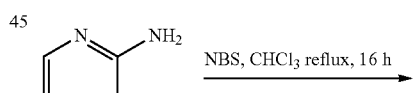

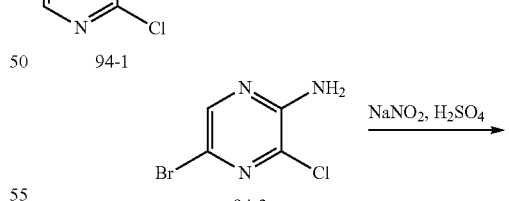

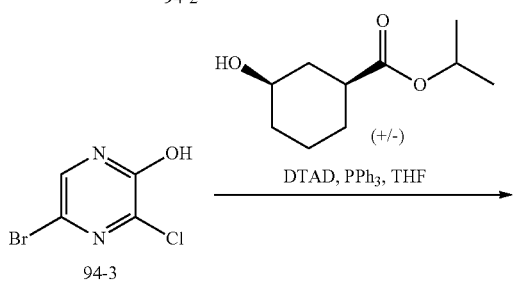

-continued

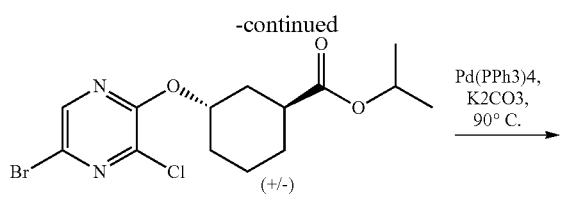

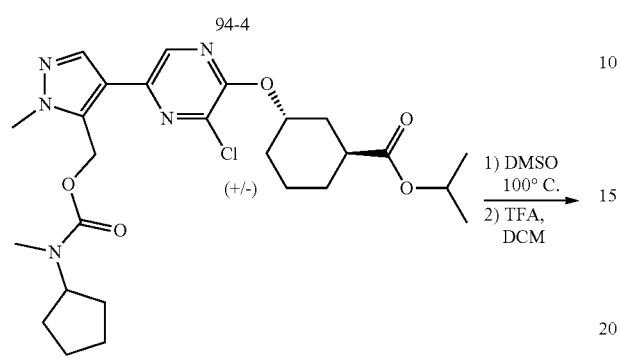

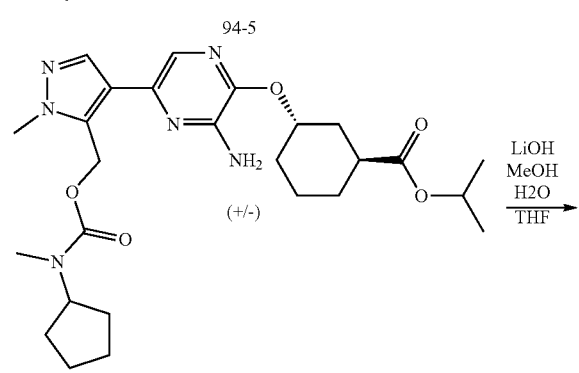

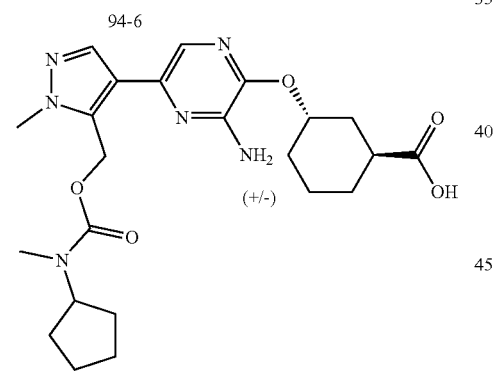

Step (1): Preparation of
5-bromo-3-chloropyrazin-2-amine

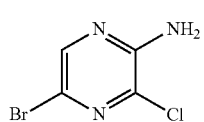

3-chloropyrazin-2-amine (3.0 g, 23.2 mmol) was dissolved in chloroform (30 mL), and the reaction system was added with N-bromosuccinimide (4.5 g, 25.5 mmol), and stirred at 60° C. for 16 h. The reaction system was quenched with water (50 mL), and a large amount of solids was precipitated and filtered. The filter cake was washed with water (30 mL×2), and dried to give intermediate 94-2 (2.7 g, 56% yield) in the form of a yellow solid. LC-MS [M+H]$^+$: 208.2.

Step (2): Preparation of
5-bromo-3-chloropyrazin-2-ol

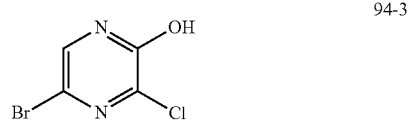

Intermediate 94-2 (2.7 g, 13.0 mmol) was dissolved in concentrated sulfuric acid (30 mL), and the reaction system was cooled to 0° C. Sodium nitrite (1.1 g, 15.6 mmol) was dissolved in concentrated sulfuric acid (30 mL), which was slowly added dropwise to the reaction system, and the reaction system was reacted at 40° C. for 1 h. After the reaction was completed, the reaction system was cooled to room temperature, poured into ice water (100 g), and extracted with ethyl acetate (40 mL×3). The organic phases were combined, washed with saturated brine (60 mL), dried over anhydrous sodium sulfate, filtered and concentrated to give intermediate 94-3 (2.0 g, 73% yield). LC-MS [M+H]$^+$: 209.1.

Step (3): Preparation of (+/−)-isopropyl (1S,3S)-3-bromo-3-chloropyrazin-2-yl)oxy)cyclohexane-1-carboxylate

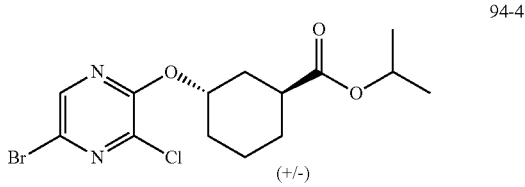 [SMILES: CC(C)OC(=O)[C@H]1CCC[C@H](Oc2ncc(Br)nc2Cl)C1]

Intermediate 94-3 (2.0 g, 9.6 mmol) was dissolved in anhydrous tetrahydrofuran (60 mL), and the reaction system was added with (+/−)-isopropyl (1S,3R)-3-hydroxycyclohexane-1-carboxylate (3.5 g, 19.2 mmol), triphenylphosphine (5.0 g, 19.2 mmol) and di-tert-butyl azodicarboxylate (4.4 g, 19.2 mmol), and reacted at room temperature for 3 h under nitrogen atmosphere. After the reaction was completed, the reaction system was diluted with water (120 mL) and extracted with ethyl acetate (100 mL×2). The organic phases were combined, washed with saturated brine (200 mL), dried over anhydrous sodium sulfate, filtered and concentrated, and the residue was separated by silica gel column chromatography to give intermediate 94-4 (2.0 g, 55% yield) in the form of a pale yellow oily liquid. LC-MS [M+H]$^+$=376.9.

Step (4): Preparation of (+/−)-isopropyl (1S,3S)-3-chloro-5-(5-(((cyclopentyl(methyl)carbamoyl) oxy) methyl)-1-methyl-1H-pyrazol-4-yl)pyrazin-2-yl)oxy) cyclohexane-1-carboxylate

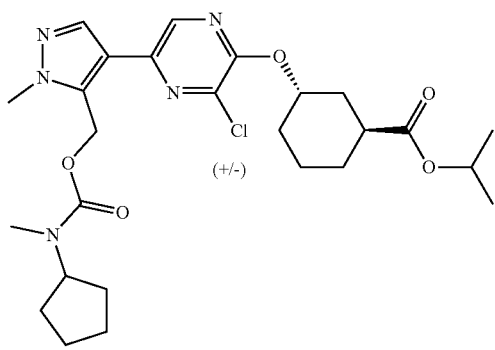

94-5

Intermediate 94-4 (1.0 g, 2.6 mmol) was dissolved in anhydrous dioxane (20 mL), and the reaction system was added with (5-(((cyclopentyl(methyl)carbamoyl)oxy) methyl)-1-methyl-1H-pyrazol-4-yl) boronic acid (730 mg, 2.6 mmol), potassium carbonate (1.1 g, 7.8 mmol) and tetrakis(triphenylphosphine)palladium(0) (305 mg, 0.26 mmol), and stirred at 90° C. for 8 h under nitrogen atmosphere. The reaction system was added with water (40 mL) to quench the reaction and extracted with ethyl acetate (25 mL×3). The organic phases were combined, washed with saturated brine (50 mL), dried over anhydrous sodium sulfate, filtered and concentrated to give a crude product, and the crude product was separated by silica gel column chromatography (PE/EA=8/1) to give intermediate 94-5 (800 mg, 57% yield) in the form of a pale yellow oily liquid. LC-MS [M+H]$^+$: 534.2.

Step (5): Preparation of (+/−)-isopropyl (1S,3S)-3-((3-amino-5-(5-(((cyclopentyl(methyl)carbamoyl) oxy)methyl)-1-methyl-1H-pyrazol-4-yl)pyrazin-2-yl) oxy)cyclohexane-1-carboxylate

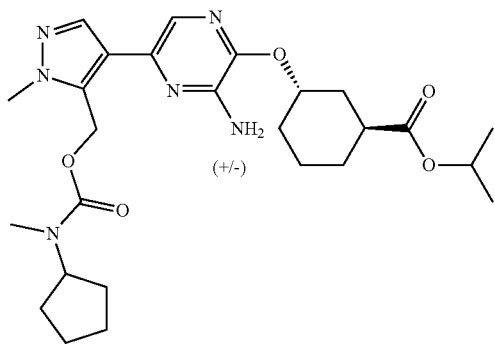

94-6

Intermediate 94-5 (400 mg, 0.75 mmol) was dissolved in dimethyl sulfoxide (5 mL), and the reaction system was added with 2,4-dimethoxybenzylamine (626 mg, 3.75 mmol) and stirred at 100° C. for 10 h. The reaction system was diluted with water (15 mL), and extracted with ethyl acetate (10 mL×2). The organic phases were combined, washed with saturated brine (20 mL), dried over anhydrous sodium sulfate, filtered and concentrated to give a crude product. The crude product was dissolved in dichloromethane (5 mL), and the reaction system was added dropwise with trifluoroacetic acid (5 mL), and stirred at room temperature for 3 h. The reaction system was concentrated under reduced pressure, and the residue was diluted with water (10 mL), and extracted with dichloromethane (10 mL×2). The aqueous phase was retained, adjusted to pH 9 with aqueous sodium hydroxide solution (2 N), and extracted with dichloromethane (10 mL×3). The organic phases were combined, dried over anhydrous sodium sulfate, filtered and concentrated, and the residue was separated by column chromatography to give intermediate 94-6 (120 mg, 30% yield) in the form of a pale yellow oily liquid. LC-MS [M+H]$^+$: 514.9.

Step (6): Preparation of (+/−)-(1S,3S)-3-((3-amino-5-(5-(((cyclopentyl(methyl)carbamoyl)oxy)methyl)-1-methyl-1H-pyrazol-4-yl)pyrazin-2-yl)oxy)cyclohexane-1-carboxylic Acid

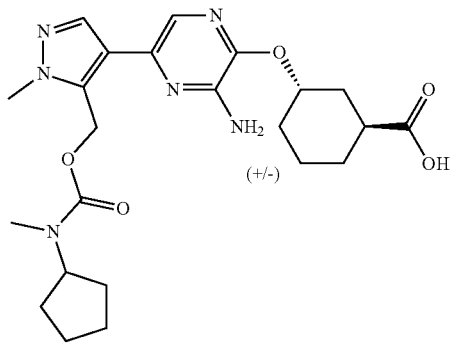

94

Intermediate 94-6 (120 mg, 0.23 mmol) and lithium hydroxide monohydrate (38 mg, 0.92 mmol) were dissolved in tetrahydrofuran (3 mL)/methanol (1 mL)/water (1 mL), and the reaction system was reacted overnight at room temperature. The reaction system was concentrated under reduced pressure, and the residue was added with water (10 mL) and extracted with ether (5 mL×3). The aqueous phase was retained, adjusted to pH 4 with diluted hydrochloric acid (1 N), and extracted with dichloromethane (10 mL×3). The organic phases were combined, dried over anhydrous sodium sulfate, filtered and concentrated, and the residue was separated by preparative chromatography to give compound 94 (50 mg) in the form of a pale yellow oil. LC-MS [M+H]$^+$: 472.8.

$^1$H NMR (400 MHz, CDCl$_3$) δ 7.82 (s, 1H), 7.53 (s, 1H), 5.59-5.54 (m, 1H), 5.27 (s, 2H), 4.60-4.30 (m, 1H), 4.04 (s, 3H), 2.95-2.85 (m, 1H), 2.79 (s, 3H), 2.32-2.22 (m, 1H), 2.08-1.95 (m, 3H), 1.85-1.45 (m, 12H).

Example 95

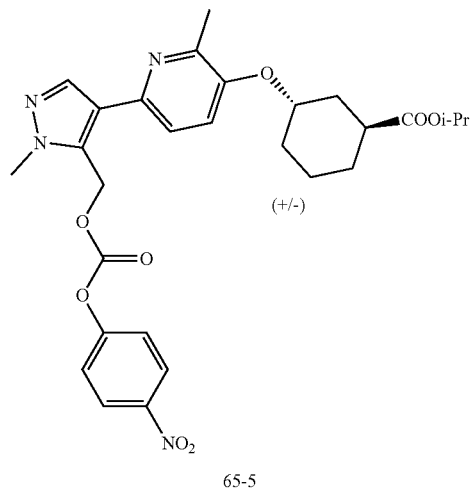

65-5

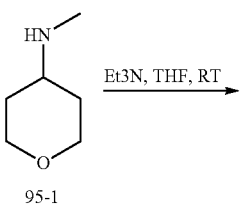

95-1

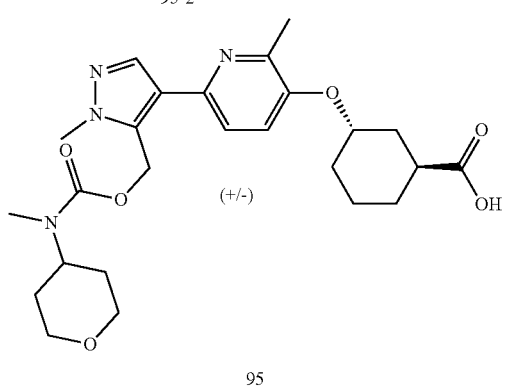

95

Step (1): Preparation of isopropyl (1S,3S)-3-((2-methyl-6-(1-methyl-5-(((methyl(tetrahydro-2H-pyran-4-yl) carbamoyl)oxy)methyl)-1H-pyrazol-4-yl)pyridin-3-yl)oxy)cyclohexane-1-carboxylate

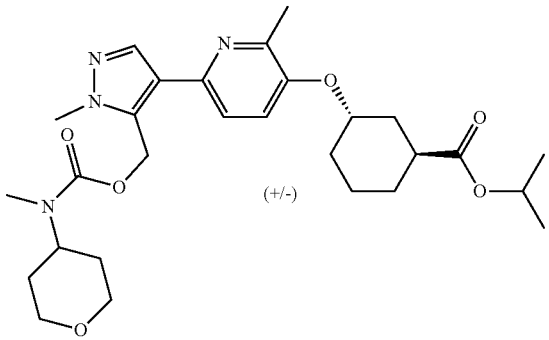

95-2

Intermediate 65-5 (200 mg, 0.36 mmol) was dissolved in anhydrous tetrahydrofuran (5 mL). The reaction system was added with N-methyltetrahydro-2H-pyran-4-amine (62 mg, 0.54 mmol) and triethylamine (109 mg, 1.08 mmol), stirred overnight at room temperature under nitrogen atmosphere and concentrated under reduced pressure, and the residue was purified by silica gel column chromatography to give intermediate 95-2 (100 mg, 52.6% yield) in the form of a yellow oil. LC-MS [M+H]$^+$: 529.2.

Step (2): Preparation of (1S,3S)-3-((2-methyl-6-(1-methyl-5-(((methyl(tetrahydro-2H-pyran-4-yl)carbamoyl) oxy)methyl)-1H-pyrazol-4-yl)pyridin-3-yl) oxy)cyclohexane-1-carboxylic Acid

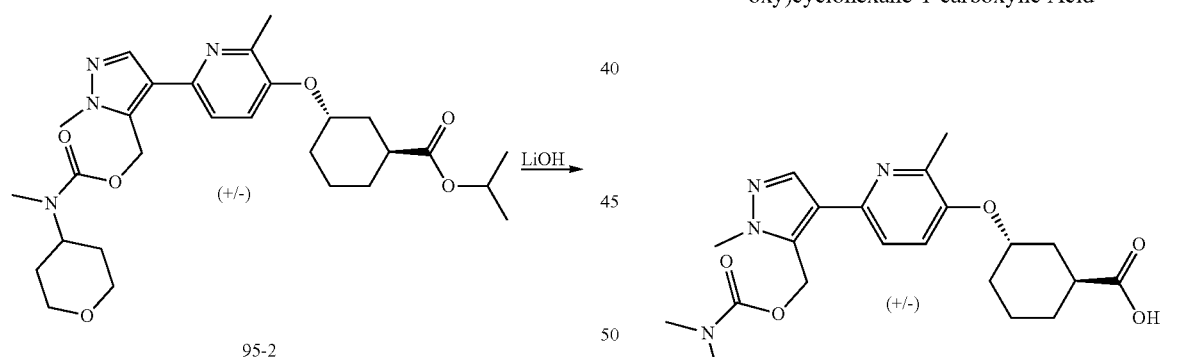

95

Intermediate 95-2 (100 mg, 0.19 mmol) was dissolved in methanol (3 mL), and the reaction system was added with aqueous lithium hydroxide solution (0.9 mL, 0.5 N) and reacted at room temperature for 12 h. The reaction system was concentrated, then adjusted to pH 5 with diluted hydrochloric acid, and extracted with dichloromethane (10 mL×3). The organic phases were combined, dried over anhydrous sodium sulfate, filtered and concentrated, and the residue was separated by silica gel column chromatography to give compound 95 (80 mg, 86% yield) in the form of a yellow oily liquid. LC-MS [M+H]$^+$: 487.1.

¹H NMR (400 MHz, DMSO-d₆) δ 10.63 (bs, 1H), 7.99 (d, J=6.8 Hz, 1H) 7.89 (s, 1H), 7.47 (d, J=6.8 Hz, 1H), 5.46 (s, 2H), 3.67 (m, 2H), 3.64 (m, 1H), 3.63 (s, 3H), 3.57 (m, 2H), 3.27 (s, 3H), 2.51 (s, 3H), 2.31 (m, 1H), 2.17 (m, 1H), 1.95 (m, 3H), 1.92 (m, 1H), 1.72 (m, 1H), 1.70 (m, 3H), 1.53 (m, 1H), 1.47 (m, 1H), 1.43 (m, 1H).
Example 96
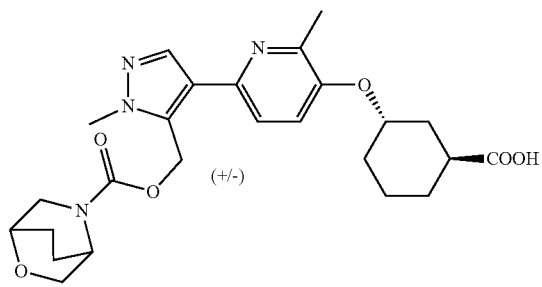
96
Refer to the method in Example 94, LC-MS [M+H]⁺: 487.02.
Example 97
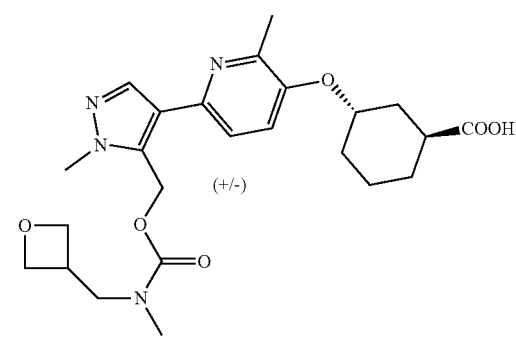
97
Refer to the method in Example 94, LC-MS [M+H]⁺: 473.25.
Example 98
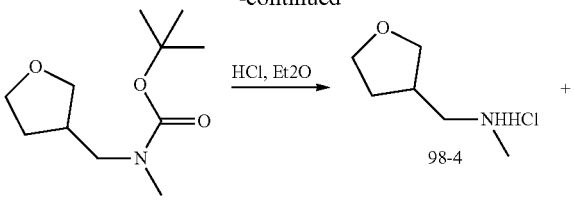
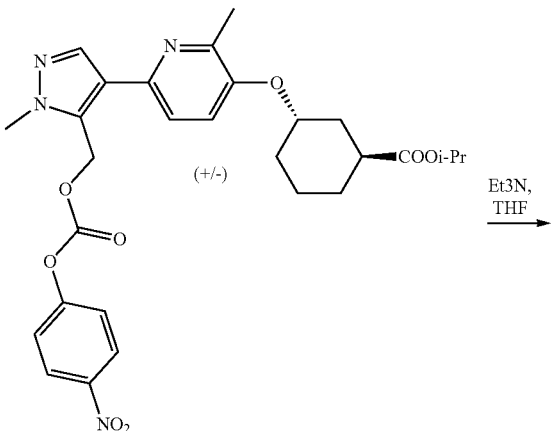
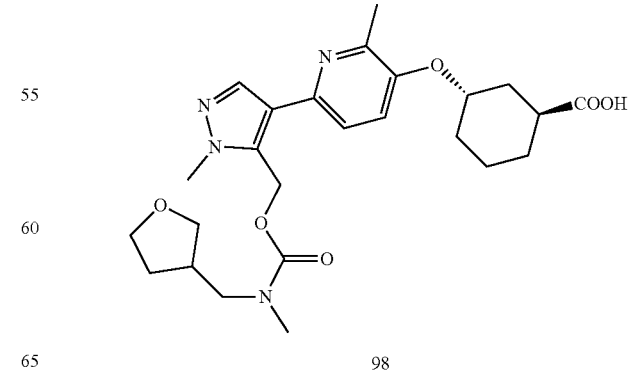
98

Step (1): Preparation of tert-butyl ((tetrahydrofuran-3-yl)methyl)carbamate

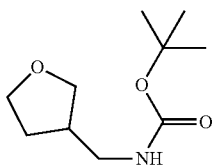

98-2

(Tetrahydrofuran-3-yl)methylamine (0.91 g, 8.99 mmol) was dissolved in anhydrous dichloromethane (30 mL), and the reaction system was cooled to 0° C., added with triethylamine (1.82 g, 17.98 mmol) and di-tert-butyl dicarbonate ester (2.16 g, 9.89 mmol), warmed to room temperature and stirred overnight. The reaction system was diluted with dichloromethane (30 mL), washed with saturated brine (30 mL×2), dried over anhydrous sodium sulfate, filtered and concentrated to give intermediate 98-2 (1.86 g, 97% yield) in the form of a colorless oil. LC-MS [M+H]$^+$: 146, 224.

Step (2): Preparation of tert-butyl methyl((tetrahydrofuran-3-yl)methyl)carbamate

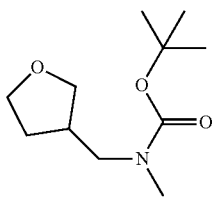

98-3

Intermediate 98-2 (1.0 g, 4.97 mmol) was dissolved in DMF (10 mL) under nitrogen atmosphere, and the reaction system was cooled to 0° C., added with NaH (400 mg, 9.94 mmol, 60% purity), warmed to room temperature, reacted for 30 min, added with methyl iodide (1.06 g, 7.46 mmol) and stirred overnight at room temperature. The reaction system was quenched with saturated ammonium chloride (20 mL) and extracted with ethyl acetate (30 mL×2). The organic phases were combined, washed with saturated brine (30 mL), dried over anhydrous sodium sulfate, filtered and concentrated to give intermediate 98-3 (1.01 g, 85% yield) in the form of a yellow oil. LC-MS [M+H]$^+$: 160, 238.

Step (3): Preparation of N-methyl-1-(tetrahydrofuran-3-yl)methylamine Hydrochloride

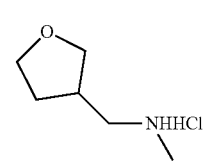

98-4

Intermediate 98-3 (250 mg, 1.16 mmol) was dissolved in dichloromethane (5 mL), and the reaction system was added with a solution of HCl in ether (2 M, 5 mL) and stirred overnight at room temperature. The reaction system was concentrated by rotary evaporation and added with tetrahydrofuran. The solids were precipitated, filtered and dried to give intermediate 98-4 (90 mg, 51% yield) in the form of a white solid. LC-MS [M+H]$^+$: 116.2.

Step (4): Preparation of (+/−)-isopropyl (1S,3S)-3-((2-methyl-6-(1-methyl-5-(((methyl((tetrahydrofuran-3-yl) methyl)carbamoyl)oxy)methyl)-1H-pyrazol-4-yl)pyridin-3-yl)oxy)cyclohexane-1-carboxylate

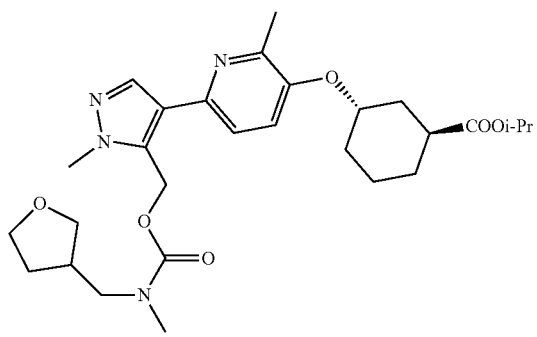

98-5

Intermediate 65-5 (100 mg, 0.18 mmol) was dissolved in tetrahydrofuran (10 mL), and the reaction system was added with triethylamine (80 mg, 0.72 mmol) and intermediate 98-4 (41 mg, 0.27 mmol), heated to 60° C. and reacted for 1 h. The reaction system was diluted with ethyl acetate (20 mL), and washed with water (10 mL×2), aqueous NaOH solution (10 mL×4, 1 N) and saturated brine (10 mL). The organic phases were dried over anhydrous sodium sulfate, filtered and concentrated, and the residue was separated by silica gel column chromatography to give intermediate 98-5 (80 mg, 78% yield) in the form of a yellow oily liquid. LC-MS [M+H]$^+$: 487.

Step (5): Preparation of (+/−)-(1S,3S)-3-((2-methyl-6-(1-methyl-5-(((methyl((tetrahydrofuran-3-yl) methyl)carbamoyl)oxy)methyl)-1H-pyrazol-4-yl) pyridin-3-yl)oxy)cyclohexane-1-carboxylic Acid

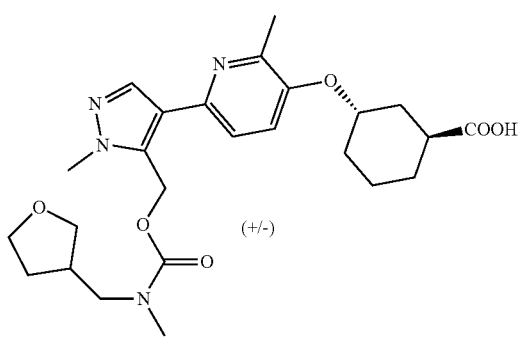

98

Intermediate 98-5 (120 mg, 0.23 mmol) was dissolved in tetrahydrofuran (6 mL), and the reaction system was added with lithium hydroxide monohydrate (48 mg, 1.15 mmol), methanol (2 mL) and water (2 mL), and stirred overnight at room temperature. The reaction system was concentrated under reduced pressure, diluted with water (15 mL), adjusted to pH 5 with diluted hydrochloric acid (1 N), extracted with dichloromethane (10 mL×2), washed with saturated brine (10 mL), dried over anhydrous sodium sulfate, filtered and concentrated, and the residue was separated by silica gel column chromatography (DCM/MeOH=20/1) and then lyophilized to give compound 98 (50 mg, 43% yield) in the form of a white solid. LC-MS [M+H]$^+$: 487.

$^1$H NMR (400 MHz, MeOD) δ 7.81 (s, 1H), 7.43-7.41 (m, 2H), 5.61-5.55 (m, 2H), 4.80-4.75 (m, 1H), 3.99 (s, 3H), 3.87-3.50 (m, 5H), 3.24-3.13 (m, 1H), 2.94-2.77 (m, 4H), 2.49 (s, 3H), 2.15-1.42 (m, 11H).

Example 99

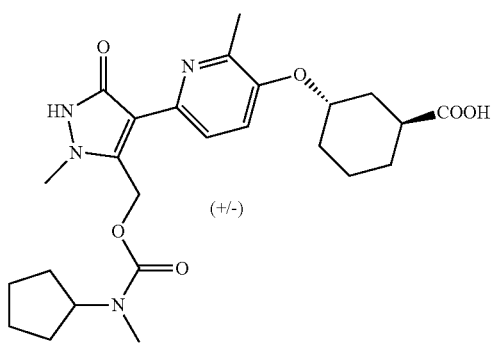

99

Refer to the method in Example 11, LC-MS [M+H]$^+$: 487.23.

Example 100

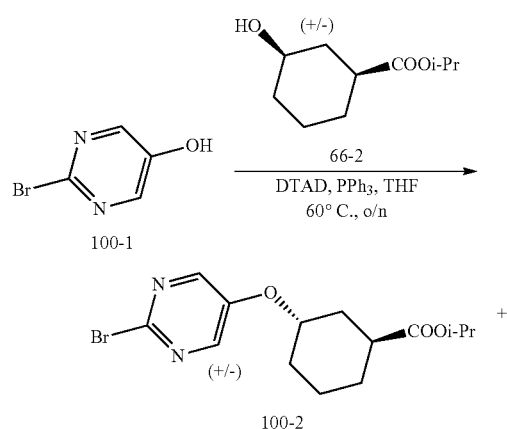

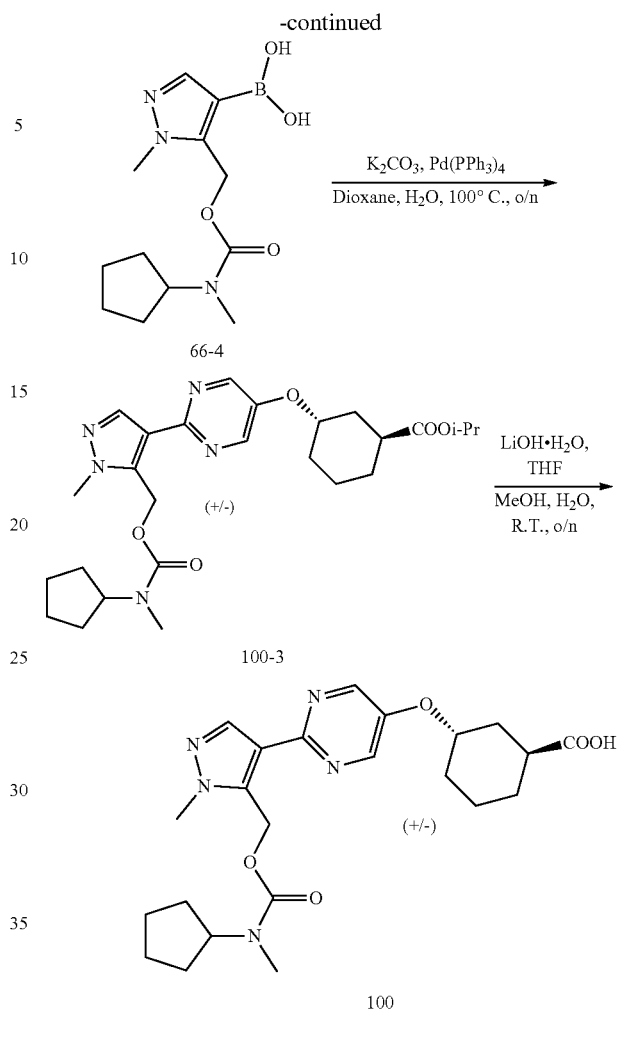

Step (1): Preparation of (+/−)-isopropyl (1S,3S)-3-((2-bromopyrimidin-5-yl)oxy)cyclohexane-1-carboxylate

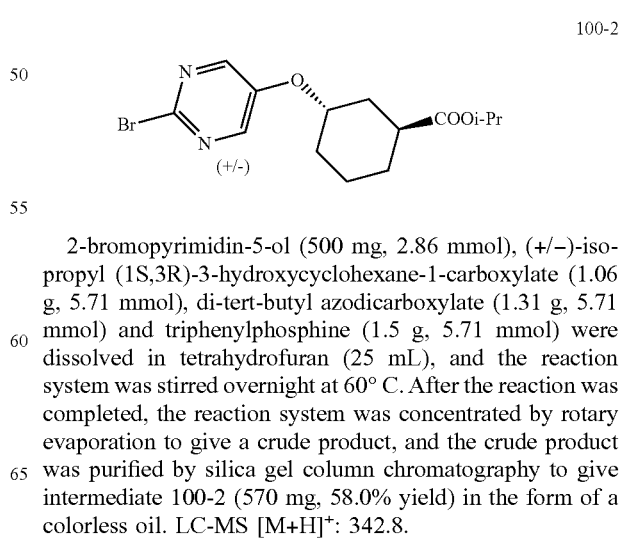

2-bromopyrimidin-5-ol (500 mg, 2.86 mmol), (+/−)-isopropyl (1S,3R)-3-hydroxycyclohexane-1-carboxylate (1.06 g, 5.71 mmol), di-tert-butyl azodicarboxylate (1.31 g, 5.71 mmol) and triphenylphosphine (1.5 g, 5.71 mmol) were dissolved in tetrahydrofuran (25 mL), and the reaction system was stirred overnight at 60° C. After the reaction was completed, the reaction system was concentrated by rotary evaporation to give a crude product, and the crude product was purified by silica gel column chromatography to give intermediate 100-2 (570 mg, 58.0% yield) in the form of a colorless oil. LC-MS [M+H]$^+$: 342.8.

Step (2): Preparation of (+/−)-isopropyl (1S,3S)-3-((2-(5-(((cyclopentyl(methyl)carbamoyl)oxy)methyl)-1-methyl-1H-pyrazol-4-yl)pyrimidin-5-yl)oxy)cyclohexane-1-carboxylate

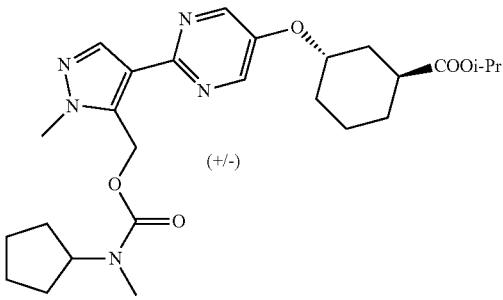

100-3

Intermediate 100-2 (250 mg, 0.71 mmol), intermediate 66-4 (200 mg, 0.71 mmol), potassium carbonate (245 mg, 1.78 mmol) and tetrakis(triphenylphosphine)palladium(0) (80 mg, 0.07 mmol) were dissolved in dioxane (15 mL) and water (3 mL) under nitrogen atmosphere, and the reaction system was warmed to 100° C. and stirred overnight. After the reaction was completed, the reaction system was diluted with water (15 mL) and filtered, and the filtrate was extracted with ethyl acetate (15 mL×3). The organic phases were combined, washed with saturated brine, dried over anhydrous sodium sulfate, filtered and concentrated to give a crude product, and the crude product was purified by silica gel column chromatography to give intermediate 100-3 (171 mg, 46.6% yield) in the form of a white solid. MS [M+H]⁺ =499.8.

Step (3): Preparation of (+/−)-(1S,3S)-3-((2-(5-(((cyclopentyl(methyl)carbamoyl)oxy)methyl)-1-methyl-1H-pyrazol-4-yl)pyrimidin-5-yl)oxy)cyclohexane-1-carboxylic Acid

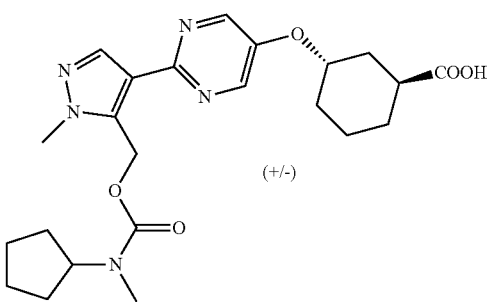

100

Intermediate 100-3 (170 mg, 0.34 mmol) was dissolved in tetrahydrofuran (3 mL)/water (3 mL)/methanol (1 mL). The reaction system was added with lithium hydroxide monohydrate (86 mg, 2.0 mmol), and stirred overnight at room temperature. After the reaction was completed, the reaction system was diluted with water (5 mL), adjusted to pH 3 with diluted hydrochloric acid (1 N), and extracted with ethyl acetate (10 mL×3). The organic phases were combined, dried over anhydrous sodium sulfate, filtered and concentrated by rotary evaporation to give a crude product, and the crude product was purified by silica gel column chromatography to give compound 100 (95 mg) in the form of a white solid. LC-MS [M+H]⁺: 458.19.

¹H NMR (400 MHz, CDCl₃) δ 8.58 (s, 2H), 8.27 (s, 1H), 5.74 (s, 2H), 4.88-4.77 (m, 1H), 4.65-4.28 (m, 1H), 4.01 (s, 3H), 2.99-2.91 (m, 1H), 2.74 (s, 3H), 2.22-2.14 (m, 1H), 2.00-1.45 (m, 15H).

Example 101

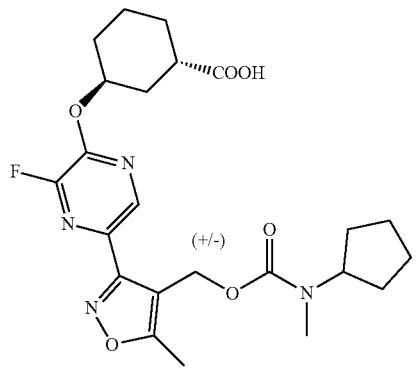

101

Refer to the method in Example 100, LC-MS [M+H]⁺: 477.20.

Example 102

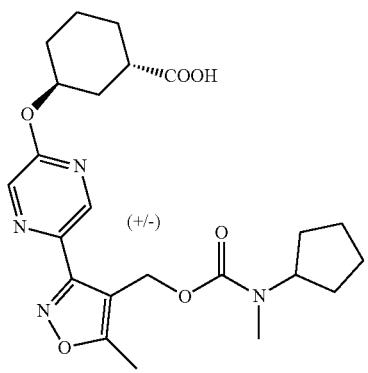

102

Refer to the method in Example 100, LC-MS [M+H]⁺: 459.20.

Example 103

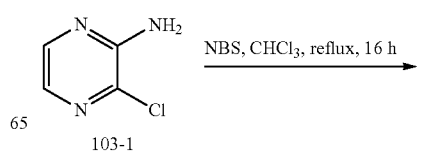

103-1

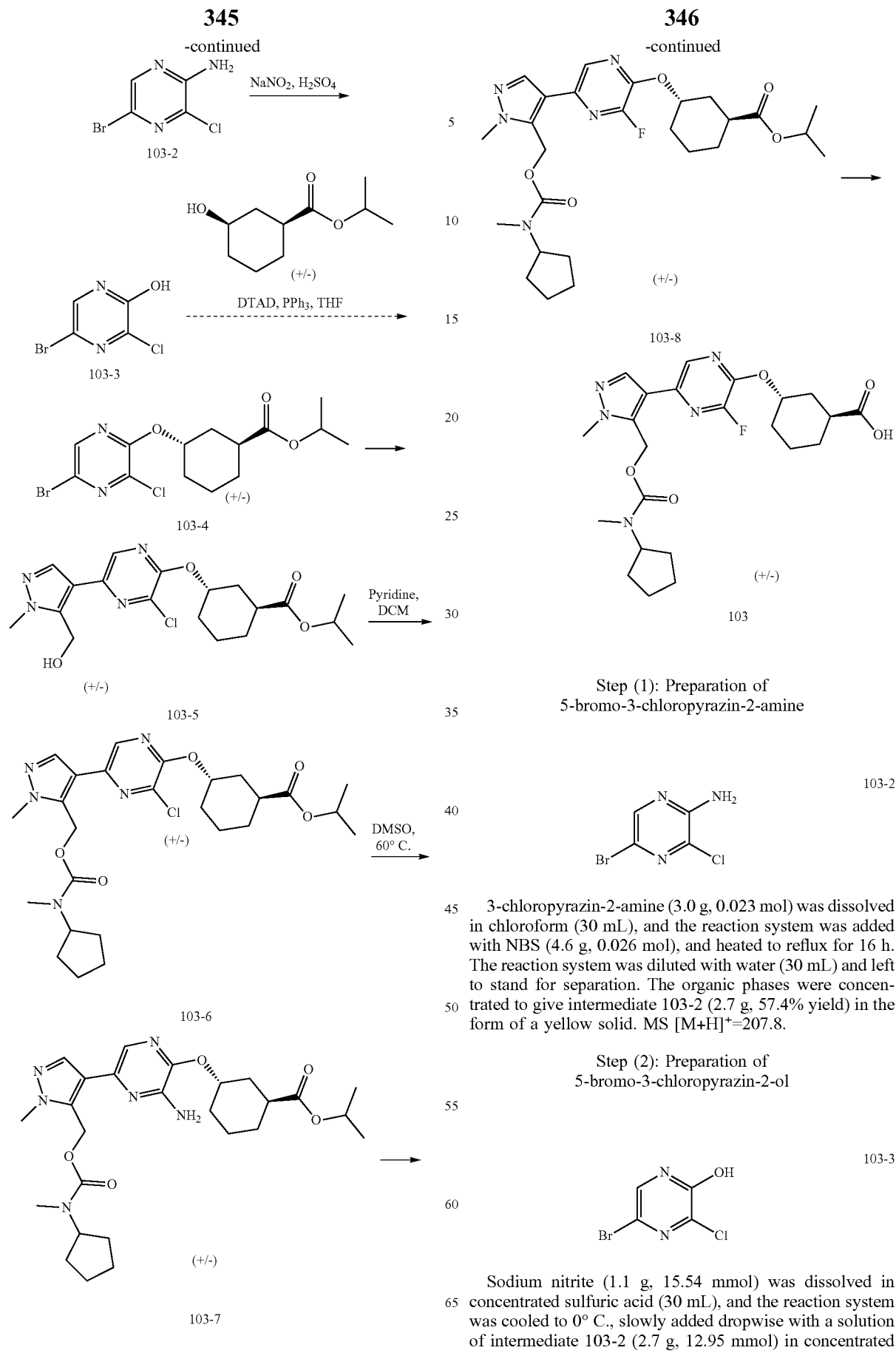

Step (1): Preparation of
5-bromo-3-chloropyrazin-2-amine 3-chloropyrazin-2-amine (3.0 g, 0.023 mol) was dissolved in chloroform (30 mL), and the reaction system was added with NBS (4.6 g, 0.026 mol), and heated to reflux for 16 h. The reaction system was diluted with water (30 mL) and left to stand for separation. The organic phases were concentrated to give intermediate 103-2 (2.7 g, 57.4% yield) in the form of a yellow solid. MS $[M+H]^+$=207.8.

Step (2): Preparation of
5-bromo-3-chloropyrazin-2-ol

Sodium nitrite (1.1 g, 15.54 mmol) was dissolved in concentrated sulfuric acid (30 mL), and the reaction system was cooled to 0° C., slowly added dropwise with a solution of intermediate 103-2 (2.7 g, 12.95 mmol) in concentrated sulfuric acid (60 mL), warmed to 40° C. and reacted for 1 h. The reaction system was poured into crushed ice (100 g), and the reaction system was extracted with ethyl acetate (40 mL×3). The organic phases were washed with saturated brine (60 mL), dried over anhydrous sodium sulfate, and concentrated to give intermediate 103-3 (2.2 g, 81.5% yield) in the form of a yellow oily liquid. MS [M+H]⁺=239.3.

Step (3): Preparation of (+/−)-isopropyl (1S,3S)-3-((5-bromo-3-chloropyrazin-2-yl)oxy)cyclohexane-1-carboxylate

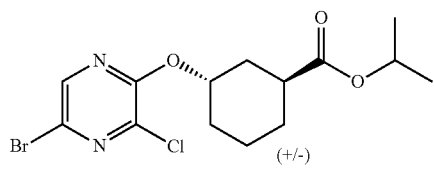

103-4

Intermediate 103-3 (2.0 g, 0.01 mol) and (+/−)-isopropyl (1S,3R)-3-hydroxycyclohexane-1-carboxylate (3.72 g, 0.02 mmol) were dissolved in anhydrous tetrahydrofuran (20 mL), and the reaction system was added with triphenylphosphine (5.25 g, 0.02 mmol), slowly added dropwise with di-tert-butyl azodicarboxylate (4.61 g, 0.02 mmol) under nitrogen atmosphere, dissolved in tetrahydrofuran (50 mL) and reacted at room temperature for 3 h. The reaction system was concentrated, and the residue was separated by silica gel column chromatography to give intermediate 103-4 (2.0 g, 53.2% yield) in the form of a yellow oily liquid. LC-MS [M+H]⁺: 377.02.

Step (4): Preparation of (+/−)-isopropyl (1S,3S)-3-((3-chloro-5-(5-(hydroxymethyl)-1-methyl-1H-pyrazol-4-yl)pyrazin-2-yl)oxy)cyclohexane-1-carboxylate

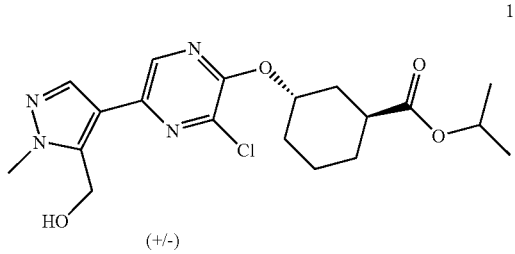

103-5

Intermediate 103-4 (2.0 g, 5.3 mmol) was added to (1-methyl-4-(4,4,5,5-tetramethyl-1,3,2-dioxaborolan-2-yl)-1H-pyrazol-5-yl)methanol (1.9 g, 7.9 mmol), and the reaction system was added with tetrakis(triphenylphosphine)palladium(0) (612 mg, 0.53 mmol) and potassium carbonate (1.6 g, 11.65 mmol), and stirred at 80° C. for 8 h under nitrogen atmosphere. The reaction system was quenched with water (100 mL) and extracted with ethyl acetate (60 mL×3). The organic phases were combined, washed with saturated brine (100 mL), dried over anhydrous sodium sulfate, filtered and concentrated to give a crude product, and the crude product was separated by silica gel column chromatography to give intermediate 103-5 (500 mg, 23% yield) in the form of a yellow oily liquid. LC-MS [M+1]⁺: 408.8.

Step (5): Preparation of (+/−)-isopropyl (1S,3S)-3-chloro-5-(5-(((cyclopentyl(methyl)carbamoyl) oxy) methyl)-1-methyl-1H-pyrazol-4-yl)pyrazin-2-yl)oxy) cyclohexane-1-carboxylate

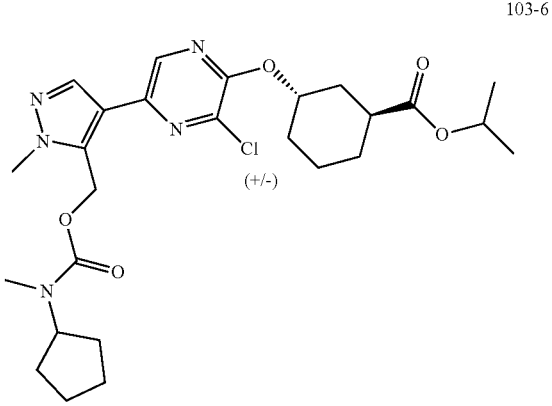 [SMILES: CC(C)OC(=O)[C@H]1CCC[C@H](Oc2ncc(-c3cnn(C)c3COC(=O)N(C)C3CCCC3)nc2Cl)C1]

103-6

4-nitrophenyl chloroformate (369 mg, 1.83 mmol) was dissolved in tetrahydrofuran (10 mL) under nitrogen atmosphere, and the reaction system was cooled to 0° C., slowly added with intermediate 103-5 (500 mg, 1.22 mmol) and pyridine (579 mg, 7.32 mmol), and stirred overnight at room temperature. The reaction system was diluted with water (20 mL), extracted with ethyl acetate (20 mL×3), washed with saturated brine (10 mL×2), dried over anhydrous sodium sulfate, filtered and concentrated to give a crude product (750 mg). The crude product and diisopropylethylamine (944 mg, 7.32 mmol) were dissolved in anhydrous tetrahydrofuran (10 mL), and the reaction system was added with N-methylcyclopentylamine hydrochloride (944 mg, 7.32 mmol), and stirred overnight at room temperature. The reaction system was diluted with water (20 mL), extracted with ethyl acetate (20 mL×3), washed with saturated brine (20 mL×5), dried over anhydrous sodium sulfate, filtered and concentrated, and the residue was separated by column chromatography to give intermediate 103-6 (900 mg, 70% yield) in the form of a pale yellow oily liquid. LC-MS [M+H]⁺: 408.3.

Step (6): Preparation of (+/−)-isopropyl (1S,3S)-3-((3-amino-5-(5-(((cyclopentyl(methyl)carbamoyl)oxy)methyl)-1-methyl-1H-pyrazol-4-yl)pyrazin-2-yl)oxy)cyclohexane-1-carboxylate

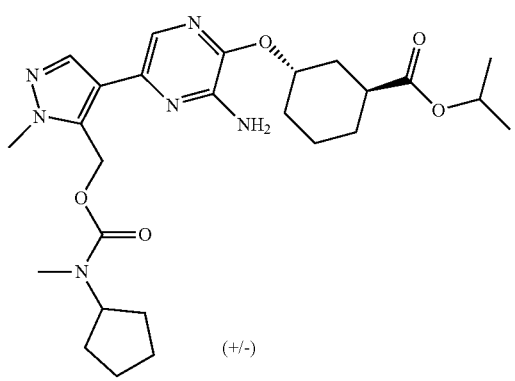

103-7

Intermediate 103-6 (350 mg, 0.65 mmol) was dissolved in anhydrous dimethyl sulfoxide (10 mL), and the reaction system was added with 2,4-dimethoxybenzylamine (219 mg, 1.31 mmol) and potassium carbonate (271 mg, 1.97 mmol), and reacted at 80° C. for 48 h. The reaction system was diluted with water (20 mL) and extracted with ethyl acetate (20 mL×3). The organic phases were combined, dried over anhydrous magnesium sulfate and concentrated to give a crude product. The crude product was dissolved in dichloromethane (6 mL), and the reaction system was added with trifluoroacetic acid (3 mL) and stirred overnight at room temperature. The reaction system was concentrated under reduced pressure, and the residue was diluted with water (20 mL), adjusted to pH 8-9 with sodium carbonate solution, and extracted with ethyl acetate (20 mL×3). The organic phases were combined, dried over anhydrous sodium sulfate, filtered and concentrated, and the residue was separated by column chromatography to give intermediate 103-7 (150 mg, 44.6% yield) in the form of a yellow oily liquid. LC-MS [M+H]⁺: 515.0.

Step (7): Preparation of (+/−)-isopropyl (1S,3S)-3-((5-(5-(((cyclopentyl(methyl)carbamoyl)oxy)methyl)-1-methyl-1H-pyrazol-4-yl)-3-fluoropyrazin-2-yl)oxy)cyclohexane-1-carboxylate 103-8

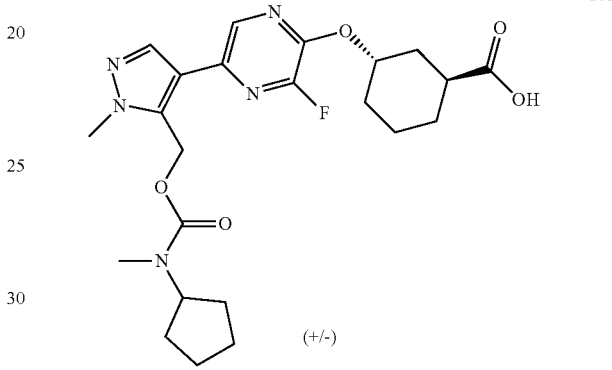

Intermediate 103-7 (150 mg, 0.31 mmol) was dissolved in acetonitrile (5 mL). The reaction system was added with a solution of boron tetrafluoride in THF (1 N, 1 mL), cooled to 0° C., added with sodium nitrite (43 mg, 0.62 mmol), stirred at room temperature for 5 h, diluted with water (15 mL) and extracted with ethyl acetate (20 mL×3). The organic phases were combined, dried over anhydrous sodium sulfate and concentrated, and the residue was separated by column chromatography to give intermediate 103-8 (50 mg, 31.2% yield) in the form of a yellow oily liquid. LC-MS [M+H]⁺: 518.2.

Step (8): Preparation of (+/−)-(1S,3S)-3-((5-(5-(((cyclopentyl(methyl)carbamoyl)oxy)methyl)-1-methyl-1H-pyrazol-4-yl)-3-fluoropyrazin-2-yl)oxy)cyclohexane-1-carboxylic Acid

103

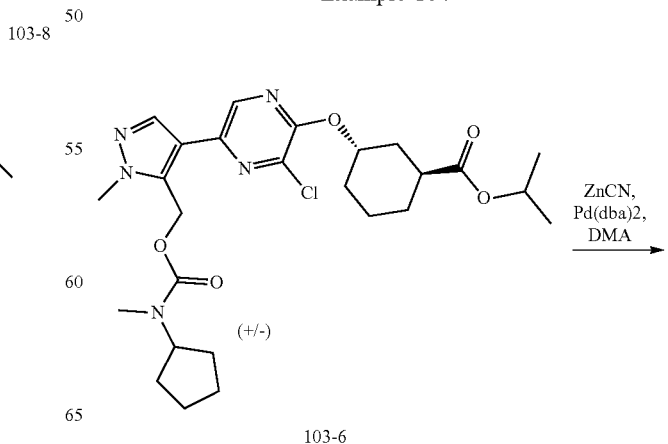

Intermediate 103-8 (120 mg, 0.23 mmol) was dissolved in dichloroethane (5 mL). The reaction system was added with trimethyltin hydroxide (42 mg, 0.23 mmol), reacted at 85° C. for 36 h and filtered, and the filtrate was added with water (15 mL), adjusted to pH 5-6 with diluted hydrochloric acid (1 N), and extracted with dichloromethane (20 mL×3). The organic phases were combined, dried over anhydrous sodium sulfate and concentrated, and the residue was separated by preparative HPLC to give compound 103 (3 mg) in the form of a white solid. LC-MS [M+H]⁺: 475.8.

¹H NMR (400 MHz, DMSO) δ 12.41 (s, 1H), 8.42 (d, J=3.6 Hz, 1H), 7.96 (s, 1H), 5.45-5.41 (m, 3H), 4.45-4.10 (m, 1H), 3.92 (s, 3H), 2.68-2.61 (m, 4H), 2.15-2.05 (m, 1H), 1.90-1.78 (m, 3H), 1.72-1.36 (m, 12H).

Example 104

351

-continued

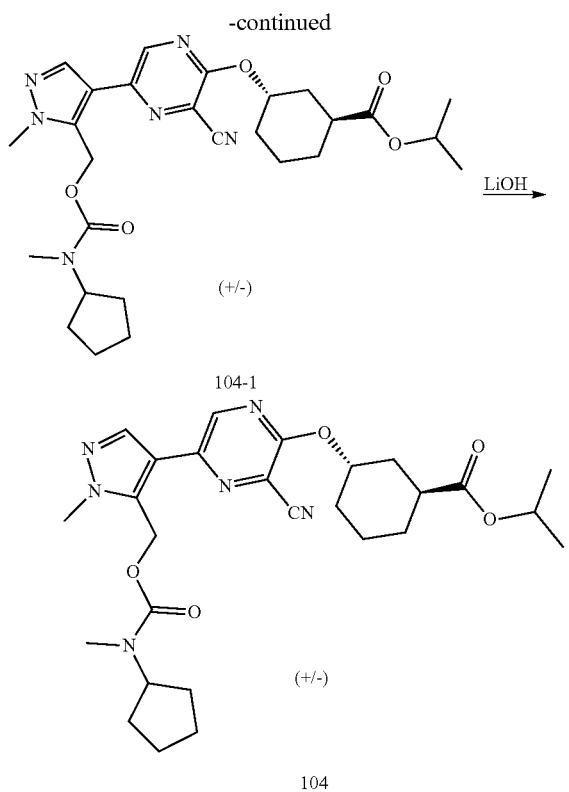

104-1

104

Step (1): Preparation of (+/−)-isopropyl (1S,3S)-3-((3-cyano-5-(5-(((cyclopentyl(methyl)carbamoyl)oxy)methyl)-1-methyl-1H-pyrazol-4-yl)pyrazin-2-yl)oxy)cyclohexane-1-carboxylate

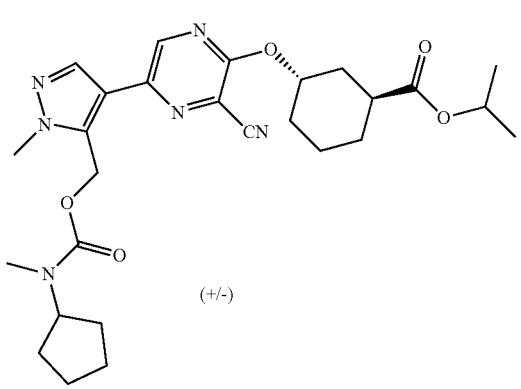

103-6

Intermediate 103-6 (300 mg, 0.56 mmol) was dissolved in N,N-dimethylacetamide (10 mL). The reaction system was added with zinc cyanide (118 mg, 1.01 mmol), tris(dibenzylideneacetone)dipalladium (97 mg, 0.17 mmol) and 1,1'-bis(diphenylphosphine)ferrocene (186 mg, 0.34 mmol), and reacted overnight at 120° C. The reaction system was diluted with water (20 mL) and extracted with ethyl acetate (20 mL×3). The organic phases were combined, dried over anhydrous sodium sulfate, filtered and concentrated, and the residue was separated by silica gel column chromatography

352 to give intermediate 104-1 (150 mg, 51.0% yield) in the form of a yellow oily liquid. LC-MS [M+H]$^+$: 525.1.

Step (2): Preparation of (+/−)-(1S,3S)-3-((3-cyano-5-(5-(((cyclopentyl(methyl)carbamoyl)oxy)methyl)-1-methyl-1H-pyrazol-4-yl)pyrazin-2-yl)oxy)cyclohexane-1-carboxylic Acid

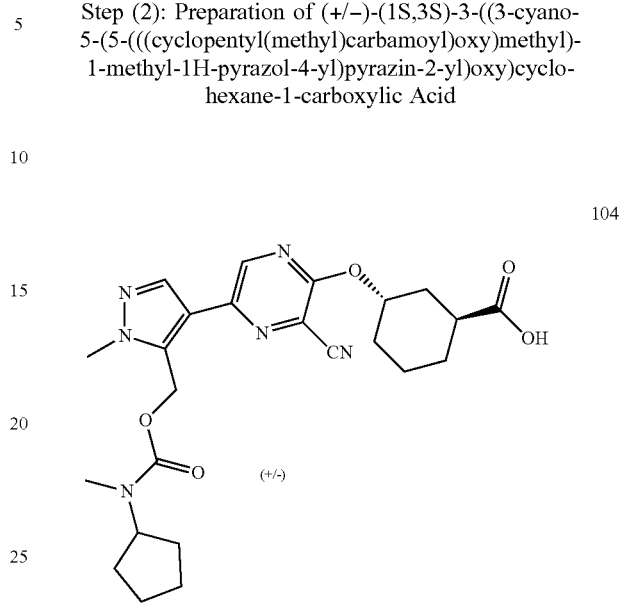

104

Intermediate 104-1 (150 mg, 0.29 mmol) and lithium hydroxide monohydrate (61 mg, 1.45 mmol) were dissolved in tetrahydrofuran (6 mL)/methanol (2 mL)/water (2 mL), and the reaction system was reacted overnight at room temperature. The reaction system was concentrated under reduced pressure, and the residue was added with water (10 mL) and extracted with ether (5 mL×3). The aqueous phase was retained, adjusted to pH 5-6 with diluted hydrochloric acid (1 N), and extracted with dichloromethane (20 mL×3). The organic phases were combined, dried over anhydrous sodium sulfate and concentrated, and the residue was separated by preparative HPLC to give compound 104 (80 mg) in the form of a white solid. LC-MS [M+H]$^+$: 483.2.

$^1$H NMR (400 MHz, MeOD) δ 8.76 (s, 1H), 8.00 (s, 1H), 5.63-5.58 (m, 1H), 5.54 (s, 2H), 4.48-4.33 (m, 1H), 4.01 (s, 3H), 2.86-2.71 (m, 4H), 2.30-2.21 (m, 1H), 2.08-1.93 (m, 3H), 1.89-1.45 (m, 12H).

Example 105

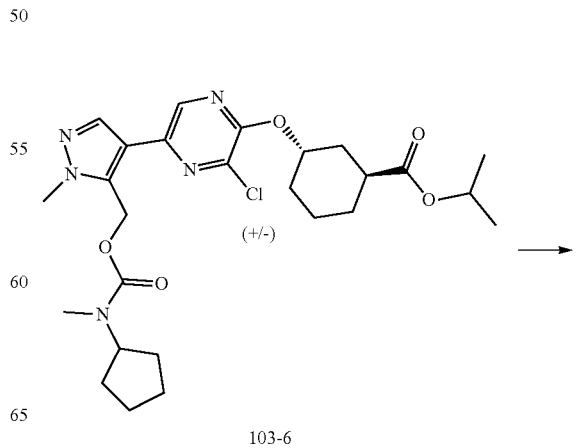

103-6

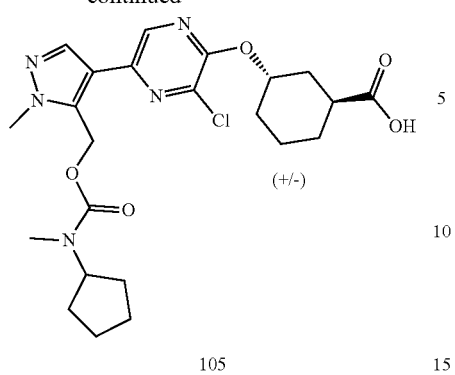

105 (+/-)

Preparation of (1S,3S)-3-chloro-5-(5-((((cyclopentyl (methyl)carbamoyl)oxy)methyl)-1-methyl-1H-pyrazol-4-yl)pyrazin-2-yl)oxy)cyclohexane-1-carboxylic Acid Intermediate 103-6 (150 mg, 0.28 mmol) and lithium hydroxide monohydrate (60 mg, 1.4 mmol) were dissolved in tetrahydrofuran (6 mL)/methanol (2 mL)/water (2 mL), and the reaction system was reacted overnight at room temperature. The reaction system was concentrated under reduced pressure, and the residue was added with water (10 mL) and extracted with ether (15 mL×3). The aqueous phase was retained, adjusted to pH 5-6 with diluted hydrochloric acid (1 N), and extracted with dichloromethane (20 mL×3). The organic phases were combined, dried over anhydrous sodium sulfate and concentrated, and the residue was separated by preparative HPLC to give compound 105 (90 mg, 66.4% yield) in the form of a white solid. LC-MS [M+H]$^+$: 492.1.

$^1$H NMR (400 MHz, MeOD) δ 8.40 (s, 1H), 7.93 (s, 1H), 5.55-5.51 (m, 3H), 4.55-4.15 (m, 1H), 4.00 (s, 3H), 2.85-2.74 (m, 4H), 2.27-2.20 (m, 1H), 2.08-1.95 (m, 2H), 1.92-1.51 (m, 13H).

Example 106

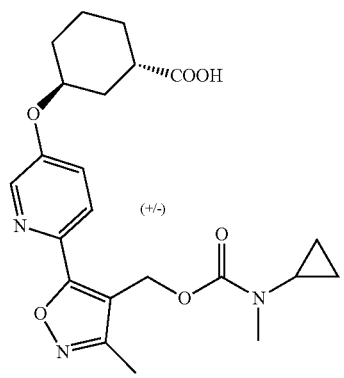

106 (+/-)

Refer to the method in Example 5, LC-MS [M+H]$^+$: 430.05.

Example 107

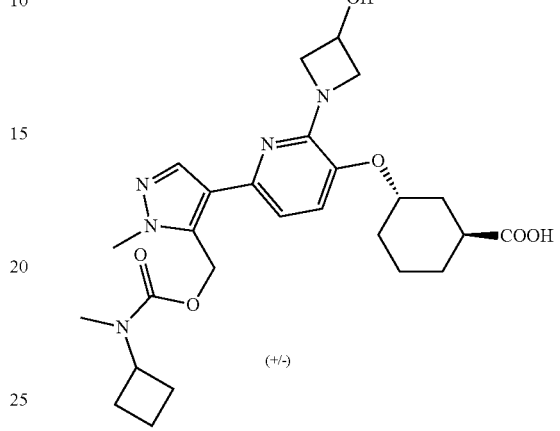

107 (+/-)

Refer to the method in Example 5, LC-MS [M+H]$^+$: 514.21.

Example 108

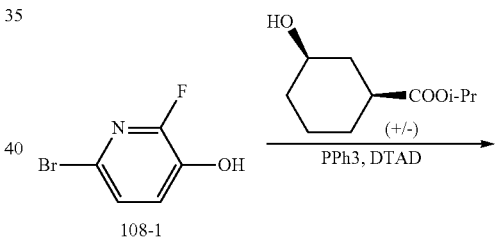

108-1

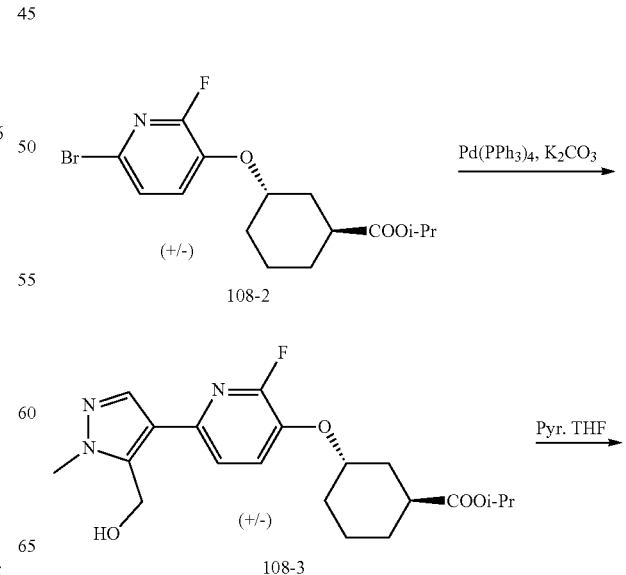

108-2

108-3

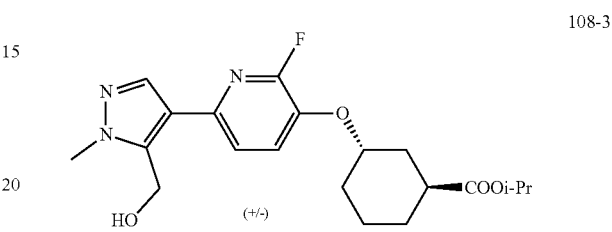

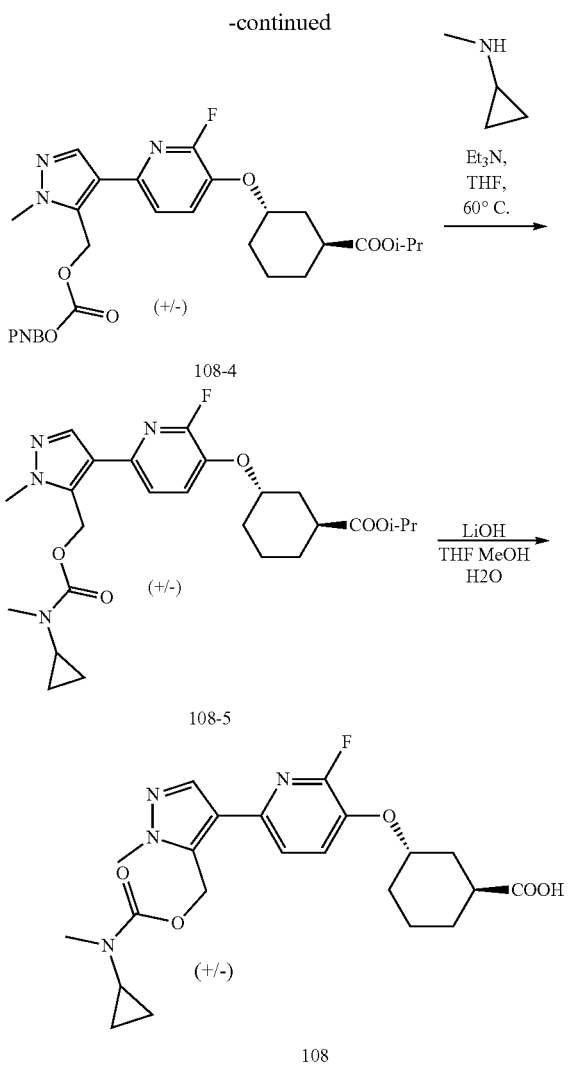

Step (1): Preparation of (+/−)-isopropyl (1S,3S)-3-((6-bromo-2-fluoropyridin-3-yl)oxy)cyclohexane-1-carboxylate 6-bromo-2-fluoropyridin-3-ol (2.02 g, 10.5 mmol) was dissolved in anhydrous tetrahydrofuran (30 mL), and the reaction system was added with (+/−)-isopropyl (1S,3R)-3-hydroxycyclohexane-1-carboxylate (3.9 g, 21.1 mmol), triphenylphosphine (5.5 g, 21.1 mmol), and a solution of di-tert-butyl azodicarboxylate (4.8 g, 21.1 mmol) in anhydrous tetrahydrofuran (10 mL), and the reaction system was reacted at 60° C. overnight under nitrogen atmosphere. The reaction system was quenched with water (100 mL) and extracted with ethyl acetate (60 mL×2). The organic phases were combined, dried over anhydrous sodium sulfate, filtered and concentrated, and the residue was separated by silica gel column chromatography to give intermediate 108-2 (2.5 g, 65% yield) in the form of a colorless oily liquid. LC-MS [M+H]$^+$: 359.8.

Step (2): Preparation of (+/−)-isopropyl (1S,3S)-3-((2-fluoro-6-(5-(hydroxymethyl)-1-methyl-1H-pyrazol-4-yl)pyridin-3-yl)oxy)cyclohexane-1-carboxylate Intermediate 108-2 (2.5 g, 6.9 mmol) was dissolved in dioxane (25 mL) and water (5 mL), and the reaction system was added with (1-methyl-4-(4,4,5,5-tetramethyl-1,3,2-dioxaborolan-2-yl)-1H-pyrazol-5-yl)methanol (42 mL, 6.4 mmol), potassium carbonate (2.1 g, 15.2 mmol) and tetrakis(triphenylphosphine)palladium(0) (797 mg, 0.69 mmol), warmed to 90° C. and stirred overnight under nitrogen atmosphere. Then the reaction system was quenched with H$_2$O (50 mL), filtered and extracted with ethyl acetate (50 mL×3). The organic phases were combined, washed with saturated brine (50 mL), dried over anhydrous sodium sulfate, filtered and concentrated, and the residue was separated by column chromatography to give intermediate 108-3 (1.5 g, 55% yield) in the form of a brown oily liquid. LC-MS [M+H]$^+$: 392.2.

Step (3): Preparation of (+/−)-isopropyl (1S,3S)-3-((2-fluoro-6-(1-methyl-5-((((4-nitrophenoxy)carbonyl) oxy)methyl)-1H-pyrazol-4-yl)pyridin-3-yl)oxy)cyclohexane-1-carboxylate

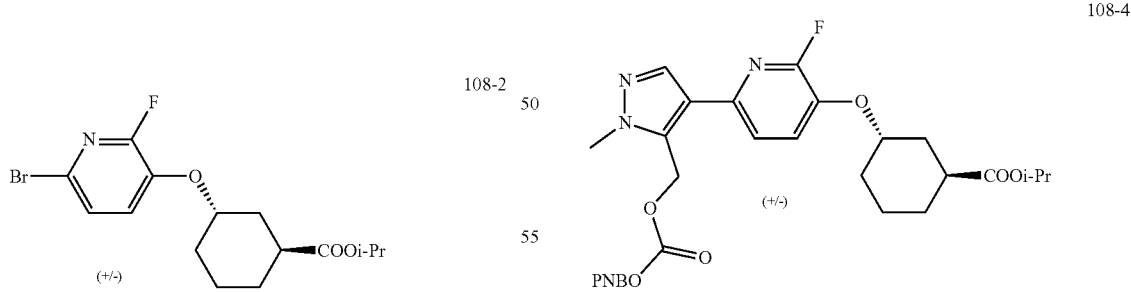

4-nitrophenyl chloroformate (115 mg, 0.57 mmol) and pyridine (60 mg, 0.76 mmol) were dissolved in tetrahydrofuran (5 mL), and the reaction system was cooled to 0° C., added with intermediate 108-3 (150 mg, 0.38 mmol), warmed to room temperature and stirred overnight. The reaction system was quenched with H$_2$O (10 mL) and extracted with ethyl acetate (10 mL×3). The organic phases were combined, washed with saturated brine (20 mL), dried over anhydrous sodium sulfate, filtered and concentrated to give intermediate 108-4 (200 mg, crude) in the form of a pale yellow solid. LC-MS [M+H]⁺: 556.9.

Step (4): Preparation of (+/−)-isopropyl (1S,3S)-3-((6-(5-(((cyclopropyl(methyl)carbamoyl)oxy)methyl)-1-methyl-1H-pyrazol-4-yl)-2-fluoropyridin-3-yl)oxy)cyclohexane-1-carboxylate

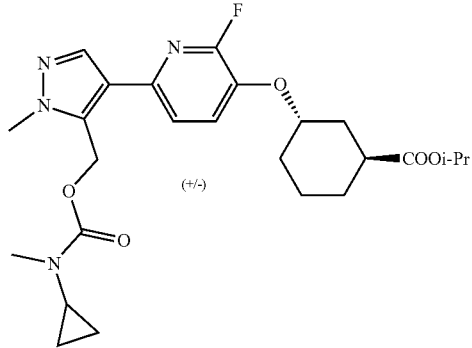

108-5

Intermediate 108-4 (200 mg) was dissolved in anhydrous tetrahydrofuran (5 mL), and the reaction system was added with triethylamine (192 mg, 1.9 mmol), then added with N-methylcyclopropylamine (81 mg, 1.14 mmol), and stirred overnight at room temperature under nitrogen atmosphere. The reaction system was diluted with water (15 mL) and extracted with ethyl acetate (15 mL×2). The organic phases were combined, washed with saturated brine (20 mL×5) until aqueous phase was colorless, dried over anhydrous sodium sulfate, filtered and concentrated, and the residue was separated by column chromatography to give intermediate 108-5 (100 mg, 55% yield over two steps) in the form of a colorless oil. LC-MS [M+H]+: 489.1.

Step (5): Preparation of (+/−) (1S,3S)-3-((6-(5-(((cyclopropyl(methyl)carbamoyl)oxy)methyl)-1-methyl-1H-pyrazol-4-yl)-2-fluoropyridin-3-yl)oxy)cyclohexane-1-carboxylic Acid

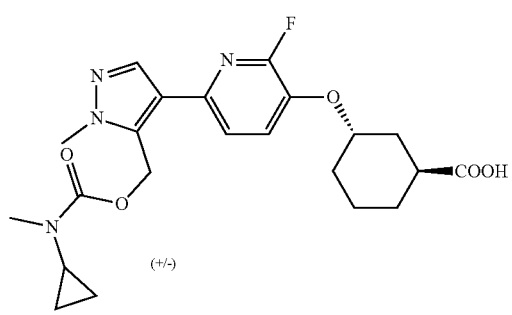

108

Intermediate 108-5 (100 mg, 0.21 mmol) was dissolved in tetrahydrofuran (3 mL)/methanol (1 mL)/water (1 mL), and then lithium hydroxide hydrate (43 mg, 0.8 mmol) was added, and the reaction system was stirred at room temperature for 5 h. Then the reaction system was concentrated, and the residue was diluted with H₂O (10 mL), adjusted to pH 2-3 by adding dropwise diluted hydrochloric acid (1 N), and then extracted with ethyl acetate (10 mL×2). The organic phases were combined, washed with saturated brine (10 mL), dried over anhydrous sodium sulfate, filtered and concentrated, and the residue was separated by column chromatography to give compound 108 (70 mg, 74% yield) in the form of a white solid. LC-MS [M+H]⁺: 446.9.

¹H NMR (400 MHz, MeOD) δ 7.86 (s, 1H), 7.63 (t, J=10.1, 1H), 7.51 (d, J=8.1 Hz, 1H), 5.58 (s, 2H), 4.83-4.73 (m, 1H), 3.99 (s, 3H), 2.87 (s, 3H), 2.85-2.79 (m, 1H), 2.58-2.54 (m, 1H), 2.08-1.63 (m, 8H), 0.68-0.59 (m, 4H).

Example 109

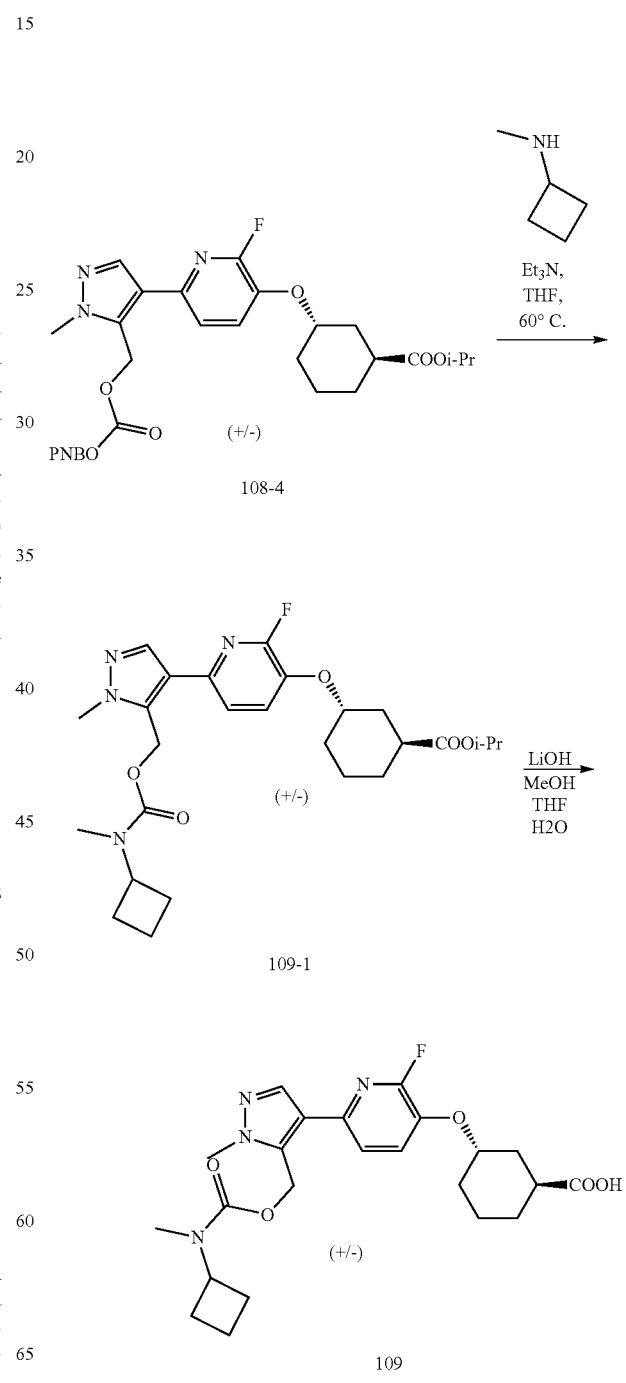

109

Step (1): Preparation of (+/−)-isopropyl (1S,3S)-3-((6-(5-(((cyclobutyl(methyl)carbamoyl)oxy)methyl)-1-methyl-1H-pyrazol-4-yl)-2-fluoropyridin-3-yl)oxy)cyclohexane-1-carboxylate

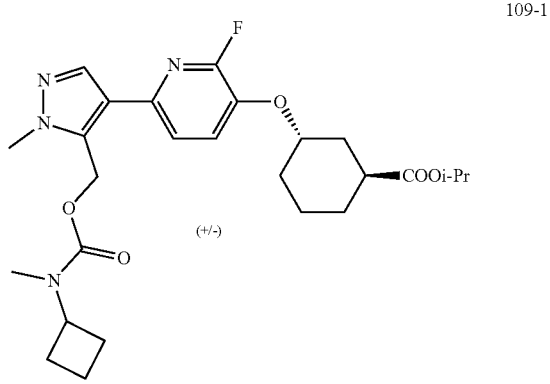

109-1

Intermediate 108-4 (250 mg) was dissolved in anhydrous tetrahydrofuran (5 mL), and the reaction system was added with triethylamine (257 mg, 2.55 mmol), then added with N-methylcyclobutanamine (186 mg, 1.53 mmol), and stirred overnight at room temperature under nitrogen atmosphere. The reaction system was diluted with water (15 mL) and extracted with ethyl acetate (15 mL×2). The organic phases were combined, washed with saturated brine (20 mL×5) until aqueous phase was colorless, dried over anhydrous sodium sulfate, filtered and concentrated, and the residue was separated by silica gel column chromatography to give intermediate 109-1 (144 mg) in the form of a colorless oil. LC-MS [M+H]⁺: 502.9.

Step (2): Preparation of (+/−)-(1S,3S)-3-((6-(5-(((cyclobutyl(methyl)carbamoyl)oxy)methyl)-1-methyl-1H-pyrazol-4-yl)-2-fluoropyridin-3-yl)oxy)cyclohexane-1-carboxylic Acid

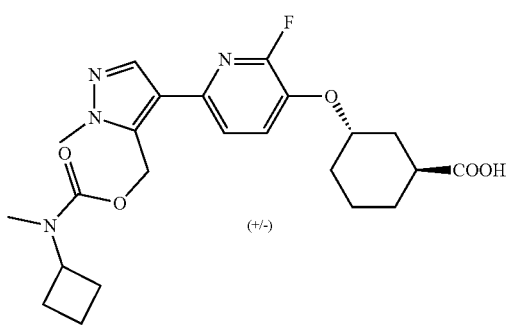

109

Intermediate 109-1 (144 mg, 0.28 mmol) was dissolved in tetrahydrofuran (3 mL)/methanol (1 mL)/water (1 mL), and then lithium hydroxide monohydrate (48 mg, 1.1 mmol) was added, and the reaction system was stirred at room temperature for 5 h. Then the reaction system was concentrated, diluted with water (10 mL), adjusted to pH 2-3 by adding diluted hydrochloric acid (1 N), and then extracted with ethyl acetate (10 mL×2). The organic phases were combined, washed with saturated brine (10 mL), dried over anhydrous sodium sulfate, filtered and concentrated, and the residue was separated by column chromatography to give compound 109 (100 mg, 77% yield) in the form of a white solid. LC-MS [M+H]⁺: 460.8.

¹H NMR (400 MHz, MeOD) δ 7.86 (s, 1H), 7.63 (t, J=10.3, 8.3 Hz, 1H), 7.49 (d, J=8.1 Hz, 1H), 5.56 (s, 2H), 4.78-4.73 (m, 1H), 4.65-4.25 (m, 1H), 3.97 (s, 3H), 2.85 (s, 3H), 2.83-2.78 (m, 1H), 2.14-1.58 (m, 14H).

Example 110

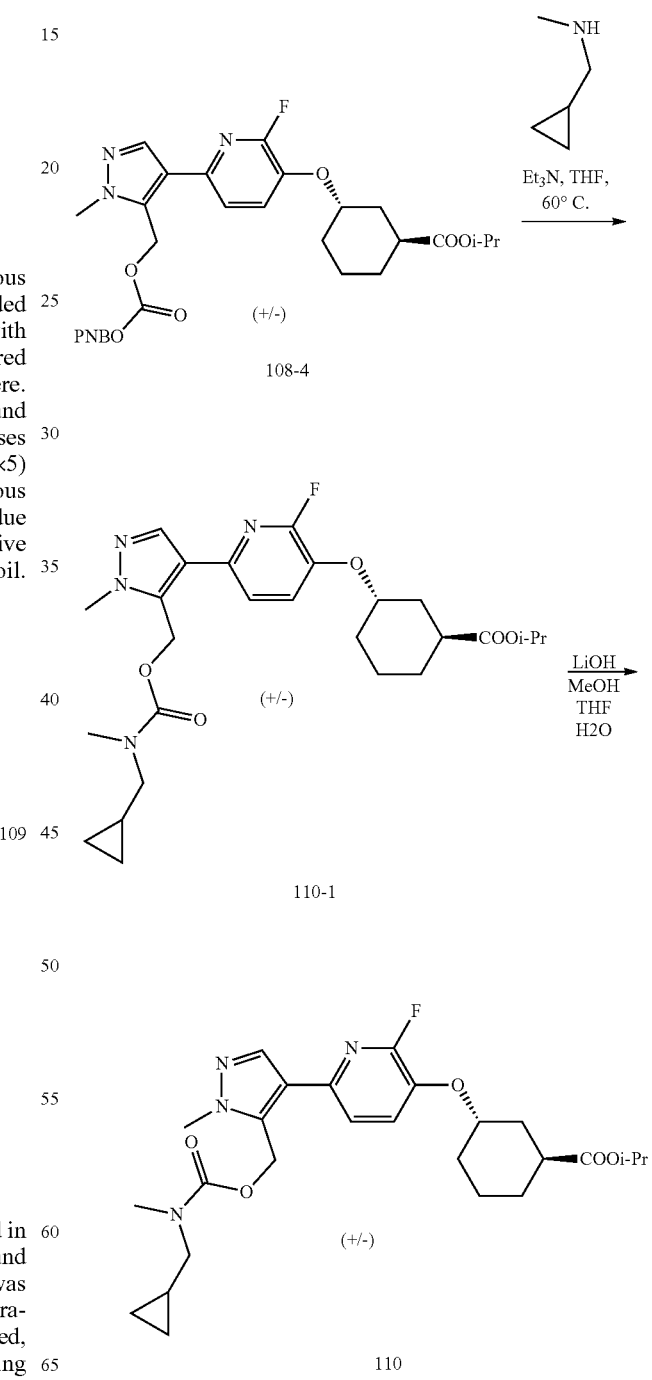

Step (1): Preparation of (+/−)-isopropyl (1S,3S)-3-((6-(5-(((((cyclopropylmethyl)(methyl)carbamoyl)oxy)methyl)-1-methyl-1H-pyrazol-4-yl)-2-fluoropyridin-3-yl)oxy)cyclohexane-1-carboxylate

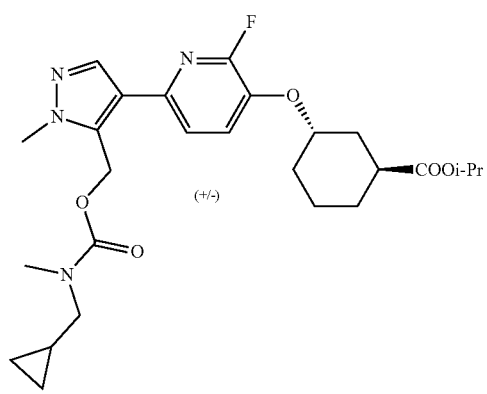

Intermediate 108-4 (250 mg) was dissolved in anhydrous tetrahydrofuran (5 mL), and the reaction system was added with triethylamine (257 mg, 2.55 mmol) and 1-cyclopropyl-N-methylmethylamine (186 mg, 1.53 mmol), and stirred overnight at room temperature under nitrogen atmosphere. The reaction system was diluted with water (15 mL) and extracted with ethyl acetate (15 mL×2). The organic phases were combined, washed with saturated brine (20 mL×5) until aqueous phase was colorless, dried over anhydrous sodium sulfate, filtered and concentrated, and the residue was separated by column chromatography (PE/EA=8/1) to give intermediate 110-1 (110 mg) in the form of a colorless oil. LC-MS [M+H]⁺: 502.9.

Step (2): Preparation of (+/−)-(1S,3S)-3-((6-(5-(((((cyclopropylmethyl)(methyl)carbamoyl)oxy)methyl)-1-methyl-1H-pyrazol-4-yl)-2-fluoropyridin-3-yl)oxy)cyclohexane-1-carboxylic Acid

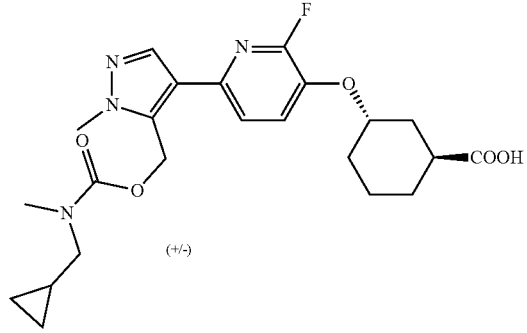

Intermediate 110-1 (110 mg, 0.22 mmol) was dissolved in tetrahydrofuran (3 mL)/methanol (1 mL)/water (1 mL), and then lithium hydroxide hydrate (37 mg, 0.88 mmol) was added, and the reaction system was stirred at room temperature for 5 h. Then the reaction system was concentrated, diluted with H₂O (10 mL), adjusted to pH 2-3 by adding diluted hydrochloric acid (1 N), and then extracted with ethyl acetate (10 mL×2). The organic phases were combined, washed with saturated brine (10 mL), dried over anhydrous sodium sulfate, filtered and concentrated, and the residue was separated by column chromatography to give compound 110 (70 mg, 69% yield) in the form of a white solid. LC-MS [M+H]⁺: 460.9.

¹H NMR (400 MHz, MeOD) δ 7.87 (s, 1H), 7.62 (t, J=10.3 H 1H), 7.49 (d, J=8.2 Hz, 1H), 5.57 (s, 2H), 4.78-4.73 (m, 1H), 3.98 (s, 3H), 3.20-3.07 (m, 2H), 2.98-2.90 (m, 3H), 2.86-2.78 (m, 1H), 2.14-1.60 (m, 8H), 1.06-0.86 (m, 1H), 0.55-0.09 (m, 4H).

Example 111

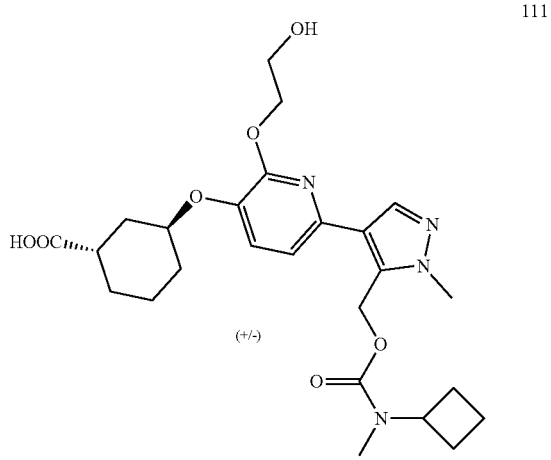 [SMILES: CN(C(=O)OCc1c(-c2ccc(O[C@H]3CCC[C@H](C(=O)O)C3)c(OCCO)n2)cnn1C)C1CCC1]

Refer to the method in Example 11, LC-MS [M+H]⁺: 503.19.

Example 112

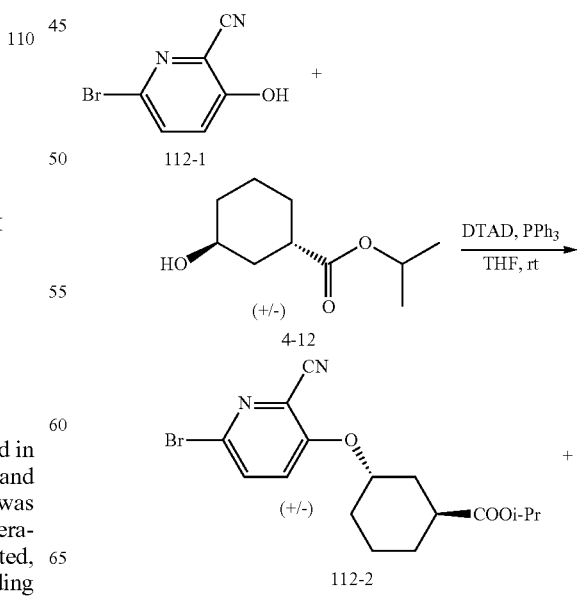

363

-continued

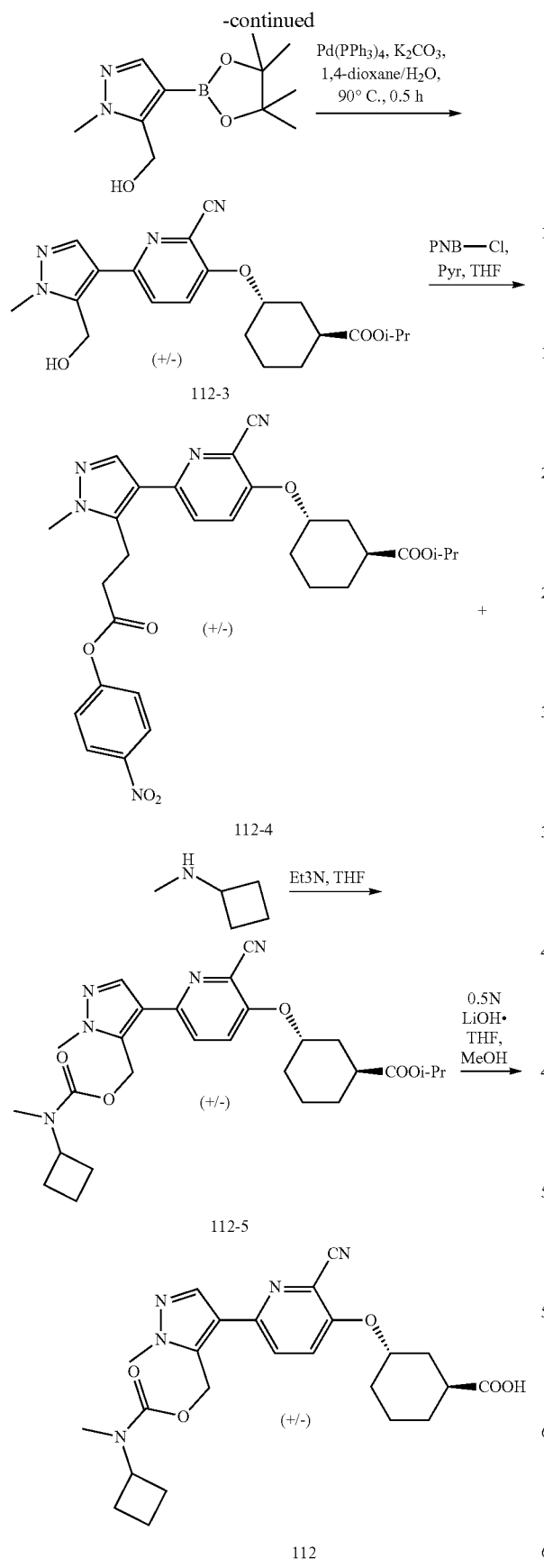

112-3

112-4

112-5

112

364

Step (1): Preparation of (+/−)-isopropyl (1S,3S)-3-((6-bromo-2-cyanopyridin-3-yl)oxy)cyclohexane-1-carboxylate

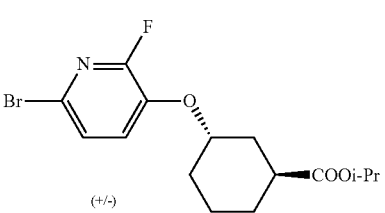

112-2

6-bromo-3-hydroxypicolinonitrile (600 mg, 3.01 mmol), (+/−)-isopropyl 3-hydroxycyclohexane-1-carboxylate (1.12 g, 6.03 mmol) and triphenylphosphine (1.58 g, 6.03 mmol) were dissolved in THF (30 mL) under nitrogen atmosphere, and the reaction system was slowly added dropwise with a solution of DTAD (1.39 g, 6.03 mmol) in THF (5 mL), and stirred overnight at room temperature. The reaction system was concentrated, and the residue was purified by silica gel column chromatography to give intermediate 112-2 (870 mg, 79% yield) in the form of a yellow oil. LC-MS [M+H]⁺: 367; 369.

Step (2) Preparation of (+/−)-isopropyl (1S,3S)-3-((2-cyano-6-(5-(hydroxymethyl)-1-methyl-1H-pyrazol-4-yl)pyridin-3-yl)oxy)cyclohexane-1-carboxylate

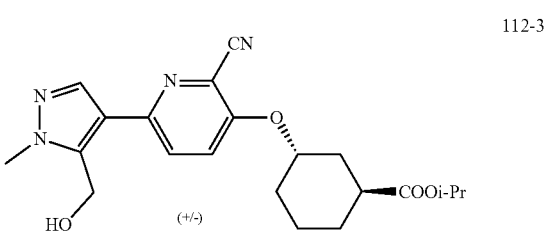

112-3

Intermediate 112-2 (2.0 g, 5.44 mmol), (1-methyl-4-(4,4,5,5-tetramethyl-1,3,2-dioxaborolan-2-yl)-1H-pyrazol-5-yl)methanol (1.95 g, 8.17 mmol) and tetrakis(triphenylphosphine)palladium(0) (0.63 g, 0.54 mmol) were dissolved in 1,4-dioxane (20 mL). The reaction system was added with potassium carbonate (1.65 g, 11.98 mmol) and water (4 mL), and reacted overnight at 80° C. under nitrogen atmosphere. The reaction system was filtered, and the filtrate was diluted with ethyl acetate (40 mL), washed with saturated brine (30 mL×2), dried over anhydrous sodium sulfate, filtered and concentrated to give a crude product, and the crude product was purified by silica gel column chromatography to give intermediate 112-3 (650 mg, 29.6% yield) in the form of a yellow oily liquid. LC-MS [M+H]⁺: 399.

Step (3): Preparation of (+/−)-isopropyl (1S,3S)-3-((2-cyano-6-(1-methyl-5-((((4-nitrophenoxy)carbonyl) oxy)methyl)-1H-pyrazol-4-yl)pyridin-3-yl)oxy) cyclohexane-1-carboxylate

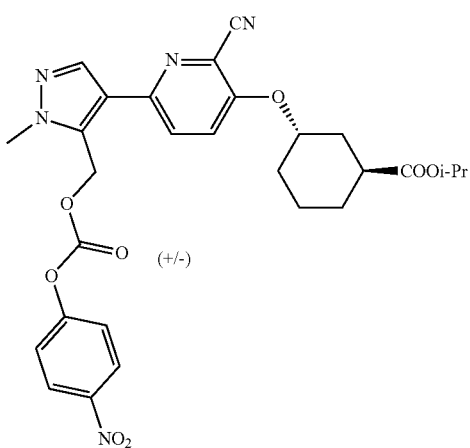

112-4

4-nitrophenyl chloroformate (364 mg, 1.8 mmol) was dissolved in tetrahydrofuran (20 mL) under nitrogen atmosphere, and the reaction system was added dropwise with a solution of intermediate 112-3 (600 mg, 1.5 mmol) and pyridine (186 mg, 3.01 mmol) in tetrahydrofuran (10 mL) at 0° C. and stirred overnight at room temperature for 3 h. The reaction system was directly concentrated to give a crude product, and the crude product was purified by silica gel column chromatography to give intermediate 112-4 (640 mg, 71.6% yield) in the form of a white solid. LC-MS [M+H]$^+$: 564.

Step (4): Preparation of (+/−)-isopropyl (1S,3S)-3-((2-cyano-6-(5-(((cyclobutyl(methyl)carbamoyl) oxy)methyl)-1-methyl-1H-pyrazol-4-yl)pyridin-3-yl) oxy)cyclohexane-1-carboxylate

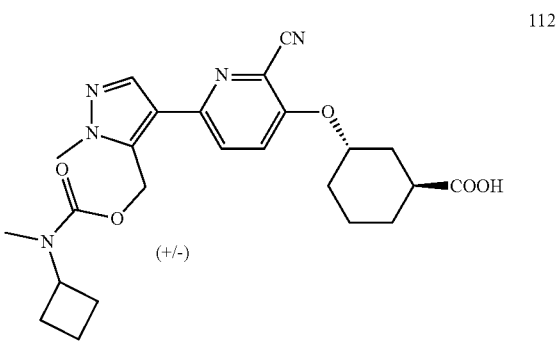 [SMILES: CN(C(=O)OCc1c(-c2ccc(O[C@H]3CCC[C@H](C(=O)O)C3)c(C#N)n2)cnn1C)C1CCC1]

112-5

Intermediate 112-4 (300 mg, 0.53 mmol) and triethylamine (107 mg, 1.06 mmol) were added to anhydrous tetrahydrofuran (20 mL), and the reaction system was added with N-methylcyclobutylamine hydrochloride (72 mg, 0.58 mmol), and reacted overnight at room temperature. The reaction system was diluted with ethyl acetate (40 mL) and washed with water (20 mL×2), aqueous NaOH solution (10 mL×5, 1 N) and saturated brine (20 mL). The organic phases were dried over anhydrous sodium sulfate, filtered and concentrated, and the residue was separated by column chromatography to give intermediate 112-5 (280 mg, 92.9% yield) in the form of a yellow solid. LC-MS [M+H]$^+$: 510.

Step (5): Preparation of (+/−)-(1S,3S)-3-((2-cyano-6-(5-(((cyclobutyl(methyl)carbamoyl)oxy)methyl)-1-methyl-1H-pyrazol-4-yl)pyridin-3-yl)oxy)cyclohexane-1-carboxylic Acid

112

Intermediate 112-5 (200 mg, 0.39 mmol) was dissolved in tetrahydrofuran (9 mL), and the reaction system was added with lithium hydroxide monohydrate (83 mg, 1.96 mmol)/methanol (3 mL)/water (3 mL), and stirred overnight at room temperature. The reaction system was diluted with water (15 mL), concentrated under reduced pressure, adjusted to pH 5 with diluted hydrochloric acid (1 N), and extracted with dichloromethane (10 mL×2). The organic phases were combined, washed with saturated brine (10 mL), dried over anhydrous sodium sulfate, filtered and concentrated, and the residue was separated by column chromatography (DCM/MeOH=20/1) to give compound 112 (120 mg, 58.8% yield) in the form of a white solid. LC-MS [M+H]$^+$: 468.

$^1$H NMR (400 MHz, MeOD) δ 7.92 (s, 1H), 7.90 (d, J=9.0 Hz, 1H), 7.76 (d, J=9.1 Hz, 1H), 5.56 (s, 2H), 4.98-4.92 (m, 1H), 4.68-4.25 (m, 1H), 4.00 (s, 3H), 2.92-2.78 (m, 4H), 2.12-1.65 (m, 14H).

Example 113

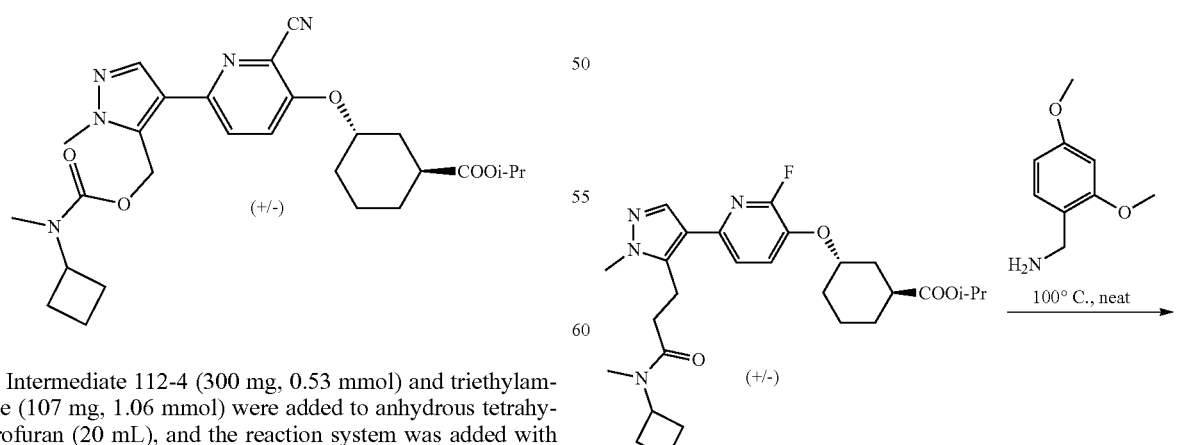

113-1

367

-continued

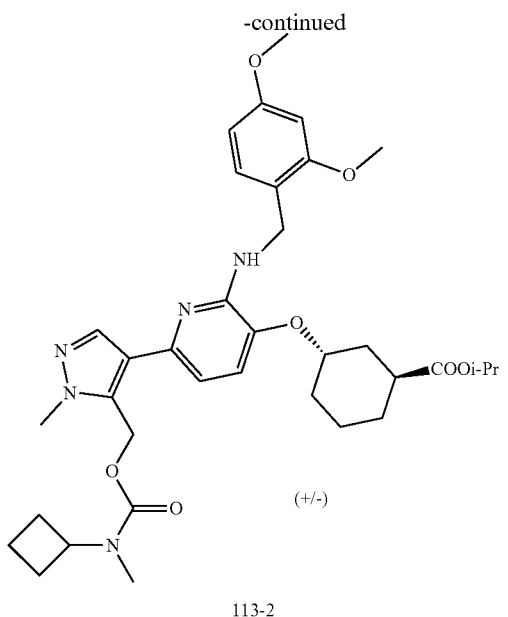

113-2

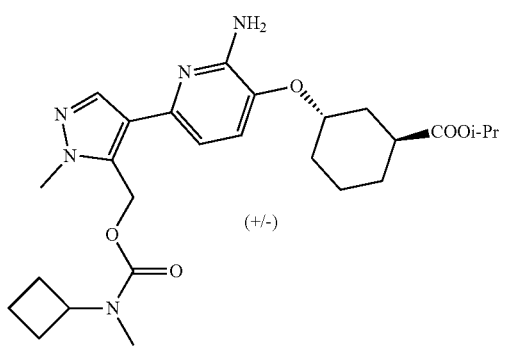

113-3

368

Step (1): Preparation of (+/−)-isopropyl (1S,3S)-3-((6-(5-(((cyclobutyl(methyl)carbamoyl)oxy)methyl)-1-methyl-1H-pyrazol-4-yl)-2-((2,4-dimethoxybenzyl)amino)pyridin-3-yl)oxy)cyclohexane-1-carboxylate

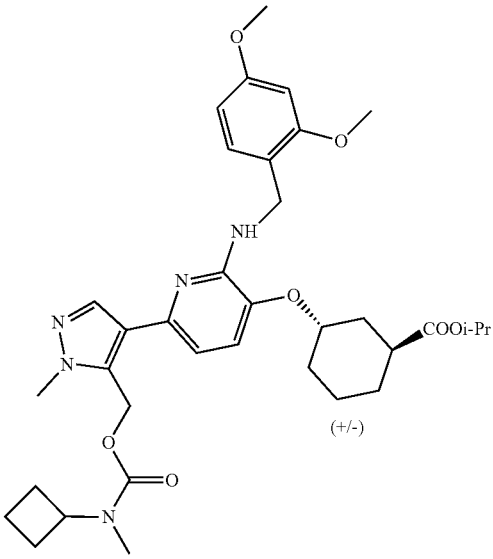

113-2

Intermediate 113-1 (250 mg, 0.49 mol) (prepared by referring to Example 13) was dissolved in 2,4-dimethoxybenzylamine (3.5 mL), and the reaction system was reacted at 100° C. for 8 h under nitrogen atmosphere. Then the reaction system was diluted with water (20 mL) and extracted with ethyl acetate (20 mL×2). The organic phases were combined, washed with saturated brine (20 mL), dried over anhydrous sodium sulfate and concentrated, and the residue was separated by column chromatography to give intermediate 113-2 (200 mg, 62% yield) in the form of a yellow oily liquid. LC-MS [M+H]⁺: 649.9.

Step (2): Preparation of (+/−)-isopropyl (1S,3S)-3-((2-amino-6-(5-(((cyclobutyl(methyl)carbamoyl)oxy)methyl)-1-methyl-1H-pyrazol-4-yl)pyridin-3-yl)oxy)cyclohexane-1-carboxylate

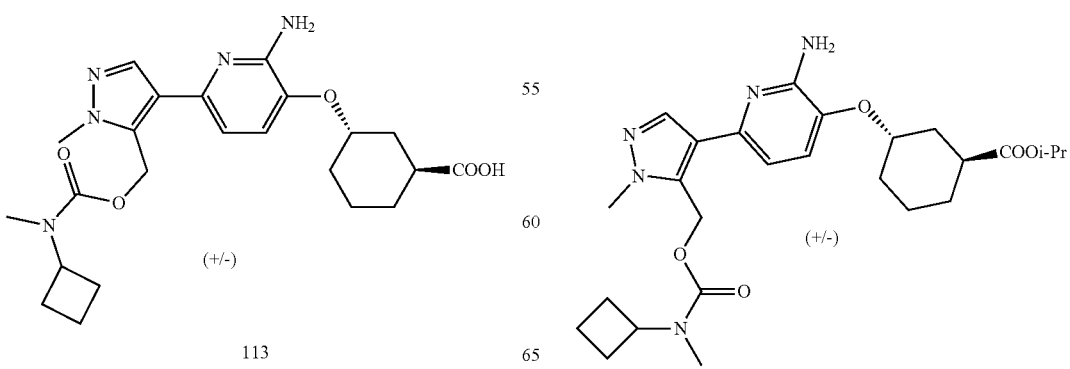

113
113-3

Intermediate 113-2 (200 mg, 0.31 mmol) was dissolved in dichloromethane (3 mL), and the reaction system was added with trifluoroacetic acid (1 mL), and reacted at room temperature for 3 h. The reaction system was concentrated under reduced pressure, and the residue was diluted with water (10 mL), and extracted with dichloromethane (10 mL). The aqueous phase was retained, adjusted to pH 8 with aqueous sodium hydroxide solution (1 N), and extracted with dichloromethane (10 mL×2). The organic phases were combined, wash with saturated brine (20 mL), dried over anhydrous sodium sulfate and concentrated, and the residue was separated by column chromatography to give intermediate 113-3 (130 mg, 84% yield) in the form of a yellow oily liquid. LC-MS [M+H]$^+$: 499.9.

Step (3): Preparation of (+/−)-(1S,3S)-3-((2-amino-6-(5-(((cyclobutyl(methyl)carbamoyl)oxy)methyl)-1-methyl-1H-pyrazol-4-yl)pyridin-3-yl)oxy)cyclohexane-1-carboxylic Acid

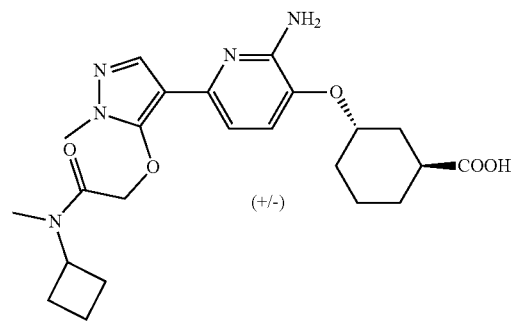

113

Intermediate 113-3 (130 mg, 0.26 mmol) was dissolved in tetrahydrofuran (3 mL)/methanol (1 mL)/water (1 mL), and the reaction system was added with lithium hydroxide monohydrate (43 mg, 1.04 mmol) and reacted at room temperature for 10 h. The reaction system was concentrated under reduced pressure, and the residue was added with water (5 mL) and extracted with ether (5 mL×2). The aqueous phase was retained, adjusted to pH 4 with diluted hydrochloric acid (1 N), and extracted with dichloromethane (10 mL×3). The organic phases were combined, dried over anhydrous sodium sulfate and concentrated, and the residue was separated by preparative HPLC to give compound 113 (60 mg, 50% yield) in the form of a white solid. LC-MS [M+H]$^+$: 457.9.

$^1$H NMR (400 MHz, MeOD) δ 7.74 (s, 1H), 7.17 (d, J=8.2 Hz, 1H), 6.84 (d, J=8.1 Hz, 1H), 5.52 (s, 2H), 4.75-4.70 (m, 1H), 4.68-4.25 (m, 1H), 3.96 (s, 3H), 2.87-2.81 (m, 4H), 2.16-1.63 (m, 14H).

Example 114

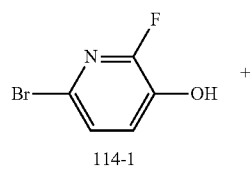

114-1

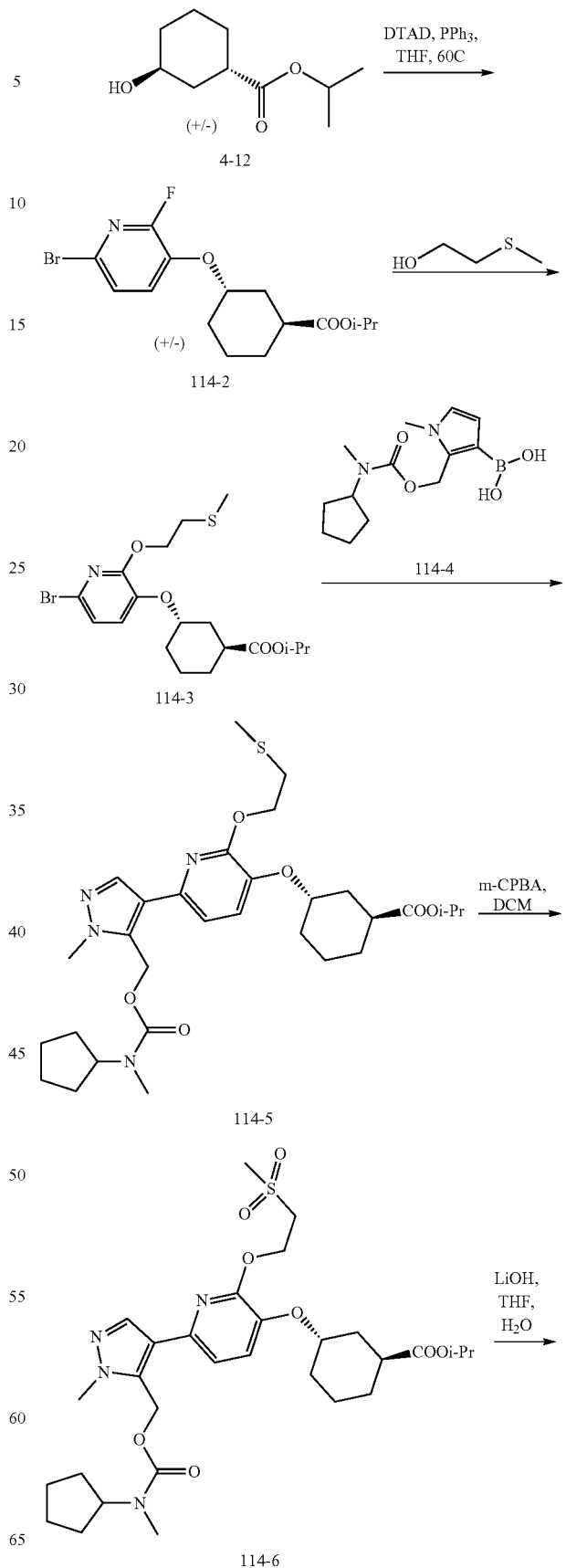

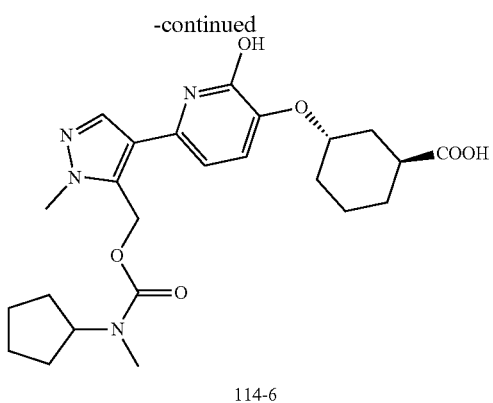

114-6

Step (1): Preparation of (+/−)-isopropyl (1S,3S)-3-((6-bromo-2-fluoropyridin-3-yl)oxy)cyclohexane-1-carboxylate

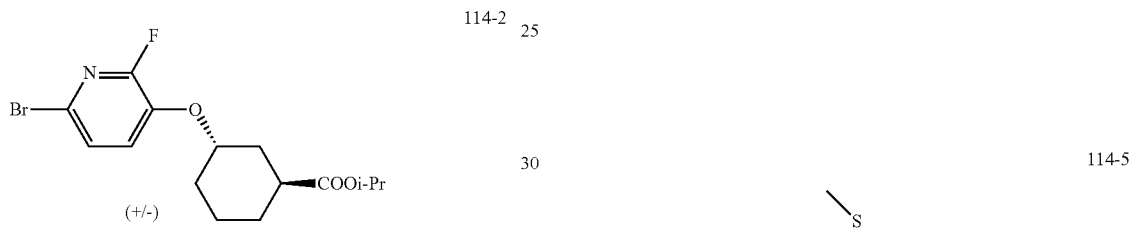

114-2

6-bromo-2-fluoropyridin-3-ol (2.0 g, 10.5 mmol), triphenylphosphine (5.5 g, 21.0 mmol) and (+/−)-isopropyl (1S, 3R)-3-hydroxycyclohexane-1-carboxylate (3.9 g, 21 mmol) were dissolved in tetrahydrofuran (20 mL). The reaction system was stirred at room temperature, added dropwise with a solution of DTAD (4.8 g, 21.0 mmol) in tetrahydrofuran (20 mL), reacted overnight at 60° C., added with water (100 mL) to quench the reaction and extracted with ethyl acetate (100 mL×3). The organic phases were combined, washed with saturated brine (100 mL), dried over anhydrous sodium sulfate and concentrated, and the residue was separated by column chromatography to give intermediate 114-2 (2.5 g, 66.3% yield) in the form of a white solid. LC-MS [M+H]⁺: 359.6.

Step (2): Preparation of (+/−)-isopropyl (1S,3S)-3-((6-bromo-2-(2-(methylthio)ethoxy)pyridin-3-yl)oxy)cyclohexane-1-carboxylate

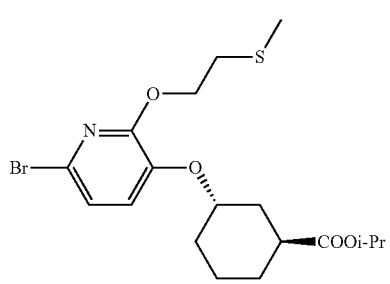

114-3

2-(methylthio)ethanol (387 mg, 4.2 mmol) and intermediate 114-2 (1.0 g, 2.8 mmol) were dissolved in anhydrous tetrahydrofuran (10 mL), and the reaction system was added with potassium tert-butoxide (471 mg, 4.2 mmol), and reacted at room temperature for 1 h. Then the reaction system was diluted with water (25 mL) and extracted with ethyl acetate (30 mL×3). The organic phases were combined, washed with saturated brine (30 mL), dried over anhydrous sodium sulfate and concentrated, and the residue was separated by column chromatography to give intermediate 114-3 (500 mg, 41.7% yield) in the form of a yellow oily liquid. LC-MS [M+H]⁺: 431.6.

Step (3): Preparation of (+/−)-isopropyl (1S,3S)-3-((6-(5-(((cyclopentyl(methyl)carbamoyl)oxy)methyl)-1-methyl-1H-pyrazol-4-yl)-2-(2-(methylthio)ethoxy)pyridin-3-yl)oxy)cyclohexane-1-carboxylate 114-5

Intermediate 114-3 (500 mg, 1.16 mmol), (5-(((cyclopentyl(methyl)carbamoyl)oxy)methyl)-1-methyl-1H-pyrazol-4-yl)boronic acid (487 mg, 1.73 mmol) and tetrakis(triphenylphosphine)palladium(0) (134 mg, 0.12 mmol) were dissolved in 1,4-dioxane (8 mL), and the reaction system was added with potassium carbonate (479 mg, 3.47 mmol) and water (2 mL), and reacted overnight at 90° C. under nitrogen atmosphere for 1 h. The reaction system was filtered, then diluted with water (20 mL) and extracted with ethyl acetate (30 mL×2). The organic phases were combined, dried over anhydrous sodium sulfate, filtered and concentrated, and the residue was separated by column chromatography (PE/EA=5/1) to give intermediate 114-5 (450 mg, 66.0% yield) in the form of a yellow oil. LC-MS [M+H]⁺: 588.7.

Step (4): Preparation of (+/−)-isopropyl (1S,3S)-3-((6-(5-(((cyclopentyl(methyl)carbamoyl)oxy)methyl)-1-methyl-1H-pyrazol-4-yl)-2-(2-(methylsulfonyl)ethoxy)pyridin-3-yl)oxy)cyclohexane-1-carboxylate

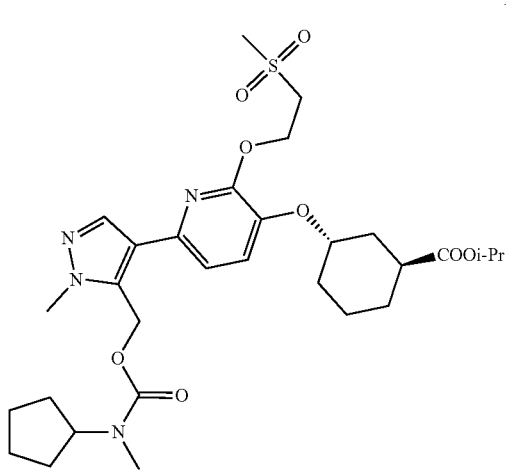

114-6

Intermediate 114-5 (450 mg, 0.76 mmol) was dissolved in anhydrous dichloromethane (10 mL). The reaction system was cooled to 0° C., added with m-chloroperoxybenzoic acid (264 mg, 1.53 mmol), reacted at 0° C. for 1 h and concentrated, and the residue was separated by column chromatography (DCM/MeOH=10/1) to give intermediate 114-6 (200 mg, 42.5% yield) in the form of a yellow solid. LC-MS [M+H]⁺: 620.8.

Step (5): Preparation of (+/−)-(1S,3S)-3-((6-(5-(((cyclopentyl(methyl)carbamoyl)oxy)methyl)-1-methyl-1H-pyrazol-4-yl)-2-hydroxypyridin-3-yl)oxy)cyclohexane-1-carboxylic Acid

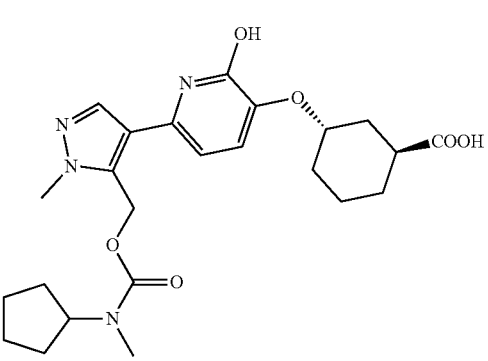

114

Intermediate 114-6 (100 mg, 0.16 mmol) was dissolved in tetrahydrofuran (6 mL), and the reaction system was added with lithium hydroxide (34 mg, 0.80 mmol)/methanol (2 mL)/water (2 mL), and stirred overnight at room temperature. The reaction system was diluted with water (10 mL), adjusted to pH 5 with diluted hydrochloric acid (1 N) and extracted with dichloromethane (20 mL×2). The organic phases were combined, washed with saturated brine (20 mL), dried over anhydrous sodium sulfate, filtered and concentrated, and the residue was separated by preparative HPLC to give compound 114 (10 mg) in the form of a white solid. LC-MS [M+H]⁺: 472.8. ¹H NMR (400 MHz, MeOD) δ 7.69 (s, 1H), 7.13 (d, J=7.8 Hz, 1H), 6.41 (d, J=7.7 Hz, 1H), 5.31 (s, 2H), 4.74-4.67 (m, 1H), 4.61-4.34 (m, 1H), 4.00 (s, 3H), 2.97-2.88 (m, 1H), 2.82 (s, 3H), 2.14-2.06 (m, 1H), 1.98-1.89 (m, 3H), 1.98-1.52 (m, 12H).

Example 115

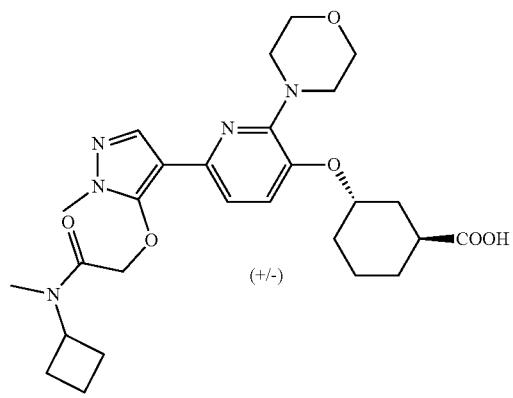

115

Refer to the method in Example 100, LC-MS [M+H]⁺: 528.21.

Example 116

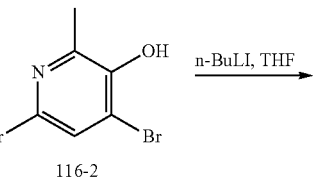

116-1

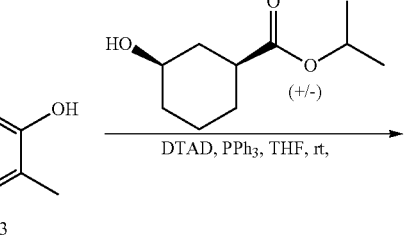

116-2

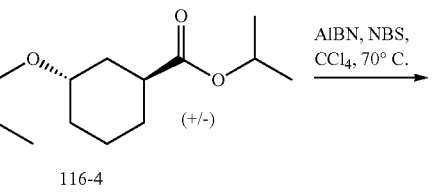

116-3

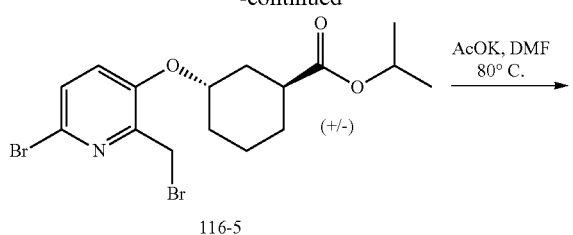
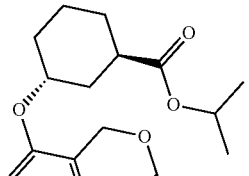
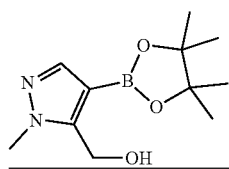
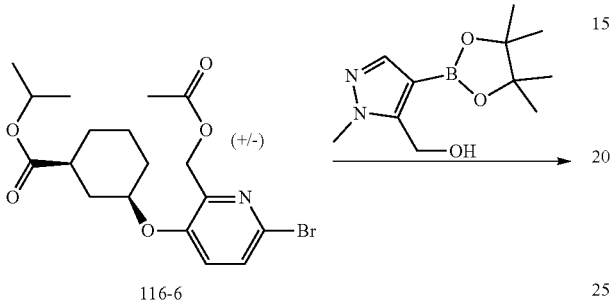
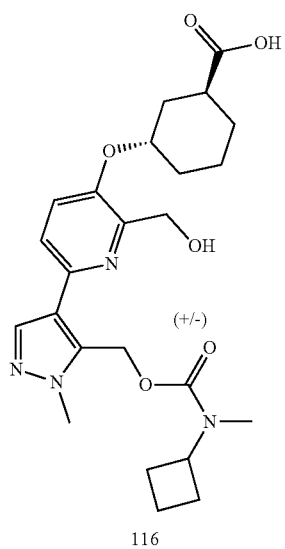 [SMILES: CN(C(=O)OCc1c(-c2ccc(O[C@H]3CCC[C@H](C(=O)O)C3)c(CO)n2)cnn1C)C1CCC1]
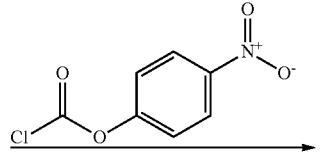
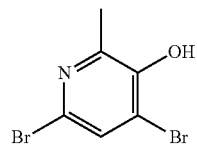

Step (1): Preparation of 4,6-dibromo-2-methylpyridin-3-ol 2-methylpyridin-3-ol (25 g, 0.23 mol) was dissolved in acetonitrile (250 mL). The reaction system was stirred at room temperature, and slowly added dropwise with a solution of NBS (81.9 g, 0.46 mol) in acetonitrile (90 mL), then heated to reflux, reacted for 1.5 h and concentrated, and the residue was separated by column chromatography to give intermediate 116-2 (42 g, 56.52% yield) in the form of a yellow solid. LC-MS [M+H]$^+$: 213.8.

Step (2): Preparation of 6-bromo-2-methylpyridin-3-ol

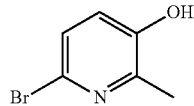

116-3

Intermediate 116-2 (42 g, 0.16 mol) was dissolved in tetrahydrofuran (500 mL) under nitrogen atmosphere, and the reaction system was cooled to −78° C., added dropwise with n-BuLi (136 mL, 0.33 mol), and reacted at −78° C. for 2 h. The reaction system was quenched with water (500 mL), adjusted to pH 6 with hydrochloric acid (2 N) and extracted with dichloromethane (300 mL×3). The organic phases were combined, washed with saturated brine (300 mL), dried over anhydrous sodium sulfate, filtered and concentrated, and the residue was separated by column chromatography to give intermediate 116-3 (22 g, 73.5% yield) in the form of a white solid. LC-MS [M+H]$^+$: 187.9.

Step (3): Preparation of (+/−)-isopropyl (1S,3S)-3-((6-bromo-2-methylpyridin-3-yl)oxy)cyclohexane-1-carboxylate

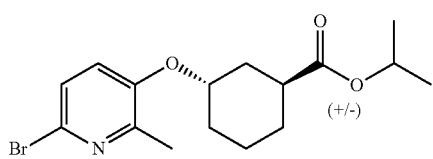

116-4

Intermediate 116-3 (20.0 g, 0.11 mol), triphenylphosphine (56.1 g, 0.22 mol), and (+/−)-isopropyl (1S,3R)-3-hydroxy-cyclohexane-1-carboxylate (39.8 g, 0.21 mol) were dissolved in tetrahydrofuran (200 mL) under nitrogen atmosphere. The reaction system was stirred at room temperature, added dropwise with a solution of DTAD (49.2 g, 0.21 mol) in tetrahydrofuran (100 mL), and stirred at room temperature for 12 h. Then the reaction system was added with water (400 mL) to quench the reaction and extracted with ethyl acetate (300 mL×3). The organic phases were combined, washed with saturated brine (300 mL), dried over anhydrous sodium sulfate and concentrated, and the residue was separated by column chromatography to give intermediate 116-4 (17.0 g, 44.7% yield) in the form of a white solid.

Step (4): Preparation of (+/−)-isopropyl (1S,3S)-3-((6-bromo-2-(bromomethyl) pyridin-3-yl)oxy)cyclohexane-1-carboxylate

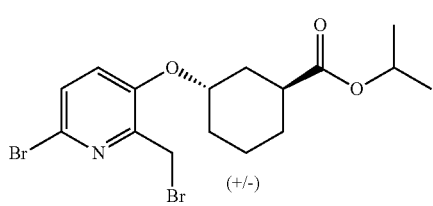

116-5

A solution of intermediate 116-4 (2.0 g, 5.6 mmol) and N-bromosuccinimide (1.5 g, 8.4 mmol) in carbon tetrachloride (30 mL) was added with azobisbutyronitrile (1.9 g, 11.2 mmol) under nitrogen atmosphere, and the reaction system was stirred in an oil bath at 70° C. for 2 h. The reaction system was filtered, and the filtrate was added with water (50 mL) and extracted with dichloromethane (20 mL×3). The organic phases were combined, washed with saturated brine (10 mL), dried over anhydrous sodium sulfate, filtered and concentrated, and the residue was purified by column chromatography to give intermediate 116-5 (2.7 g, 99% yield) in the form of a white solid. MS [M+H]$^+$=435.6.

Step (5): Preparation of (+/−)-isopropyl (1S,3R)-3-((2-(acetoxymethyl)-6-bromopyridin-3-yl)oxy)cyclohexane-1-carboxylate

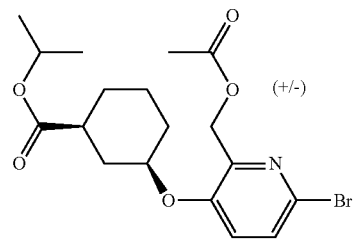

116-6

Potassium acetate (1.8 g, 18.6 mmol) was added to a solution of intermediate 116-5 (2.7 g, 6.2 mmol) in DMF (25 mL) under nitrogen atmosphere, and the reaction system was stirred in an oil bath at 80° C. for 5 h. The reaction system was diluted with water (100 mL) and extracted with ethyl acetate (30 mL×3). The organic phases were combined, washed with saturated brine (80 mL), dried over anhydrous sodium sulfate, and concentrated by rotary evaporation, and the residue was purified by column chromatography to give intermediate 116-6 (1.7 g, 65% yield) in the form of a white solid. MS [M+H]$^+$=415.7.

Step (6): Preparation of (+/−)-isopropyl (1S,3S)-3-((2-(acetoxymethyl)-6-(5-(hydroxymethyl)-1-methyl-1H-pyrazol-4-yl)pyridin-3-yl)oxy)cyclohexane-1-carboxylate

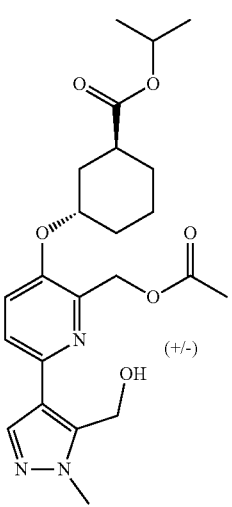

116-7

A solution of intermediate 116-6 (420 mg, 1 mmol), (1-methyl-4-(4,4,5,5-tetramethyl-1,3,2-dioxaborolan-2-yl)-1H-pyrazol-5-yl)methanol (483 mg, 2.02 mmol) and NaHCO$_3$ (340 mg, 4.1 mmol) in dioxane (20 mL) and water (3 mL) was added with tetrakis(triphenylphosphine)palladium(0) (117 mg, 0.05 mmol) under nitrogen atmosphere, and the reaction system was stirred at 60° C. for 5 h. The reaction system was added with water (20 mL) and extracted with ethyl acetate (20 mL×3). The organic phases were combined, washed with saturated brine (30 mL), dried over anhydrous sodium sulfate, filtered and concentrated, and the residue was purified by column chromatography to give intermediate 116-7 (240 mg, 53% yield) in the form of a brown oil. MS [M+H]$^+$=445.8.

Step (7): Preparation of (+/−)-isopropyl (1S,3S)-3-((2-(acetoxymethyl)-6-(1-methyl-5-(((((4-(nitrophenoxy) carbonyl)oxy)methyl)-1H-pyrazol-4-yl)pyridin-3-yl)oxy)cyclohexane-1-carboxylate

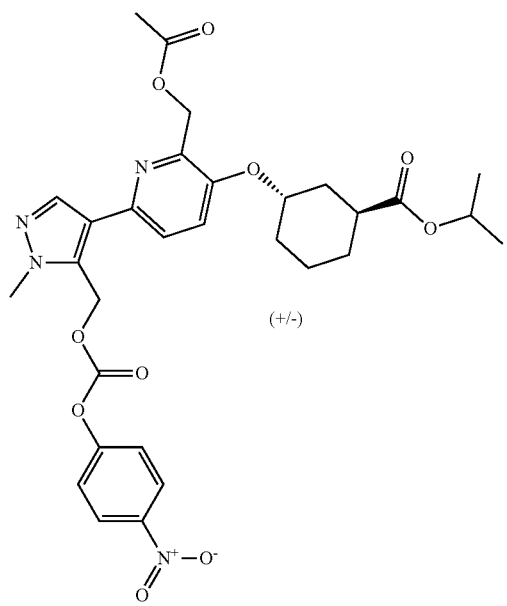

116-8

A solution of intermediate 116-7 (240 mg, 0.54 mmol) and pyridine (171 mg, 2.15 mmol) in tetrahydrofuran (2 mL) was added to a solution of 4-nitrophenyl chloroformate (217 mg, 1.07 mmol) in tetrahydrofuran (8 mL) under nitrogen atmosphere. The reaction mixture was stirred overnight at room temperature. After the reaction was completed, intermediate 116-8 was obtained, which was directly used in the next step. MS [M+H]$^+$=610.6.

Step (8): Preparation of (+/−)-isopropyl (1R,3R)-3-((2-(acetoxymethyl)-6-(5-(((cyclobutyl(methyl) carbamoyl)oxy)methyl)-1-methyl-1H-pyrazol-4-yl)pyridin-pyridin-3-yl)oxy)cyclohexane-1-carboxylate

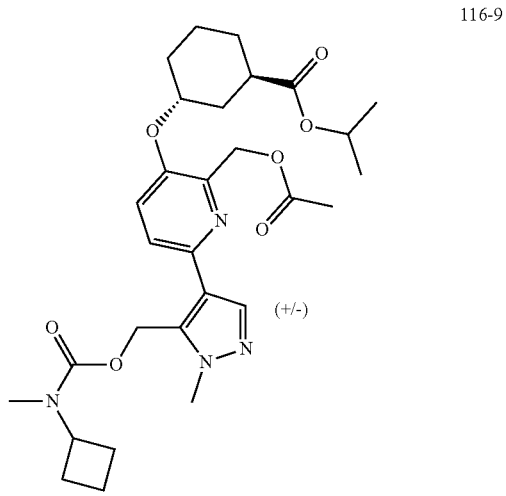 [SMILES: CC(=O)OCc1nc(-c2cnn(C)c2COC(=O)N(C)C2CCC2)ccc1O[C@@H]1CCC[C@@H](C(=O)OC(C)C)C1]

116-9

The above reaction system was added with DIEA (278 mg, 2.15 mmol) and N-methylcyclobutylamine hydrochloride (196 mg, 1.6 mmol), and the reaction system was stirred overnight at room temperature. The reaction system was concentrated, and the residue was separated by column chromatography to give intermediate 116-9 (150 mg, 50% yield) in the form of a pale yellow oil. MS [M+H]$^+$=556.8.

Step (9): Preparation of (+/−)-(1S,3S)-3-((6-(5-(((cyclobutyl(methyl)carbamoyl)oxy)methyl)-1-methyl-1H-pyrazol-4-yl)-2-(hydroxymethyl)pyridin-3-yl)oxy)cyclohexane-1-carboxylic Acid

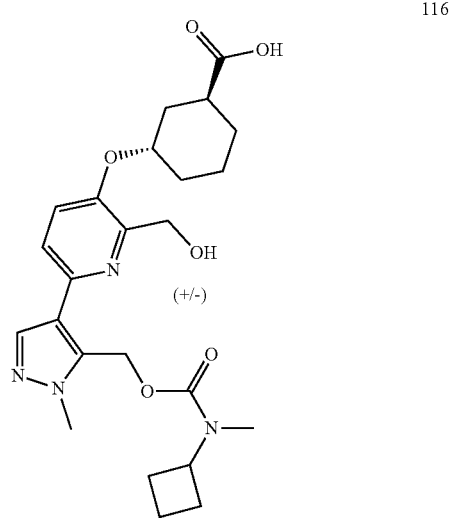 [SMILES: CN(C(=O)OCc1c(-c2ccc(O[C@H]3CCC[C@H](C(=O)O)C3)c(CO)n2)cnn1C)C1CCC1]

116

A solution of sodium hydroxide (72 mg, 1.80 mmol) in water (2 mL) was added to a solution of intermediate 116-9 (200 mg, 0.36 mmol) in a mixed solvent of tetrahydrofuran and methanol (5 mL, 1 mL) while stirring at room temperature, and the reaction system was stirred overnight at room temperature. The reaction system was diluted with water (10 mL), adjusted to pH 6 with diluted hydrochloric acid and extracted with ethyl acetate (10 mL×3). The organic phases were combined, dried over anhydrous sodium sulfate, filtered and concentrated, and the residue was separated by column chromatography to give compound 116 (150 mg, 83% yield) in the form of a colorless oil. LC-MS [M+H]$^+$: 472.8.

$^1$H NMR (400 MHz, CDCl$_3$) δ 7.80 (s, 1H), 7.39 (d, J=8.5 Hz, 1H), 7.22 (d, J=8.5 Hz, 1H), 5.55 (s, 2H), 4.80 (s, 2H), 4.74-4.68 (m, 1H), 4.46-4.14 (m, 1H), 4.01 (s, 3H), 2.91-2.79 (m, 4H), 2.16-2.05 (m, 4H), 2.03-1.85 (m, 4H), 1.79-1.56 (m, 6H).

Example 117

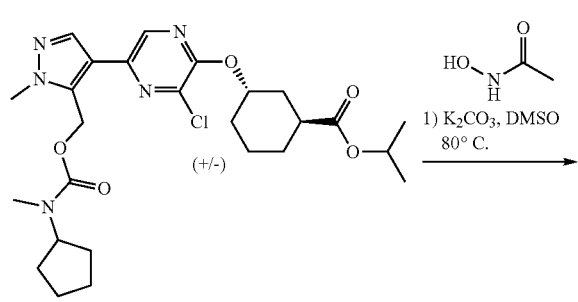

103-6

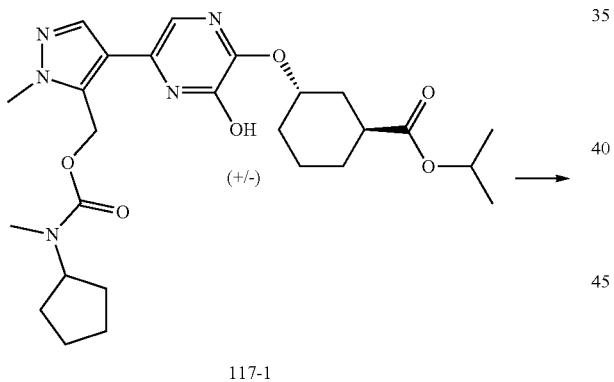

117-1

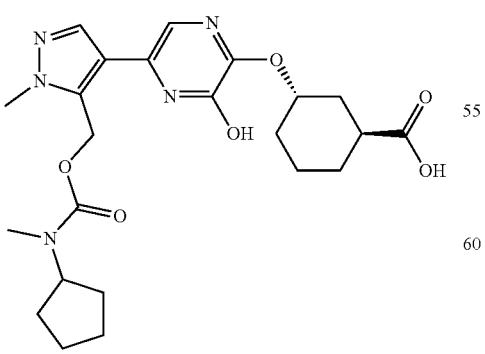

117

Step (1): Preparation of (+/−)-isopropyl (1S,3S)-3-((5-(5-(((cyclopentyl(methyl)carbamoyl)oxy)methyl)-1-methyl-1H-pyrazol-4-yl)-3-hydroxypyrazin-2-yl)oxy)cyclohexane-1-carboxylate

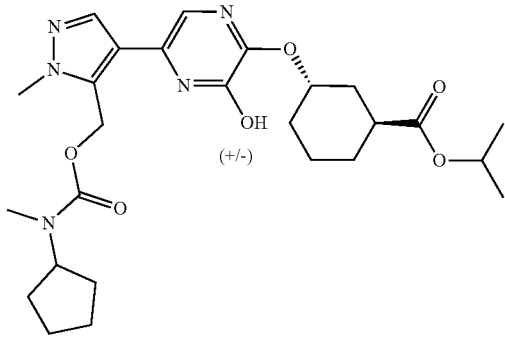

117-1

Intermediate 103-6 (400 mg, 0.75 mmol) was dissolved in dimethyl sulfoxide (5 mL), and the reaction system was added with acetohydroxamic acid (281 mg, 3.75 mmol) and potassium carbonate (310 mg, 2.25 mmol) and stirred at 80° C. for 3 h. Then the reaction system was diluted with water (15 mL) and extracted with ethyl acetate (20 mL×2). The organic phases were combined, washed with saturated brine (20 mL), dried over anhydrous sodium sulfate, filtered and concentrated, and the residue was separated by silica gel column chromatography to give intermediate 117-1 (150 mg, 38.9% yield) in the form of a pale yellow oily liquid. LC-MS [M+H]$^+$: 515.7.

Step (2): Preparation of (+/−)-(1S,3S)-3-(5-(((cyclopentyl(methyl)carbamoyl)oxy)methyl)-1-methyl-1H-pyrazol-4-yl)-3-hydroxypyrazin-2-yl) oxy)cyclohexane-1-carboxylic Acid

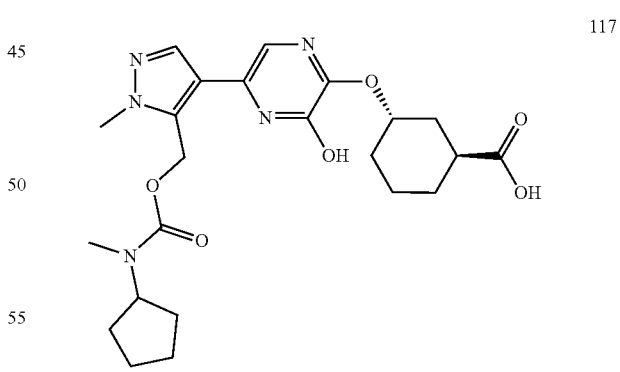

117

Intermediate 117-1 (100 mg, 0.19 mmol) and lithium hydroxide monohydrate (41 mg, 0.97 mmol) were dissolved in tetrahydrofuran (3 mL)/methanol (1 mL)/water (1 mL), and the reaction system was reacted overnight at room temperature. The reaction system was concentrated under reduced pressure, and the residue was added with water (10 mL) and extracted with ether (10 mL×2). The aqueous phase was retained, adjusted to pH 4 with diluted hydrochloric acid (1 N), and extracted with dichloromethane (15 mL×3). The organic phases were combined, dried over anhydrous sodium sulfate, filtered and concentrated, and the residue was separated by preparative chromatography to give compound 117 (20 mg) in the form of a pale yellow oil. LC-MS [M+H]$^+$: 473.9.

$^1$H NMR (400 MHz, MeOD) δ 7.68 (s, 1H), 7.00 (s, 1H), 5.43-5.38 (m, 1H), 5.30 (s, 2H), 4.58-4.32 (s, 1H), 4.00 (s, 3H), 2.93-2.85 (m, 1H), 2.81 (s, 3H), 2.29-2.19 (m, 1H), 2.03-1.95 (m, 2H), 1.90-1.55 (m, 13H).

Biological Experiments

Example A: In Vitro Evaluation of Biological Activity

The antagonist property of the compounds disclosed herein was determined using the FLIPR (fluorescence imaging plate reader) method, wherein the compounds are inhibitors for the intracellular calcium increase induced by activation of hLPAR1 (human lysophosphatidic acid receptor 1, accession No. NM_001401.4) expressed in CHO-K1 cells (Chinese hamster ovary cells K1, ATCC).

CHO-K1 cells stably expressing hLPAR1 were cultured in F-12 medium containing 10% FBS (fetal bovine serum, Gibco, 10099-141), 1% penicillin-streptomycin (Gibco, 15140-122) and 0.4 mg/mL hygromycin B (Gibco, 10687010) in a cell incubator (37° C., 5% humidity). Cells at 250,000 cells/mL were seeded into a 96-well plate (25,000 cells/well) 18-24 h prior to the FLIPR experiment and then incubated overnight in a cell incubator. On the day of the experiment, the medium was discarded and the cells were washed in an FLIPR buffer (0.3 mL of probenecid (Thermo, P36400), 0.6 mL of 1 M HEPES (Invitrogen, 15630080) and 29.1 mL of HBSS (Invitrogen, 14065056) per 30 mL of the buffer). Each well was added with 75 μL of 1 mM Fluo-4 AM fluorescent dye (Thermo, F14202) and then the cells were subjected to dye-loading incubation at 37° C. for 1.0 h. The 96-well plate was then washed once with buffer, added with a buffer containing a test compound or a vehicle at 50 μL per well and then incubated for 30 min at room temperature. The cell plate was then placed in the FLIPR for baseline fluorescence measurements (excitation at 485 nm and emission at 525-535 nm). An agonist (oleoyl-L-α-lysophosphatidic acid sodium salt (Sigma, L7260)) at a final concentration of 1 μM or a vehicle (ultrapure water) was then added at 50 μL/well, fluorescence values were measured for 2 min at 1-second intervals, and finally the output fluorescence counts were analyzed.

IC$_{50}$ values obtained using the above method are shown in Table 1.

TABLE 1

IC$_{50}$ values of the compounds of Examples 1-117 for LPAR1 receptor

| Compound | Example No. | LPAR1 IC$_{50}$ (μM) |
| --- | --- | --- |
| Compound 1 | Example 1 | C |
| Compound 2 | Example 2 | C |
| Compound 3 | Example 3 | C |
| Compound 4 | Example 4 | A |
| Compound 5 | Example 5 | C |
| Compound 6 | Example 6 | C |
| Compound 7 | Example 7 | A |
| Compound 8 | Example 8 | C |
| Compound 9 | Example 9 | C |
| Compound 10 | Example 10 | C |
| Compound 11 | Example 11 | A |
| Compound 12 | Example 12 | C |
| Compound 13 | Example 13 | B |
| Compound 14 | Example 14 | C |
| Compound 15 | Example 15 | C |
| Compound 16 | Example 16 | A |
| Compound 17 | Example 17 | B |
| Compound 18 | Example 18 | B |
| Compound 19 | Example 19 | C |
| Compound 20 | Example 20 | A |
| Compound 21 | Example 21 | C |
| Compound 22 | Example 22 | C |
| Compound 23 | Example 23 | C |
| Compound 24 | Example 24 | C |
| Compound 25 | Example 25 | C |
| Compound 26 | Example 26 | C |
| Compound 27 | Example 27 | A |
| Compound 28 | Example 28 | A |
| Compound 29 | Example 29 | A |
| Compound 30 | Example 30 | A |
| Compound 31 | Example 31 | A |
| Compound 32 | Example 32 | B |
| Compound 33 | Example 33 | A |
| Compound 34 | Example 34 | B |
| Compound 35 | Example 35 | A |
| Compound 36 | Example 36 | A |
| Compound 37 | Example 37 | A |
| Compound 38 | Example 38 | A |
| Compound 39 | Example 39 | A |
| Compound 40 | Example 40 | A |
| Compound 41 | Example 41 | A |
| Compound 42 | Example 42 | A |
| Compound 43 | Example 43 | A |
| Compound 44 | Example 44 | A |
| Compound 45 | Example 45 | A |
| Compound 46 | Example 46 | A |
| Compound 47 | Example 47 | A |
| Compound 48 | Example 48 | A |
| Compound 49 | Example 49 | A |
| Compound 50 | Example 50 | A |
| Compound 51 | Example 51 | A |
| Compound 52 | Example 52 | A |
| Compound 53 | Example 53 | A |
| Compound 54 | Example 54 | A |
| Compound 55 | Example 55 | A |
| Compound 56 | Example 56 | A |
| Compound 57 | Example 57 | A |
| Compound 58 | Example 58 | A |
| Compound 59 | Example 59 | A |
| Compound 61 | Example 61 | A |
| Compound 62 | Example 62 | A |
| Compound 63 | Example 63 | A |
| Compound 64 | Example 64 | C |
| Compound 65 | Example 65 | C |
| Compound 66 | Example 66 | A |
| Compound 67 | Example 67 | C |
| Compound 68 | Example 68 | C |
| Compound 69 | Example 69 | C |
| Compound 70 | Example 70 | C |
| Compound 71 | Example 71 | C |
| Compound 72 | Example 72 | C |
| Compound 73 | Example 73 | C |
| Compound 74 | Example 74 | C |
| Compound 75 | Example 75 | C |
| Compound 76 | Example 76 | C |
| Compound 77 | Example 77 | A |
| Compound 78 | Example 78 | B |
| Compound 79 | Example 79 | A |
| Compound 80 | Example 80 | A |
| Compound 81 | Example 81 | B |
| Compound 82 | Example 82 | A |
| Compound 83 | Example 83 | B |
| Compound 84 | Example 84 | A |
| Compound 85 | Example 85 | B |
| Compound 86 | Example 86 | A |
| Compound 87 | Example 87 | B |
| Compound 88 | Example 88 | B |

TABLE 1-continued

IC$_{50}$ values of the compounds of Examples 1-117 for LPAR1 receptor

| Compound | Example No. | LPAR1 IC$_{50}$ (μM) |
|---|---|---|
| Compound 89 | Example 89 | B |
| Compound 90 | Example 90 | A |
| Compound 91 | Example 91 | A |
| Compound 92 | Example 92 | A |
| Compound 93 | Example 93 | C |
| Compound 94 | Example 94 | C |
| Compound 95 | Example 95 | C |
| Compound 96 | Example 96 | C |
| Compound 97 | Example 97 | C |
| Compound 98 | Example 98 | C |
| Compound 99 | Example 99 | C |
| Compound 100 | Example 100 | C |
| Compound 101 | Example 101 | A |
| Compound 102 | Example 102 | A |
| Compound 103 | Example 103 | A |
| Compound 104 | Example 104 | A |
| Compound 105 | Example 105 | A |
| Compound 106 | Example 106 | C |
| Compound 107 | Example 107 | C |
| Compound 108 | Example 108 | C |
| Compound 109 | Example 109 | B |
| Compound 110 | Example 110 | B |
| Compound 111 | Example 111 | C |
| Compound 112 | Example 112 | B |
| Compound 113 | Example 113 | C |
| Compound 114 | Example 114 | C |
| Compound 115 | Example 115 | C |
| Compound 116 | Example 116 | C |
| Compound 117 | Example 117 | C |

A: IC$_{50}$ ≤ 50 nM;
B: 50 < IC$_{50}$ ≤ 300 nM;
C: 300 < IC$_{50}$ ≤ 10000 nM.

The results show that the above compounds have good inhibitory activity against LPAR1. The IC$_{50}$ value of some of the compounds was 10000 nM or less, 300 nM or less, or even 50 nM or less. In view of such an excellent inhibitory activity, application thereof as LPAR1 inhibitors to the diseases or disorders described above is anticipated.

Example B: In Vitro Evaluation of Biological Activity (Cell Activity)

The activity of the compounds disclosed herein at the cell level in vitro is evaluated by A2058 (human melanoma cells, Beina Bio, BNCC341099) cell scratch assay. The inhibitory activity of the compounds against LPAR1 can be reflected by inhibition of cell scratch healing.

A2058 cells in a T75 cm$^2$ cell culture flask were digested and gently pipetted into single cells, adjusted to a cell density of $4\times10^5$ cells/mL, and then seeded into a 24-well plate. After the cell confluence reached 80%, the cell culture plate was taken out and the original medium was discarded. Serum-free medium was then added, and the cells were starved overnight in an incubator (37° C., 5% CO$_2$). The cell culture plate was then taken out, and cell scratches were made along the diameter of the wells using a 200 μL pipette tip. The cell culture plate was then added with 500 μL of serum-free medium and then shaken gently to wash away the residual cells on the scratched surface, and this was repeated twice. The medium was discarded and 500 μL of 1% FBS medium containing the compound was then added, and the mixture was incubated at 37° C. for 30 min. The medium was discarded, and 500 μL of 1% FBS medium containing 10 μM compound and 10 μM LPA was added. Olympus CKX53 was used to observe the scratches, and MShot image analysis system was used to take pictures and measure the scratch area at 0 h. The plate was incubated in the incubator under the conditions of 37° C. and 5% CO$_2$. 24 h later, the scratches were observed again with Olympus CKX53, and MShot image analysis system was used to take pictures and measure the scratch area at 24 h. Cell migration inhibition rate was calculated according to the following formula:

$$\text{Cell migration inhibition rate (\%)} = 1 - \frac{\text{scratch area of compound group at 0 h} - \text{scratch area of compound group at 24 h}}{\text{scratch area of control group at 0 h} - \text{scratch area of control group at 24 h}}$$

TABLE 2

Inhibition rate of example compounds against scratch migration of A2058 cells

| Compound | Example No. | Cell migration inhibition rate (%20 μM) |
|---|---|---|
| Compound 1 | Example 1 | C |
| Compound 2 | Example 2 | C |
| Compound 3 | Example 3 | C |
| Compound 4 | Example 4 | B |
| Compound 5 | Example 5 | C |
| Compound 6 | Example 6 | C |
| Compound 7 | Example 7 | A |
| Compound 8 | Example 8 | C |
| Compound 9 | Example 9 | C |
| Compound 10 | Example 10 | C |
| Compound 11 | Example 11 | A |
| Compound 12 | Example 12 | C |
| Compound 13 | Example 13 | B |
| Compound 14 | Example 14 | C |
| Compound 15 | Example 15 | C |
| Compound 16 | Example 16 | A |
| Compound 17 | Example 17 | C |
| Compound 18 | Example 18 | B |
| Compound 19 | Example 19 | C |
| Compound 20 | Example 20 | B |
| Compound 21 | Example 21 | C |
| Compound 22 | Example 22 | C |
| Compound 23 | Example 23 | C |
| Compound 24 | Example 24 | C |
| Compound 25 | Example 25 | B |
| Compound 26 | Example 26 | C |
| Compound 27 | Example 27 | B |
| Compound 28 | Example 28 | A |
| Compound 29 | Example 29 | B |
| Compound 30 | Example 30 | B |
| Compound 31 | Example 31 | B |
| Compound 32 | Example 32 | B |
| Compound 33 | Example 33 | B |
| Compound 34 | Example 34 | B |
| Compound 35 | Example 35 | B |
| Compound 36 | Example 36 | A |
| Compound 37 | Example 37 | A |
| Compound 38 | Example 38 | A |
| Compound 39 | Example 39 | B |
| Compound 40 | Example 40 | A |
| Compound 41 | Example 41 | B |
| Compound 42 | Example 42 | A |
| Compound 43 | Example 43 | A |
| Compound 44 | Example 44 | B |
| Compound 45 | Example 45 | A |
| Compound 46 | Example 46 | A |
| Compound 47 | Example 47 | B |
| Compound 48 | Example 48 | B |
| Compound 49 | Example 49 | B |
| Compound 50 | Example 50 | A |
| Compound 51 | Example 51 | A |

TABLE 2-continued

Inhibition rate of example compounds against scratch migration of A2058 cells

| Compound | Example No. | Cell migration inhibition rate (%20 μM) |
|---|---|---|
| Compound 52 | Example 52 | B |
| Compound 53 | Example 53 | A |
| Compound 54 | Example 54 | B |
| Compound 55 | Example 55 | A |
| Compound 56 | Example 56 | A |
| Compound 57 | Example 57 | A |
| Compound 58 | Example 58 | A |
| Compound 59 | Example 59 | B |
| Compound 61 | Example 61 | A |
| Compound 62 | Example 62 | A |
| Compound 63 | Example 63 | B |
| Compound 64 | Example 64 | C |
| Compound 65 | Example 65 | C |
| Compound 66 | Example 66 | B |
| Compound 88 | Example 88 | C |
| Compound 89 | Example 89 | A |
| Compound 91 | Example 91 | C |
| Compound 92 | Example 92 | B |
| Compound 93 | Example 93 | B |
| Compound 94 | Example 94 | C |
| Compound 95 | Example 95 | C |
| Compound 97 | Example 97 | C |
| Compound 98 | Example 98 | C |
| Compound 100 | Example 100 | B |
| Compound 102 | Example 102 | A |
| Compound 104 | Example 104 | C |
| Compound 105 | Example 105 | B |
| Compound 106 | Example 106 | B |
| Compound 108 | Example 108 | B |
| Compound 109 | Example 109 | A |
| Compound 110 | Example 110 | B |
| Compound 112 | Example 112 | B |
| Compound 113 | Example 113 | C |
| Compound 114 | Example 114 | C |
| Compound 115 | Example 115 | C |
| Compound 116 | Example 116 | B |
| Compound 117 | Example 117 | B |

A: 50-70%;
B: 30-50%;
C: 0-30%.

It can be seen from the data in Table 2 that the above-mentioned compounds have relatively good inhibitory activity against LPAR1, wherein some compounds have an inhibitory rate of 30-50% against A2058 cell migration, some compounds have an inhibitory rate of 50-70%, and cell migration is remarkably inhibited.

Example C: In Vitro Cytotoxicity Assay

In vitro cytotoxicity assay for the compounds disclosed herein was performed in HepG2 cells using the CCK-8 method. HepG2 cells (Beina Bio) in the logarithmic growth phase were collected, the concentration of cell suspension was adjusted, and then the cells were plated on a 96-well cell culture plate at 50,000 cells/well. The cells were then incubated overnight in a cell incubator (5% $CO_2$, 37° C.), and after 80-90% cell confluence was achieved, test compounds or vehicle (DMSO) at various concentration gradients were added after medium change. The resulting mixture was incubated in the cell incubator (5% $CO_2$, 37° C.) for 48 h. After the treatment, the medium in the plate was discarded. The plate was washed twice with PBS, added with CCK-8 working solution (Beyotime) at 100 μL per well, and then incubated at 37° C. for 1.5 h away from the light. Absorbance at $OD_{450\,nm}$ was measured for each well on a microplate reader, and $CC_{50}$ value of each compound was analyzed and calculated.

$CC_{50}$ values obtained using the above method are shown in Table 3.

TABLE 3

$CC_{50}$ values obtained for some of the compounds

| Compound | Example No. | HepG2 $CC_{50}$ (μM) |
|---|---|---|
| Compound 1 | Example 1 | >200 |
| Compound 2 | Example 2 | >200 |
| Compound 3 | Example 3 | >200 |
| Compound 4 | Example 4 | >200 |
| Compound 5 | Example 5 | >200 |
| Compound 6 | Example 6 | >200 |
| Compound 7 | Example 7 | >200 |
| Compound 8 | Example 8 | >200 |
| Compound 9 | Example 9 | >200 |
| Compound 10 | Example 10 | >200 |
| Compound 11 | Example 11 | >200 |
| Compound 12 | Example 12 | >200 |
| Compound 13 | Example 13 | >200 |
| Compound 14 | Example 14 | >200 |
| Compound 15 | Example 15 | >200 |
| Compound 16 | Example 16 | >200 |
| Compound 17 | Example 17 | >200 |
| Compound 18 | Example 18 | >200 |
| Compound 19 | Example 19 | >200 |
| Compound 20 | Example 20 | >200 |
| Compound 21 | Example 21 | >200 |
| Compound 22 | Example 22 | >200 |
| Compound 23 | Example 23 | >200 |
| Compound 24 | Example 24 | >200 |
| Compound 25 | Example 25 | >200 |
| Compound 26 | Example 26 | >200 |
| Compound 27 | Example 27 | >200 |
| Compound 28 | Example 28 | >200 |
| Compound 29 | Example 29 | >200 |
| Compound 30 | Example 30 | >200 |
| Compound 31 | Example 31 | >200 |
| Compound 32 | Example 32 | >200 |
| Compound 33 | Example 33 | >200 |
| Compound 34 | Example 34 | >200 |
| Compound 35 | Example 35 | >200 |
| Compound 36 | Example 36 | >200 |
| Compound 37 | Example 37 | >200 |
| Compound 38 | Example 38 | >200 |
| Compound 39 | Example 39 | >200 |
| Compound 40 | Example 40 | >200 |
| Compound 41 | Example 41 | >200 |
| Compound 42 | Example 42 | >200 |
| Compound 43 | Example 43 | >200 |
| Compound 44 | Example 44 | >200 |
| Compound 45 | Example 45 | >200 |
| Compound 46 | Example 46 | >200 |
| Compound 47 | Example 47 | >200 |
| Compound 48 | Example 48 | >200 |
| Compound 49 | Example 49 | >200 |
| Compound 50 | Example 50 | >200 |
| Compound 51 | Example 51 | >200 |
| Compound 52 | Example 52 | >200 |
| Compound 53 | Example 53 | >200 |
| Compound 54 | Example 54 | >200 |
| Compound 55 | Example 55 | >200 |
| Compound 56 | Example 56 | >200 |
| Compound 57 | Example 57 | >200 |
| Compound 58 | Example 58 | >200 |
| Compound 59 | Example 59 | >200 |
| Compound 61 | Example 61 | >200 |
| Compound 62 | Example 62 | >200 |
| Compound 63 | Example 63 | >200 |
| Compound 89 | Example 89 | 14.29 |
| Compound 100 | Example 100 | >200 |

It can be seen from the data in Table 3 that most of the compounds disclosed herein all have good safety, and the $CC_{50}$ ranges of the compounds are all greater than 200 μM.

Example D: Test of In Vitro Metabolic Stability

The in vitro metabolic stability of the compounds disclosed herein was determined through incubation of liver microsomes of various species. A proper amount of test compound was added into a liver microsome reaction system (1 mg/mL liver microsome protein, 25 U/mL glucose-6 phosphate dehydrogenase, 1 mM NADP, 6 mM D-glucose 6-phosphate and 5 mM $MgCl_2$), and then the mixture was incubated in a water bath kettle at 37° C. to start reaction. At each time point, 100 µL of the reaction system was added into a centrifuge tube containing 400 µL of internal standard working solution (containing a 200 ng/mL solution of dexamethasone, diclofenac, tolbutamide and labetalol in acetonitrile) precooled at 0° C. so as to stop the reaction, and the mixture was then centrifuged at 10,000 g for 10 min at 4° C. The supernatant was collected for LC-MS assay so as to obtain the values of in vitro metabolic half-life of the test compounds in liver microsomes of various species.

The metabolic half-life data obtained using the above method are shown in Table 4.

TABLE 4

Metabolic stability data obtained for some of the compounds

| Compound | Example No. | Metabolism in human liver microsome T½ min | Metabolism in rat liver microsome T½ min | Metabolism in mouse liver microsome T½ min |
|---|---|---|---|---|
| Compound 4 | Example 4 | 131.44 | 13.09 | 167.16 |
| Compound 7 | Example 7 | 108.59 | 2.81 | 148.51 |
| Compound 8 | Example 8 | >30 | >30 | >30 |
| Compound 11 | Example 11 | >30 | >30 | >30 |
| Compound 13 | Example 13 | 68.81 | 17.2 | 213.01 |
| Compound 14 | Example 14 | >30 | >30 | >30 |
| Compound 15 | Example 15 | >30 | >30 | >30 |
| Compound 16 | Example 16 | 618.8 | 108.74 | NA |
| Compound 18 | Example 18 | 1044.12 | 92.66 | 349.63 |
| Compound 20 | Example 20 | >30 | >30 | >30 |
| Compound 28 | Example 28 | >30 | <30 | >30 |
| Compound 36 | Example 36 | 145.36 | 28.4 | 339.73 |
| Compound 62 | Example 62 | >30 | ~30 | >30 |
| Compound 63 | Example 63 | 385.83 | 44.92 | 537.42 |
| Compound 66 | Example 66 | 492.32 | 93.37 | 703.34 |
| Compound 89 | Example 89 | 448.92 | 57.45 | 3670.49 |

NA: no obvious metabolism found and T½ unable to be fitted

Studies have shown that the compounds disclosed herein have relatively good metabolic stability in human, rat and mouse, and some of the compounds have $T_{1/2}$>30 min, even $T_{1/2}$>90 min in human liver microsome.

Example E: Pharmacodynamic Evaluation on Bleomycin-Induced Mouse Lung Fibrosis Models Pharmacodynamic evaluation of the compounds disclosed herein was performed using bleomycin-induced mouse lung fibrosis models.

The bleomycin-induced pulmonary fibrosis models of C57BL/6 mice were established by administering 3 mg/kg of bleomycin in a single rapid spray (tracheal spray) with a nebulizer. For the normal control group, normal saline was used instead. Immediately after injection, the animals were erected at a 90-degree angle and rotated left and right for 2 min to allow the medical solution to be evenly distributed in the lungs. On day 0, the bleomycin induction group was randomly divided into a model group and an administration group (divided into low, medium, and high dosage groups) according to body weight. On days 0-20 of the experiment, animals in the normal control group and the model control group were intragastrically administered with vehicle (0.5% CMC-Na) once daily, and animals in the administration group was administered with a corresponding dosage of the compound. After 21 days of consecutive administration, the mice were anesthetized by intraperitoneal injection of 1% sodium pentobarbital (0.06 mL/10 g) and then put to death by bleeding at abdominal aorta. The thoracic cavity was cut open, the whole lungs of the mice were taken out, and the residual blood on the surface was washed away with normal saline. The left lung was soaked in 4% paraformaldehyde for use in the detection of pulmonary inflammation and fibrosis using HE and Masson staining. After the upper bronchus and blood vessels were removed as much as possible, the remaining lung was weighed, added with 1× Ripa lysate (containing protease inhibitor cocktail and PMSF) at a ratio of 2 mL/100 mg, homogenized with a homogenizer, and then stored in a refrigerator at −80° C. for use in the detection of the levels of hydroxyproline, Collagen I and α-SMA in lung tissue.

The results show that the compounds disclosed herein can alleviate bleomycin-induced lung fibrosis in mice by inhibiting the fibrogenic mechanism mediated by LPAR1.

In the specification, terms such as "one embodiment", "some embodiments", "examples", "a specific example", or "some examples", means that a particular feature, structure, material or characteristic described in reference to the embodiment or example is included in at least one embodiment or example of the present invention. In this specification, the schematic descriptions of the terms described above do not necessarily refer to the same embodiment or example. Moreover, the specific features, materials, structures and other characteristics described may be combined in any one or more embodiments or examples in an appropriate manner. Moreover, various embodiments or examples and features of various embodiments or examples described in this specification can be combined by one skilled in the art to the extent that they do not contradict each other.

Although examples of the present invention are illustrated and described above, it will be appreciated that the above examples are exemplary and not to be construed as limiting the present invention, and that changes, modifications, substitutions and alterations can be made to the above examples by those of ordinary skill in the art within the scope of the present invention.

The invention claimed is:

1. A compound, a stereoisomer, a tautomer, a nitrogen oxide, a solvate, a polymorph, an ester, or a pharmaceutically acceptable salt thereof, wherein the compound is selected from the following compounds:

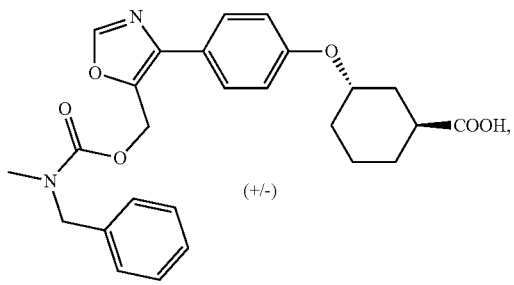

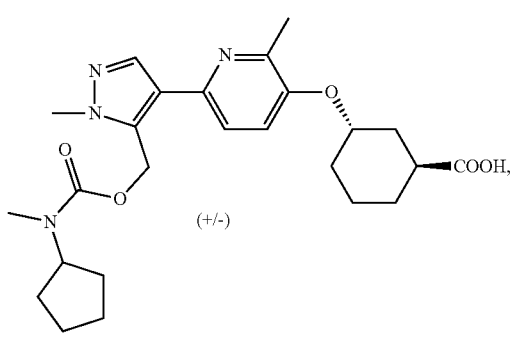

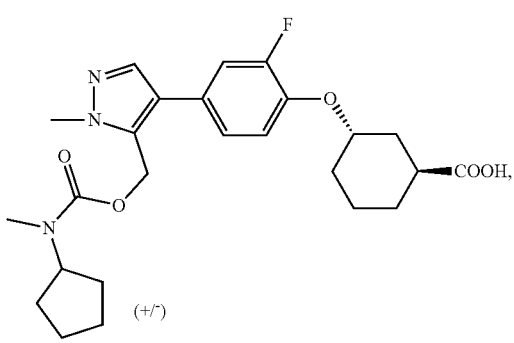

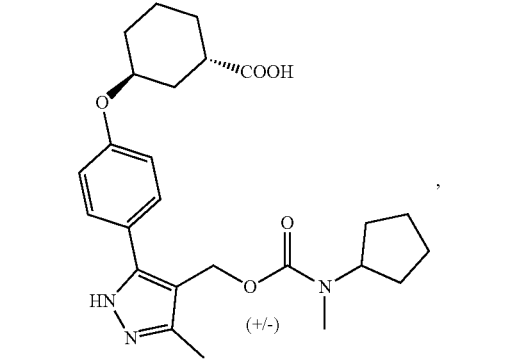

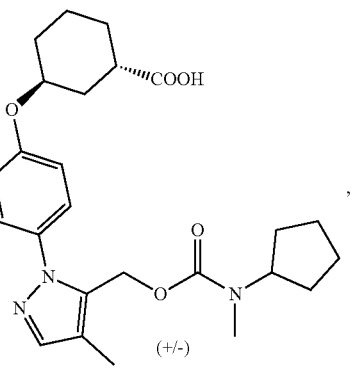

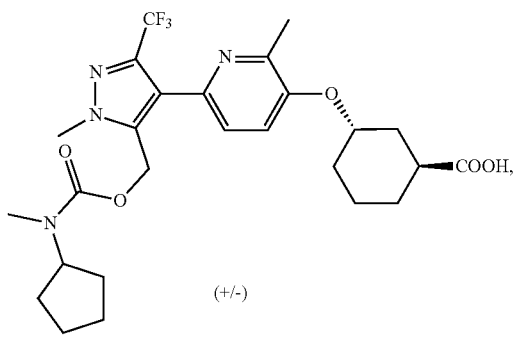

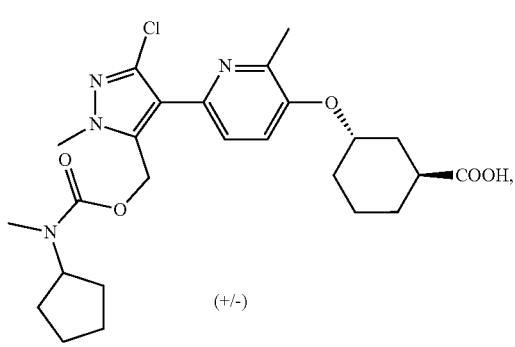

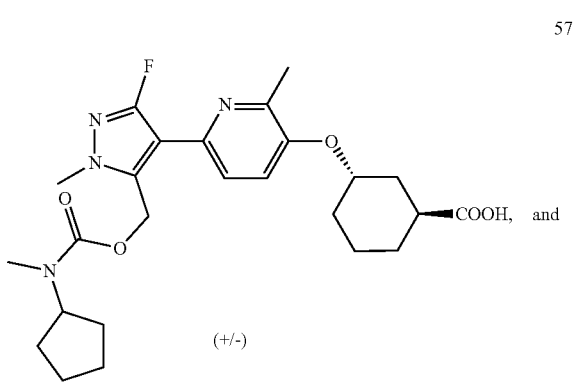

-continued

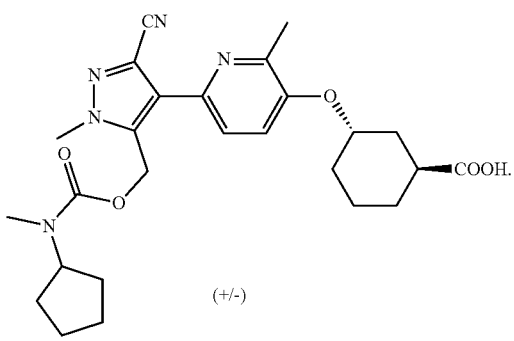

58

(+/-)

2. A pharmaceutical composition comprising one, two or more selected from the compound, the stereoisomer, the tautomer, the nitrogen oxide, the solvate, the polymorph, the ester, and the pharmaceutically acceptable salt according to claim 1.

3. A method for treating LPAR1-mediated conditions or diseases, comprising administering a therapeutically effective amount of the compound according to claim 1, the stereoisomer, the tautomer, the nitrogen oxide, the solvate, the polymorph, the ester, or the pharmaceutically acceptable salt thereof to a subject in need thereof, wherein the conditions or diseases are selected from organ fibrotic diseases, respiratory diseases, renal diseases, hepatic diseases, inflammatory diseases, neurological diseases, cardiovascular and cerebrovascular diseases, gastrointestinal diseases, pains, urinary system diseases, ophthalmic diseases, metabolic diseases, cancers, and rejection of transplanted organs.

* * * * *